United States Patent
Nie et al.

(10) Patent No.: US 11,827,615 B2
(45) Date of Patent: *Nov. 28, 2023

(54) NITROGEN-CONTAINING COMPOUND, ELECTRONIC ELEMENT AND ELECTRONIC DEVICE

(71) Applicant: Shaanxi Lighte Optoelectronics Materials Co., Ltd., Shaanxi (CN)

(72) Inventors: Qiqi Nie, Shaanxi (CN); Jiamei Cao, Shaanxi (CN); Tiantian Ma, Shaanxi (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/528,554

(22) Filed: Nov. 17, 2021

(65) Prior Publication Data

US 2022/0081408 A1     Mar. 17, 2022

Related U.S. Application Data

(63) Continuation of application No. 17/109,611, filed on Dec. 2, 2020, now Pat. No. 11,203,584.

(30) Foreign Application Priority Data

Dec. 31, 2019    (CN) .......................... 201911415821.0

(51) Int. Cl.
    *C07D 333/76*       (2006.01)
    *C07C 211/54*       (2006.01)
    (Continued)

(52) U.S. Cl.
    CPC .......... *C07D 333/76* (2013.01); *C07C 211/54* (2013.01); *C07D 209/82* (2013.01);
    (Continued)

(58) Field of Classification Search
    CPC .. C07D 333/76; C07D 209/82; C07D 209/86; C07D 209/88; C07D 213/36;
    (Continued)

(56) References Cited

U.S. PATENT DOCUMENTS 11,203,584 B2 * 12/2021 Nie ................... C07D 307/91
2004/0124766 A1    7/2004 Nakagawa et al.
(Continued)

FOREIGN PATENT DOCUMENTS

CN       107459466 A     12/2017
CN       110128279 A      8/2019
(Continued)

OTHER PUBLICATIONS

Gu, Yu, et al. "Tetrasubstituted adamantane derivatives with arylamine groups: Solution-processable hole-transporting and host materials with high triplet energy and good thermal stability for organic light-emitting devices." Organic Electronics 25 (2015): 193-199. (Year: 2015).*

(Continued)

*Primary Examiner* — Dawn L Garrett
(74) *Attorney, Agent, or Firm* — TUCKER ELLIS LLP

(57) ABSTRACT

The present disclosure provides a nitrogen-containing compound, an electronic element and an electronic device, which belongs to the technical field of organic materials. The nitrogen-containing compound has a structure of Chemical Formula 1, wherein $R_1$ and $R_2$ are each independently selected from hydrogen or a group represented by Chemical Formula 1-1, and one and only one of $R_1$ and $R_2$ has the group of Chemical Formula 1-1; when $R_1$ or $R_2$ is selected from hydrogen, said $R_1$ and $R_2$ may be replaced by $R_4$. The nitrogen-containing compound can improve the performance of electronic elements.

(Continued)

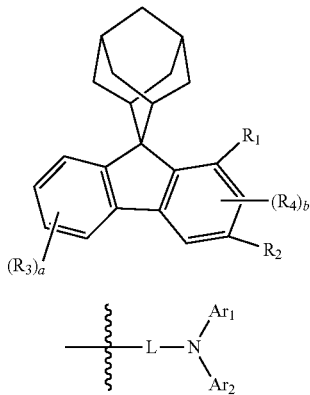

Chemical Formula 1

Chemical Formula 1-1

12 Claims, 2 Drawing Sheets

(51) Int. Cl.
C07D 209/82 (2006.01)
C07D 209/86 (2006.01)
C07D 209/88 (2006.01)
C07D 213/36 (2006.01)
C07D 215/12 (2006.01)
C07D 265/38 (2006.01)
C07D 307/91 (2006.01)
C07D 311/80 (2006.01)
C07D 319/24 (2006.01)
C07D 339/08 (2006.01)
C07D 403/12 (2006.01)
C07D 405/12 (2006.01)
C07D 409/12 (2006.01)
C07D 471/04 (2006.01)
C07F 7/08 (2006.01)
H10K 85/60 (2023.01)
H10K 50/15 (2023.01)

(52) U.S. Cl.
CPC ......... C07D 209/86 (2013.01); C07D 209/88 (2013.01); C07D 213/36 (2013.01); C07D 215/12 (2013.01); C07D 265/38 (2013.01); C07D 307/91 (2013.01); C07D 311/80 (2013.01); C07D 319/24 (2013.01); C07D 339/08 (2013.01); C07D 403/12 (2013.01); C07D 405/12 (2013.01); C07D 409/12 (2013.01); C07D 471/04 (2013.01); C07F 7/0816 (2013.01); H10K 85/631 (2023.02); H10K 85/633 (2023.02); H10K 85/636 (2023.02); H10K 85/654 (2023.02); H10K 85/6572 (2023.02); H10K 85/6574 (2023.02); H10K 85/6576 (2023.02); H10K 50/156 (2023.02)

(58) Field of Classification Search
CPC .. C07D 215/12; C07D 265/38; C07D 307/91; C07D 311/80; C07D 319/24; C07D 339/08; C07D 403/12; C07D 405/12; C07D 409/12; C07D 471/04; C07D 407/12; C07D 213/38; C07D 213/74; C07D 215/38; C07D 215/44; C07D 311/82; C07D 327/08; C07C 211/54; C07C 211/56; C07C 211/58; C07C 2603/18; C07C 2603/26; C07C 2603/94; C07C 211/61; C07C 255/58; C07C 2601/14; C07F 7/0816; C07F 7/081; C07F 7/0812; H10K 85/631; H10K 85/633; H10K 85/636; H10K 85/654; H10K 85/6572; H10K 85/6574; H10K 85/6576; H10K 50/156; H10K 85/615; H10K 85/626; H10K 30/80; H10K 50/18; H10K 85/40; H10K 85/624; H10K 85/657; C07B 59/001; C07B 2200/05; Y02E 10/549; C09K 11/06; C09K 2211/1007; C09K 2211/1011; C09K 2211/1014; C09K 2211/1029; C09K 2211/1033; C09K 2211/1044; C09K 2211/1088; C09K 2211/1092; C09K 2211/1096

See application file for complete search history.

(56) References Cited

U.S. PATENT DOCUMENTS

2009/0302758 A1 12/2009 Saitoh et al.
2014/0291586 A1 10/2014 Buesing et al.
2016/0126469 A1 5/2016 Nakano
2016/0133849 A1 5/2016 Miyake et al.
2016/0372677 A1 12/2016 Miyake
2021/0130295 A1 5/2021 Kim et al.

FOREIGN PATENT DOCUMENTS

| CN | 111138298 A | 5/2020 |
| CN | 111995533 A | 11/2020 |
| EP | 2194110 A1 | 6/2010 |
| KR | 20190035567 A | 4/2019 |
| KR | 20190118514 A | 10/2019 |
| KR | 20190118515 A | 10/2019 |
| KR | 20200037732 A | 4/2020 |
| WO | 2020050623 A1 | 3/2020 |
| WO | 2020080849 A1 | 4/2020 |
| WO | 2020080872 A1 | 4/2020 |
| WO | 2020248943 A1 | 12/2020 |

OTHER PUBLICATIONS

Ching-Hsin Chen et al.: "Synthesis and characteriation of spiro(adamantane-2,9-fluorene)-based triaryldiamines: thermally stable hole-transporing materials"; Synthetic Metal; dated 2004, pp. 215-220.

* cited by examiner

NITROGEN-CONTAINING COMPOUND, ELECTRONIC ELEMENT AND ELECTRONIC DEVICE

CROSS-REFERENCE OF RELATED APPLICATIONS

This application is a continuation of U.S. patent application Ser. No. 17/109,611, filed Dec. 2, 2010, which claims priority to Chinese patent application No. 201911415821.0, filed Dec. 31, 2019, which are incorporated herein by reference in their entireties.

TECHNICAL FIELD

The present disclosure relates to the technical field of organic materials, in particular to a nitrogen-containing compound, an electronic element using the nitrogen-containing compound, and an electronic device using the electronic element.

BACKGROUND

With the development of electronic technology and the advancement of materials science, the application range of electronic components for realizing electroluminescence or photoelectric conversion becomes more and more extensive. Such electronic component usually includes a cathode and an anode disposed opposite to each other, and a functional layer disposed between the cathode and the anode. The functional layer is composed of multiple organic or inorganic film layers, and generally includes an energy conversion layer, a hole transporting layer disposed between the energy conversion layer and the anode, and an electron transporting layer disposed between the energy conversion layer and the cathode.

For example, when the electronic component is an organic electroluminescent device, it generally includes an anode, a hole transporting layer, an electroluminescent layer as an energy conversion layer, an electron transporting layer and a cathode, which are sequentially stacked. When a voltage is applied to between anode and cathode, the two electrodes generate an electric field. Under the action of the electric field, the electrons on the cathode side move to the electroluminescent layer, while the holes on the anode side move to the electroluminescent layer, so the electrons and the holes combine in the electroluminescent layer to form excitons, and the excitons are in an excited state and release energy outwards, which in turn makes the electroluminescent layer emit light outward. In order to improve the performance of electronic components that realize electroluminescence or photoelectric conversion, an electron blocking layer may also be provided between the energy conversion layer and the hole transporting layer.

In electronic components that realize electroluminescence or photoelectric conversion, the hole transport performance of the film layer disposed between the anode and the energy conversion layer has an important influence on the performance of the electronic components. As recited in patent documents such as Chinese Patent Application CN201710407382.3, the fluorene group-containing compound may be used for the hole transporting layer. However, the performance of the existing hole transporting layer materials containing fluorene groups needs to be further improved.

The above information disclosed in the background is only for enhancing the understanding of the background of the present disclosure, so it may include information that does not constitute prior art known to those skilled in the art.

SUMMARY

The object of the present disclosure is to provide a nitrogen-containing compound, an electronic element and an electronic device to improve the performance of the electronic element and the electronic device.

In order to achieve the above-mentioned object of the disclosure, the present disclosure adopts the following technical solutions:

According to the first aspect of the present disclosure, there is provided a nitrogen-containing compound having the structure shown in Chemical Formula 1:

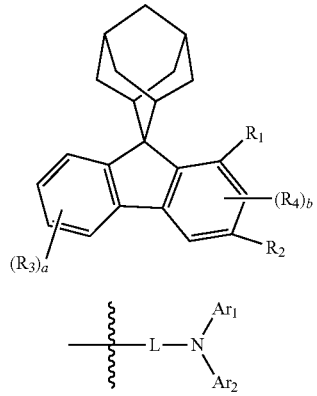

Chemical Formula 1

Chemical Formula 1-1 wherein represents a chemical bond;

$R_1$ and $R_2$ are each independently selected from hydrogen or a group represented by Chemical Formula 1-1, and one and only one of $R_1$ and $R_2$ has the group represented by Chemical Formula 1-1; when $R_1$ or $R_2$ is selected from hydrogen, said $R_1$ and $R_2$ may be replaced by $R_4$;

$R_3$, $R_4$ are each independently selected from the group consisting of deuterium, halogen, cyano, a heteroaryl having 3 to 20 carbon atoms, an aryl having 6 to 20 carbon atoms, a trialkylsily having 3 to 12 carbon atoms, an arylsilyl having 8 to 12 carbon atoms, an alkyl having 1 to 10 carbon atoms, a haloalkyl having 1 to 10 carbon atoms, an alkenyl having 2 to 6 carbon atoms, an alkynyl having 2 to 6 carbon atoms, a cycloalkyl having 3 to 20 carbon atoms, a heterocycloalkyl having 2 to 10 carbon atoms, a cycloalkenyl having 5 to 10 carbon atoms, a heterocycloalkenyl having 4 to 10 carbon atoms, an alkoxy having 1 to 10 carbon atoms, an alkylthio having 1 to 10 carbon atoms, an aryloxy having 6 to 18 carbon atoms, an arylthio having 6 to 18 carbon atoms and a phosphoroxy having 6 to 18 carbon atoms;

a is selected from 0, 1, 2, 3, or 4; when a is greater than or equal to 2, any two $R_3$ are the same or different;

b is selected from 0, 1, 2, or 3; when b is greater than or equal to 2, any two $R_4$ are the same or different;

L is selected from single bond, a substituted or unsubstituted arylene having 6 to 30 carbon atoms, or a substituted or unsubstituted heteroarylene having 3 to 30 carbon atoms;

$Ar_1$ and $Ar_2$ are each independently selected from the following substituted or unsubstituted groups: an alkyl having 1 to 20 carbon atoms, a cycloalkyl having 3 to 20 carbon atoms, an aryl having 6 to 30 carbon atoms, or a heteroaryl having 3 to 30 carbon atoms, and $Ar_1$ and $Ar_2$ are not 9,9-diphenyl fluorenyl.

According to the second aspect of the present disclosure, there is provided an electronic element including an anode and a cathode disposed opposite to each other, and a functional layer disposed between the anode and the cathode, wherein the functional layer contains the above-mentioned nitrogen-containing compound. According to an embodiment of the present disclosure, the electronic element is an organic electroluminescence device. According to another embodiment of the present disclosure, the electronic element is a solar cell.

According to the third aspect of the present disclosure, there is provided an electronic device including the above-mentioned electronic element.

The nitrogen-containing compound of the present disclosure introduces an adamantane structure at the side of the fluorene to enhance the electron density of the fluorene ring and the conjugate system of the entire compound through the hyperconjugation effect, which can enhance the hole conductivity and electron tolerance of the nitrogen-containing compound. At the same time, the luminous efficiency and lifetime of the organic electroluminescent device using the nitrogen-containing compound may be improved, and the conversion efficiency and lifetime of the photoelectric conversion device using the nitrogen-containing compound may be improved. The adamantyl group is introduced between the branches of the triarylamine which is originally a near-plane structure, rather than at the end of it. The large steric hindrance of the adamantyl group can finely adjust the bonding angle and conjugation degree of the amine and each aryl group, thereby obtain HOMO value suitable for the material of the adjacent layer. It reduces the operating voltage of the organic electroluminescent device, and increases the open circuit voltage of the photoelectric conversion device. In addition, the introduction of adamantyl can also increase the molecular weight of the nitrogen-containing compound and reduce the molecular symmetry, increase the glass transition temperature and evaporation temperature of the compound of the present disclosure, and can control the crystallinity of the nitrogen-containing compound, makes the nitrogen-containing compound have better physical and thermal stability when being mass-produced, which facilitates the mass production stability of the electronic elements such as organic electroluminescent devices and photoelectric conversion devices.

BRIEF DESCRIPTION OF THE DRAWINGS

The above and other features and advantages of the present disclosure will become more apparent by describing in detail exemplary embodiments thereof with reference to the drawings.

Figure 1:
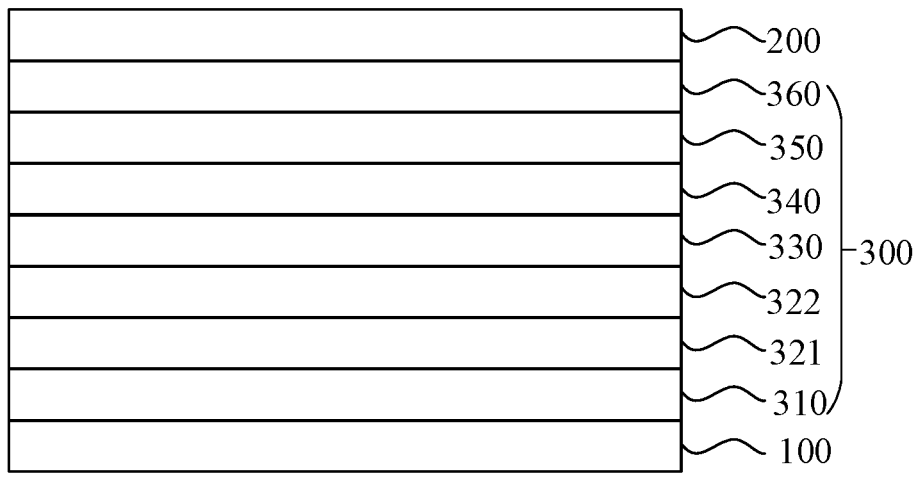
FIG. 1 is a schematic structural diagram of an organic electroluminescent device according to an embodiment of the present disclosure.

The reference symbols of the main elements in the figure are as follows:

100, anode;
200, cathode;
300, functional layer;
310, hole injecting layer;
321, hole transporting layer;
322, electron blocking layer;
330, organic electroluminescent layer;
340, hole blocking layer;
350, electron transporting layer;
360, electron injecting layer;
370, photoelectric conversion layer;
400, the first electronic device;
500, the second electronic device.

DETAILED DESCRIPTION

Exemplary embodiments will now be described more fully with reference to the drawings. However, the exemplary embodiments may be implemented in various forms, and should not be construed as being limited to the examples set forth herein; on the contrary, providing these embodiments makes the present disclosure more comprehensive and complete, and will fully convey the concept of the exemplary embodiments to those skilled in the art. The described features, structures, or characteristics may be combined in one or more embodiments in any suitable manner. In the following description, many specific details are provided to give a full understanding of the embodiments of the present disclosure.

In the figures, the area and layer thickness may be exaggerated for clarity. The same reference symbols in the figures denote the same or similar structures, and thus their detailed description will be omitted.

The described features, structures, or characteristics may be combined in one or more embodiments in any suitable manner. In the following description, many specific details are provided to give a full understanding of the embodiments of the present disclosure. However, those skilled in the art will realize that the technical solutions of the present disclosure may be practiced without one or more of the specific details, or other methods, components, materials, etc. may be used. In other cases, well-known structures, materials, or operations are not shown or described in detail to avoid obscuring the main technical ideas of the present disclosure.

In the present disclosure, when $R_1$ or $R_2$ is selected from hydrogen, said $R_1$ and $R_2$ may be replaced by $R_4$. It means that when one of $R_1$ and $R_2$ is selected from hydrogen, the one selected from hydrogen may be replaced by $R_4$ or not. For example, when $R_2$ is selected from Chemical Formula 1-1 and $R_1$ is selected from hydrogen, $R_1$ may or may not be replaced by $R_4$. Specifically, Chemical Formula 1 may include, but not limit to,

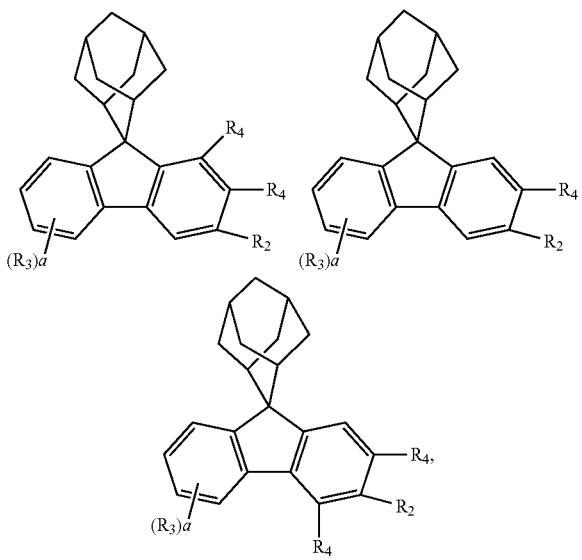

in which any two R₄ are the same or different.

In the present disclosure, since adamantane has a three-dimensional structure, in the structure diagram of the compound, because of the different drawing angles, it will show different plane shapes, among which, the ring structures formed on each 9,9-dimethylfluorene all refer to adamantine, and the connection location between the two group is the same. For example, the following four structures are the same:

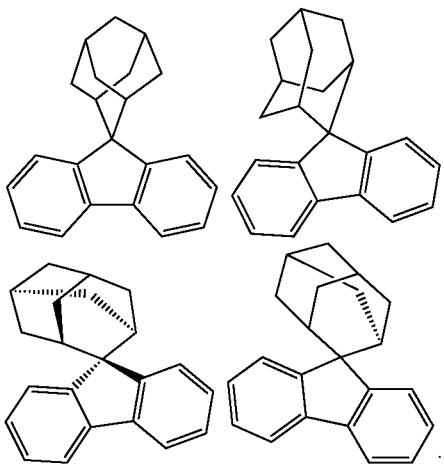

The present disclosure provides a nitrogen-containing compound having a structure shown in Chemical Formula 1:

Chemical Formula 1

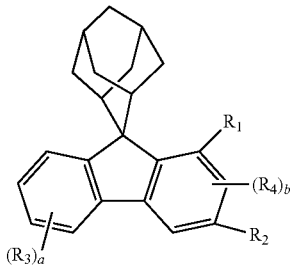

-continued

Chemical Formula 1-1

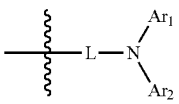

wherein

represents a chemical bond;

$R_1$ and $R_2$ are each independently selected from hydrogen or a group represented by Chemical Formula 1-1, and one and only one of $R_1$ and $R_2$ has the group represented by Chemical Formula 1-1; when $R_1$ or $R_2$ is selected from hydrogen, said $R_1$ and $R_2$ may be replaced by $R_4$;

$R_3$, $R_4$ are each independently selected the group consisting of deuterium, halogen, cyano, a heteroaryl having 3 to 20 carbon atoms, an aryl having 6 to 20 carbon atoms, a trialkylsily having 3 to 12 carbon atoms, an arylsilyl having 8 to 12 carbon atoms, an alkyl having 1 to 10 carbon atoms, a haloalkyl having 1 to 10 carbon atoms, an alkenyl 2 to 6 carbon atoms, an alkynyl having 2 to 6 carbon atoms, a cycloalkyl having 3 to 20 carbon atoms, a heterocycloalkyl having 2 to 10 carbon atoms, a cycloalkenyl having 5 to 10 carbon atoms, a heterocycloalkenyl having 4 to 10 carbon atoms, an alkoxy having 1 to 10 carbon atoms, an alkylthio having 1 to 10 carbon atoms, an aryloxy having 6 to 18 carbon atoms, an arylthio having 6 to 18 carbon atoms and a phosphoroxy having 6 to 18 carbon atoms;

a is selected from 0, 1, 2, 3, or 4; when a is greater than or equal to 2, any two $R_3$ are the same or different;

b is selected from 0, 1, 2, or 3, when b is greater than or equal to 2, any two $R_4$ are the same or different;

L is selected from single bond, a substituted or unsubstituted arylene having 6 to 30 carbon atoms, a substituted or unsubstituted heteroarylene having 3 to 30 carbon atoms;

$Ar_1$ and $Ar_2$ are each independently selected from the following substituted or unsubstituted groups: an alkyl having 1 to 20 carbon atoms, a cycloalkyl having 3 to 20 carbon atoms, an aryl having 6 to 30 carbon atoms, or a heteroaryl having 3 to 30 carbon atoms, and $Ar_1$ and $Ar_2$ are not 9,9-diphenyl fluorenyl. Alternatively, neither $Ar_1$ nor $Ar_2$ is spirobifluorenyl.

Optionally, the substituents of L, $Ar_1$ and $Ar_2$ are each independently selected from deuterium, halogen, cyano, a heteroaryl having 3 to 18 carbon atoms, an aryl having 6 to 18 carbon atoms, a haloaryl having 6 to 20 carbon atoms, a trialkylsilyl having 3 to 12 carbon atoms, an arylsilyl having 8 to 12 carbon atoms, an alkyl having 1 to 10 carbon atoms, a haloalkyl having 1 to 10 carbon atoms, an alkenyl having 2 to 6 carbon atoms, an alkynyl having 2 to 6 carbon atoms, a cycloalkyl having 3 to 10 carbon atoms, a heterocycloalkyl having 2 to 10 carbon atoms, a cycloalkenyl having 5 to 10 carbon atoms, a heterocyclic alkenyl having 4 to 10 carbon atoms, an alkoxy having 1 to 10 carbon atoms, an alkylthio having 1 to 10 carbon atoms, an aryloxy having 6 to 18 carbon atoms, an arylthio having 6 to 18 carbon atoms, and a phosphoryloxy having 6 to 18 carbon atoms.

Also optionally, the substituents of $Ar_1$ and/or $Ar_2$ are triphenylsilyl.

In the present disclosure, the number of carbon atoms of L, $Ar_1$ and $Ar_2$ refers to all the number of carbon atoms. For example, if L is selected from substituted arylene having 12 carbon atoms, all the carbon atoms of the arylene and the substituents thereon are 12.

In the present disclosure, the expressions "each . . . independently" and " . . . each independently" and " . . . independently selected" may be interchangeable, and should be interpreted broadly. They may mean that in different groups, specific options expressed between the same symbols do not affect each other, or it can mean that in the same group, specific options expressed between the same symbols do not affect each other. For example,

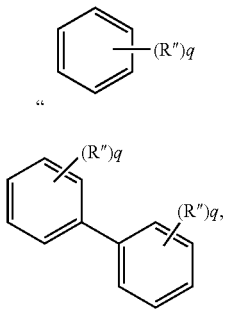

formula Q-1 formula Q-2 wherein each q is independently 0, 1, 2, or 3, and each R" is independently selected from hydrogen, deuterium, fluorine, or chlorine", means that: formula Q-1 represents that there are q substituents R" on the benzene ring, each R" may be the same or different, and the options of each R" do not affect each other; formula Q-2 represents that there are q substituents R" on each benzene ring of the biphenyl. The number q of the R" substituents on the two benzene rings may be the same or different, each R" may be the same or different, and the options of each R" do not affect each other.

In the present disclosure, the term "substituted or unsubstituted" means that there is no substituent or is substituted by one or more substituents. These substituents include, but are not limited to, deuterium (D), halogen (such as, F, Cl, Br), cyano, alkyl, alkenyl, alkynyl, haloalkyl, aryl, heteroaryl, aryloxy, arylthio, cycloalkyl, heterocycloalkyl, etc.

In the present disclosure, unless otherwise indicated, "hetero" means that at least one heteroatom such as B, N, O, S, or P is included in one functional group and the remaining atoms are carbon and hydrogen. The unsubstituted alkyl group may be a "saturated alkyl group" without any double or triple bonds.

In the present disclosure, "alkyl" may include linear or branched alkyl. The alkyl group may have 1 to 20 carbon atoms. In the present disclosure, a numerical range such as "1 to 20" refers to each integer in the given range. For example, "1 to 20 carbon atoms" refers to an alkyl having 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The alkyl group may also be a alkyl group with 1 to 10 carbon atoms. The alkyl group may also be a lower alkyl group with 1 to 6 carbon atoms. In addition, the alkyl group may be substituted or unsubstituted.

Preferably, the alkyl group is selected from alkyl groups with 1 to 10 carbon atoms, and specific examples thereof include, but are not limited to, methyl, ethyl, propyl, isopropyl, n-butyl, isobutyl, sec-butyl, tert-butyl, pentyl and hexyl.

In the present disclosure, "alkenyl" refers to a hydrocarbon group containing one or more double bonds in a linear or branched hydrocarbon chain. The alkenyl group may be unsubstituted or substituted. An alkenyl group can have 1 to 20 carbon atoms, and whenever it appears herein, a numerical range such as "1 to 20" refers to each integer in the given range. For example, "1 to 20 carbon atoms" means that it can include alkenyl having 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. For example, the alkenyl group may be vinyl, butadienyl, or 1,3,5-hexatrienyl.

In the present disclosure, "cycloalkyl" refers to a saturated hydrocarbon containing an alicyclic structure, which includes monocyclic and fused ring structures. The cycloalkyl group may have 3 to 20 carbon atoms, and a numerical range such as "3 to 20" refers to each integer in the given range. For example, "3 to 20 carbon atoms" means that it can include a cycloalkyl having 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The cycloalkyl group may be a small ring, an ordinary ring, or a large ring with 3 to 20 carbon atoms. Cycloalkyl groups may have a structure selected from monocyclic rings (single ring), bicyclic rings (two rings), polycyclic rings (three or more rings). Cycloalkyl may also have a structure of spiro ring (two rings sharing one carbon atom-spiro ring), fused ring (two rings sharing two carbon atoms), and bridge ring (two rings sharing more than two carbon atoms). In addition, the cycloalkyl group may be substituted or unsubstituted.

Preferably, the cycloalkyl group is selected from cycloalkyl groups having 3 to 10 carbon atoms, and specific examples thereof include, but are not limited to, cyclopropyl, cyclobutyl, cyclopentyl, cyclohexyl, and adamantyl.

In the present disclosure, "aryl" refers to an optional functional group or substituent derived from an aromatic hydrocarbon ring. The aryl group may be a monocyclic aryl group or a polycyclic aryl group. In other words, the aryl group may be a monocyclic aryl group, or a fused ring aryl group, and the aryl group may also be a polycyclic aryl group, which is formed by two or more monocyclic aryls conjugatedly connected through a carbon-carbon bond, formed by a monocyclic aryl and a fused ring aryl conjugatedly connected by a carbon-carbon bond, or formed by two or more fused ring aryl groups conjugatedly connected by a carbon-carbon bond. That is, two or more aryl groups conjugatedly connected through a carbon-carbon bond can also be regarded as aryl groups in the present disclosure. Among them, the aryl group does not contain heteroatoms such as B, N, O, S, or P. For example, biphenyl, terphenyl and the like are aryl groups in the present disclosure. Examples of aryl groups may include phenyl, naphthyl, fluorenyl, anthryl, phenanthryl, biphenyl, terphenyl, quaterphenyl, quinquephenyl, sexiphenyl, benzo[9,10]phenanthryl, pyrenyl, benzofluoranthenyl, chrysen, fluorenyl, etc., which are not limited thereto. The "aryl" in the present disclosure may contain 6 to 30 carbon atoms. In some embodiments, the number of carbon atoms in the aryl group may be 6 to 25; and in other embodiments, the number of carbon atoms in the aryl group may be 6 to 18; and in another embodiments, the number of carbon atoms in the aryl group may be 6 to 13. For example, the number of carbon atoms in the aryl group may be 6, 12, 13, 18, 20, 25, or 30. Of course, the number of carbon atoms may be other numbers, which will not be listed here.

In the present disclosure, the number of ring-forming carbon atoms refers to the number of carbon atoms located on the aromatic ring of a substituted or unsubstituted aryl and a substituted or unsubstituted heteroaryl. It should be noted that the carbon atoms of the aryl and heteroaryl as substituents are also considered on the ring-forming carbon atoms, and the number of carbon atoms of other substituents is not counted. For example, the number of ring-forming carbon atoms of fluorenyl is 13, the number of ring-forming carbon atoms of 9,9-dimethylfluorenyl is 13, and the number of ring-forming carbon atoms of diphenylfluorenyl is 25. The number of ring-forming carbon atoms of the aryl having 6 to 20 ring-forming carbon atoms may be, for example, 6 to 20, 6 to 18, 6 to 14, or 6 to 10, but it is not limited thereto.

In the present disclosure, substituted aryl refers to one or more hydrogen atoms in the aryl group being substituted by other groups. For example, at least one hydrogen atom is substituted by deuterium, F, Cl, I, CN, hydroxyl, amino, branched alkyl, linear alkyl, cycloalkyl, alkoxy, alkylamino, or other groups. It should be understood that the substituted aryl group having 18 carbon atoms means that the total number of carbon atoms of the aryl group and the substituents on the aryl group is 18. For example, the number of carbon atoms in 9,9-dimethylfluorenyl is 15, and the number of carbon atoms in both 9,9-diphenylfluorenyl and spirodifluorenyl is 25. Among them, biphenyl may be interpreted as aryl or substituted phenyl.

In the present disclosure, the fluorenyl group may be substituted, and the substituted fluorenyl group may be

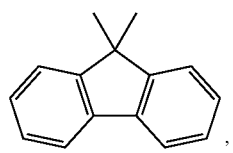, and may also be

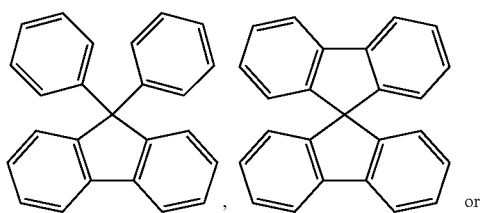,  or

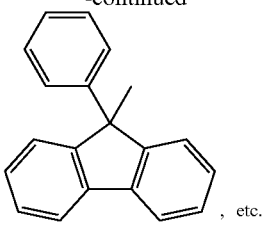, etc.

In the present disclosure, the "heteroaryl" refers to a heteroaryl group including at east one of B, O, N, P, Si, and S as a hetero atom. The heteroaryl group may be a monocyclic heteroaryl group or a polycyclic heteroaryl group. In other words, the heteroaryl group may be a single aromatic ring system or a polycyclic ring system formed by more aromatic rings conjugatedly connected through a carbon-carbon bond where any aromatic ring is an aromatic monocyclic ring or an aromatic fused ring. Exemplary the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, N-arylcarbazolyl, N-heteroarylcarbazolyl, N-alkylcarbazolyl, benzoxazolyl, benzimidazoly, benzothiazolyl, benzocarbazolyl, benzothienyl, dibenzothienyl, thienothienyl, benzofuranyl, phenanthrolinyl, isoxazolyl, thiadiazolyl, benzothiazoly, phenothiazinyl, dibenzosilyl, dibenzofuranyl, phenyl substituted dibenzofuranyl, dibenzofuranyl substituted phenyl, etc., which are not limited thereto. Among them, thienyl, furyl, phenanthrolinyl, etc. are heteroaryl groups of a single aromatic ring system, and N-arylcarbazolyl, N-heteroarylcarbazolyl, phenyl substituted dibenzofuranyl, diphenylfuranyl substituted phenyl and the like are heteroaryl groups of multiple aromatic ring systems conjugatedly connected through a carbon-carbon bond.

In the present disclosure, the number of ring-forming carbon atoms refers to the total number of carbon atoms on the aromatic ring. For example, the heteroaryl group having 3 to 20 ring-forming carbon atoms refers to the number of carbon atoms of the heteroaryl ring in the heteroaryl group is 3 to 20, and the carbon atoms of the substituent on the heteroaryl group are not counted. The number of ring-forming carbon atoms in the heteroaryl group may be 3 to 20, 3 to 18, 4 to 18, 3 to 12, 3 to 8, but not limited thereto.

In the present disclosure, substituted heteroaryl means that one or more hydrogen atoms in the heteroaryl group being substituted by other group. For example, at least one hydrogen atom is substituted by deuterium, F, Cl, Br, CN, amino, alkyl, haloalkyl, cycloalkyl, aryloxy, arylthio, silyl, alkylamino, arylamino, boranyl, phosphino, or other groups.

In the present disclosure, the interpretation of aryl may be applied to arylene, and the interpretation of heteroaryl may also be applied to heteroarylene.

In the present disclosure, the halogen may be fluorine, chlorine, bromine, or iodine.

The nitrogen-containing compound of the present disclosure may be used in the preparation of organic electroluminescent devices and photoelectric conversion devices, especially suitable for the preparation of the electron blocking layer (also known as hole assist layer, or second hole transporting layer, etc.) of the organic electroluminescent devices and photoelectric conversion devices, so as to improve the efficiency and lifetime of the organic electroluminescent devices and photoelectric conversion devices, reduce the operating voltage of organic electroluminescent devices, increase the open circuit voltage of photoelectric conversion devices, and improve the mass production stability of the photoelectric conversion devices and the organic electroluminescent devices.

Optionally, $Ar_1$ and $Ar_2$ are each independently selected from the following substituted or unsubstituted groups: an aryl group having 6 to 20 carbon atoms or a heteroaryl group having 3 to 20 carbon atoms.

Preferably, L is selected from single bond, a substituted or unsubstituted arylene group having 6 to 20 ring-forming carbon atoms, or a substituted or unsubstituted heteroarylene group having 3 to 20 ring-forming carbon atoms.

In some embodiments, L is selected from the group consisting of single bond and the following groups:

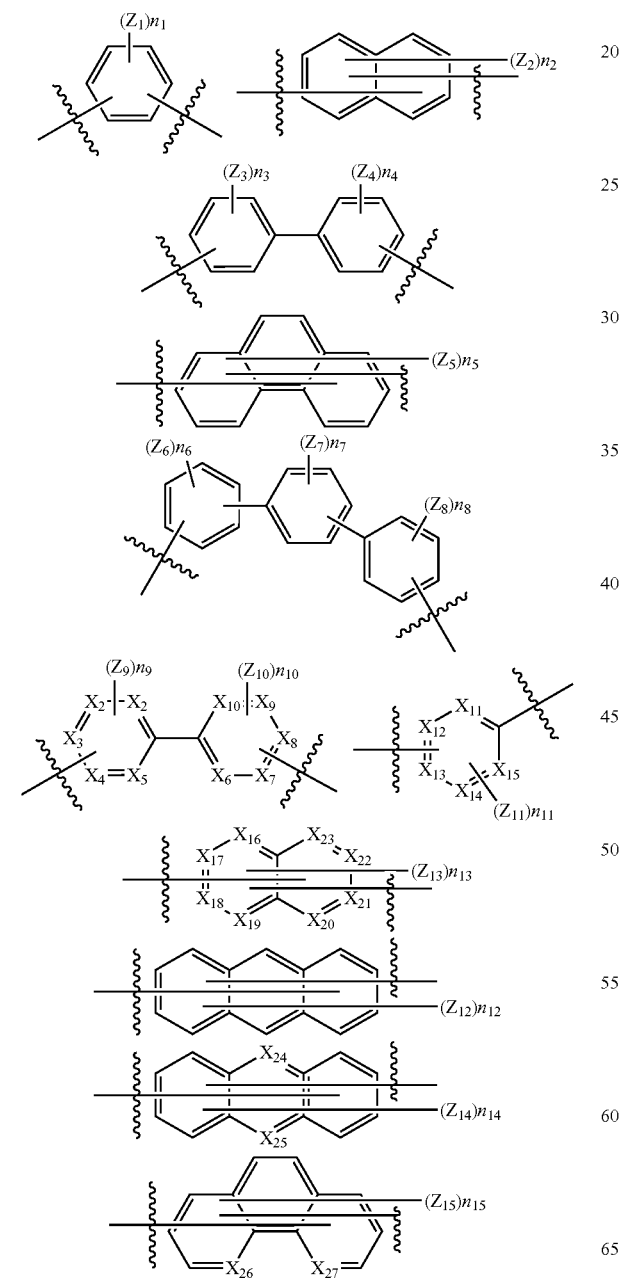

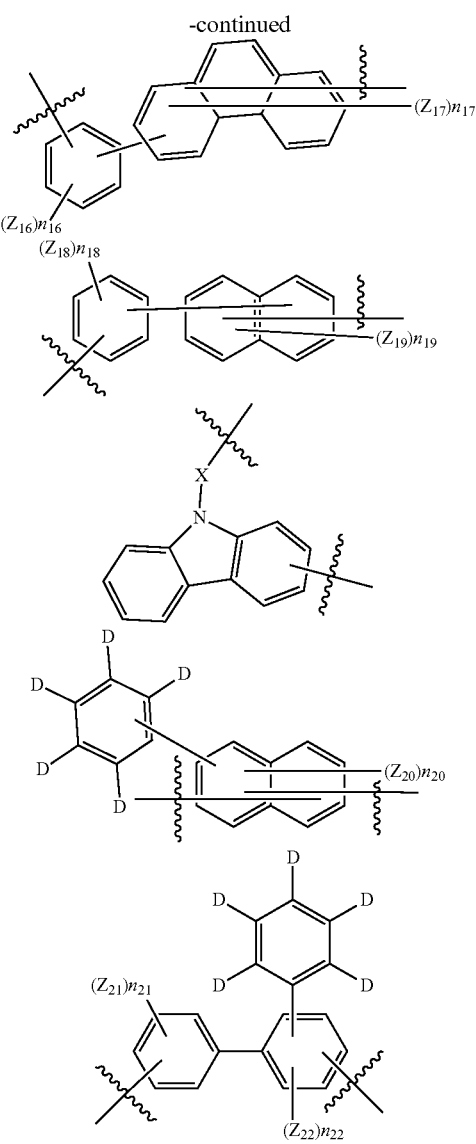

wherein

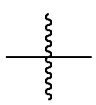

represents a chemical bond, $Z_1$ to $Z_{22}$ are each independently selected from hydrogen, deuterium, halogen, cyano, an alkyl having 1 to 6 carbon atoms, a haloalkyl having 1 to 6 carbon atoms, an alkoxy having 1 to 6 carbon atoms, an aryloxy having 6 to 18 carbon atoms, an arylthio having 6 to 18 carbon atoms, an aryl having 6 to 20 carbon atoms, a haloaryl having 6 to 20 carbon atoms, a heteroaryl having 3 to 20 carbon atoms, a silyl having 3 to 12 carbon atoms, or a cycloalkyl having 3 to 10 carbon atoms;

X is selected from a substituted or unsubstituted alkylene having 1 to 10 carbon atoms, a substituted or unsubstituted cycloalkylene having 3 to 10 carbon atoms, a substituted or unsubstituted arylene having 6 to 20 carbon atoms, or a substituted or unsubstituted heteroarylene having 3 to 20 carbon atoms;

$X_1$ to $X_{10}$ are each independently selected from C or N, and at least one of $X_1$ to $X_{10}$ is N;

$X_{11}$ to $X_{15}$ are each independently selected from C or N, and at least one of $X_{11}$ to $X_{15}$ is N;

$X_{16}$ to $X_{23}$ are each independently selected from C or N, and at least one of $X_{16}$ to $X_{23}$ is N;

$X_{24}$ and $X_{25}$ are each independently selected from single bond, $C(R_5R_6)$, $N(R_7)$, O, S, $Si(R_5R_6)$, or Se; preferably, $X_{24}$ and $X_{25}$ are not single bonds at the same time;

$R_5$ to $R_7$ are each selected from hydrogen, deuterium, a substituted or unsubstituted alkyl having 1 to 10 carbon atoms, a substituted or unsubstituted aryl having 6 to 20 carbon atoms, or a substituted or unsubstituted heteroaryl having 3 to 20 carbon atoms;

$X_{26}$ and $X_{27}$ are each independently selected from C or N, and at least one of $X_{26}$ and $X_{27}$ is N;

$n_1$, $n_3$, $n_4$, $n_6$, $n_7$, $n_8$, $n_9$, $n_{16}$, $n_{18}$, and $n_{21}$ are each independently selected from 1, 2, 3, or 4;

$n_{10}$, $n_{11}$ and, $n_{22}$ are each independently selected from 1, 2, or 3;

$n_{13}$ and $n_{20}$ are selected from 1, 2, 3, 4, or 5;

$n_2$, $n_{14}$ and $n_{19}$ are each independently selected from 1, 2, 3, 4, 5, or 6;

$n_{15}$ is selected from 1, 2, 3, 4, 5, 6, or 7;

$n_5$, $n_{12}$ and $n_{17}$ are each independently selected from 1, 2, 3, 4, 5, 6, 7, or 8.

Optionally, X is an alkylene group having 1 to 4 carbon atoms, a cycloalkylene group having 5 to 10 carbon atoms, an arylene group having 6 to 12 carbon atoms, or a heteroarylene having 3 to 12 carbon atoms. Specific examples of X include, but are not limited to, methylene, phenylene and the like.

Optionally, $R_5$ to $R_7$ are each independently selected from hydrogen, deuterium, an alkyl group having 1 to 4 carbon atoms, an aryl group having 6 to 12 carbon atoms, or a heteroaryl group having 3 to 12 carbon atoms. Specific examples of $R_5$ to $R_7$ include, but are not limited to, methyl, tert-butyl, phenyl and the like.

Also optionally, $Z_1$ is an aryl group having 6 to 20 carbon atoms substituted by deuterium, for example, a phenyl group substituted by deuterium.

According to an embodiment, L is selected from the group consisting of single bond and the following groups:

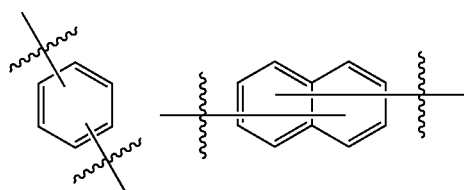

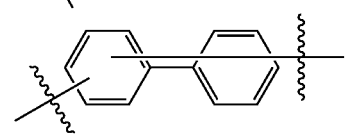

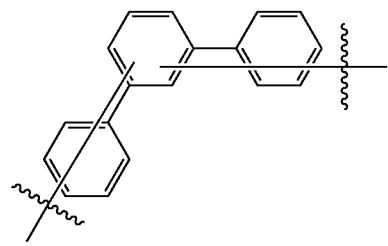

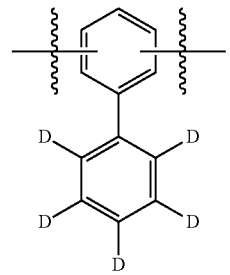

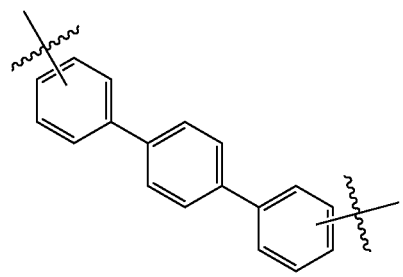

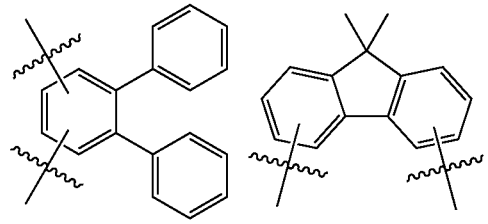

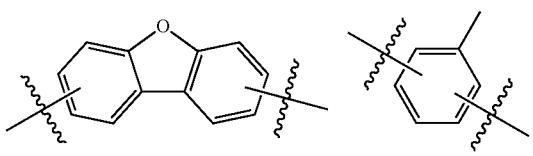

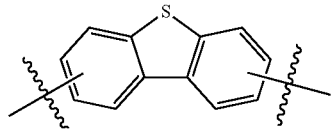

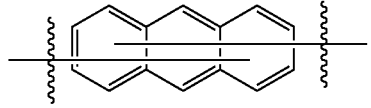

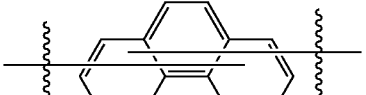

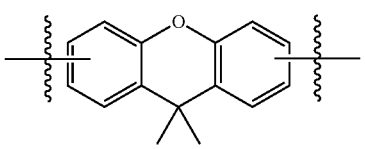

-continued
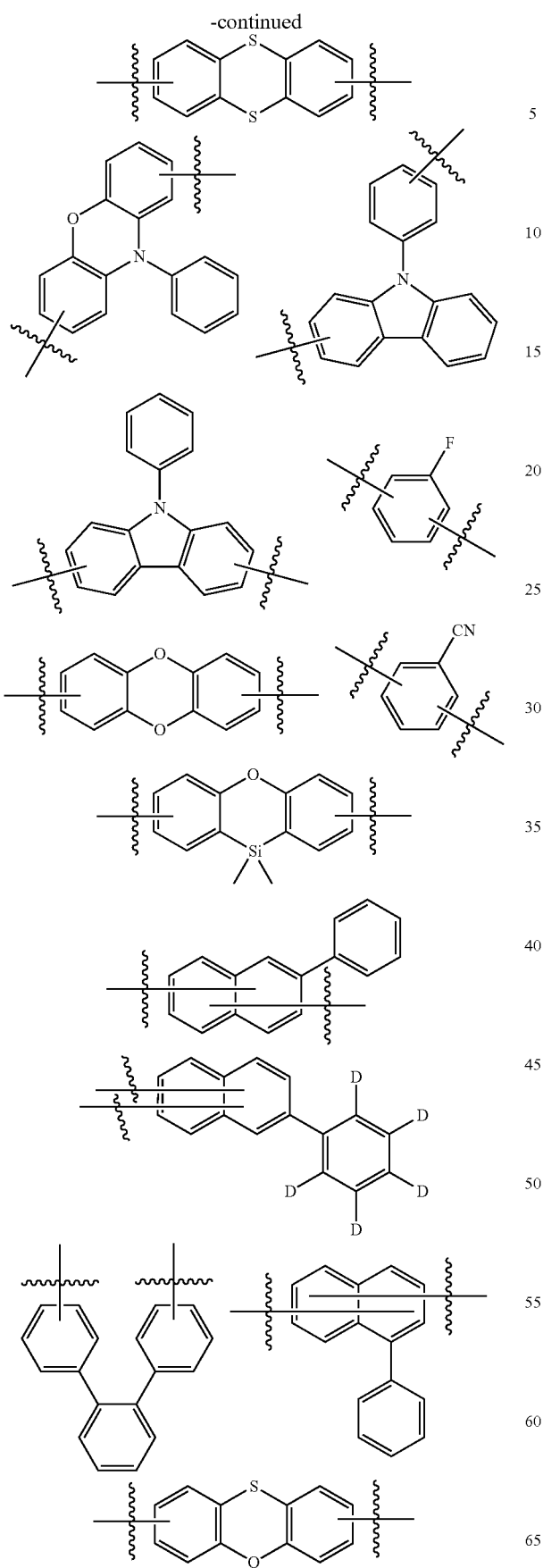
-continued
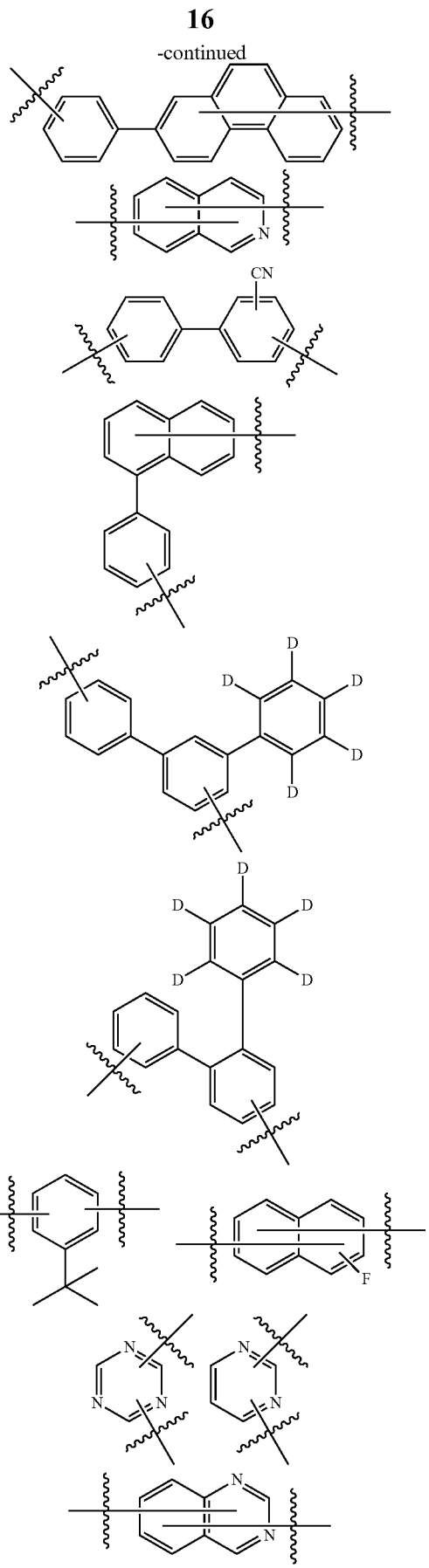

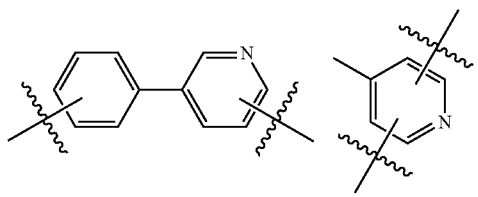
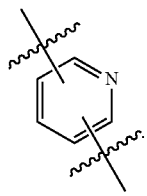
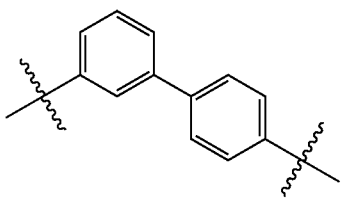
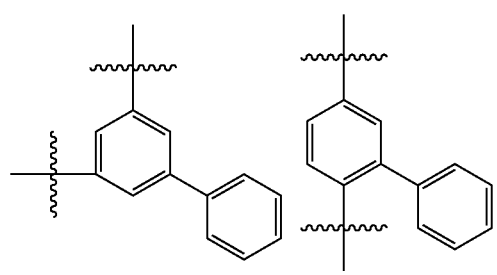
Further optionally, L is selected from the group consisting of single bond and the following groups:
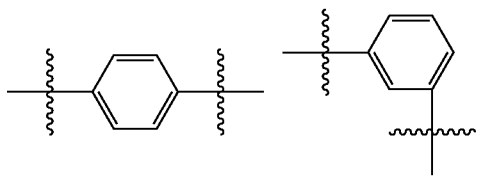
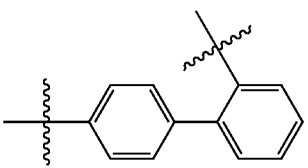
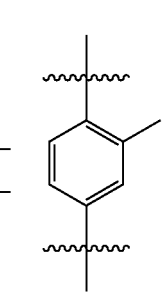
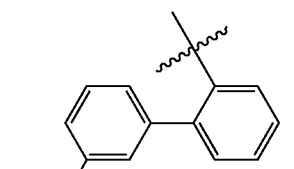
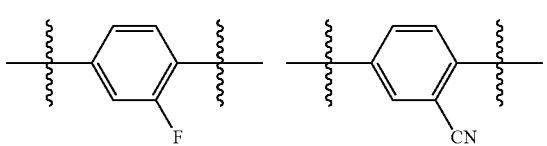
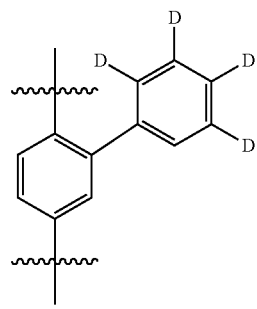
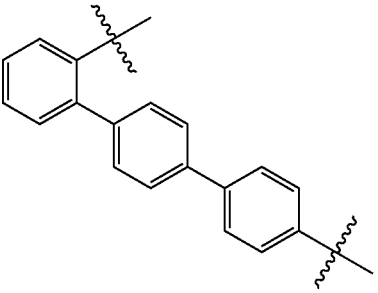
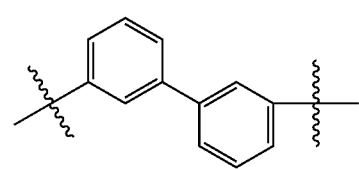
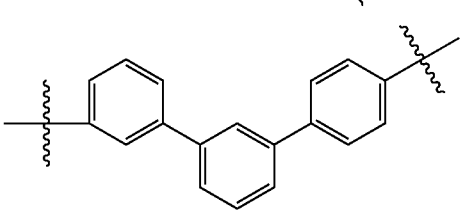

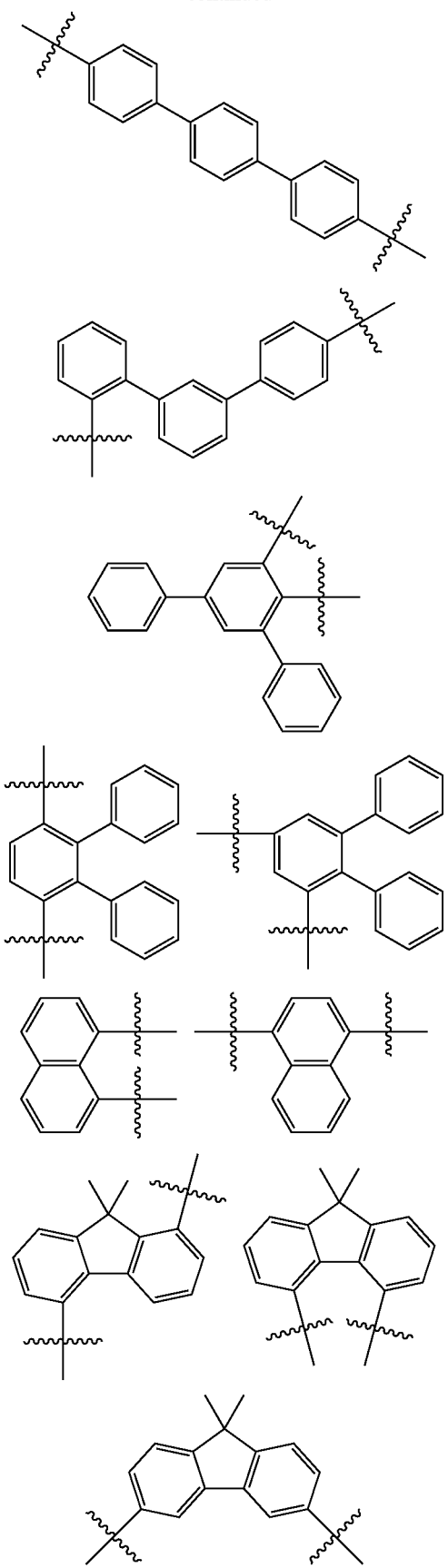
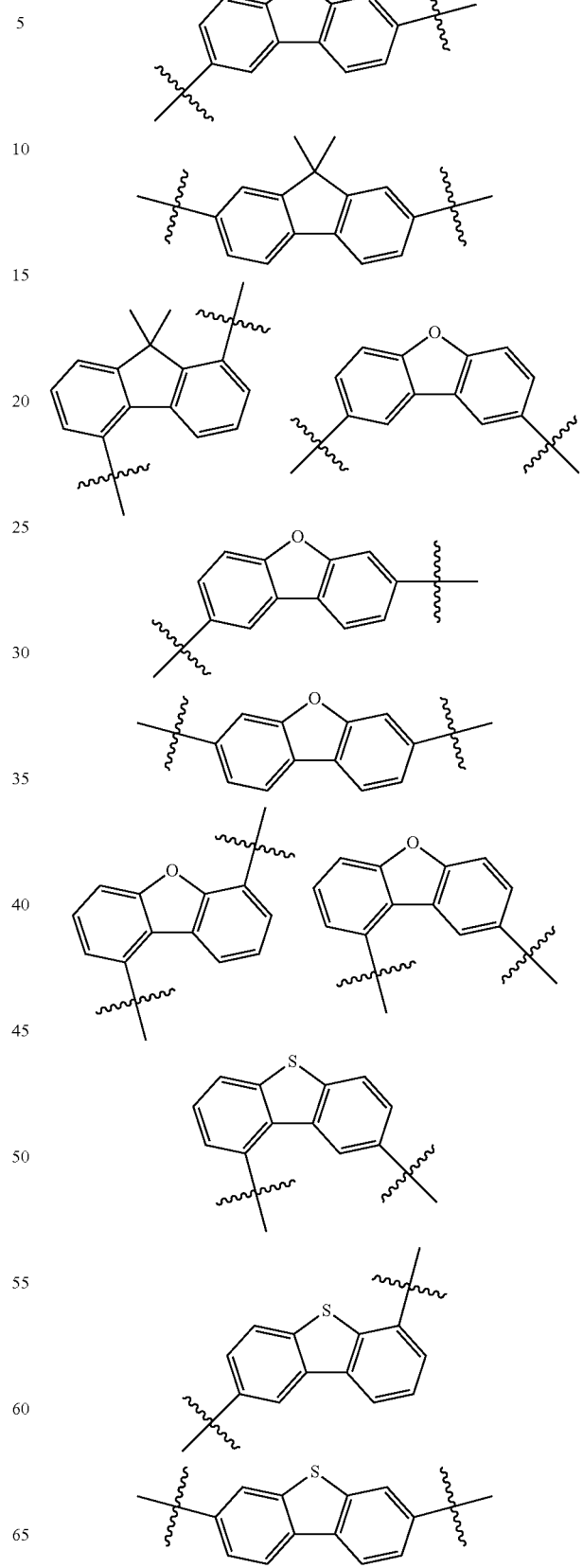

-continued
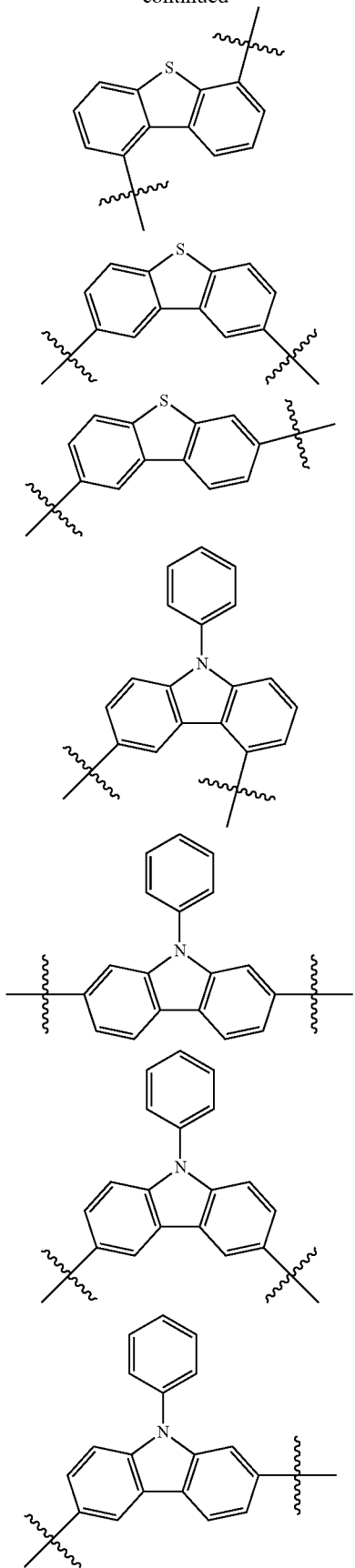
-continued
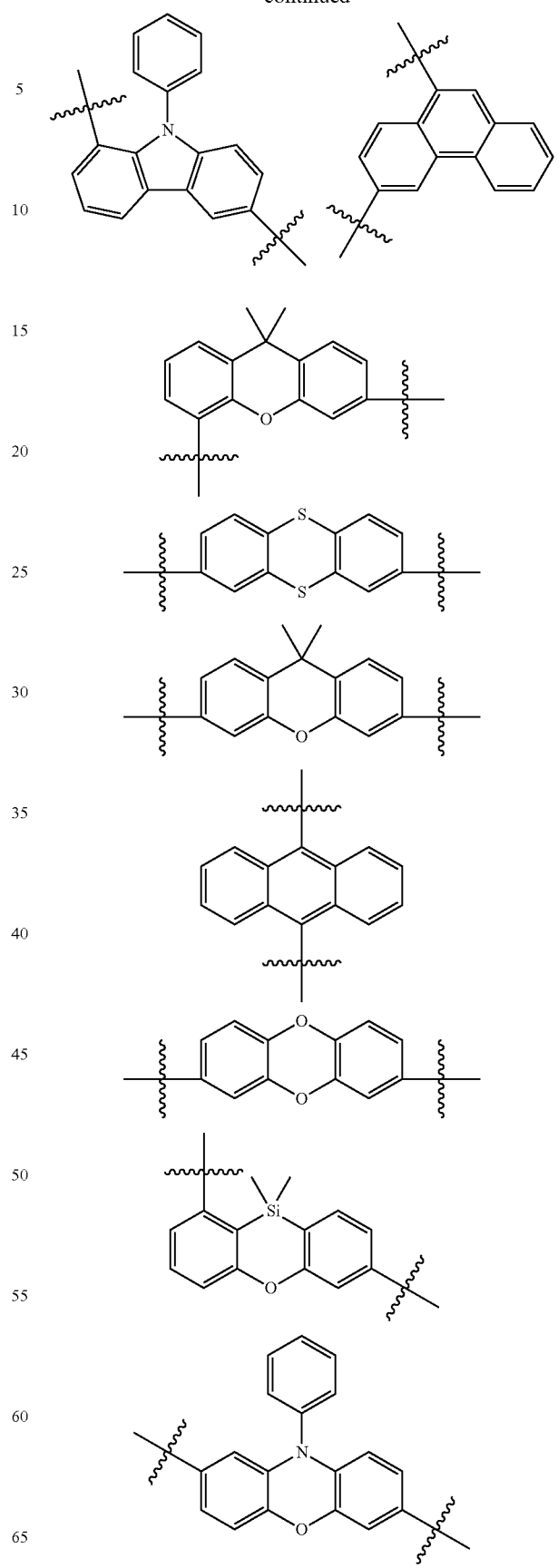

-continued

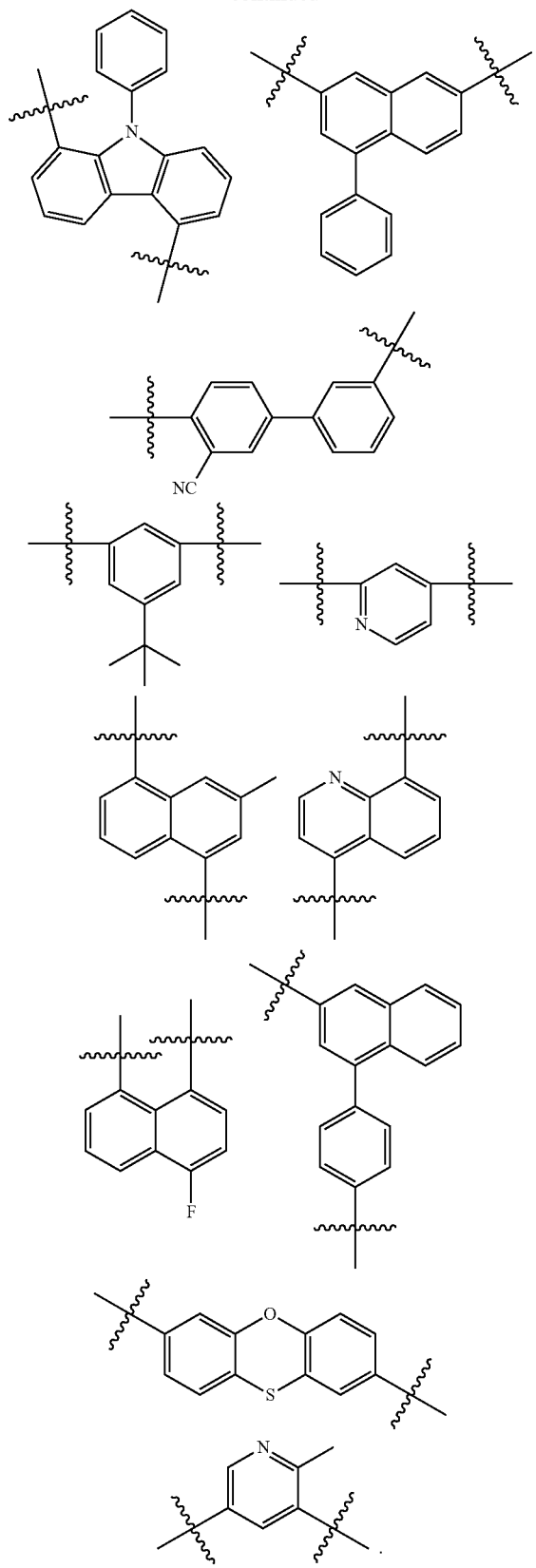

Optionally, $Ar_1$ and $Ar_2$ are each independently selected from the following substituted or unsubstituted groups: an aryl group having 6 to 20 carbon atoms, or a heteroaryl group having 3 to 20 carbon atoms.

Optionally, $Ar_1$ and $Ar_2$ are each independently selected from the following substituted or unsubstituted groups: an aryl group having 6 to 20 ring-forming carbon atoms, or a heteroaryl group having 5 to 20 ring-forming carbon atoms.

In some embodiments, $Ar_1$ and $Ar_2$ are each independently selected from the group consisting of the following groups:

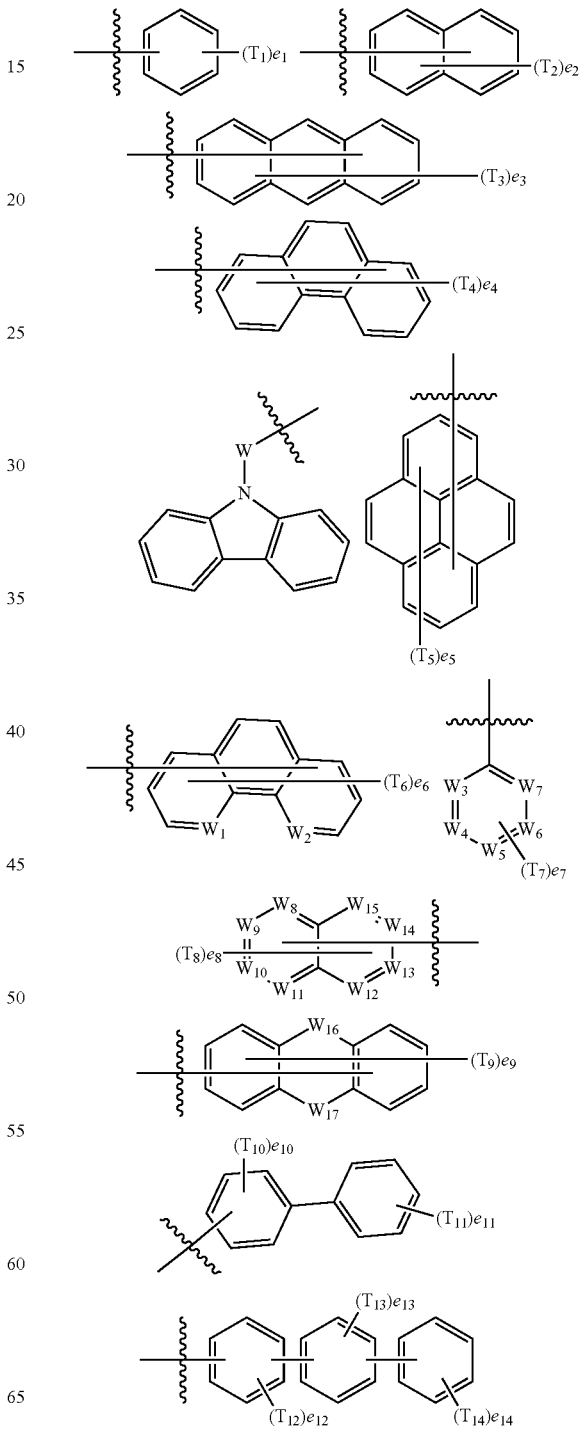

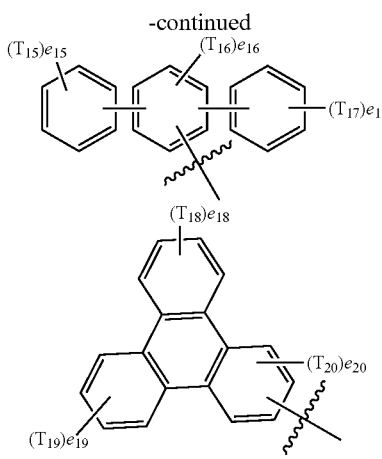

wherein

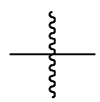

represents a chemical bond;

$T_1$ to $T_{20}$ are each independently selected from hydrogen, deuterium, halogen, cyano, an alkyl having 1 to 6 carbon atoms, a haloalkyl having 1 to 6 carbon atoms, an alkoxy having 1 to 6 carbon atoms, an aryloxy group having 6 to 18 carbon atoms, an arylthio having 6 to 18 carbon atoms, an aryl having 6 to 20 carbon atoms, a haloaryl having 6 to 20 carbon atoms, a heteroaryl having 3 to 20 carbon atoms, a silyl having 3 to 12 carbon atoms, or a cycloalkyl having 3 to 10 carbon atoms;

W is selected from a substituted or unsubstituted alkylene having 1 to 10 carbon atoms, a substituted or unsubstituted cycloalkylene having 3 to 10 carbon atoms, a substituted or unsubstituted arylene having 6 to 20 carbon atoms, or a substituted or unsubstituted heteroarylene having 3 to 20 carbon atoms;

$W_1$ and $W_2$ are each independently selected from C or N, and at least one of $W_1$ and $W_2$ is N;

$W_3$ to $W_7$ are each independently selected from C or N, and at least one of $W_3$ to $W_7$ is N;

$W_8$ to $W_{15}$ are each independently selected from C or N, and at least one of $W_8$ to $W_{15}$ is N; $W_{16}$ and $W_{17}$ are each independently selected from single bond, $C(R_9R_{10})$, $N(R_{11})$, O, S, $Si(R_9R_{10})$, or Se; preferably, $W_{16}$ and $W_{17}$ are not single bonds at the same time;

$R_9$ and $R_{10}$ are the same or different, and each independently selected from hydrogen, deuterium, a substituted or unsubstituted alkyl having 1 to 6 carbon atoms, a substituted or unsubstituted aryl having 7 to 18 carbon atoms, or a substituted or unsubstituted heteroaryl having 3 to 18 carbon atoms;

$R_8$ is selected from hydrogen, deuterium, a substituted or unsubstituted alkyl having 1 to 6 carbon atoms, a substituted or unsubstituted aryl having 6 to 20 carbon atoms, or a substituted or unsubstituted heteroaryl having 3 to 20 carbon atoms;

$e_1$, $e_{11}$, $e_{14}$, $e_{15}$ and $e_{17}$ are each independently selected from 1, 2, 3, 4, or 5;

$e_{16}$ and $e_{20}$ are each independently selected from 1, 2, or 3;

$e_2$ and $e_9$ are each independently selected from 1, 2, 3, 4, 5, 6, or 7;

$e_3$, $e_4$ and $e_5$ are each independently selected from 1, 2, 3, 4, 5, 6, 7, 8, or 9;

$e_6$ is selected from 1, 2, 3, 4, 5, 6, 7 or 8;

$e_7$, $e_{10}$, $e_{12}$, $e_{13}$, $e_{18}$ and $e_{19}$ are each independently selected from 1, 2, 3, or 4;

$e_8$ is selected from 1, 2, 3, 4, 5, or 6.

Optionally, W is an alkylene group having 1 to 4 carbon atoms, a cycloalkylene group having 5 to 10 carbon atoms, an arylene group having 6 to 12 carbon atoms, or a heteroarylene group having 3 to 12 carbon atoms. Specific examples of W include, but are not limited to, methylene, phenylene and the like.

Optionally, $R_9$ and $R_{10}$ are each independently selected from hydrogen, deuterium, or an alkyl group having 1 to 4 carbon atoms. Specific examples of $R_9$ and $R_{10}$ include, but are not limited to, methyl, tert-butyl and the like.

Optionally, $R_8$ is selected from hydrogen, deuterium, an alkyl group having 1 to 6 carbon atoms, an aryl group having 6 to 12 carbon atoms, or a heteroaryl group having 3 to 12 carbon atoms. Specific examples of $R_8$ include, but are not limited to, methyl, phenyl and the like.

Further optionally, $T_1$ is an aryl group having 6 to 20 carbon atoms substituted by deuterium, for example, a phenyl group substituted by deuterium.

Optionally, $Ar_1$ and $Ar_2$ are each independently selected from the group consisting of the following groups:

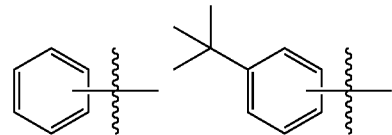

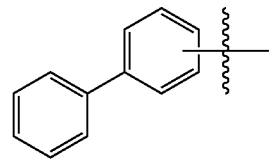

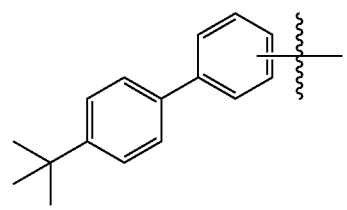

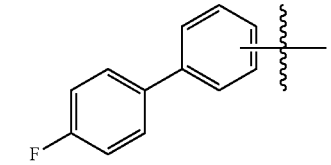

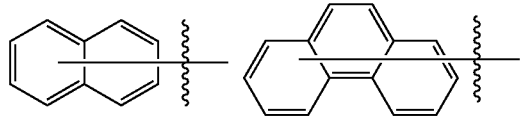

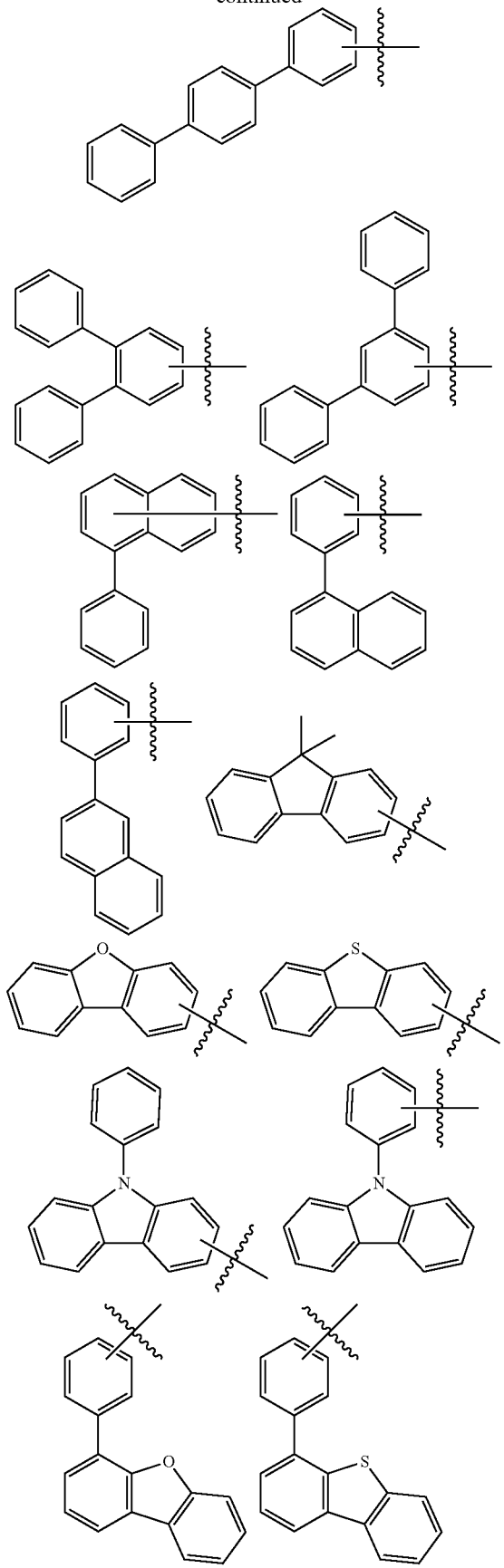
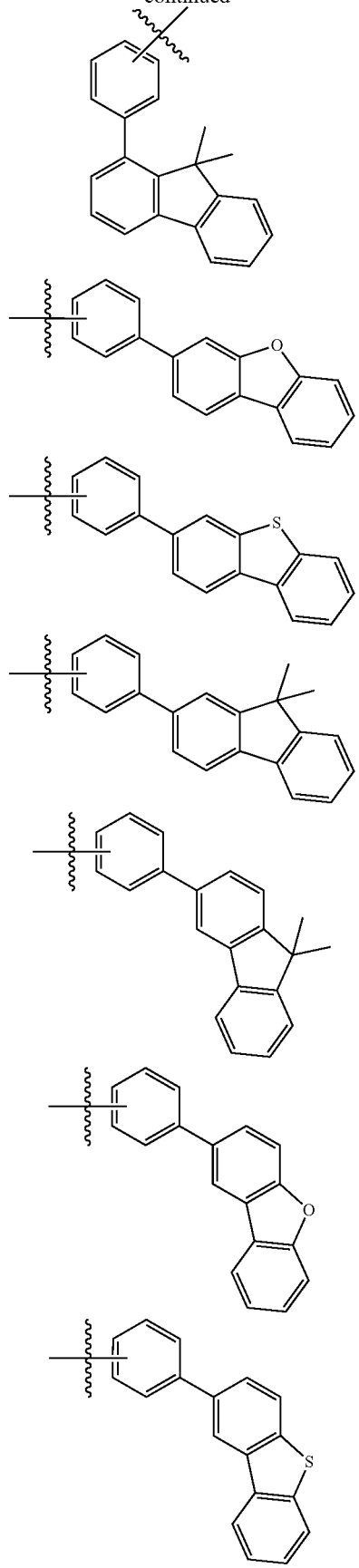

-continued
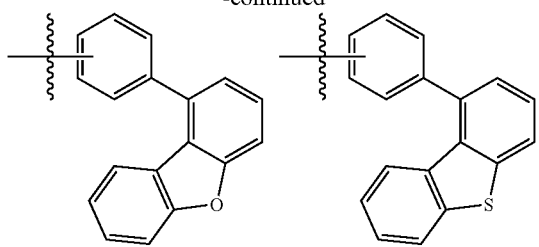
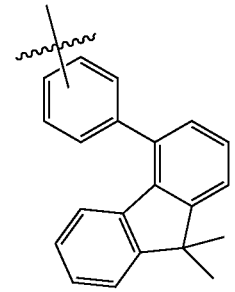
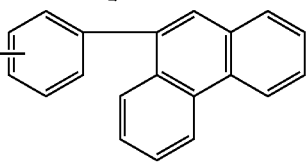
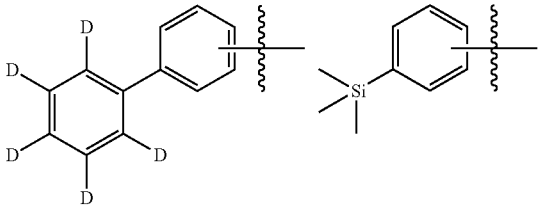
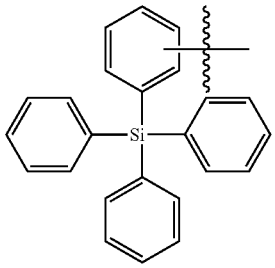
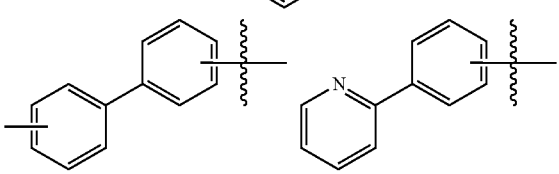
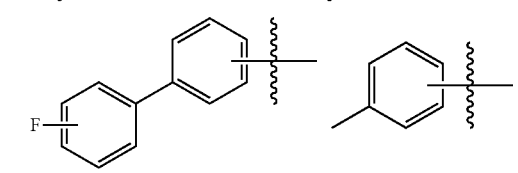
-continued
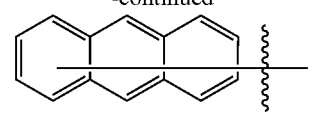
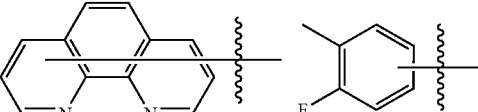
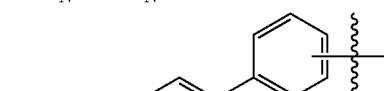
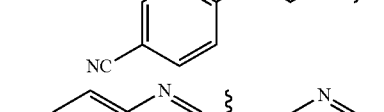
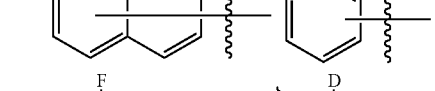
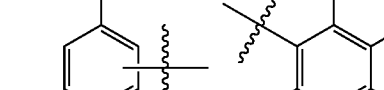
Further optionally, $Ar_1$ and $Ar_2$ are each independently selected from the group consisting of the following groups:
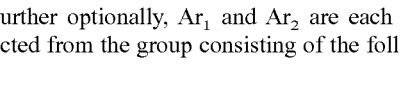
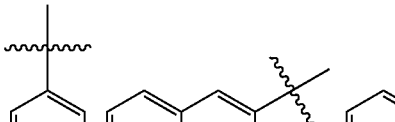
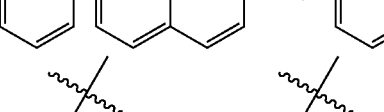
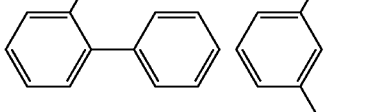
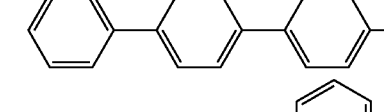
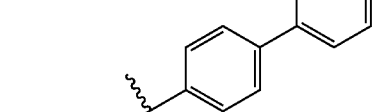
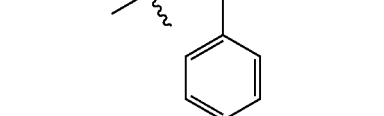

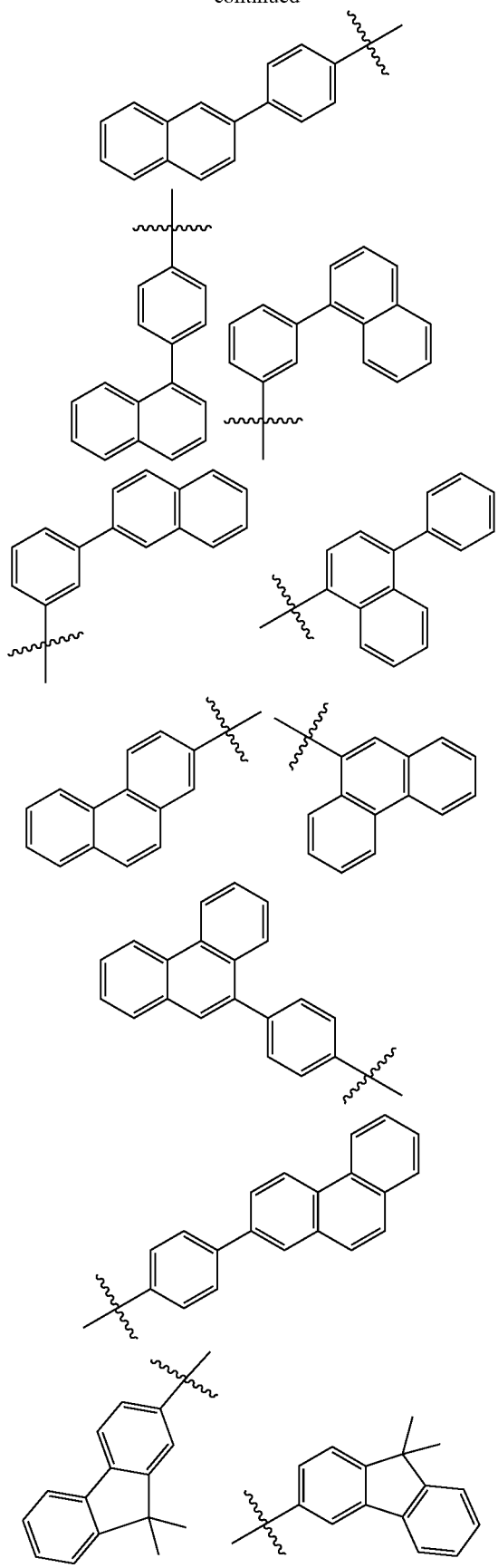
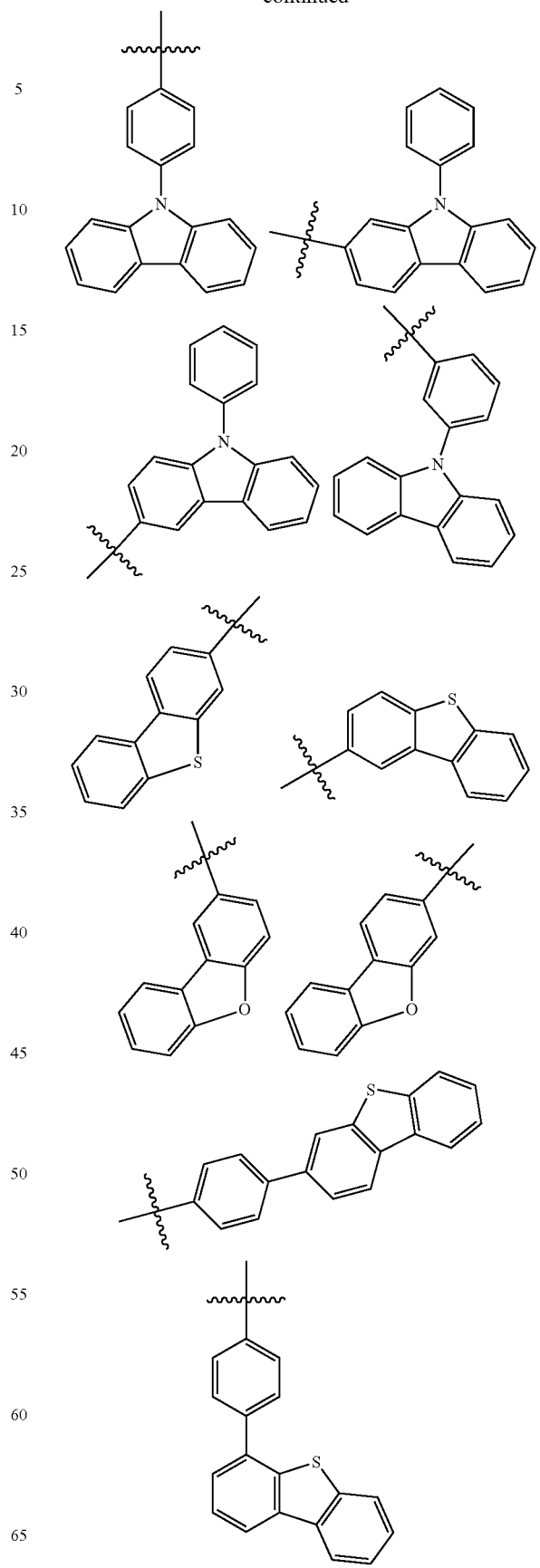

33
-continued
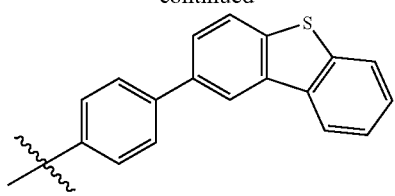
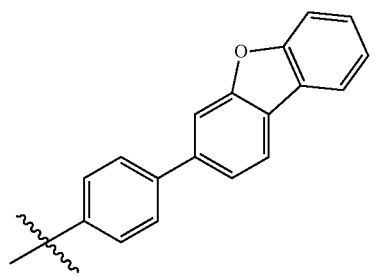
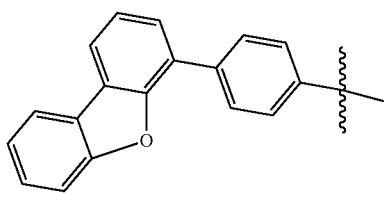
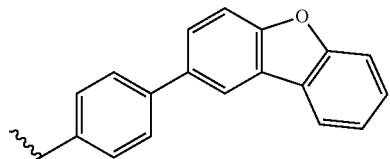
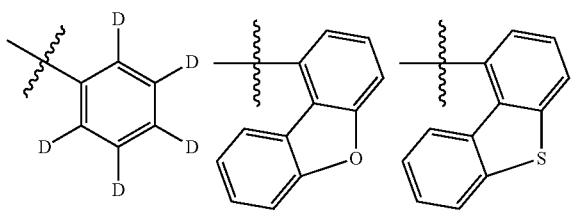
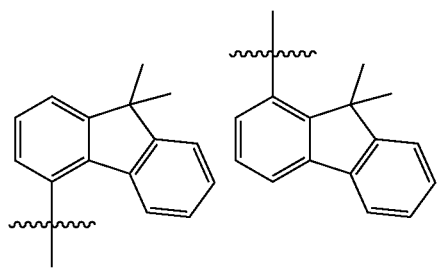
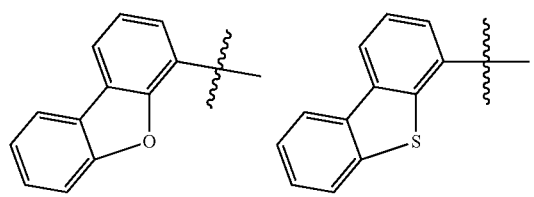
34
-continued
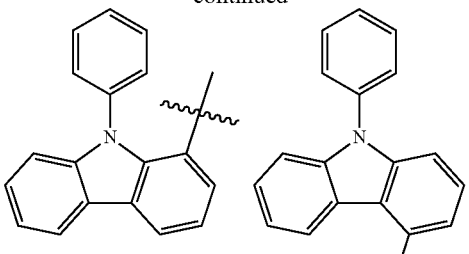
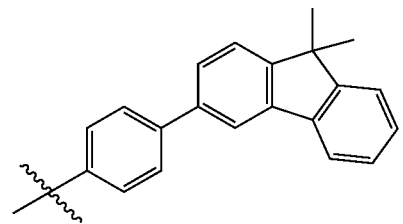
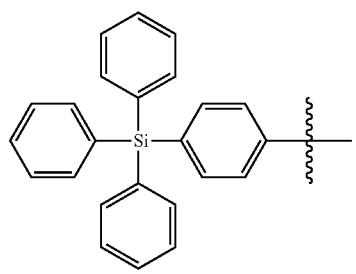
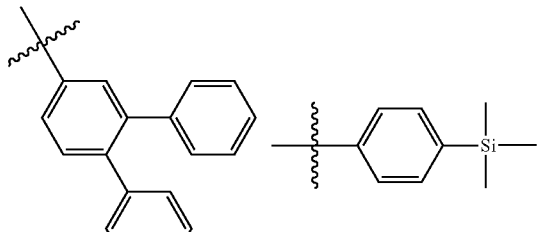
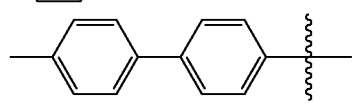
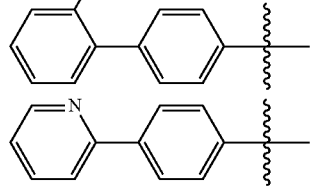
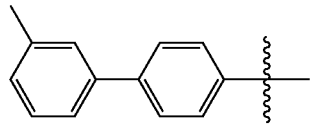
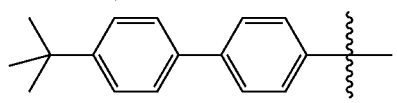

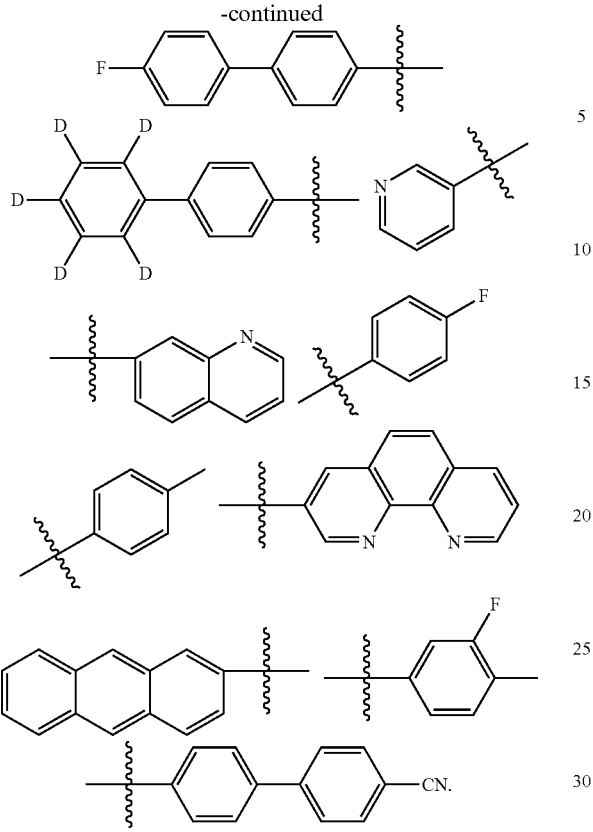

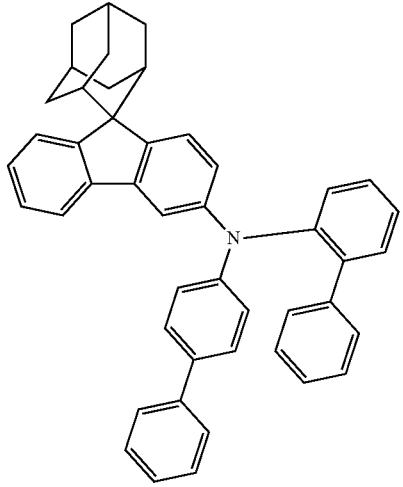

Optionally, $R_3$ and $R_4$ are each independently selected from deuterium, fluorine, cyano, an aryl group having 6 to 18 carbon atoms, a heteroaryl group having 5 to 18 carbon atoms, an alkyl group having 1 to 6 carbon atoms, or a cycloalkyl group having 3 to 10 carbon atoms. Specific examples of $R_3$ and $R_4$ include, but are not limited to, deuterium, fluorine, cyano, methyl, tert-butyl, phenyl, cyclopentyl, cyclohexyl, pyridyl and the like.

Also optionally, $R_3$ and/or $R_4$ are phenyl substituted by deuterium.

Optionally, the nitrogen-containing compound is selected from the group consisting of the following compounds:

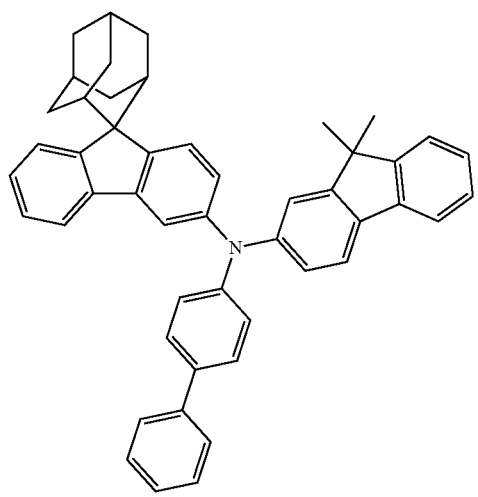

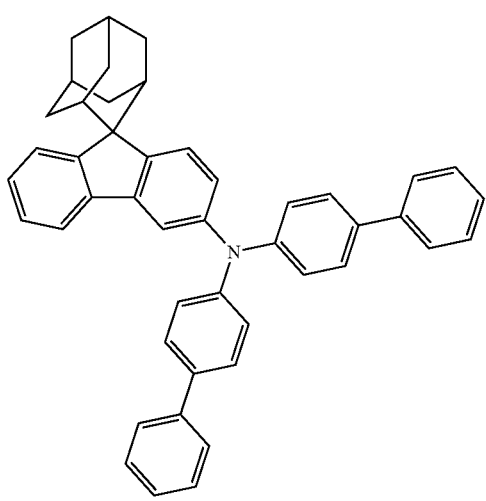

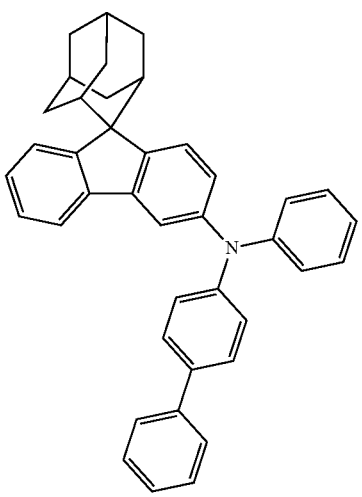

37
-continued
5
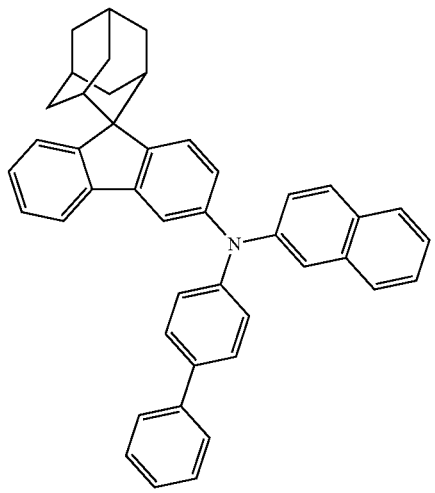
6
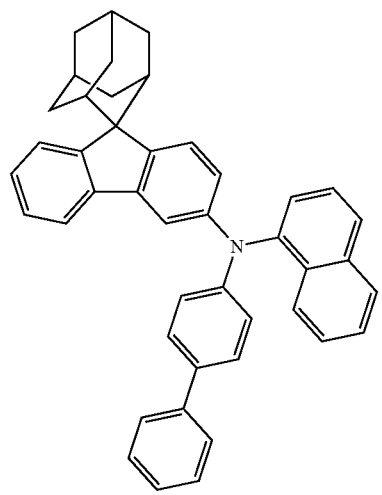
7
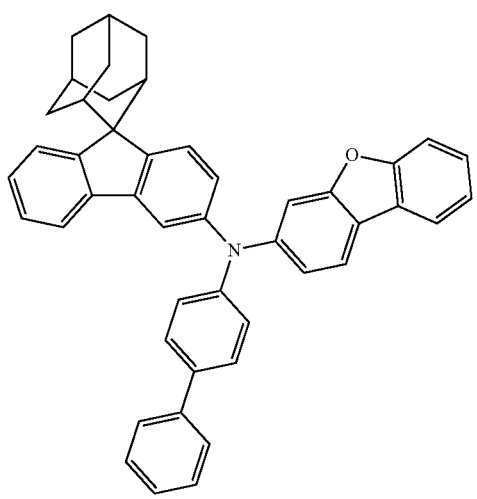
38
-continued
8
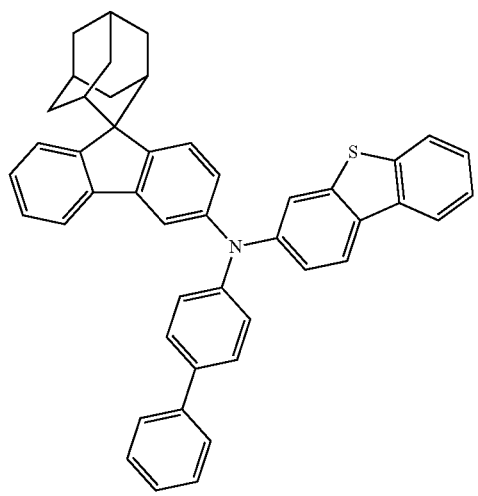
9
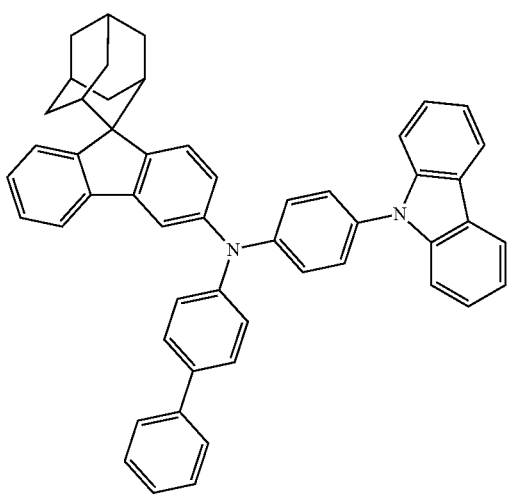
10
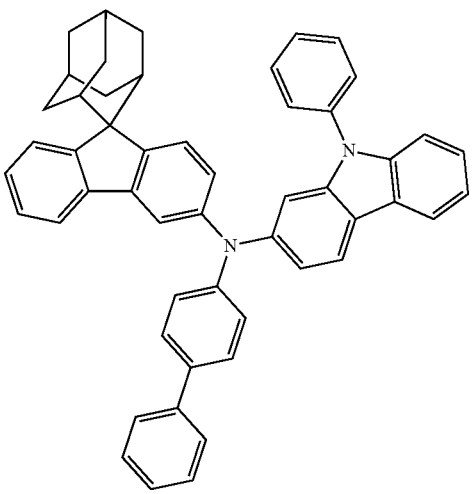

11
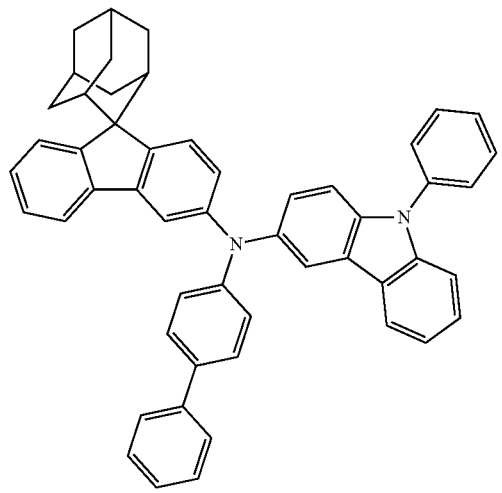
14
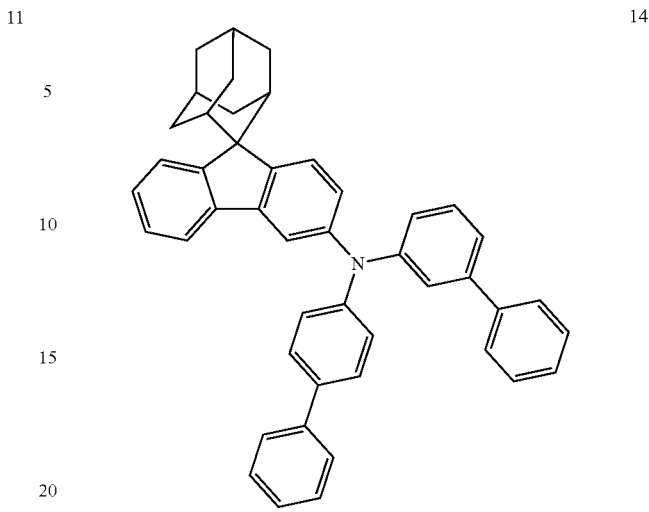
12
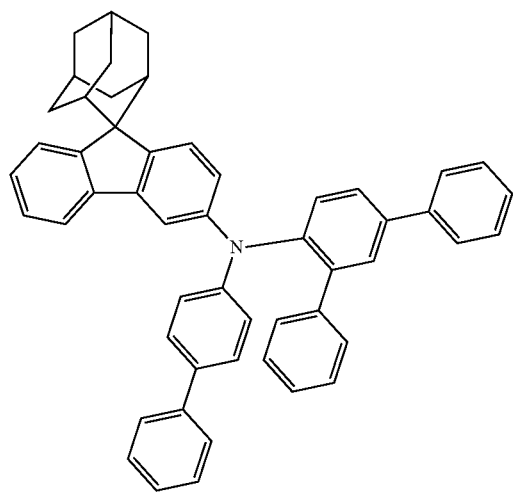
15
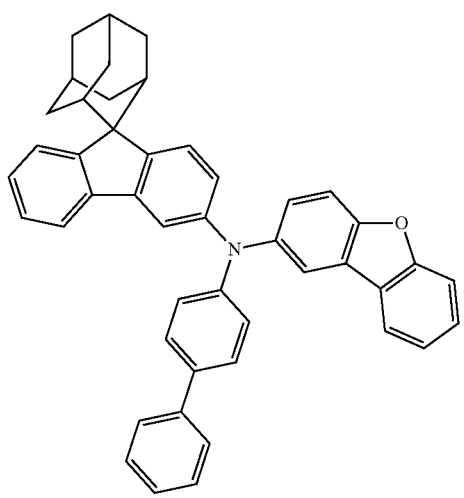
13
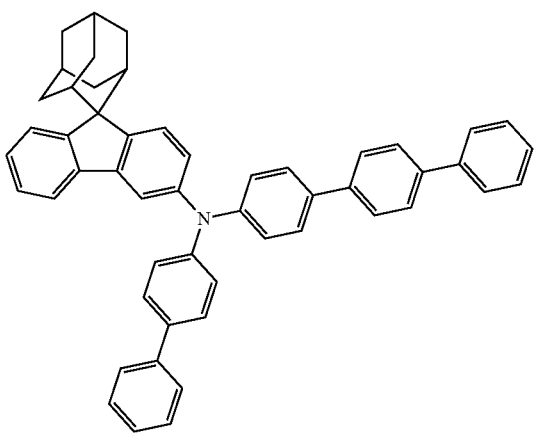
16
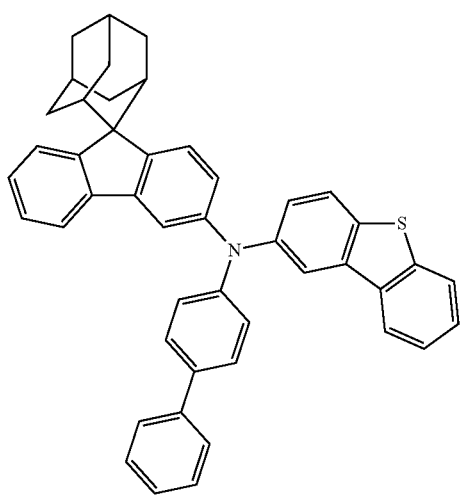

17
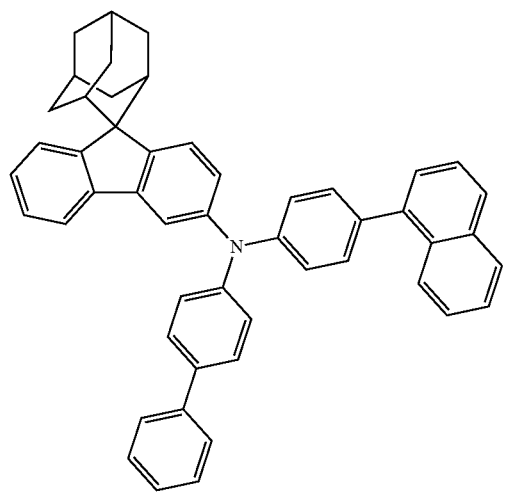
18
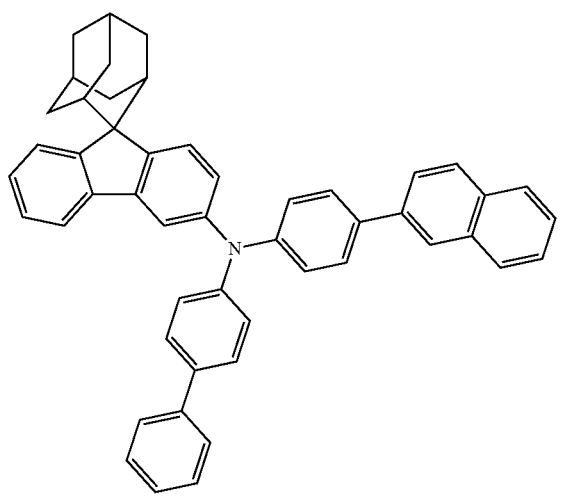
19
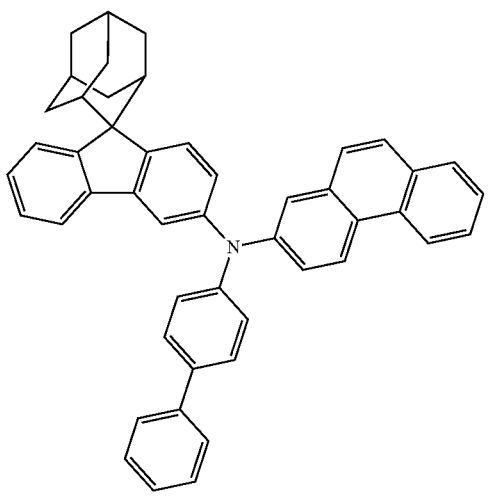
20
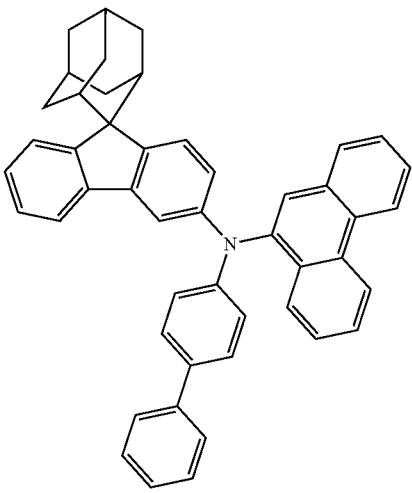
21
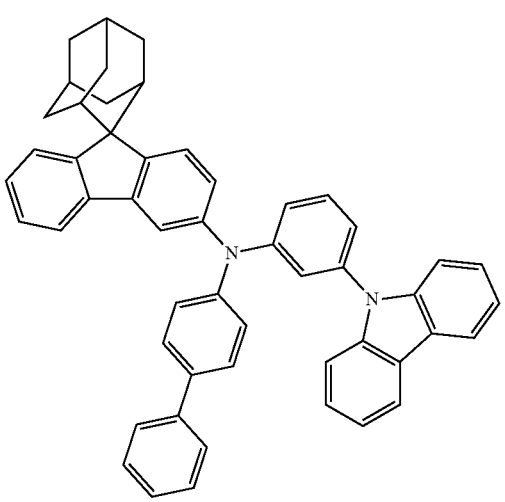
22
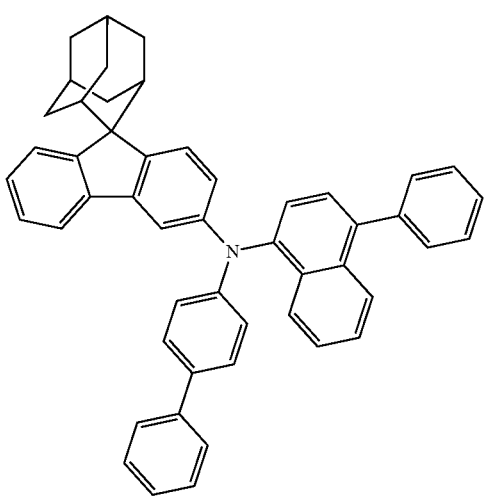

23
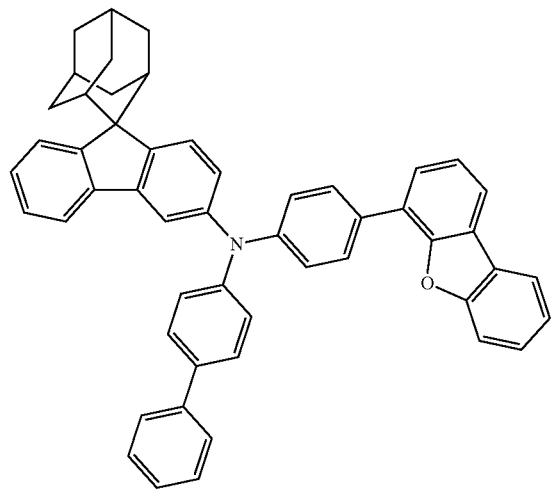
24
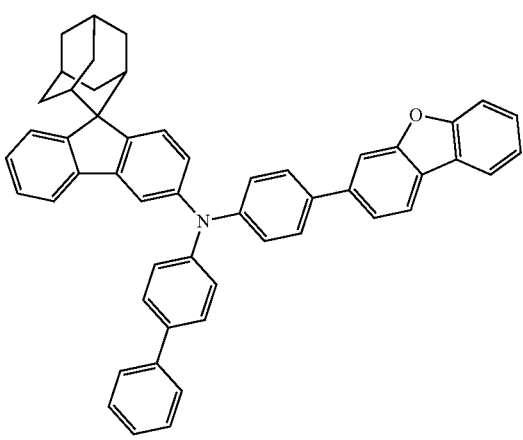
25
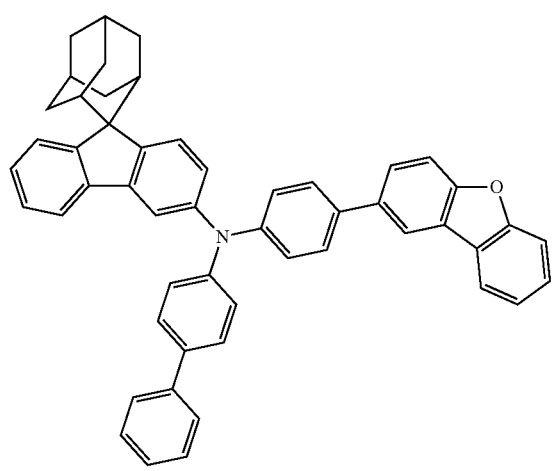
26
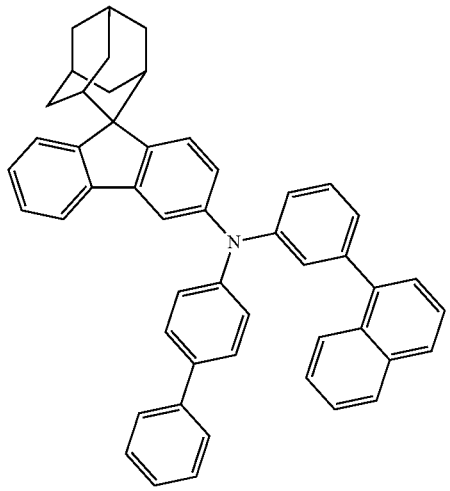
27
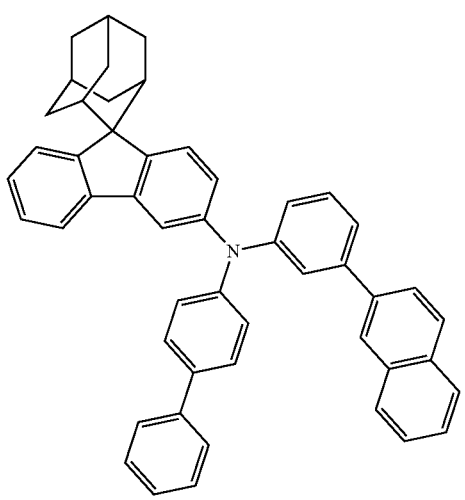
28
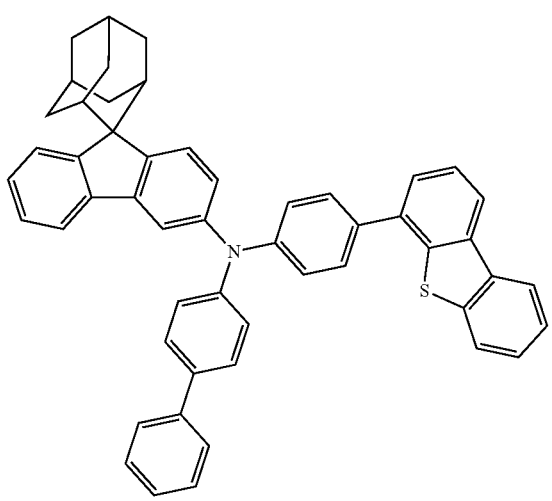

29
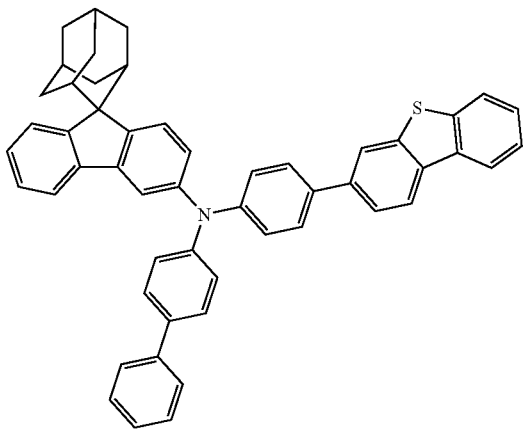
30
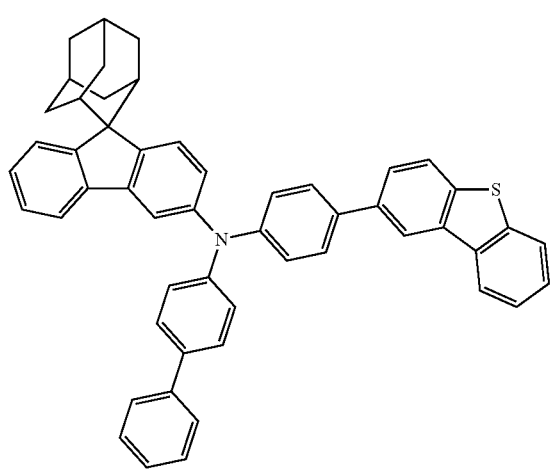
31
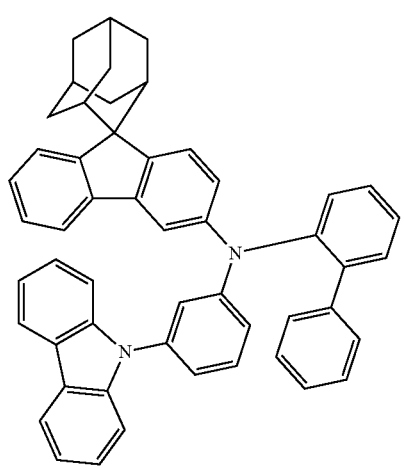
32
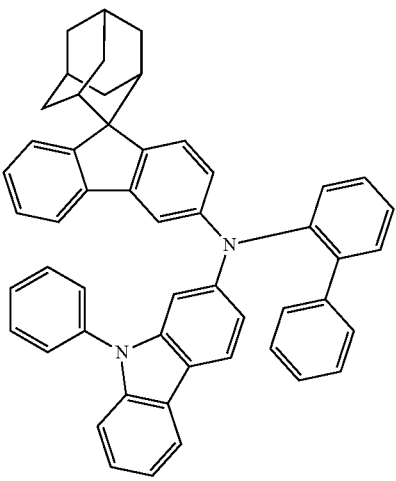
33
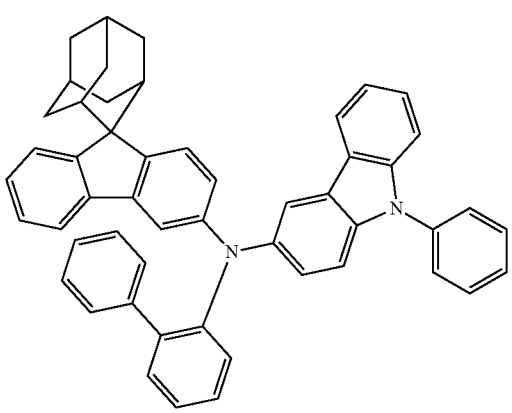
34
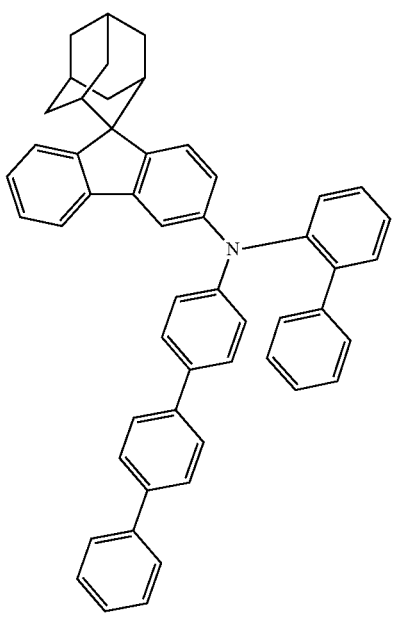

35
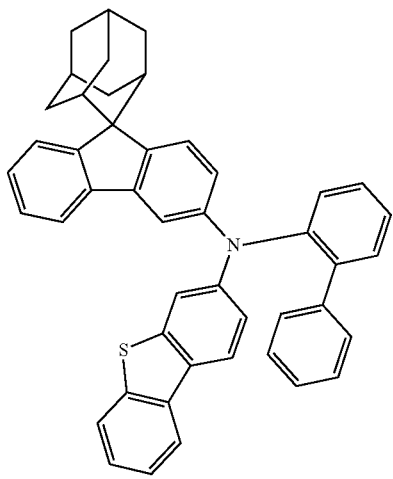
36
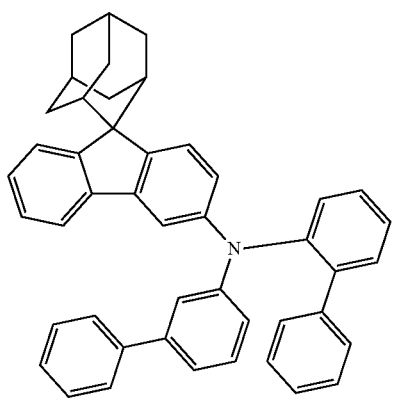
37
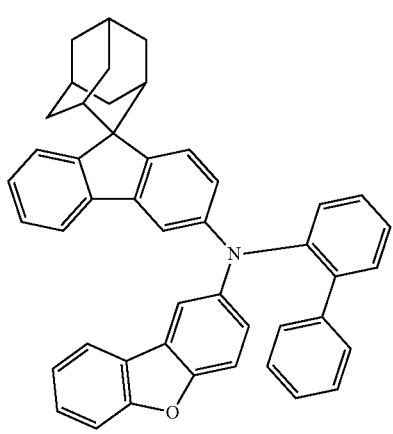
38
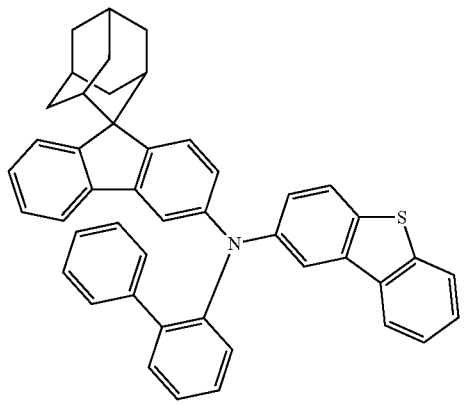
39
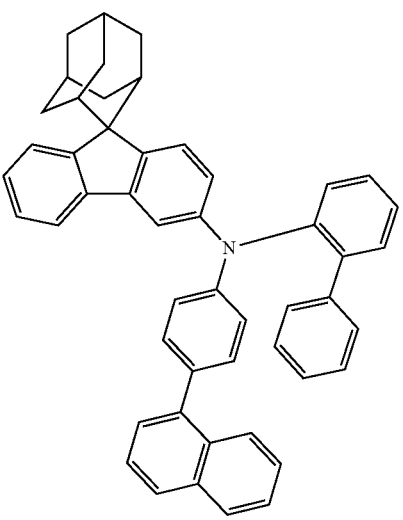
40
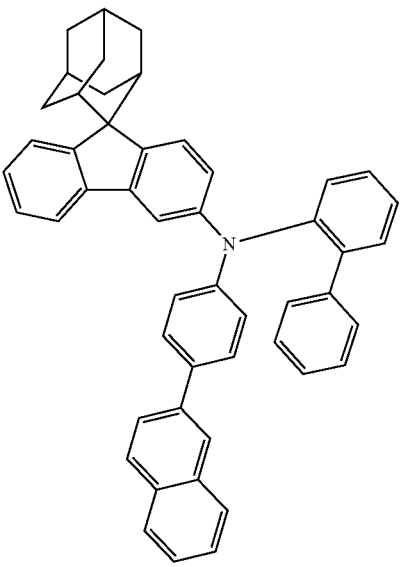

41
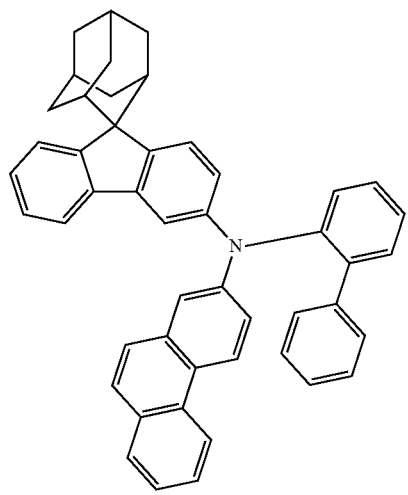
42
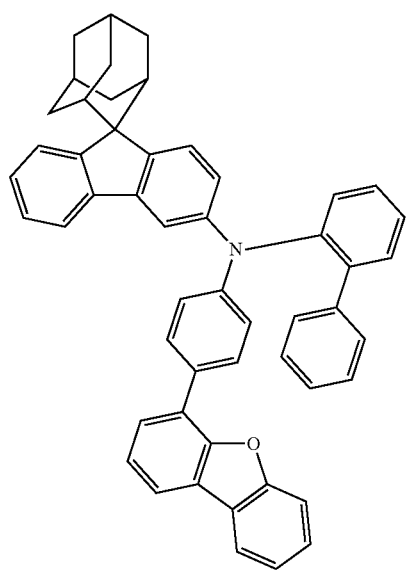
43
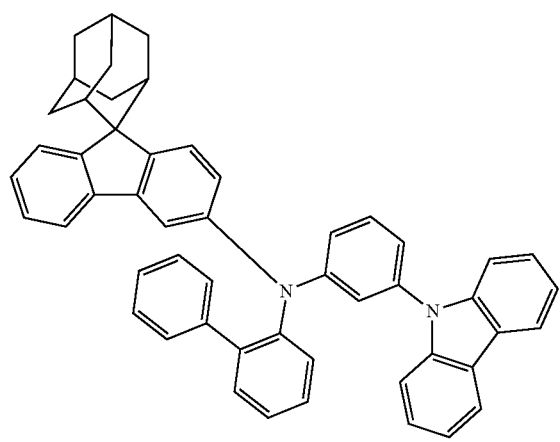
44
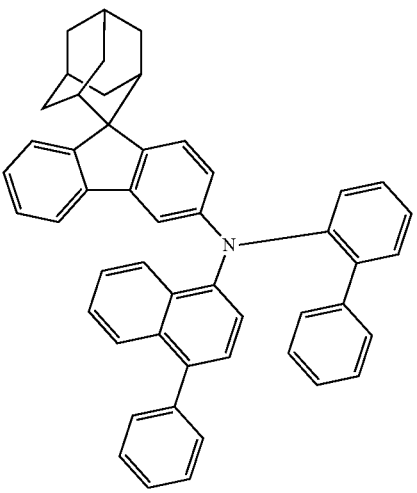
45
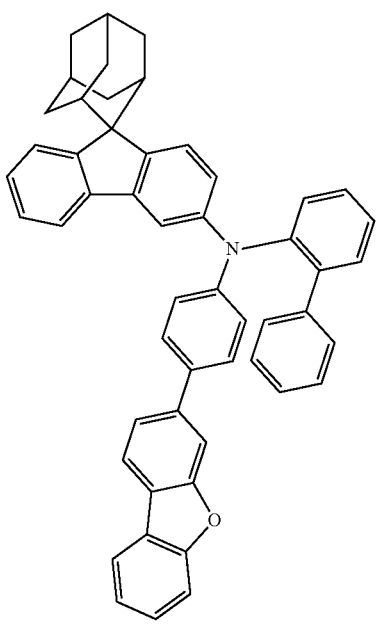

46
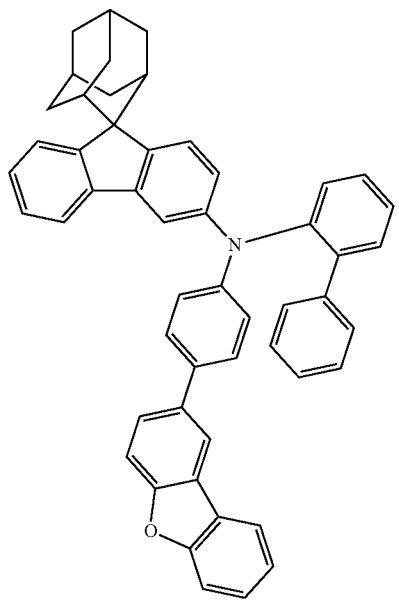
47
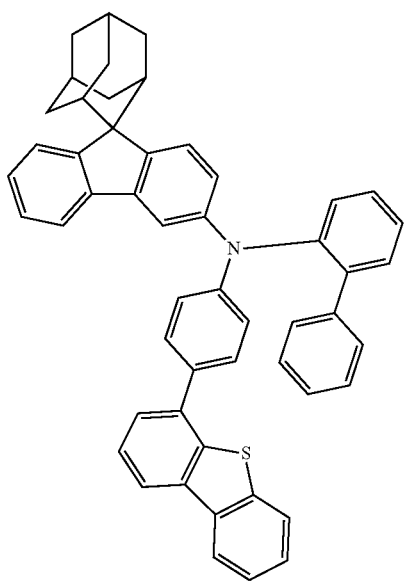
48
49
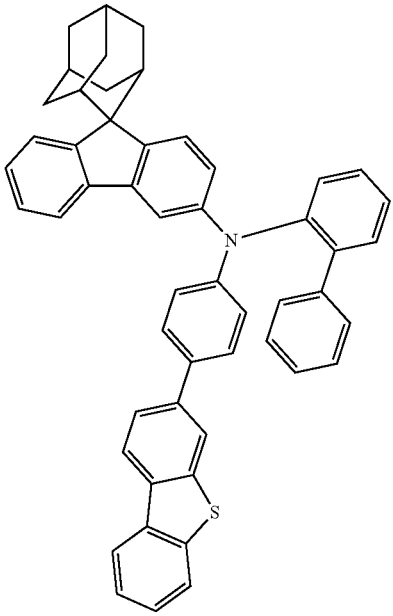
50
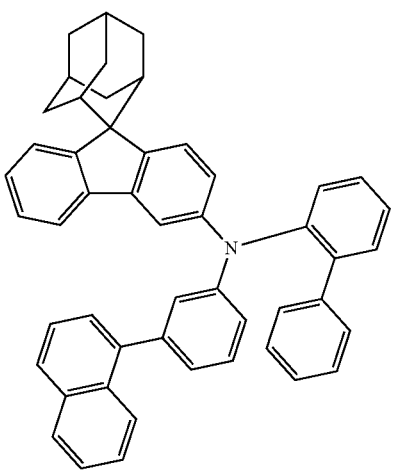
51
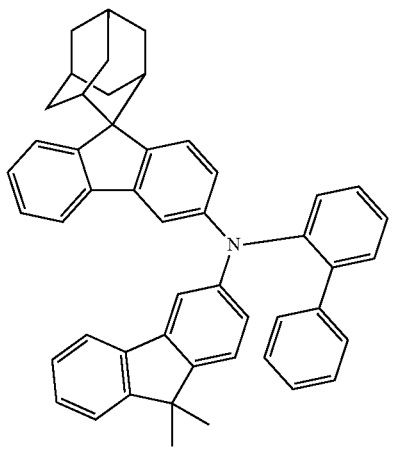

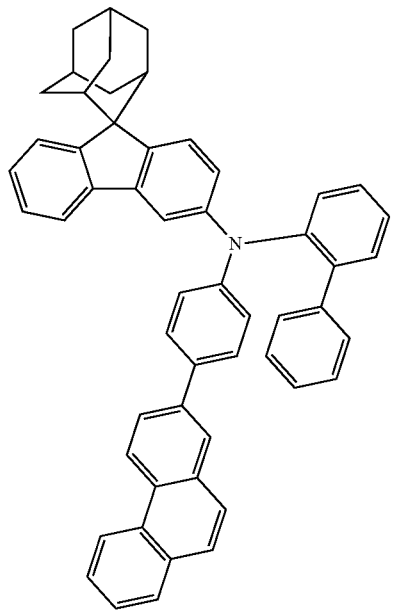
52
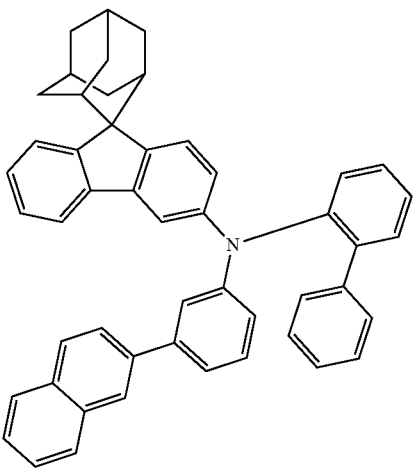
55
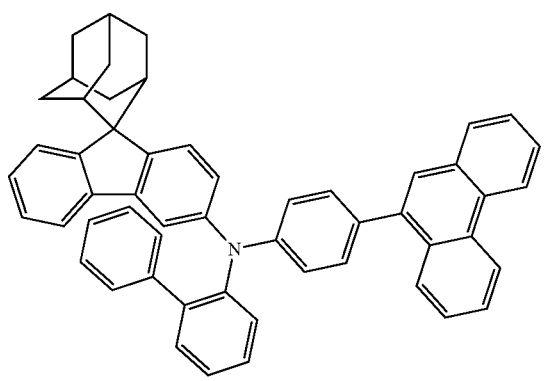
53
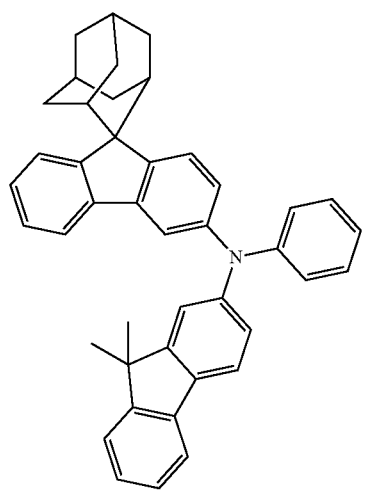
56
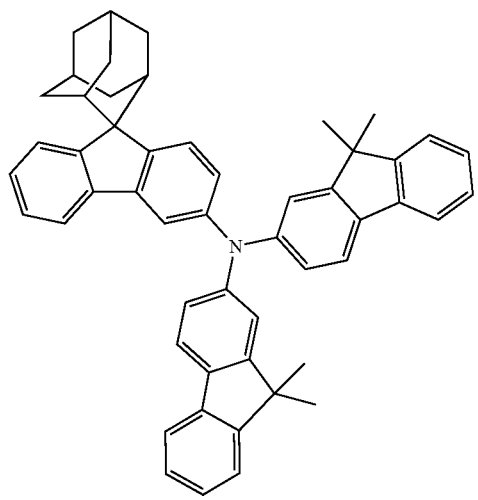
54
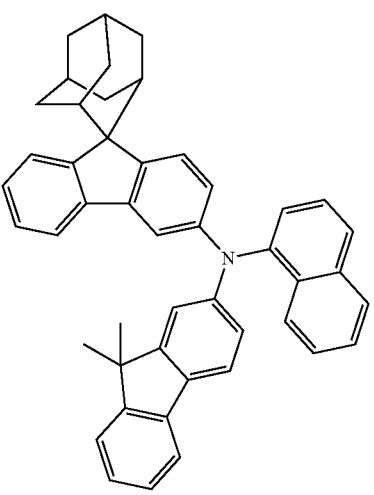
57

58
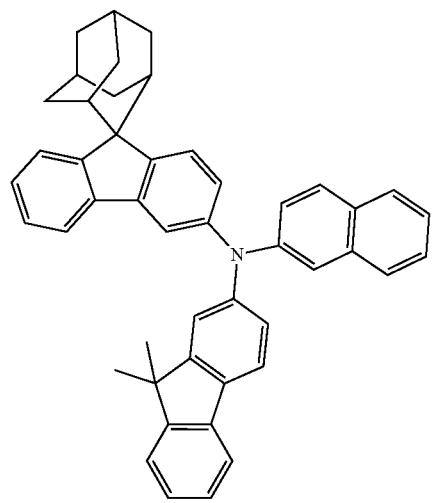
59
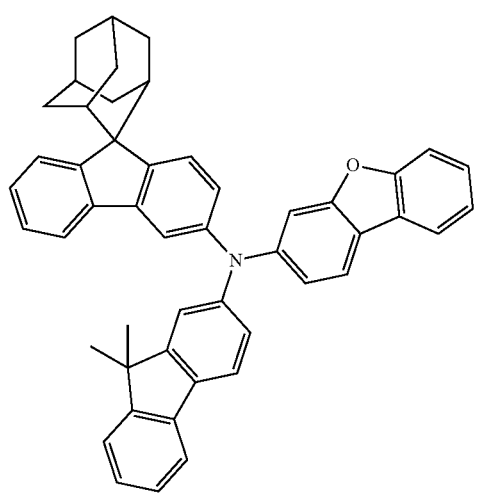
60
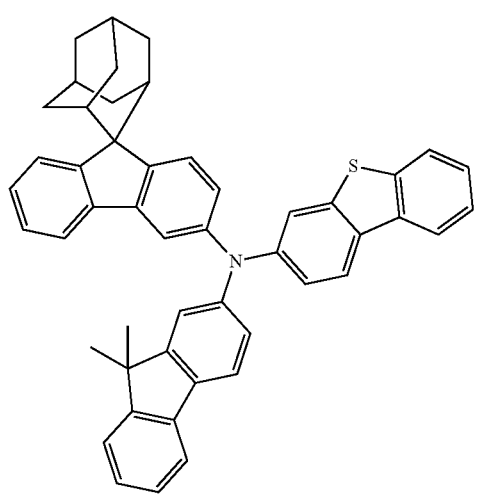
61
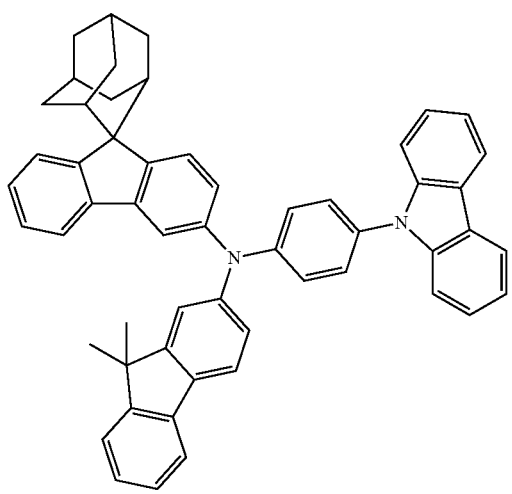
62
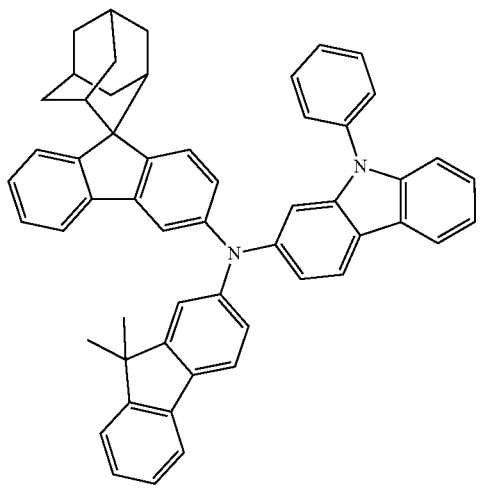
63
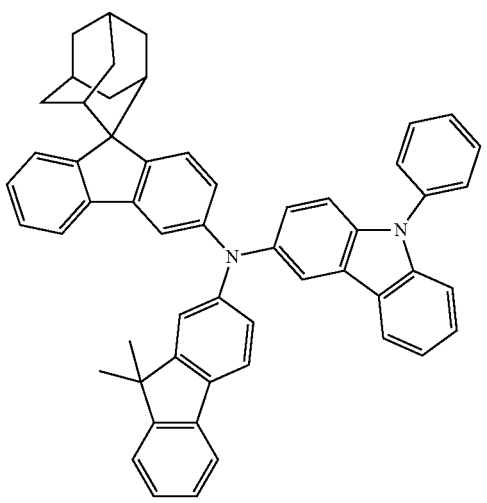

64
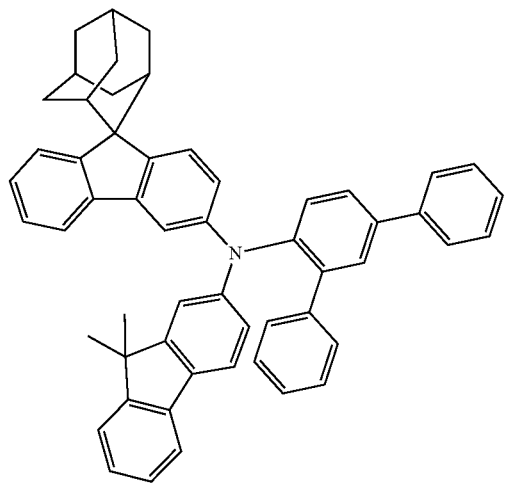
65
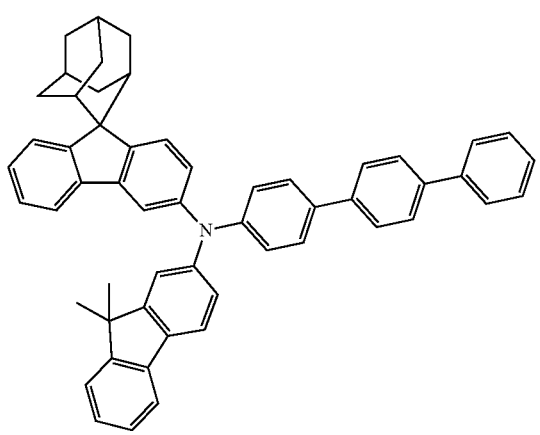
66
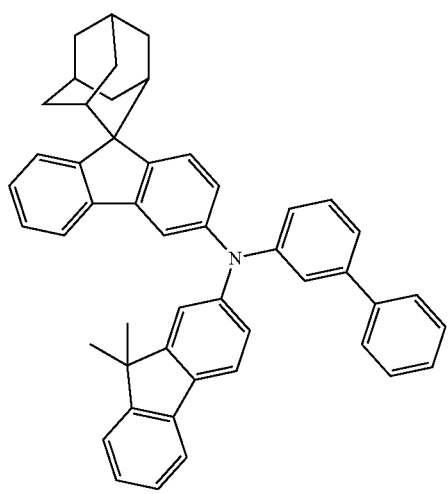
67
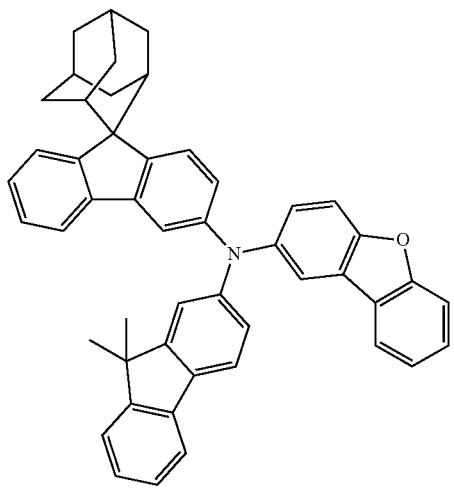
68
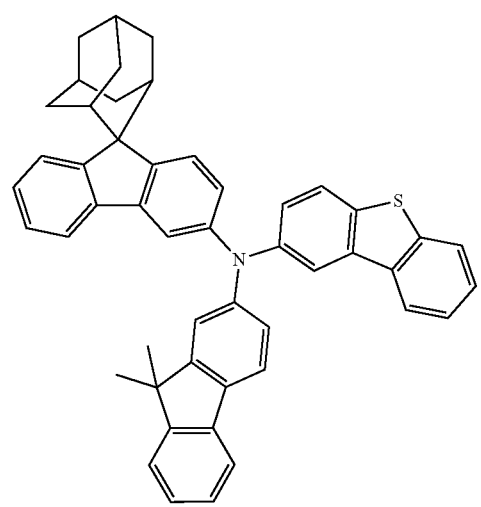
69
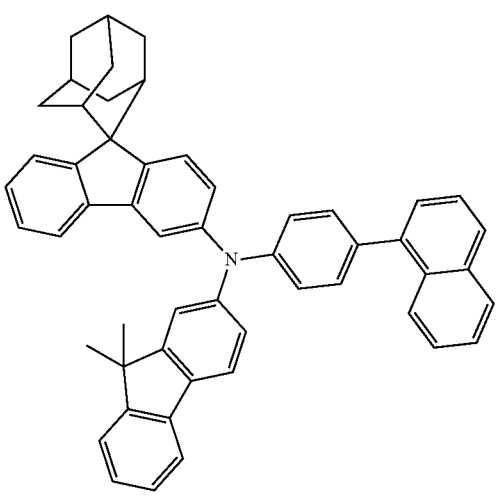

70
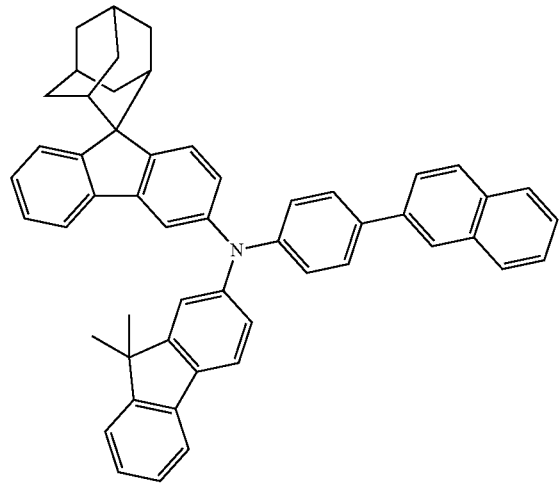
71
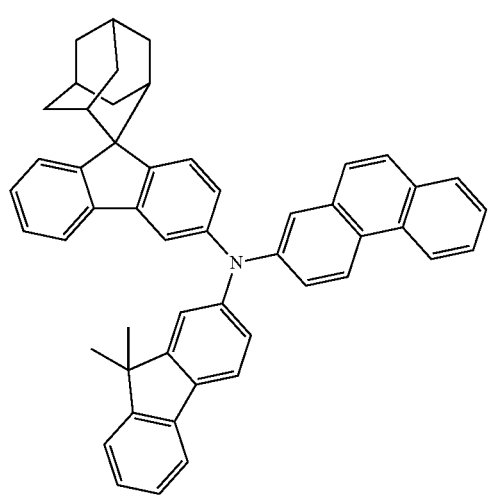
72
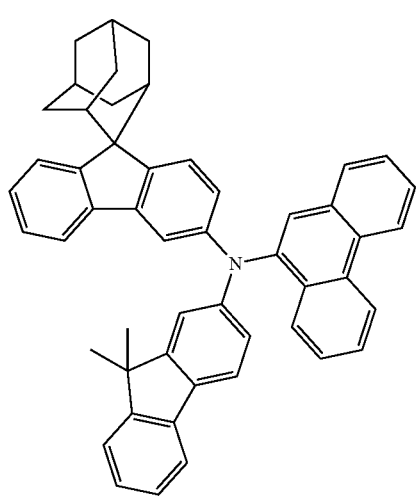
73
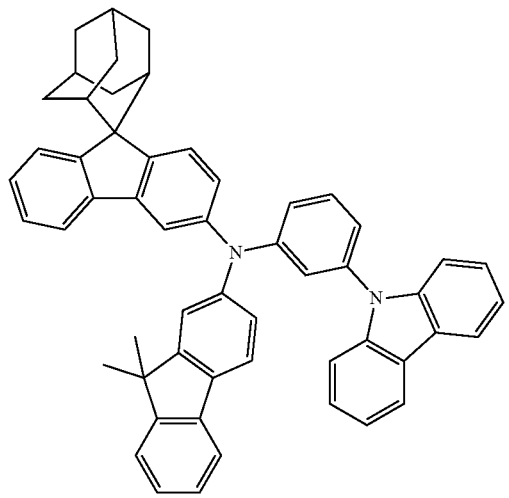
74
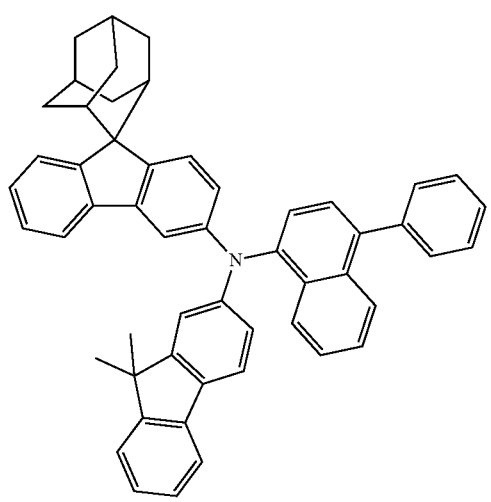
75
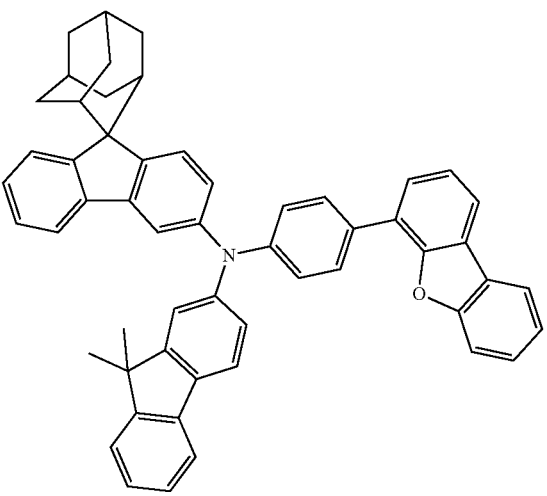

76
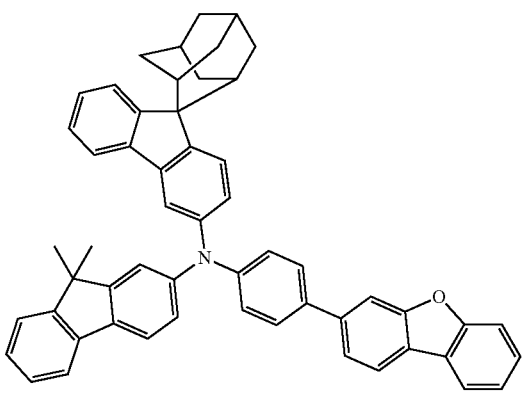
77
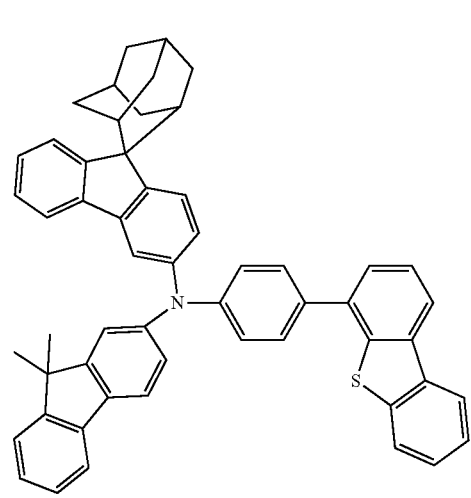
79
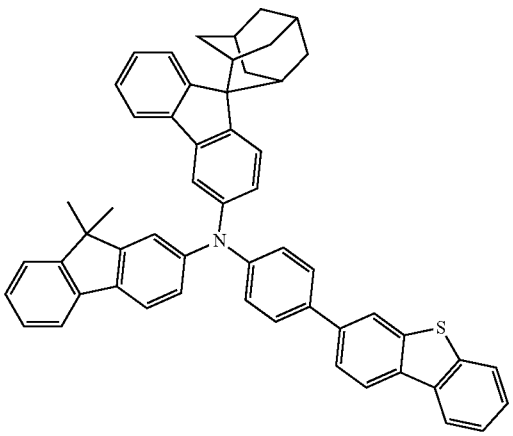
80
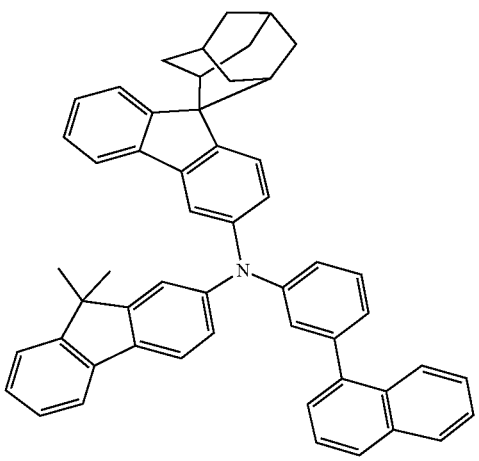
78
81

82
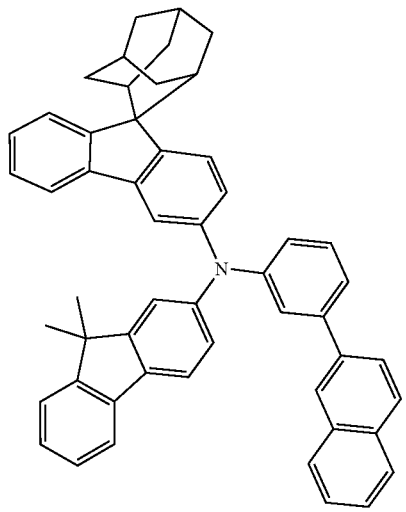
83
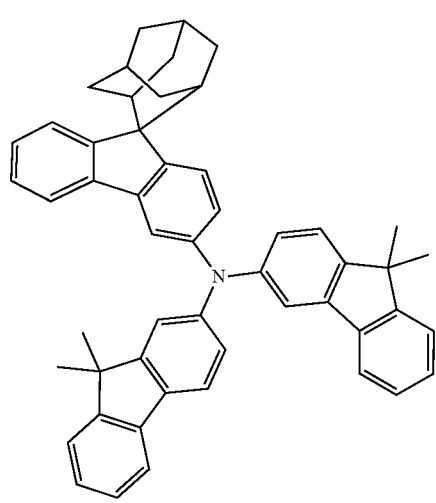
84
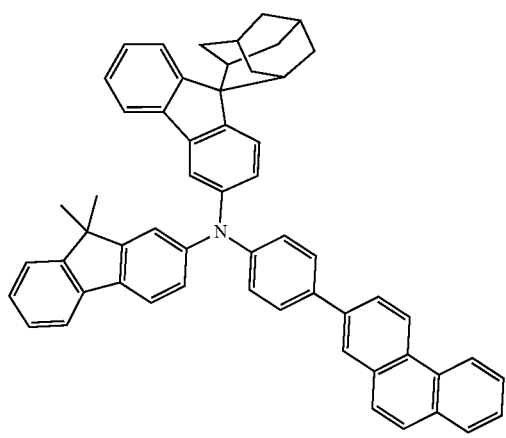
85
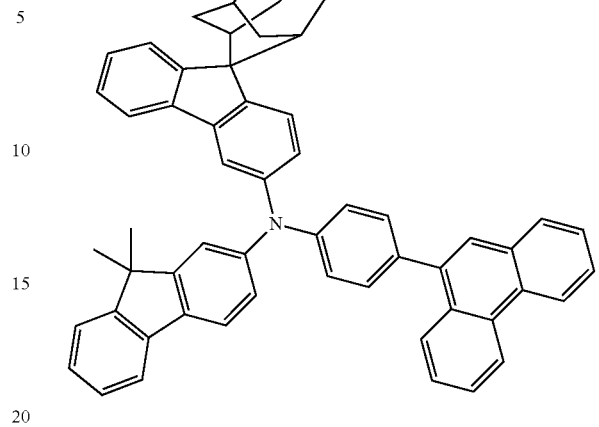
86
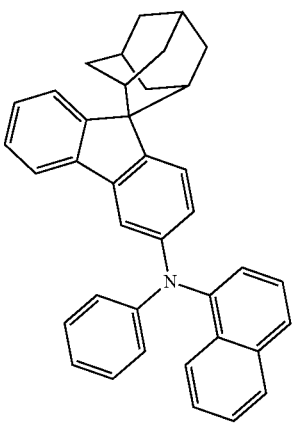
87
88
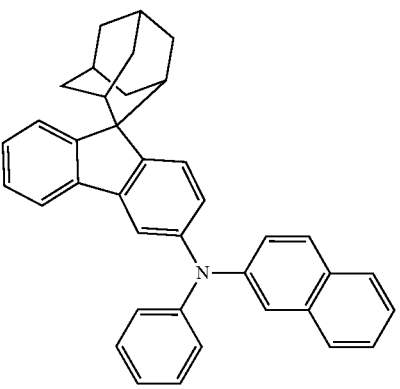

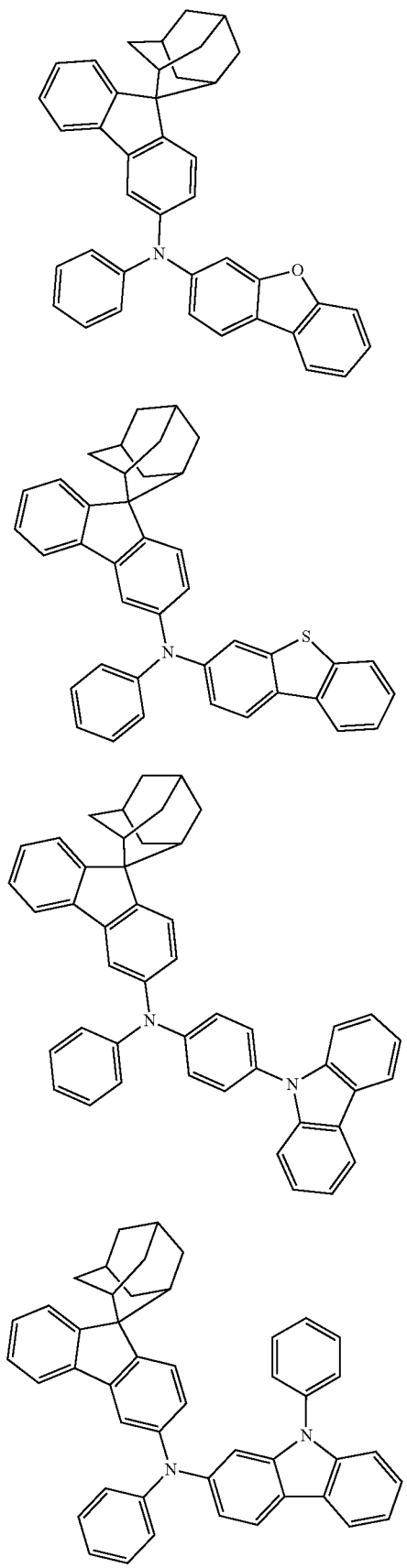
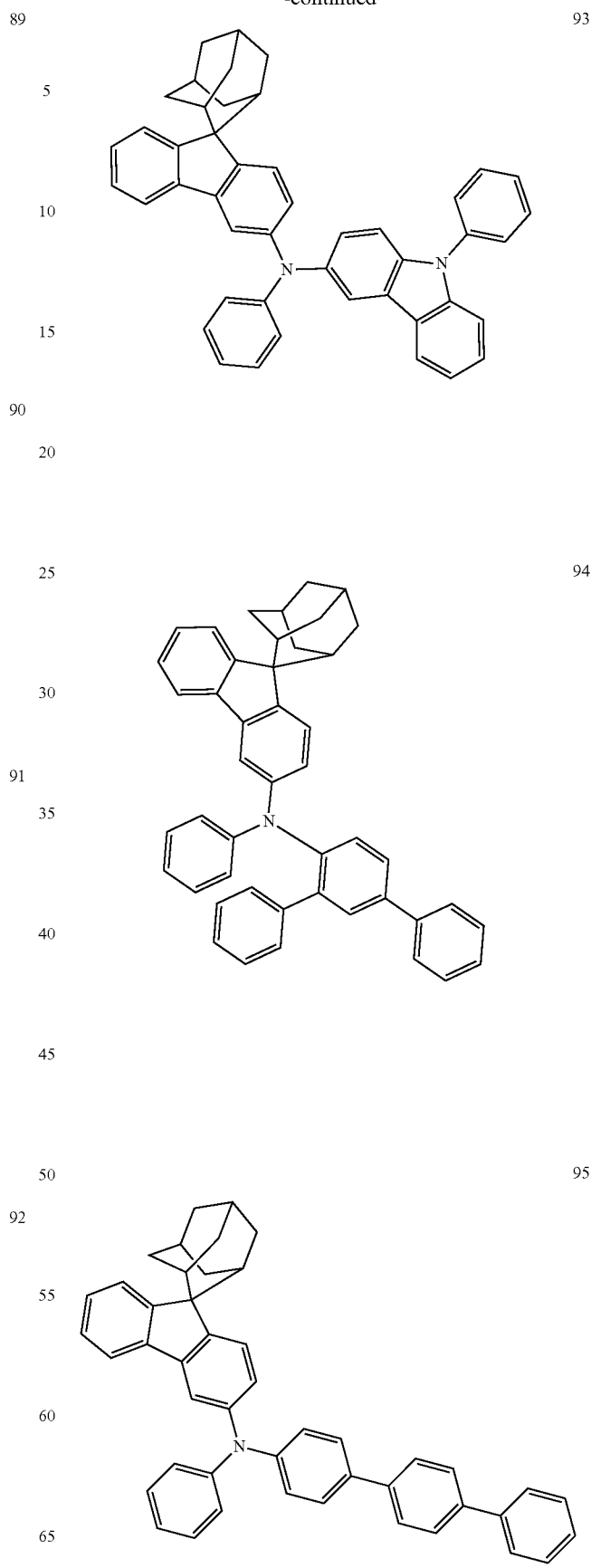

96
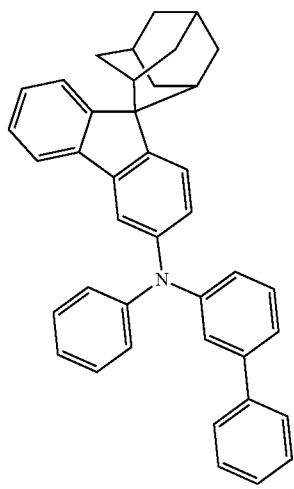
97
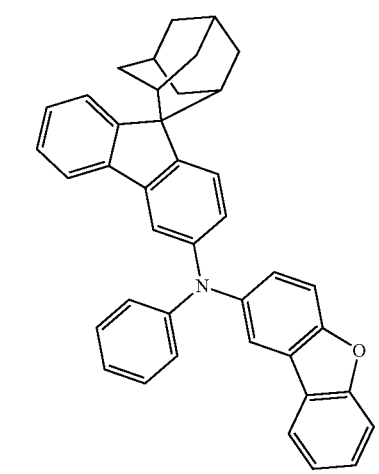
98
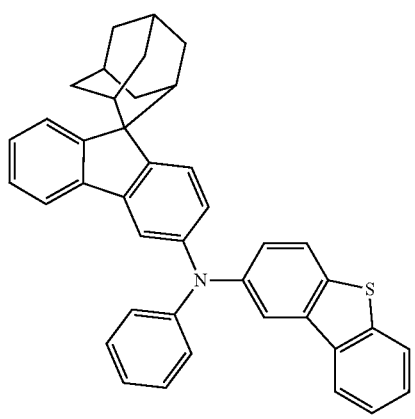
99
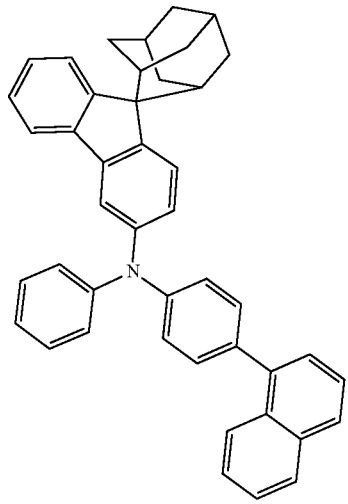
100
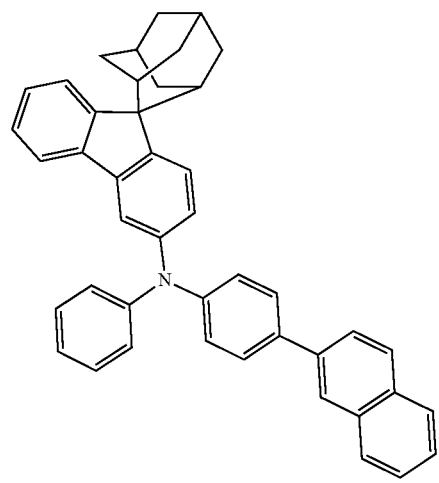
101
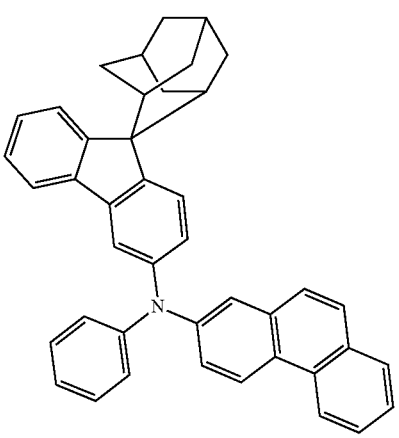

69
-continued
102
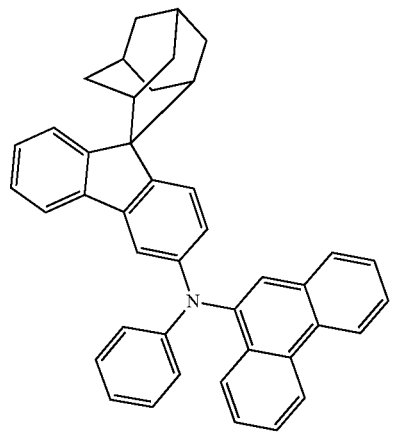
103
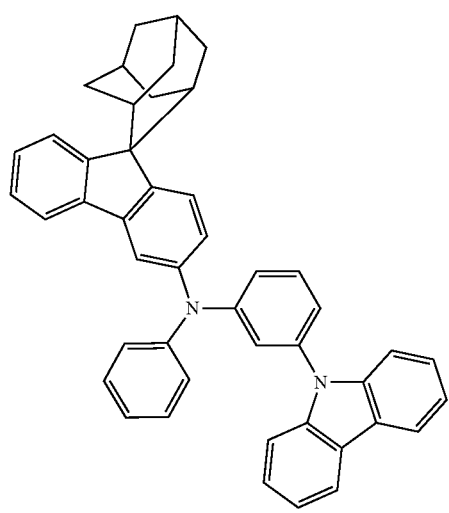
104
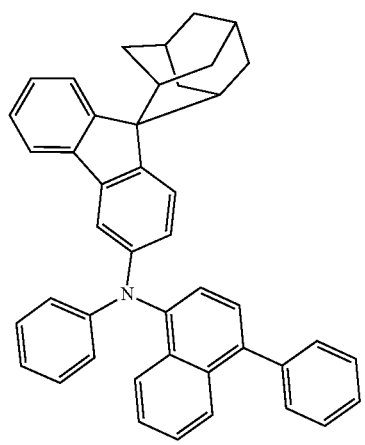
70
-continued
105
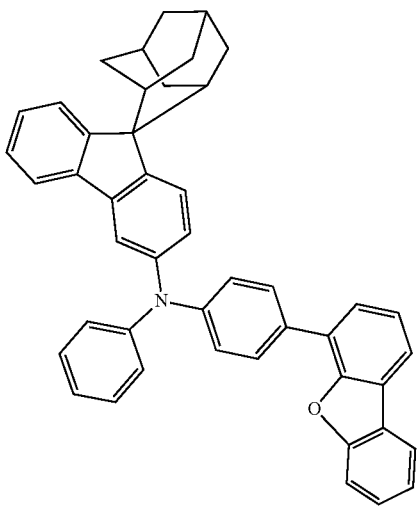
106
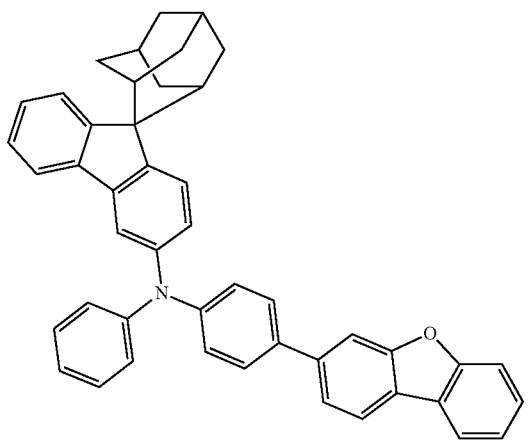
107
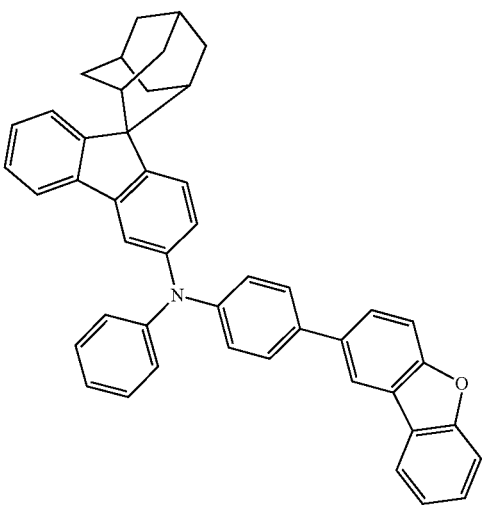

108
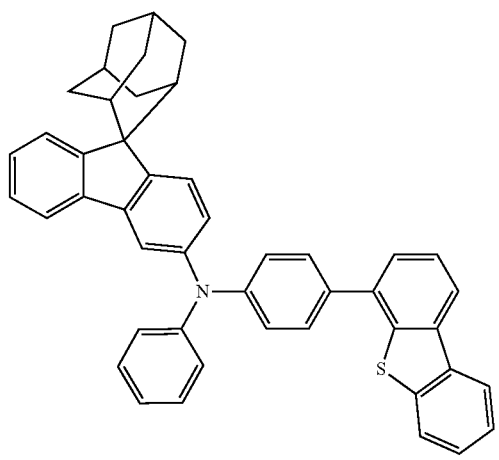
109
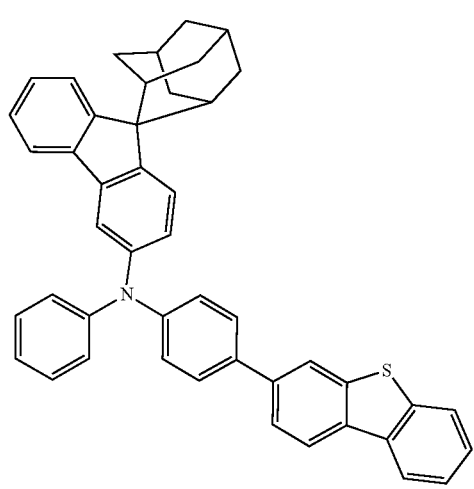
110
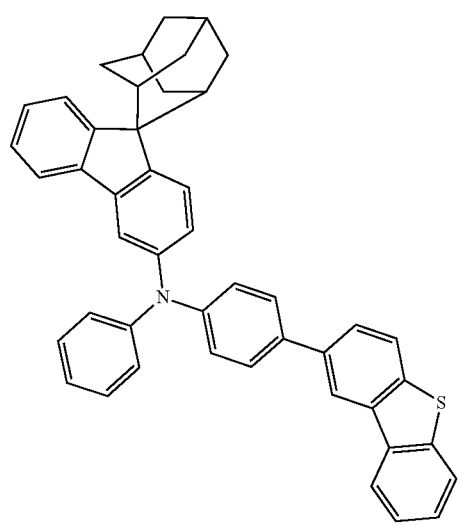
111
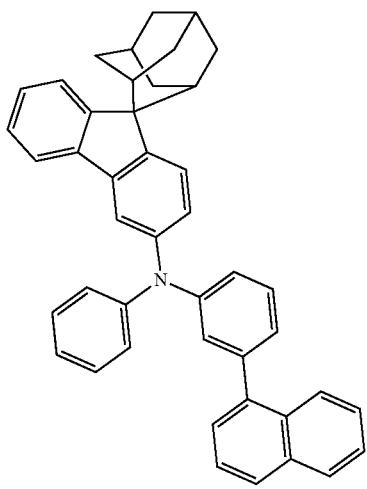
112
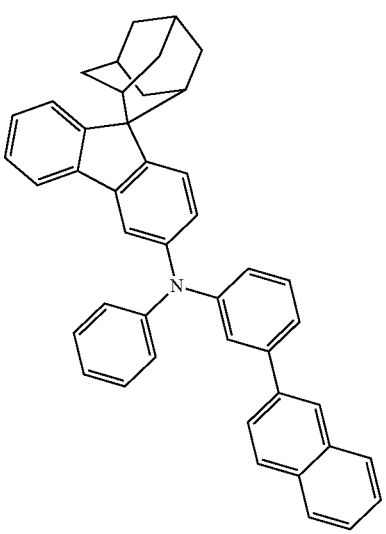
113
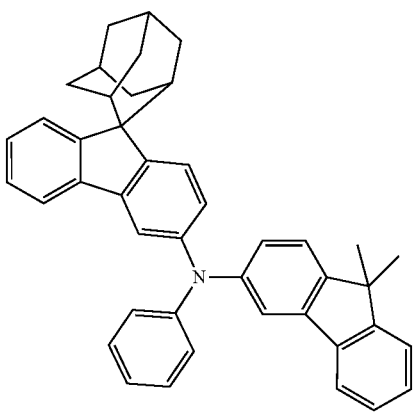

114
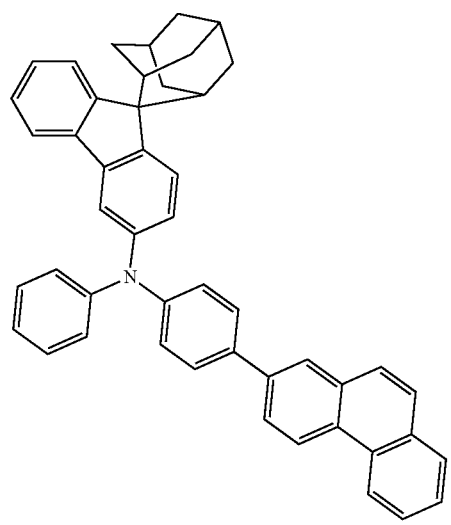
117
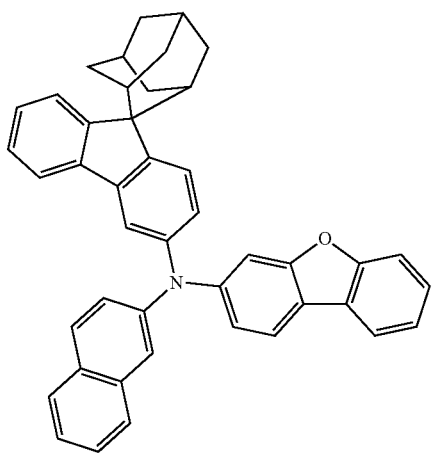
115
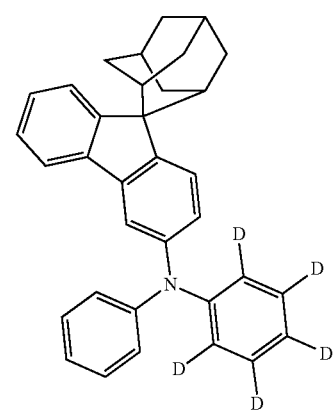
118
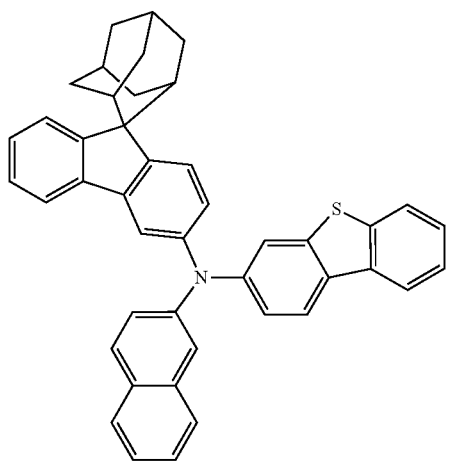
116
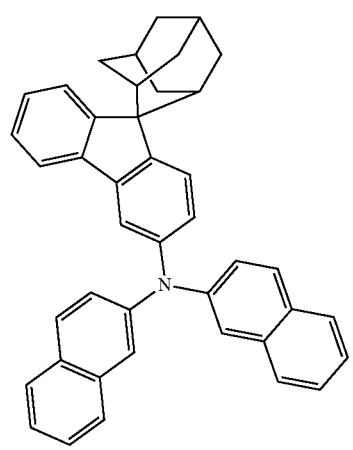
119
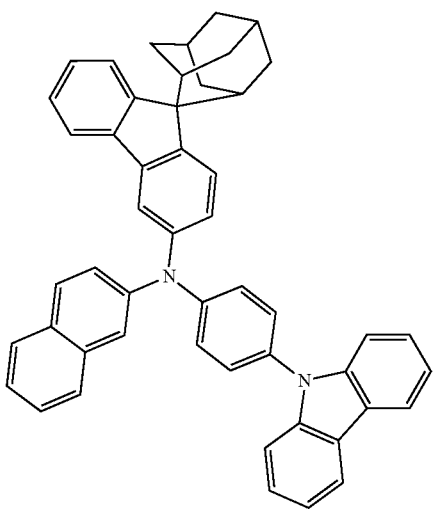

120
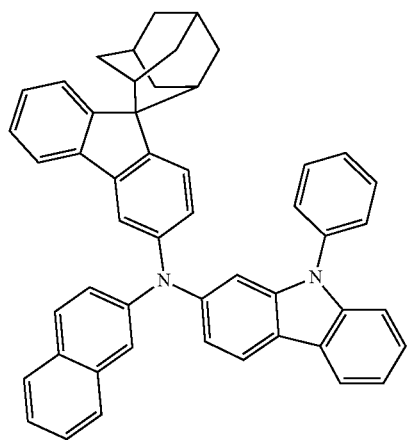
121
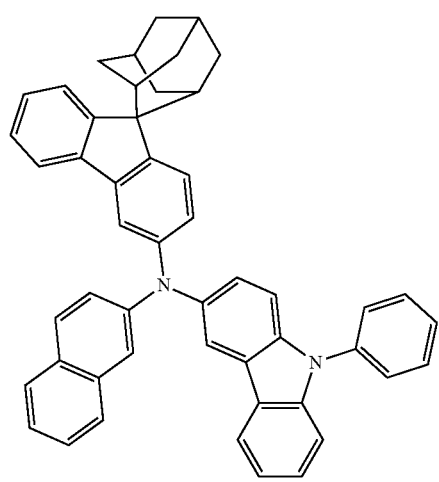
122
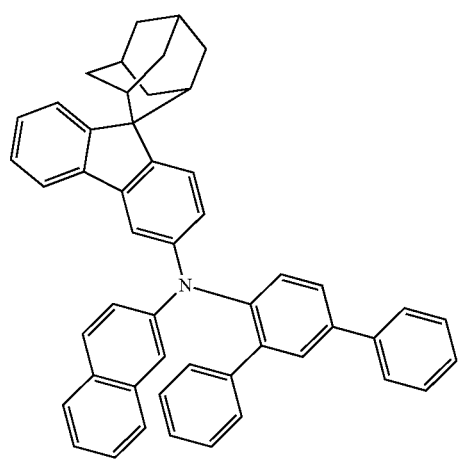
123
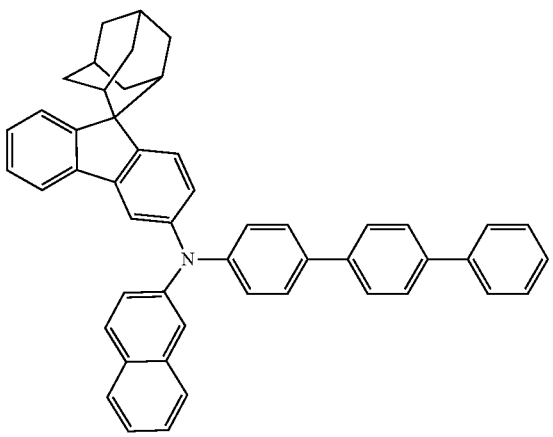
124
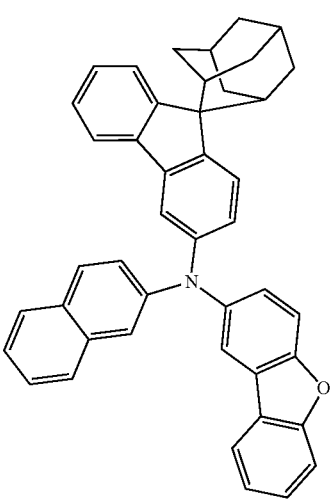
125
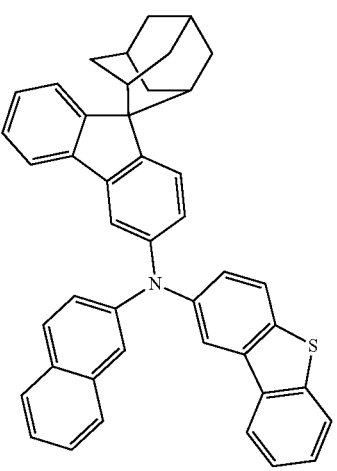

77
-continued
126
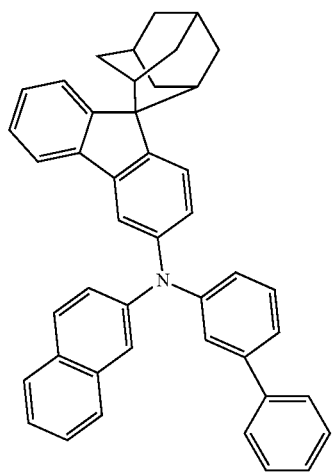
127
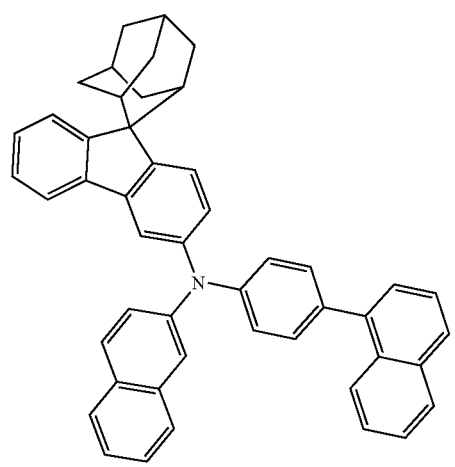
128
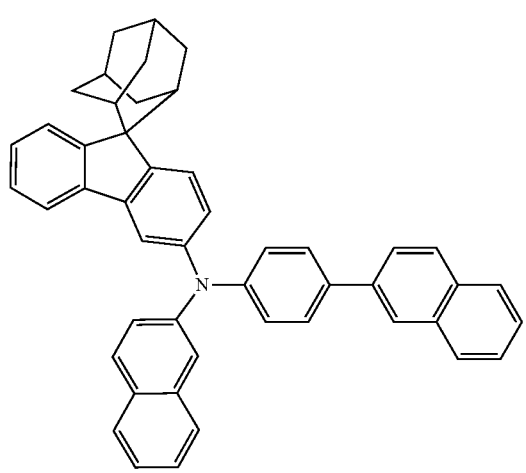
78
-continued
129
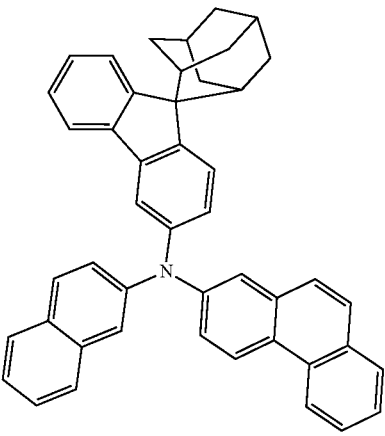
130
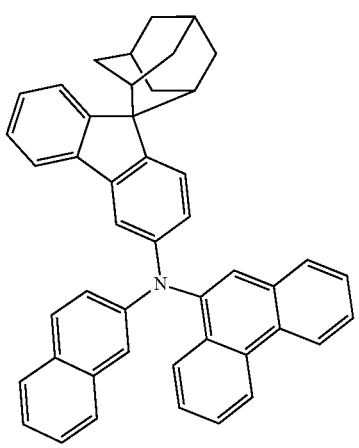
131
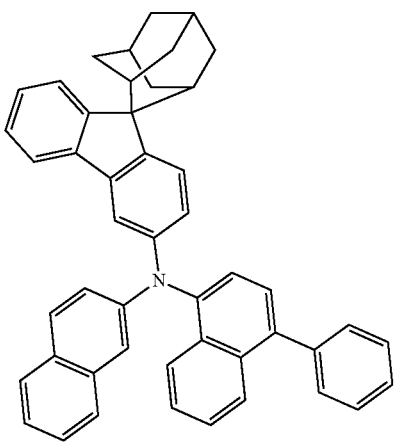

132
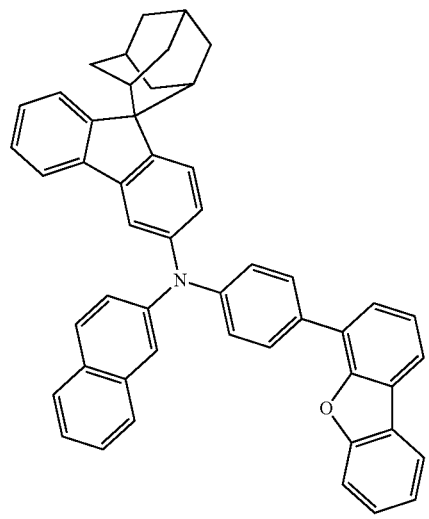
133
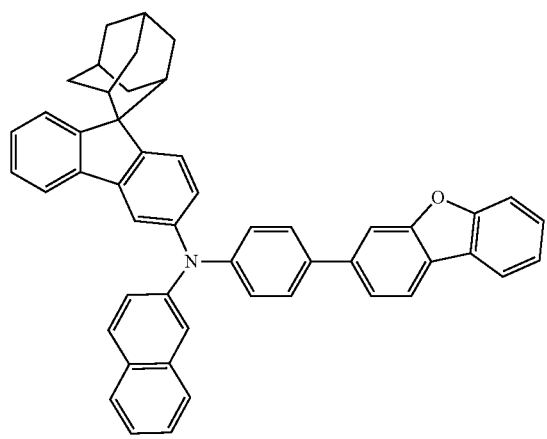
134
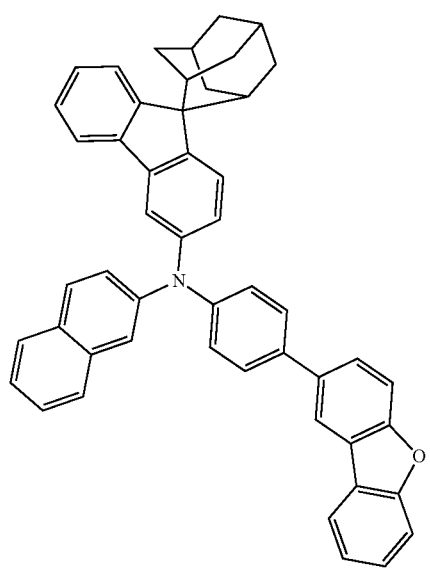
135
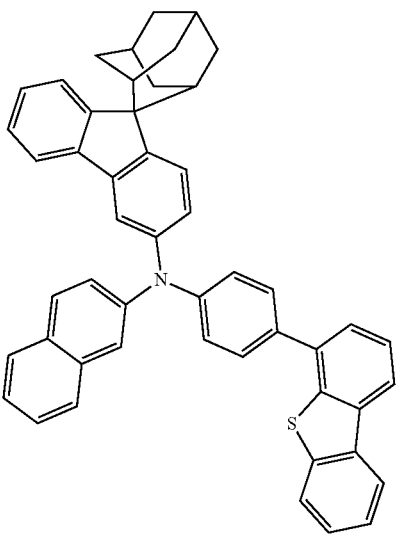
136
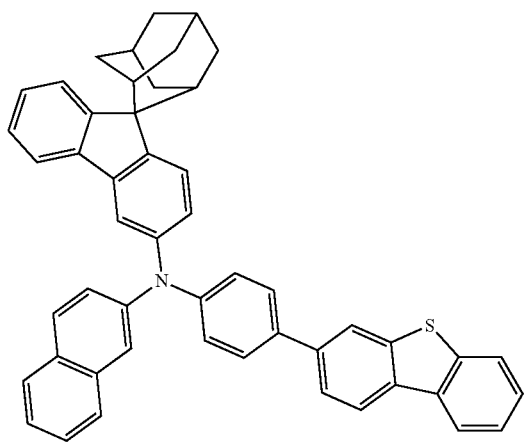
137
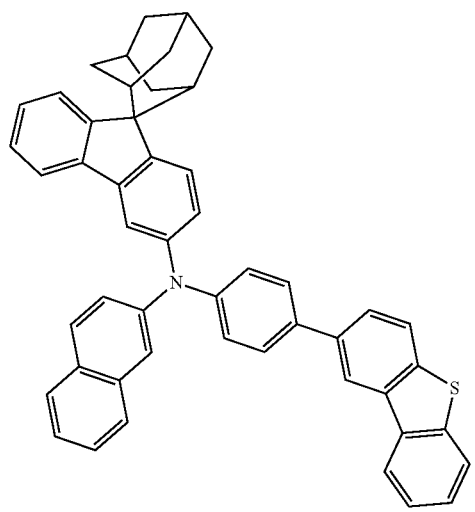

138
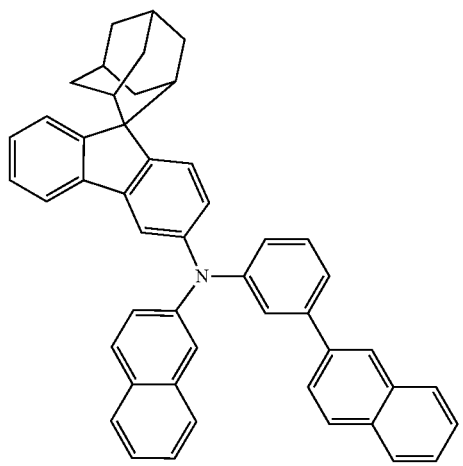
139
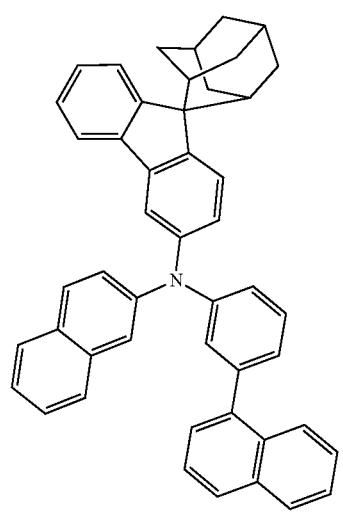
140
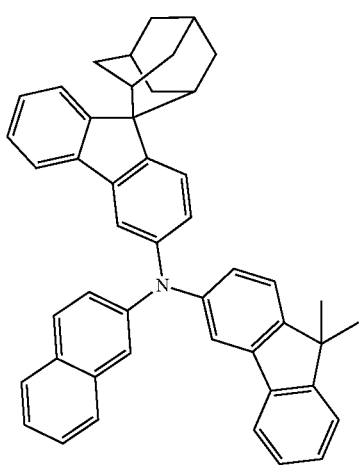
141
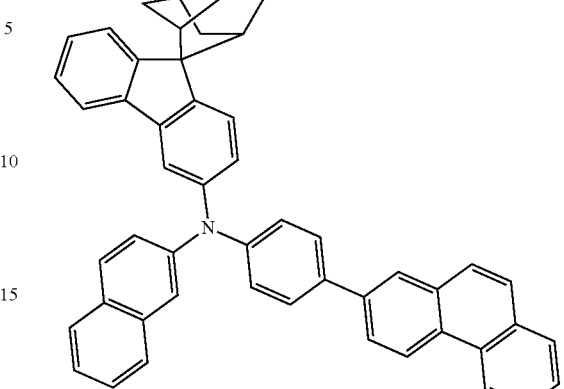
142
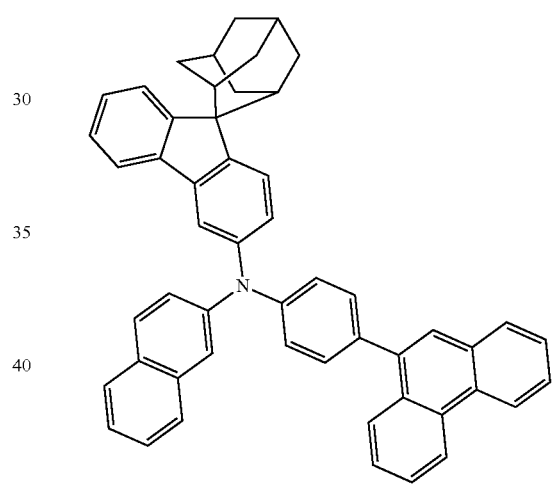
143
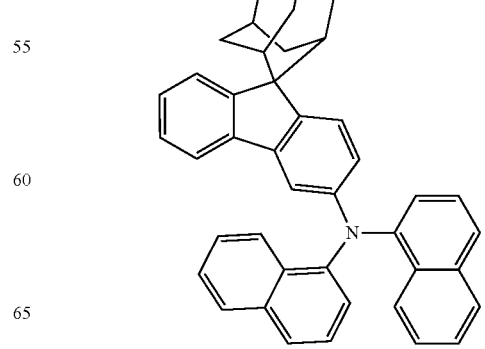

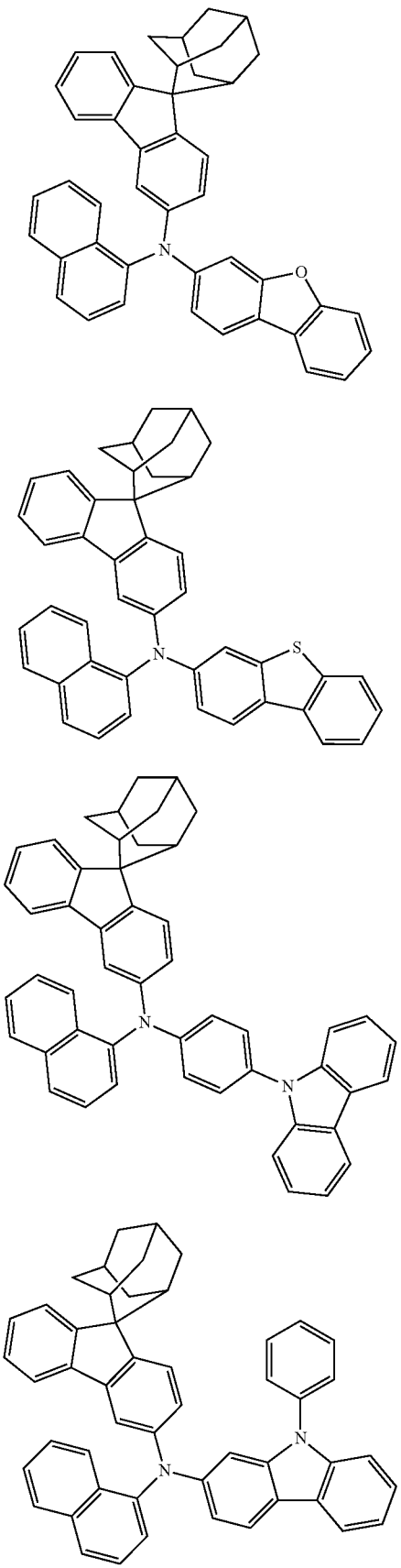
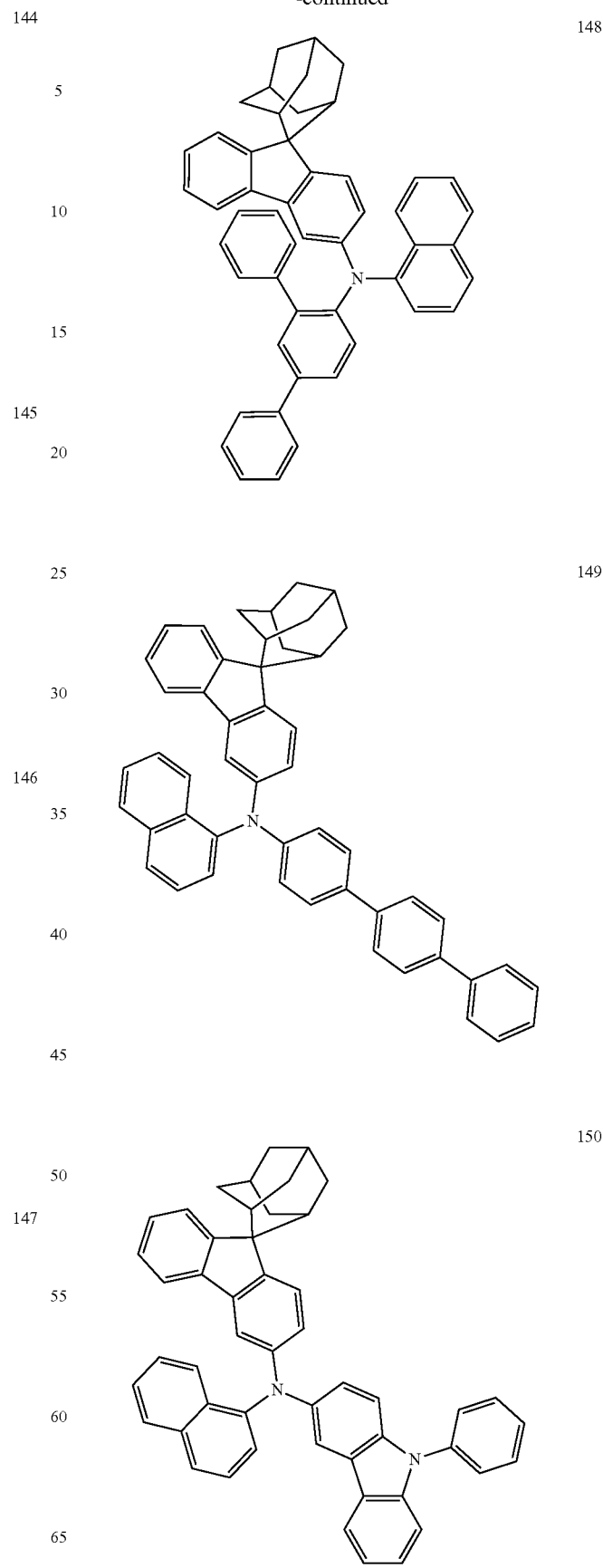

151 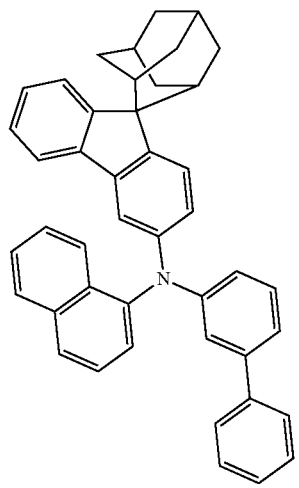
154 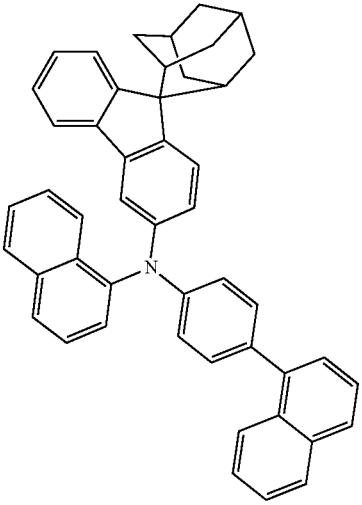
152 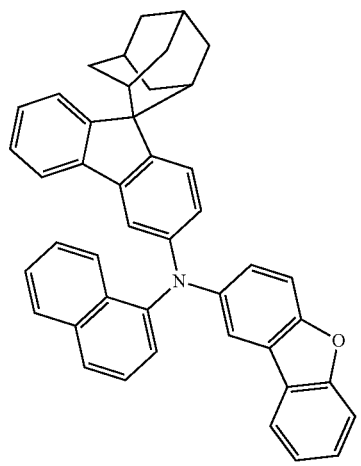
155 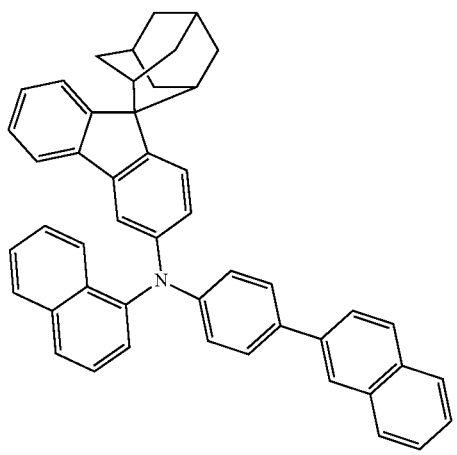
153 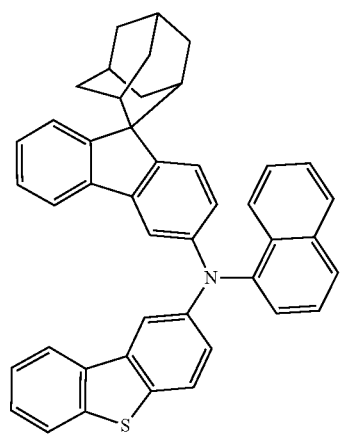
156 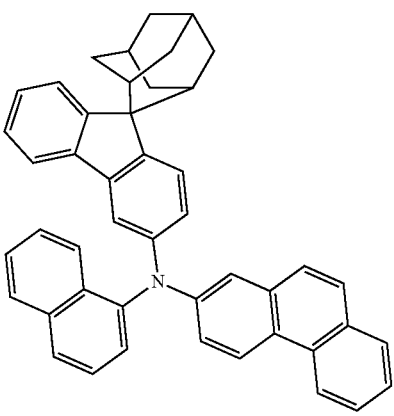

157
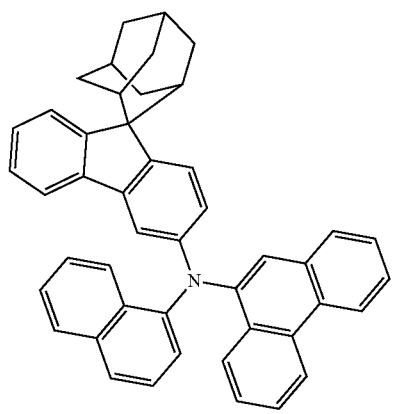
158
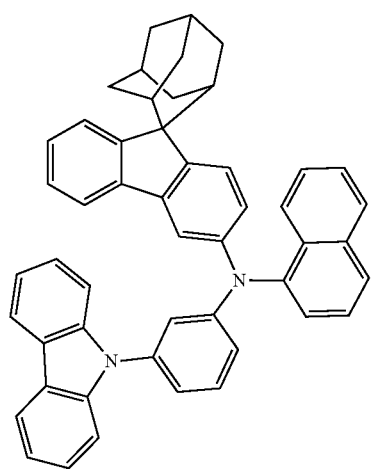
159
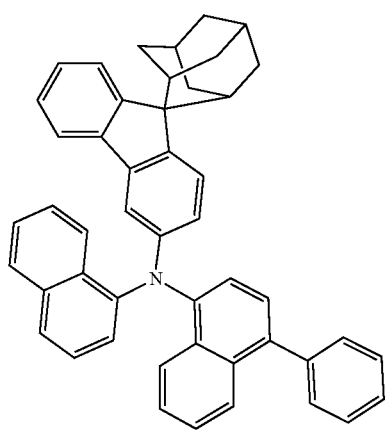
160
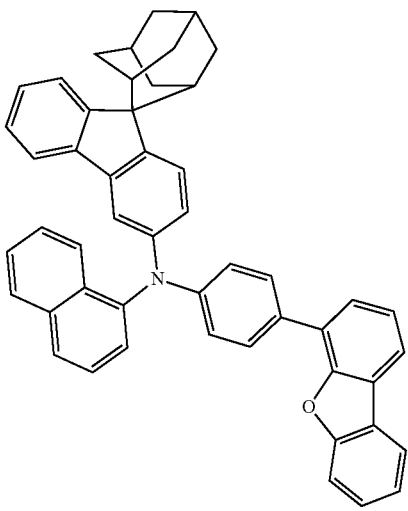
161
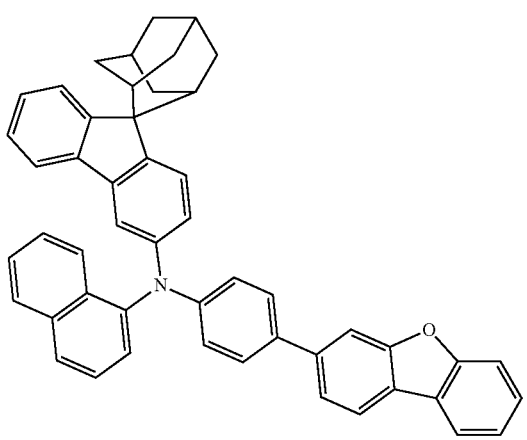
162
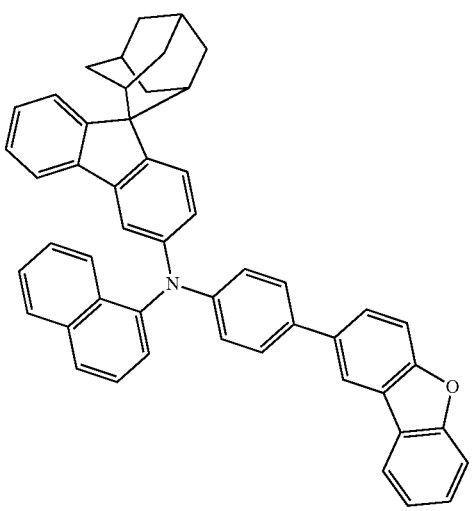

163 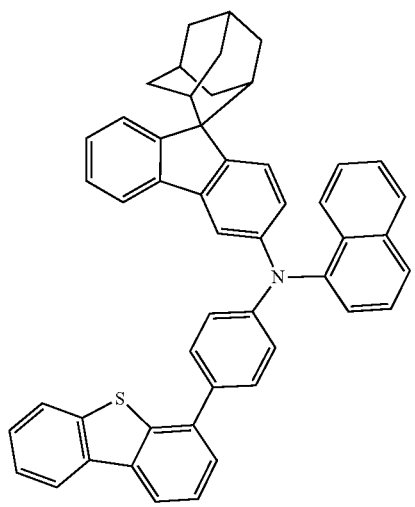
164 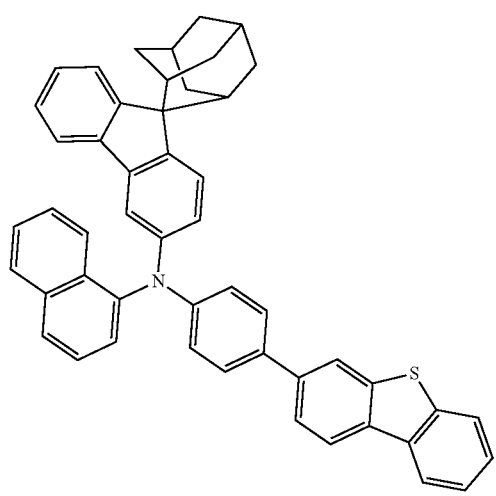
165 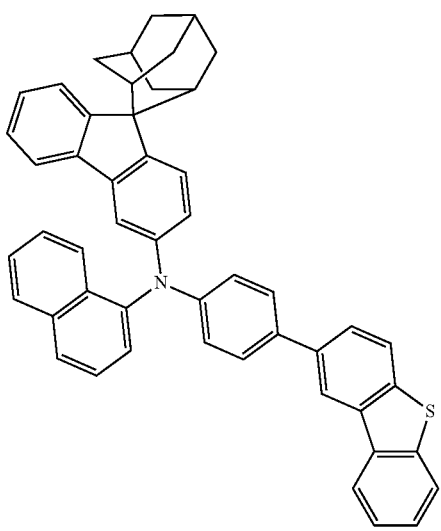
166 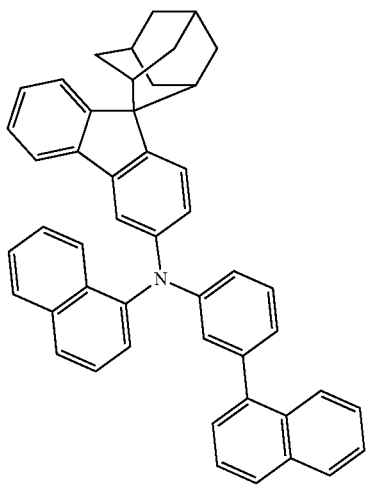
167 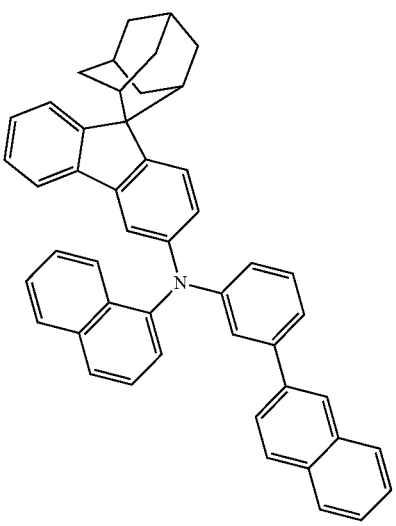
168 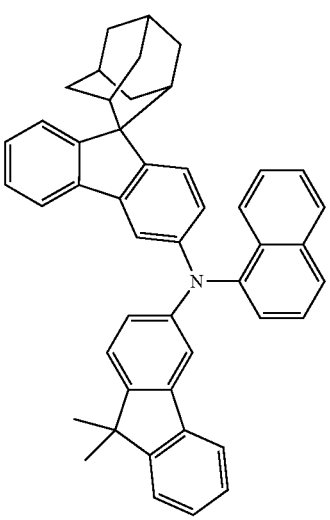

169
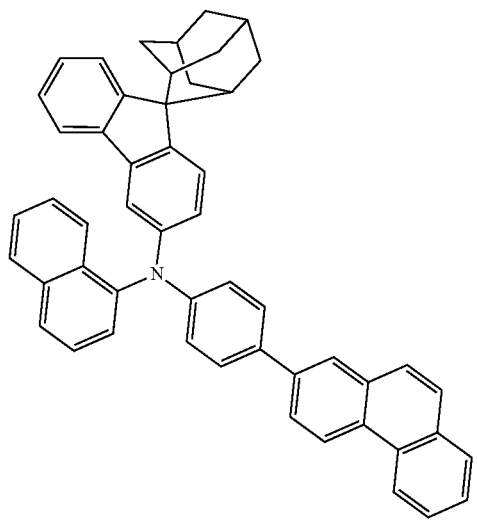
170
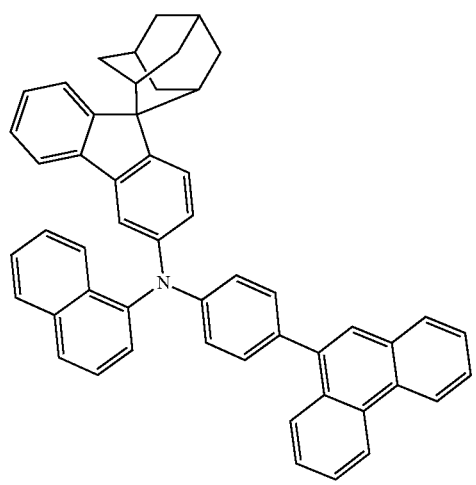
171
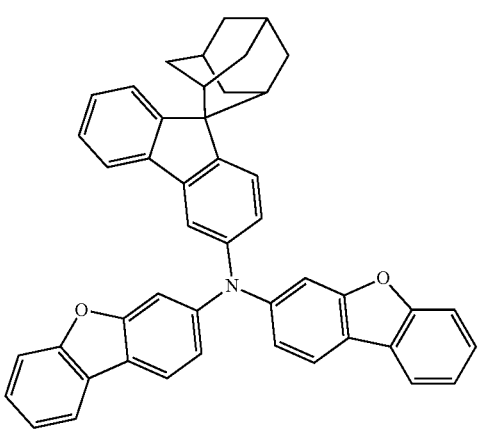
172
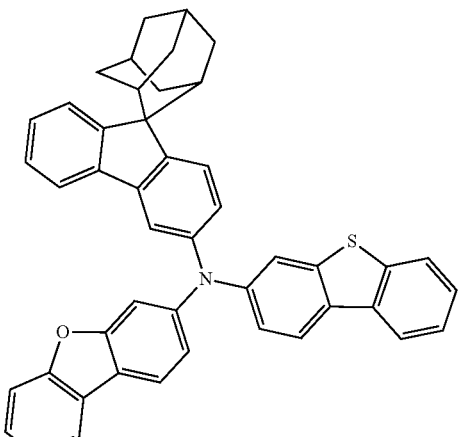
173
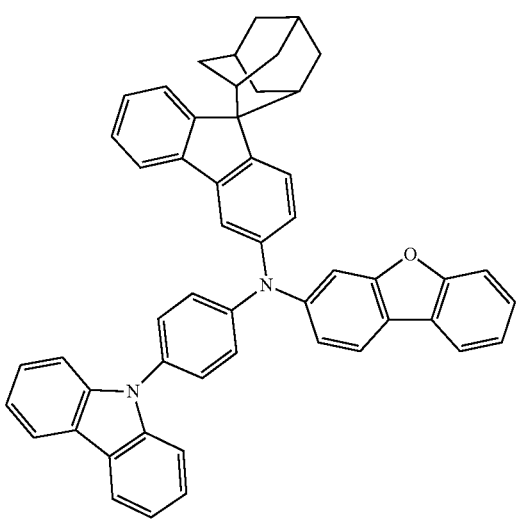
174
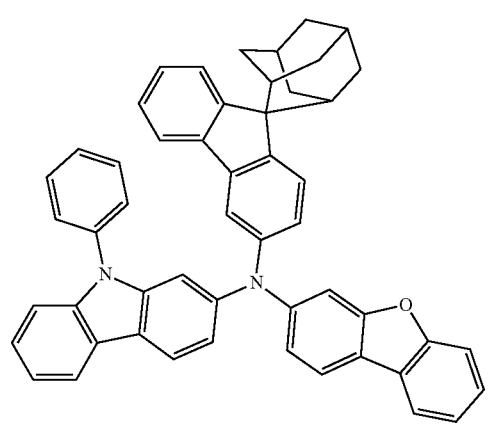

175
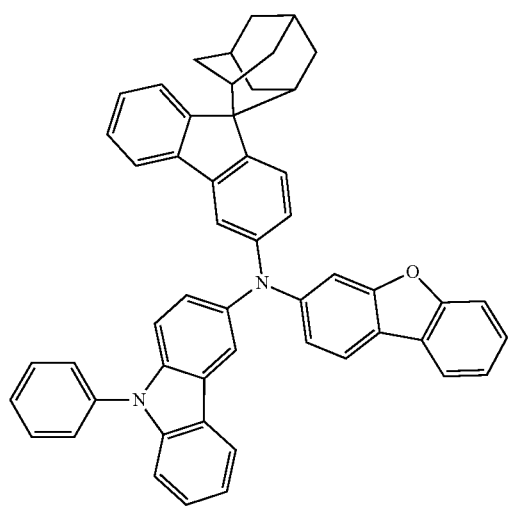
176
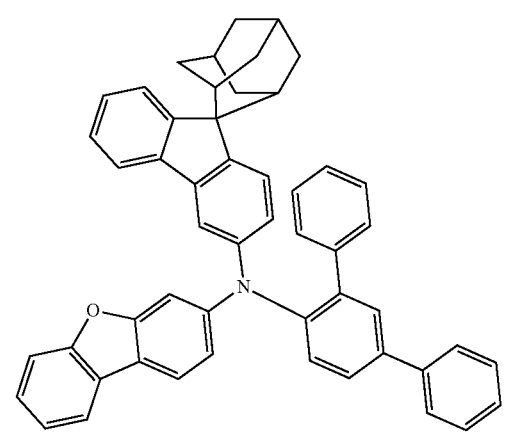
177
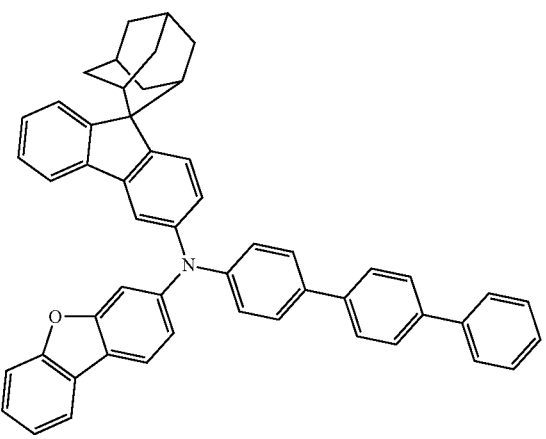
178
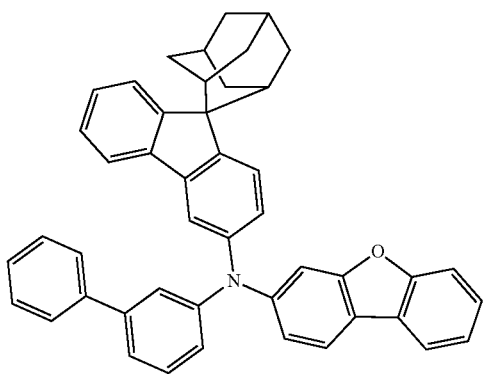
179
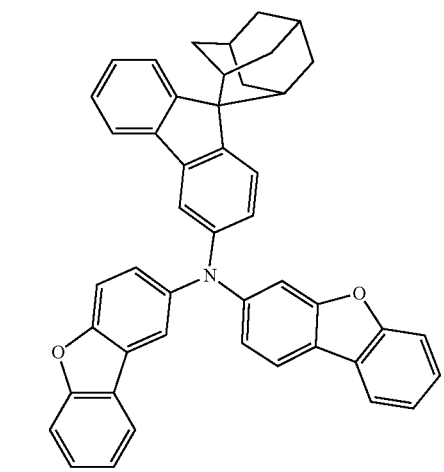
180
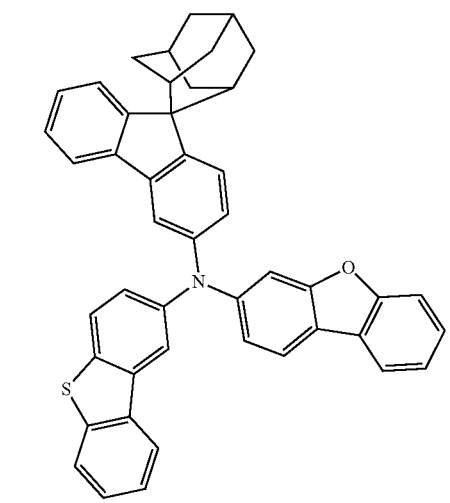

95
-continued
181
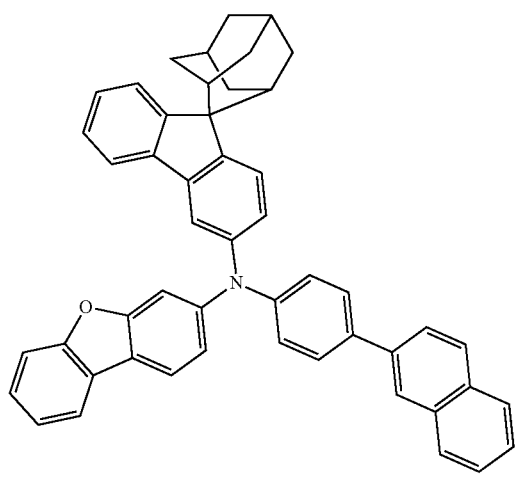
182
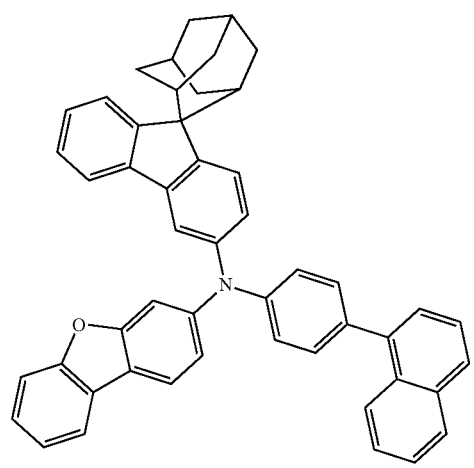
183
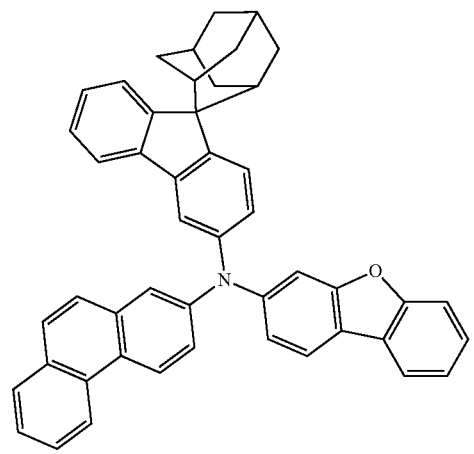
96
-continued
184
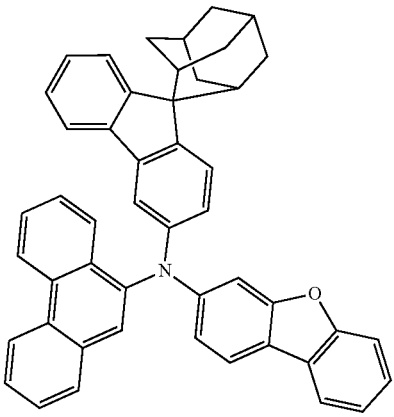
185
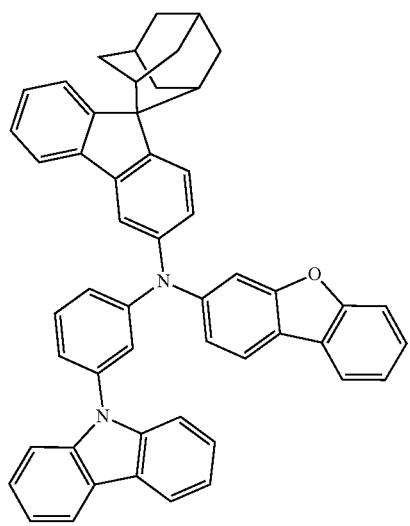
186
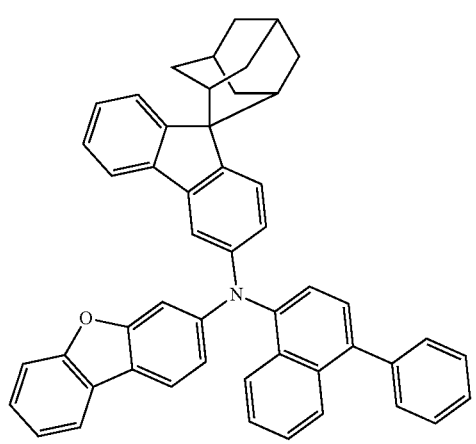

187
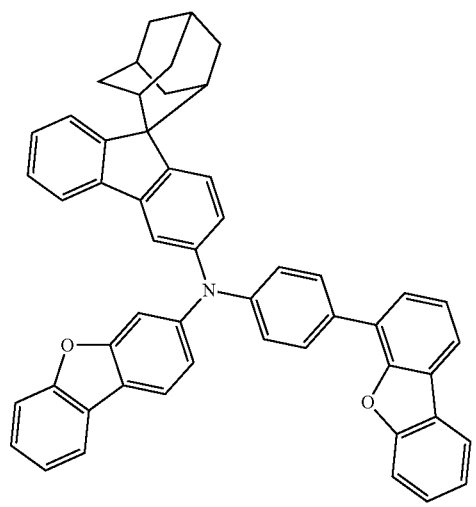
188
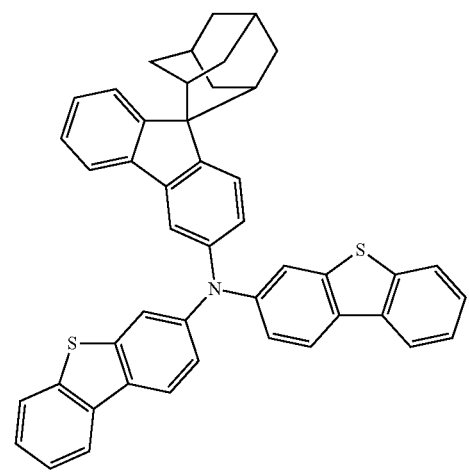
189
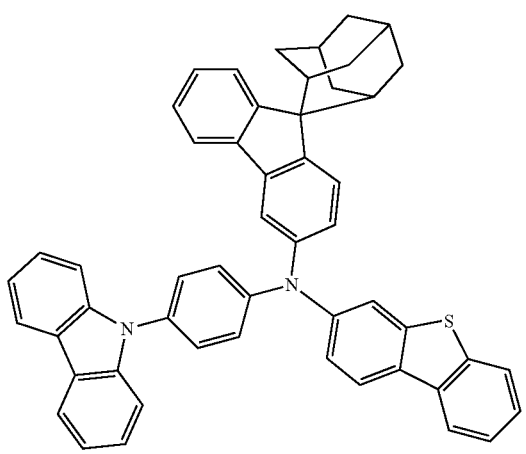
190
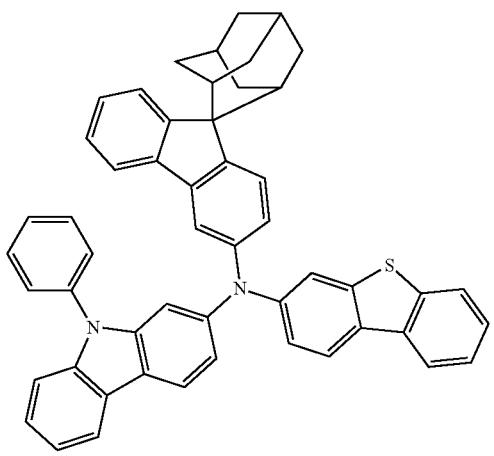
191
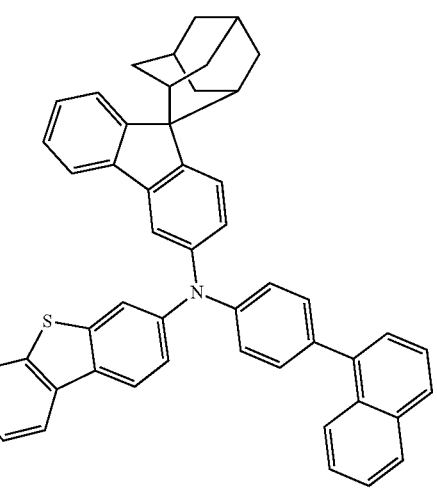
192
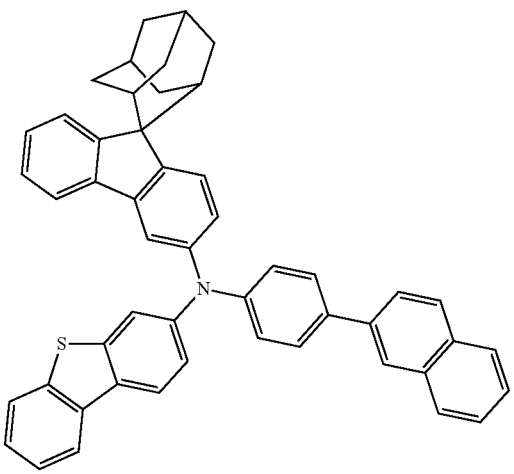

99
-continued
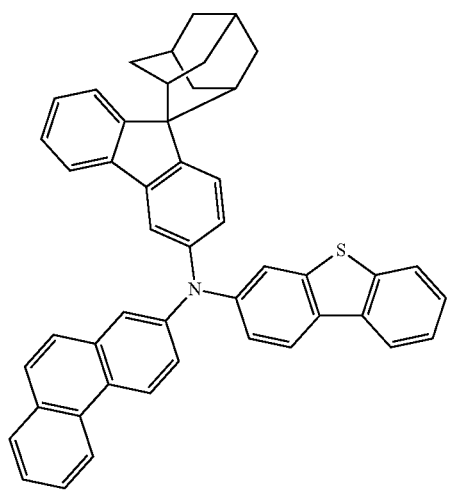
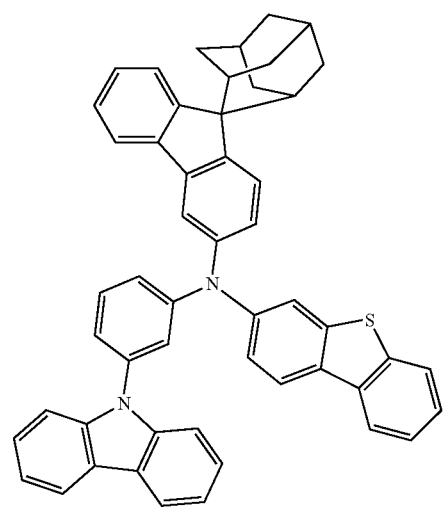
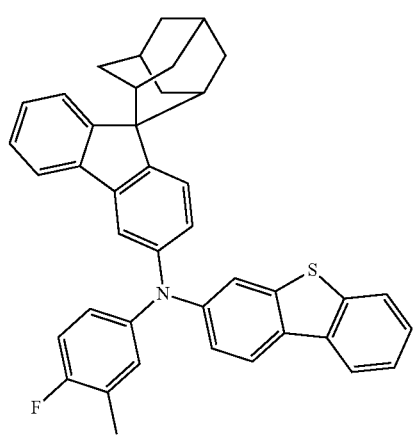
100
-continued
193
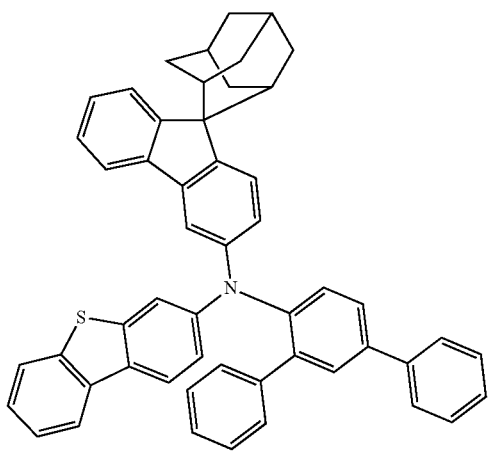
194
197
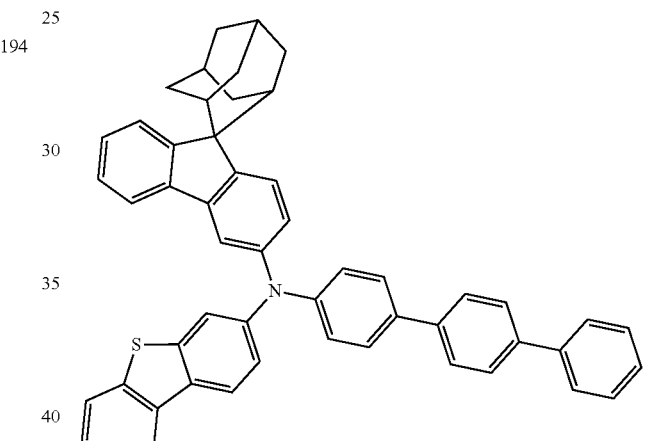
195
198
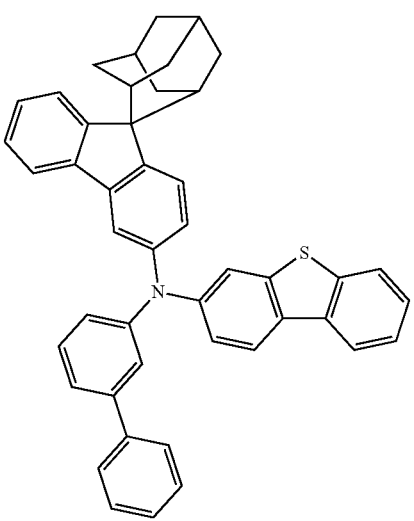

101
-continued
199
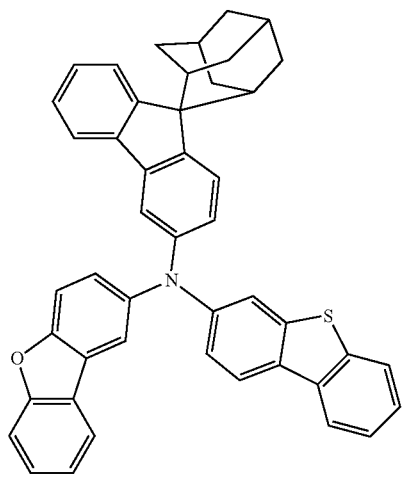
200
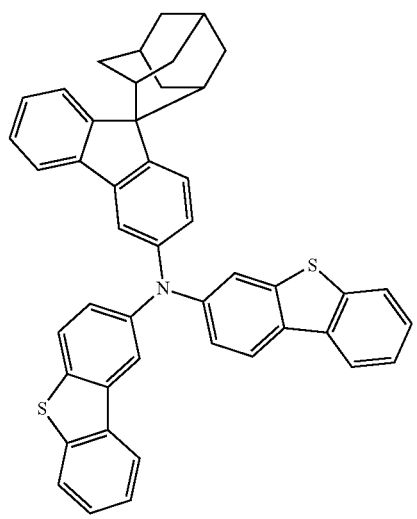
201
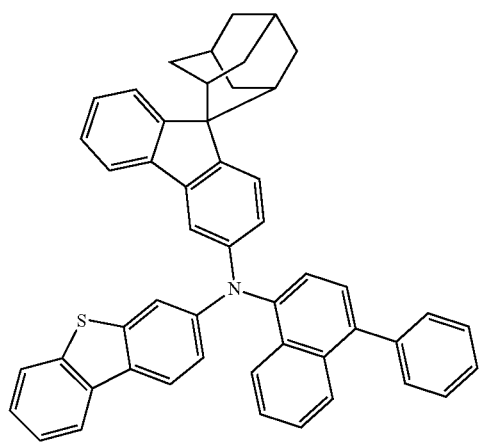
102
-continued
202
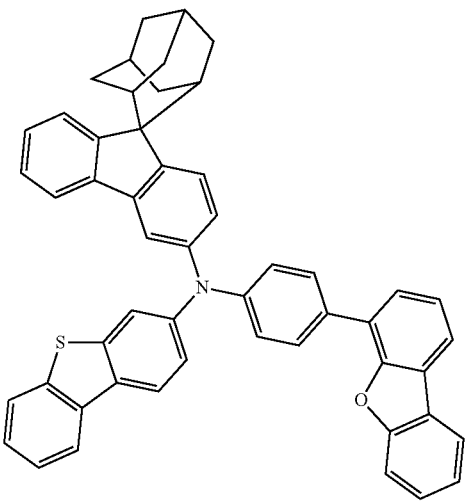
203
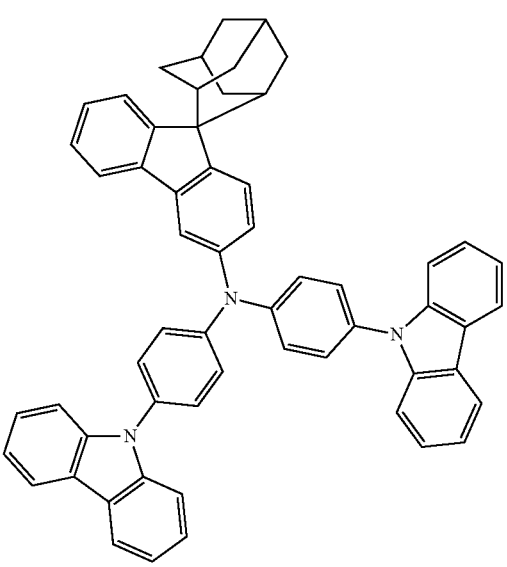
204
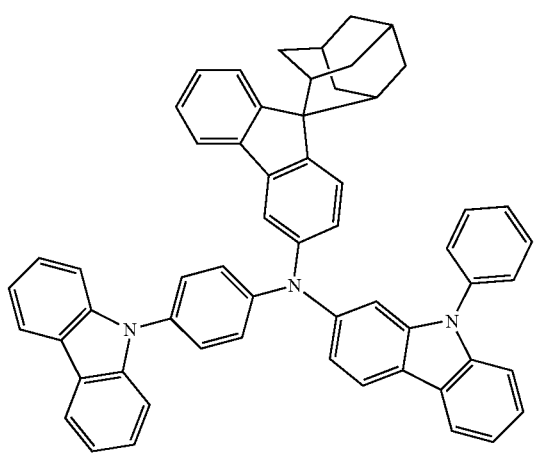

205
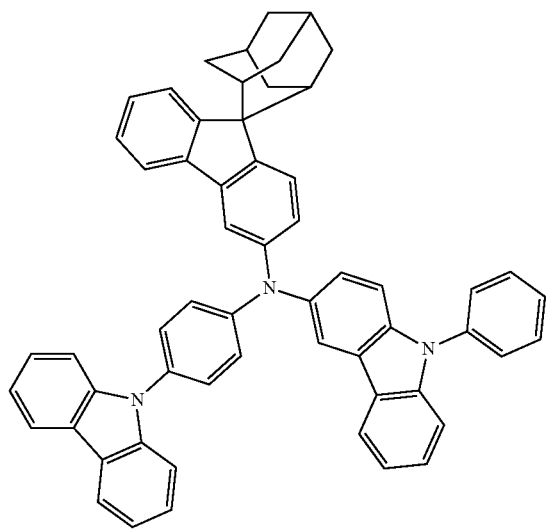
206
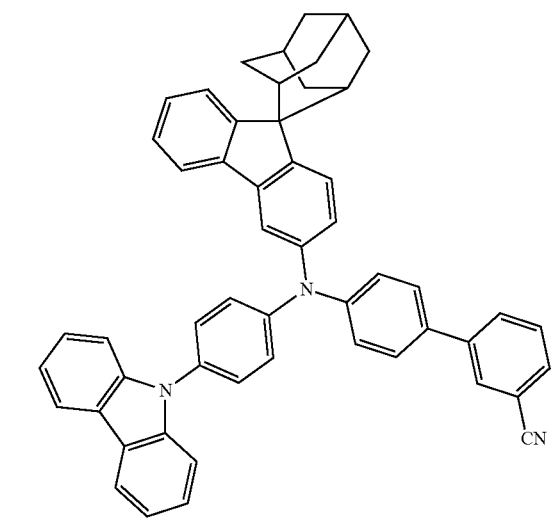
207
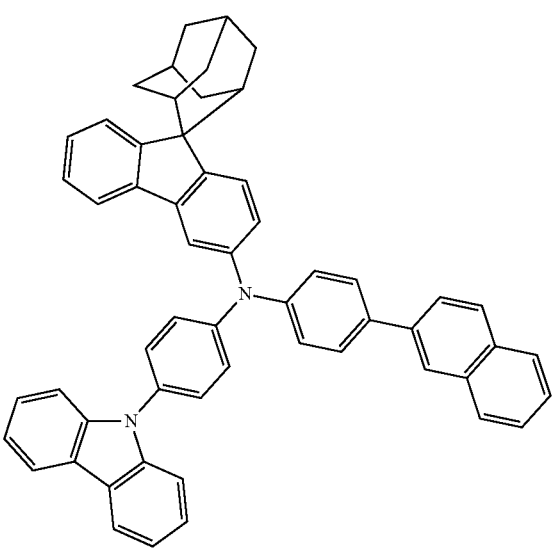
208
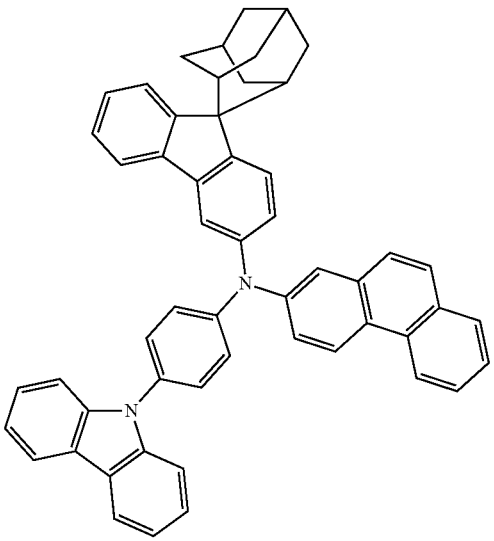
209
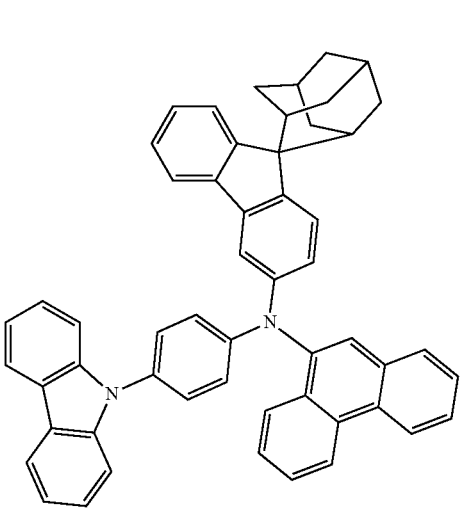
210
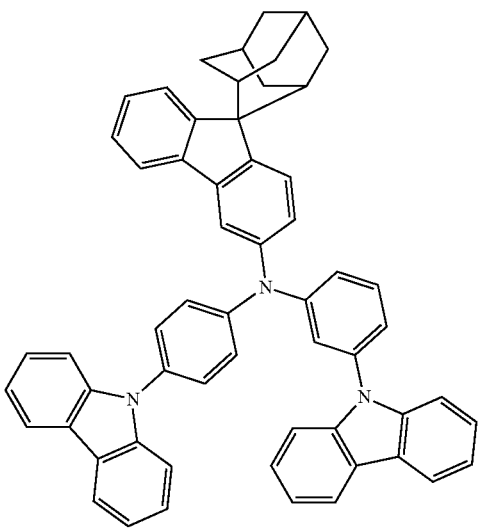

211
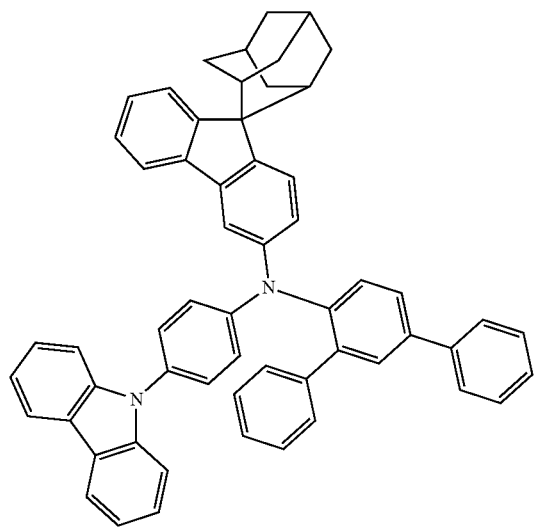
212
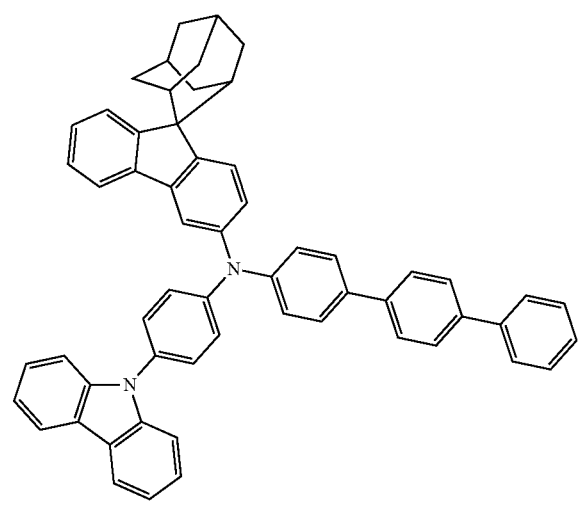
213
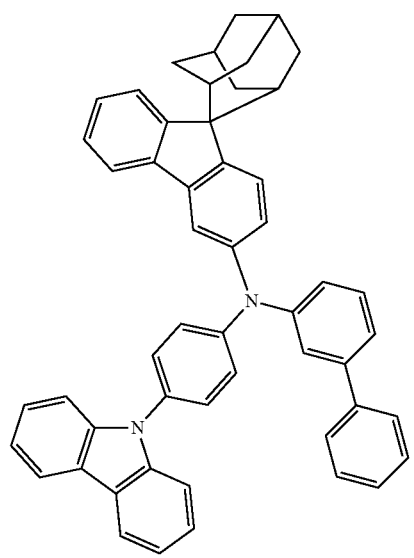
214
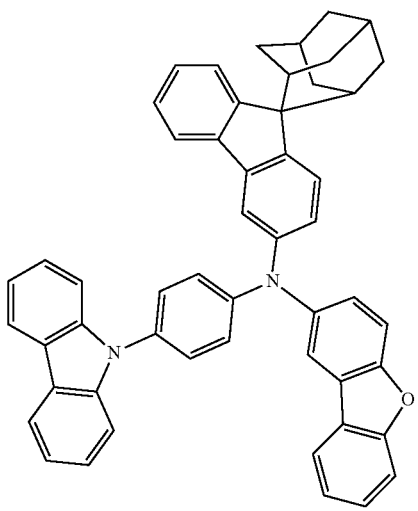
215
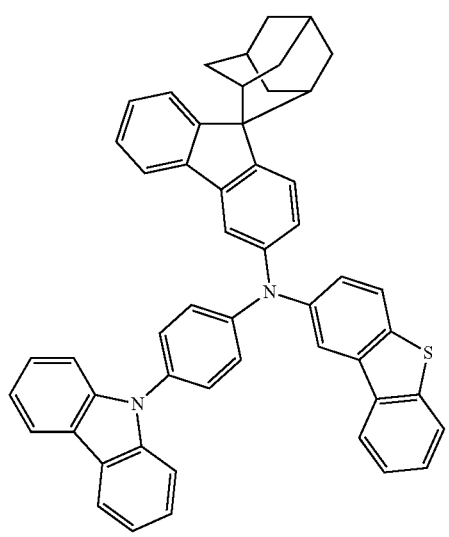
216
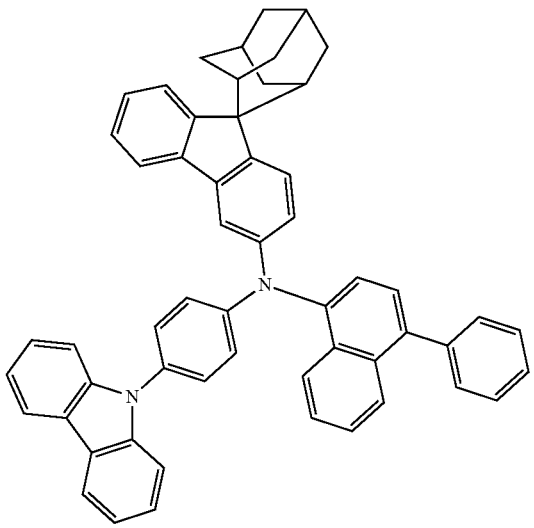

217
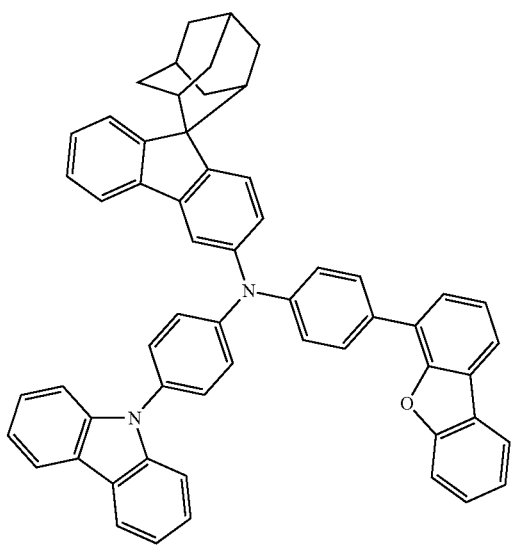
220
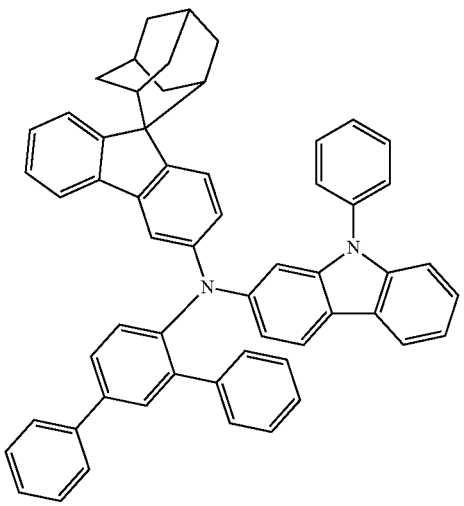
218
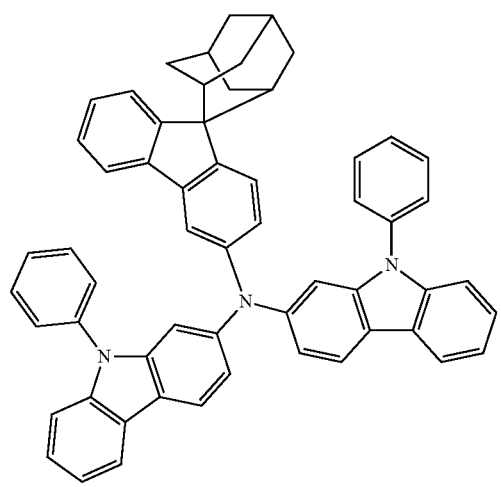
221
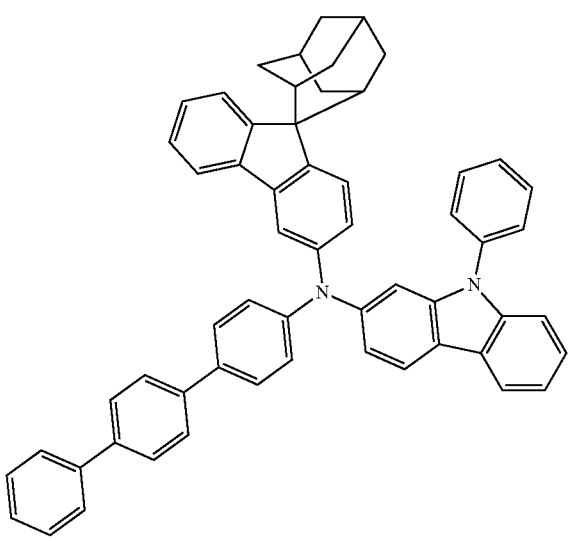
219
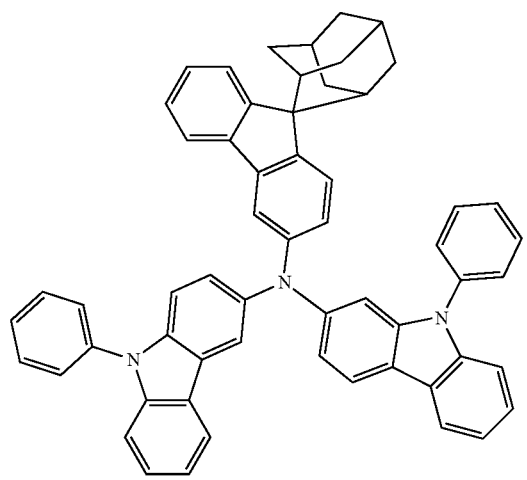
222
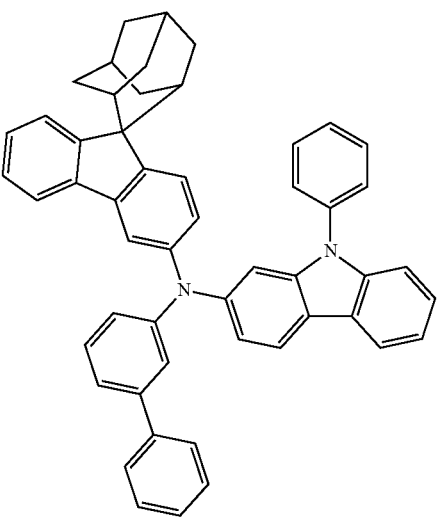

223
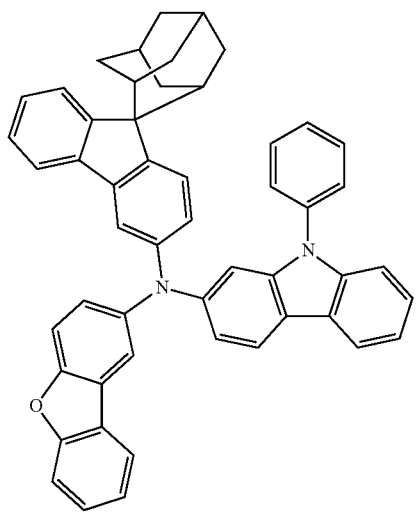
224
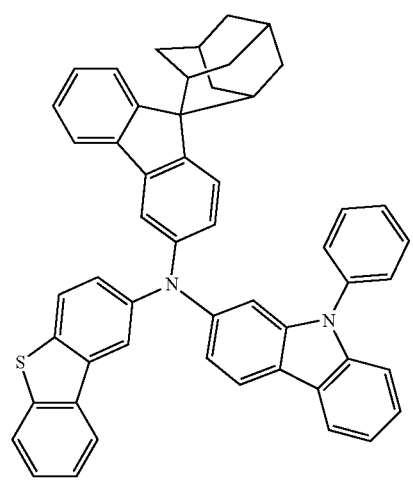
225
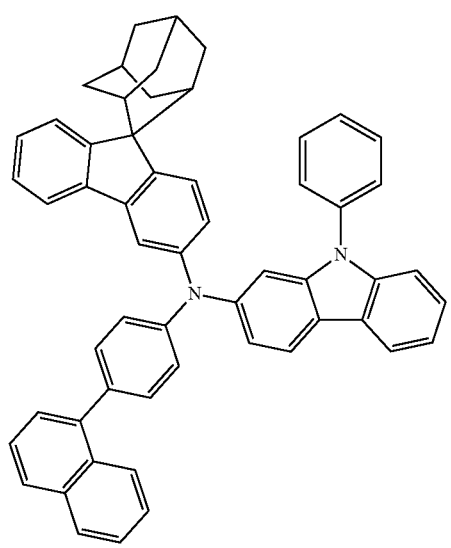
226
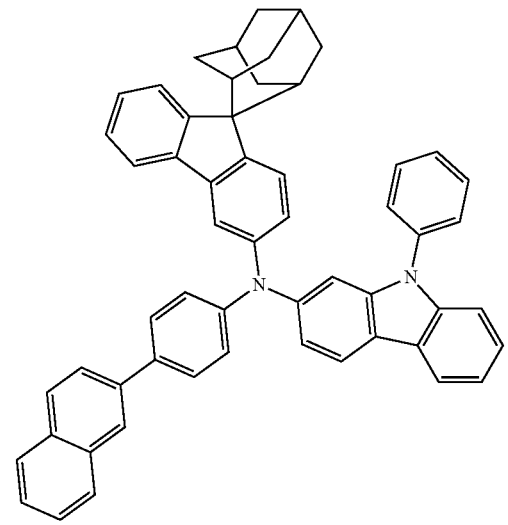
227
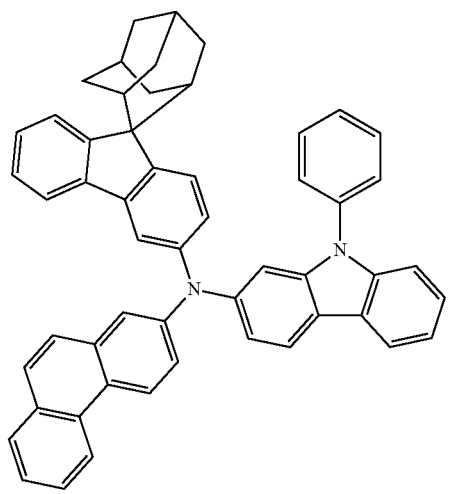
228
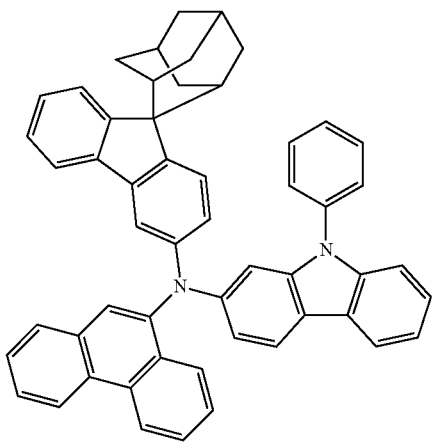

229 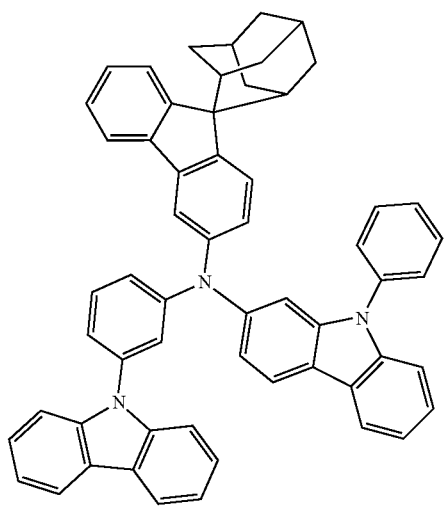
230 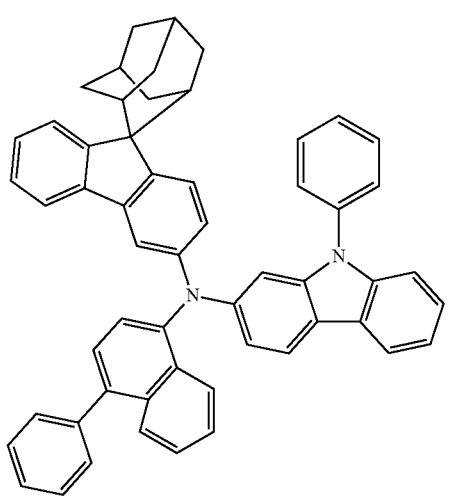
231 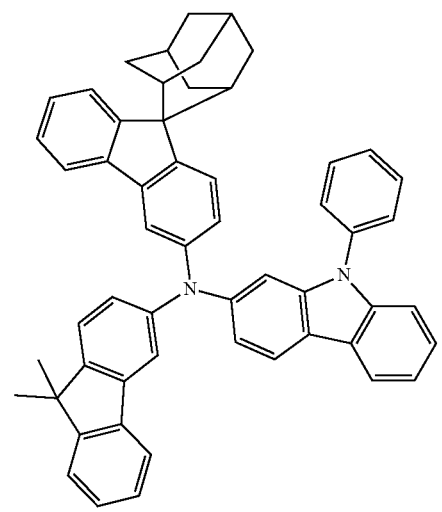
232 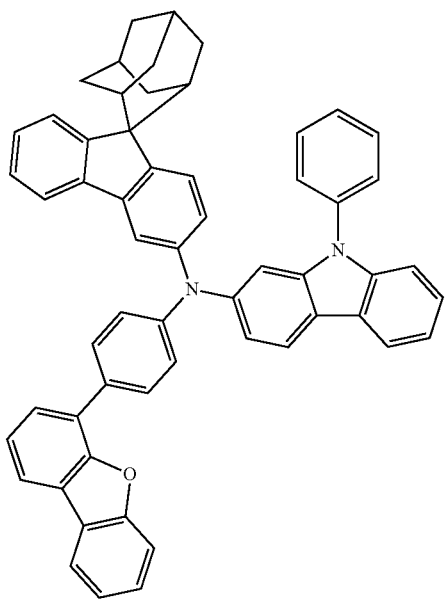
233 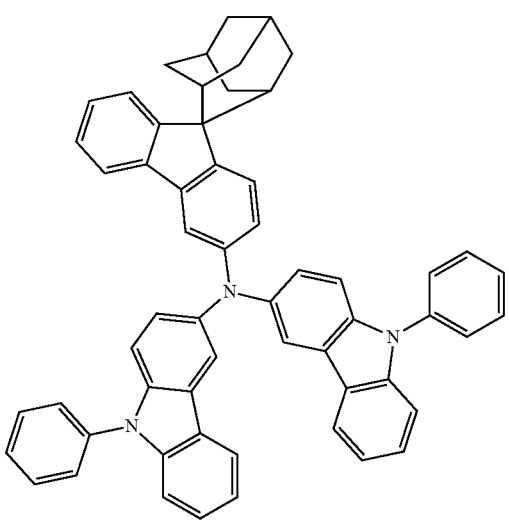
234 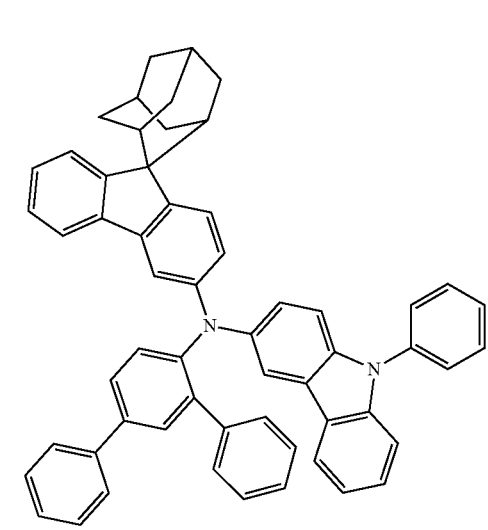

235
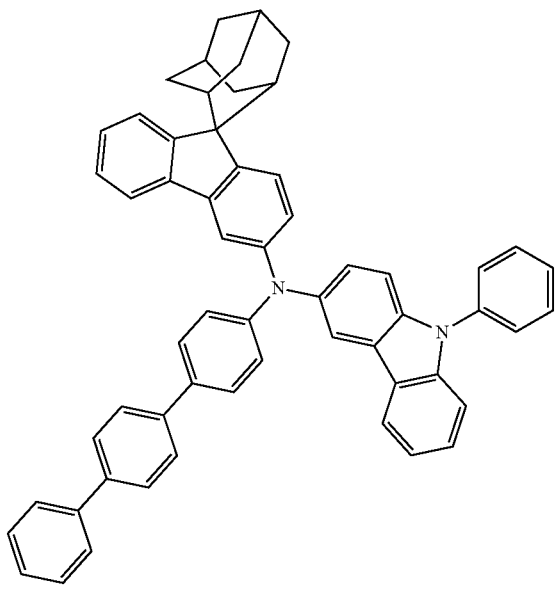
236
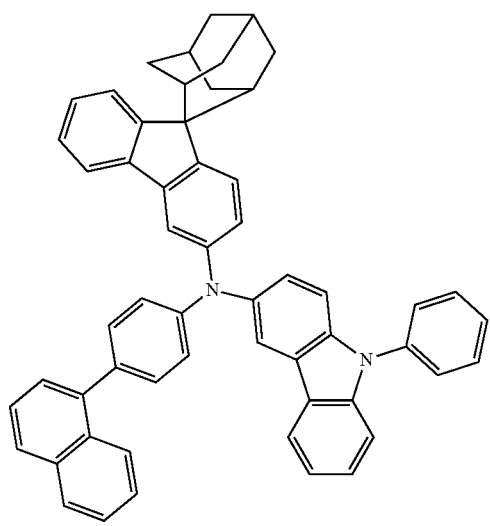
237
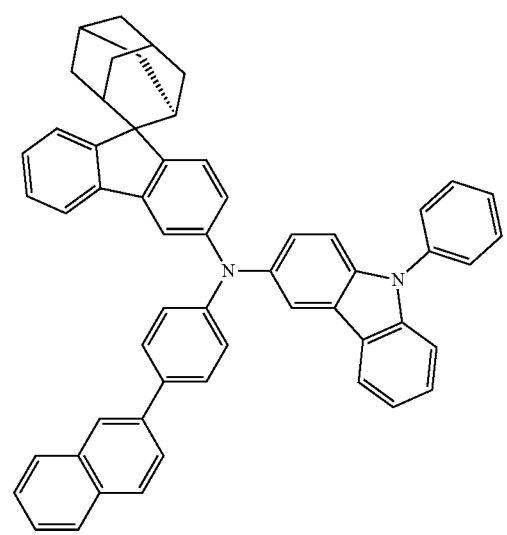
238
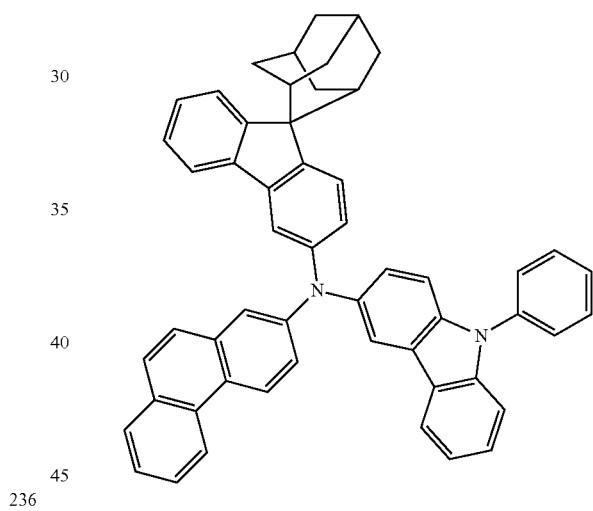
239
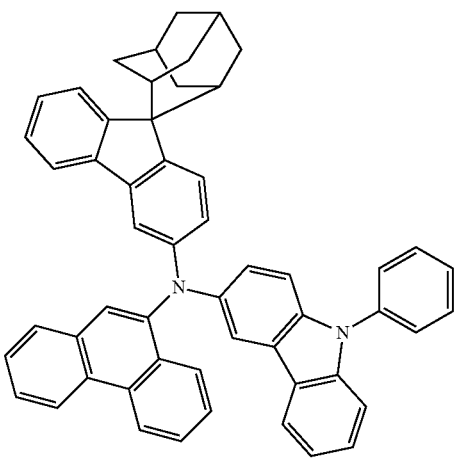

240
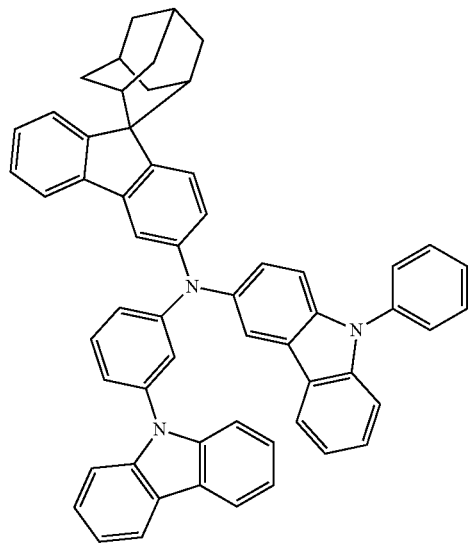
241
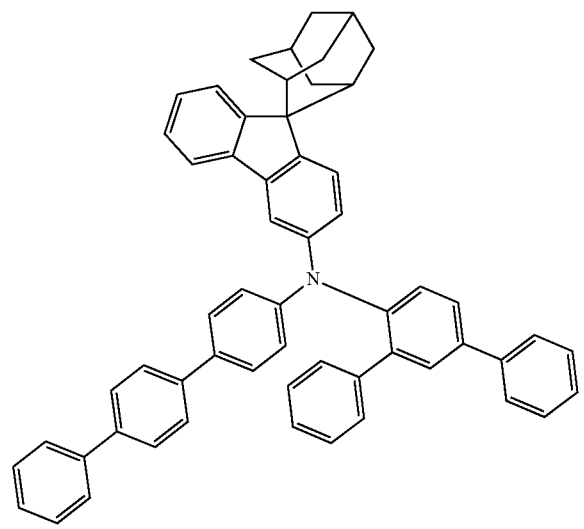
242
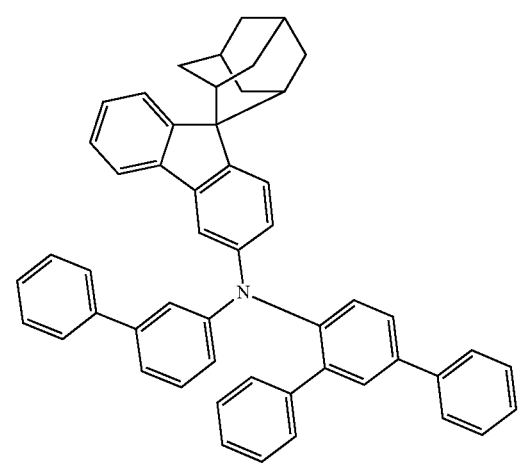
243
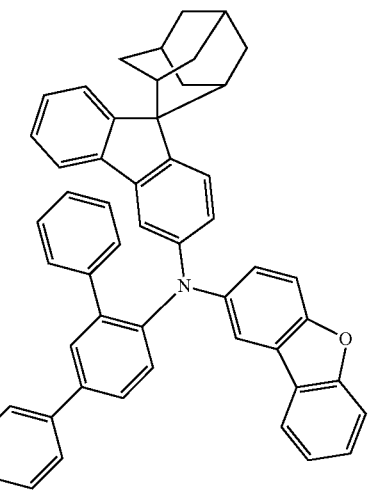
244
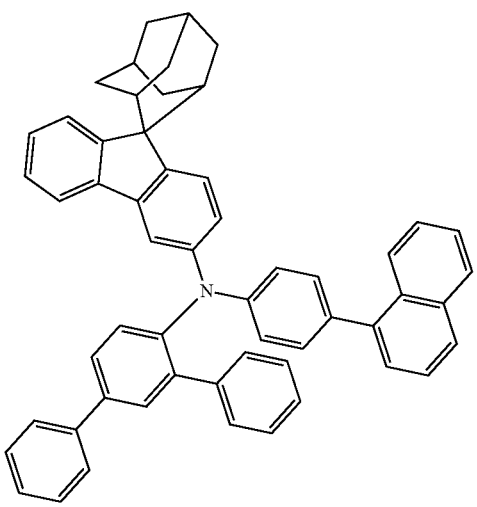
245
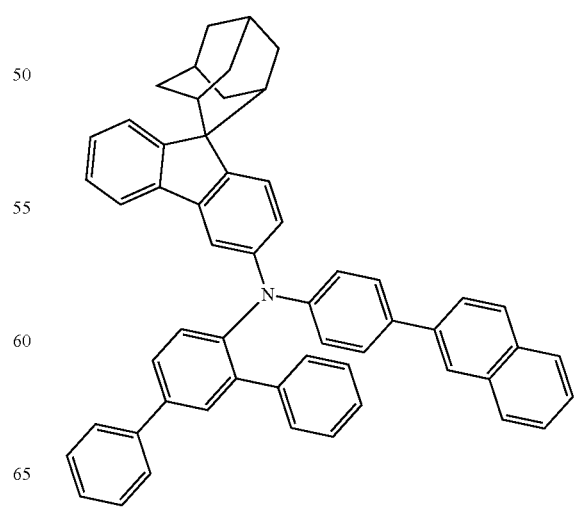

246
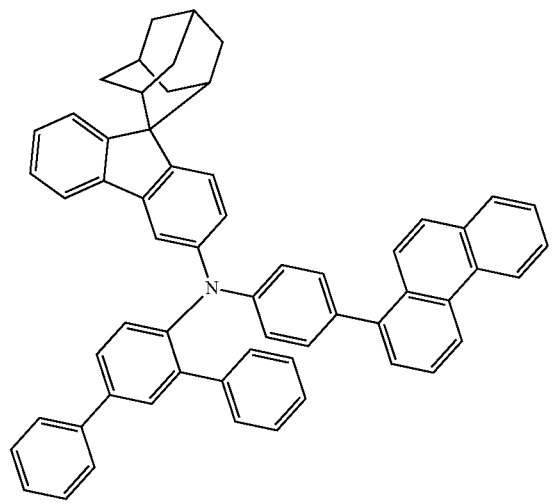
247
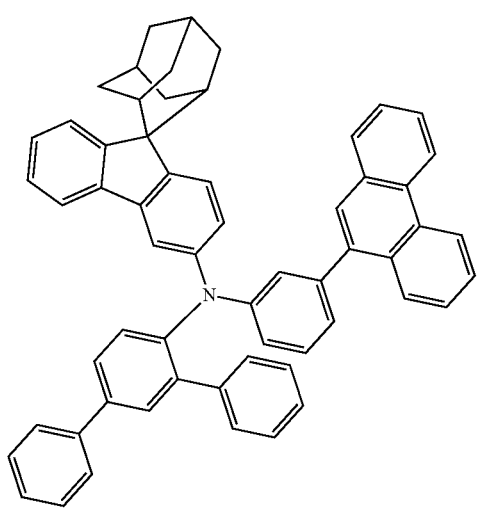
248
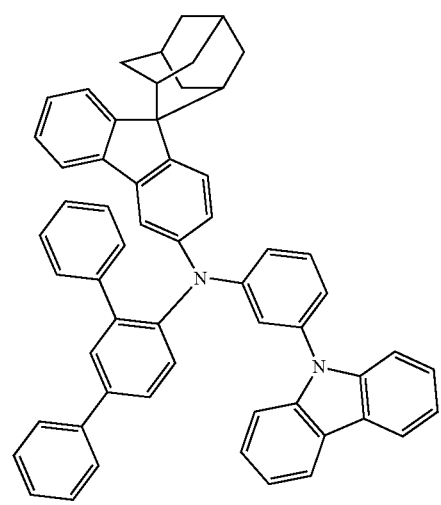
249
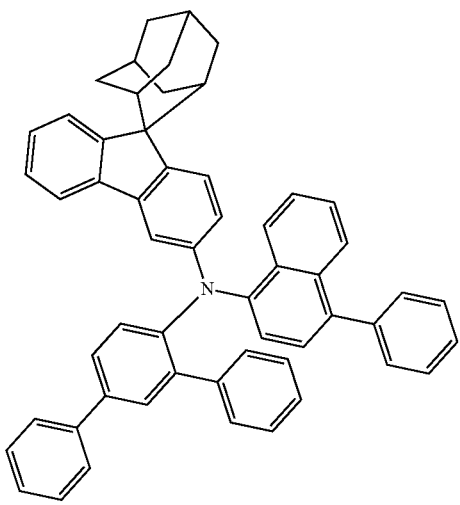
250
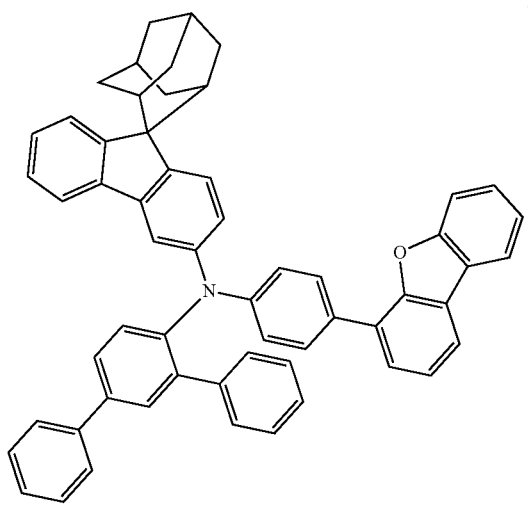
251
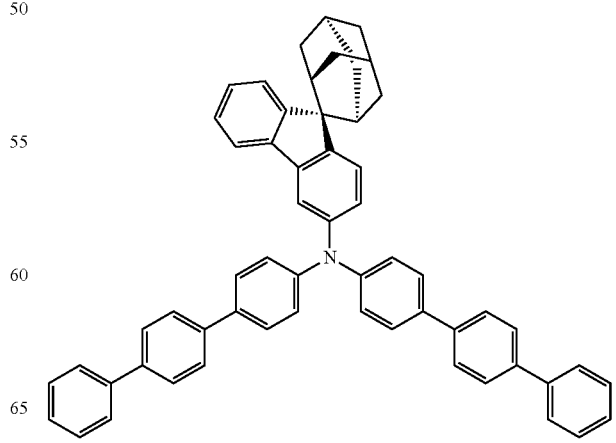

252
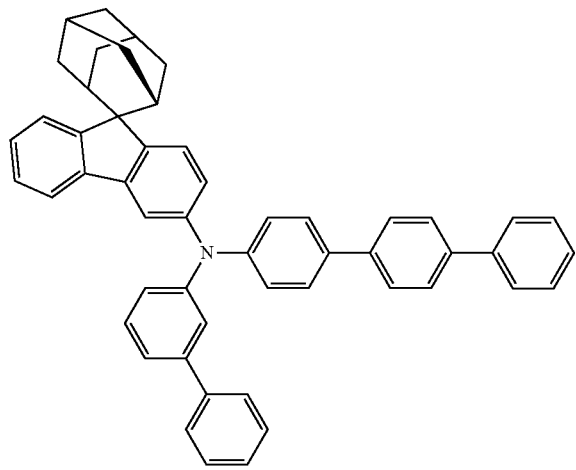
253
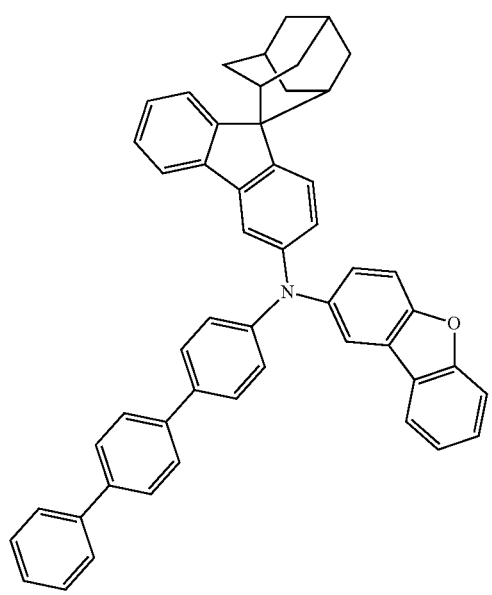
254
255
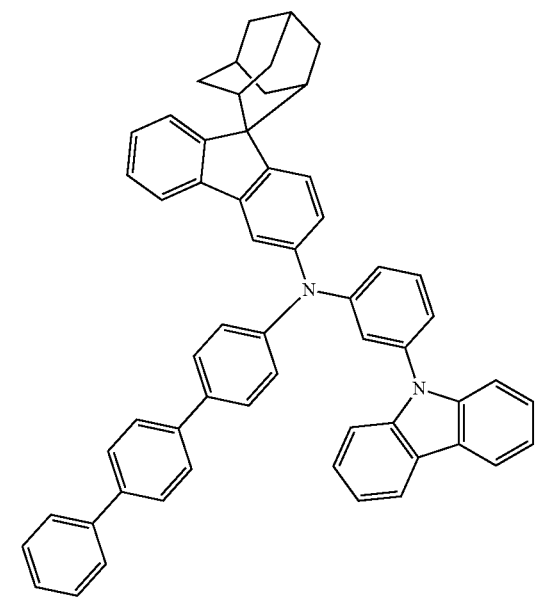
256
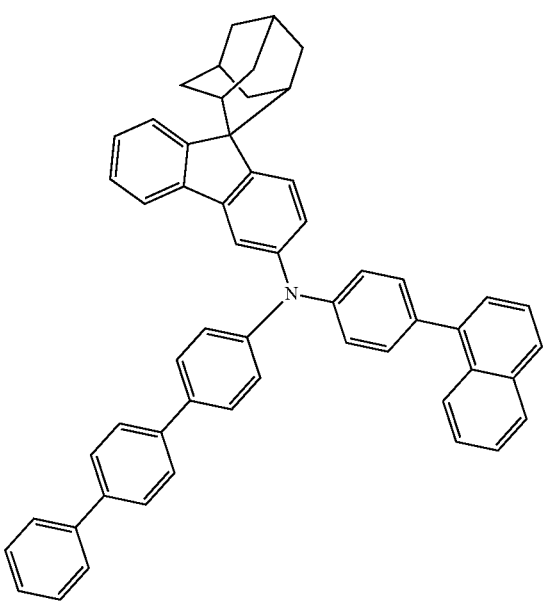

257
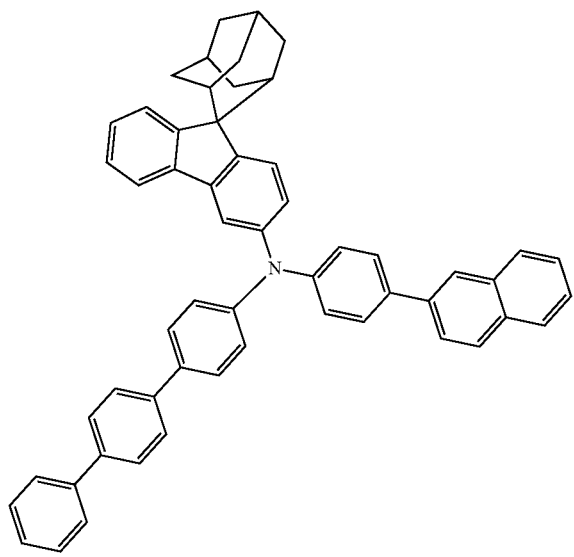
258
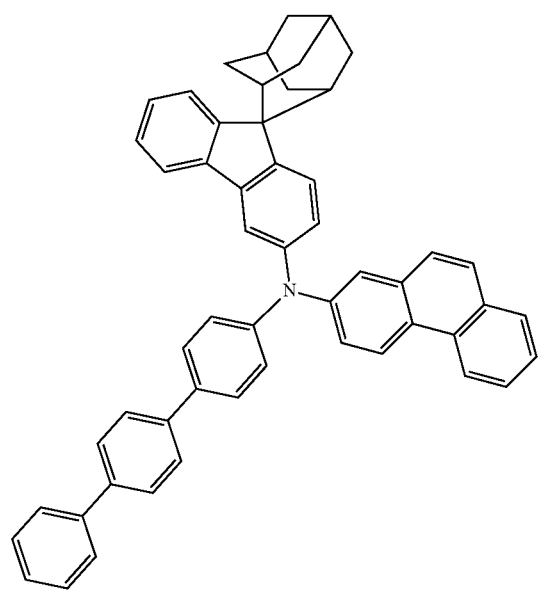
259
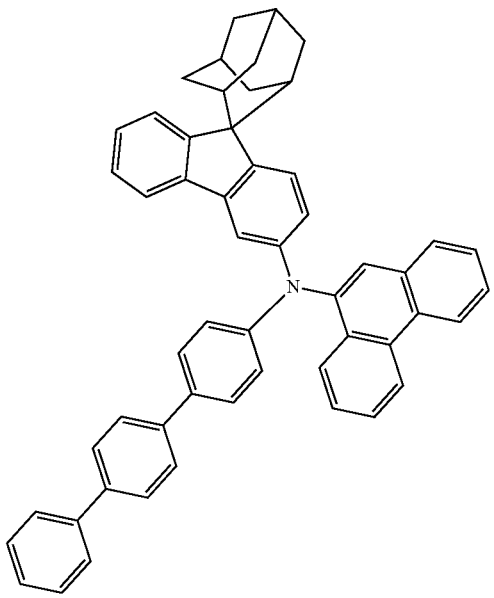
260
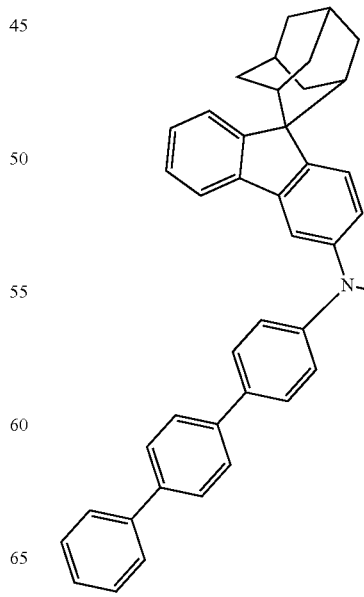

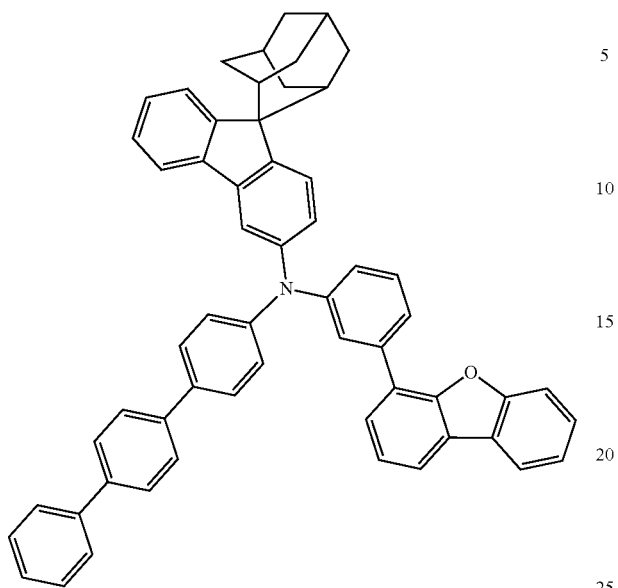
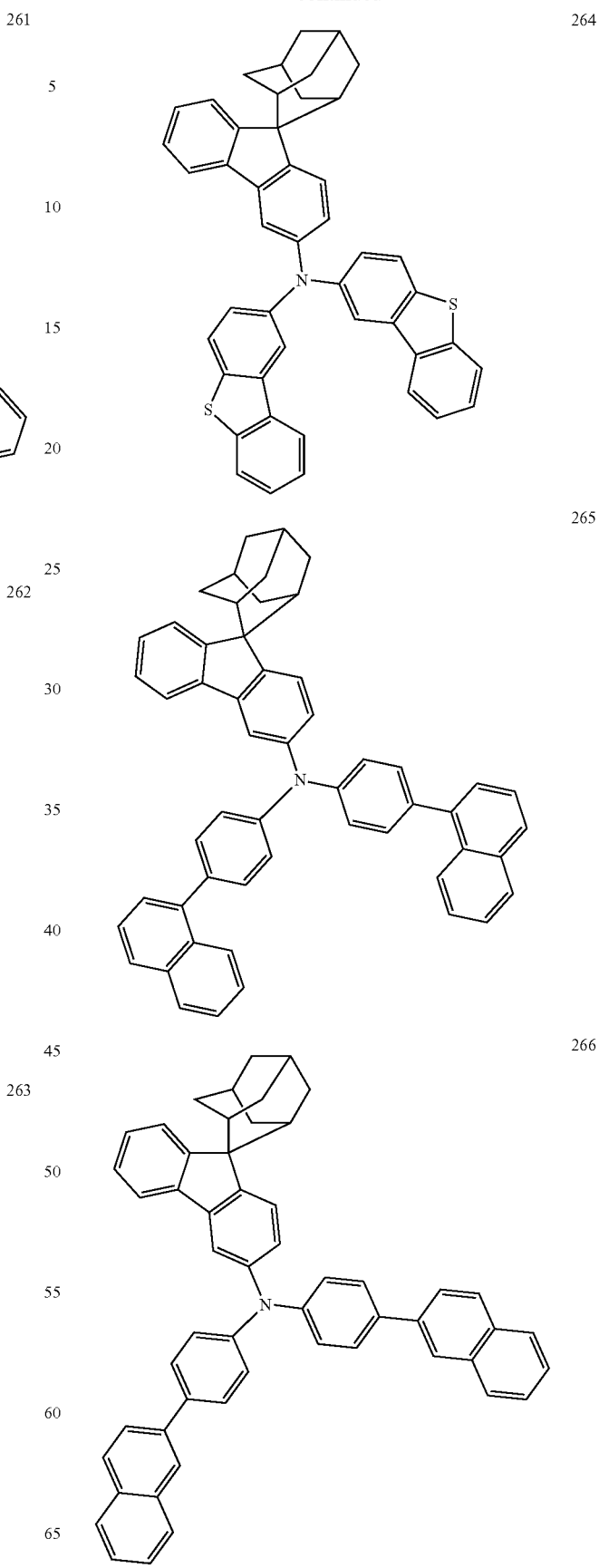

125
-continued
267
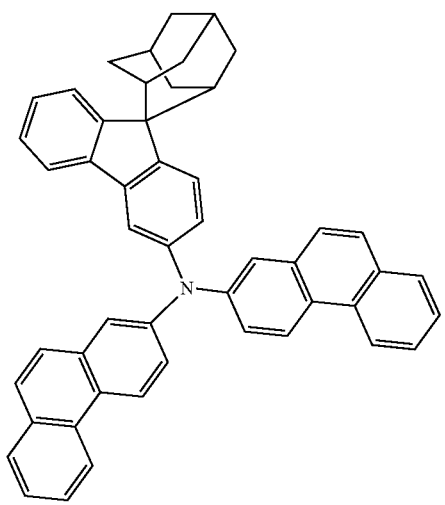
268
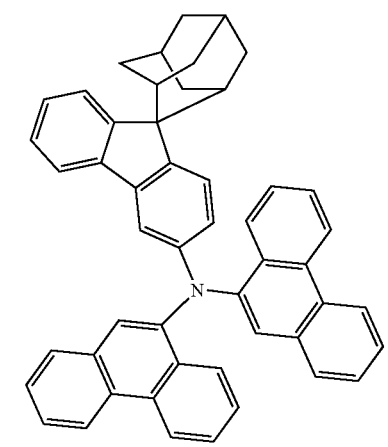
269
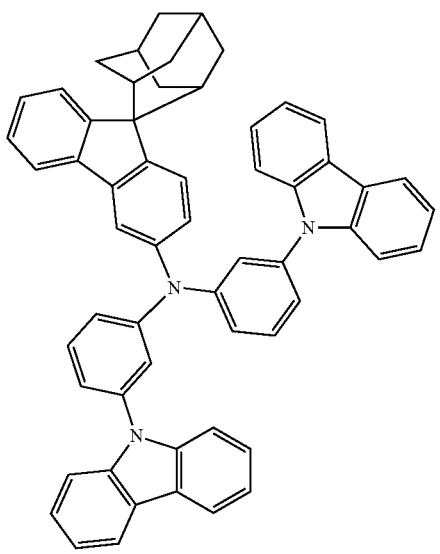
126
-continued
270
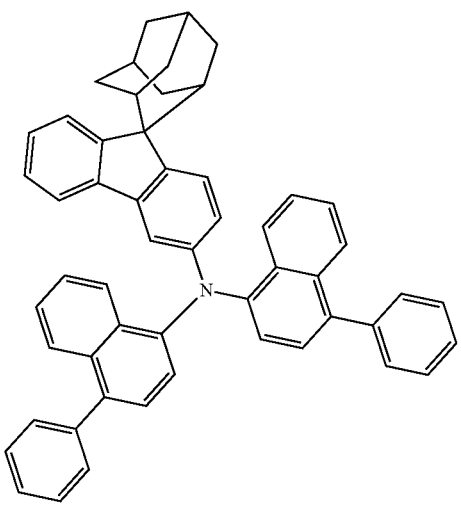
271
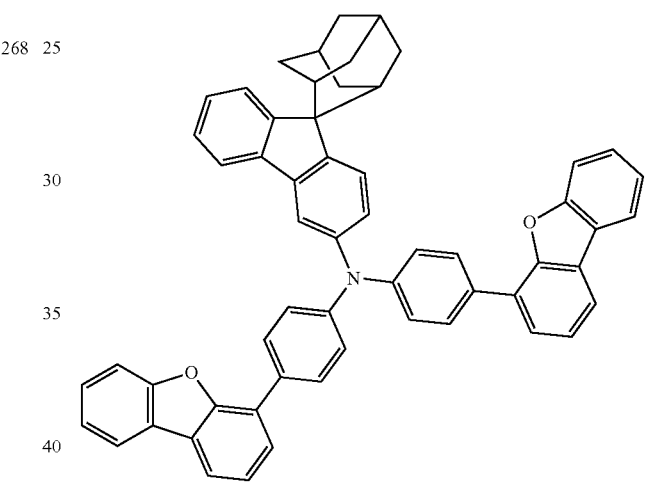
272

273
-continued
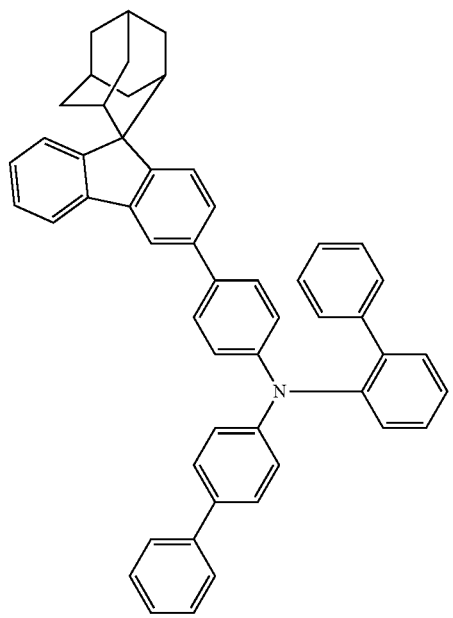
274
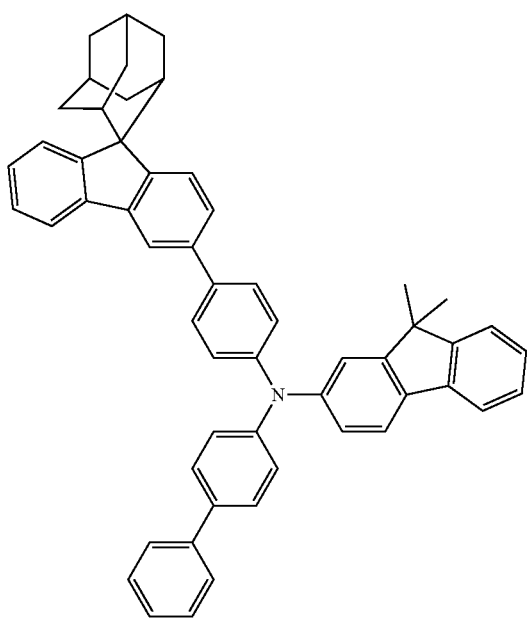
275
-continued
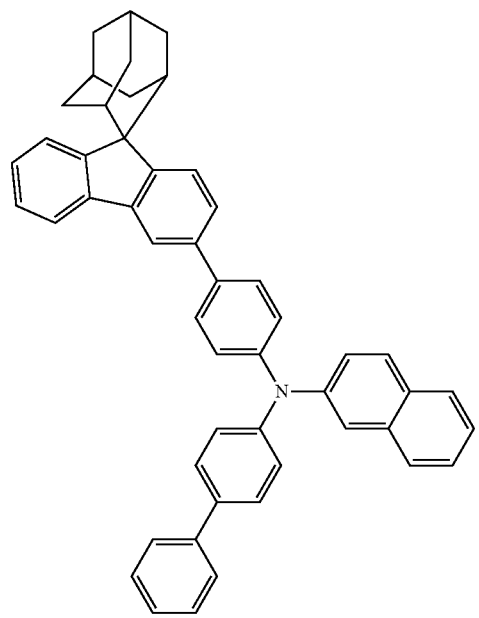
276
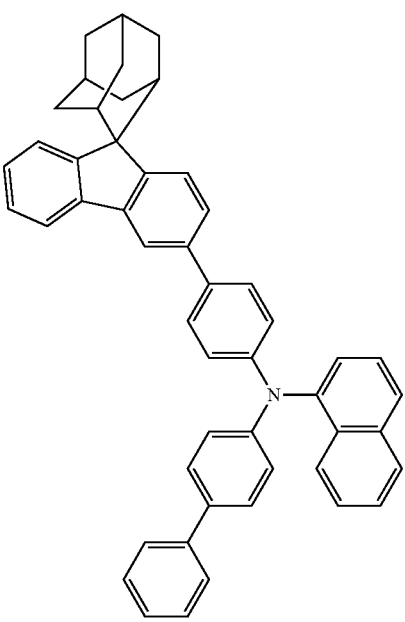

277
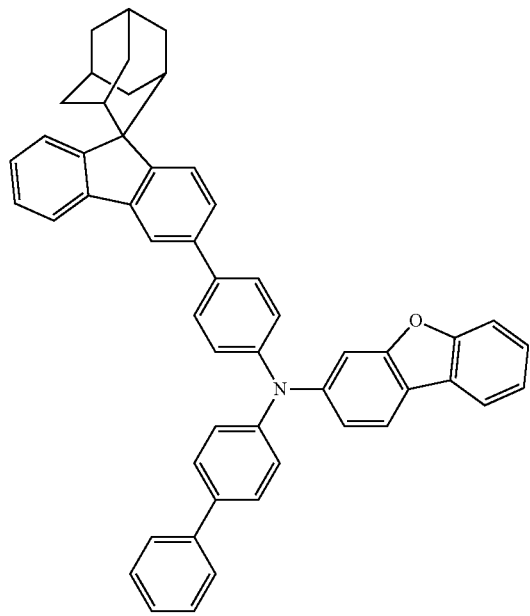
279
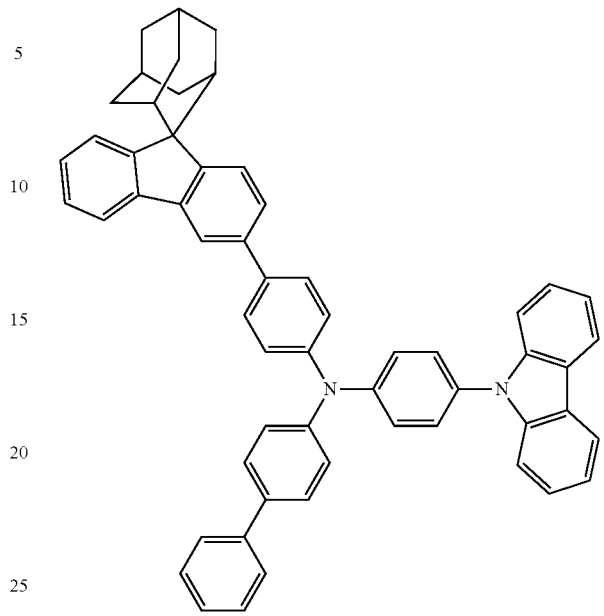
278
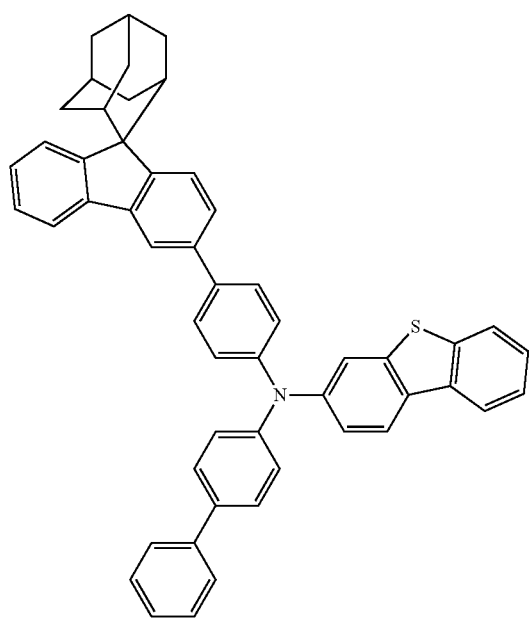
280
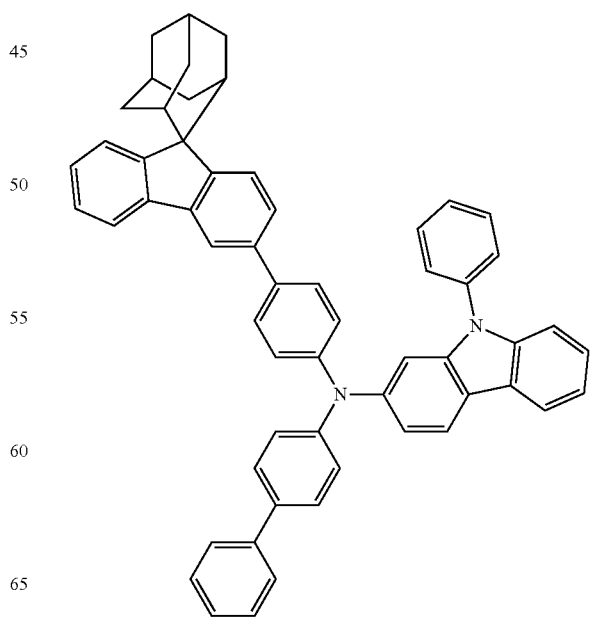

281
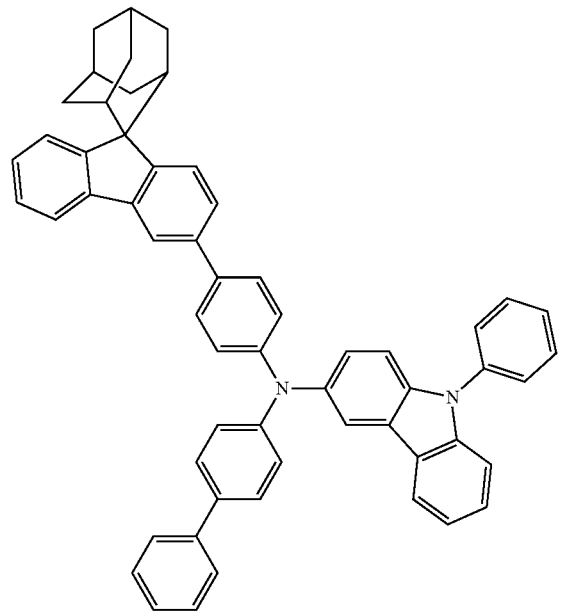
282
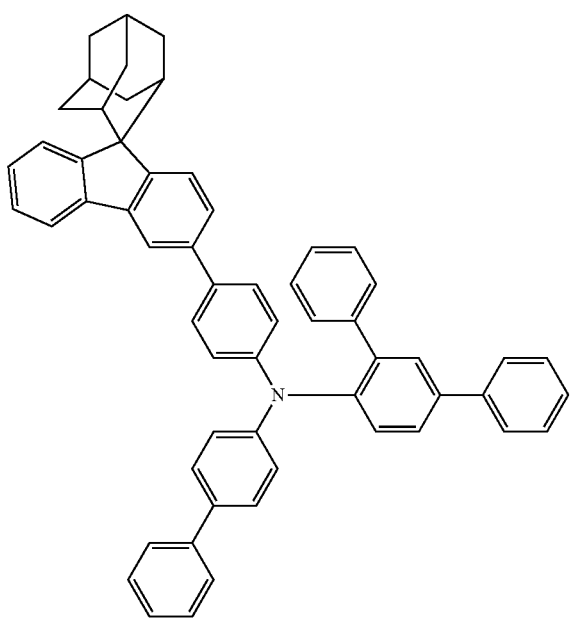
283
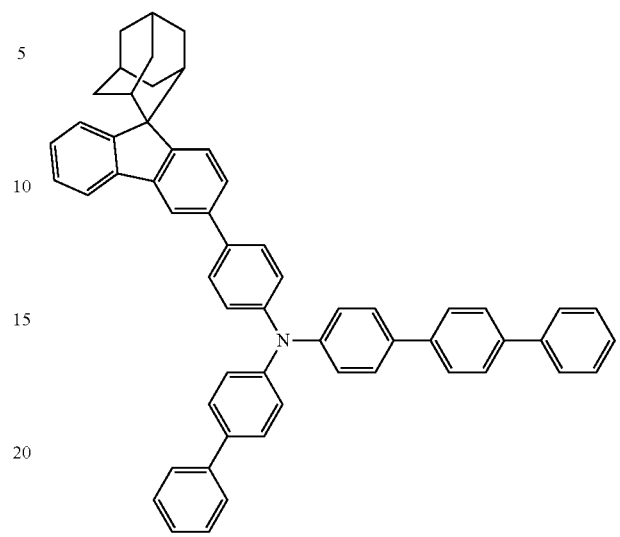
284
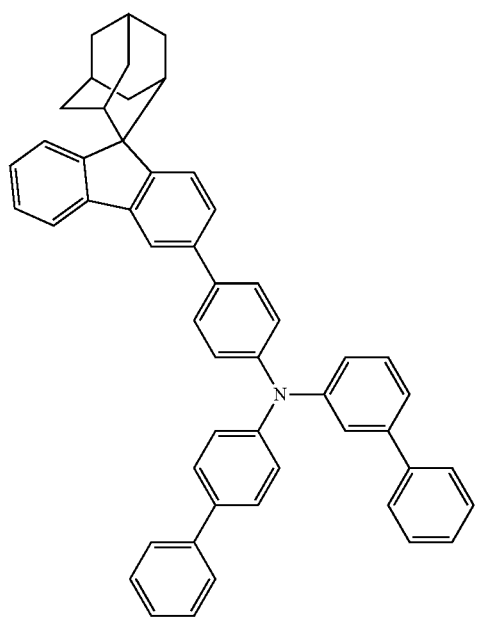

285
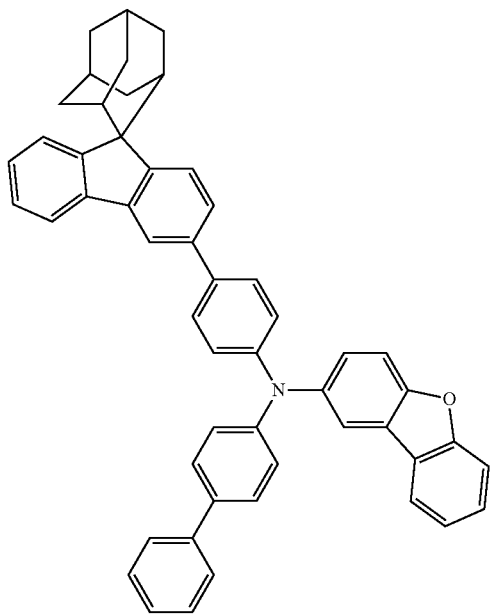
286
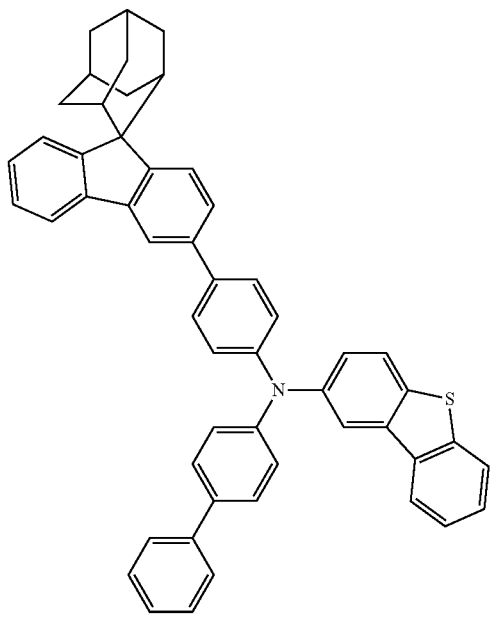
287
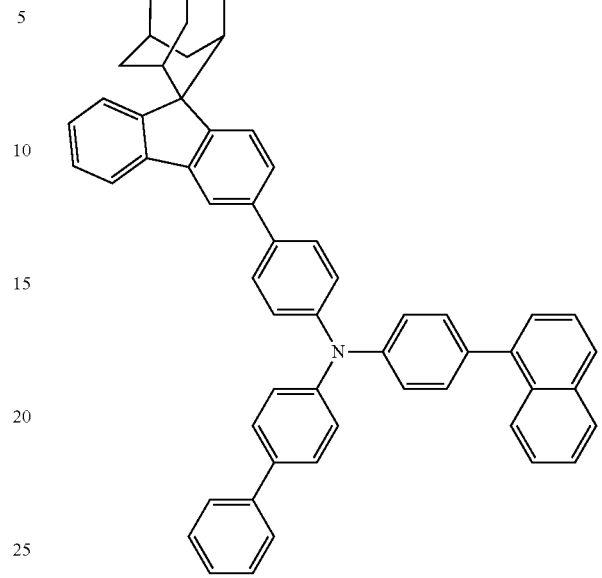
288
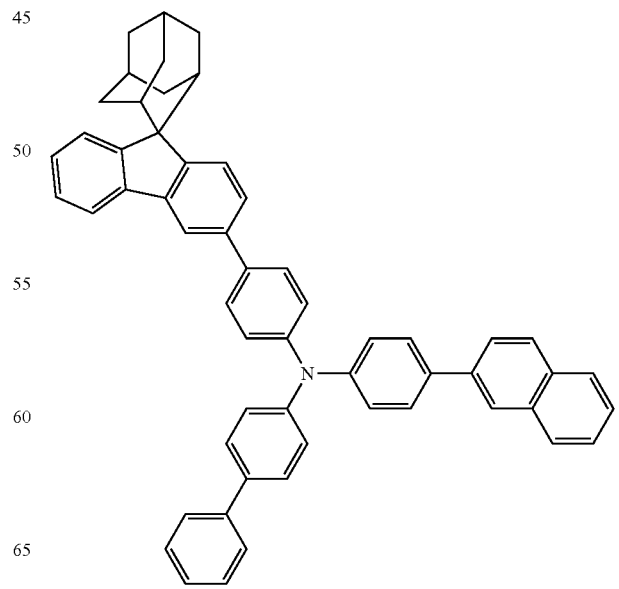

289
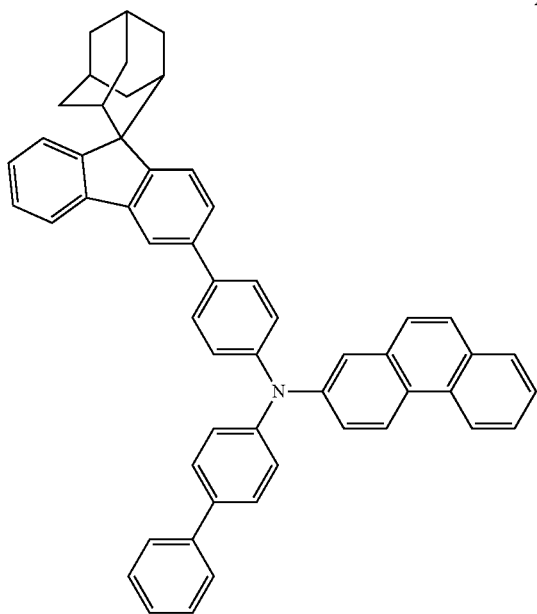
290
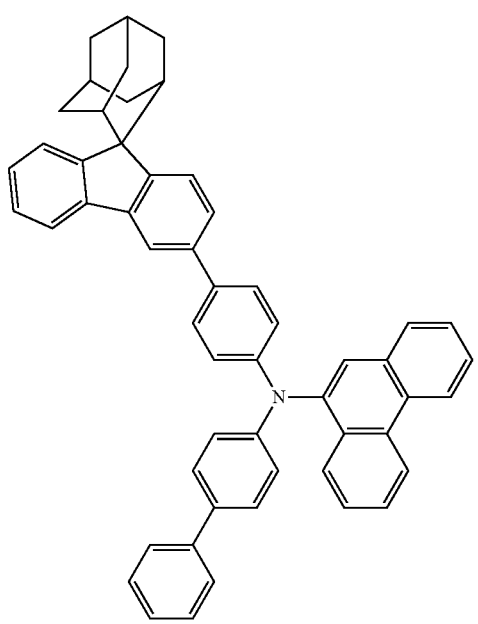
291
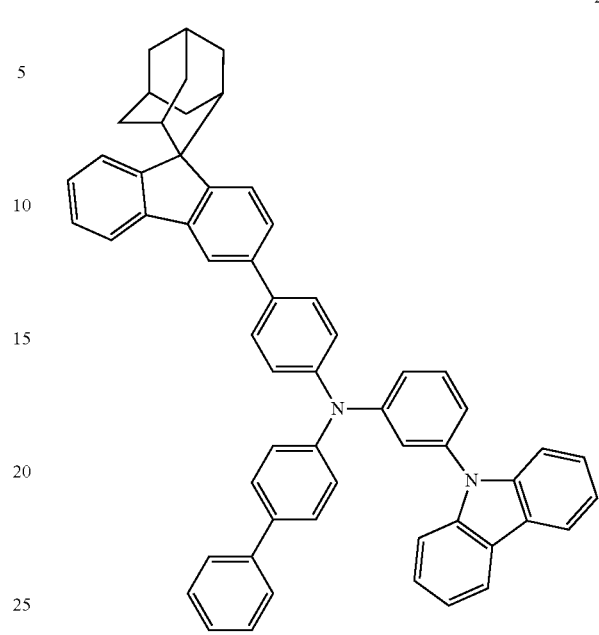
292
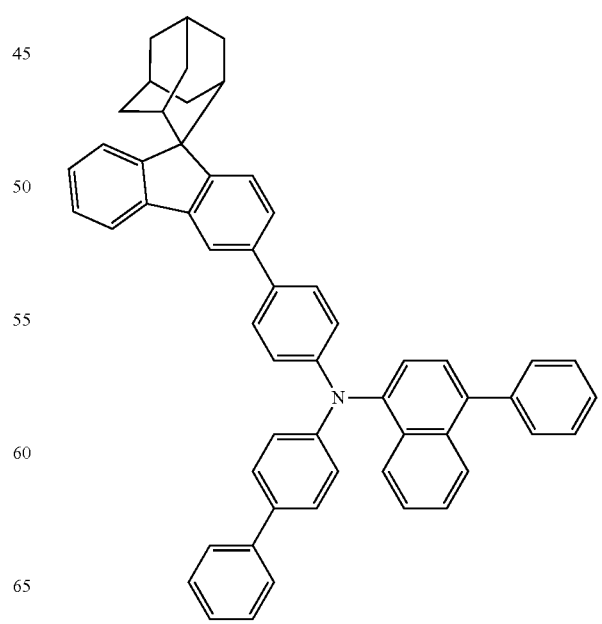

293
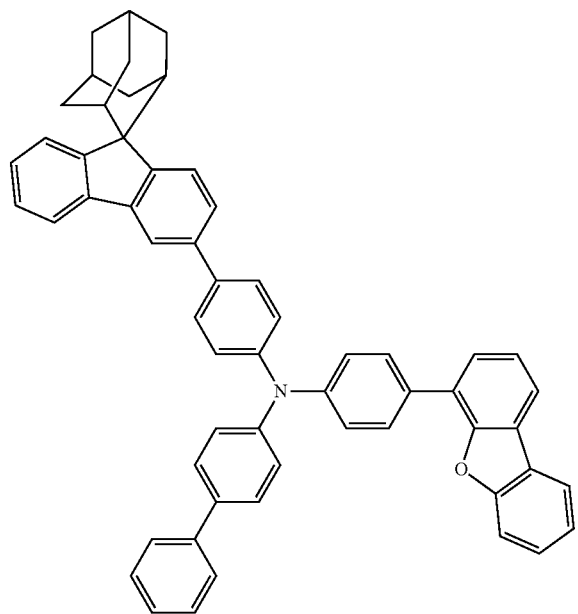
294
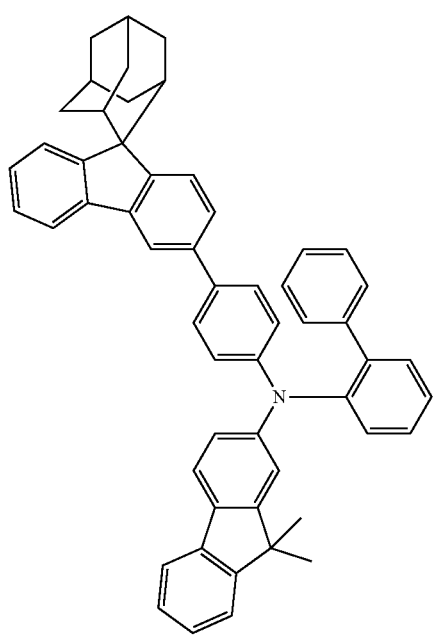
295
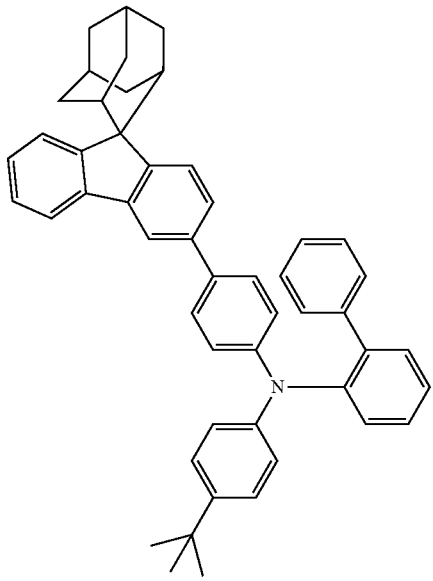
296
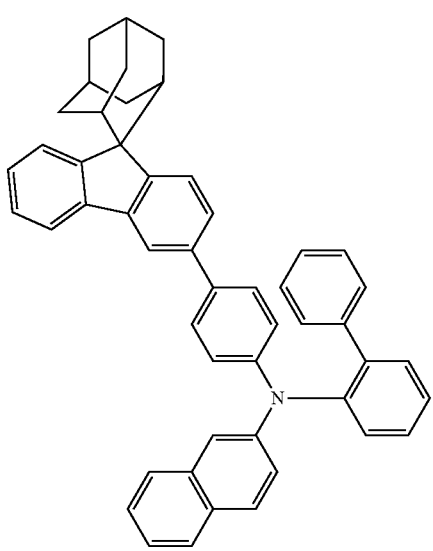
297
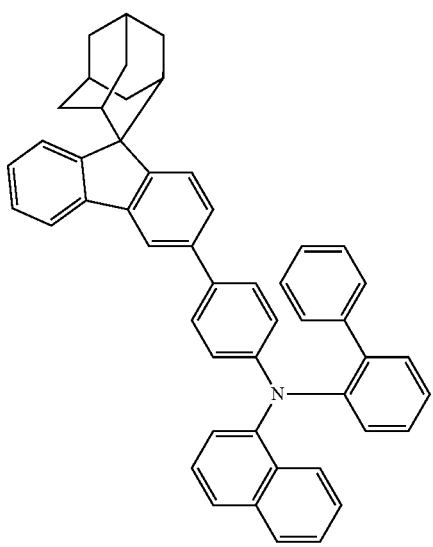

298
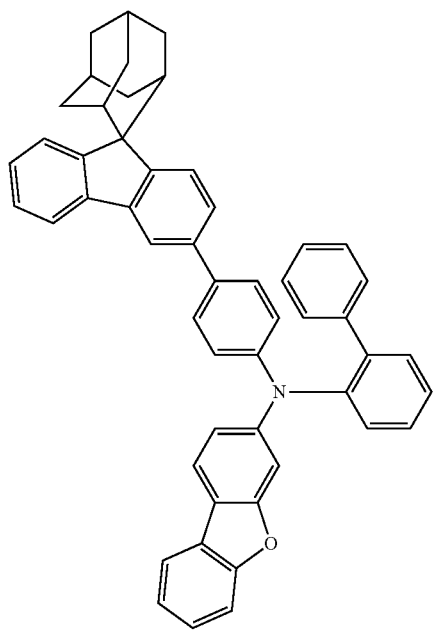
299
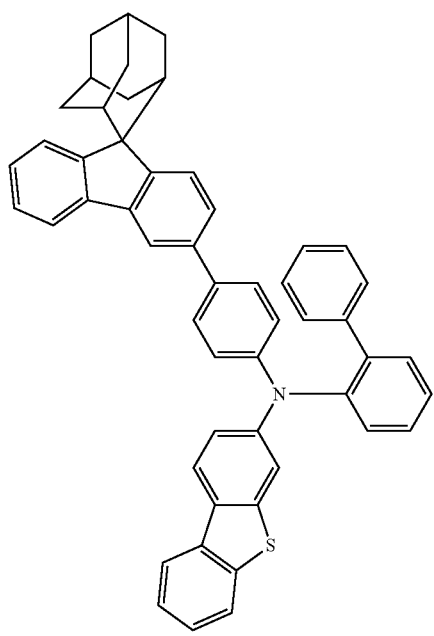
300
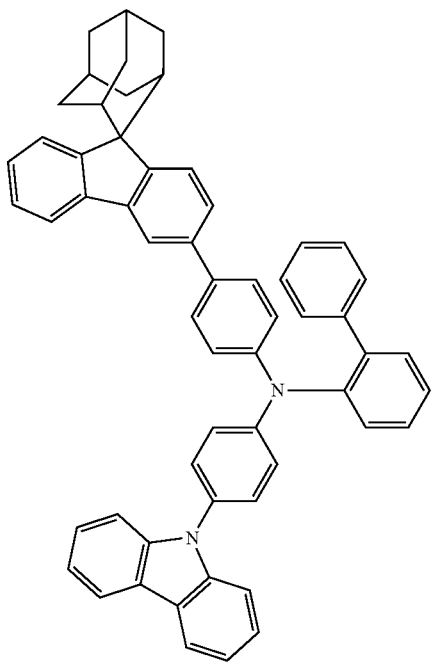
301
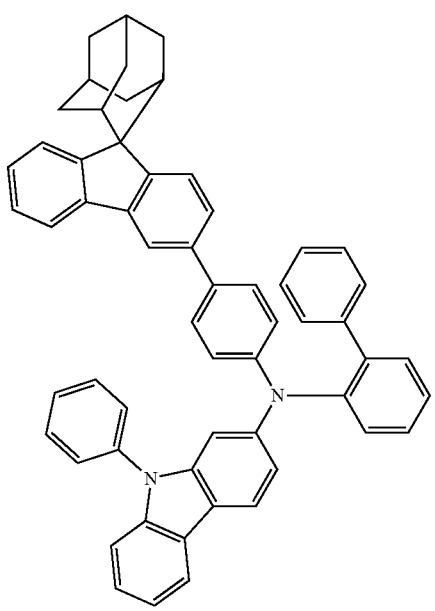

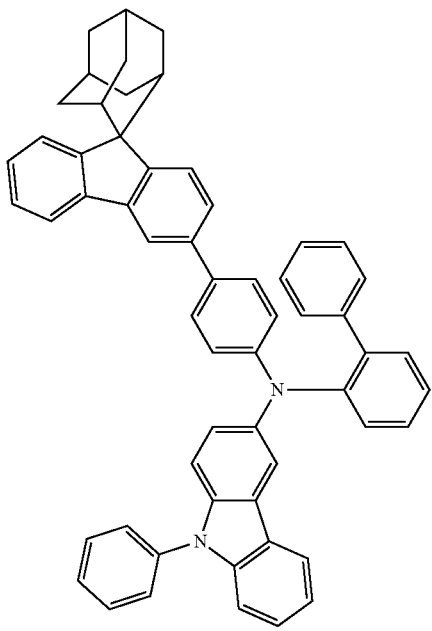
302
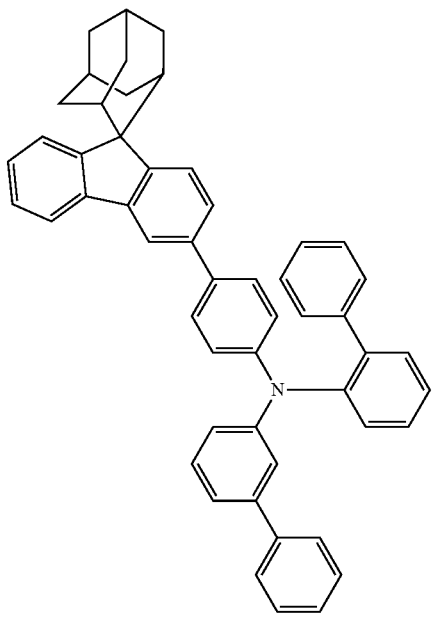
304
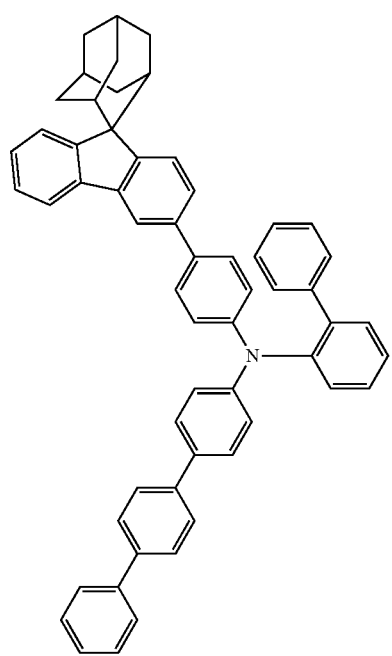
303
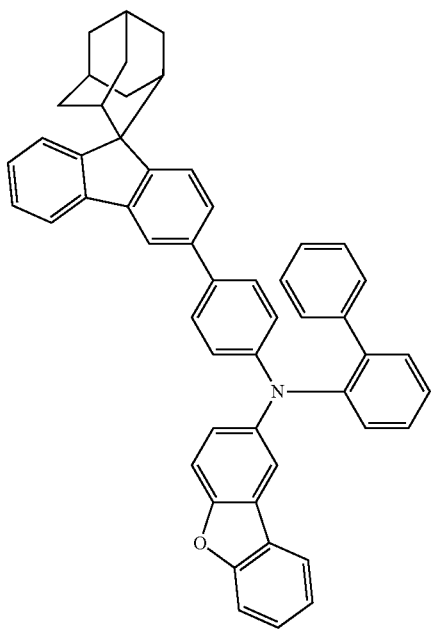
305

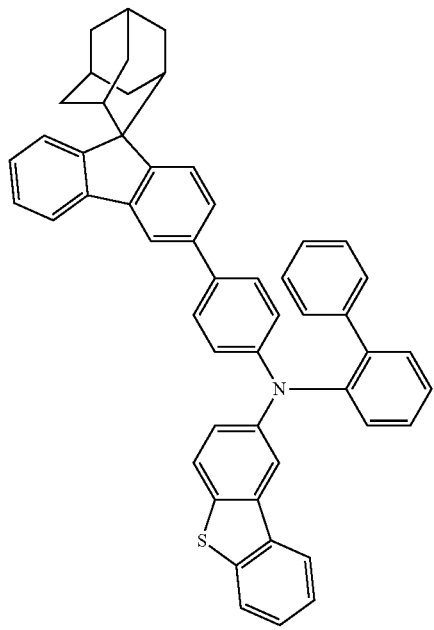
306
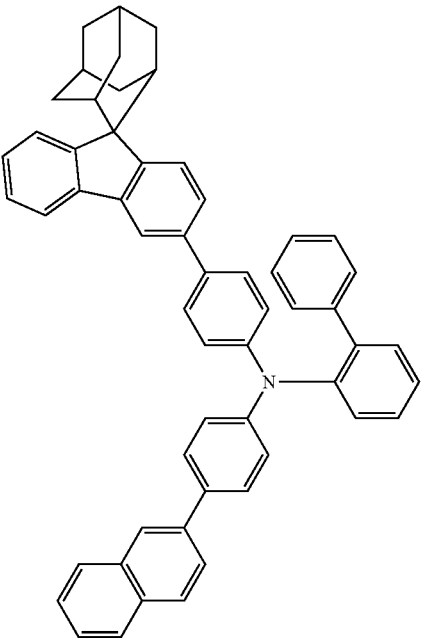
308
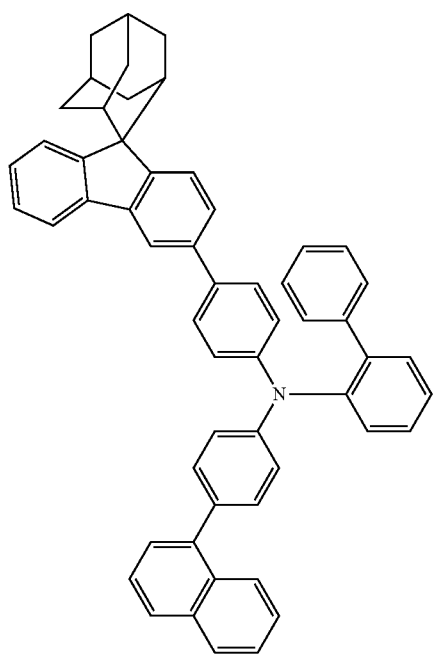
307
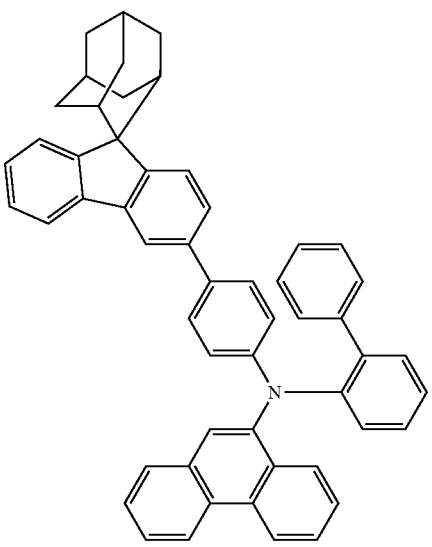
309

310
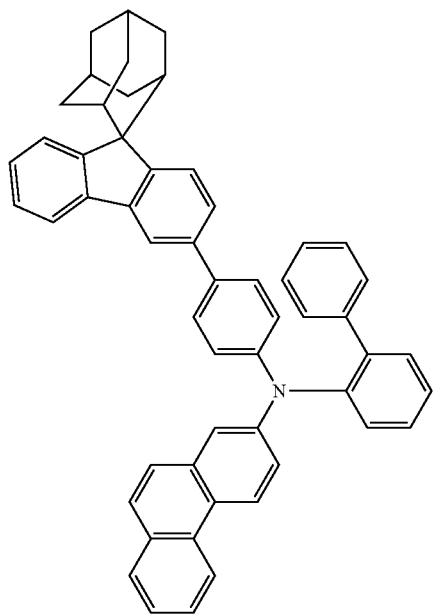
311
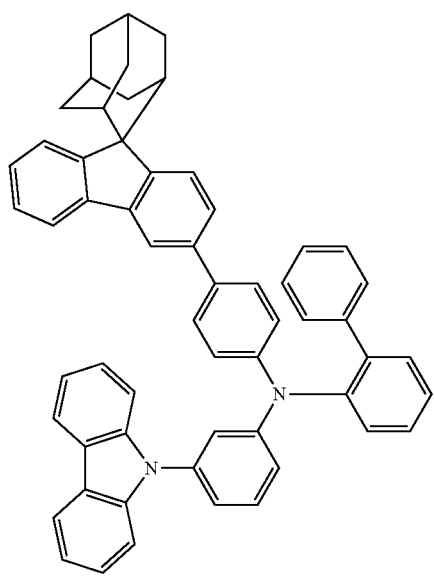
312
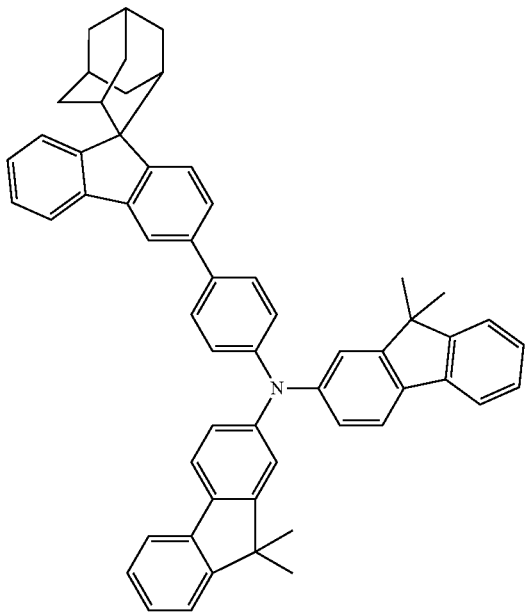
313
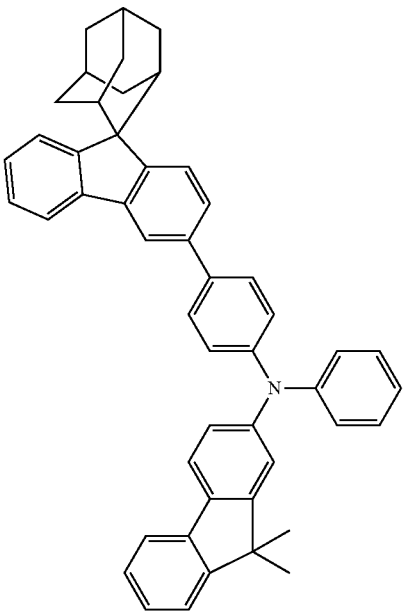

314
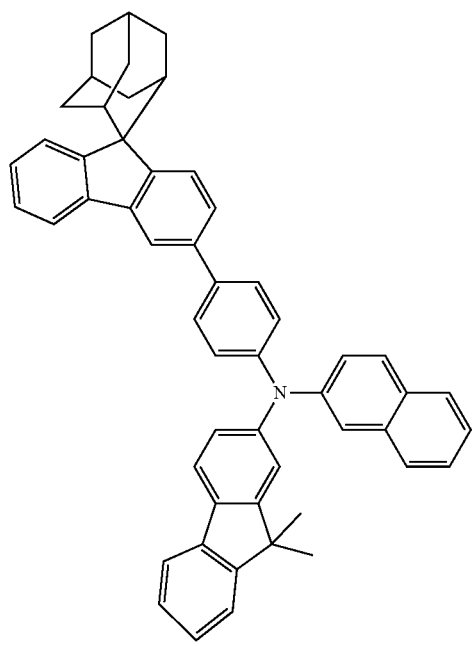
316
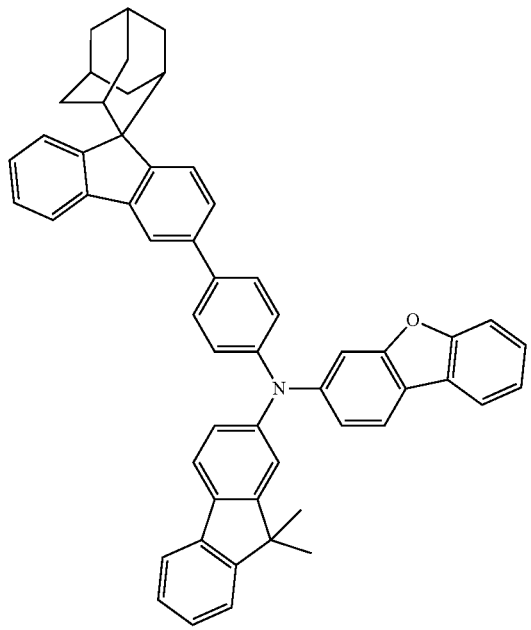
315
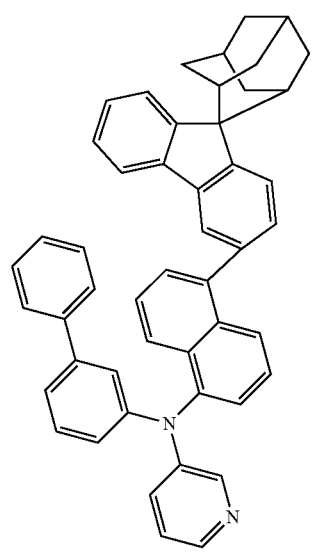
317
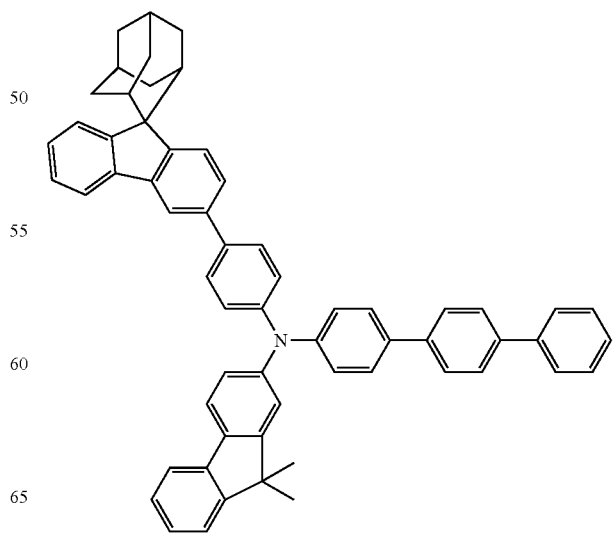

149
-continued
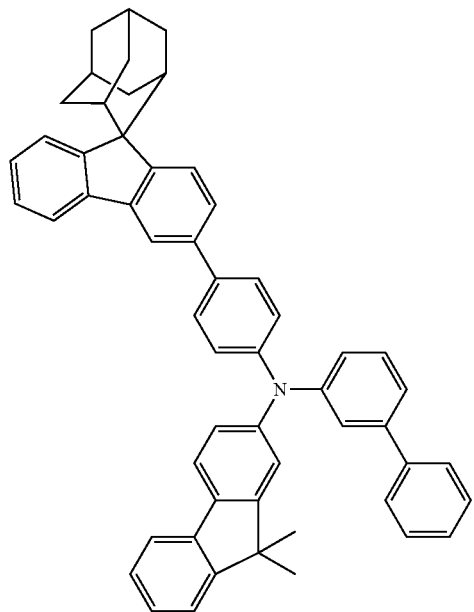
318
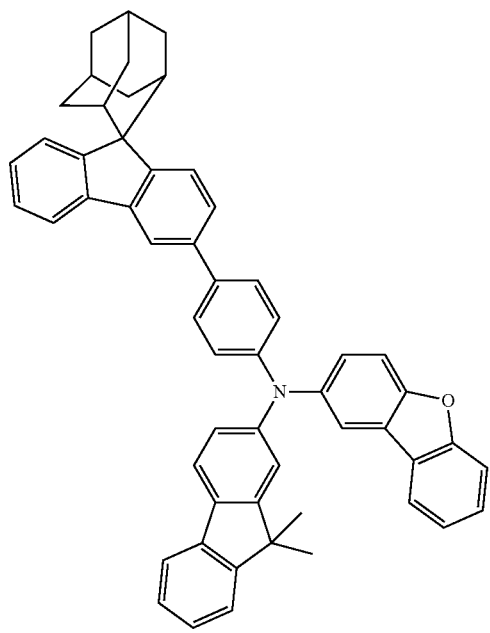
319
150
-continued
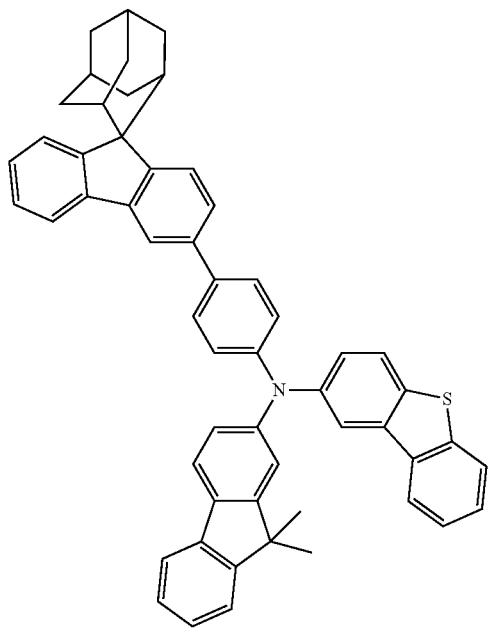
320
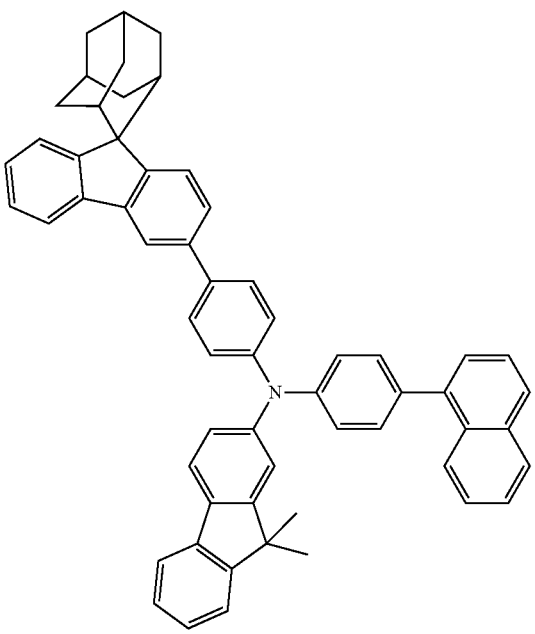
321

322
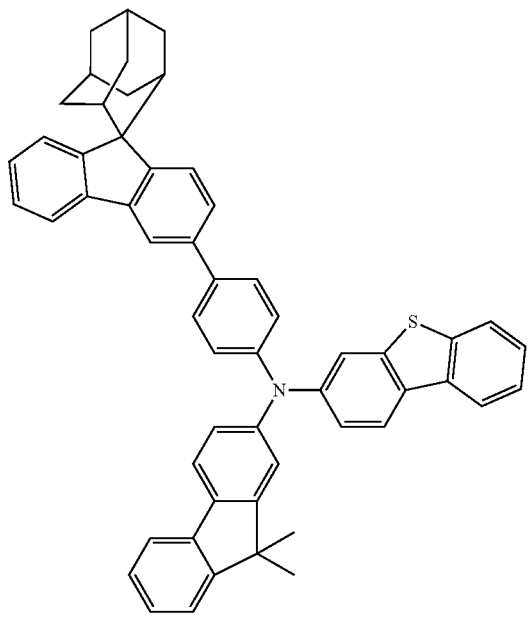
323
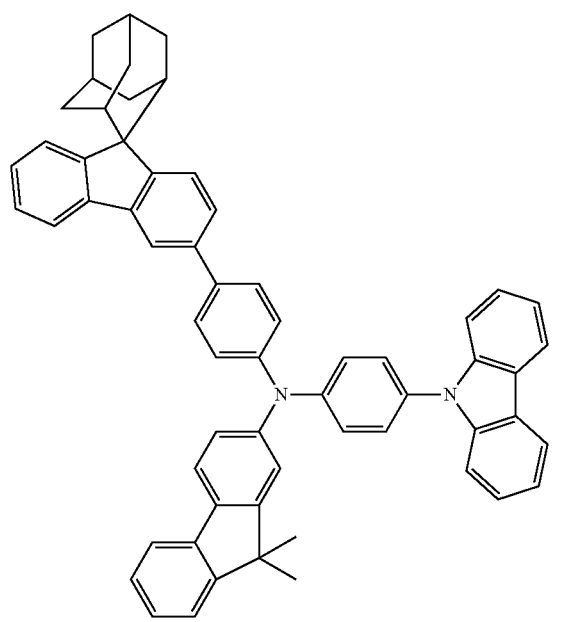
324
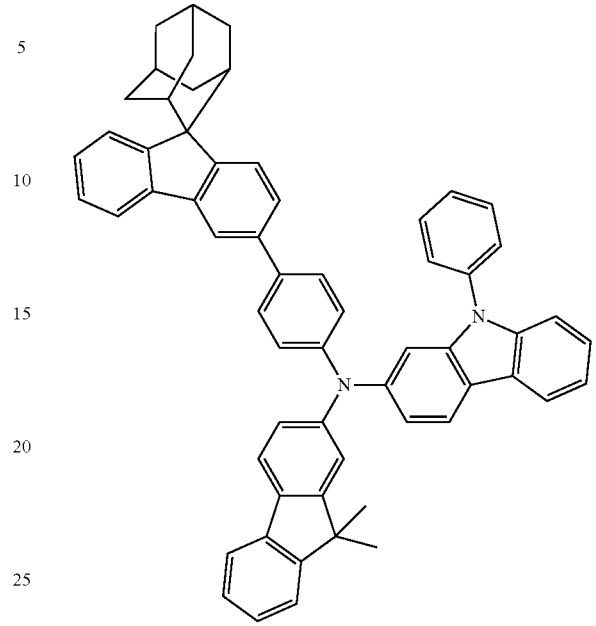
325
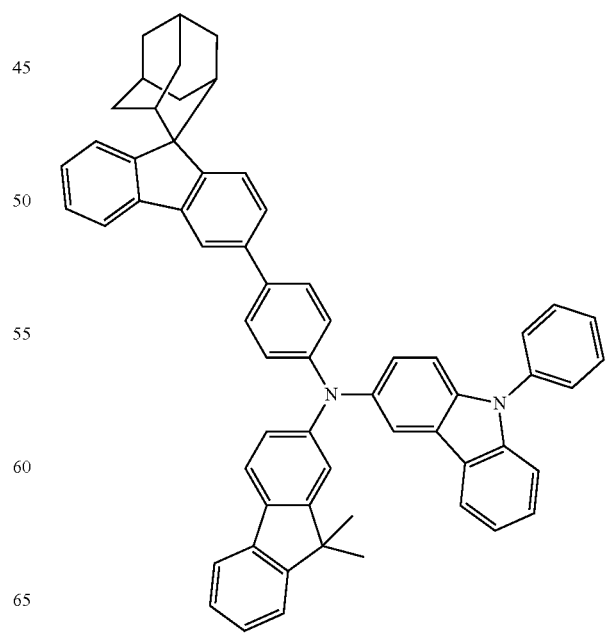

326
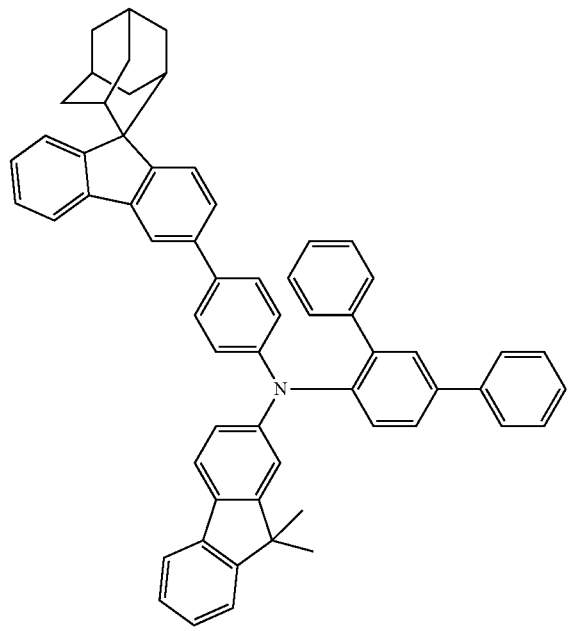
327
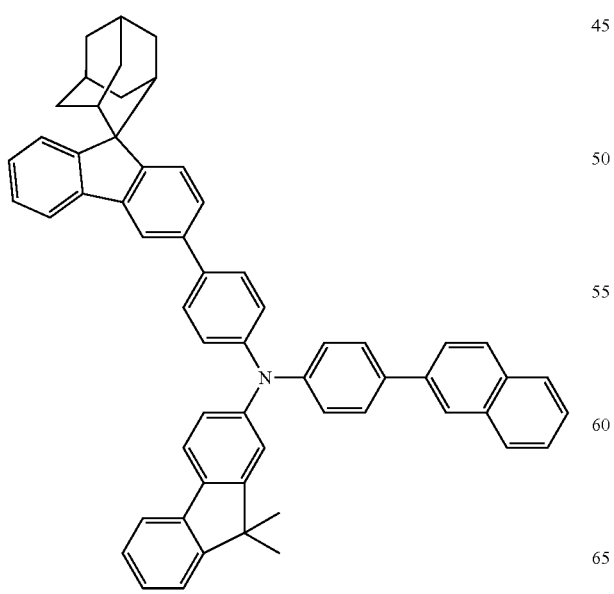
328
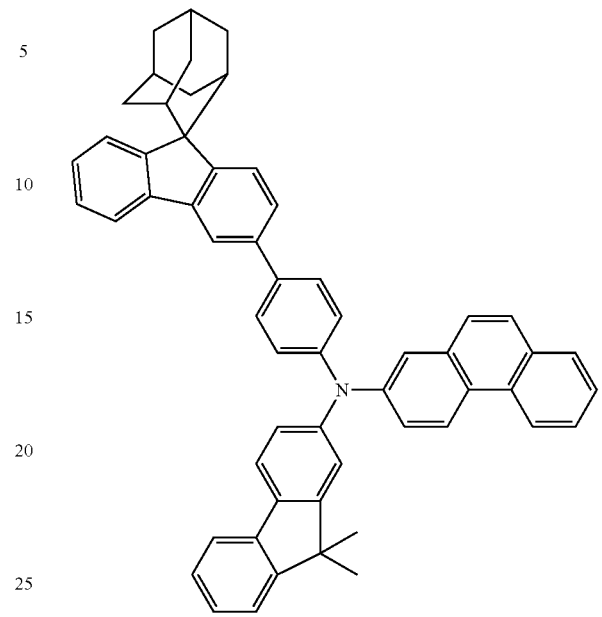
329
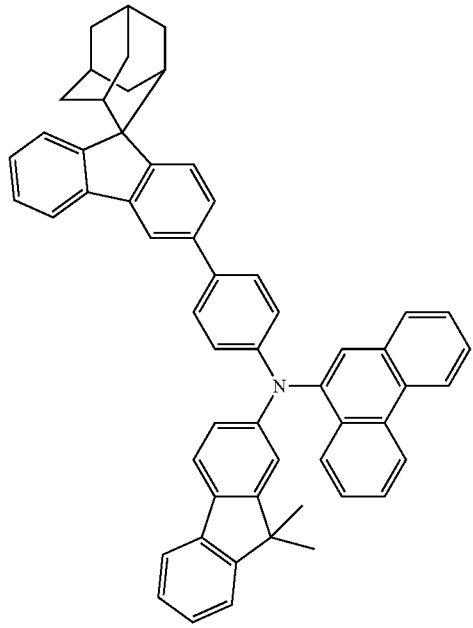

155
-continued
330
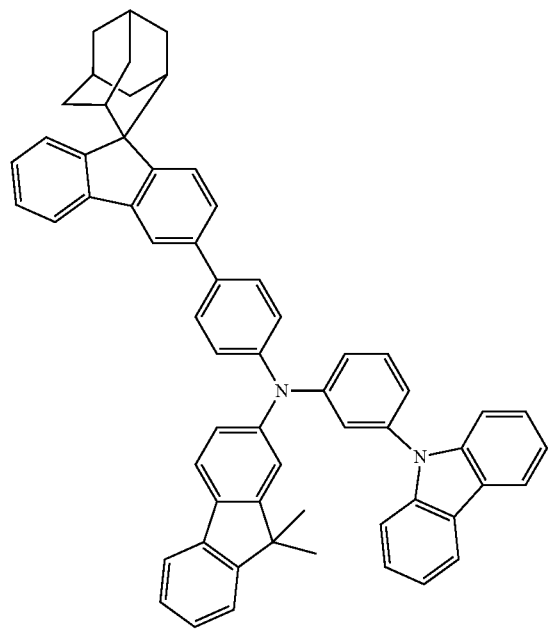
331
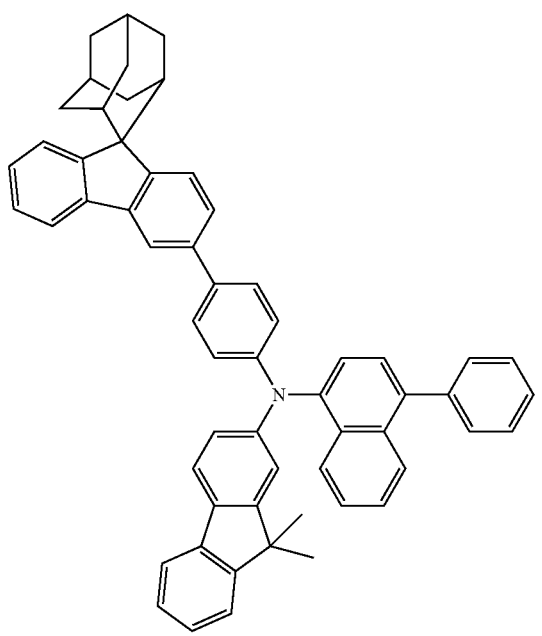
156
-continued
332
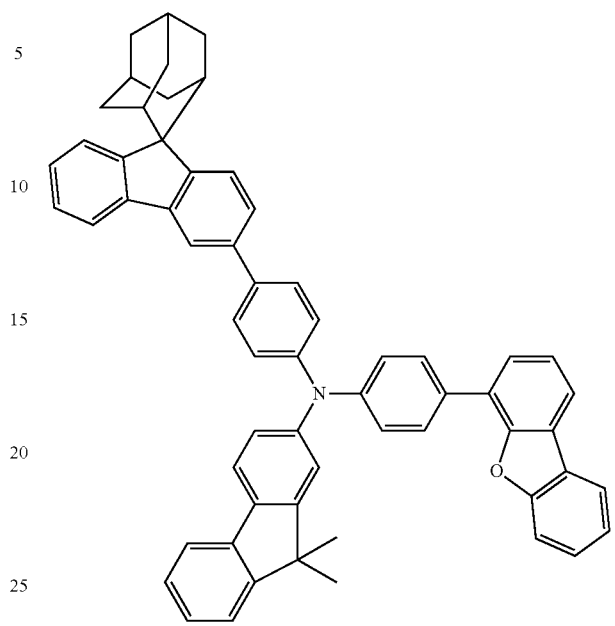
333
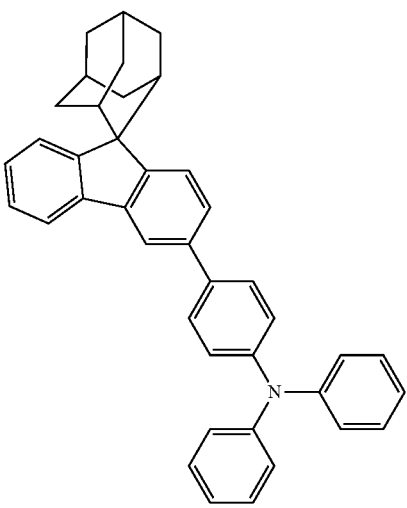
334

335
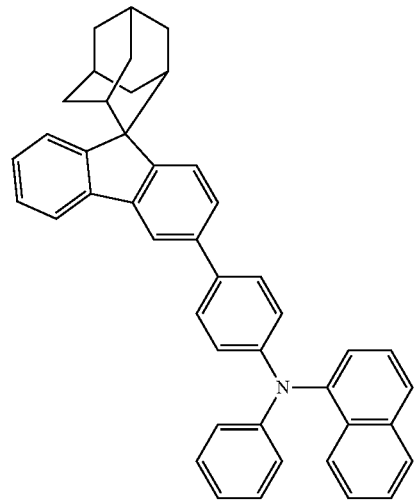
336
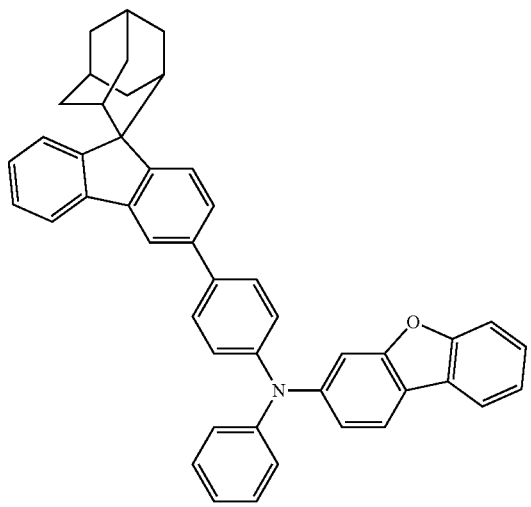
337
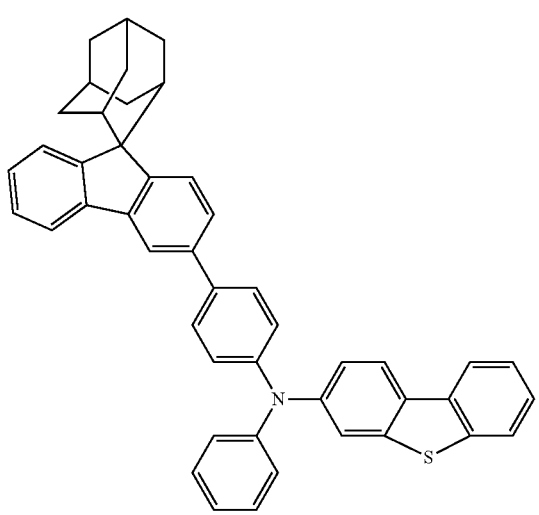
338
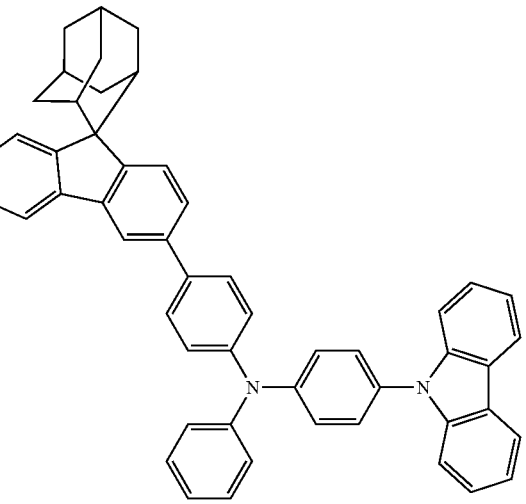
339
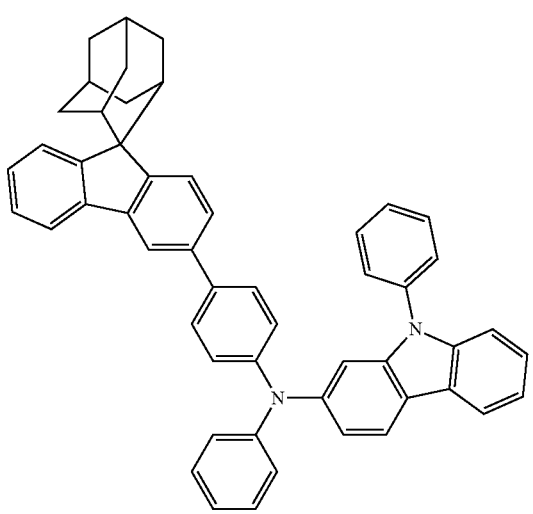
340
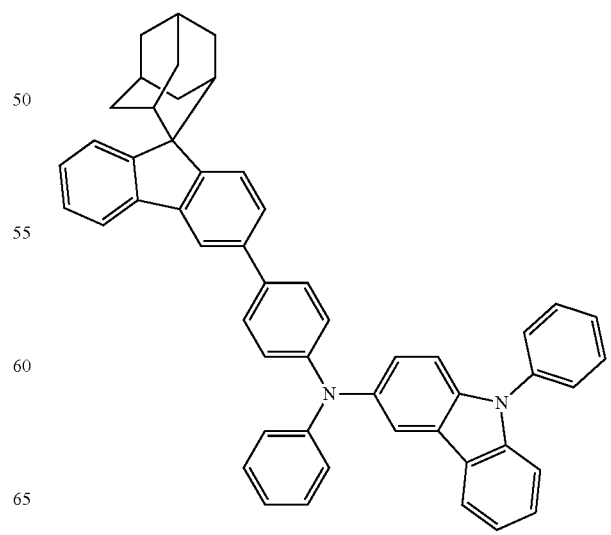

341
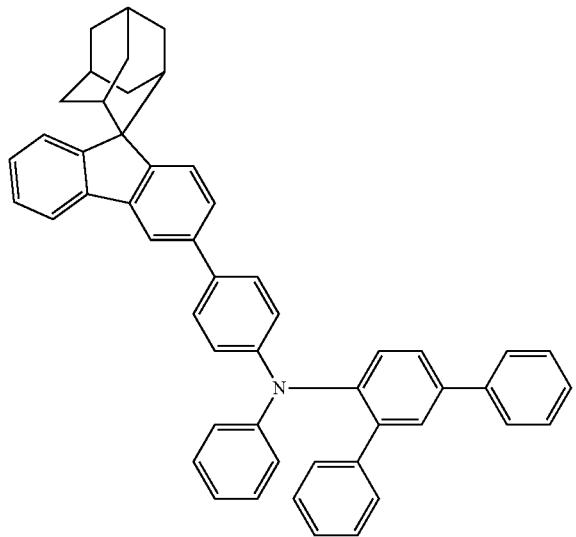
344
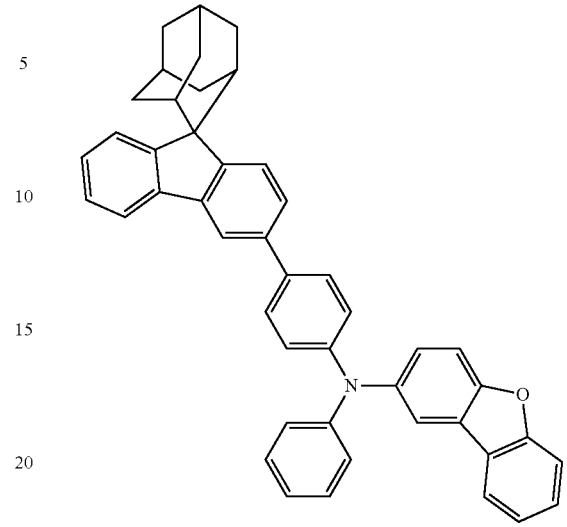
342
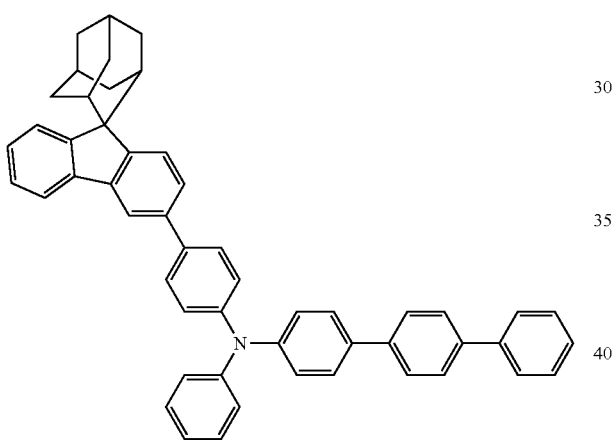
345
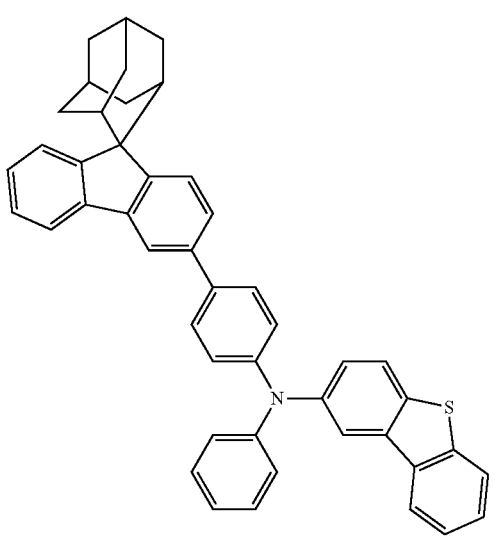
343
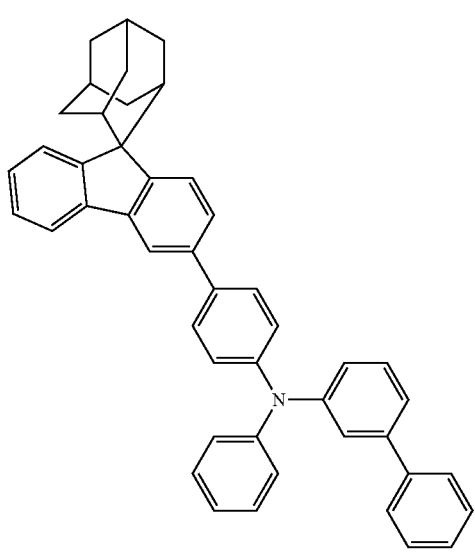
346
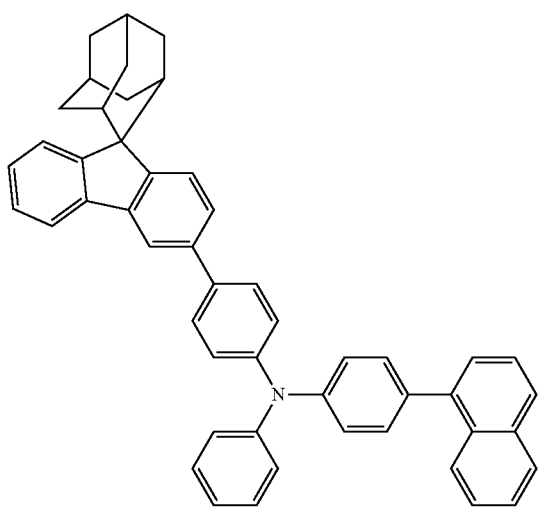

-continued
347
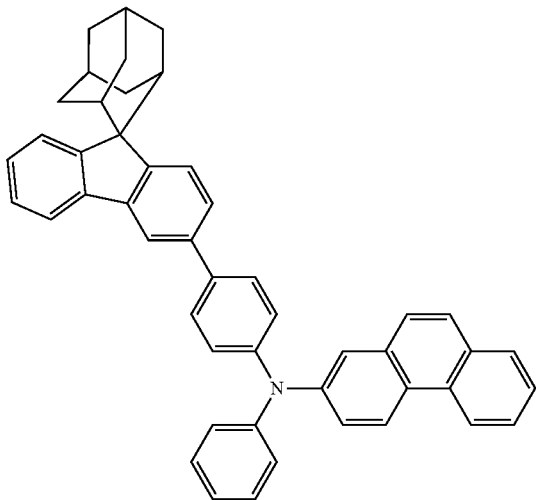
348
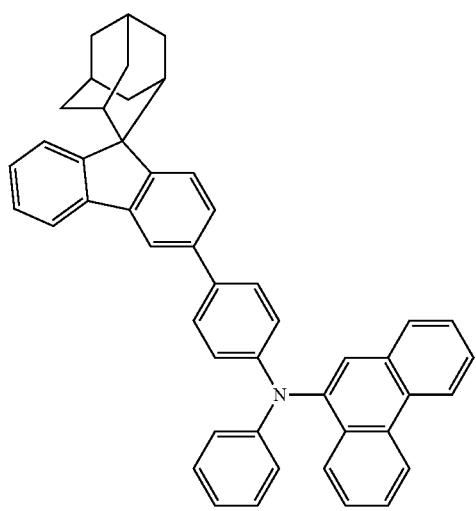
349
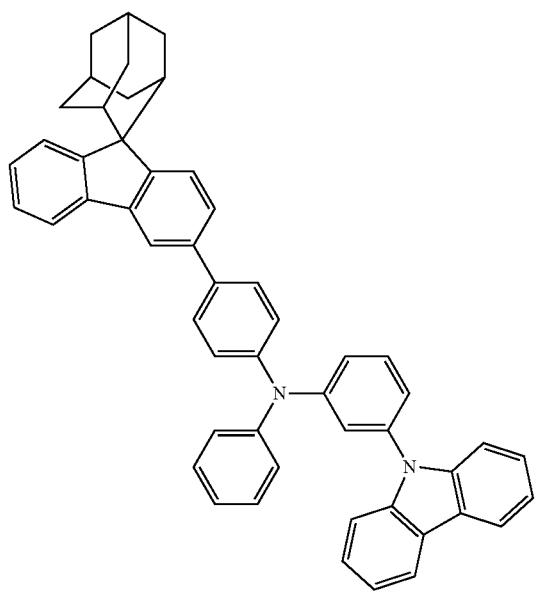
-continued
350
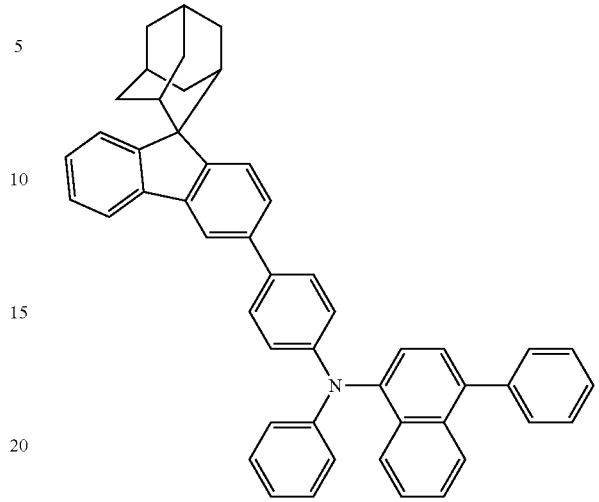
351
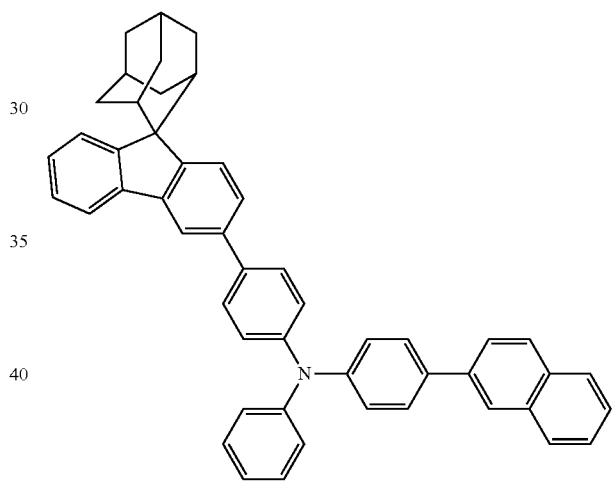
352
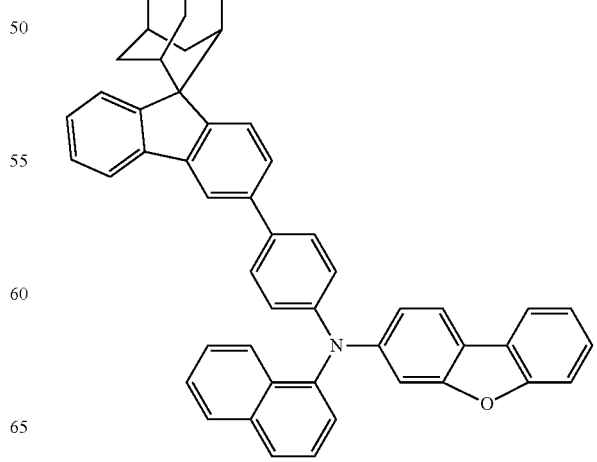

353 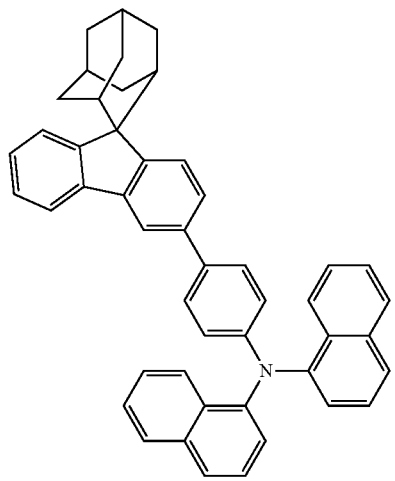
356 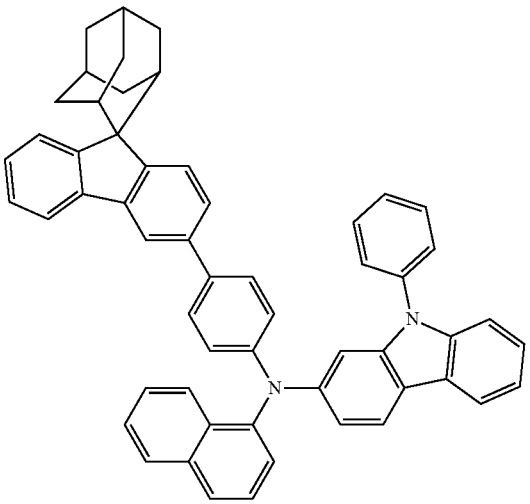
354 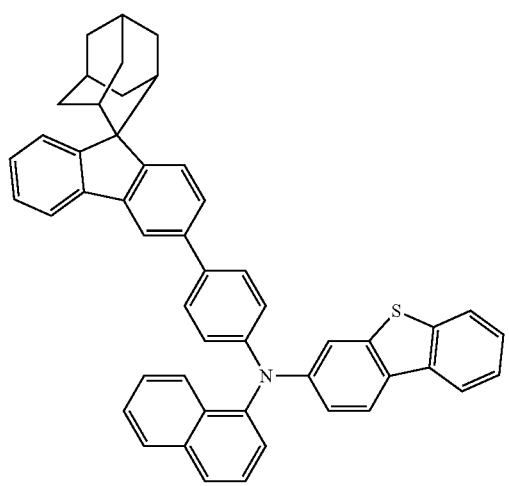
357 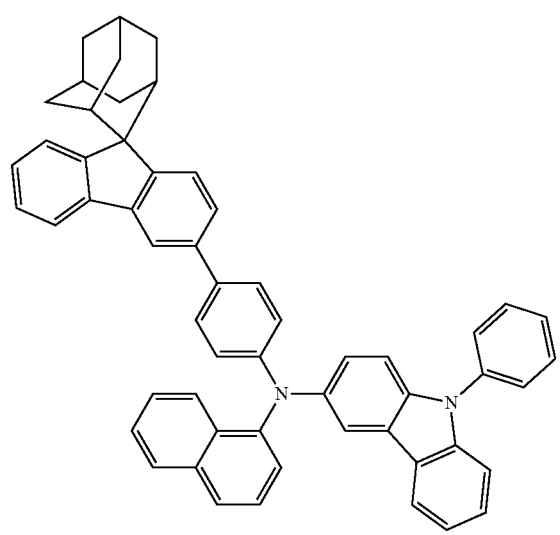
355 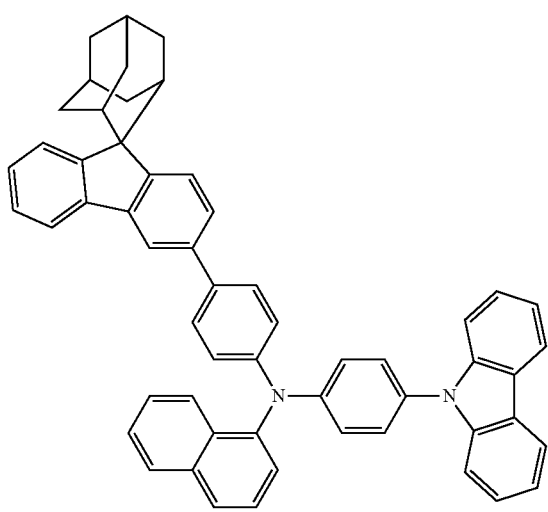
358 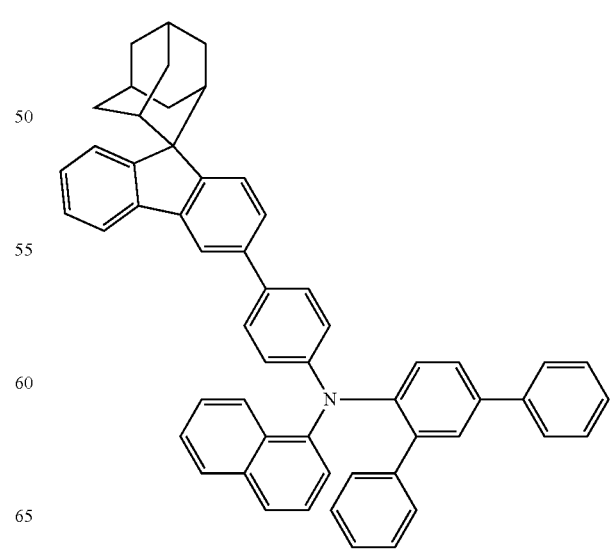

359
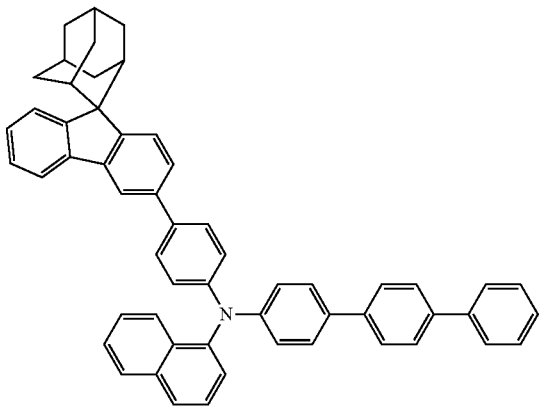
360
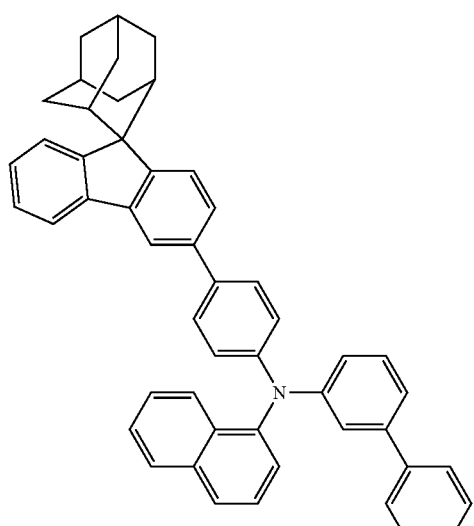
361
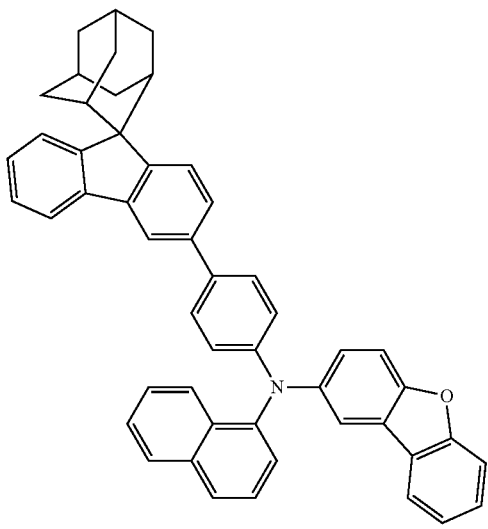
362
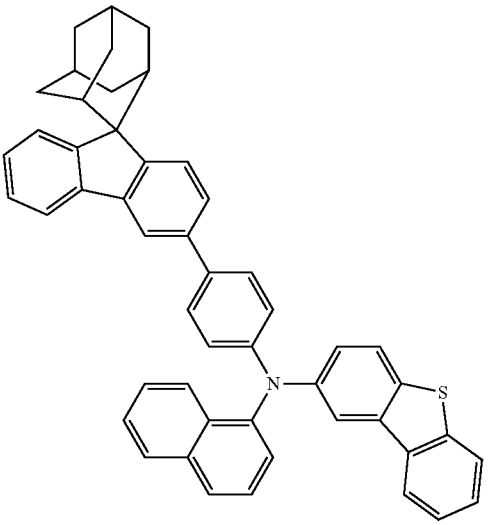
363
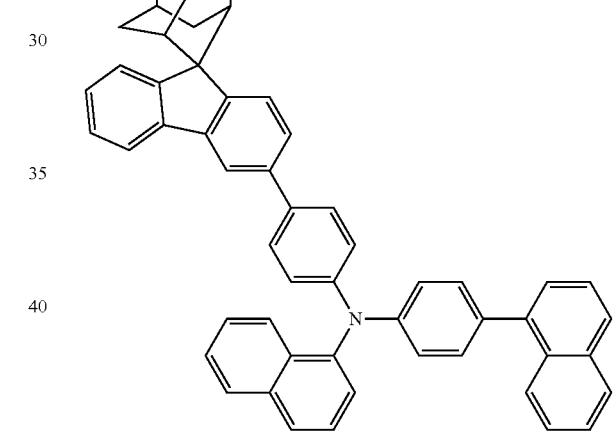
364
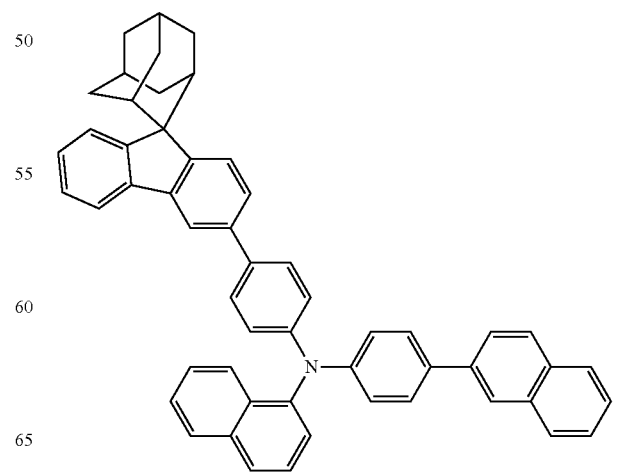

365
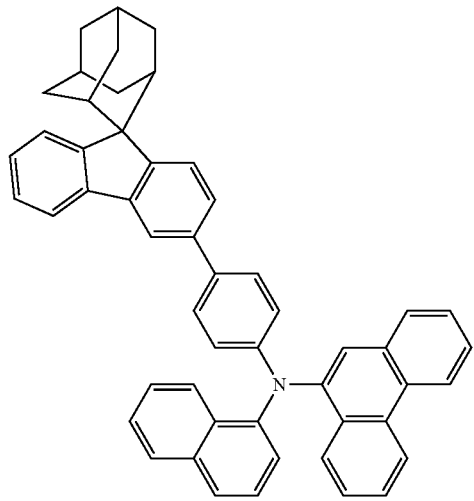
366
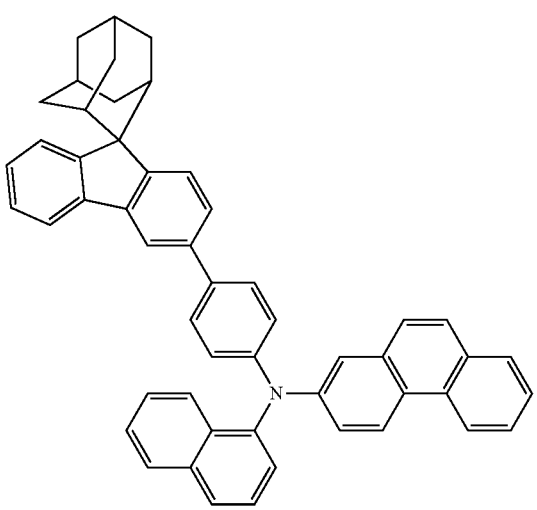
367
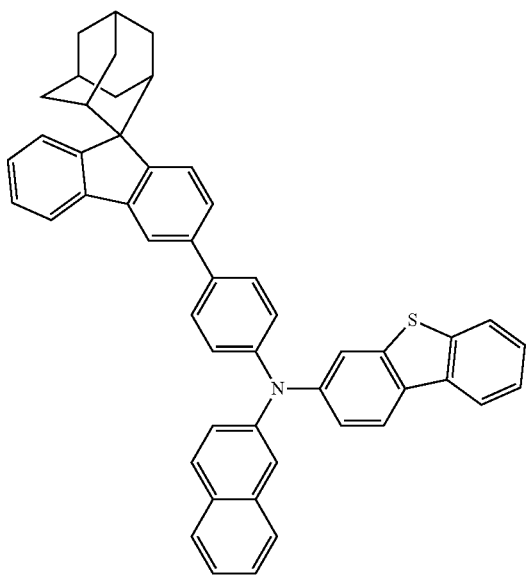
368
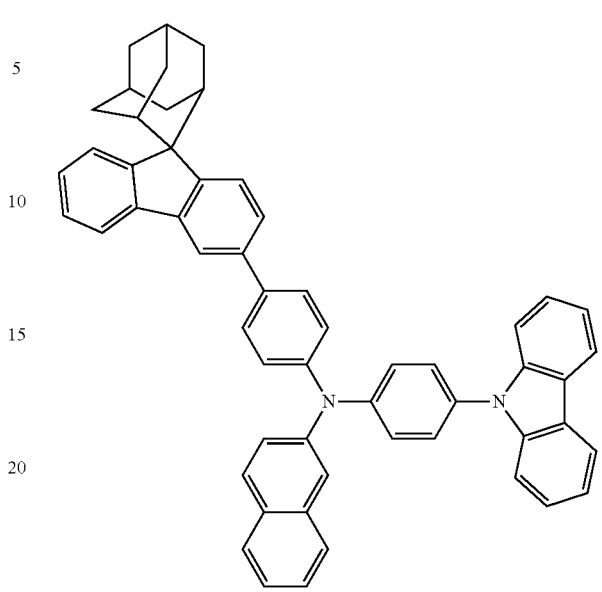
369
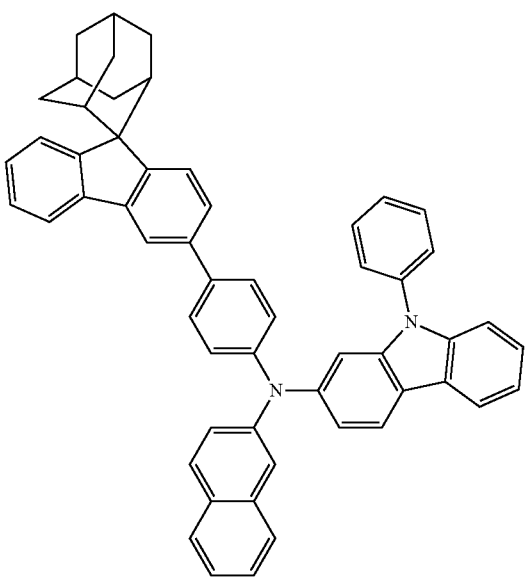

169
-continued
370
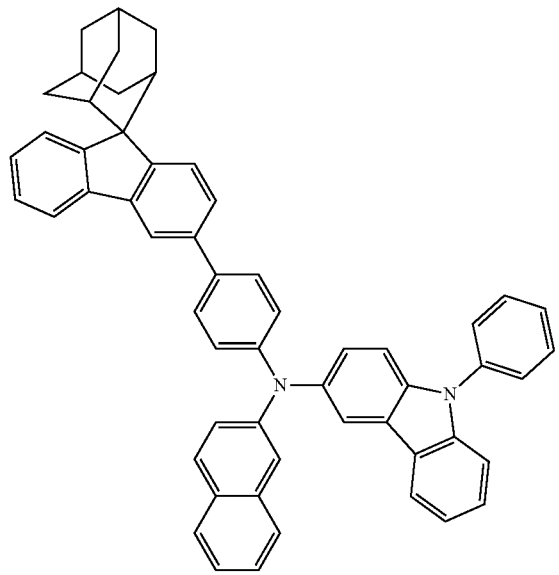
371
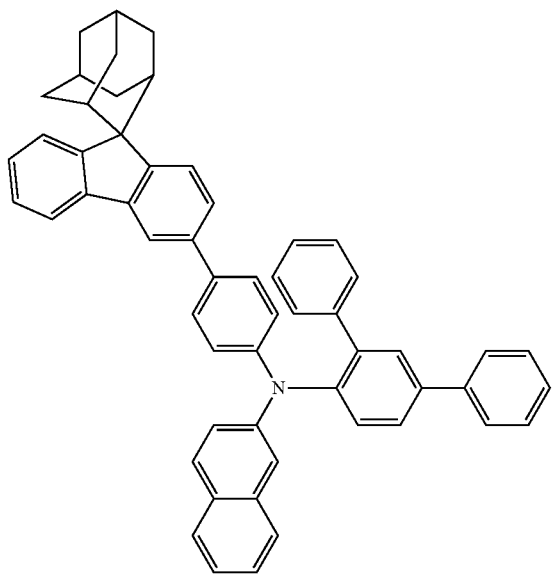
170
-continued
372
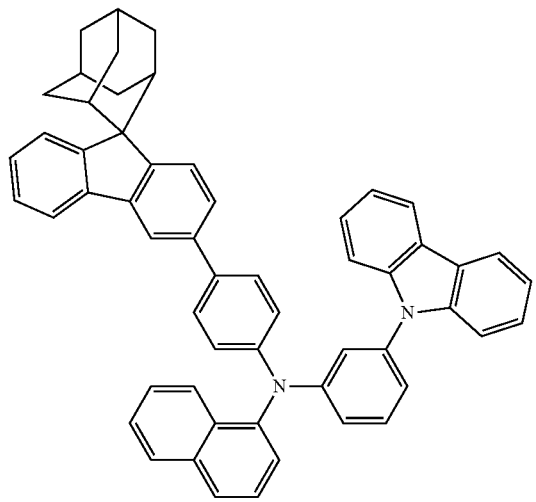
373
374
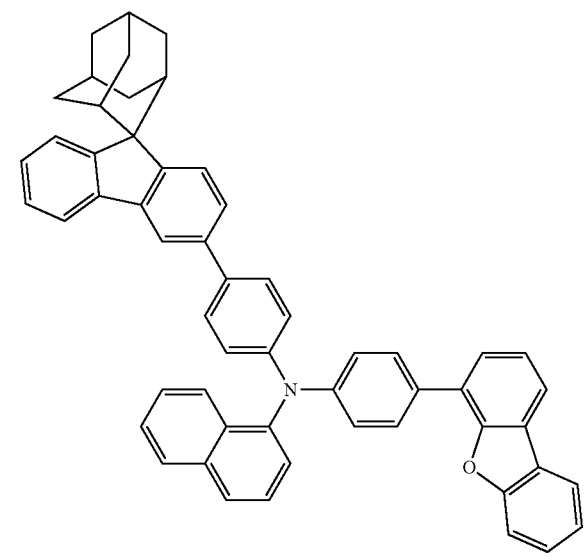

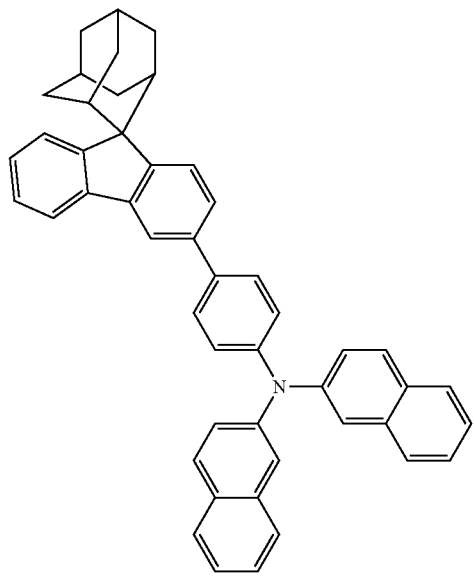
375
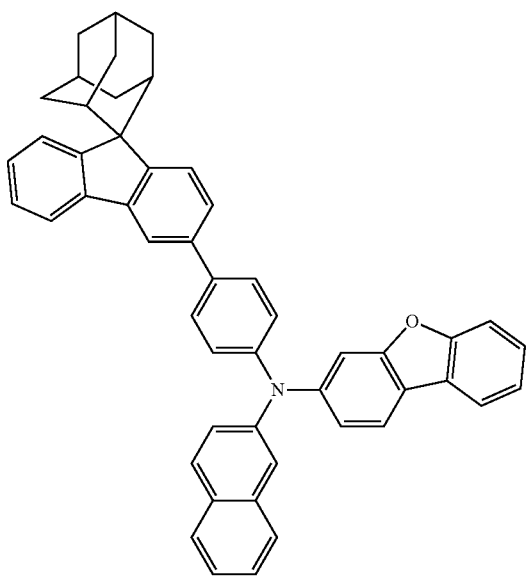
376
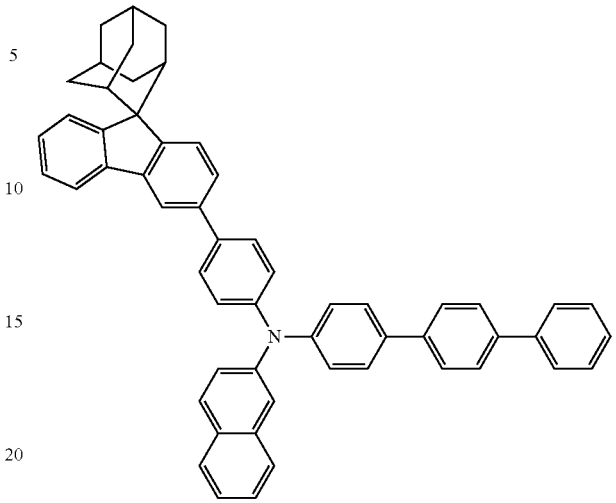
377
378
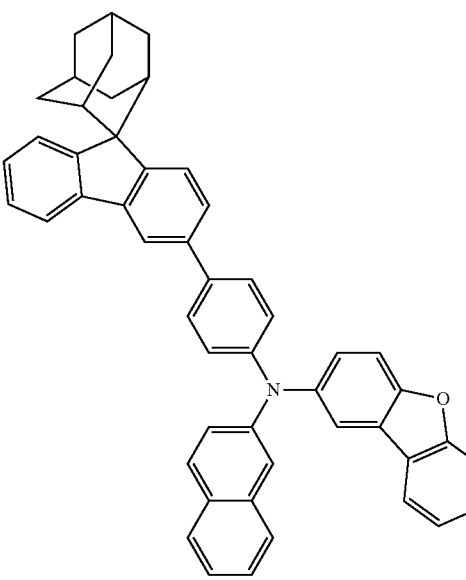
379

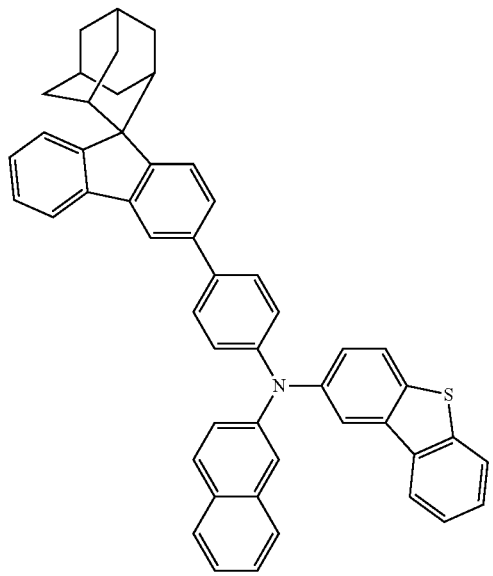
380
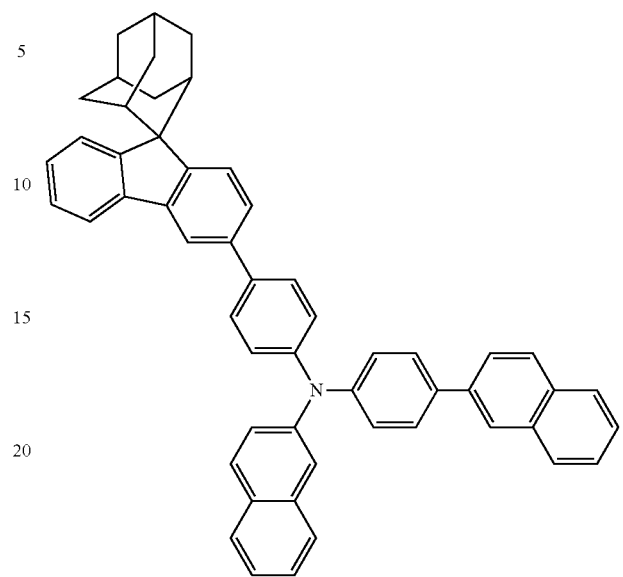
382
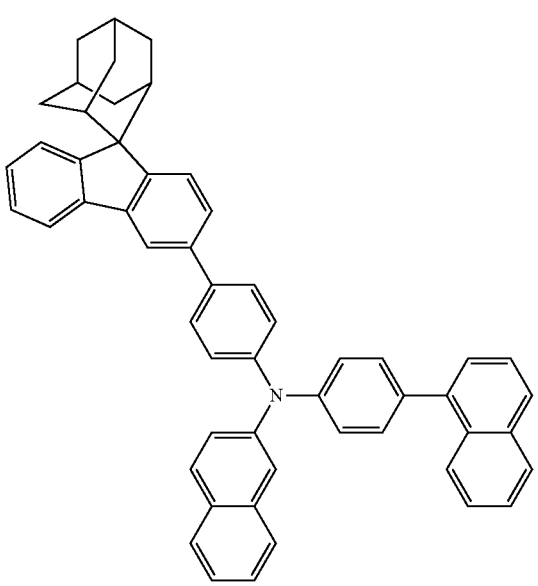
381
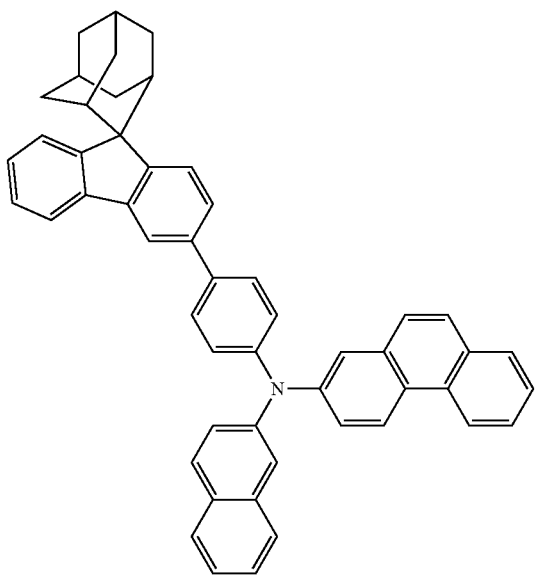
383

384
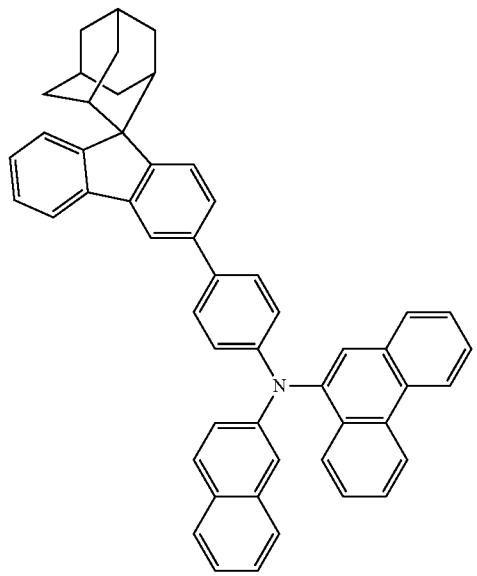
386
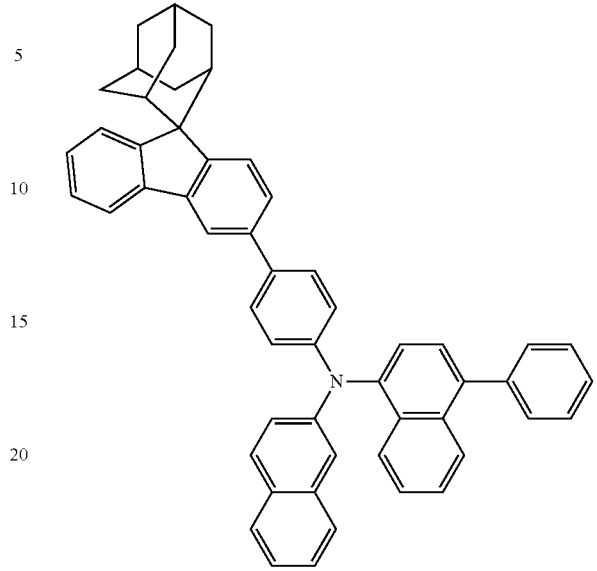
385
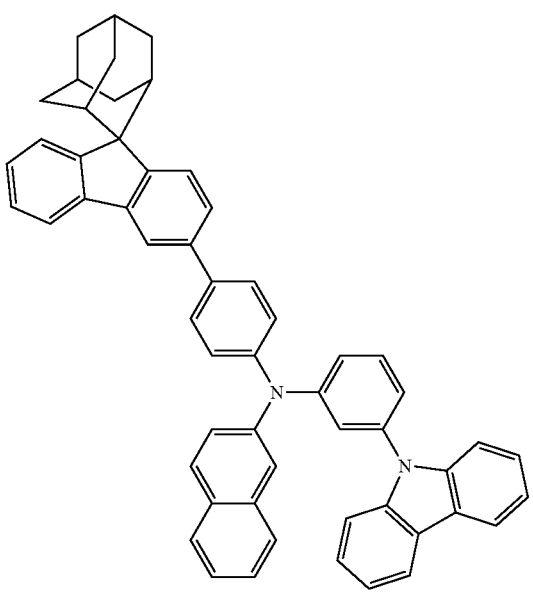
387
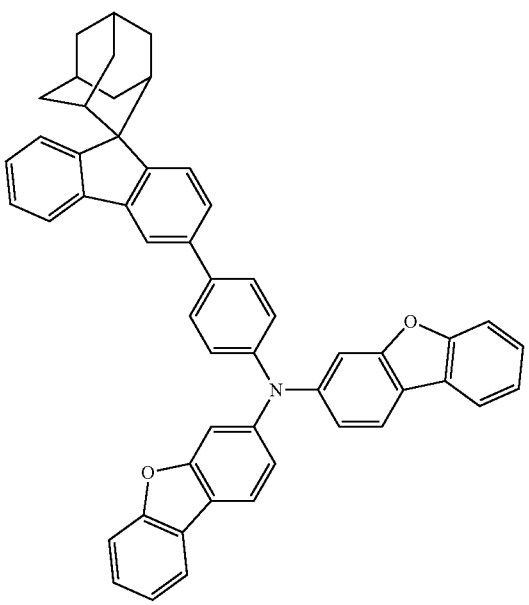

388
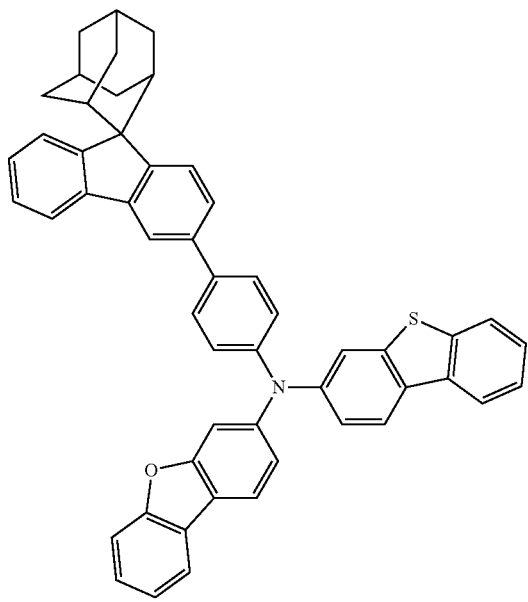
389
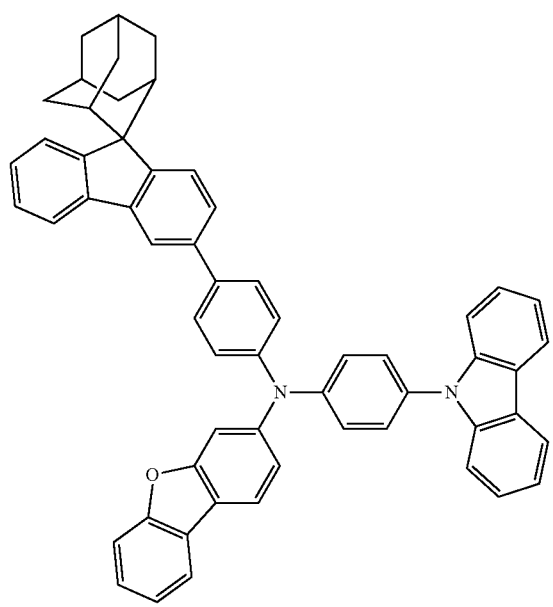
390
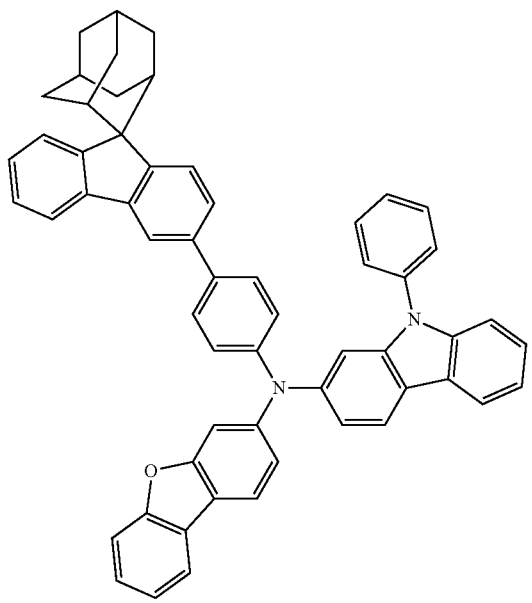
391
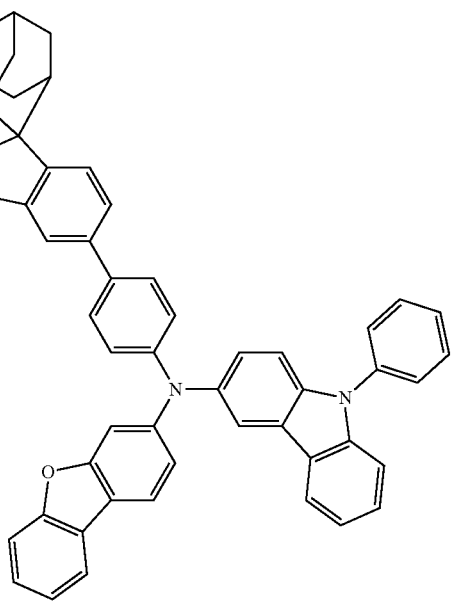

392
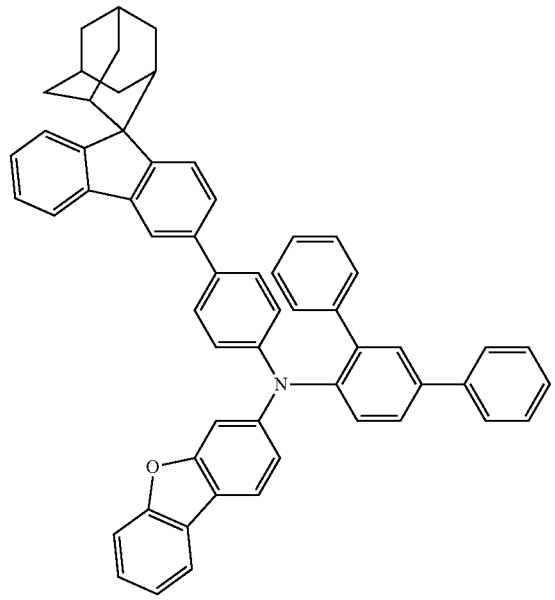
393
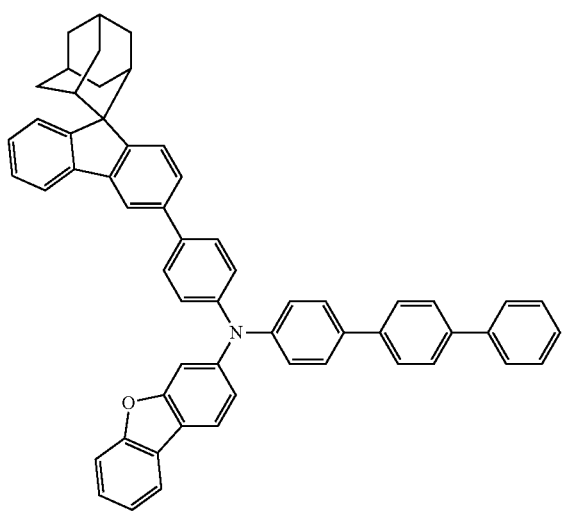
394
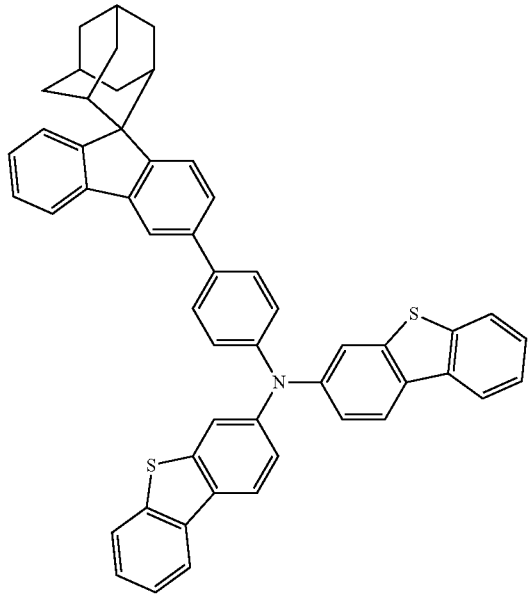
395
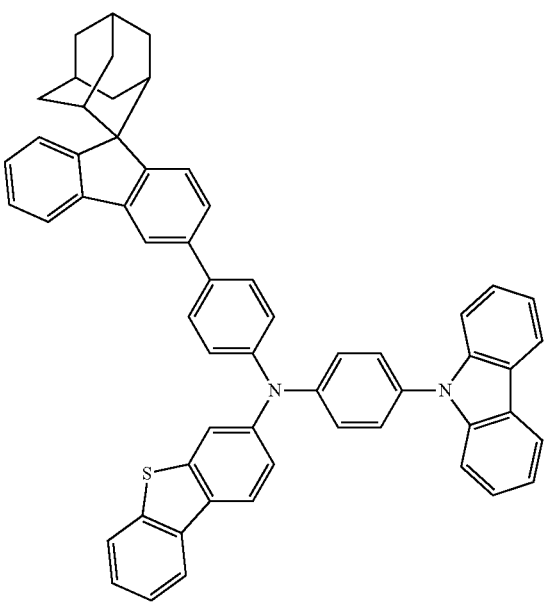

181
-continued
396
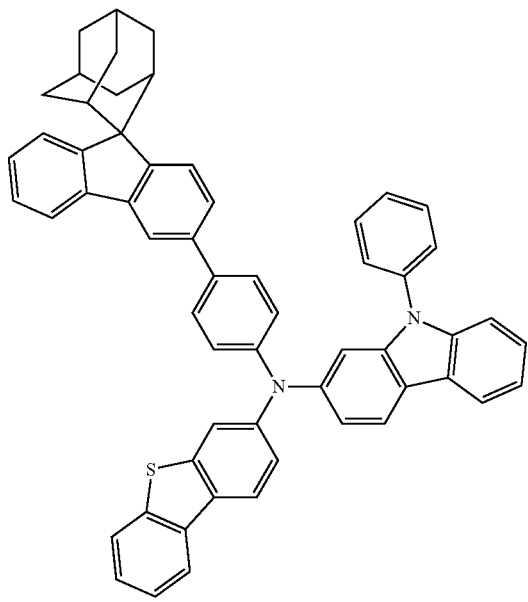
397
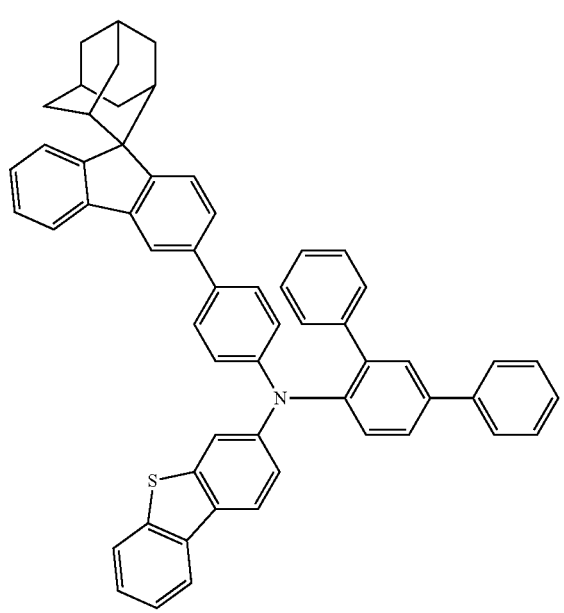
182
-continued
398
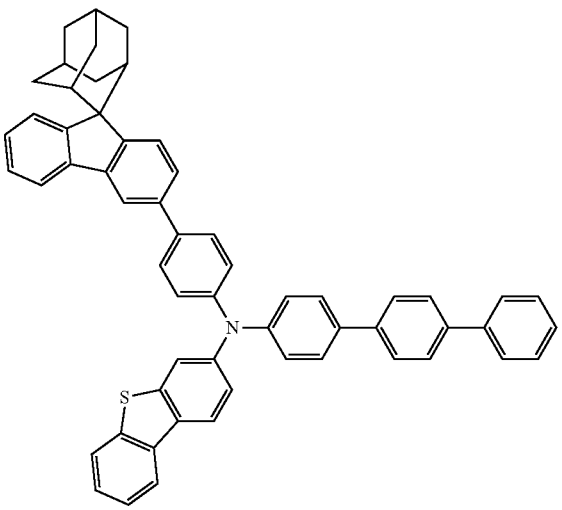
399
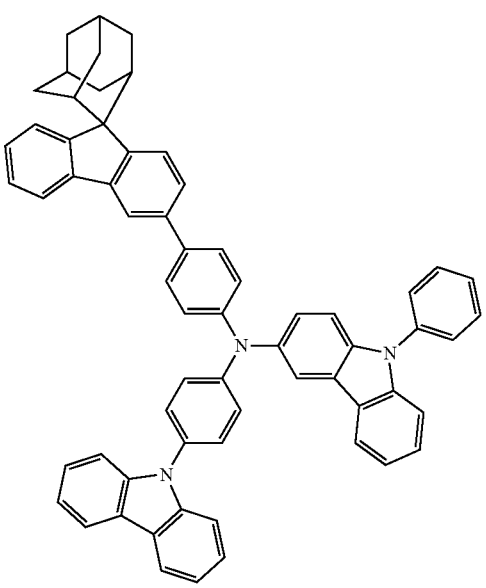

183
-continued
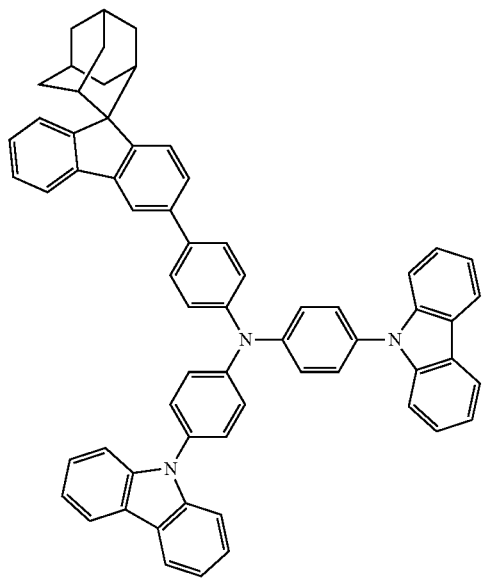
400
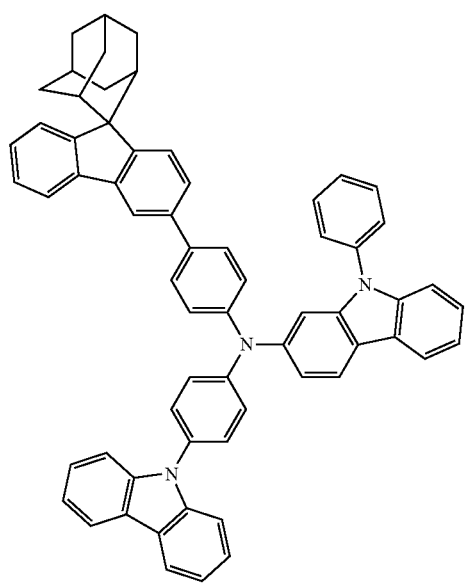
401
184
-continued
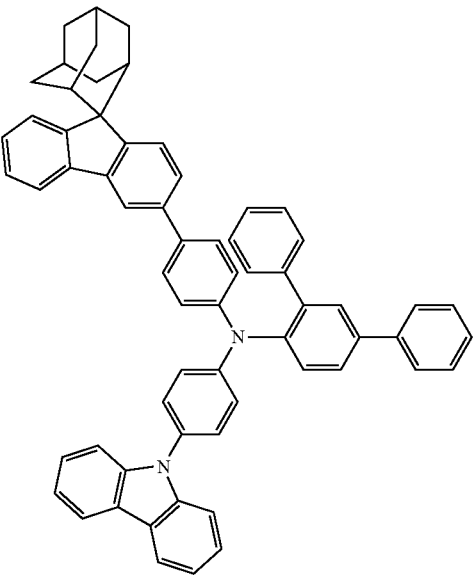
402
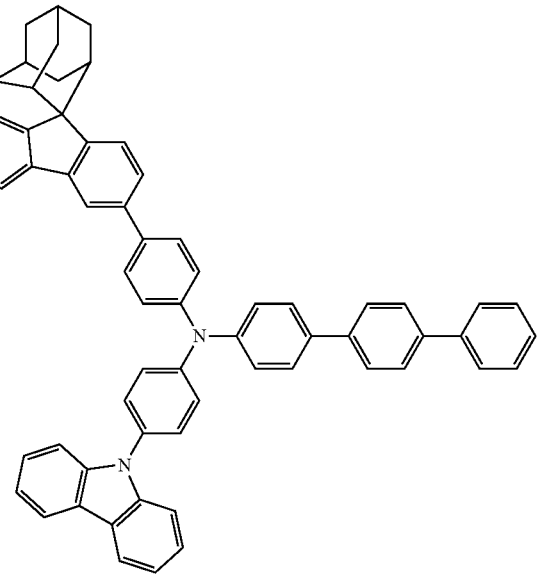
403

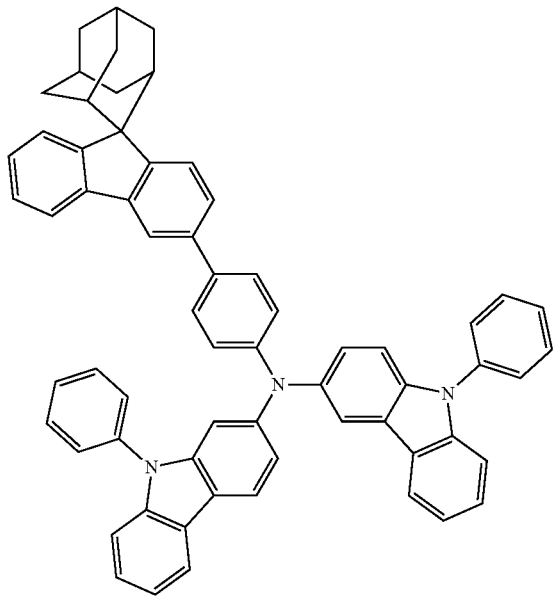
404
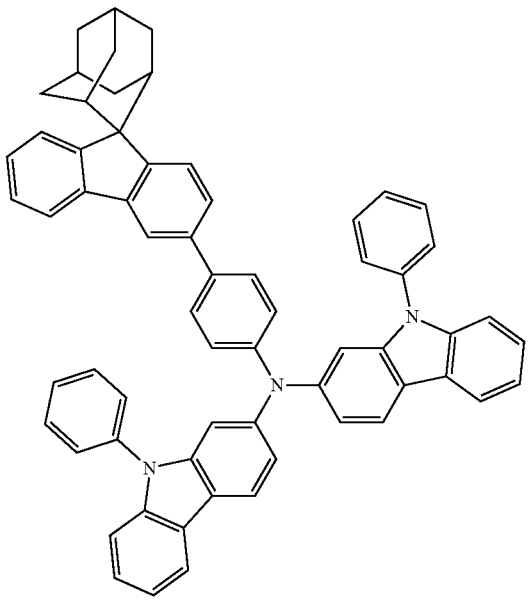
406
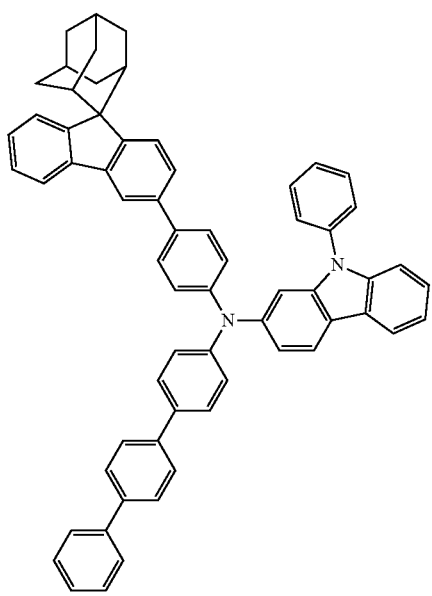
405
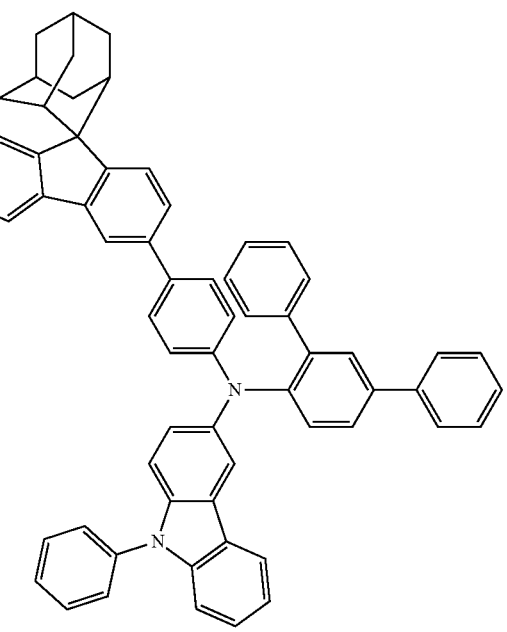
407

-continued
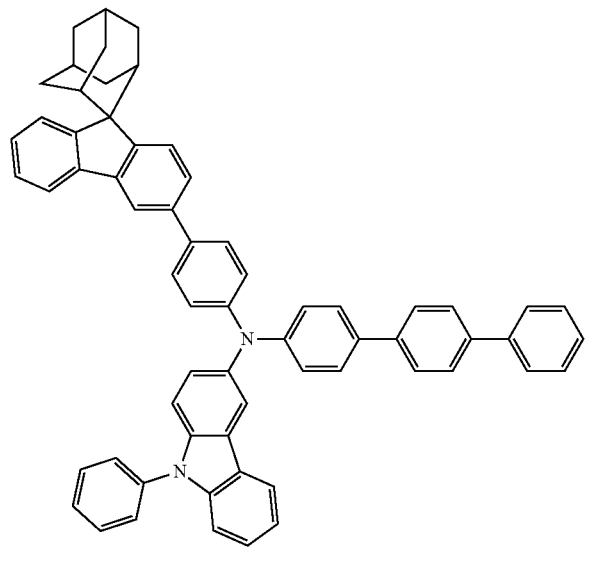
408
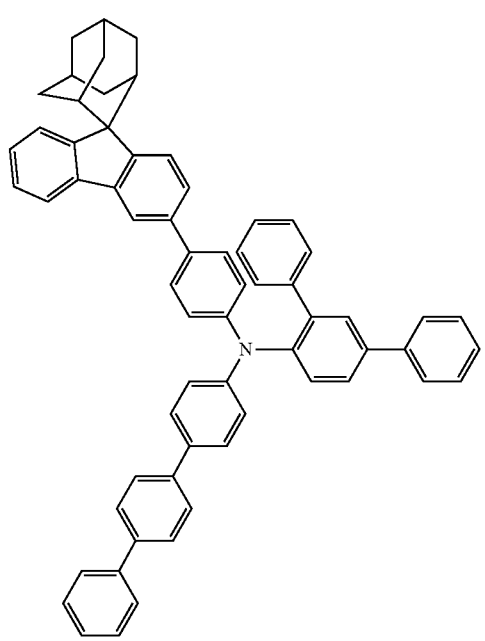
409
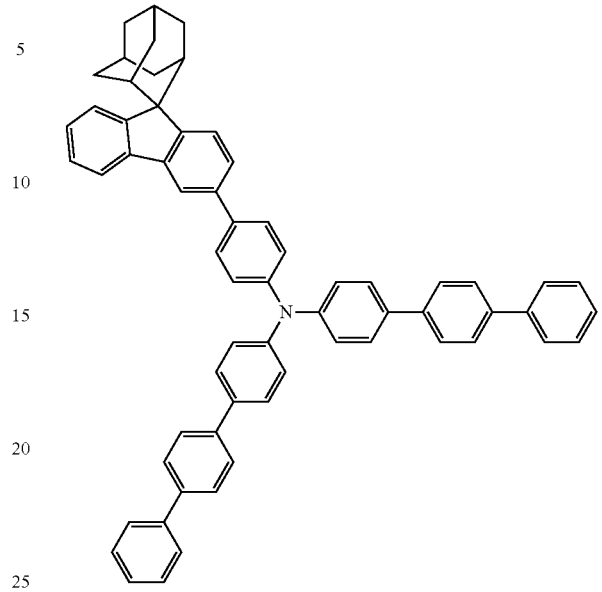
410
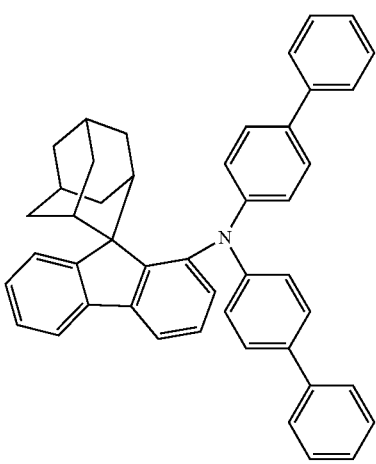
411
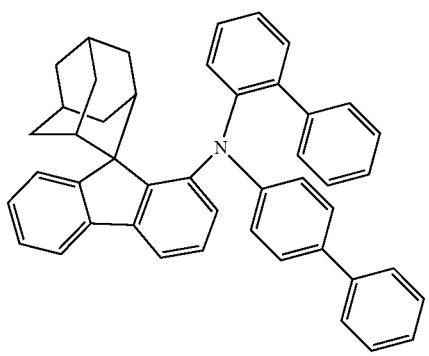
412

413
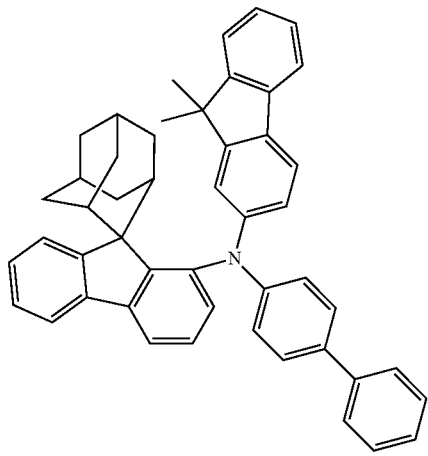
414
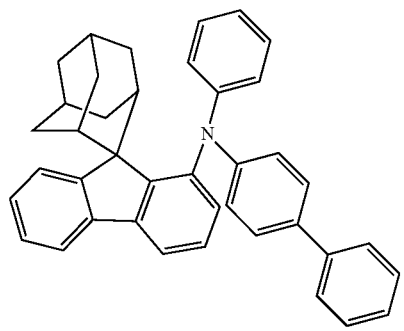
415
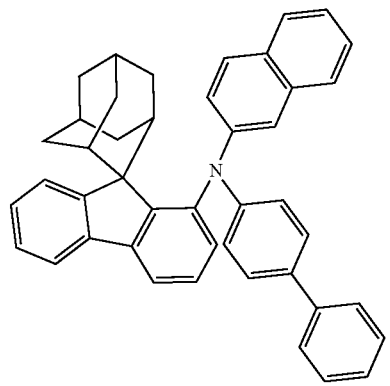
416
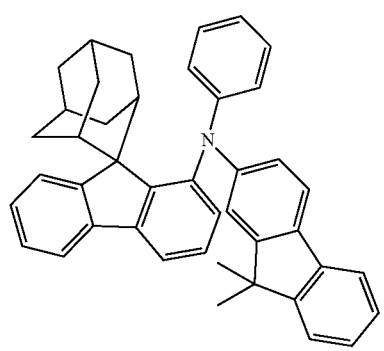
417
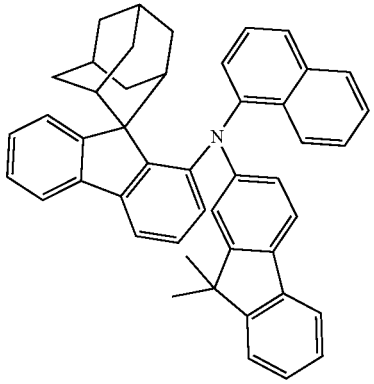
418
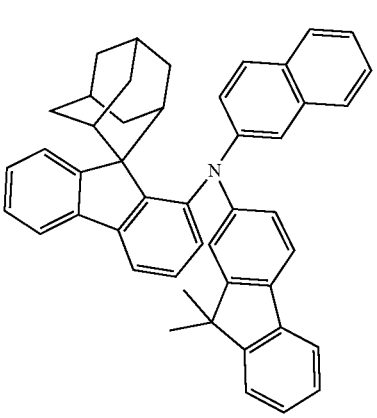
419
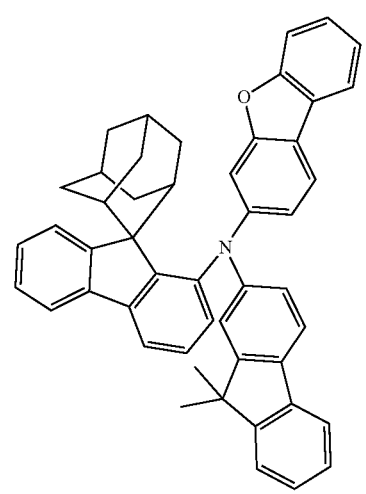

191
-continued
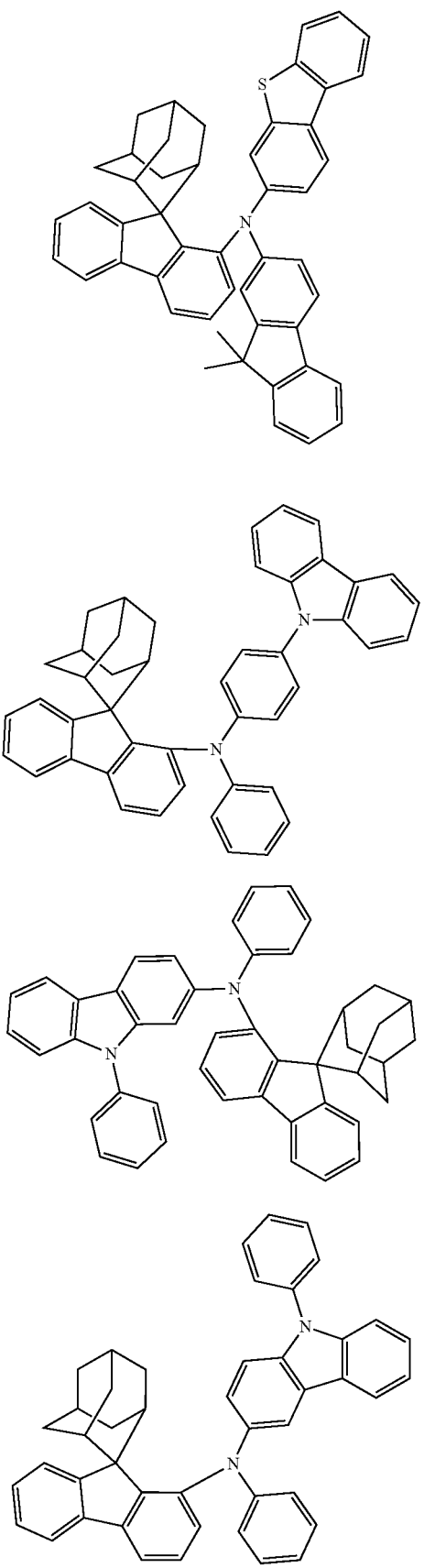
420
421
422
423
192
-continued
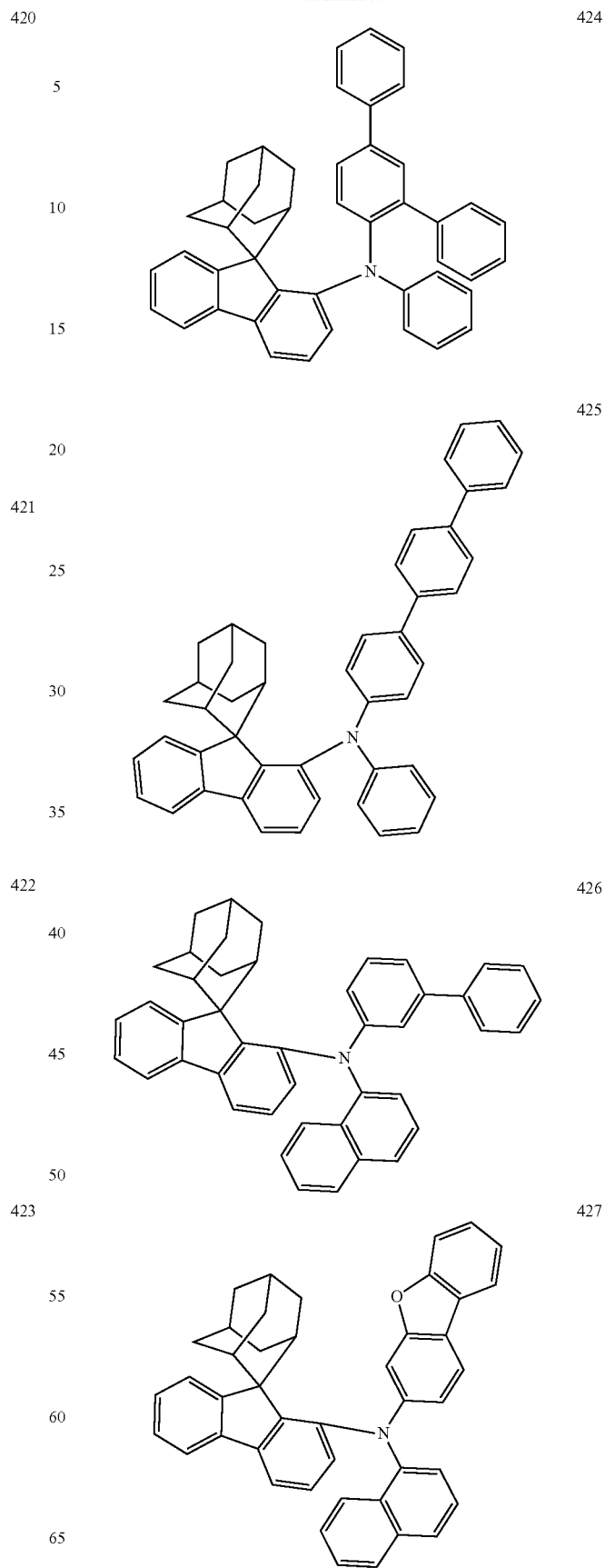
424
425
426
427

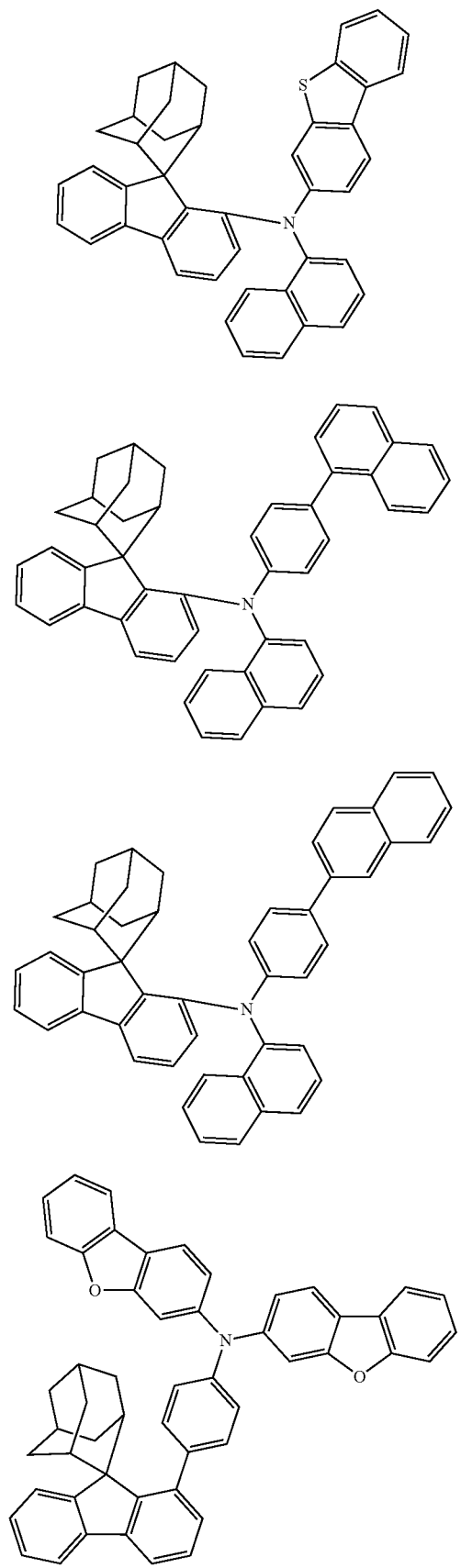
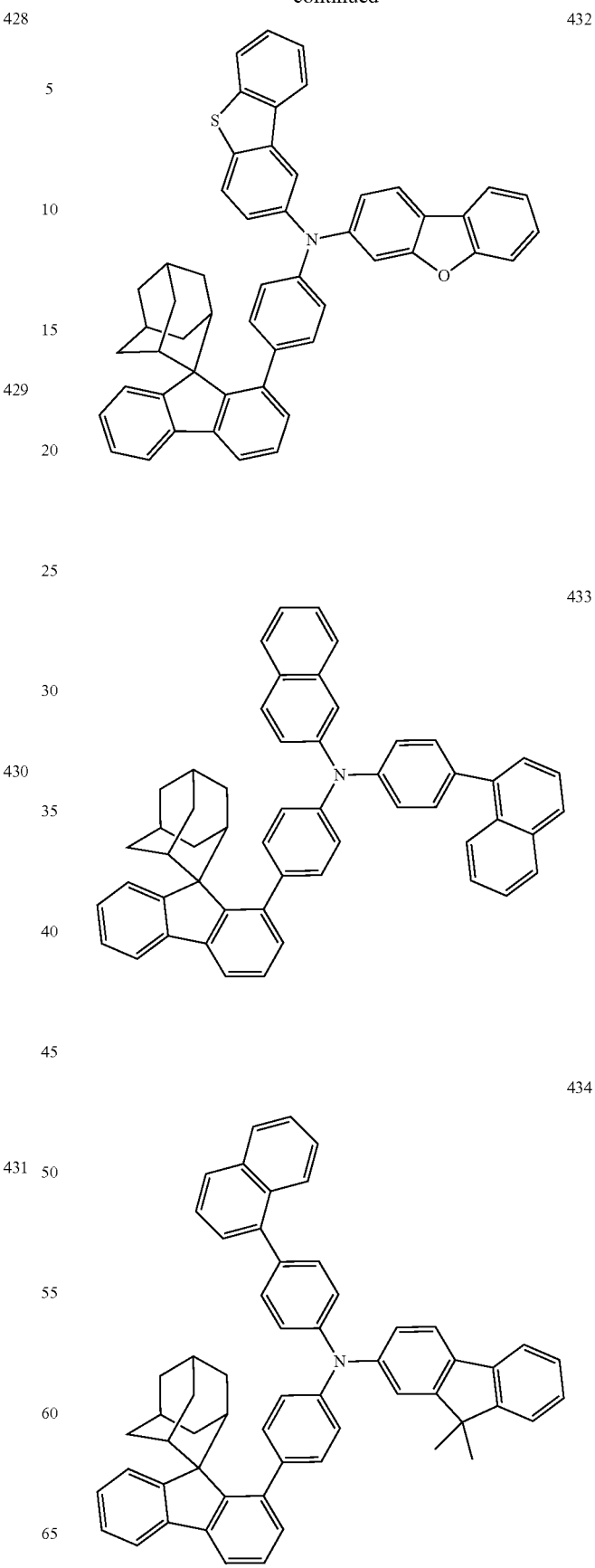

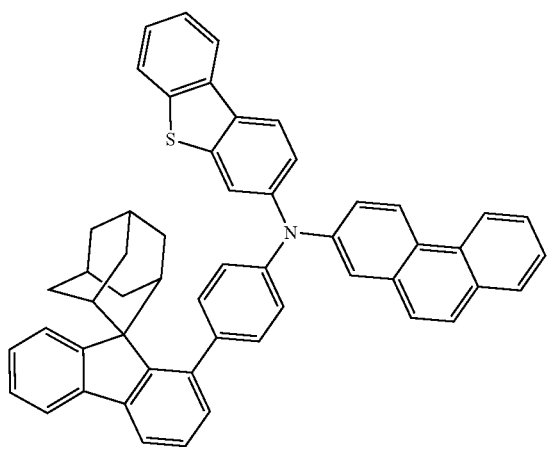
435
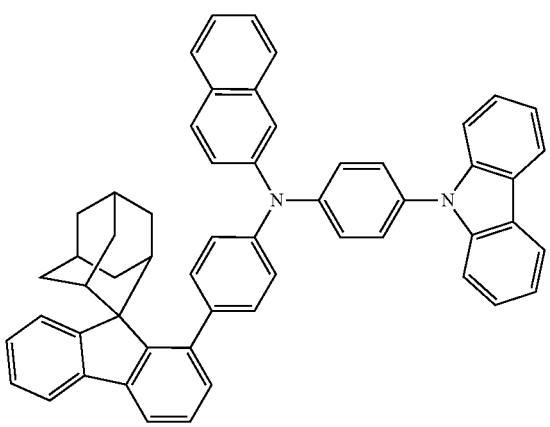
438
436
439
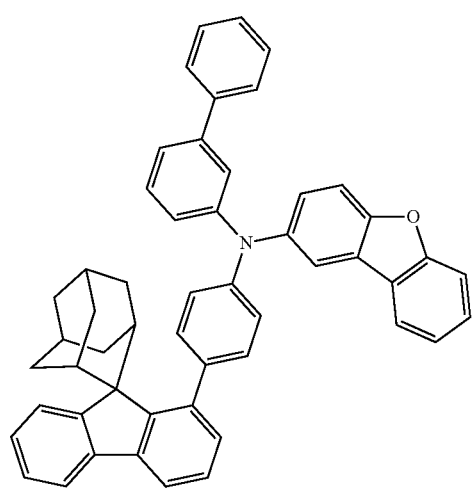
437
440

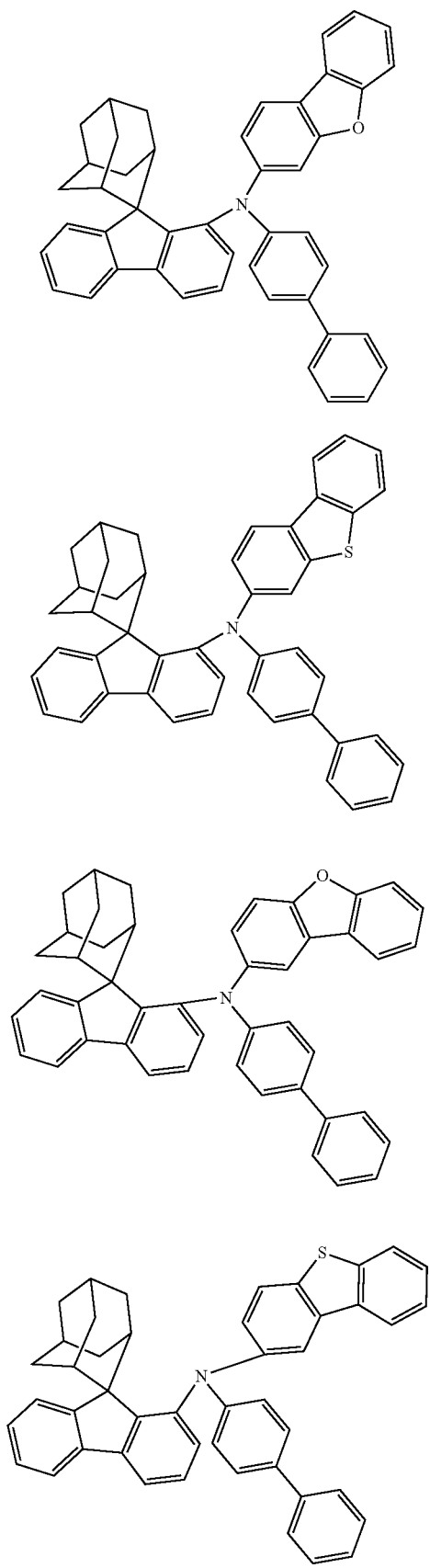
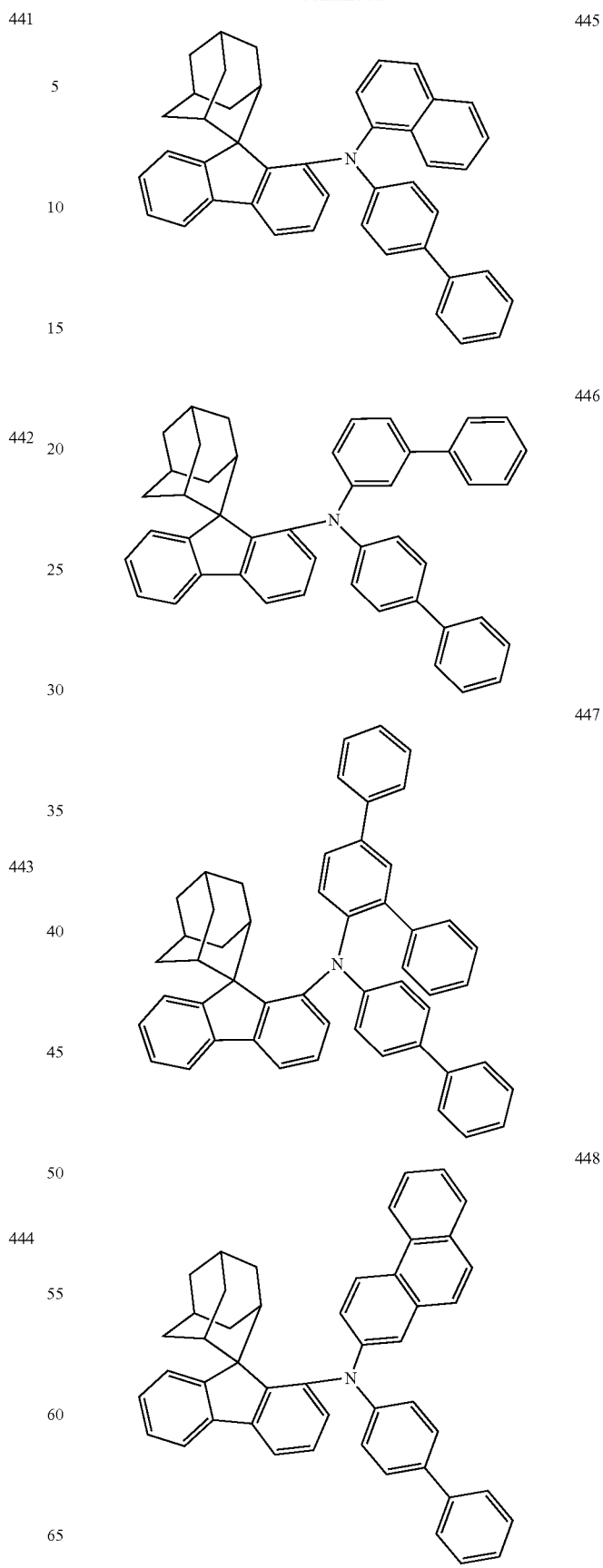

449
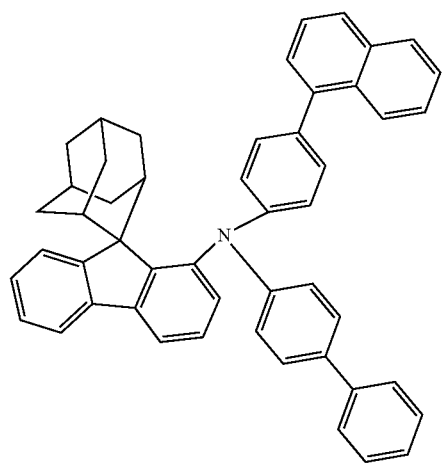
450
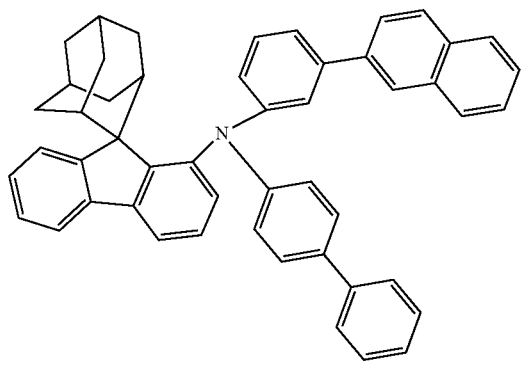
451
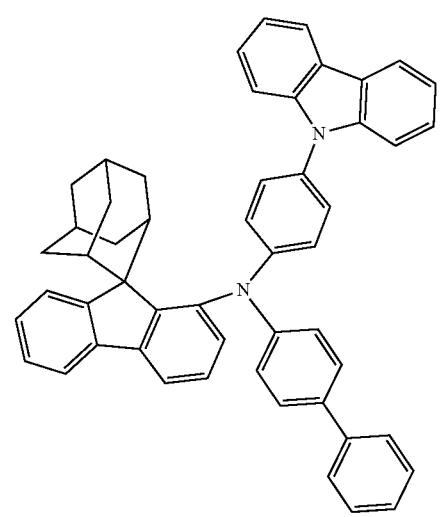
452
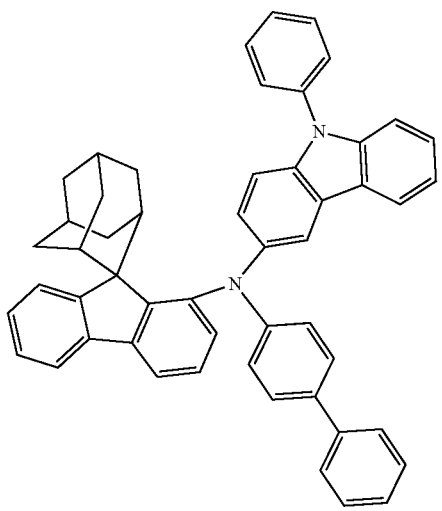
453
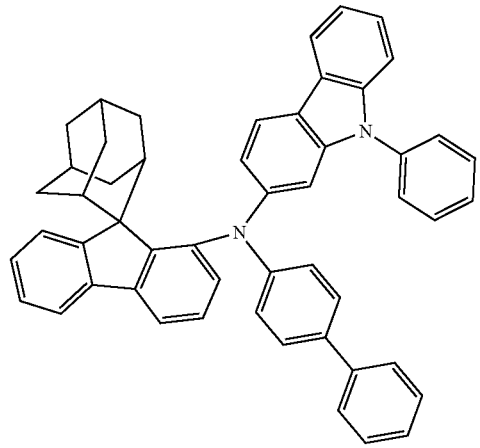
454
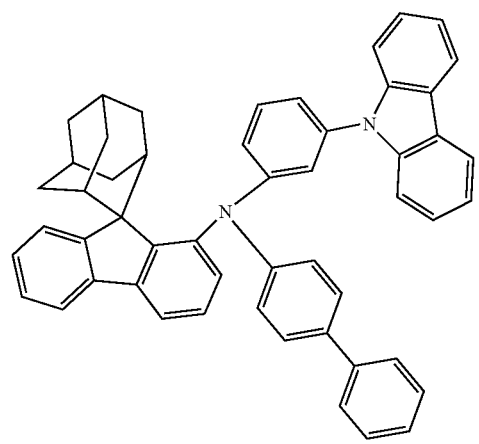

201
-continued
455
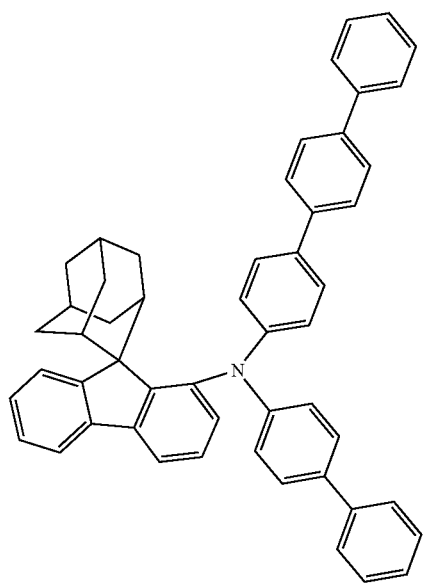
456
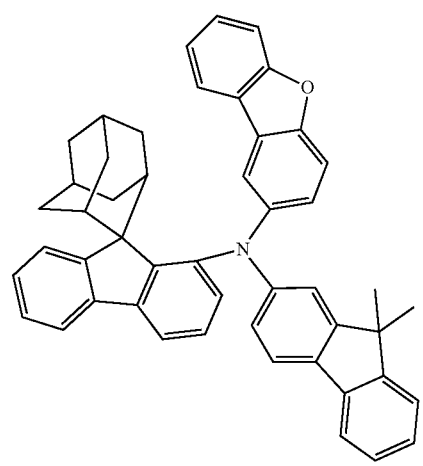
457
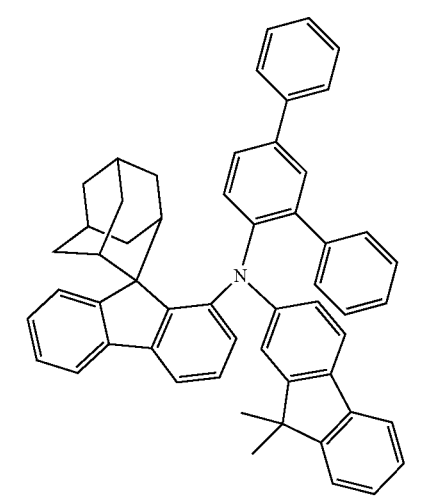
202
-continued
458
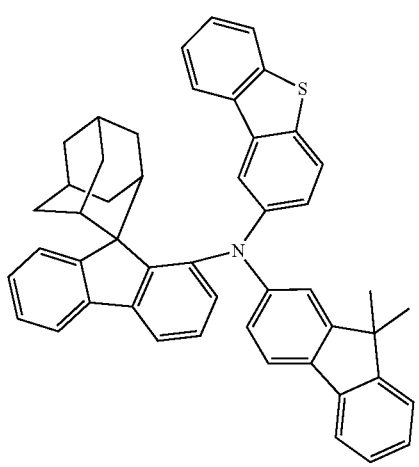
459
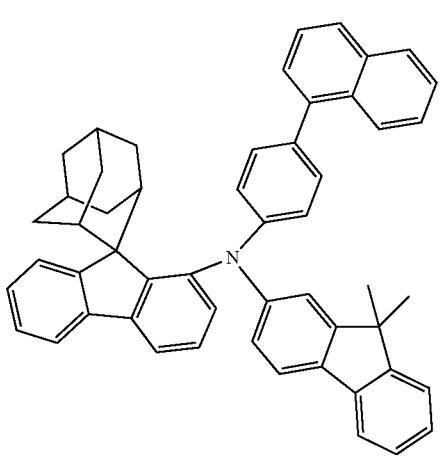
460
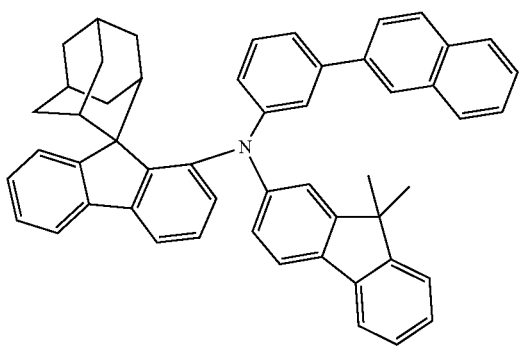

203
-continued
204
-continued
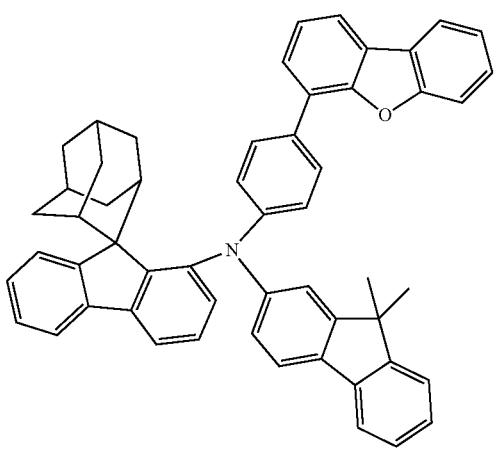
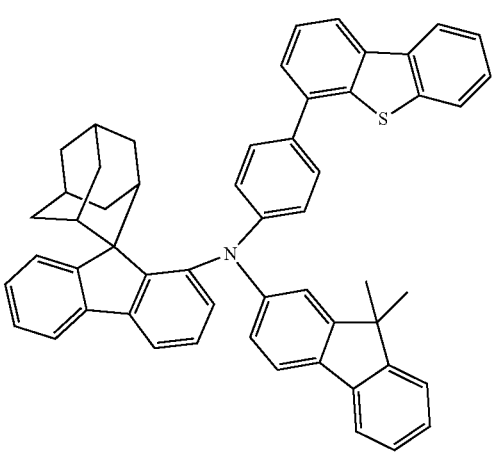

467 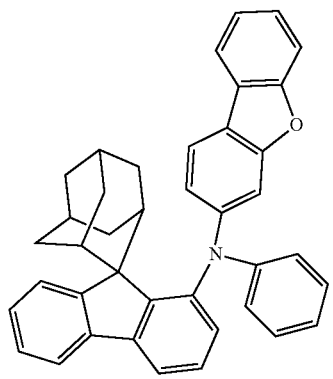
468 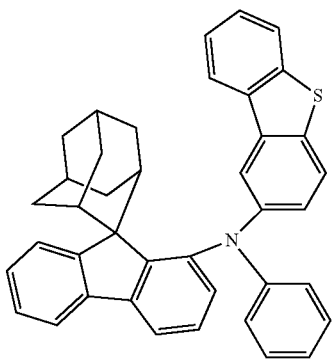
469 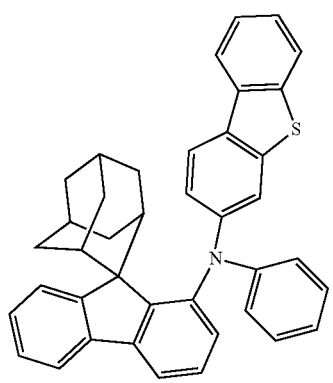
470 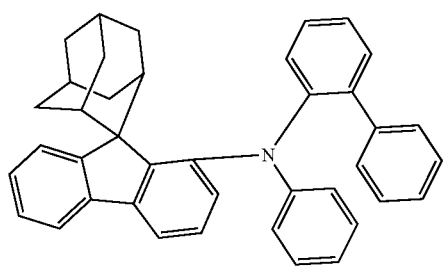
471 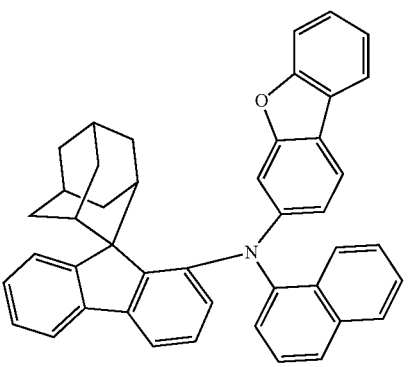
472 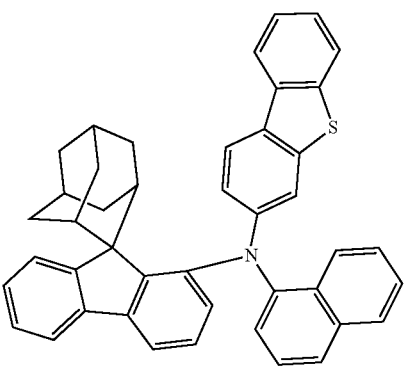
473 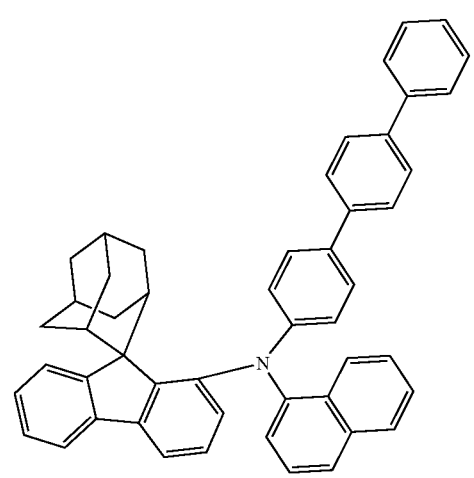
474 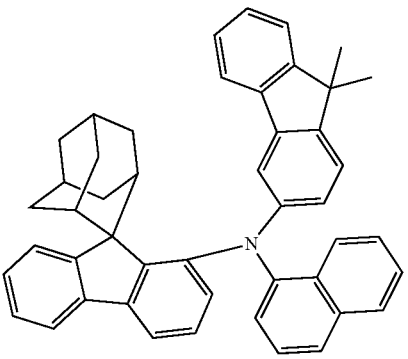

-continued
475
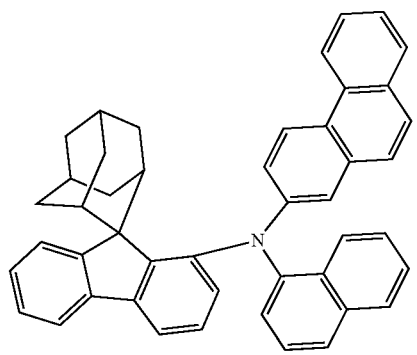
476
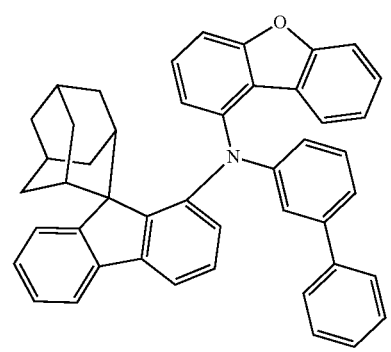
477
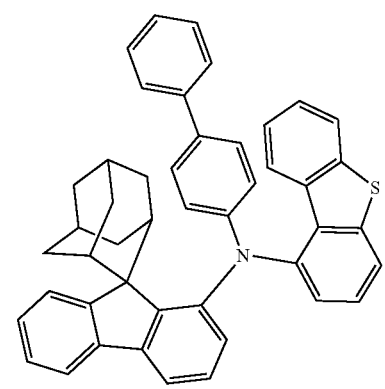
478
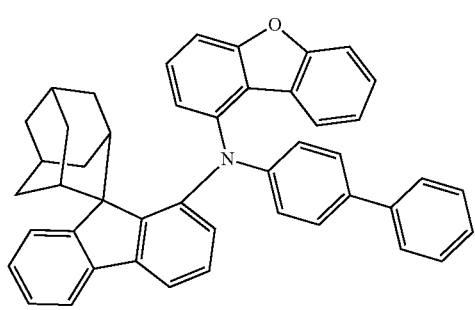
-continued
479
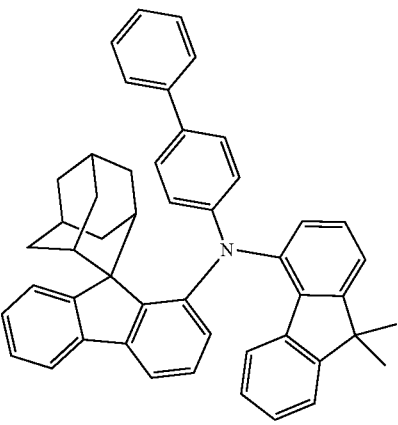
480
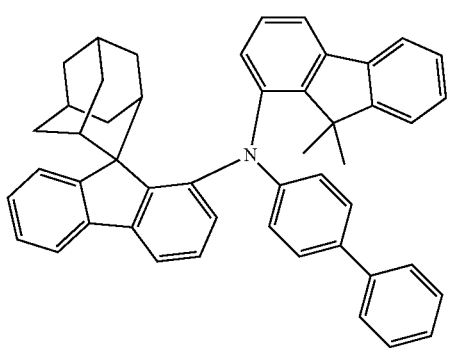
481
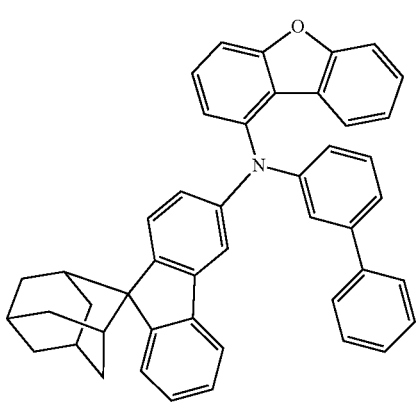
482
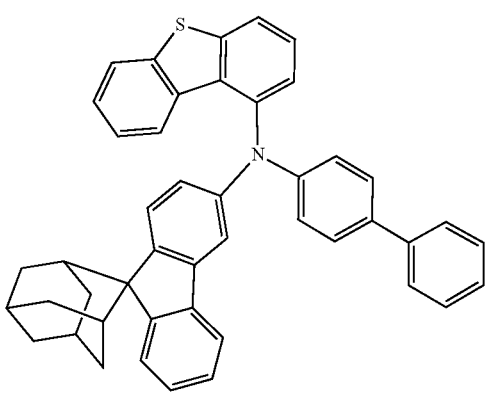

483
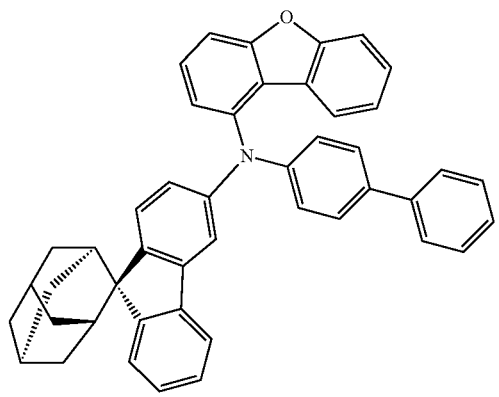
484
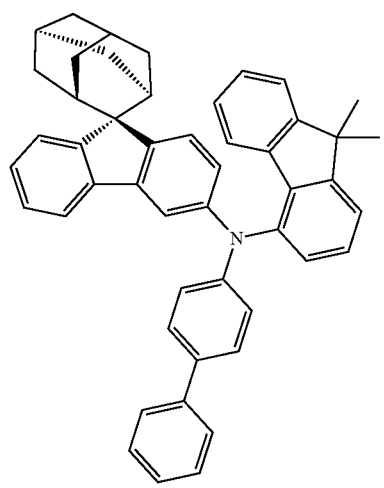
485
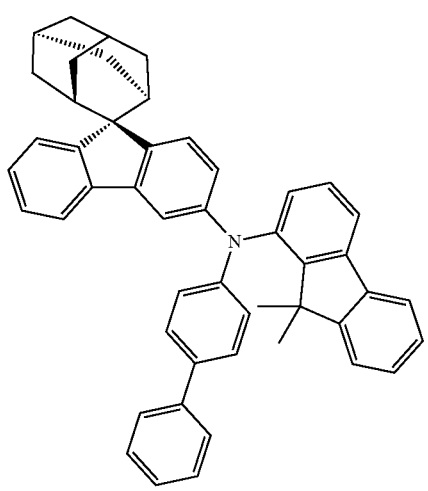
486
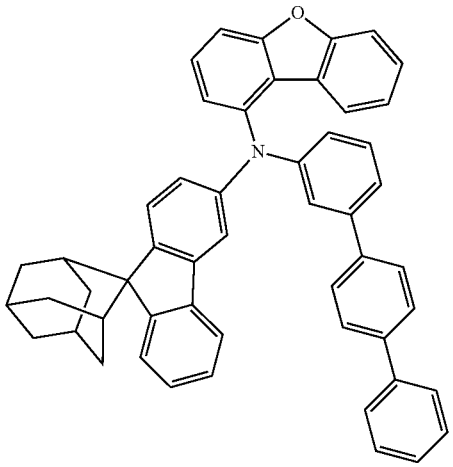
487
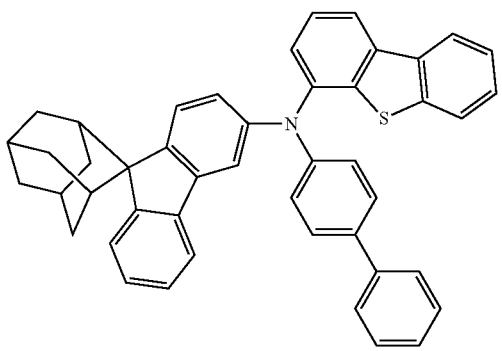
488
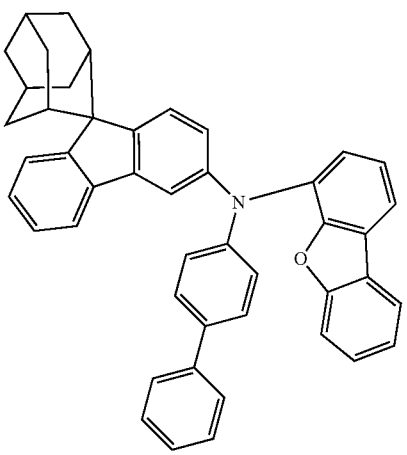

211
-continued
489
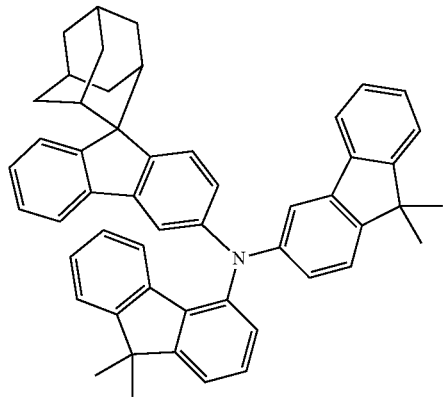
490
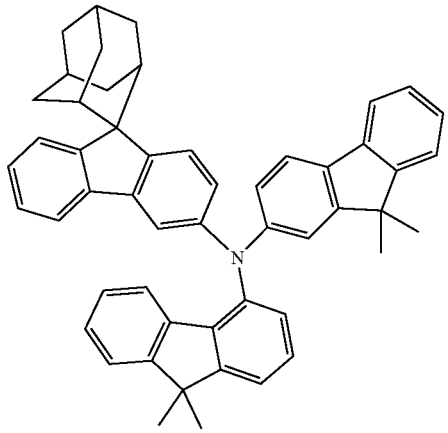
491
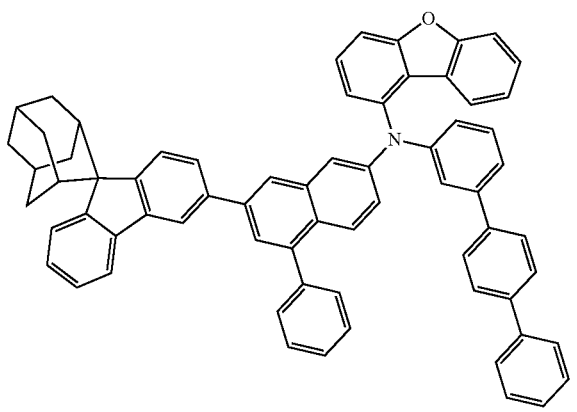
212
-continued
492
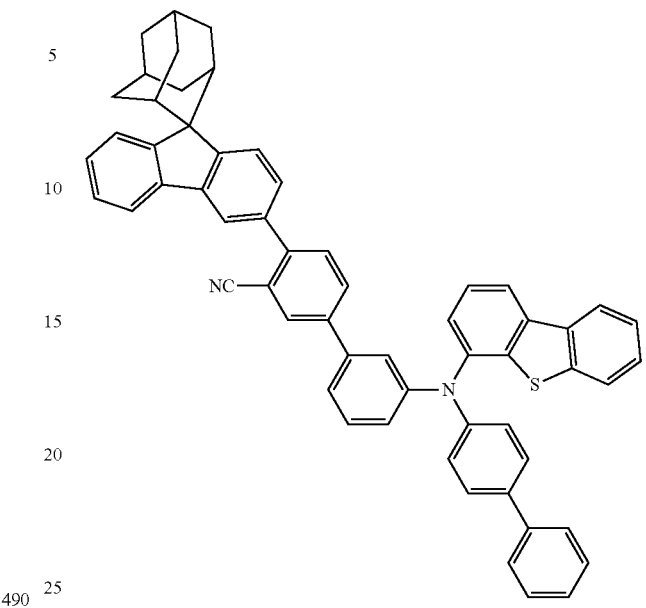
493
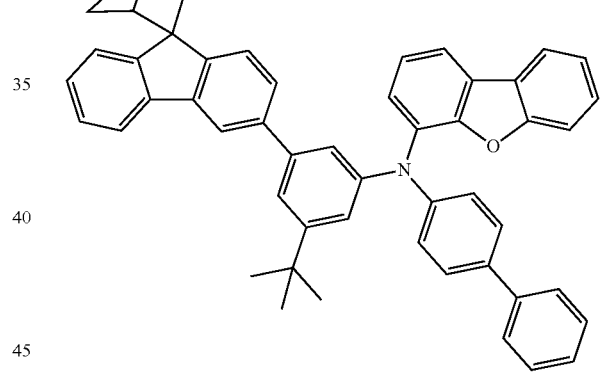
494
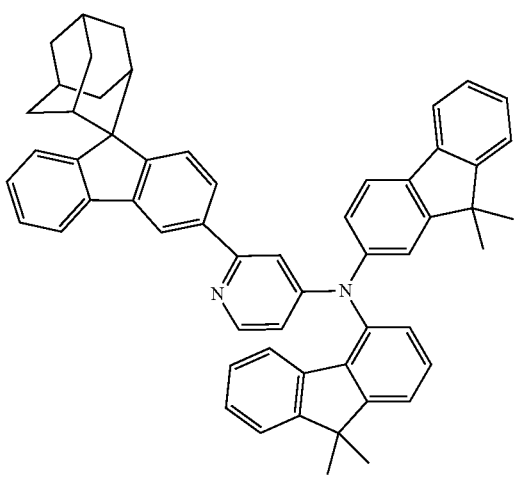

495
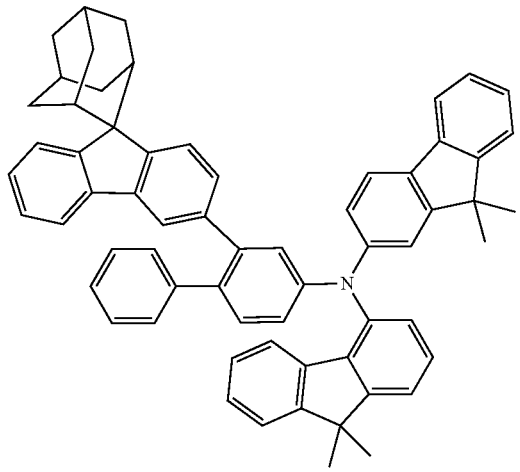
496
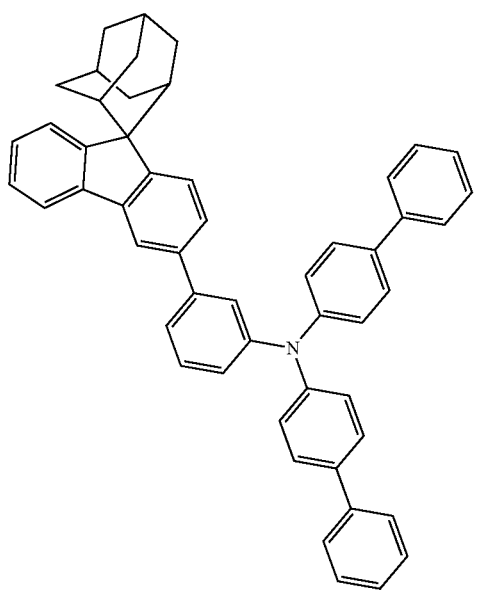
497
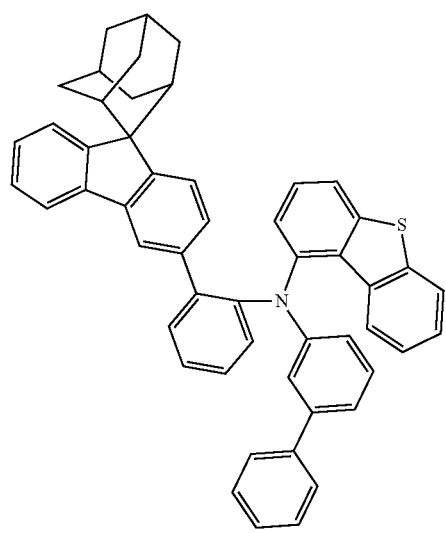
498
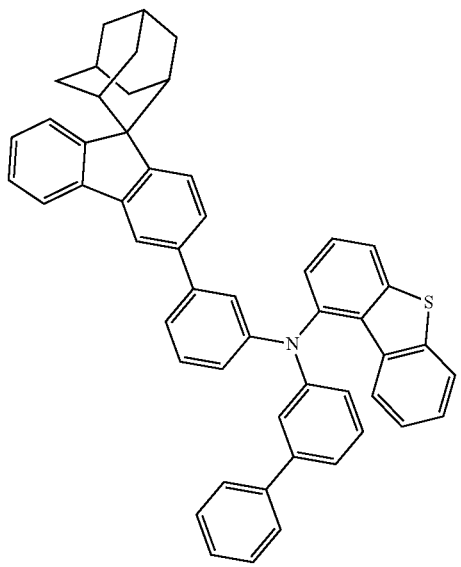
499
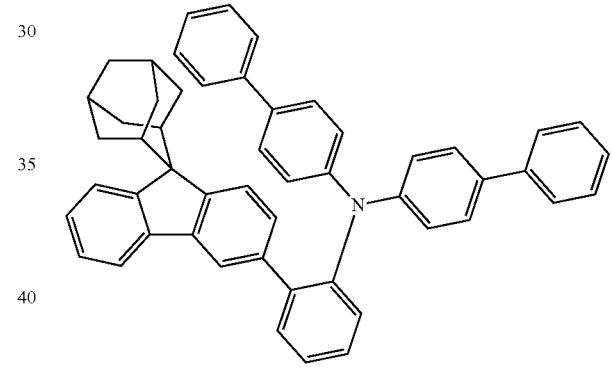
500
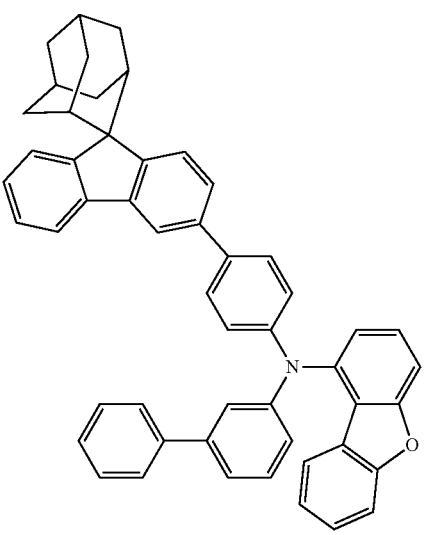

215
-continued
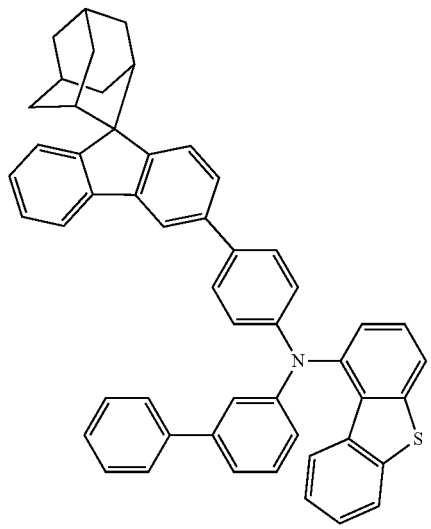
501
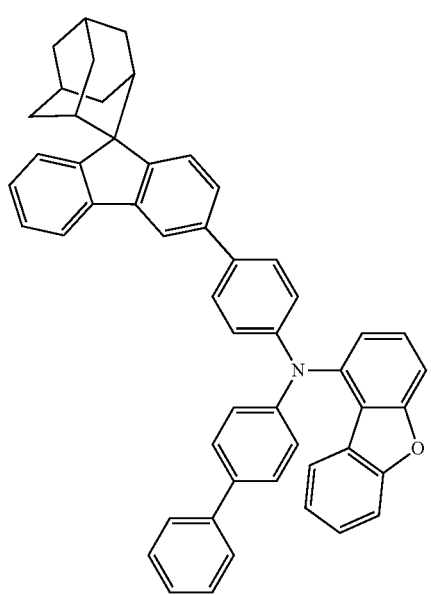
502
216
-continued
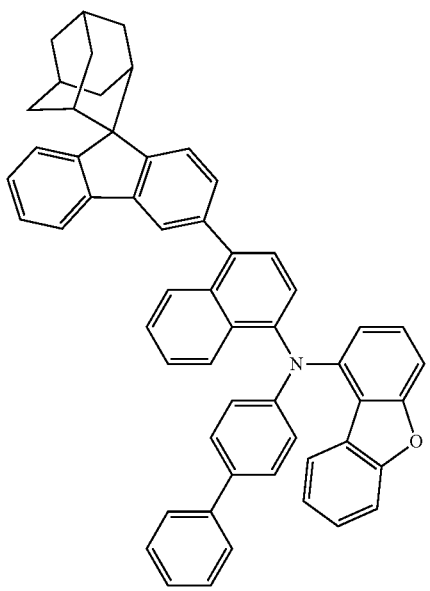
503
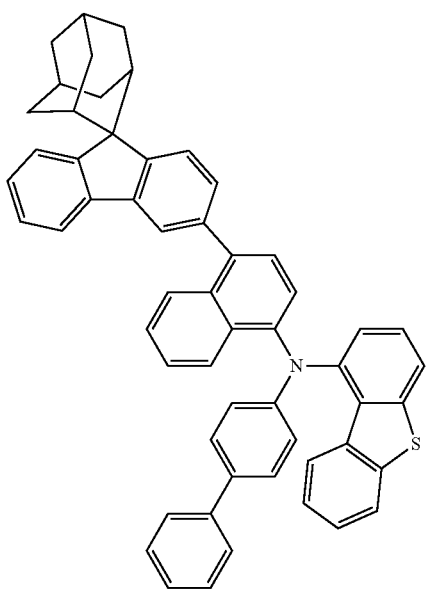
504

217
-continued
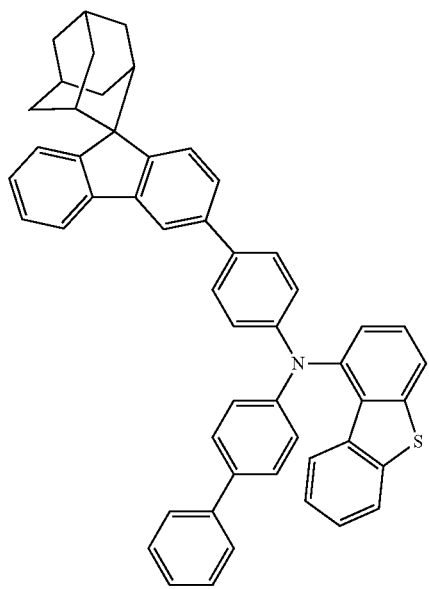
505
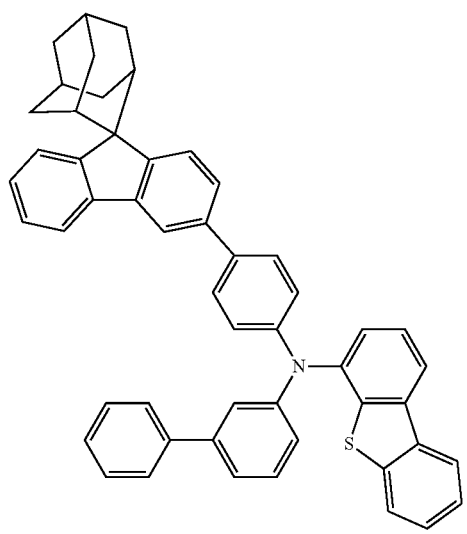
506
218
-continued
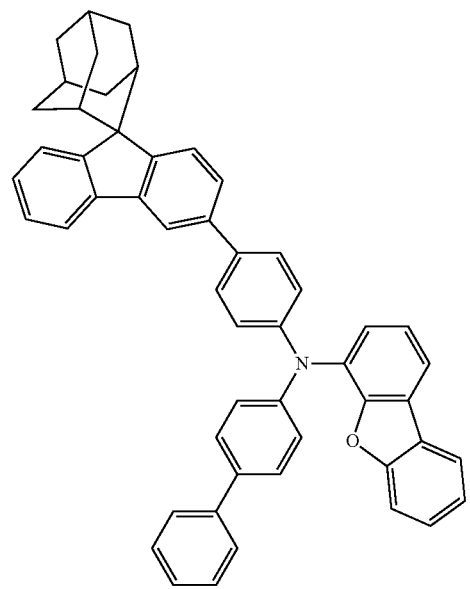
507
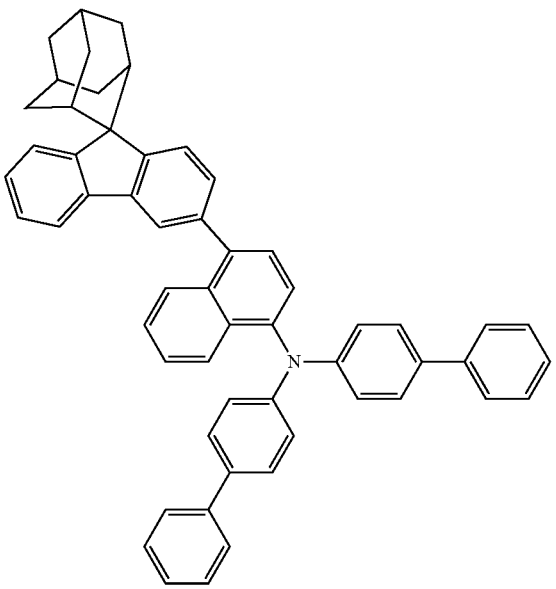
508

219
-continued
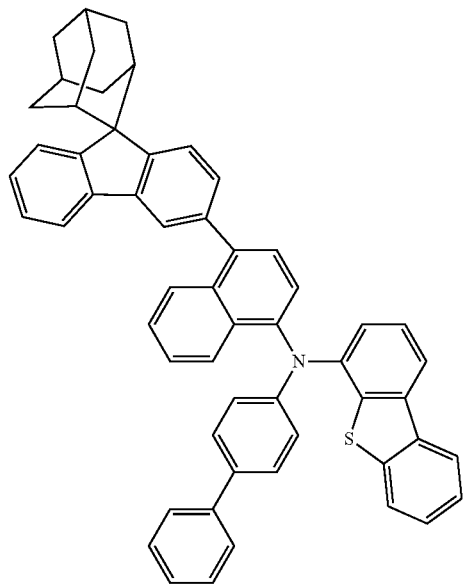
509
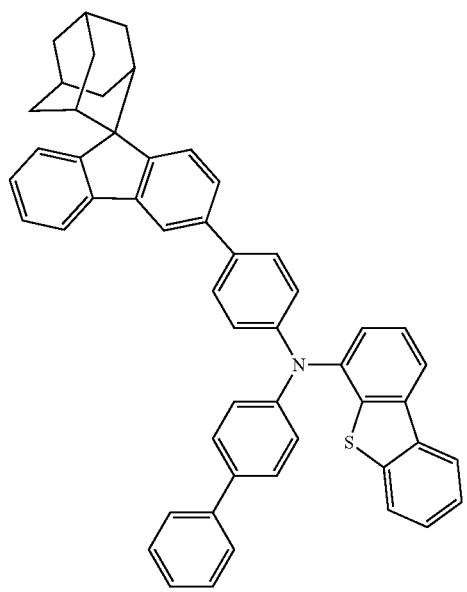
510
220
-continued
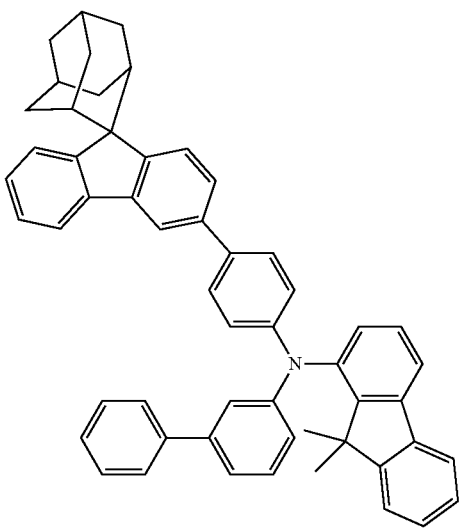
511
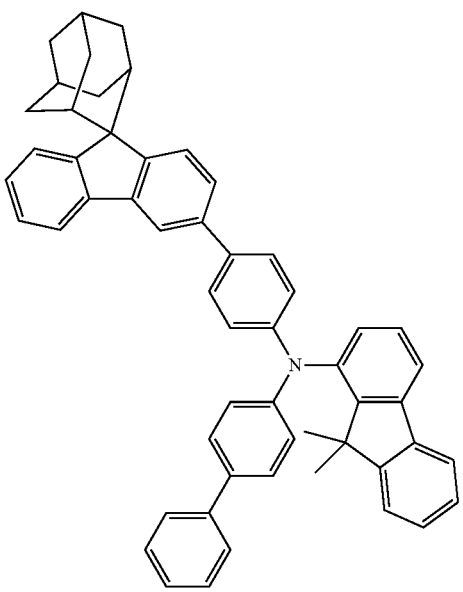
512

221
-continued
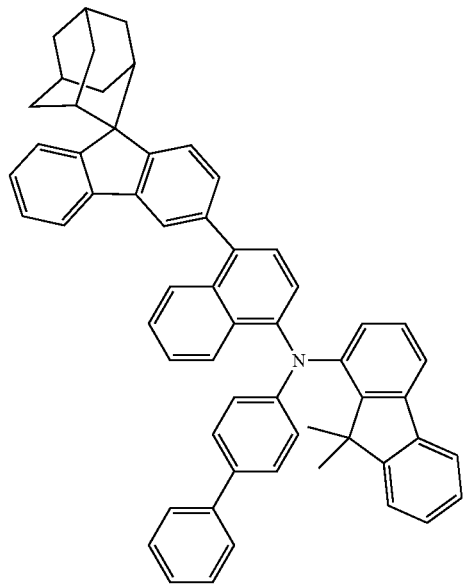
513
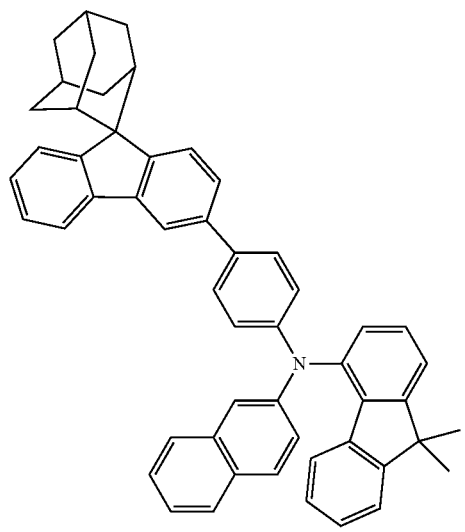
515
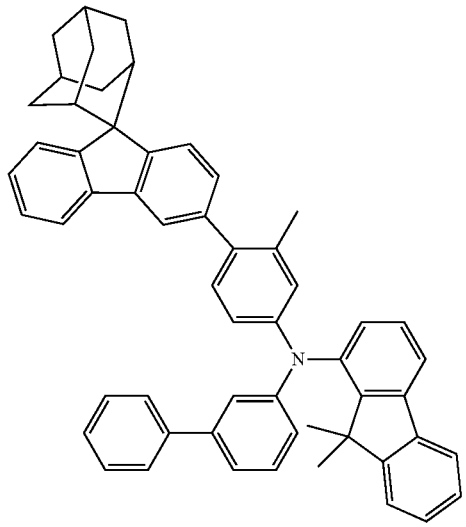
516
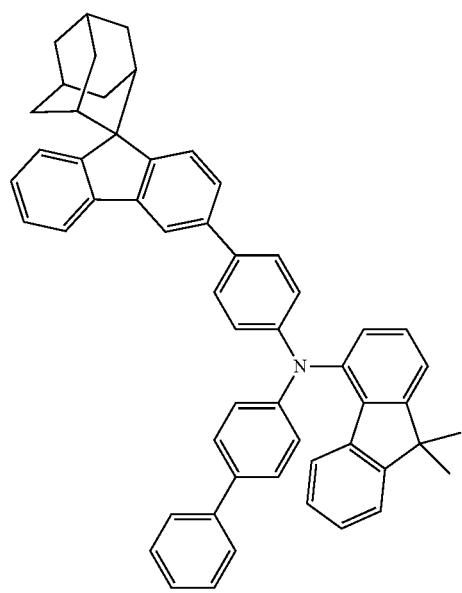
514
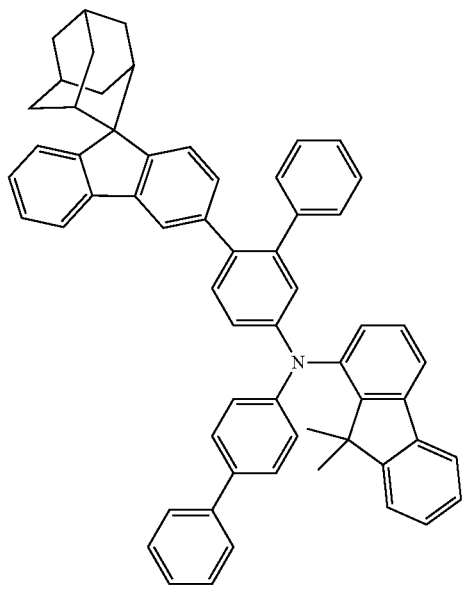
517
222
-continued

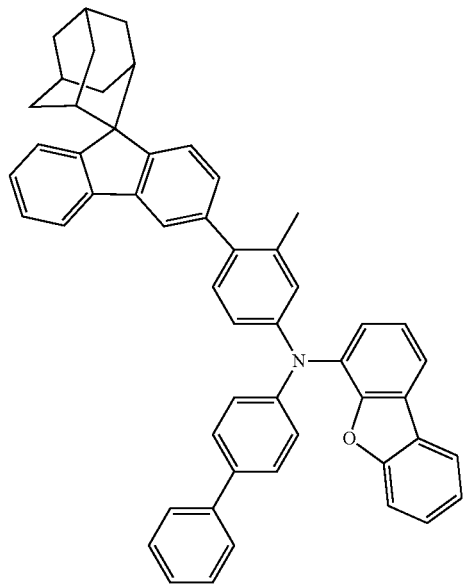
518
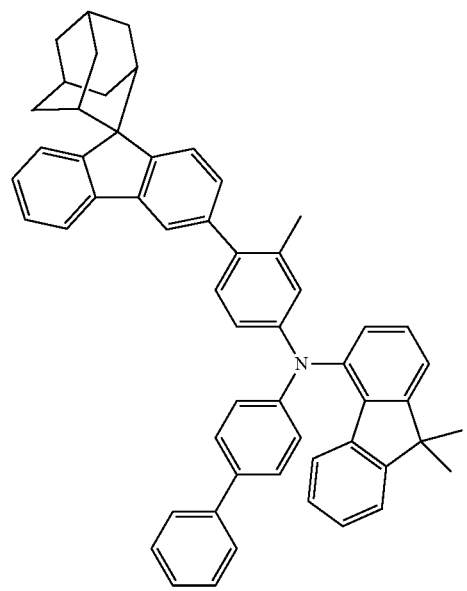
520
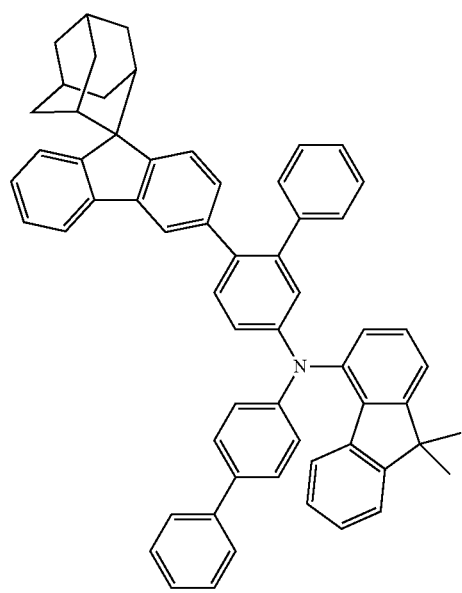
519
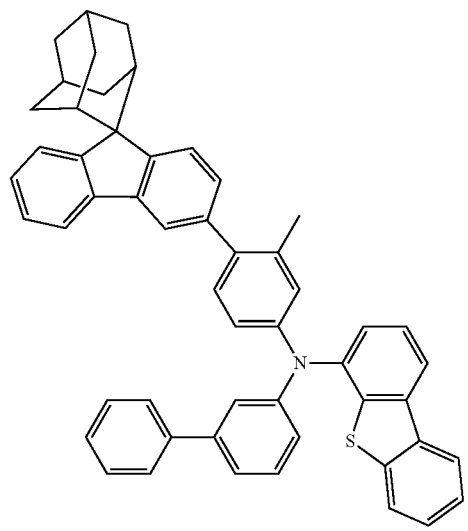
521

225
522
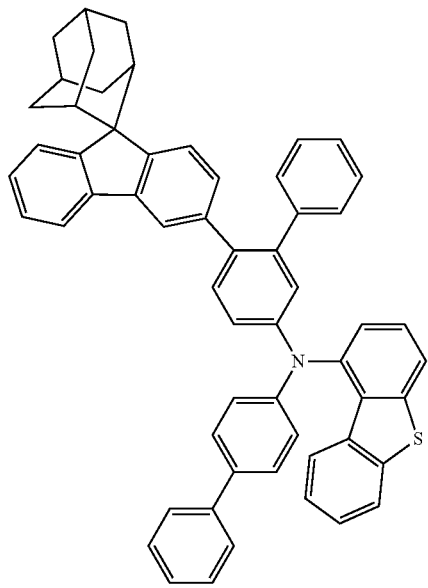
523
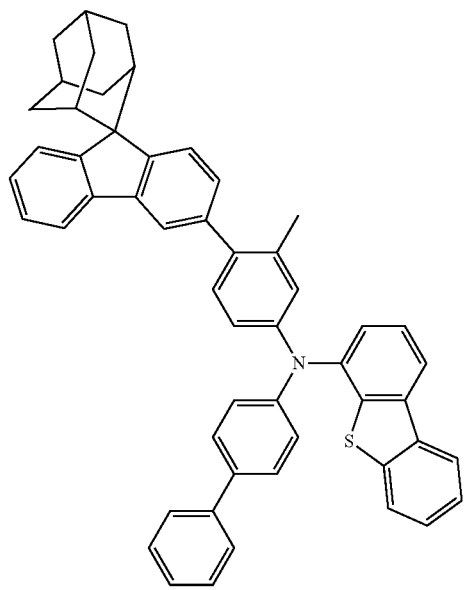
226
524
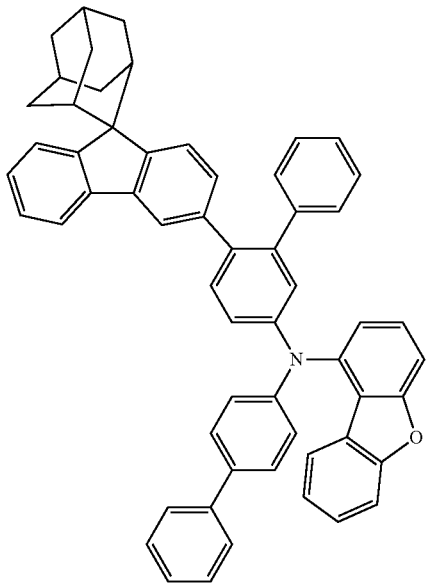
525
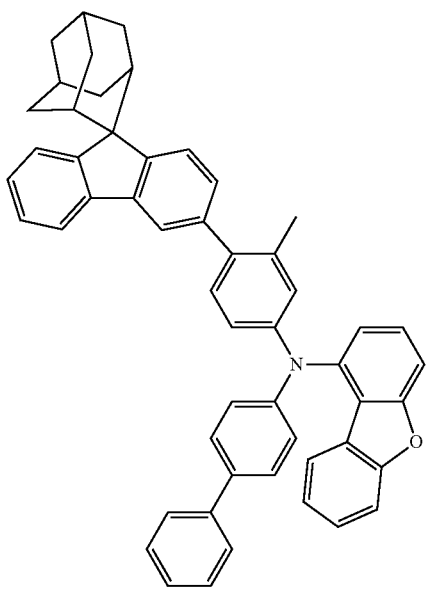

227
-continued
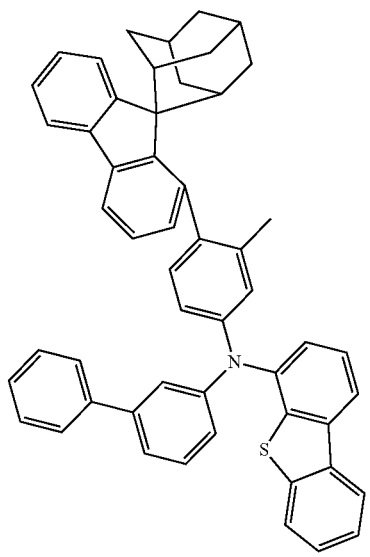
526
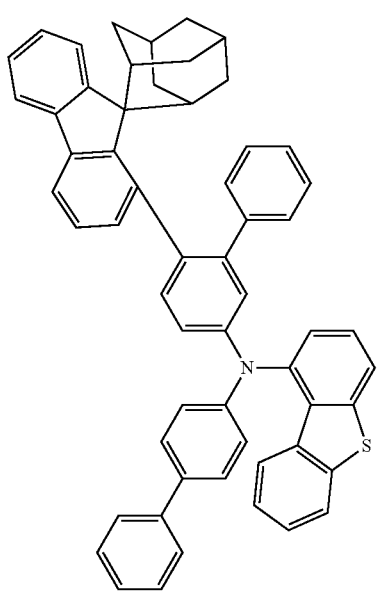
527
228
-continued
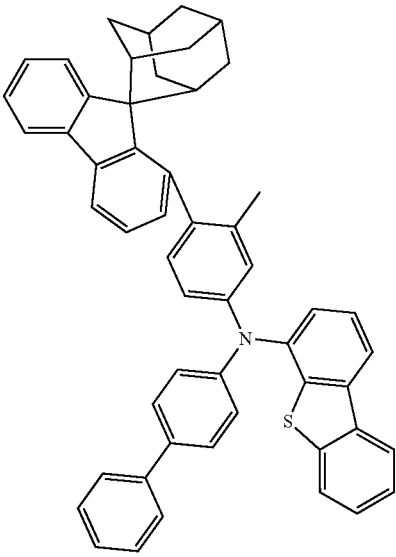
528
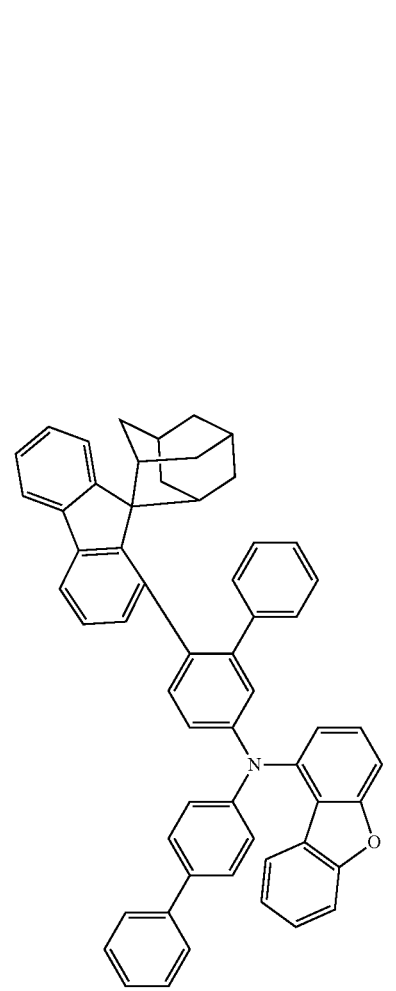
529

229
-continued
530
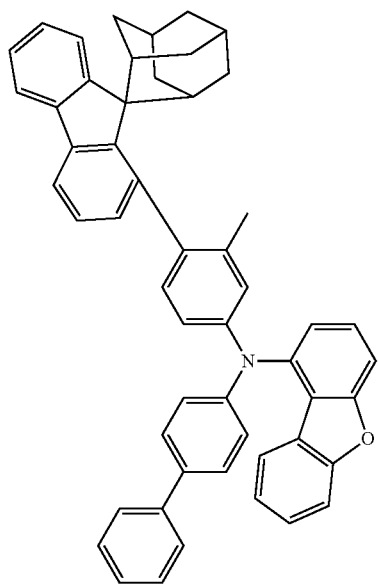
531
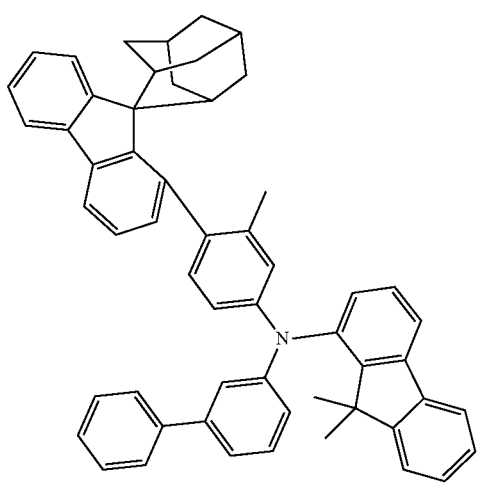
230
-continued
532
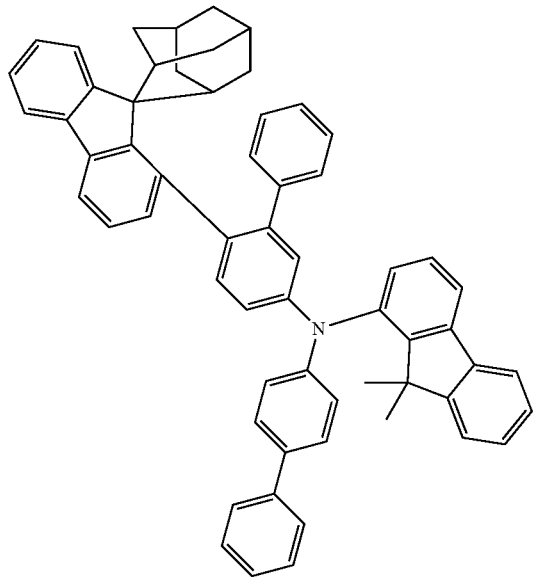
533
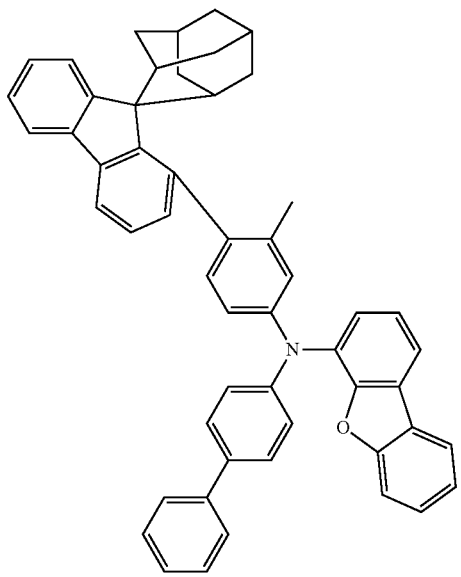

534
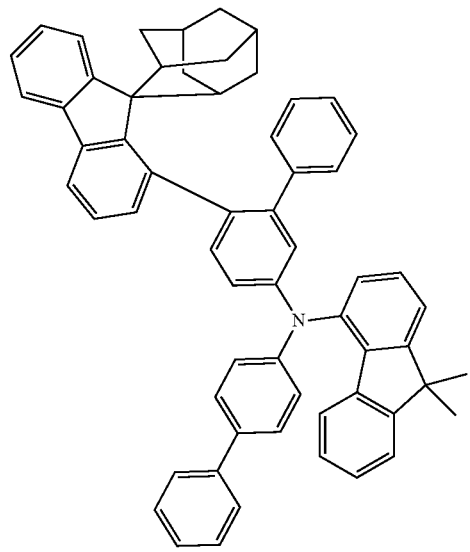
535
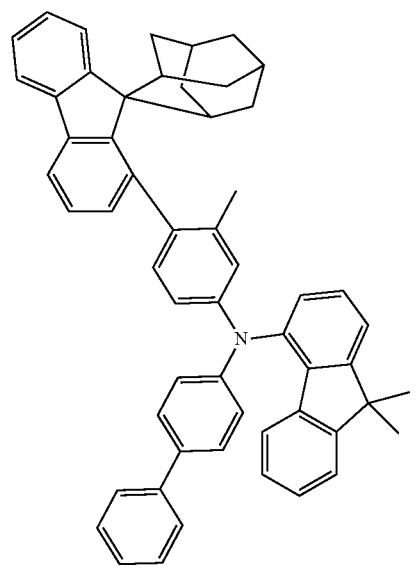
536
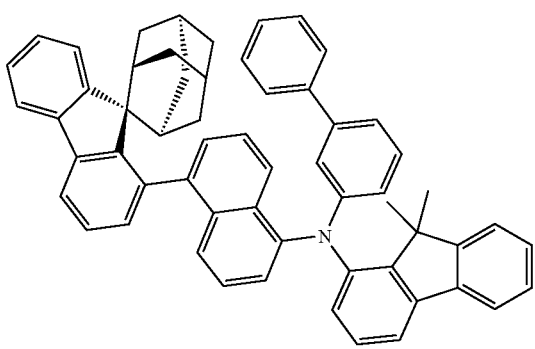
537
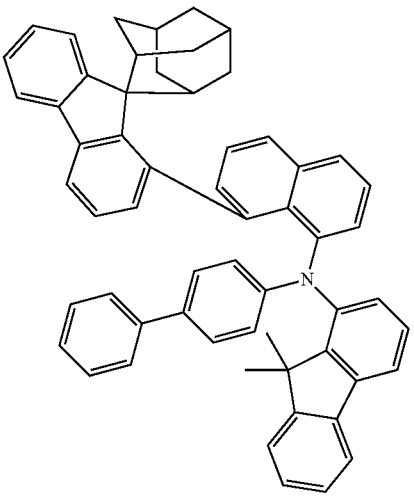
538
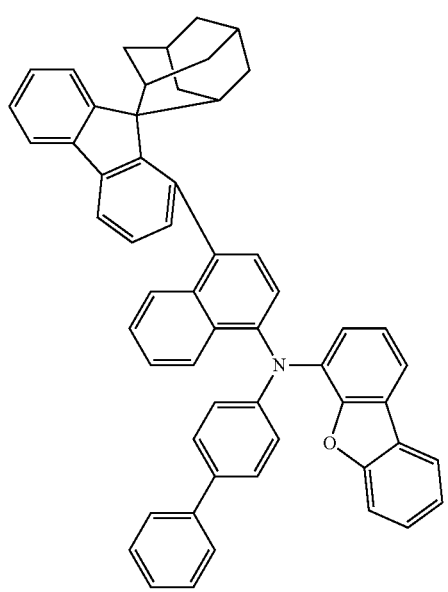
539
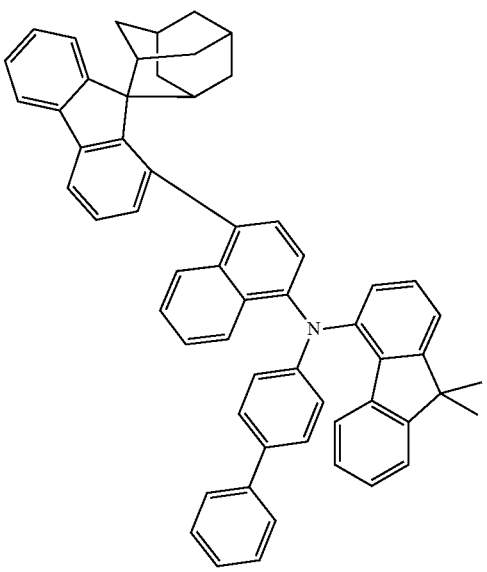

233
-continued
540
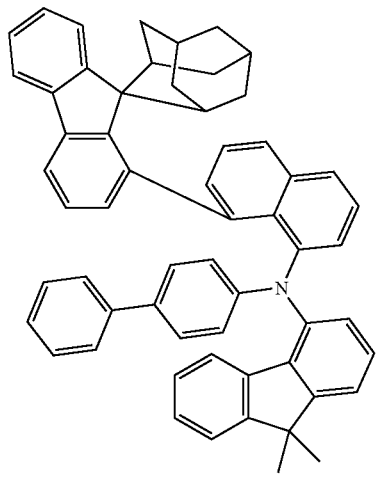
541
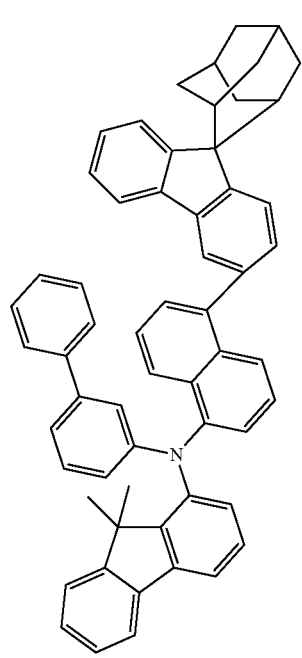
234
-continued
542
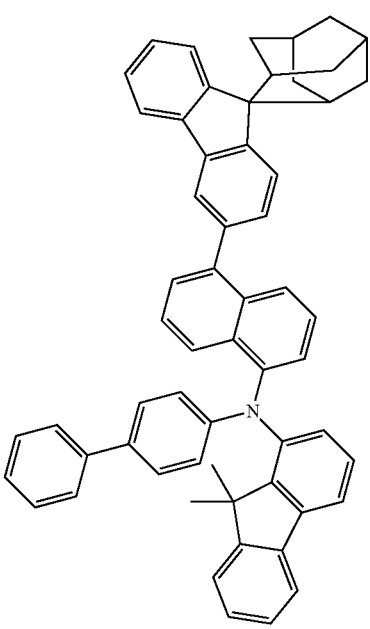
543
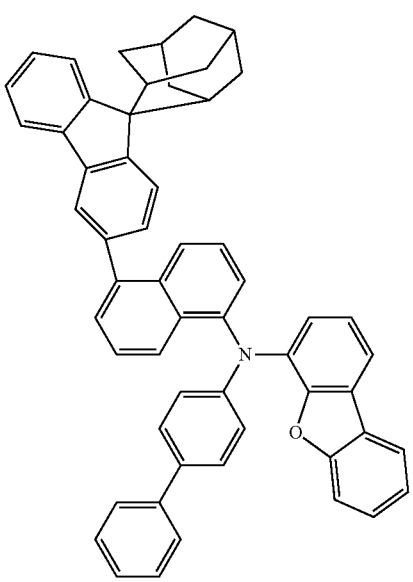

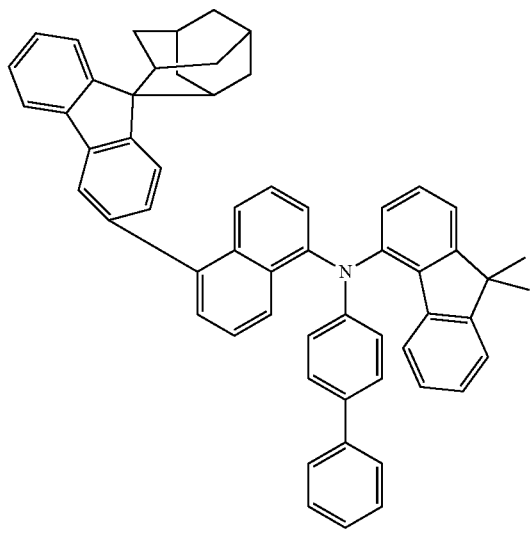
544
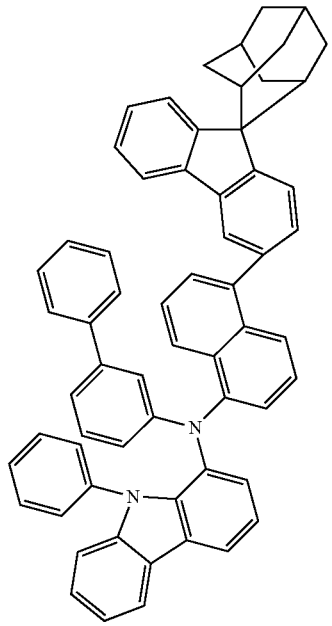
546
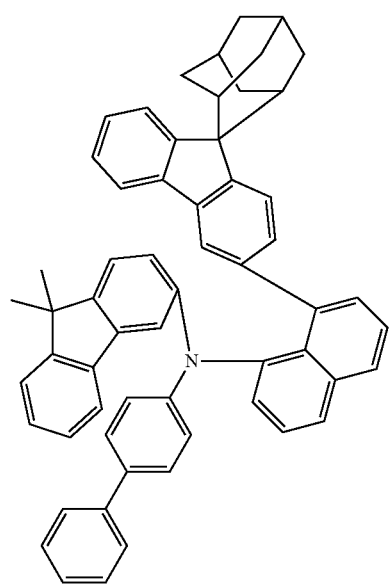
545
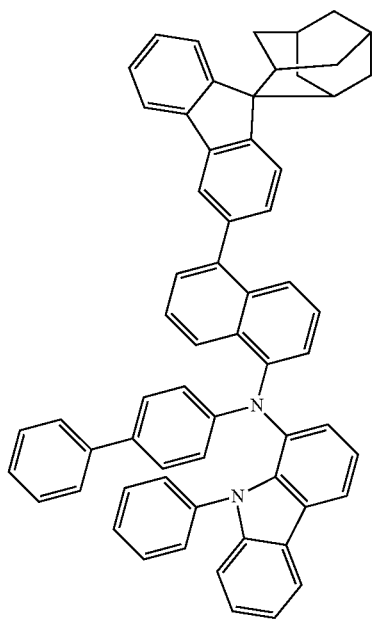
547

548
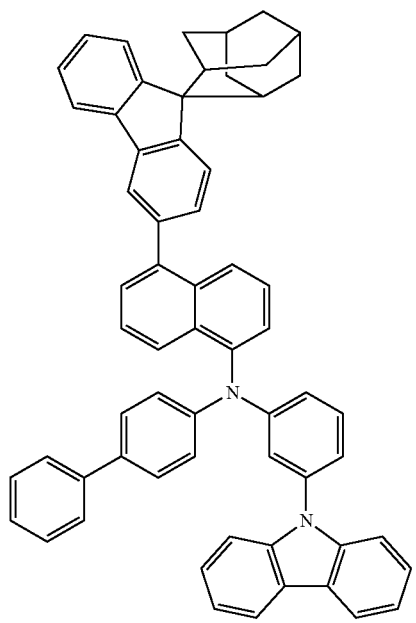
549
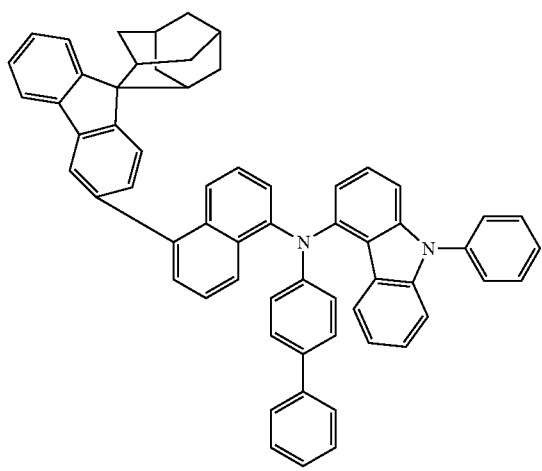
550
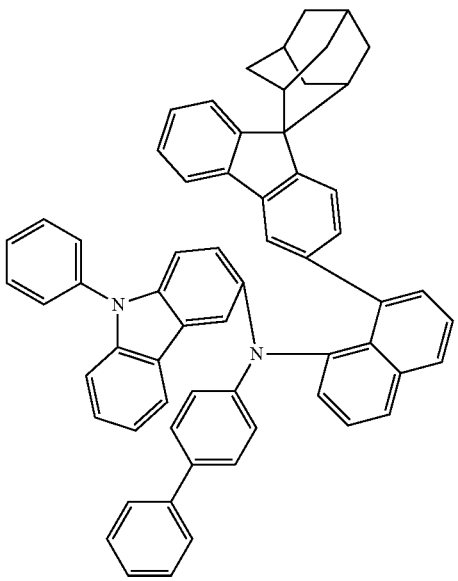
551
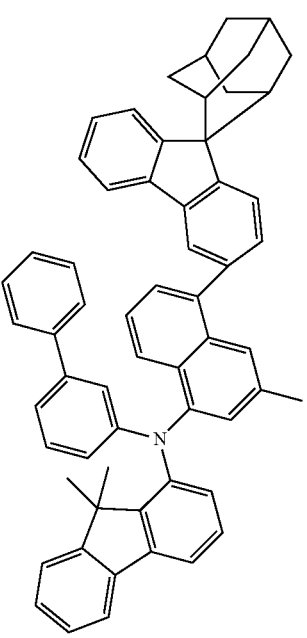

239
-continued
552
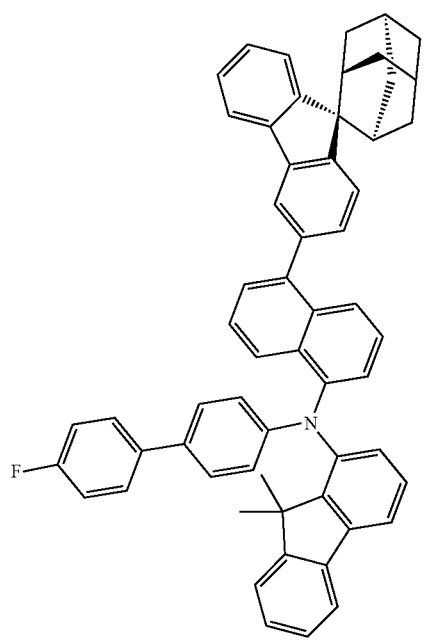
553
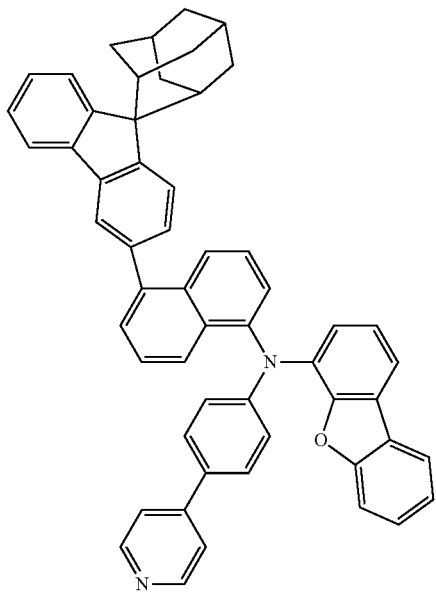
240
-continued
554
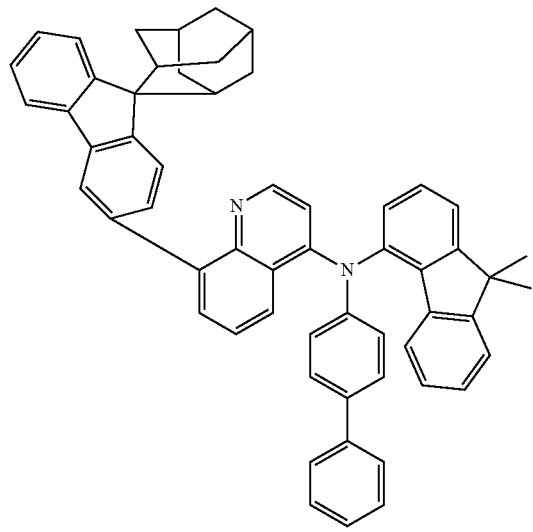
555
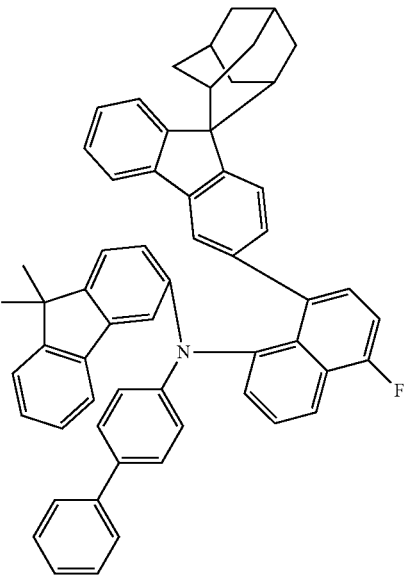

556 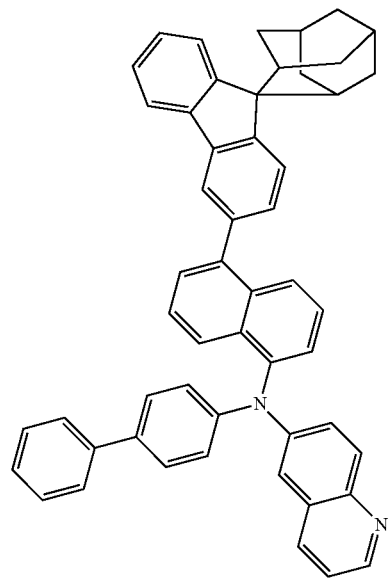
557 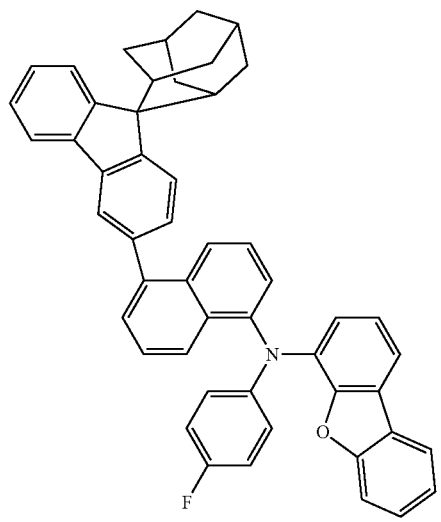
558 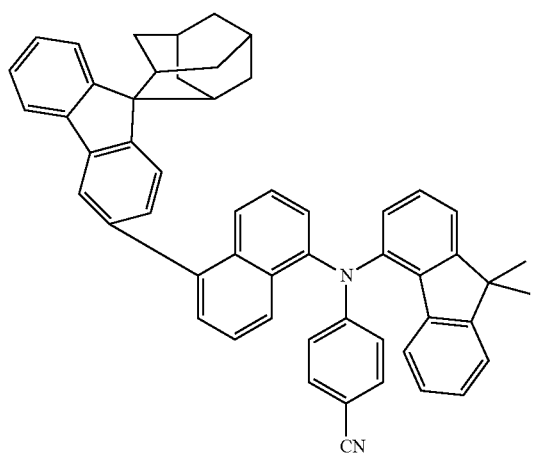
559 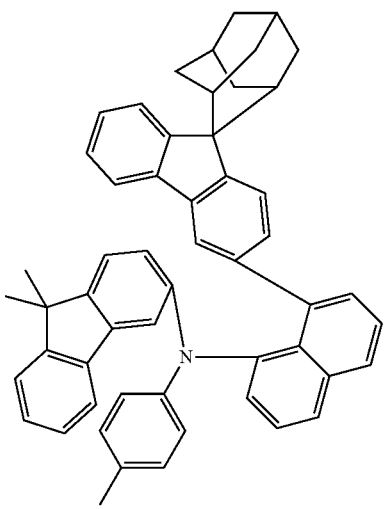
560 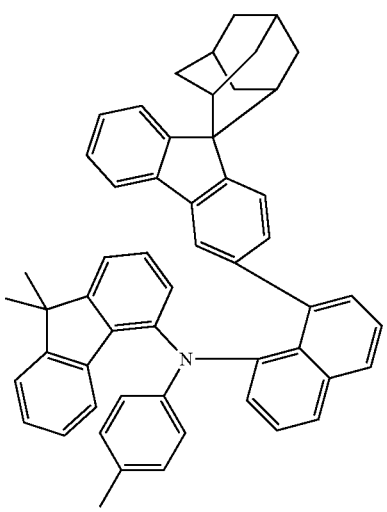
561 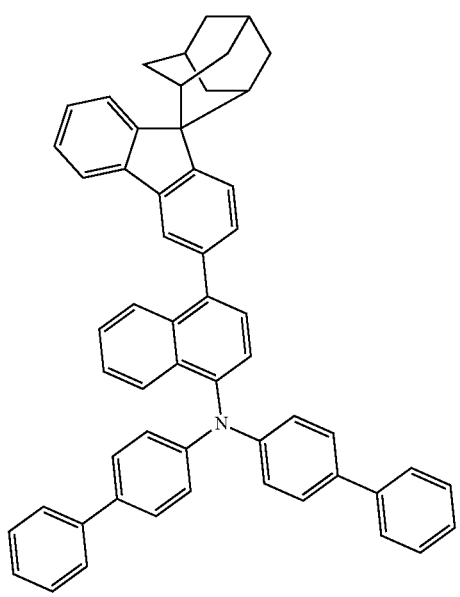

562
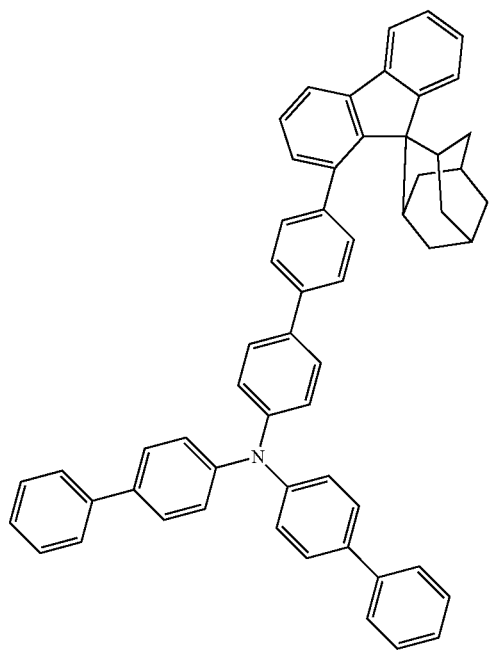
563
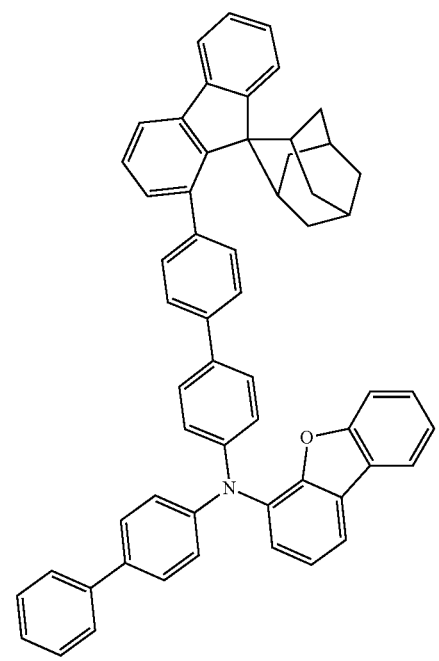
564
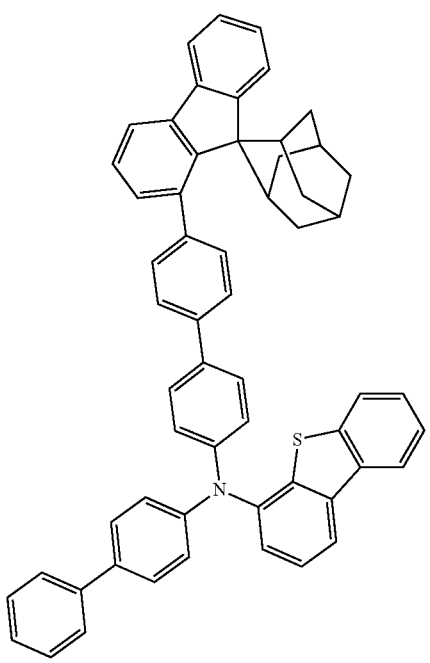
565
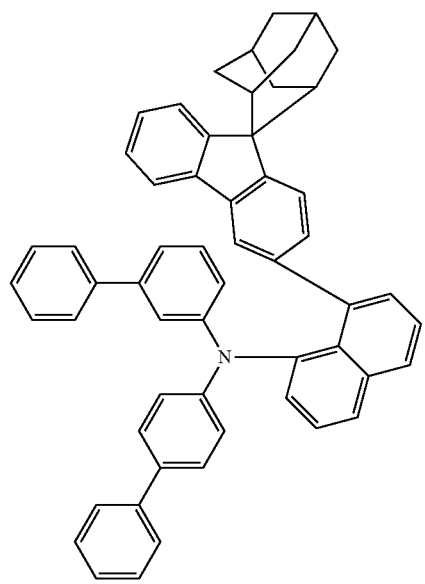

566
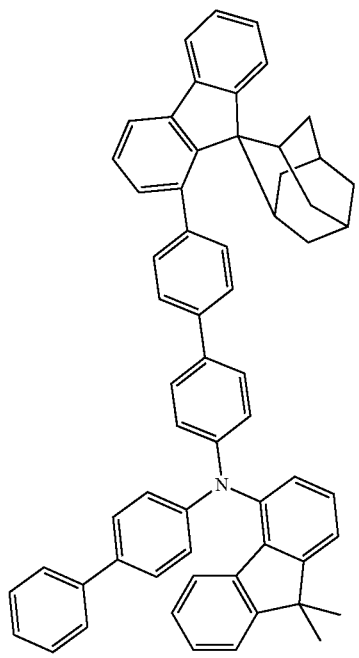
568
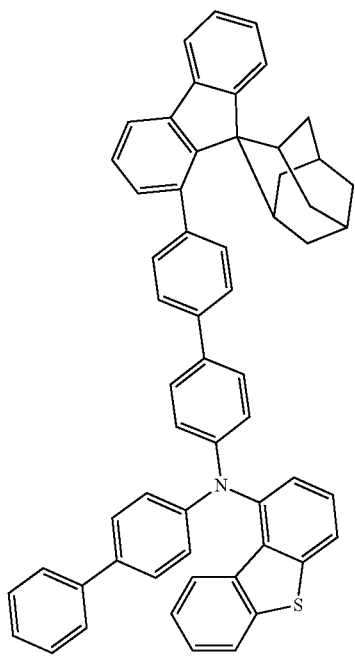
567
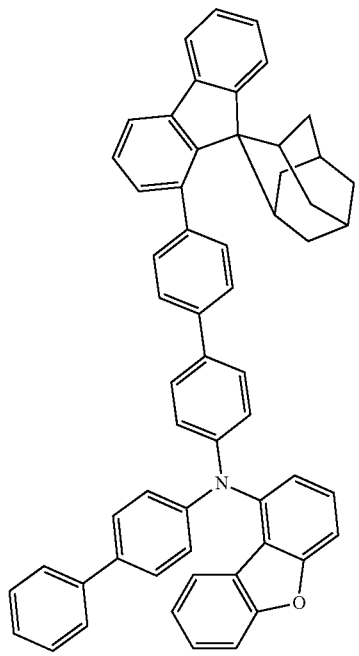
569
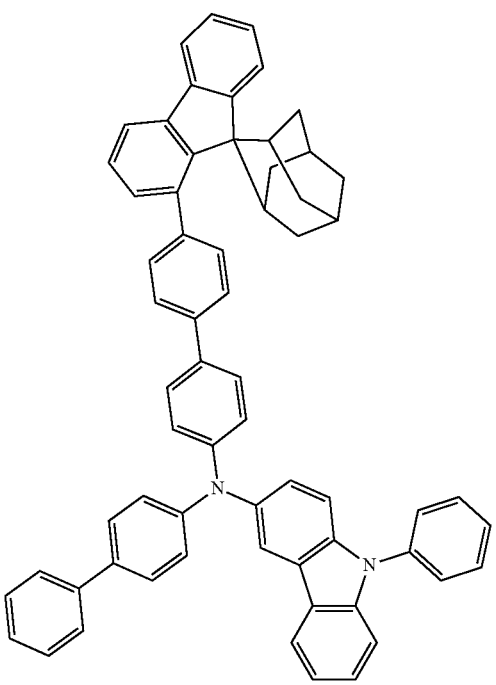

247
-continued
570
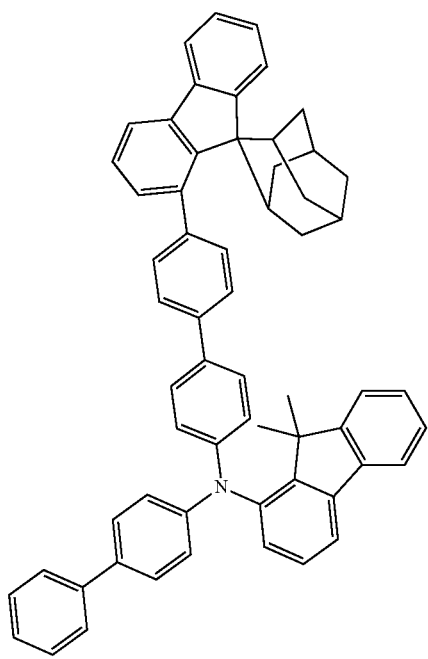
571
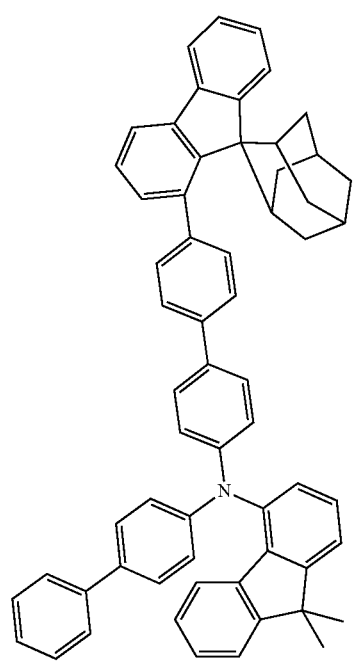
248
-continued
572
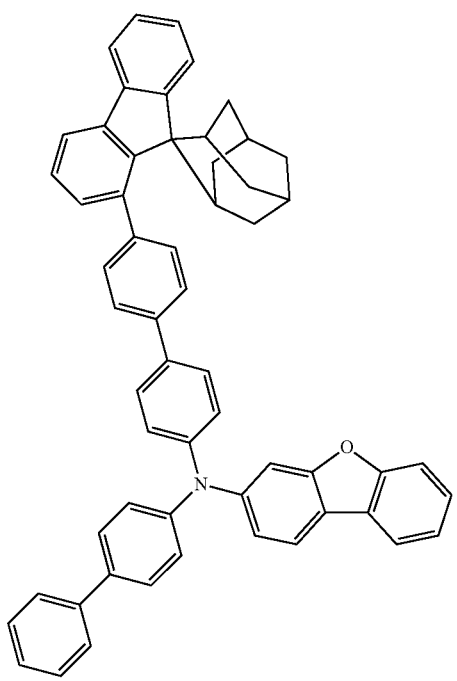
573
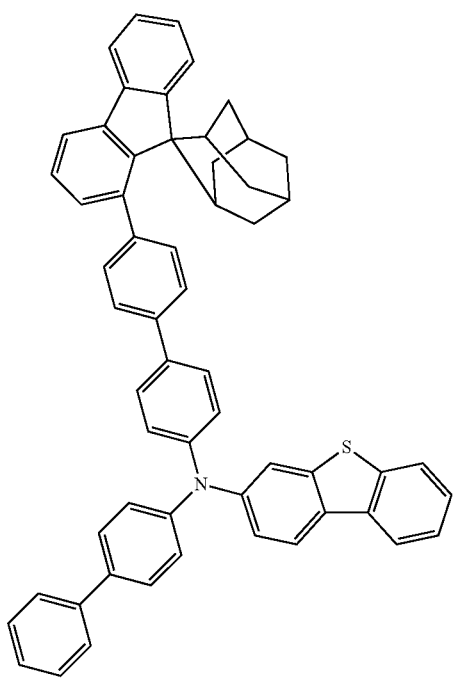

249
-continued
574
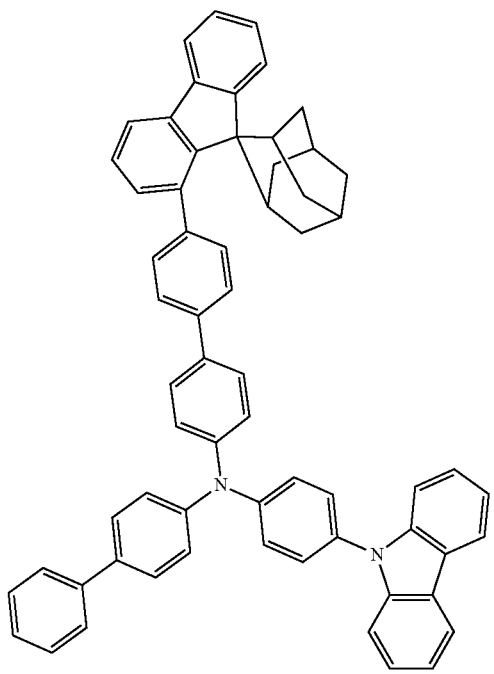
575
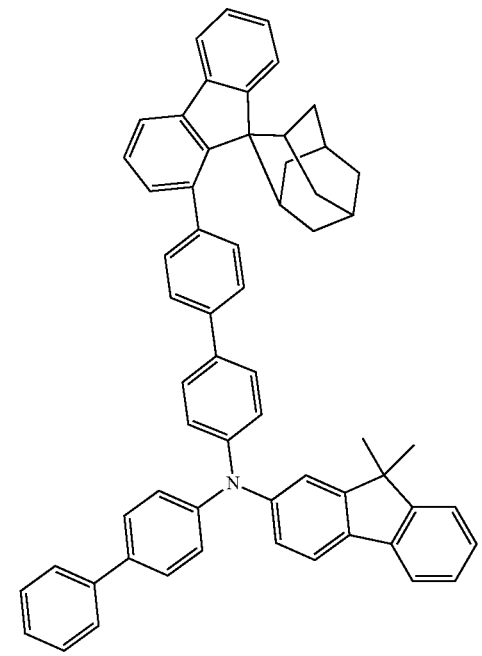
250
-continued
576
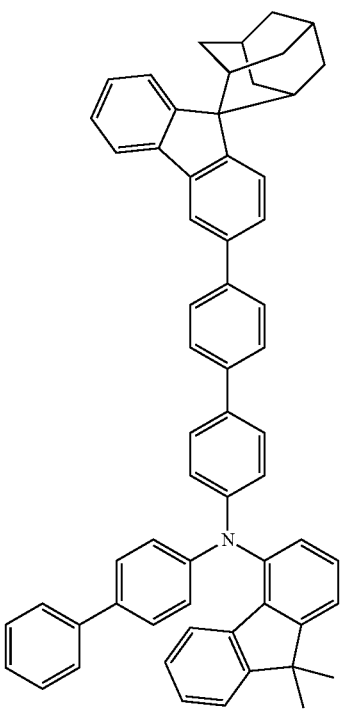
577
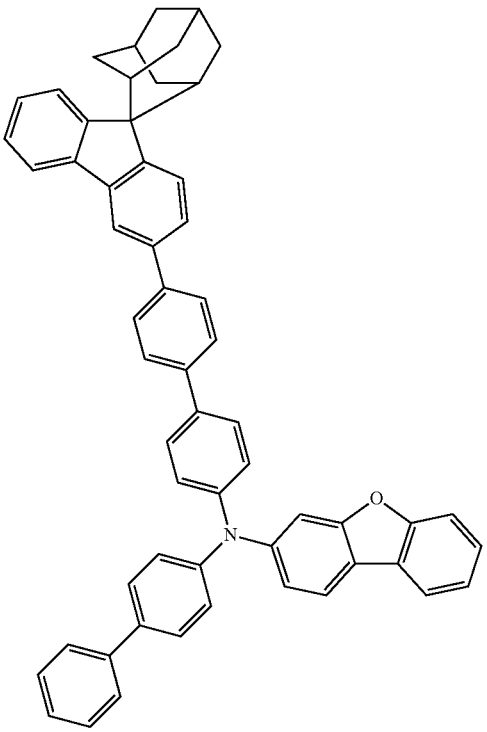

251
-continued
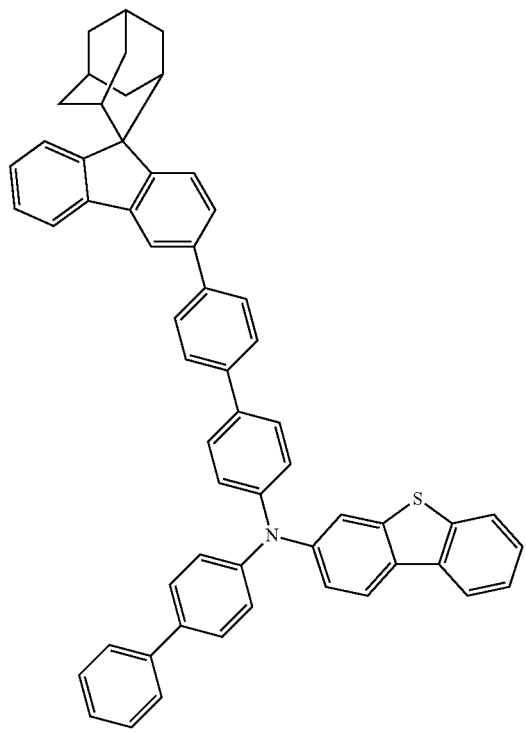
578
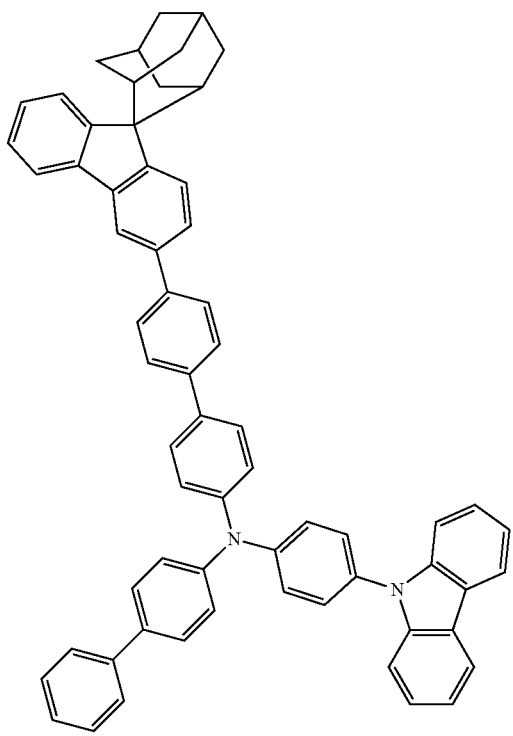
579
252
-continued
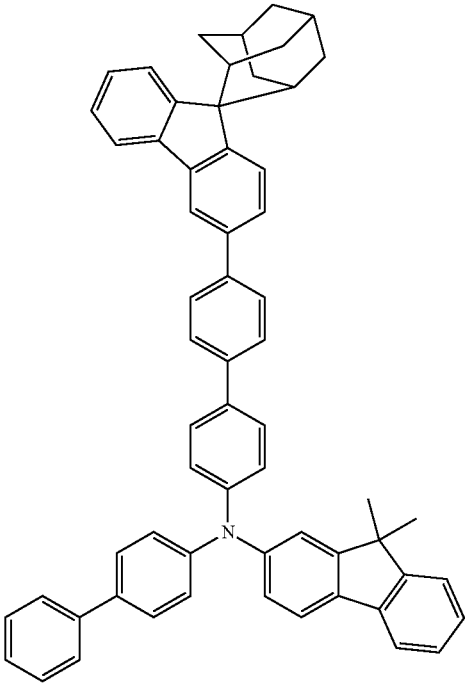
580
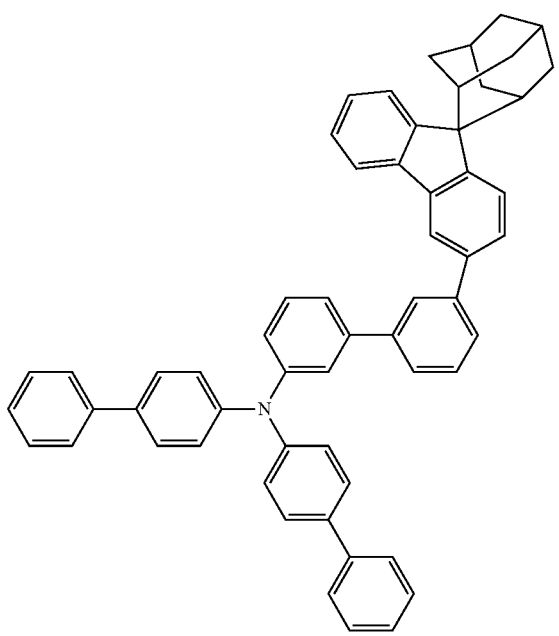
581

253
-continued
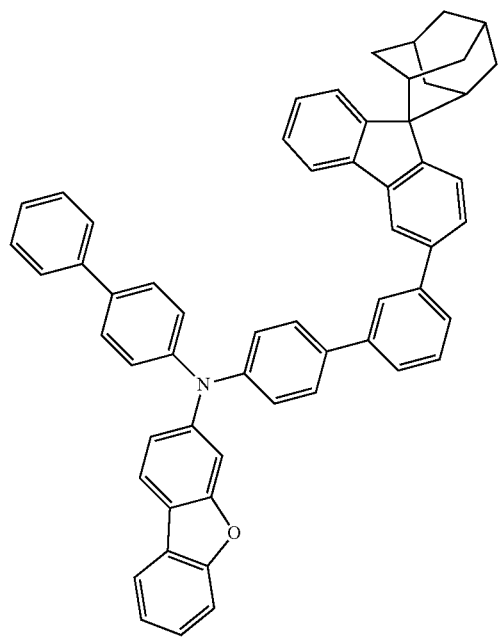
582
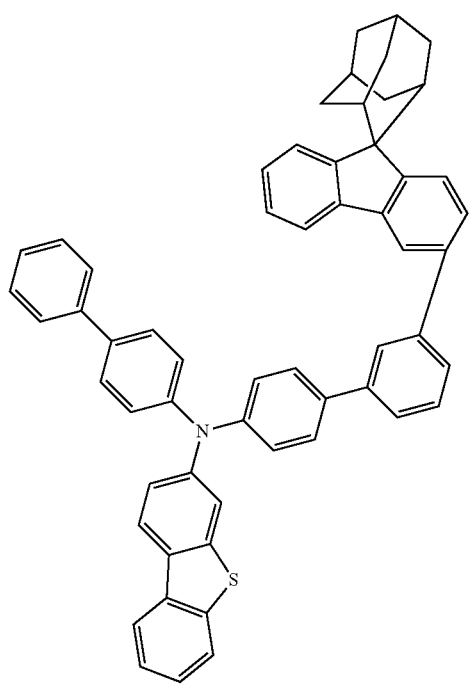
583
254
-continued
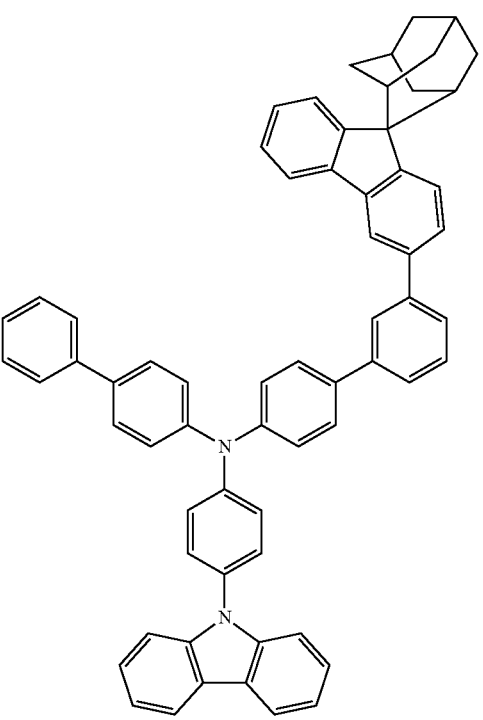
584
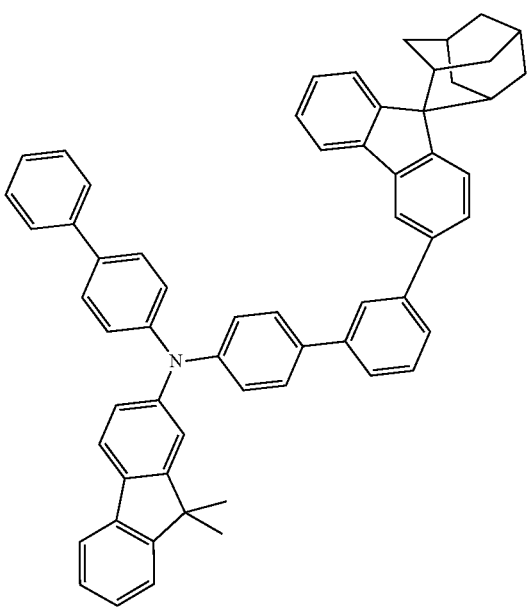
585

255
-continued
586 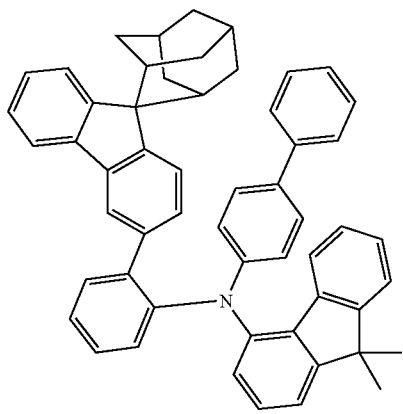
587 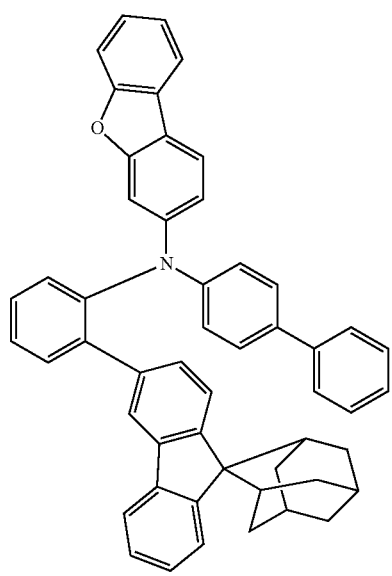
588 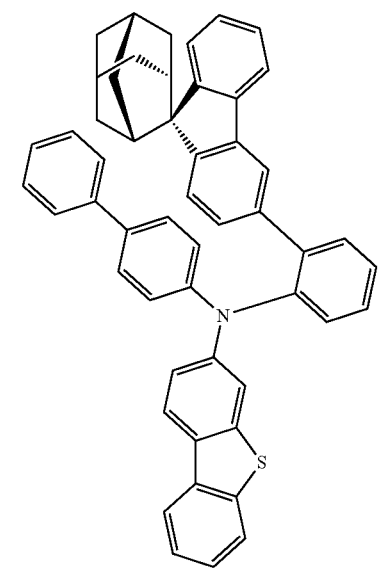
256
-continued
589 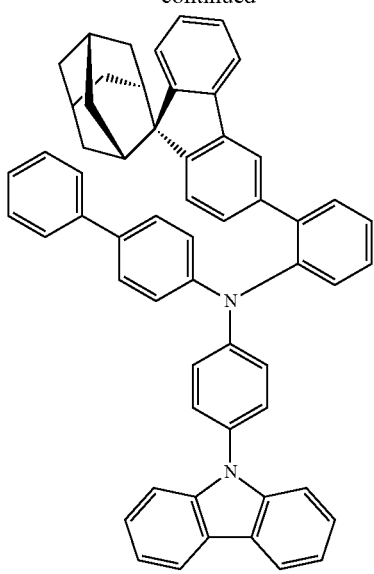
590 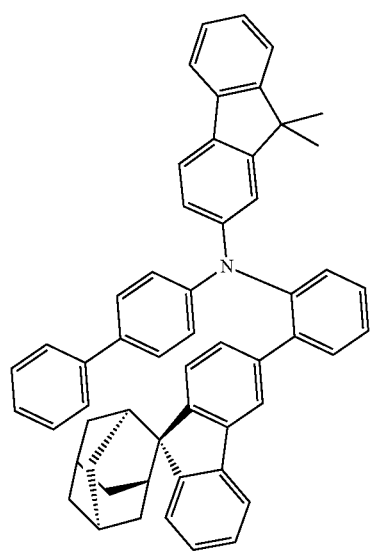
591 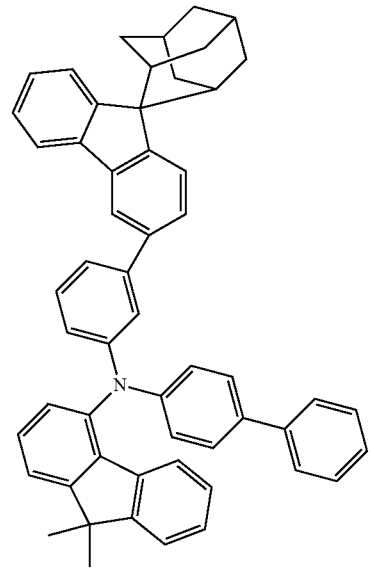

592
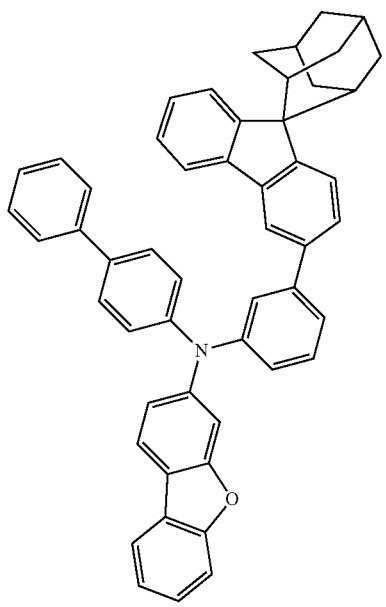
593
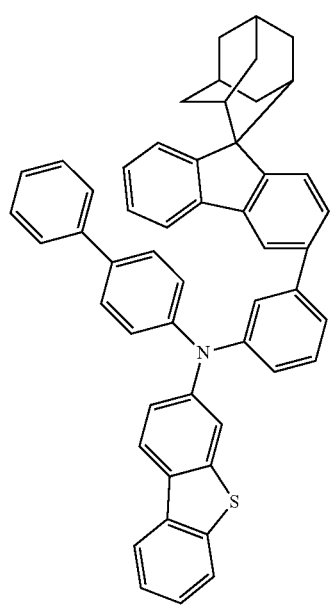
594
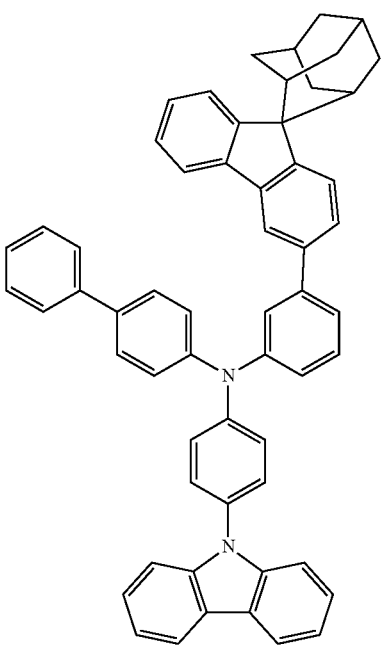
595
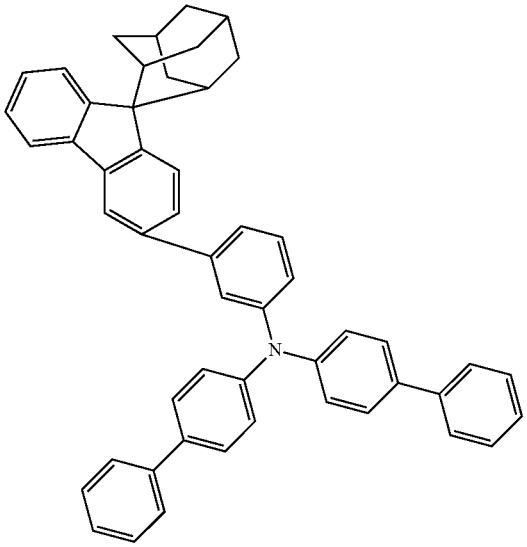
596

259
-continued
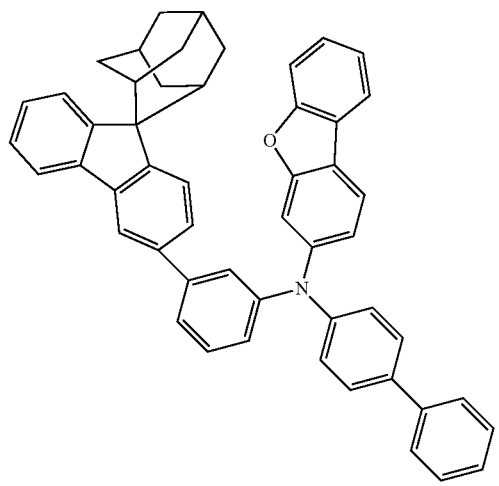
597
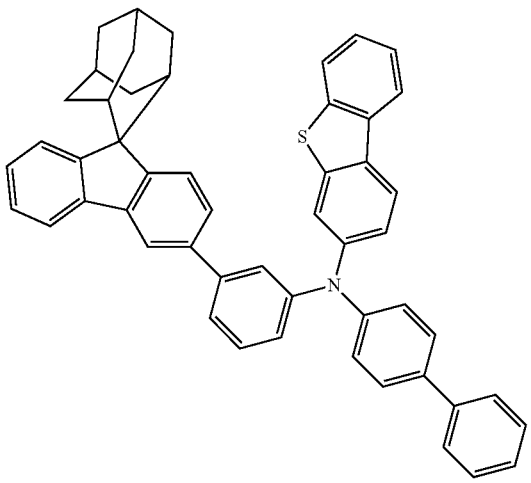
598
599
260
-continued
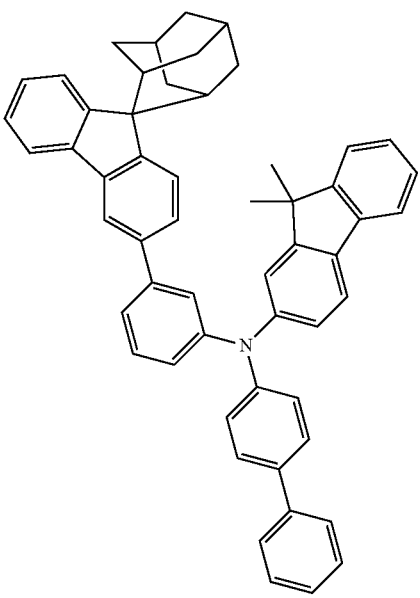
600
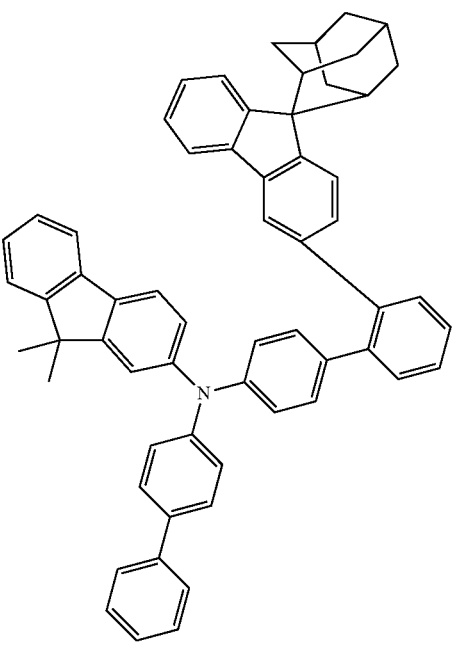
601

261
-continued
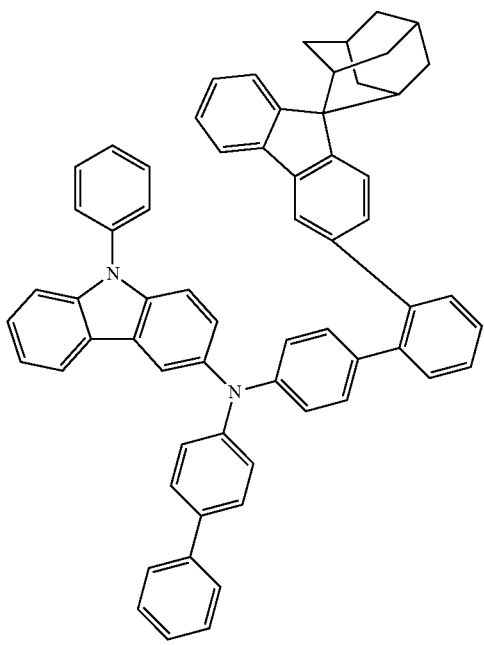
602
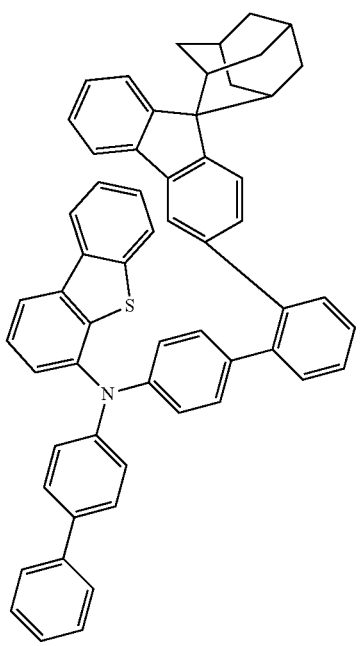
604
262
-continued
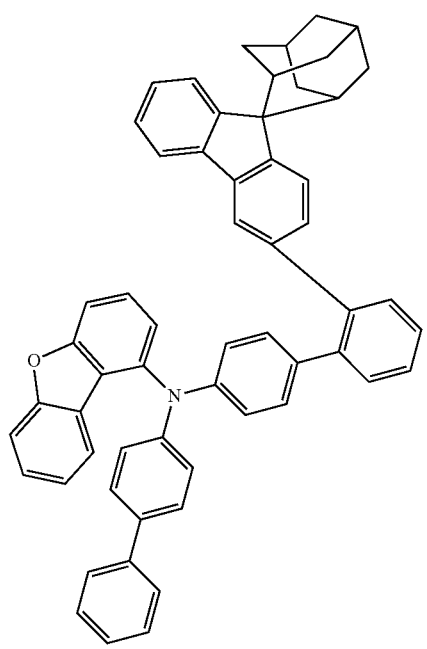
603
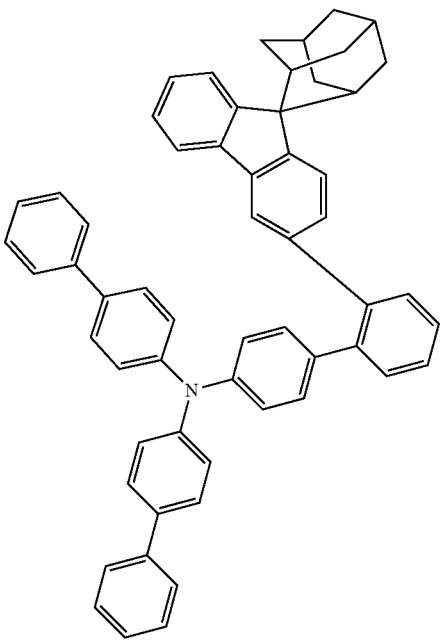
605

-continued
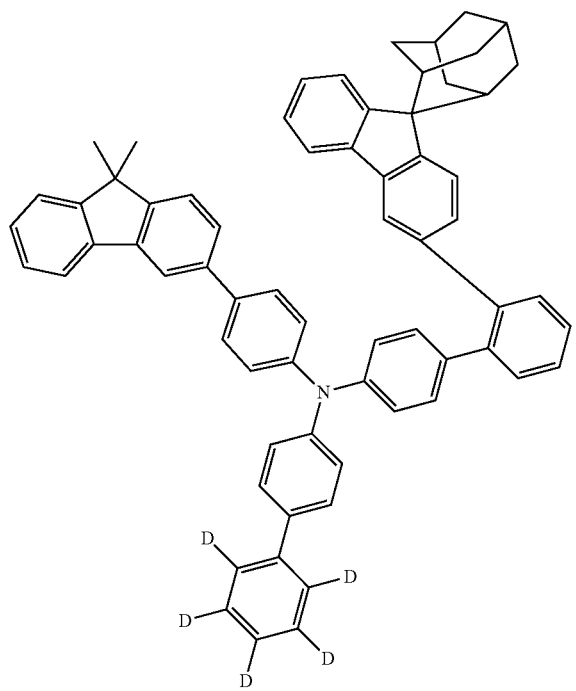
606
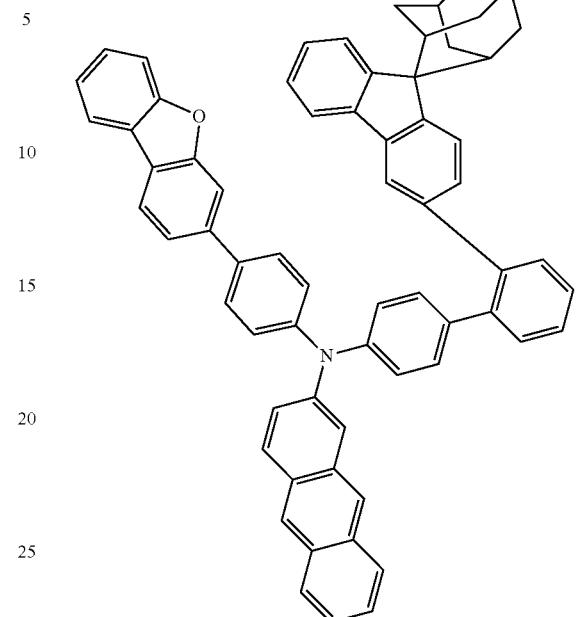
608
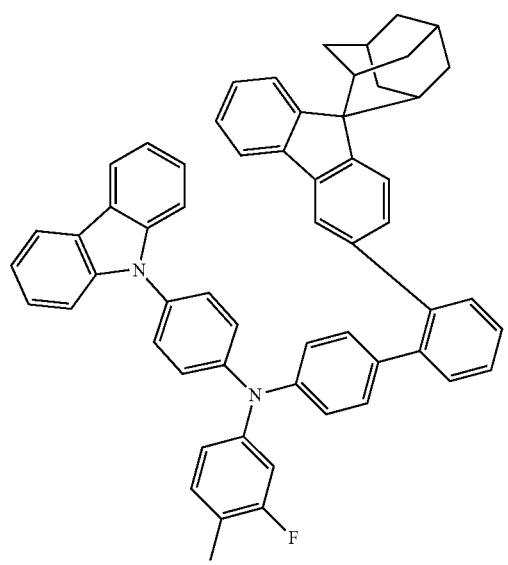
607
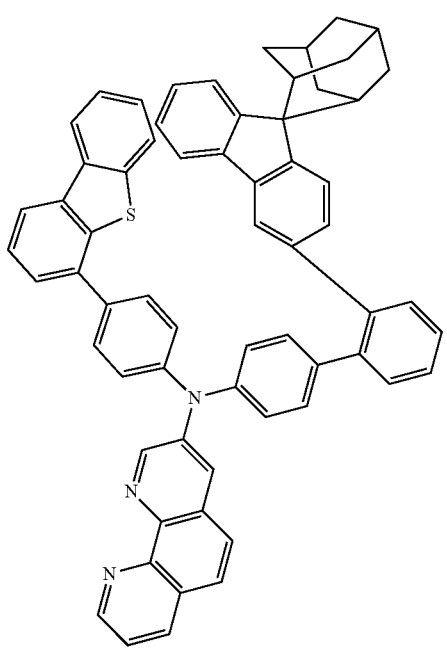
609

265
-continued
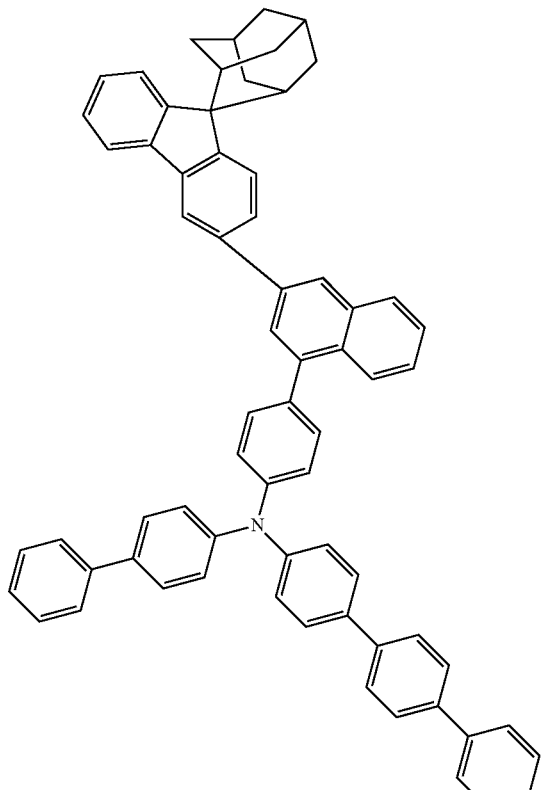
610
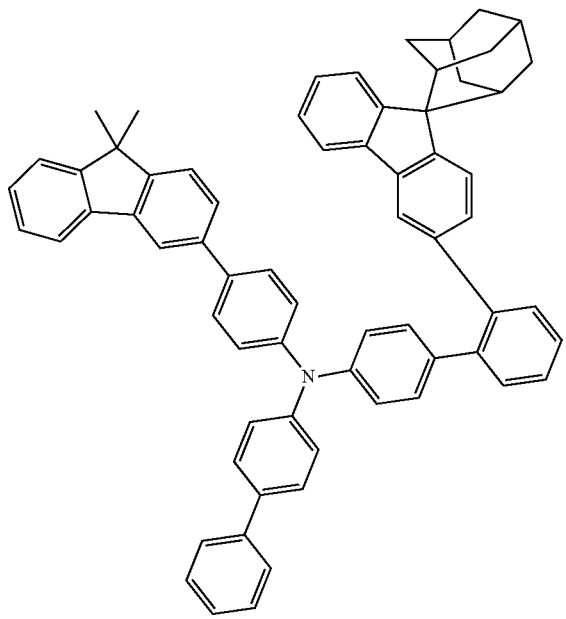
611
266
-continued
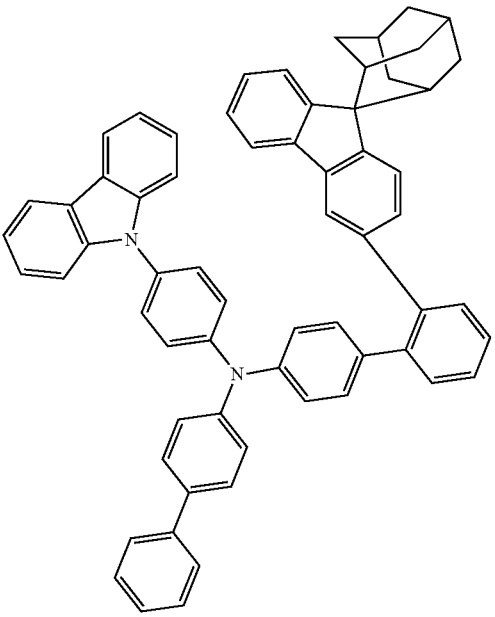
612
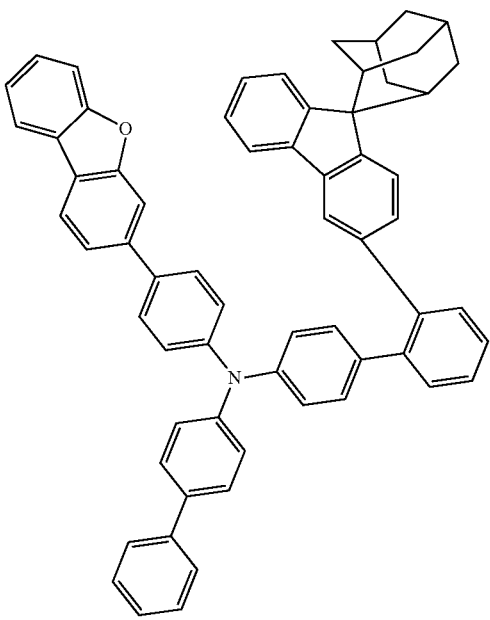
613

267
-continued
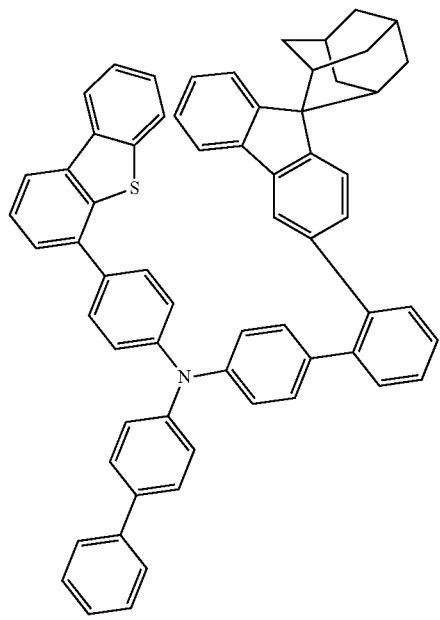
614
268
-continued
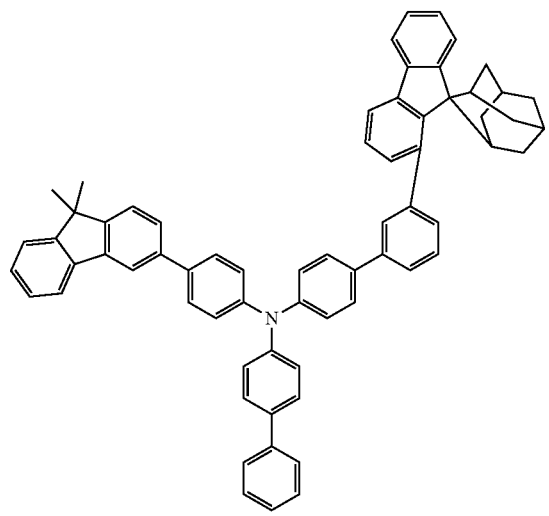
616
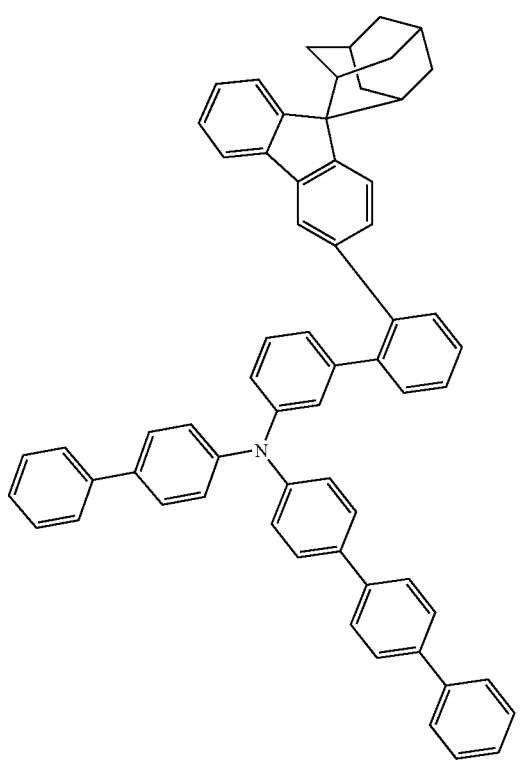
615
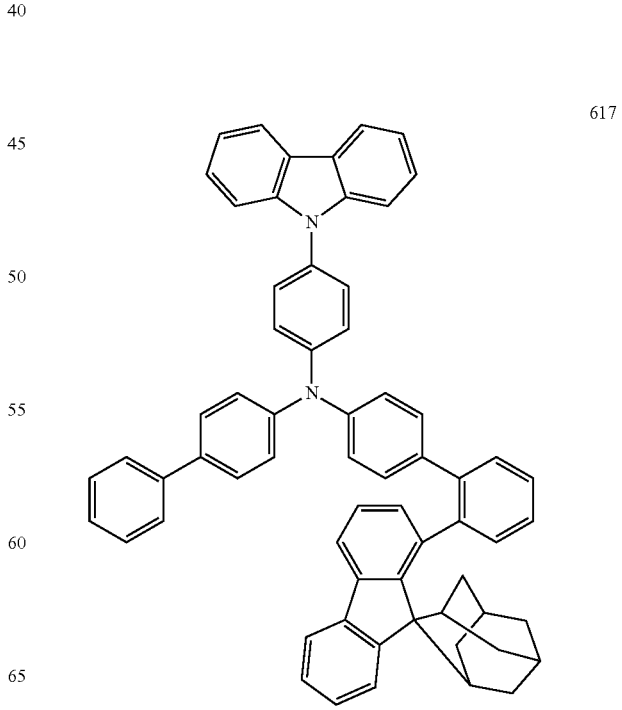
617

269
-continued
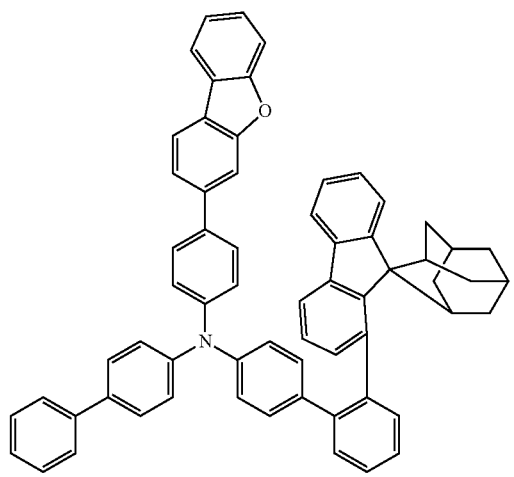
618
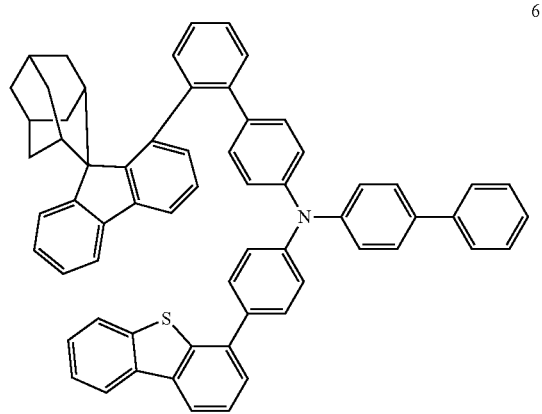
619
270
-continued
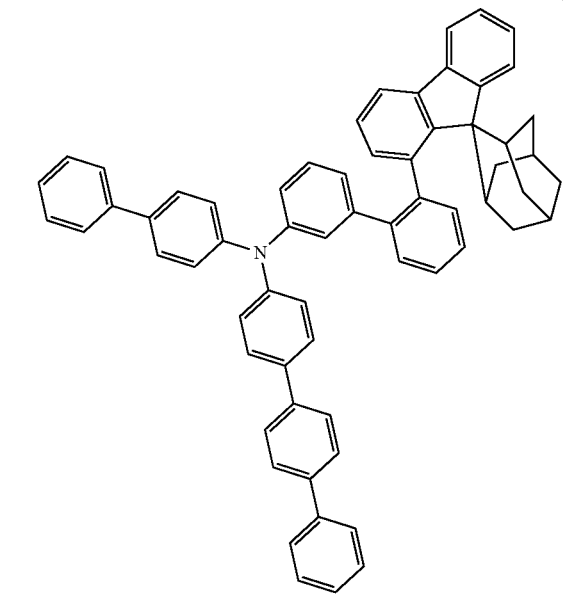
620
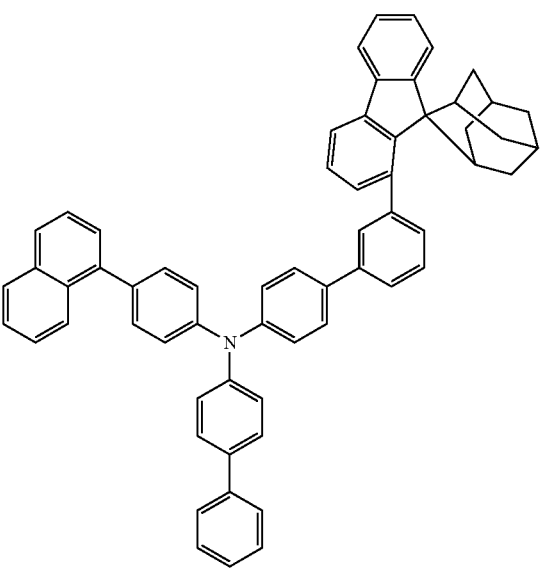
621

271
-continued
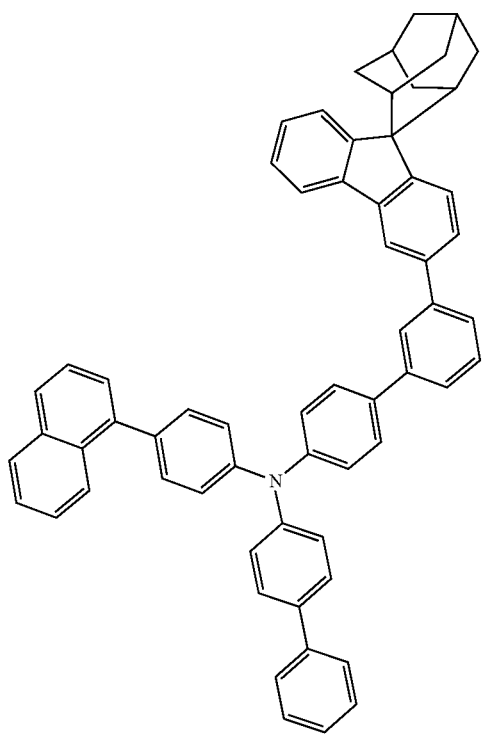
622
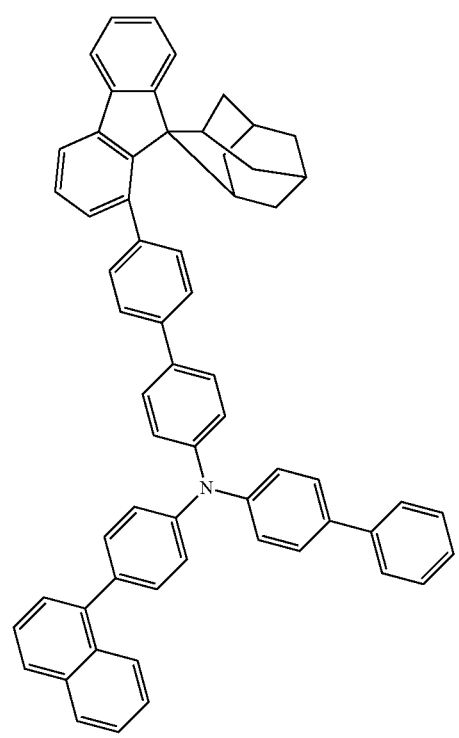
623
272
-continued
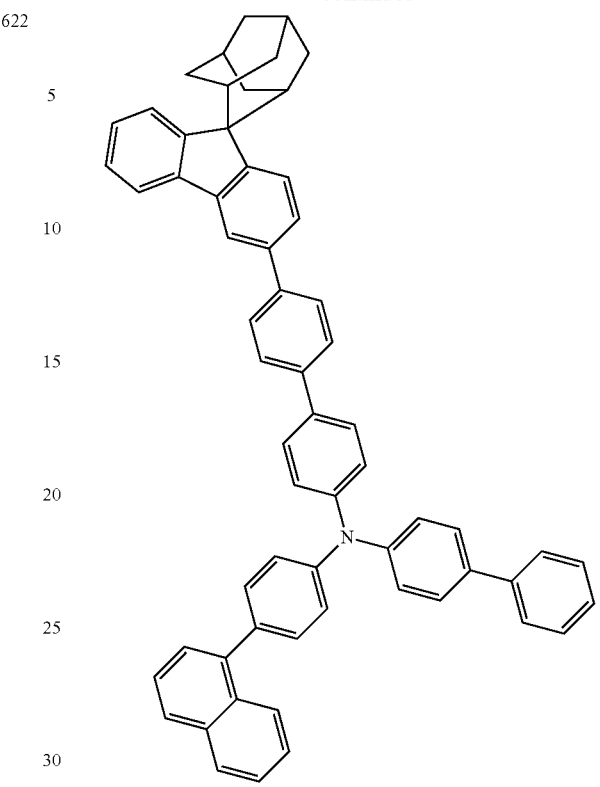
624
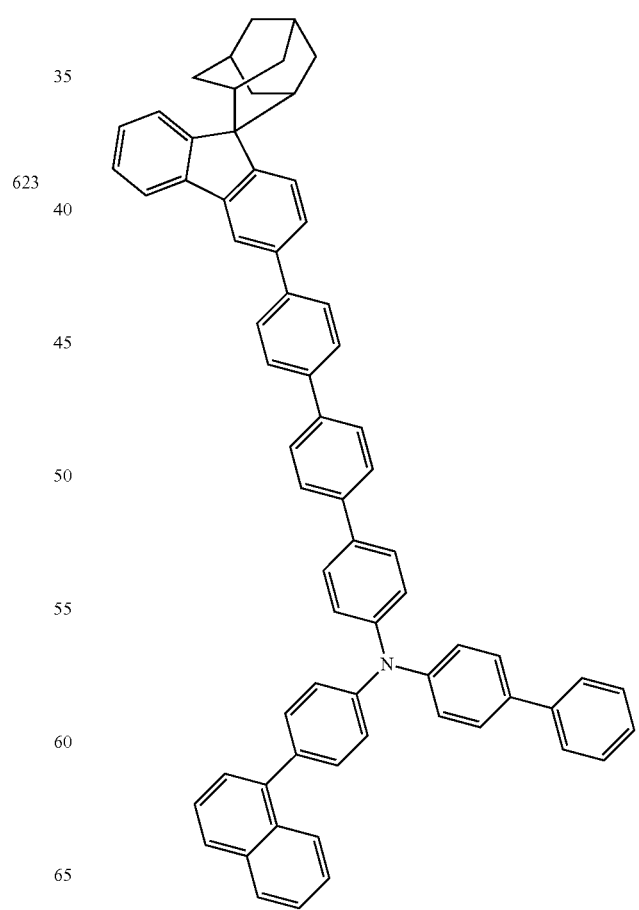
625

273
-continued
274
-continued
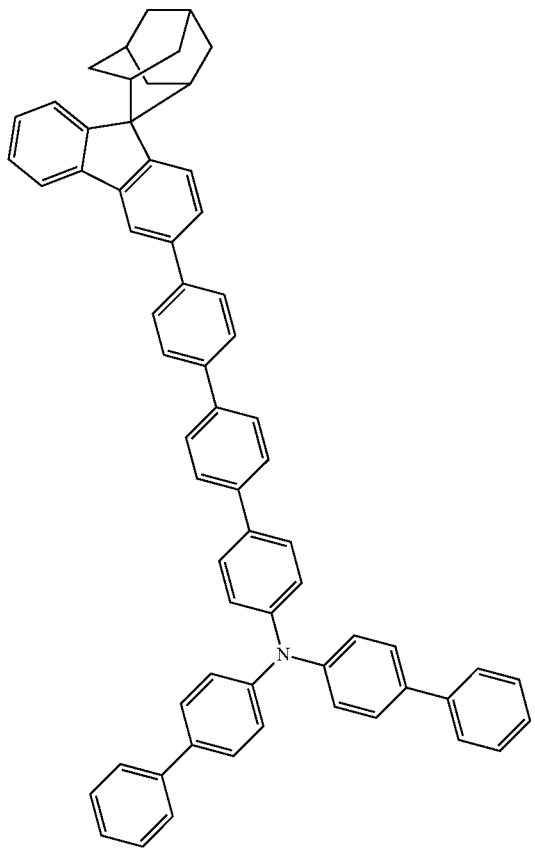
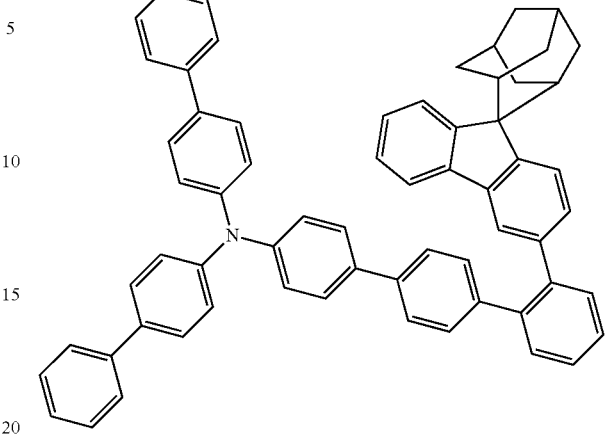
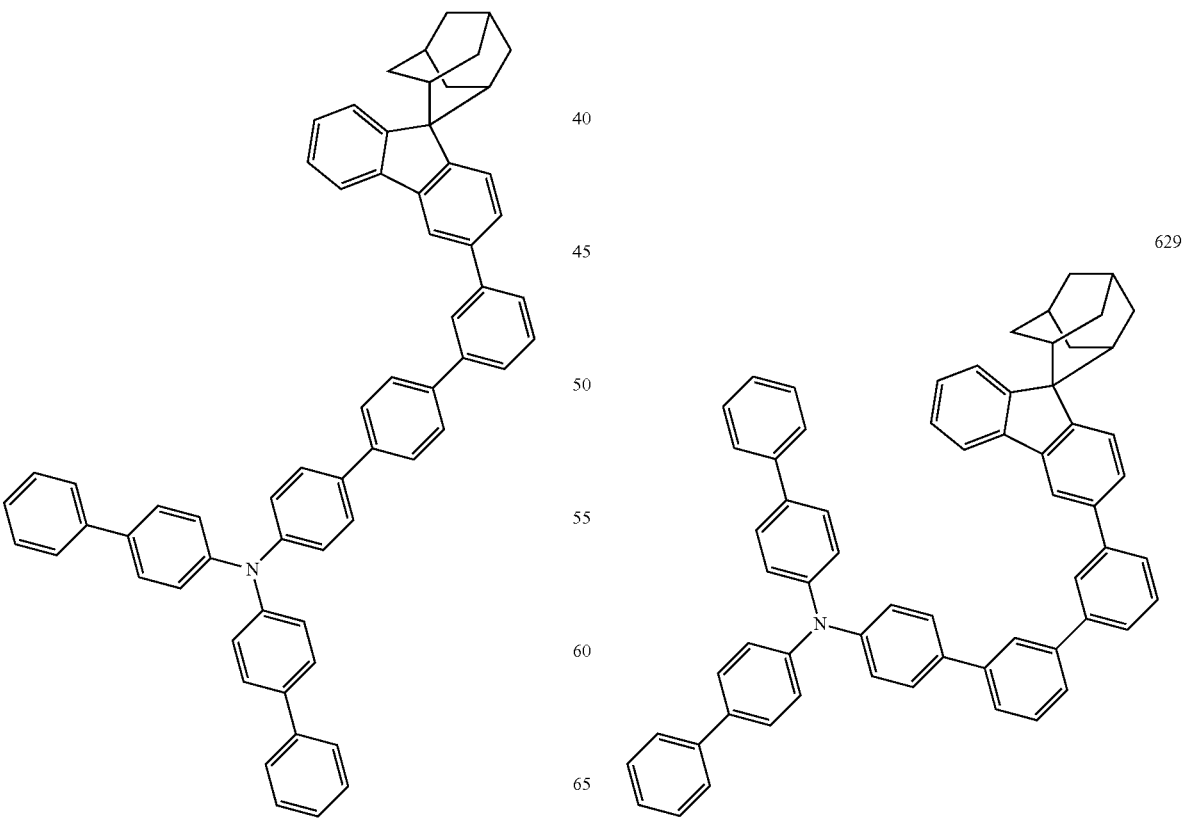

275
-continued
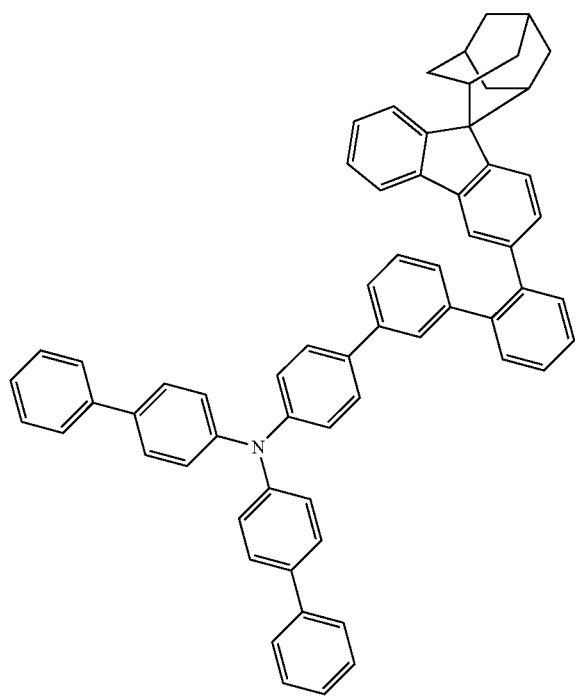
630
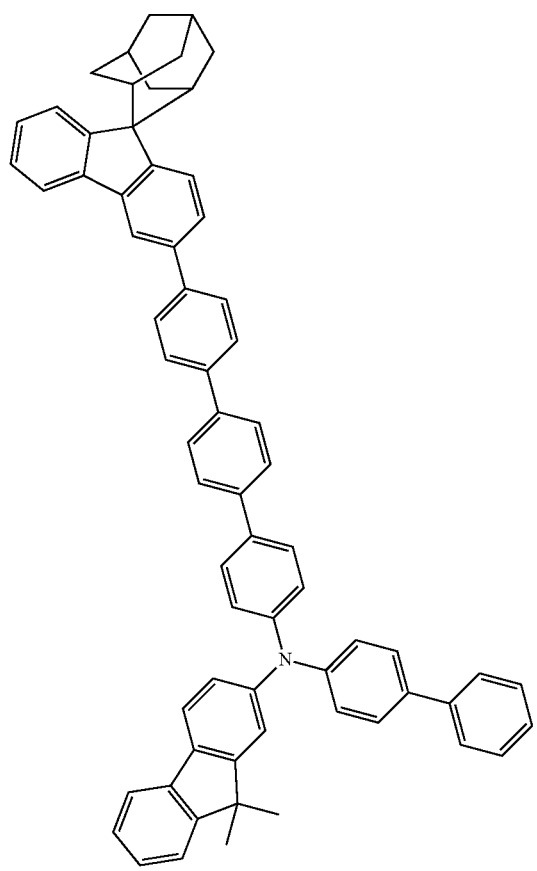
631
276
-continued
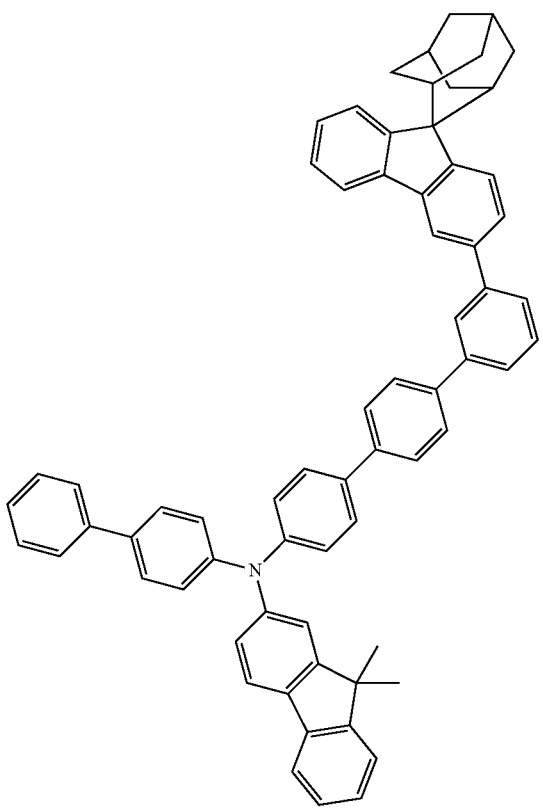
632
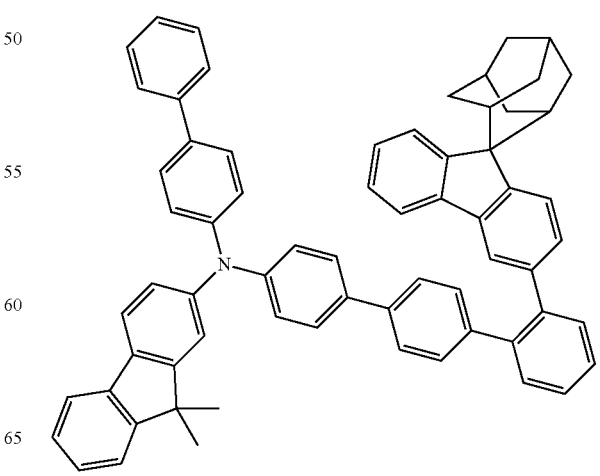
633

277
-continued
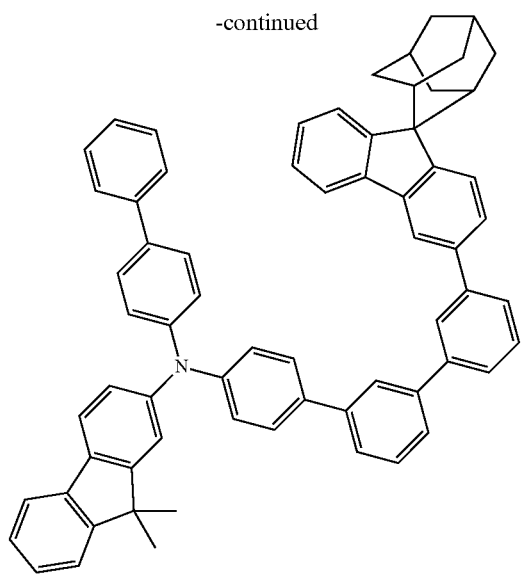
634
278
-continued
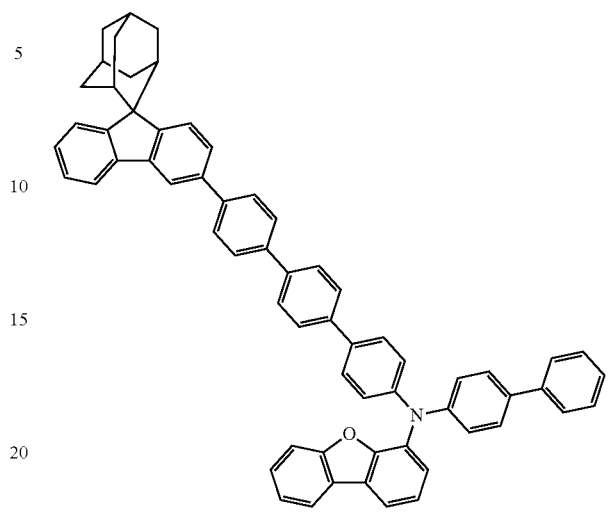
636
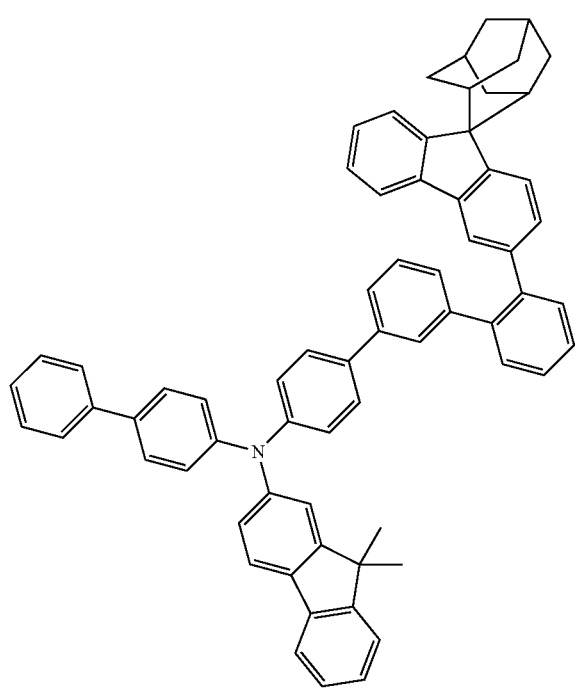
635
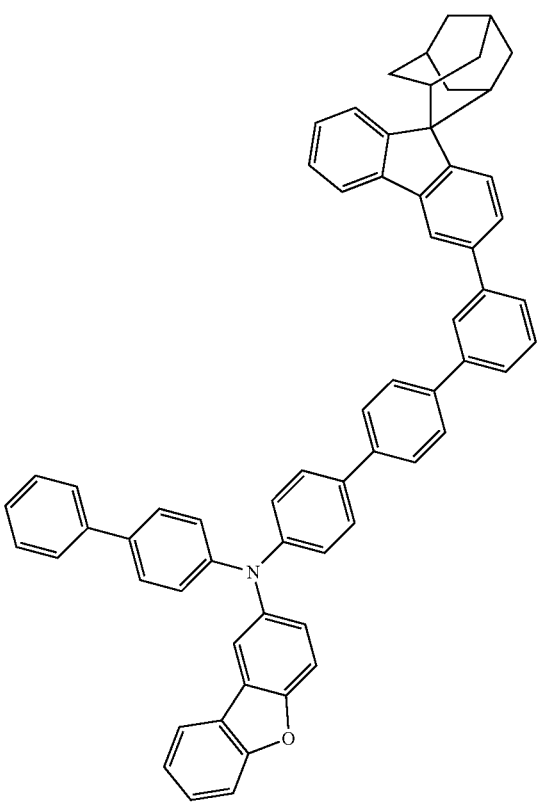
637

279
-continued
638
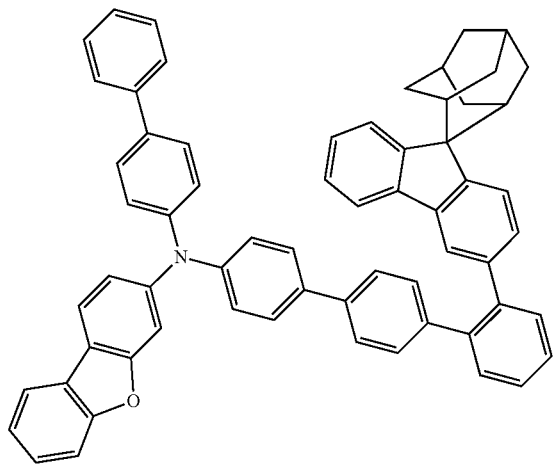
639
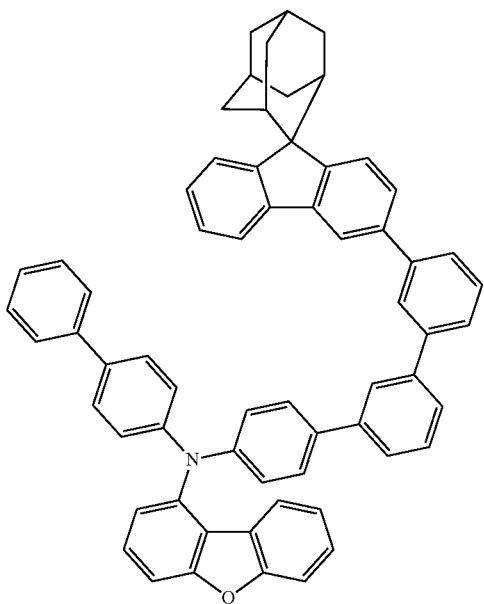
280
-continued
640
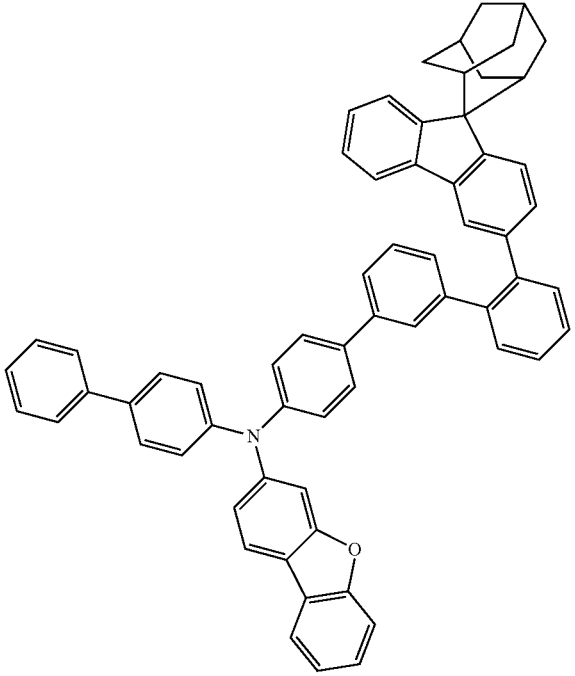
641
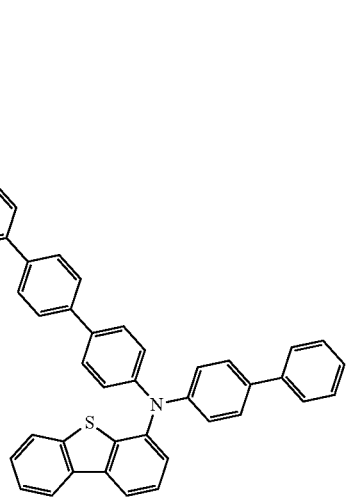

281
-continued
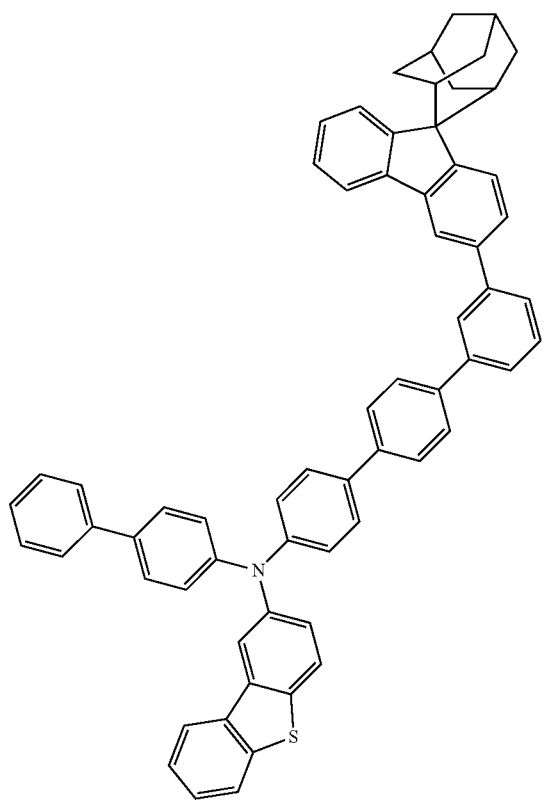
642
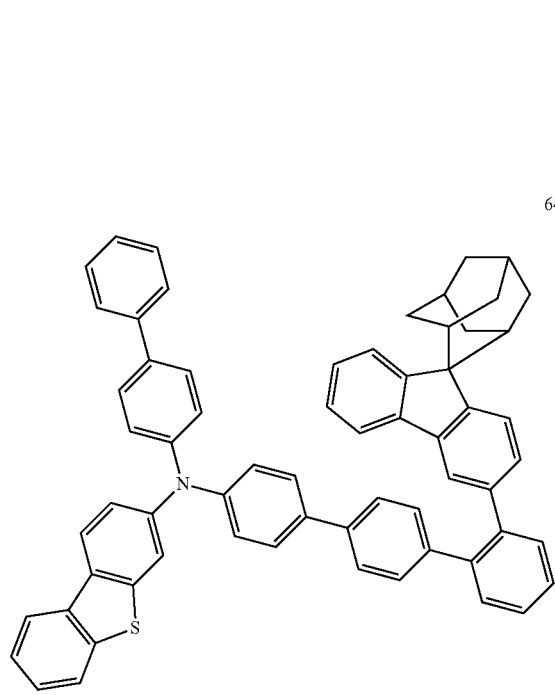
643
282
-continued
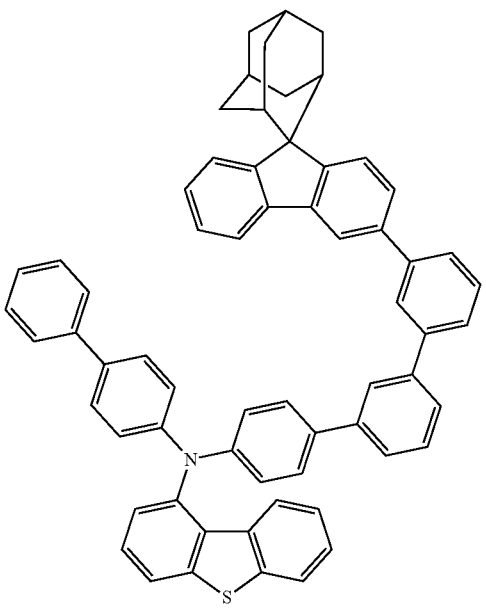
644
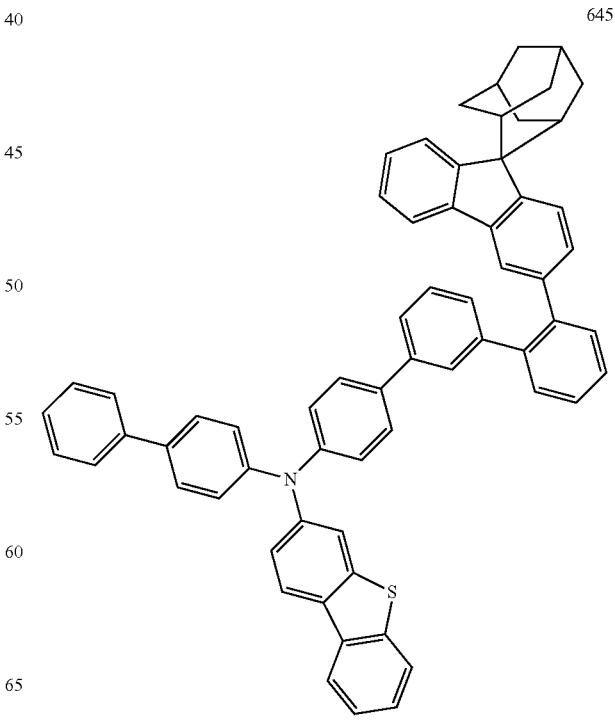
645

283
-continued
646
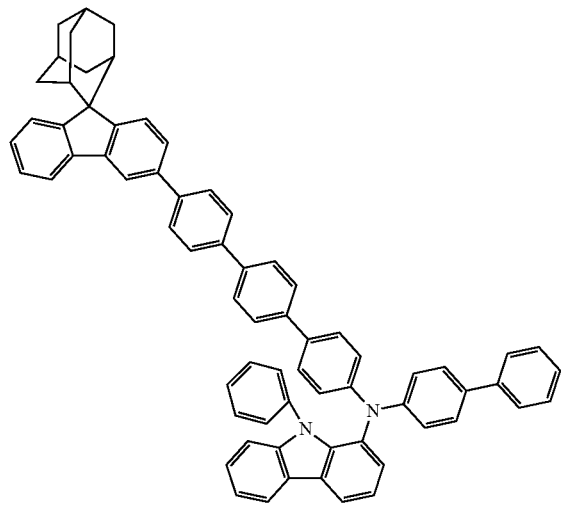
647
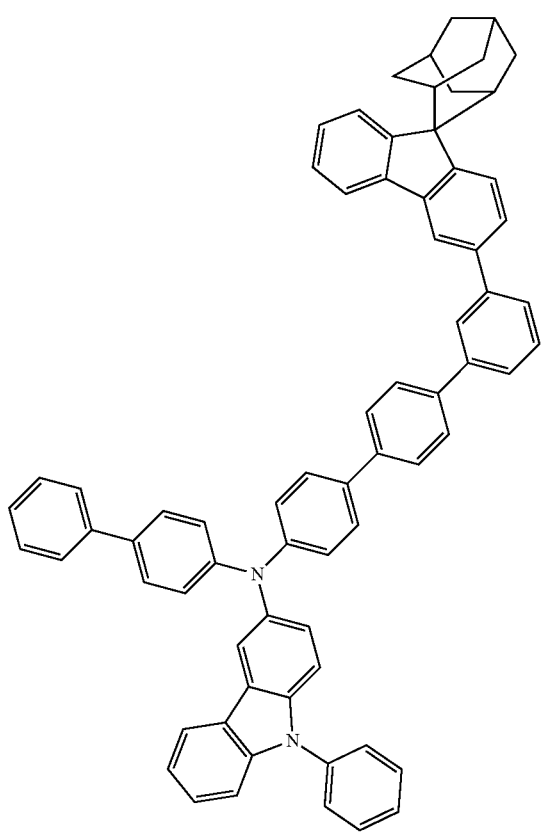
284
-continued
648
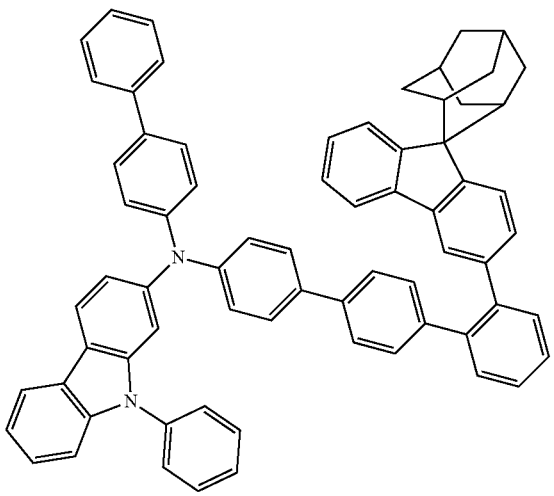
649
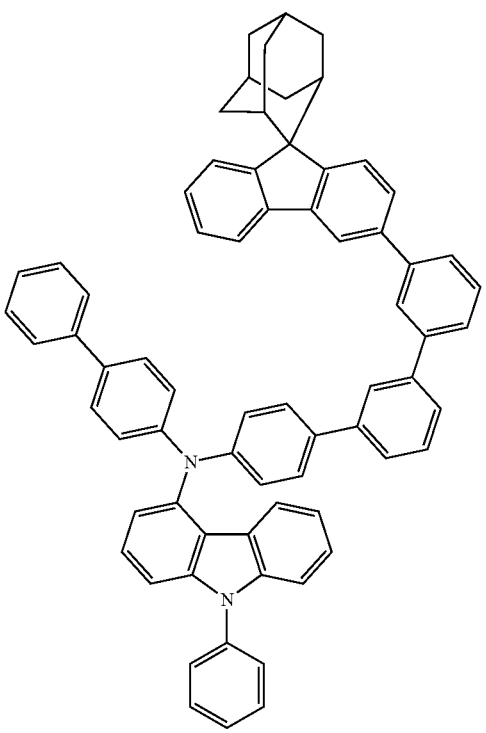

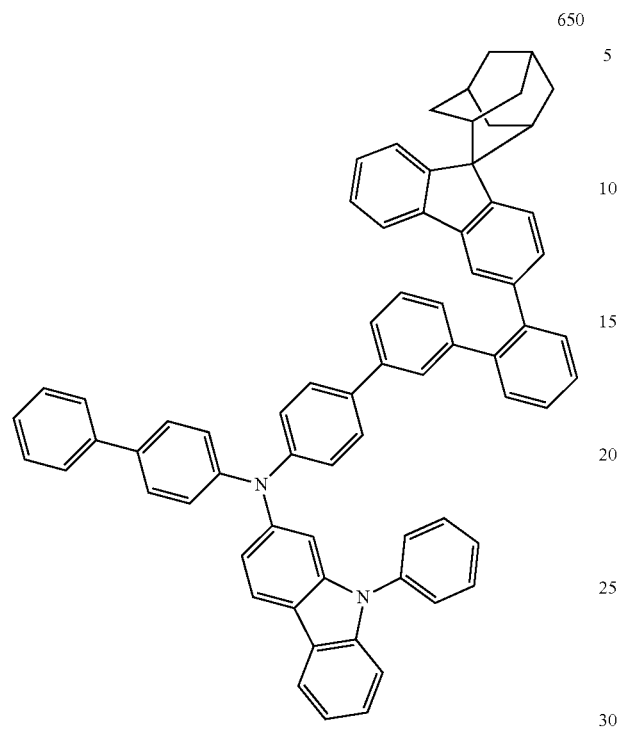
650
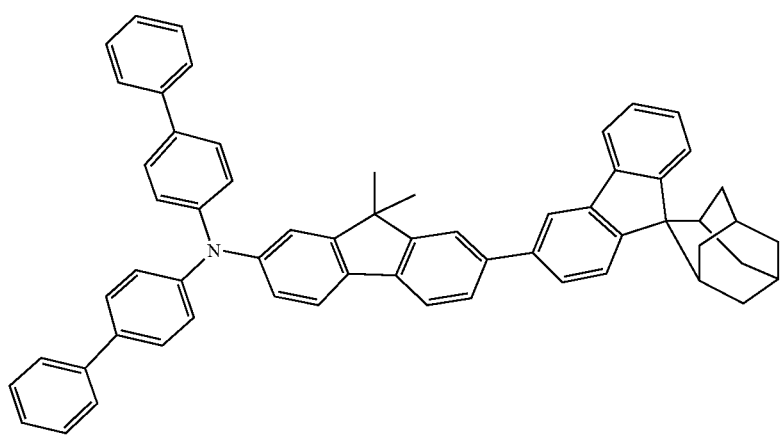
651

652
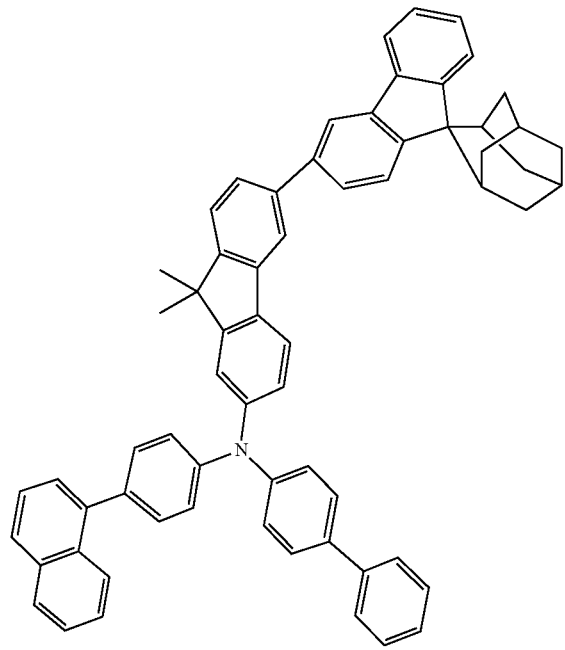
653
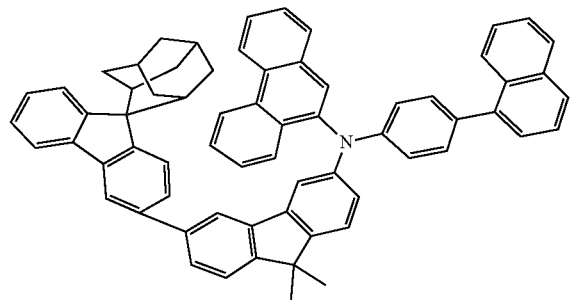
654
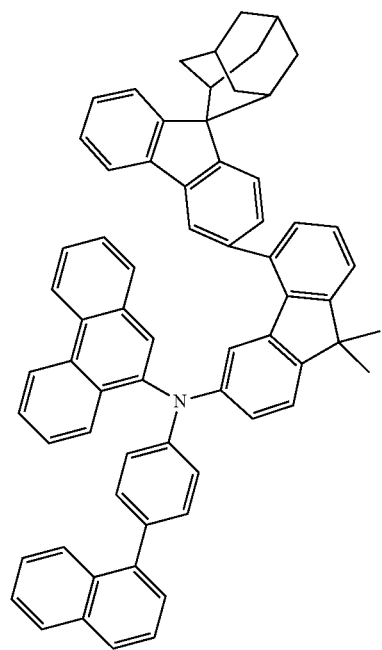
655
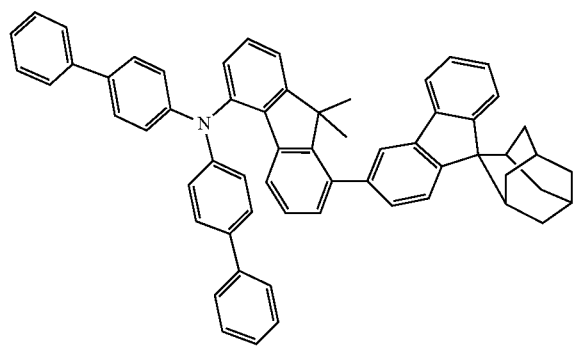

-continued
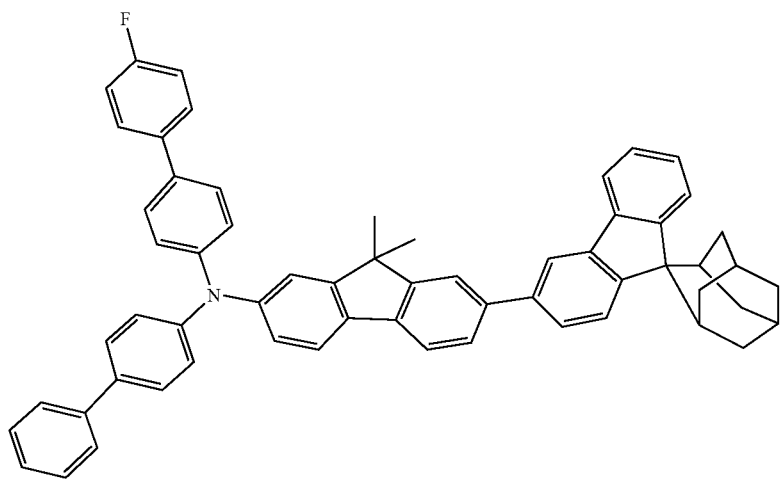
656
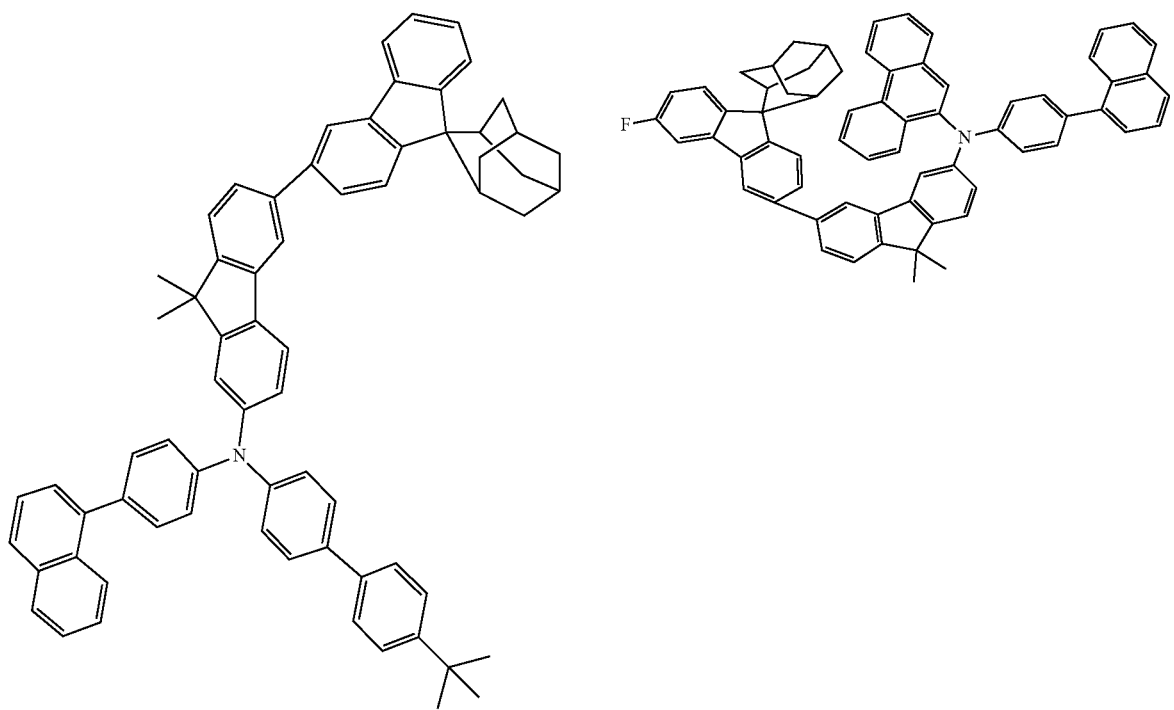
657 658

291
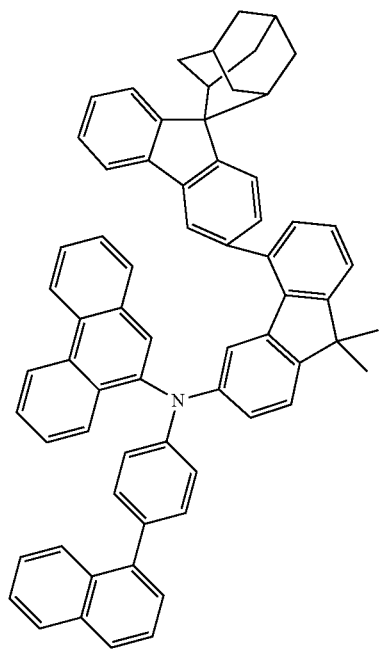
659
292
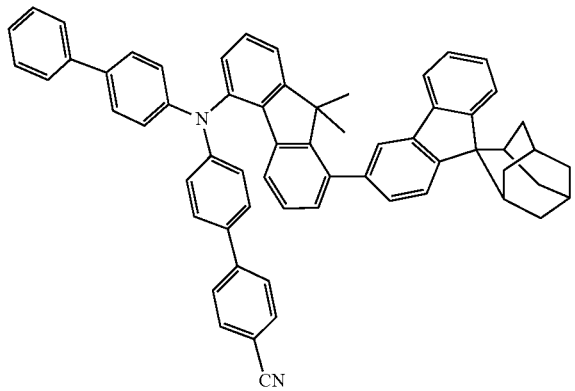
660
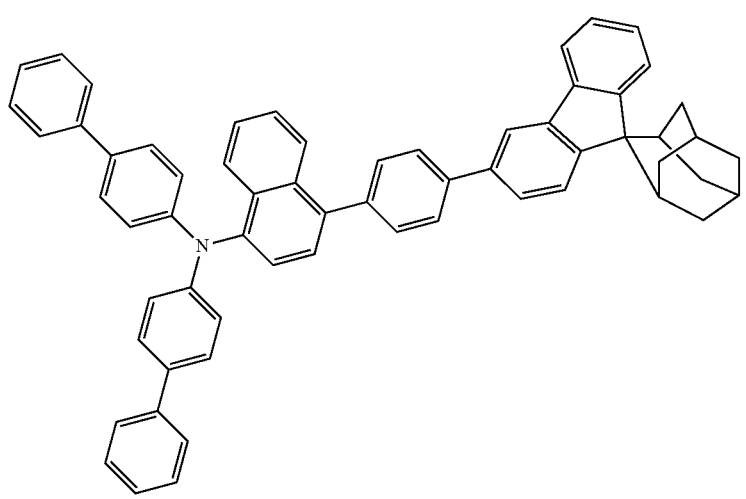
661

-continued
293
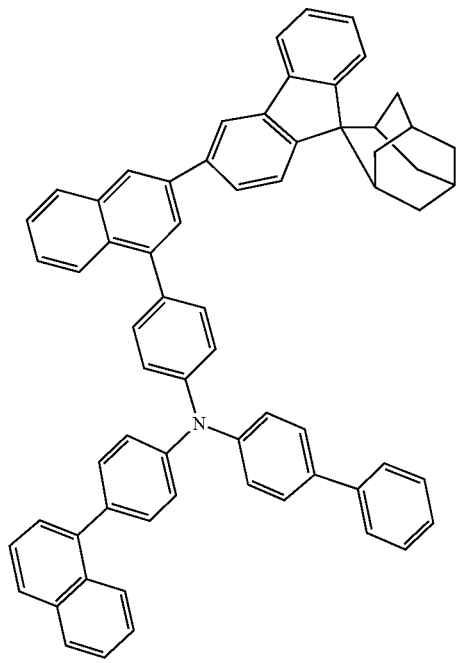
662
294
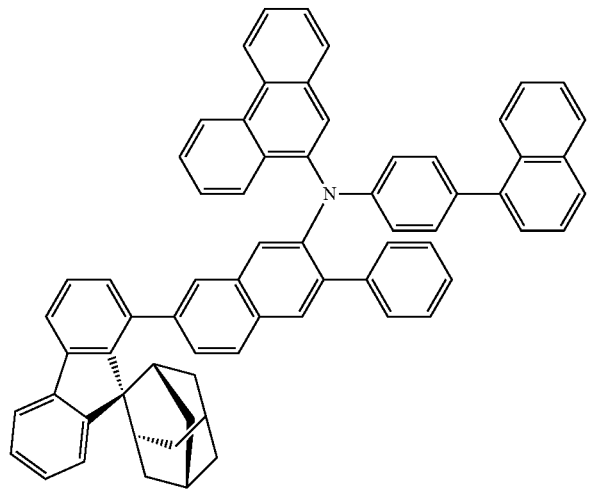
663
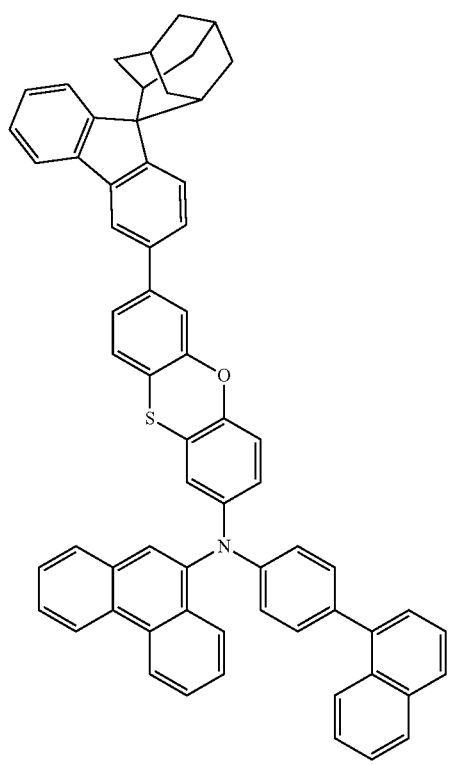
664
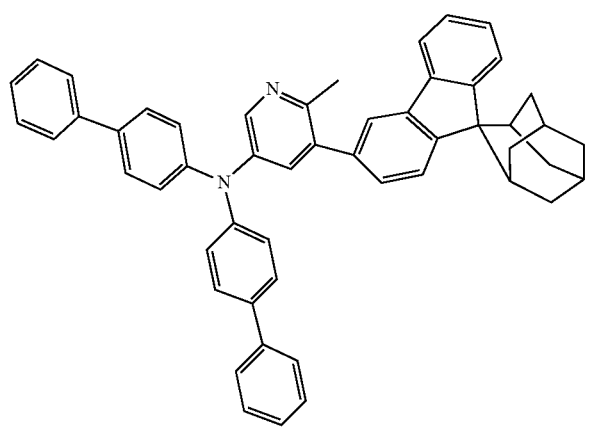
665

666
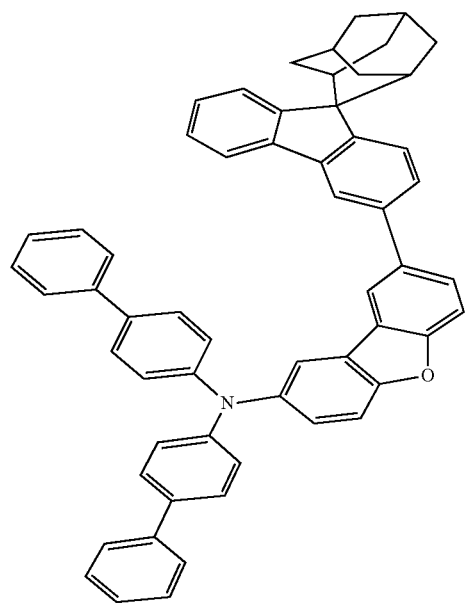
667
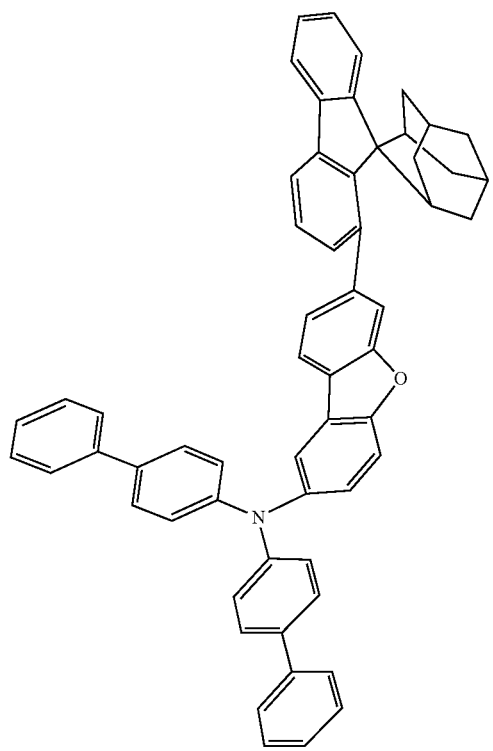
668
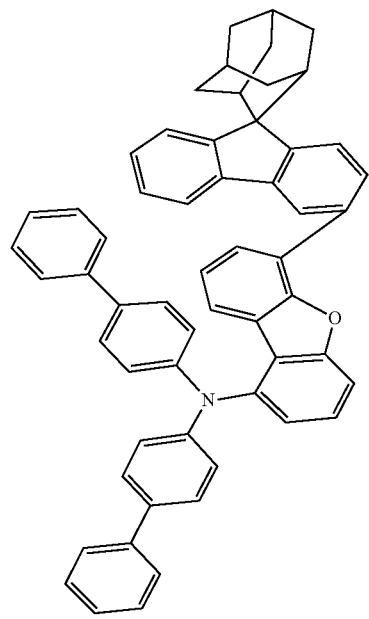
669
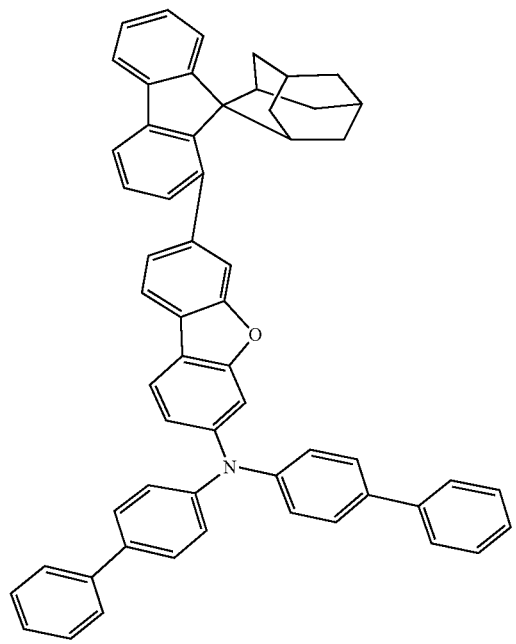

-continued
670
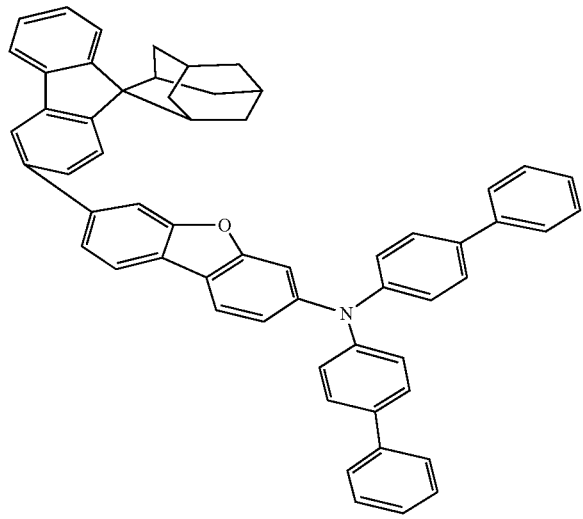
671
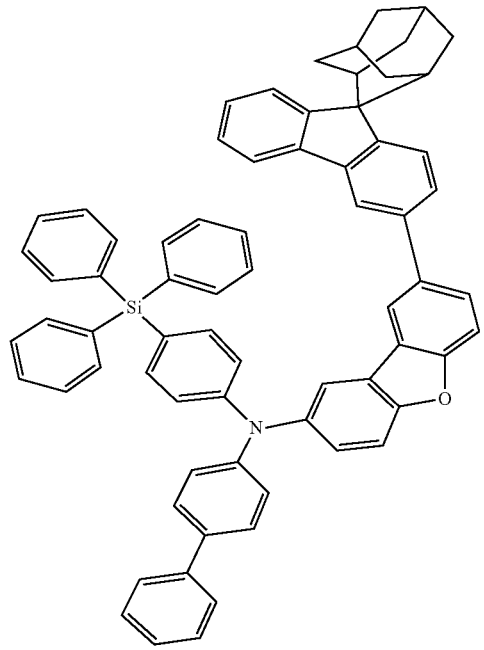
672
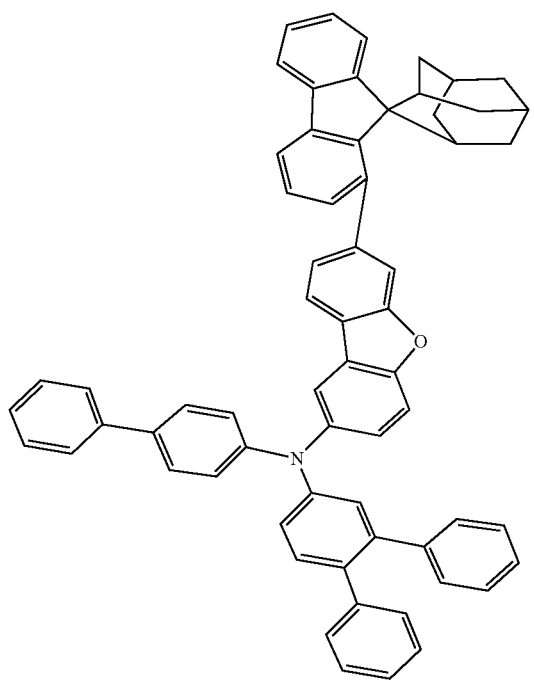
673
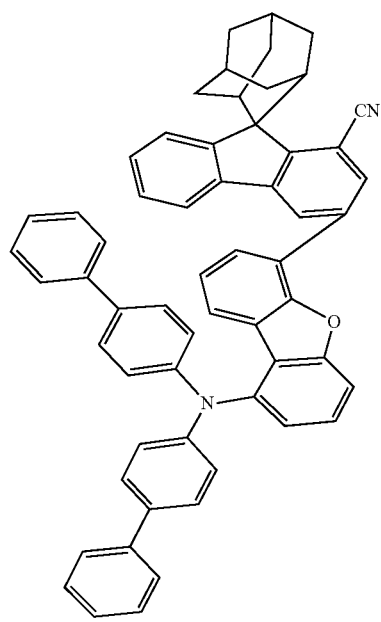

299
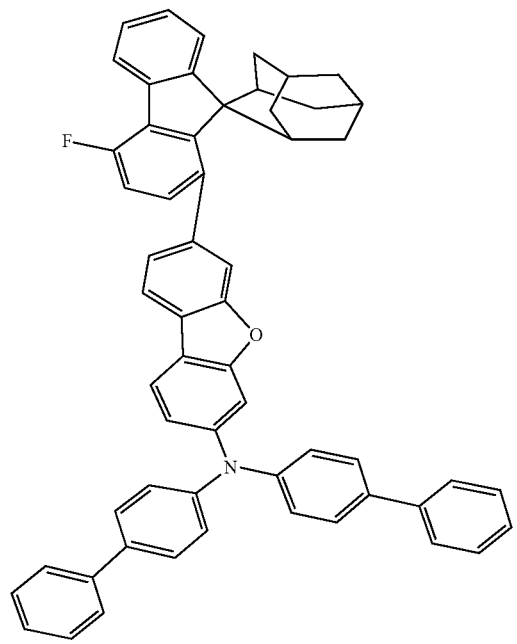
674
-continued
300
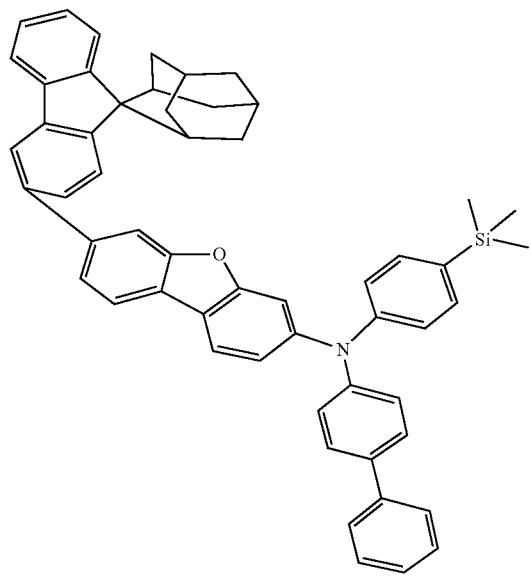
675
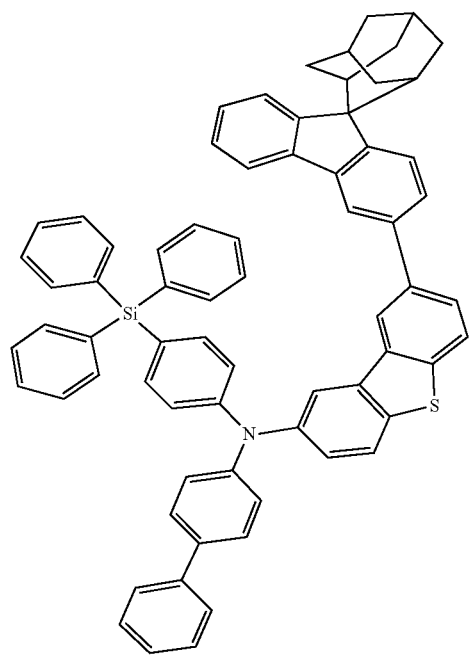
676
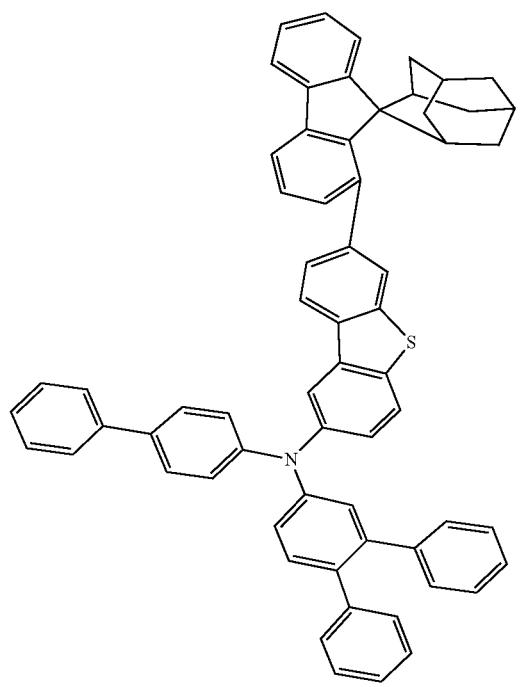
677

301 302
-continued
678 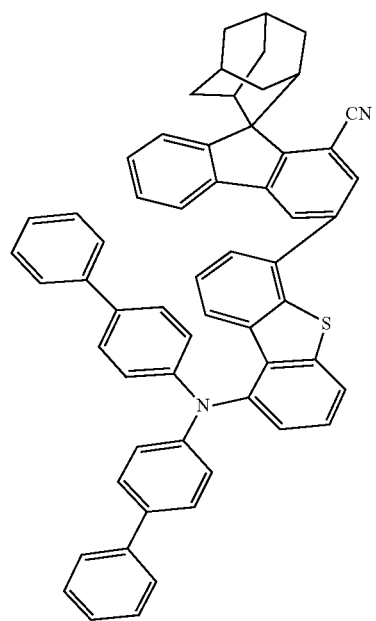 679 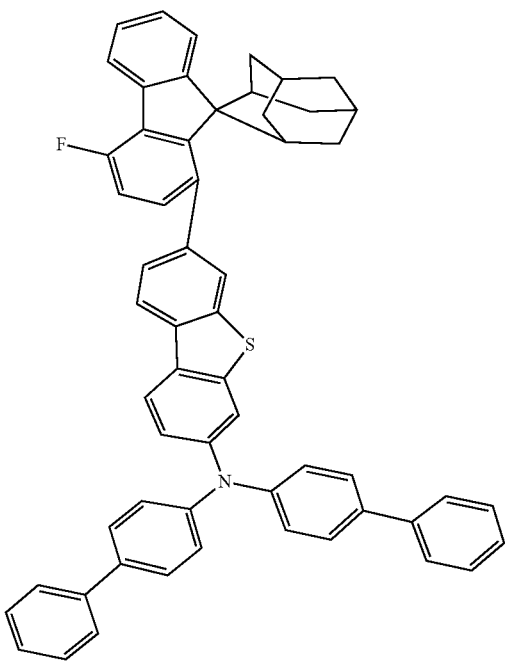
680 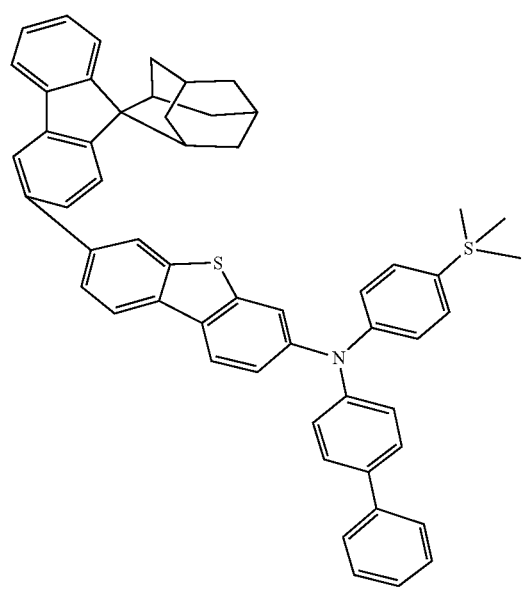 681 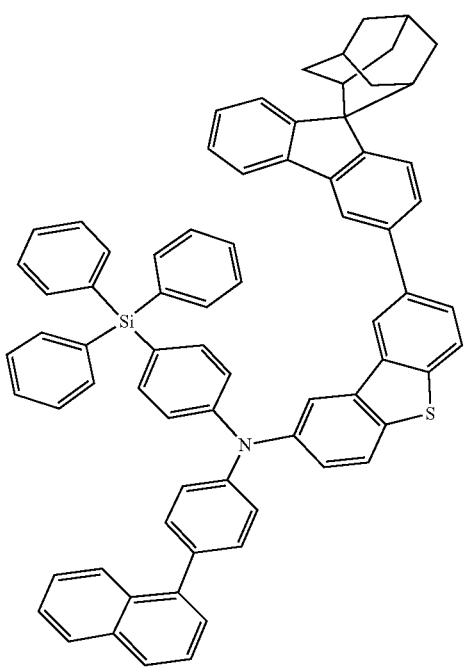

303 304
-continued
682
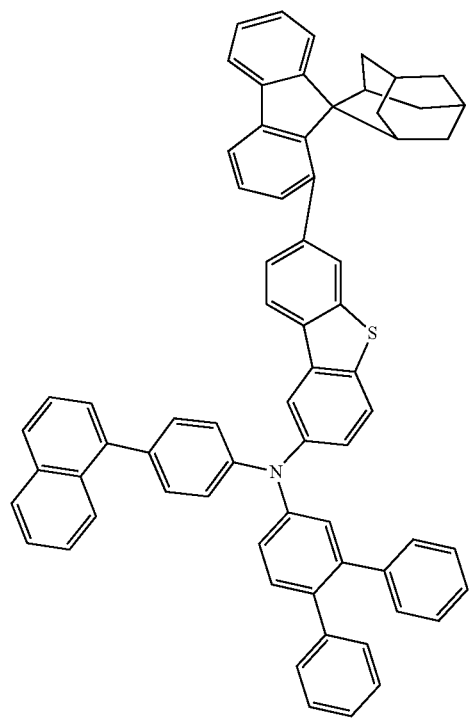
683
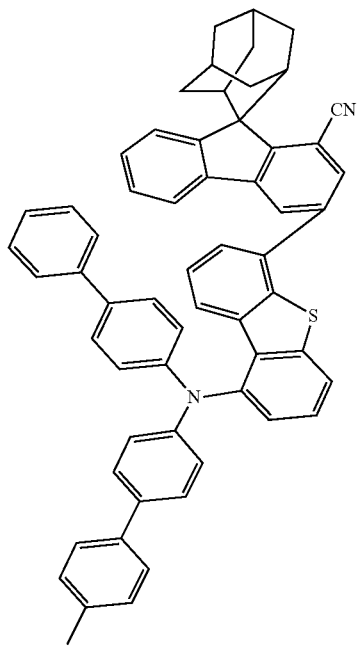
684
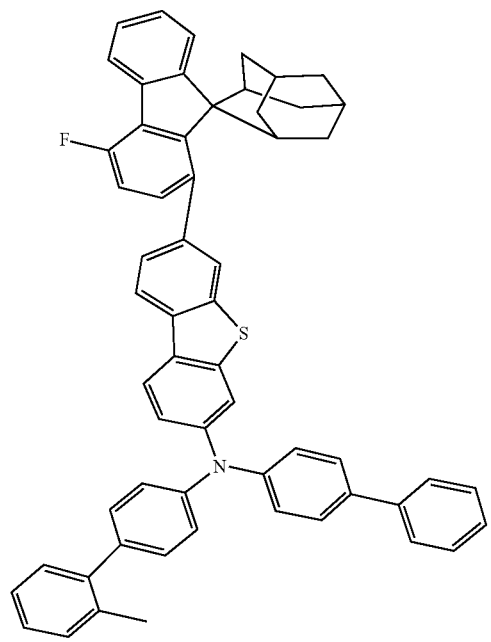
685
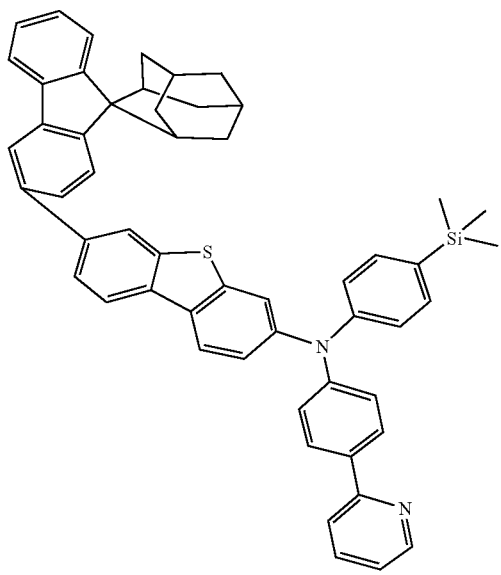

-continued
686
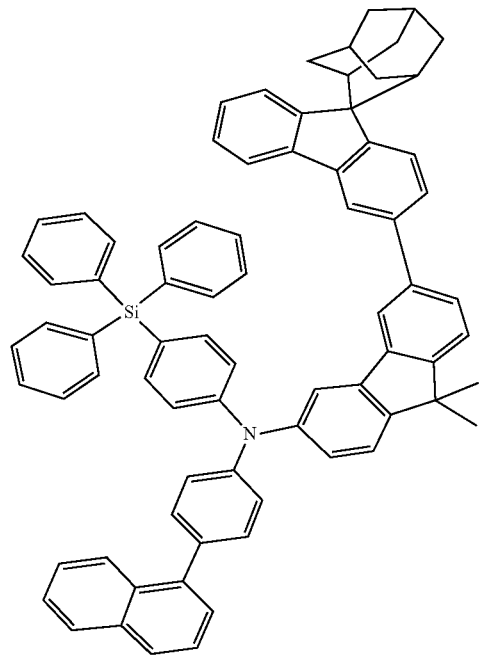
687
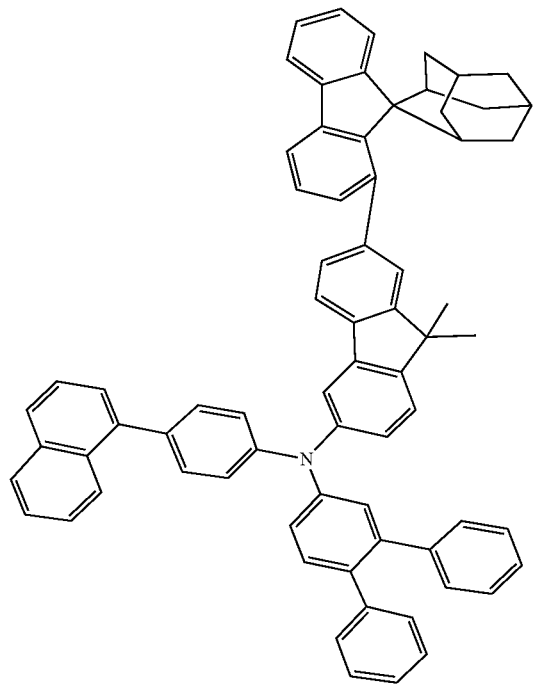
688
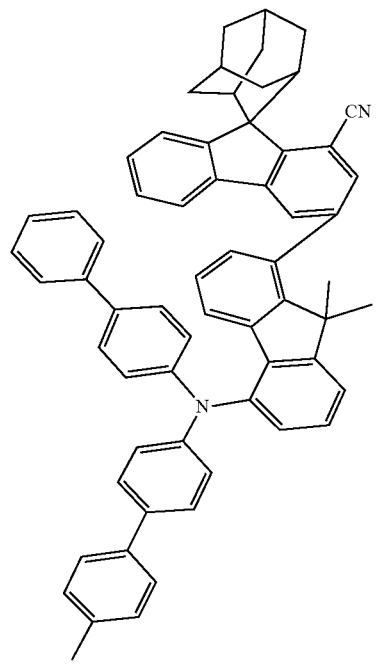
689
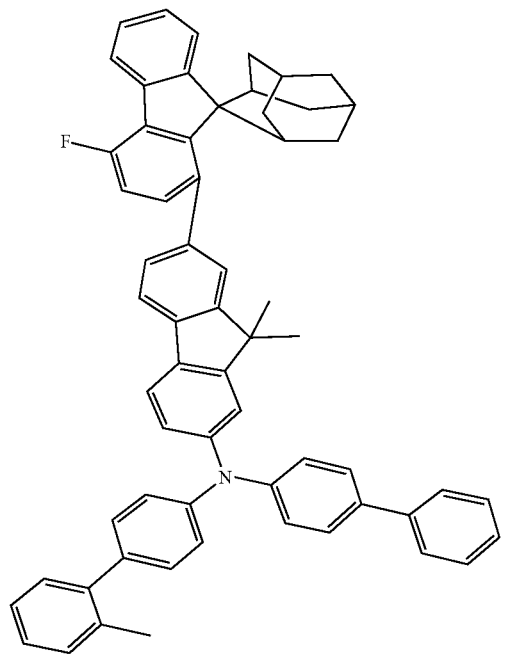

-continued
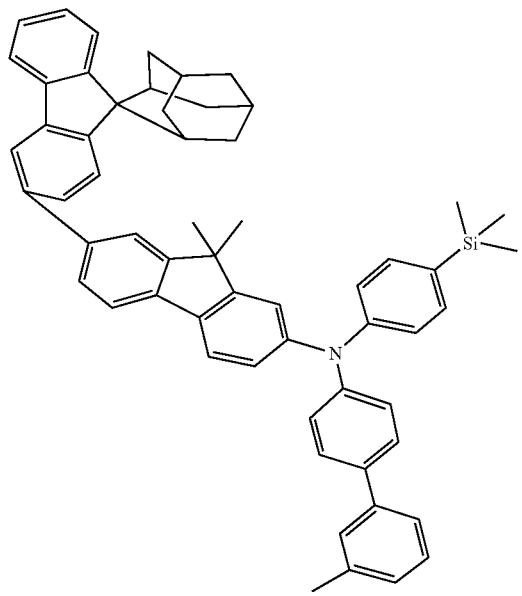
690
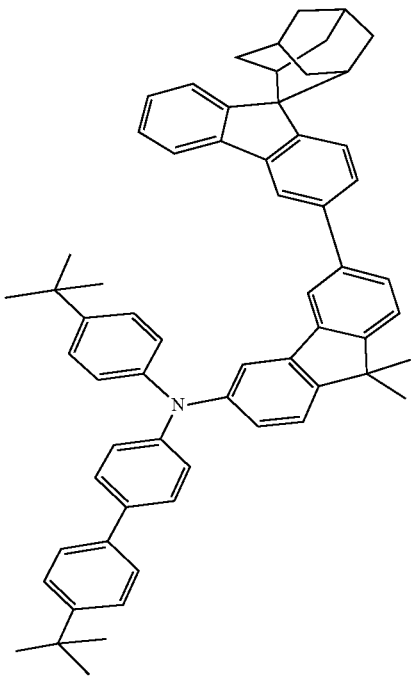
691
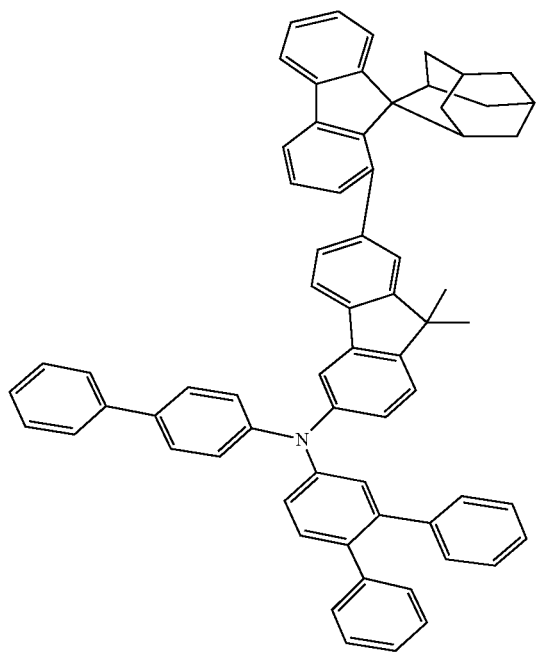
692
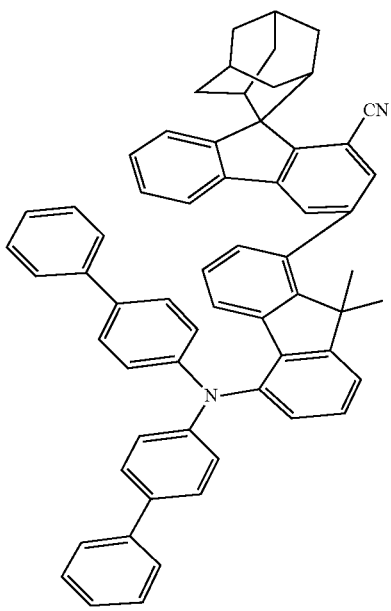
693

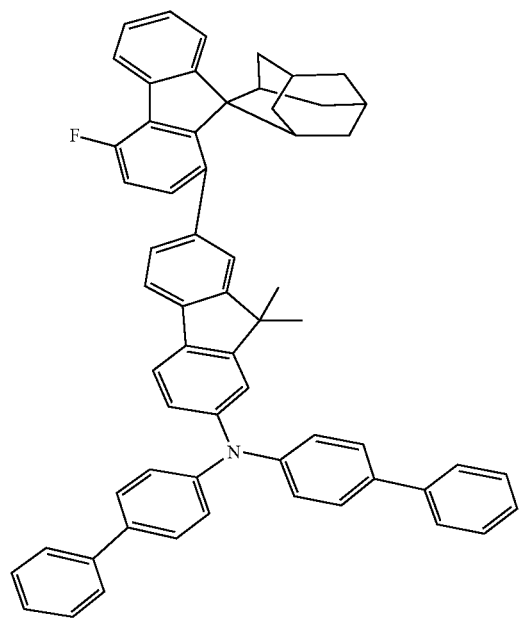
694
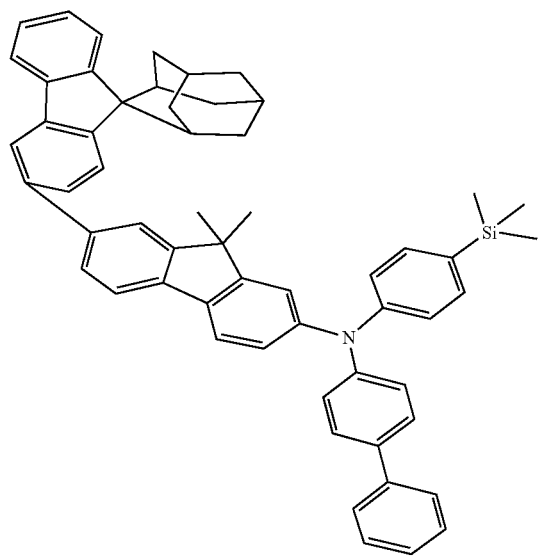
695
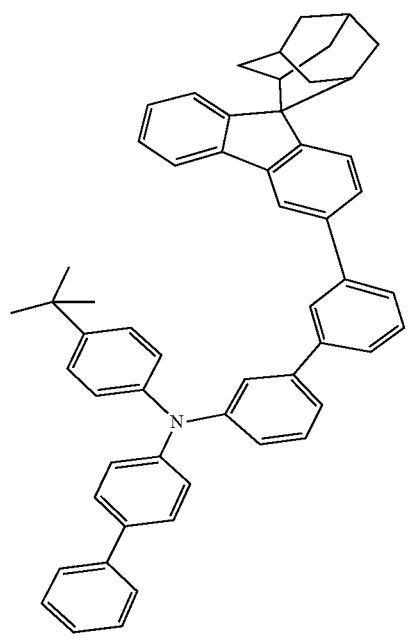
696
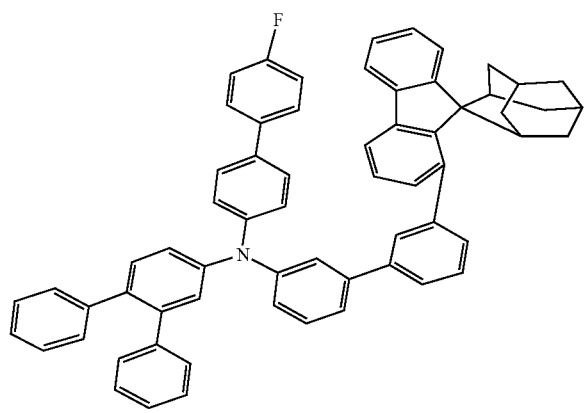
697

-continued
311
698
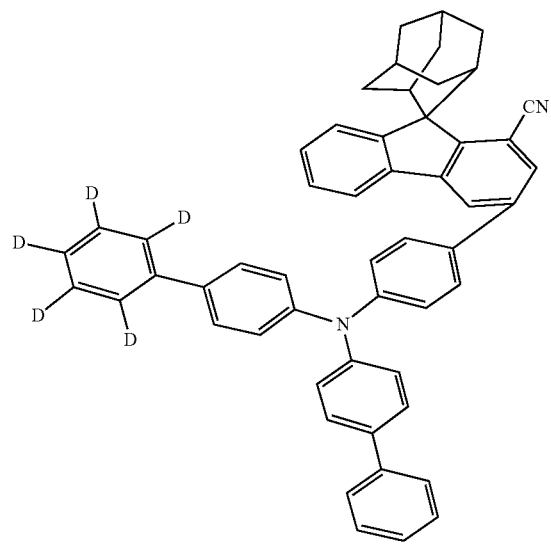
312
699
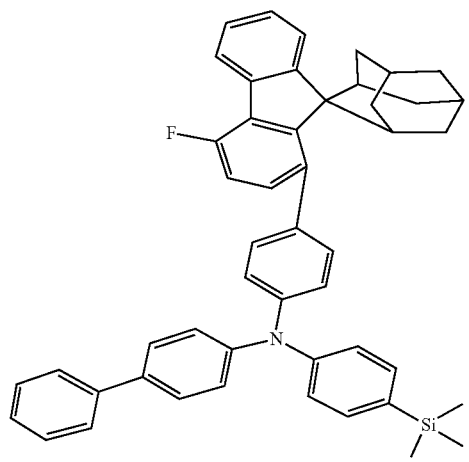
700
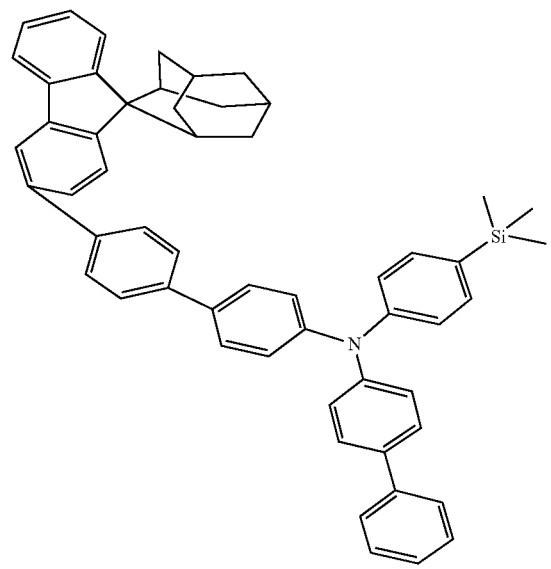
701
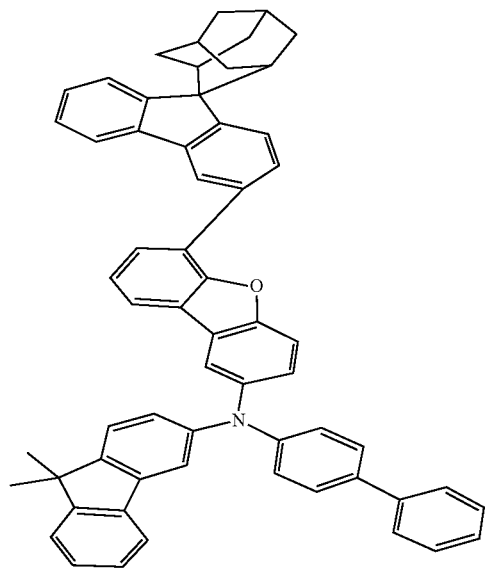

313
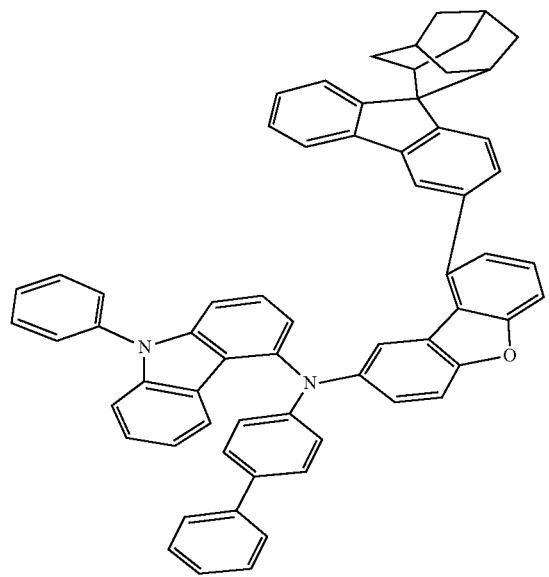
702
314
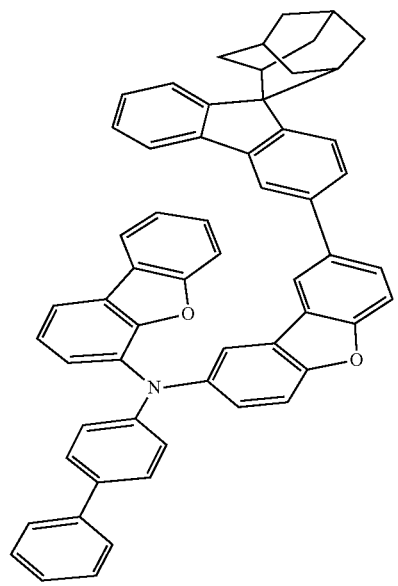
703
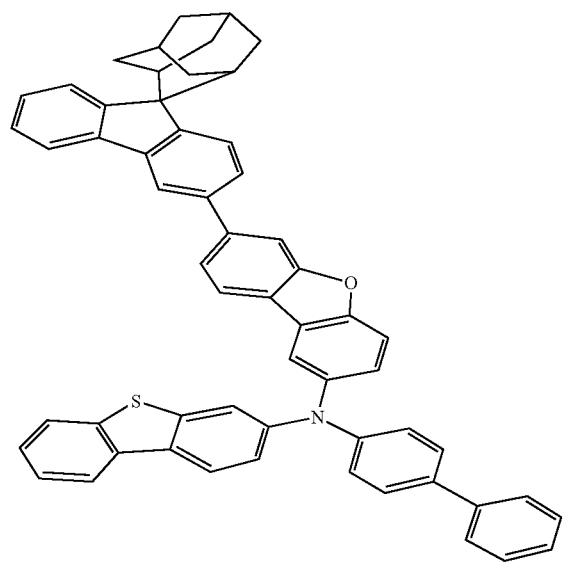
704
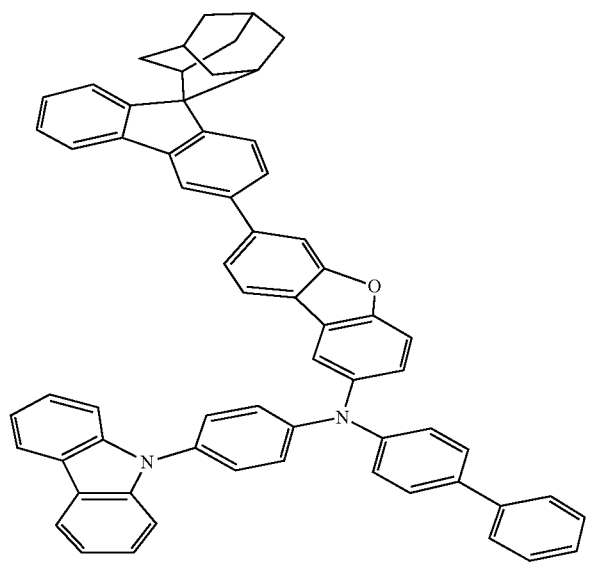
705

-continued
315
706
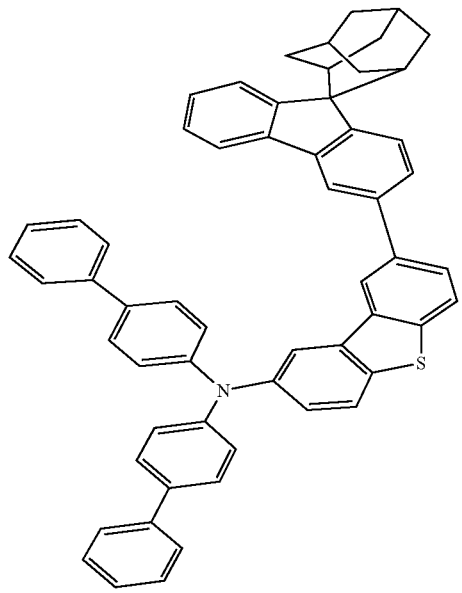
316
707
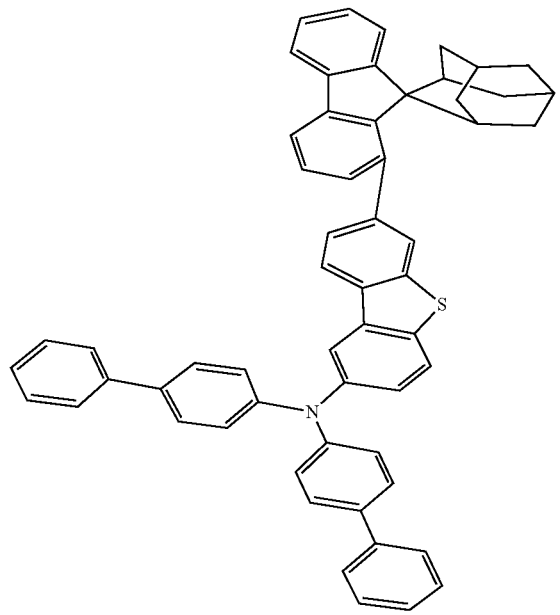
708
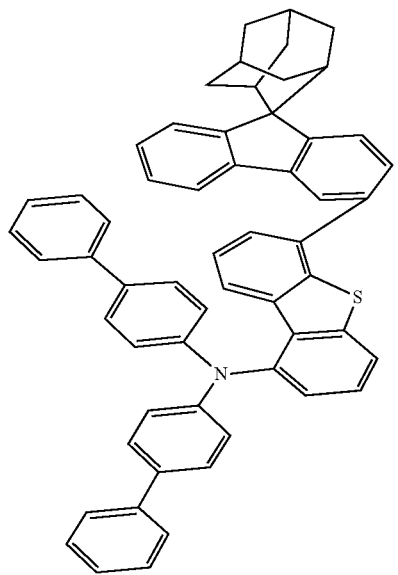
709
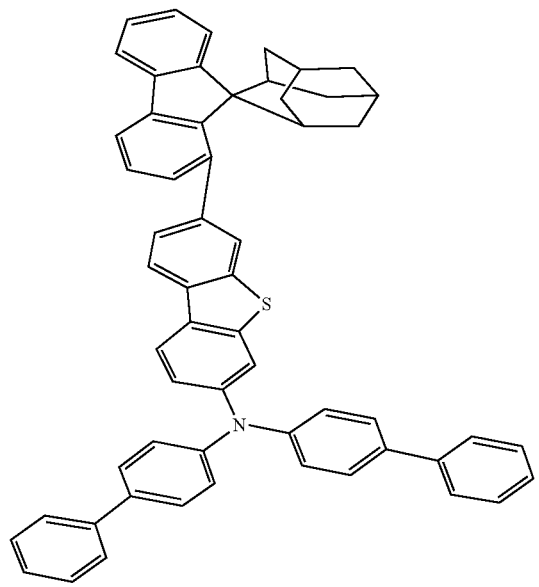

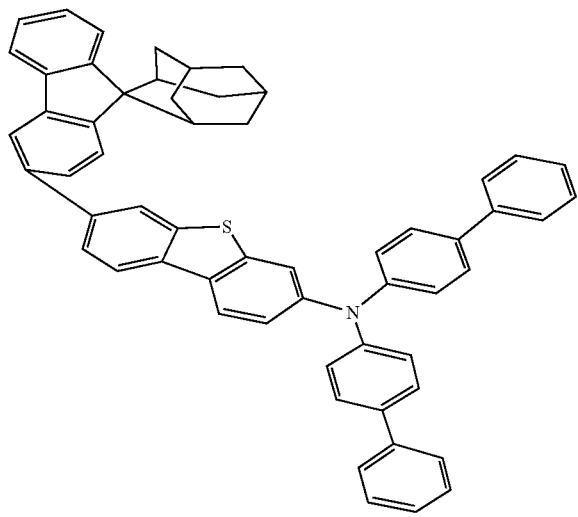
710
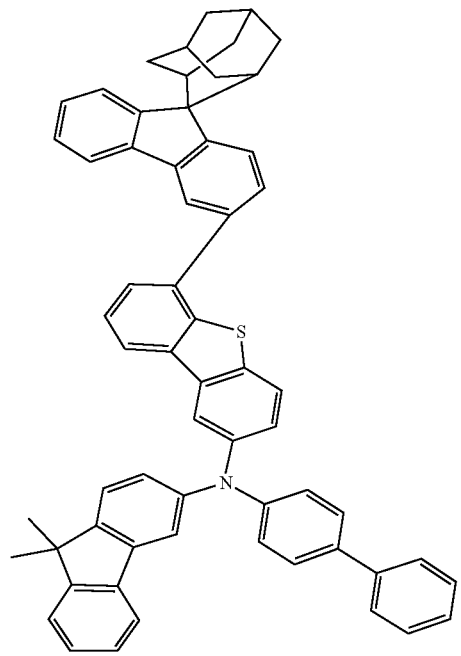
711
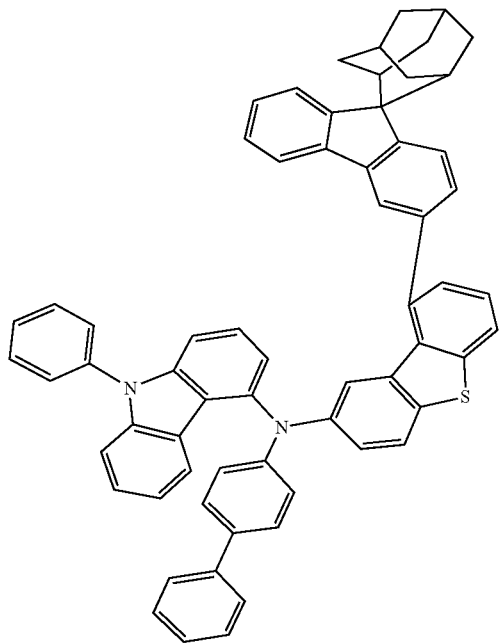
712
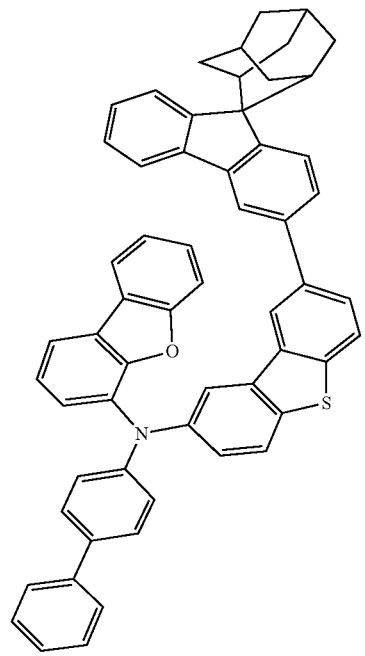
713

-continued
714
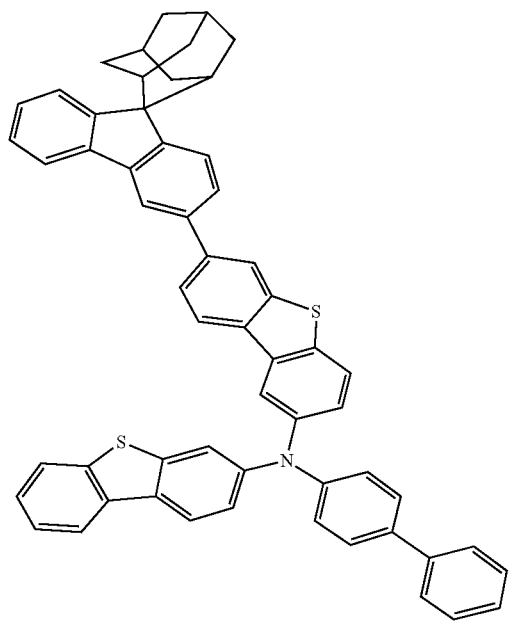
715
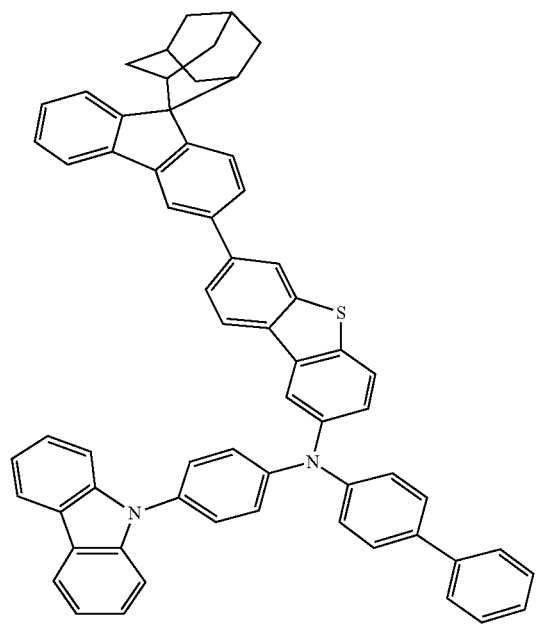
716
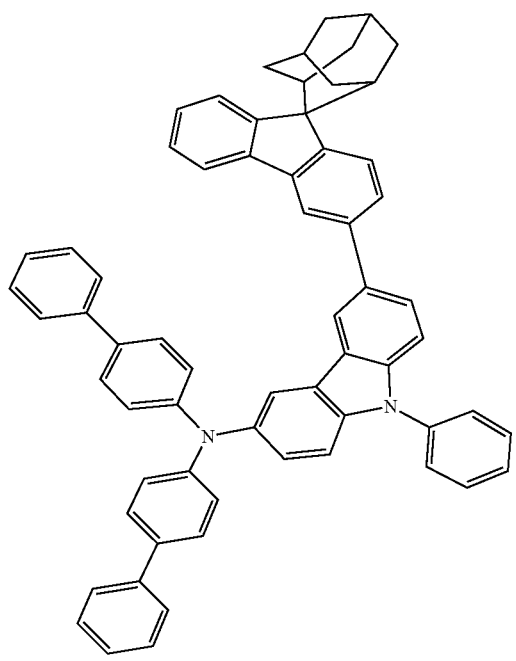
717
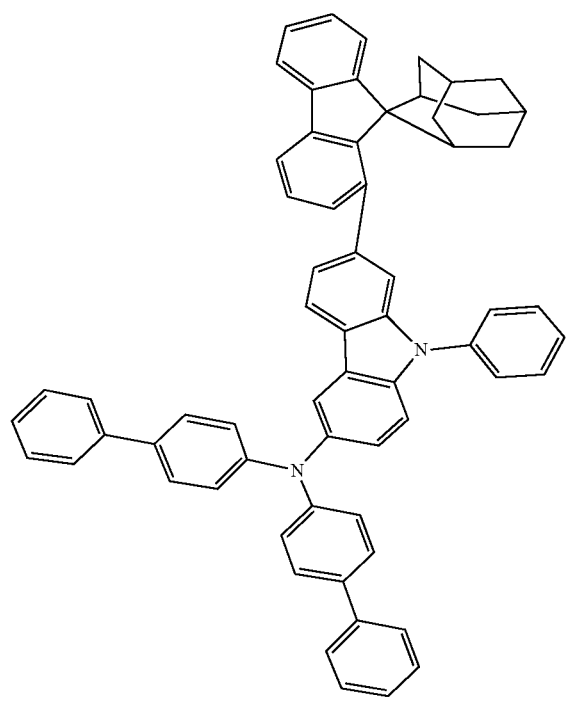

-continued
321
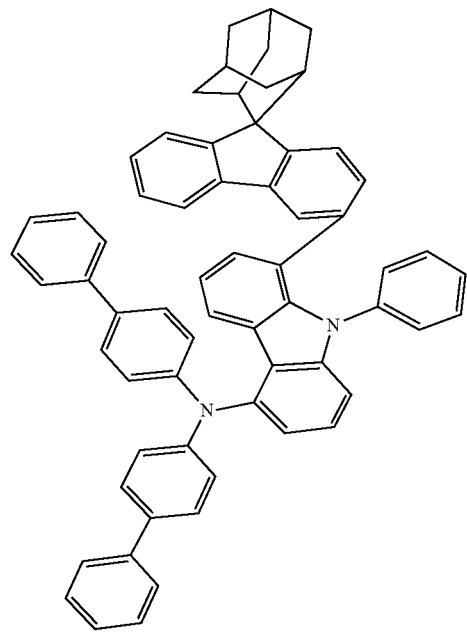
718
322
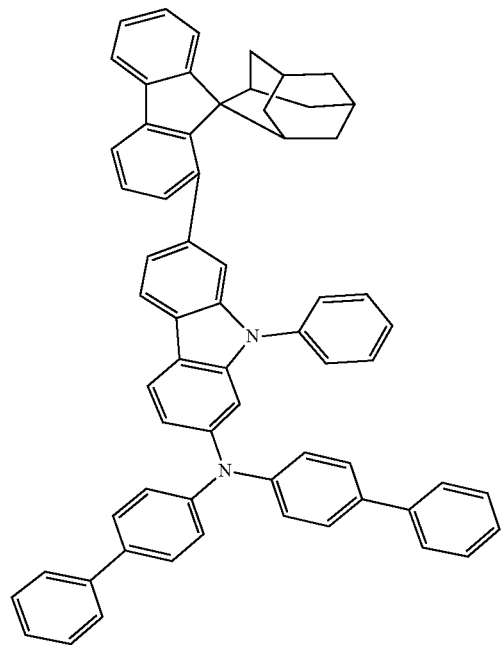
719
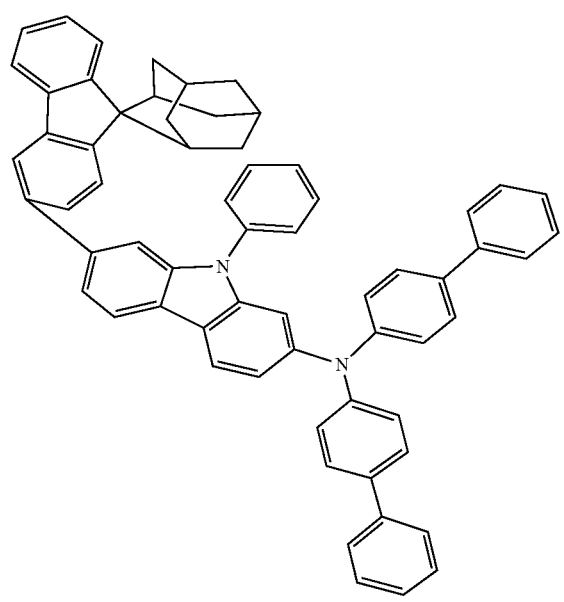
720
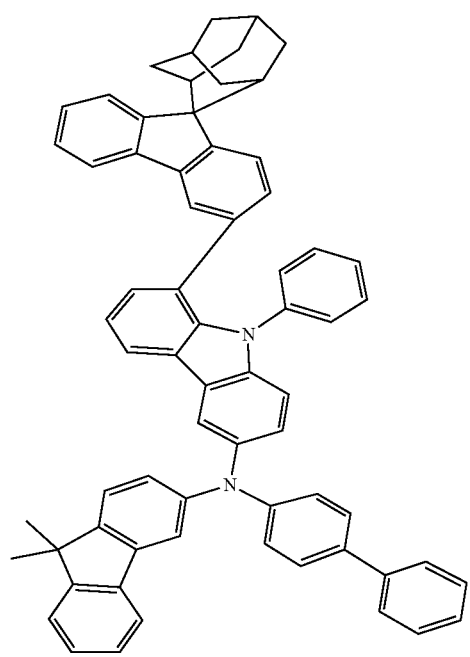
721

| 323 | 324 |
|---|---|
| 722 | 723 |
| 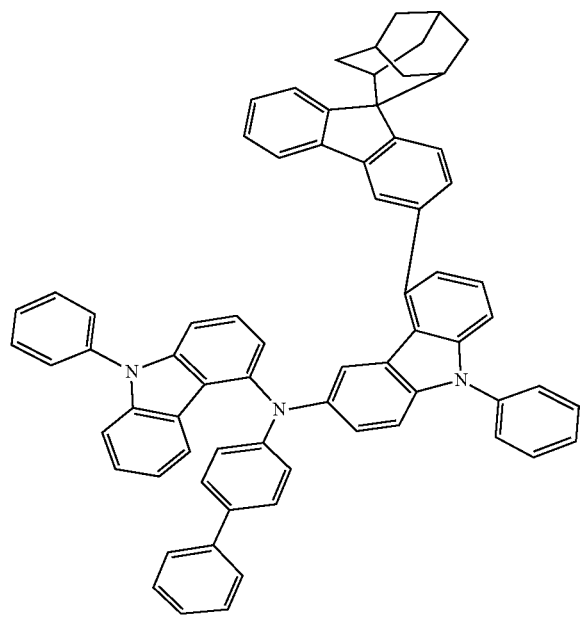 | 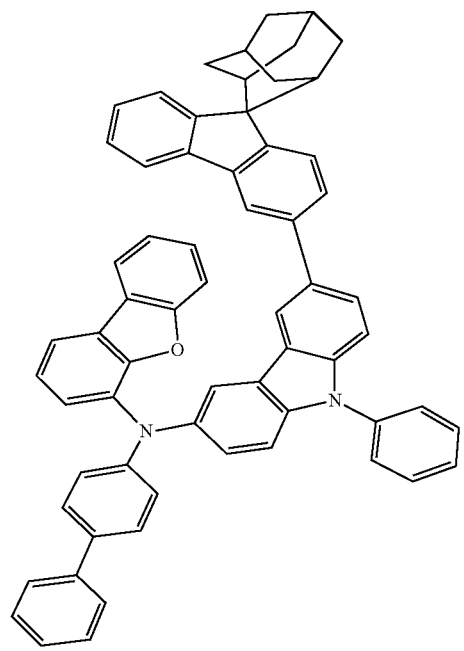 |
| 724 | 725 |
| 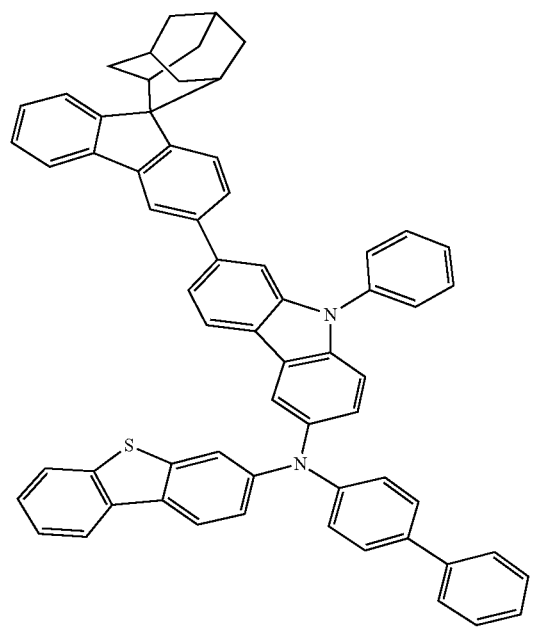 | 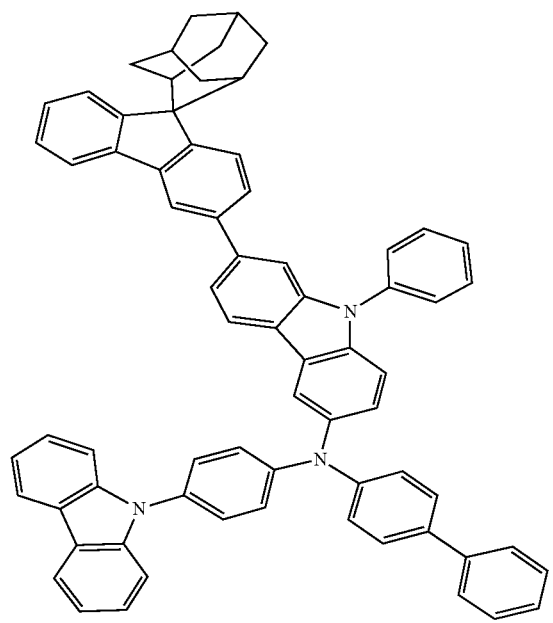 |

-continued
726
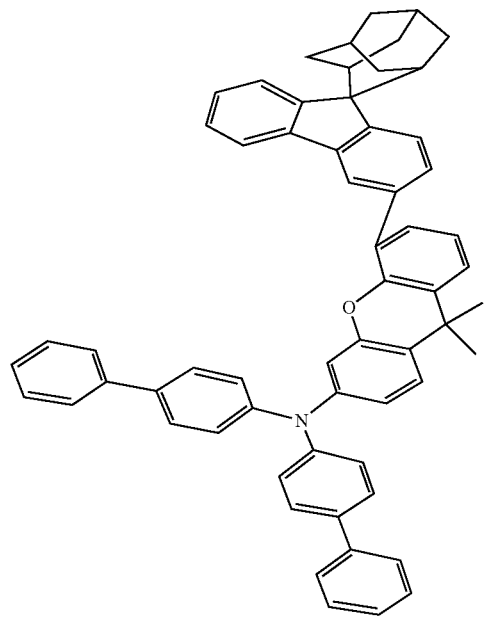
727
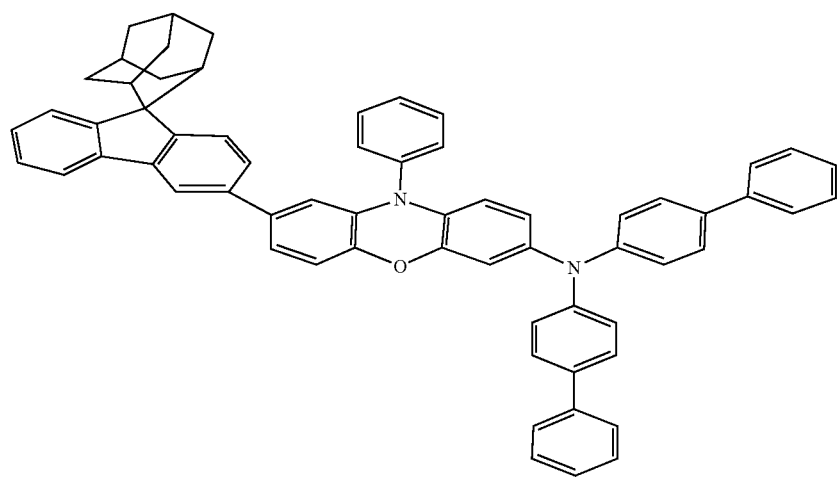

327 328
728 729
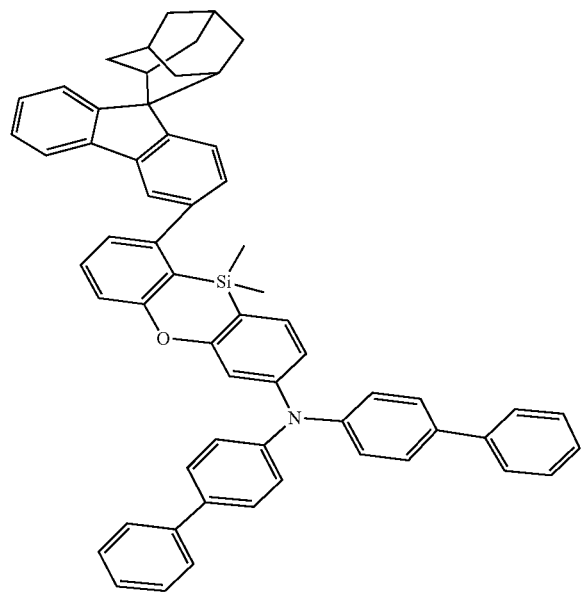 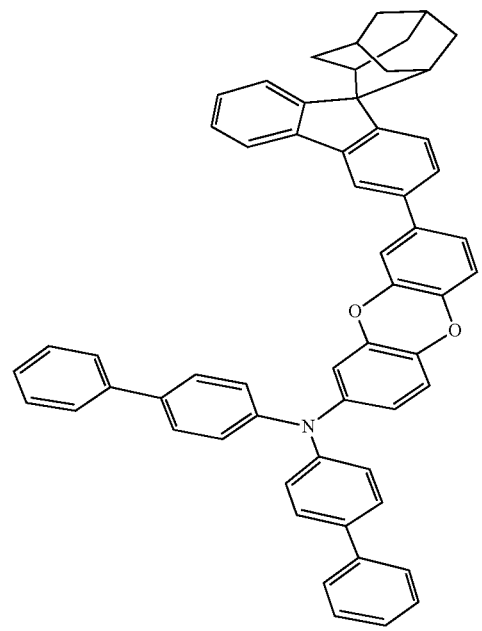
730 731
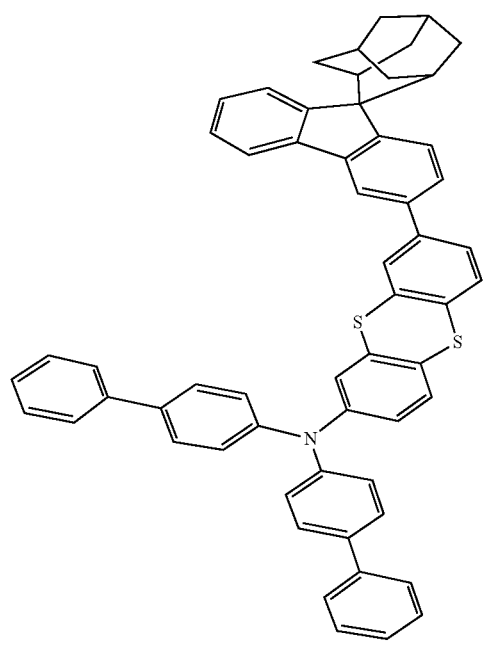 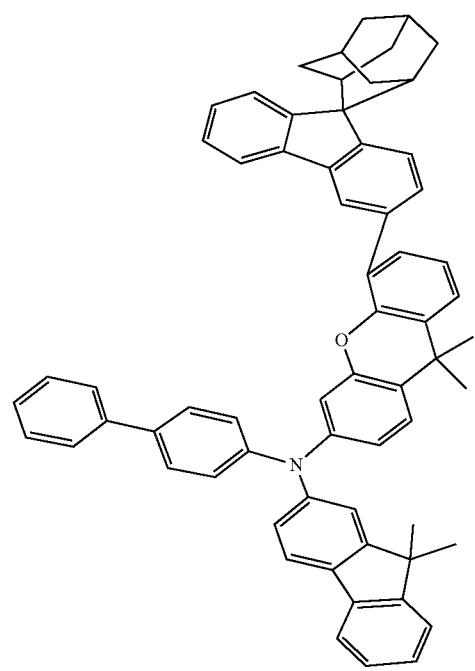

732
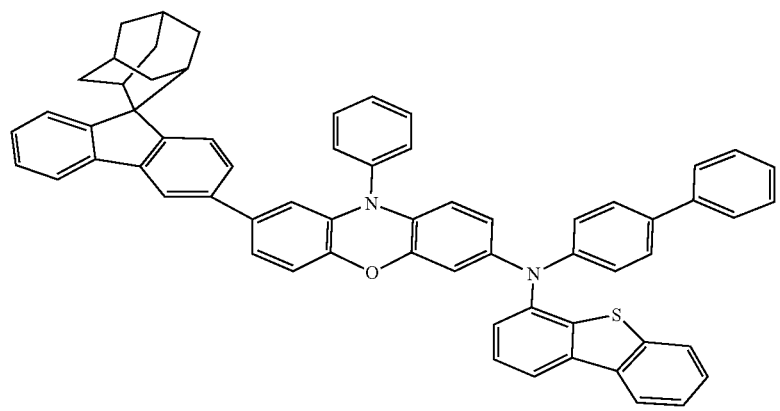
733
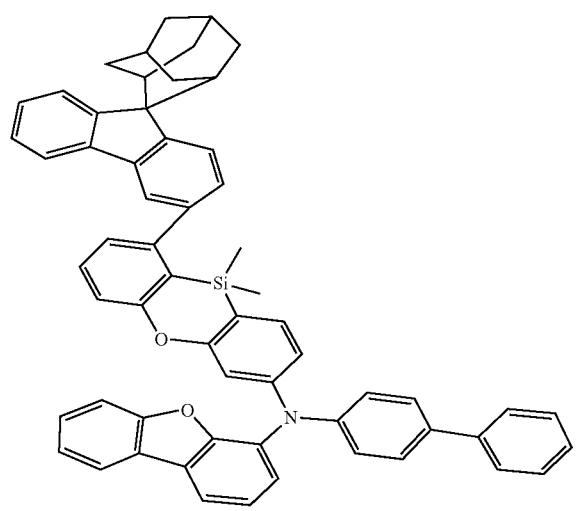
734
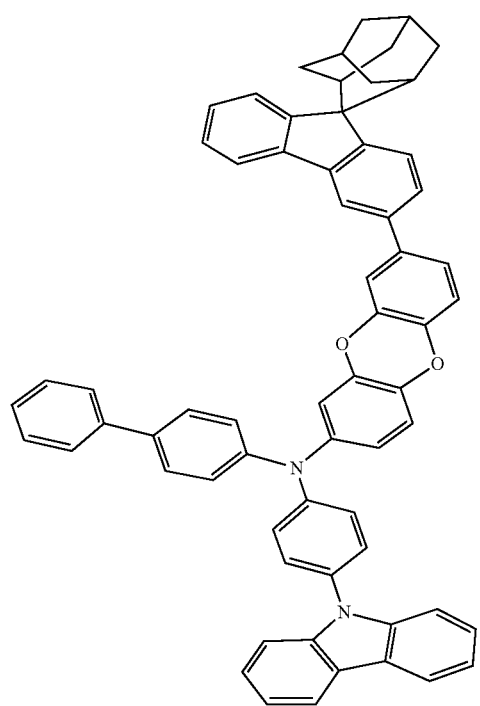

-continued
331
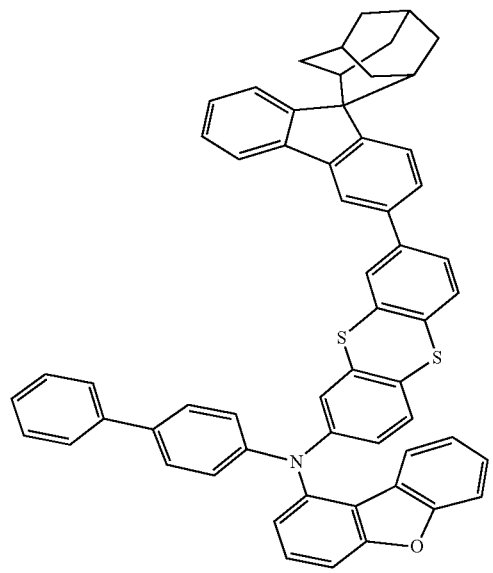
735
332
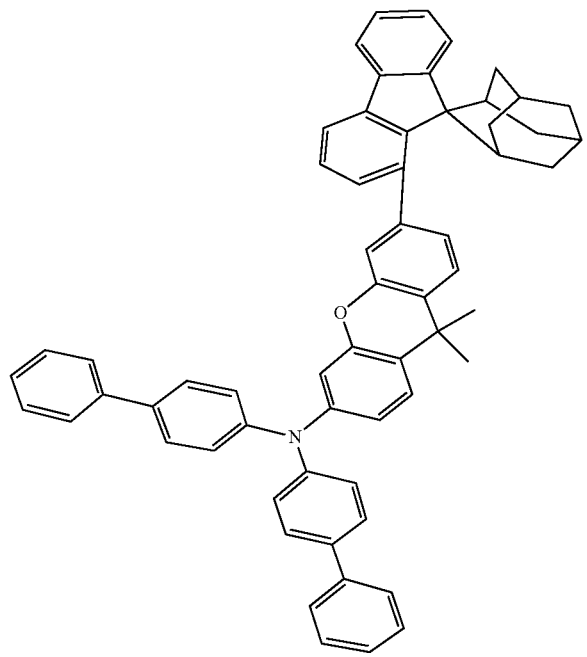
736
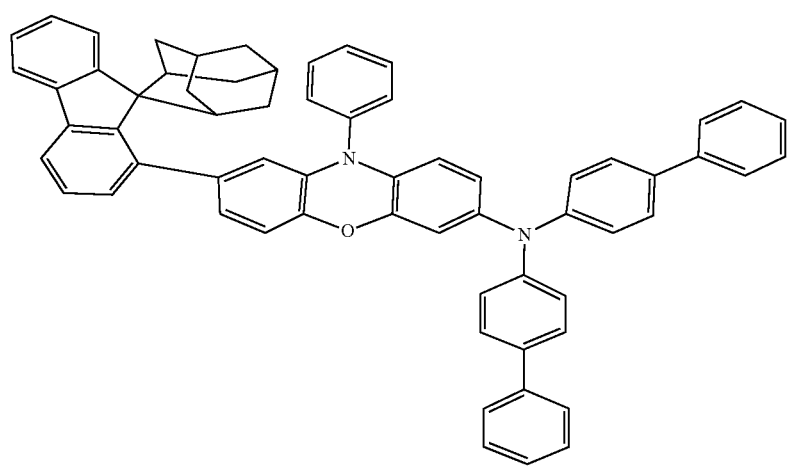
737

-continued
738
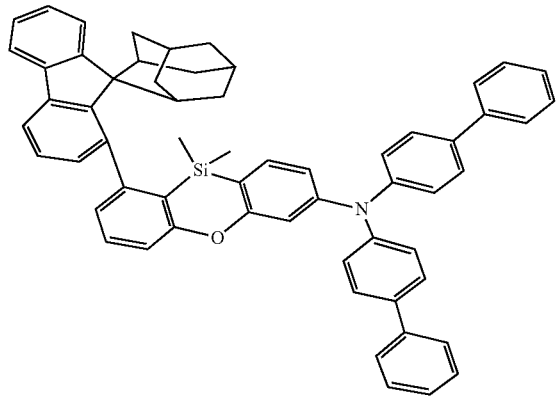
739
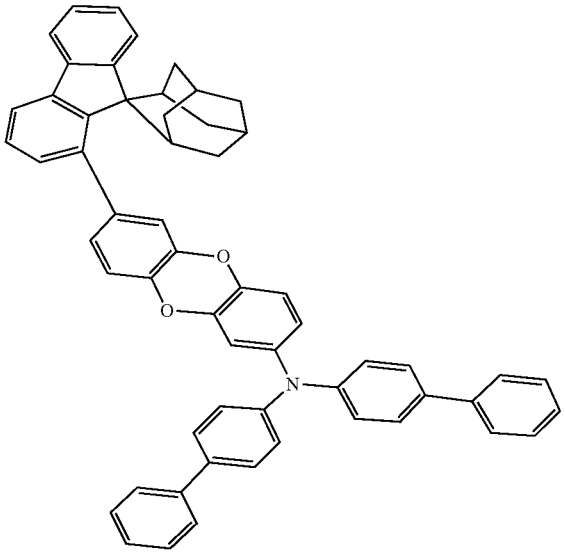
740
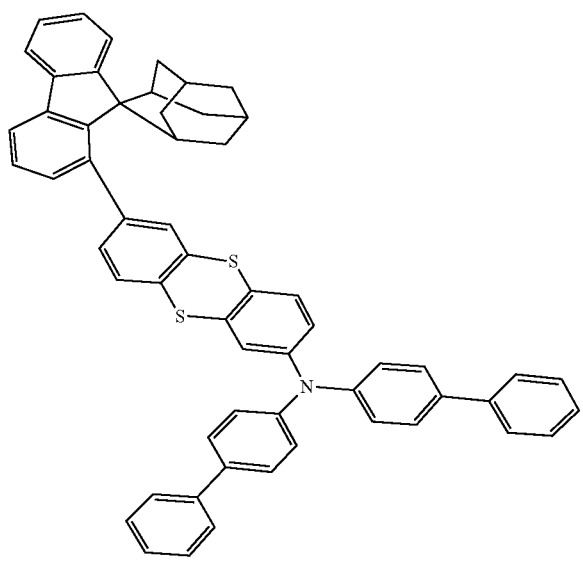
741
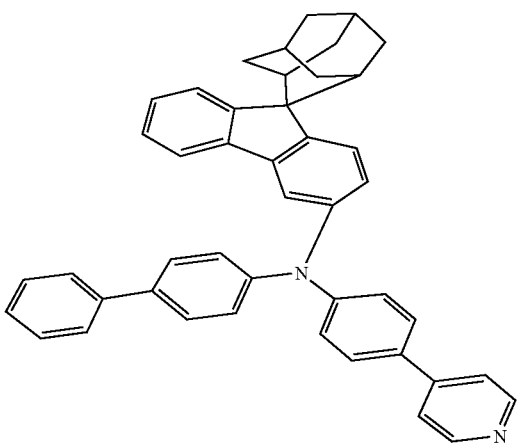
742
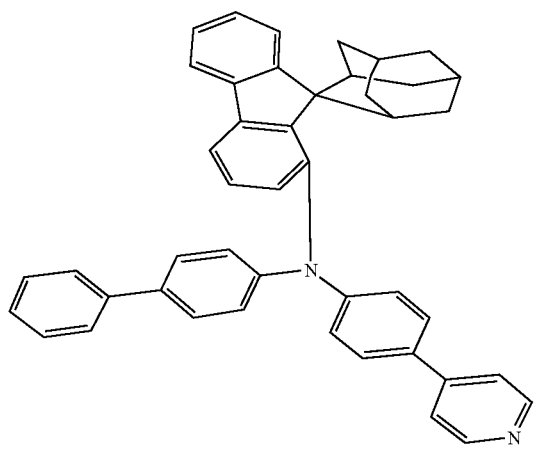
743
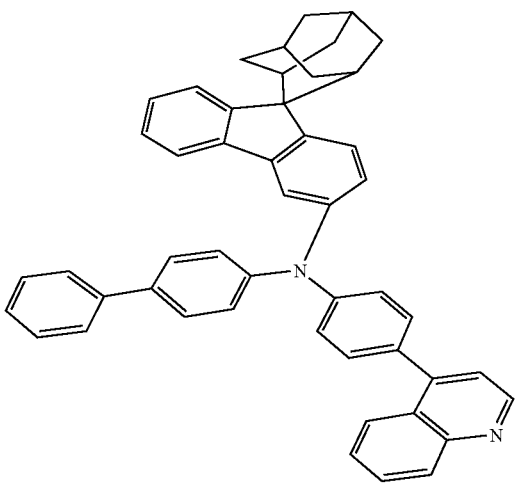

-continued
744
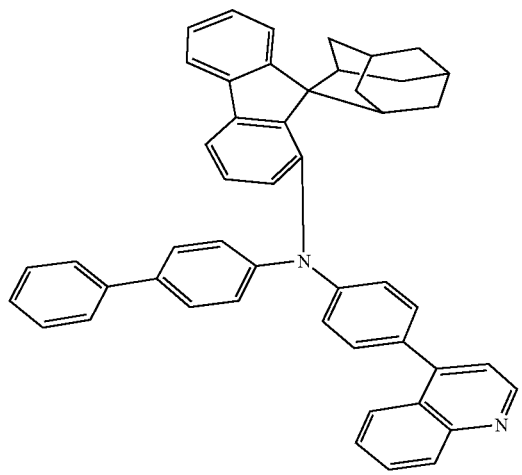
745
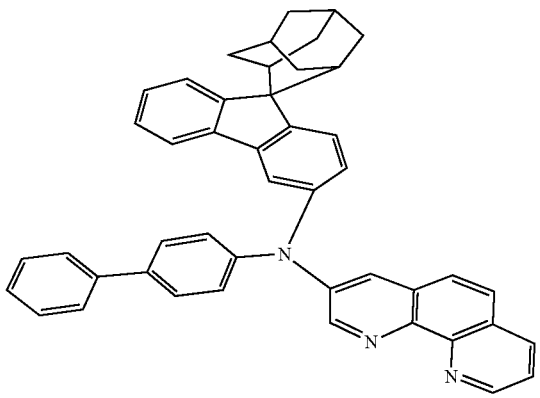
746
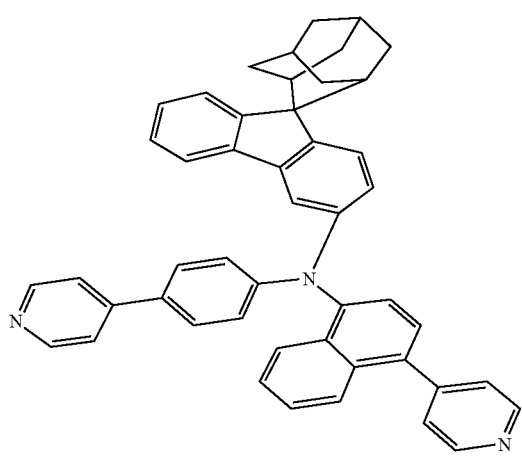
747
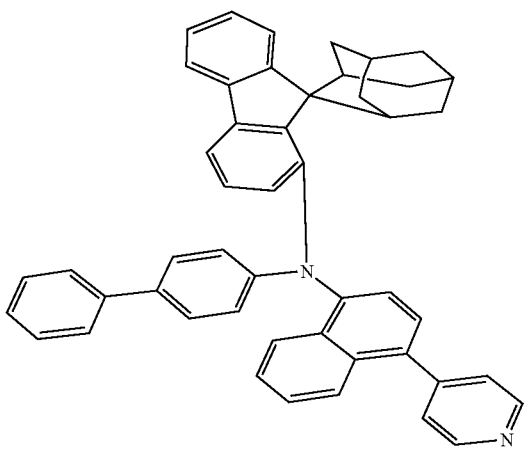
748
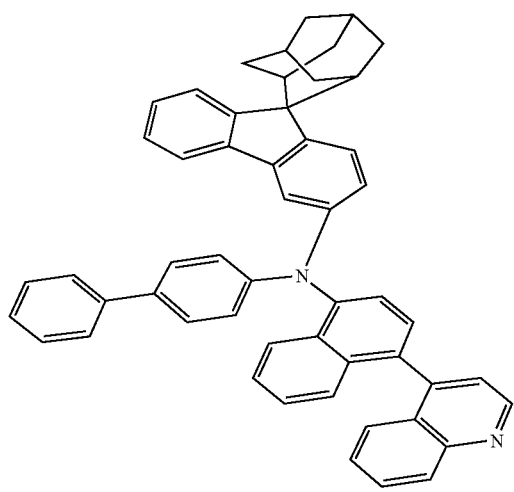
749
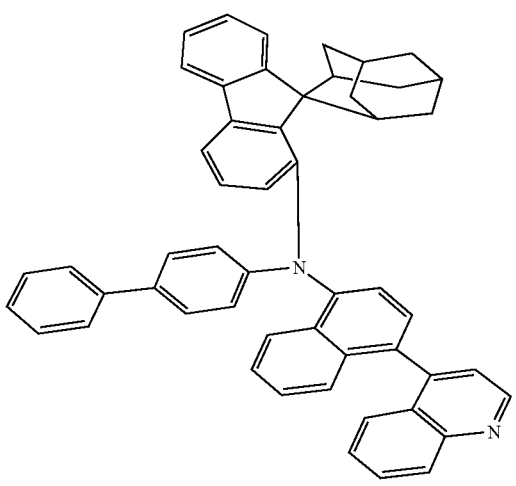

-continued
750
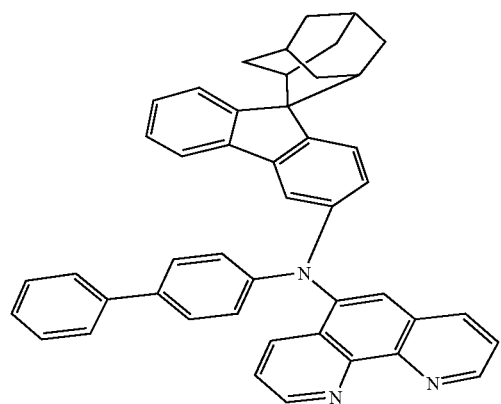
751
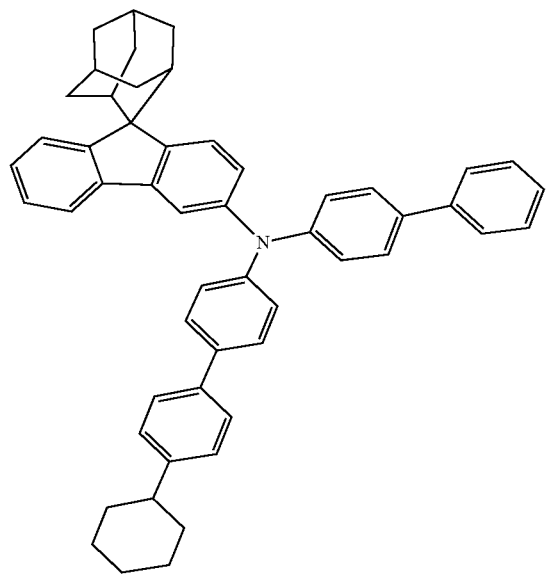
752
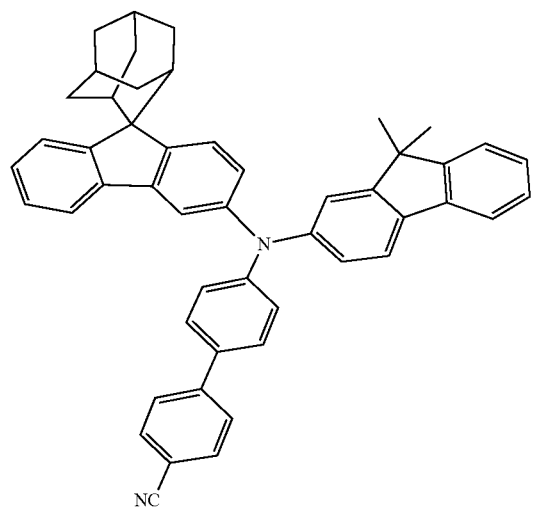
753
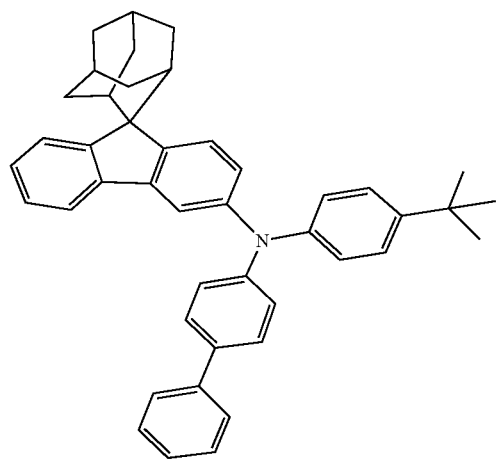
754
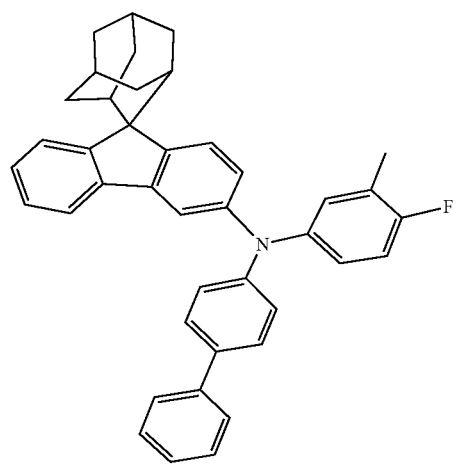
755
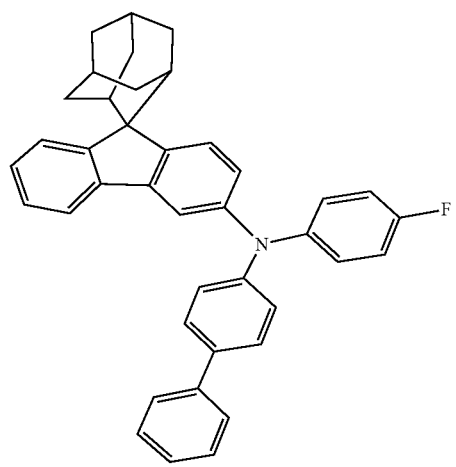

-continued
756
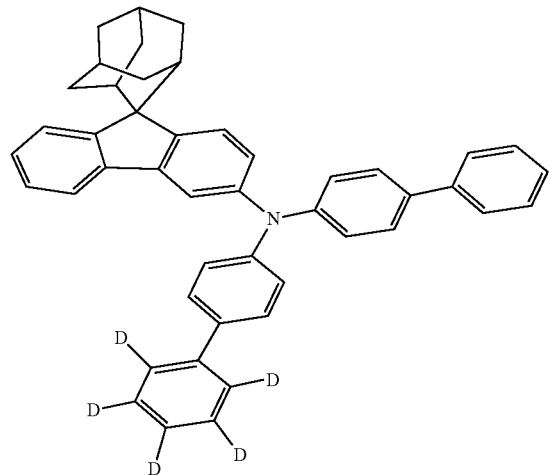
757
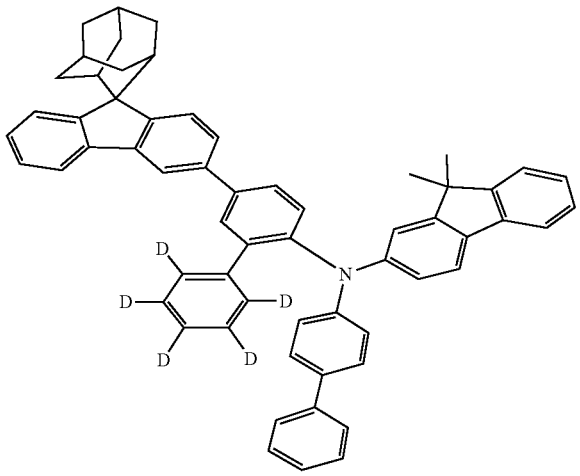
758
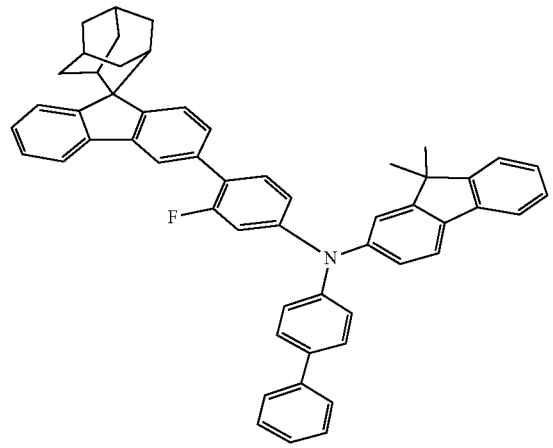
759
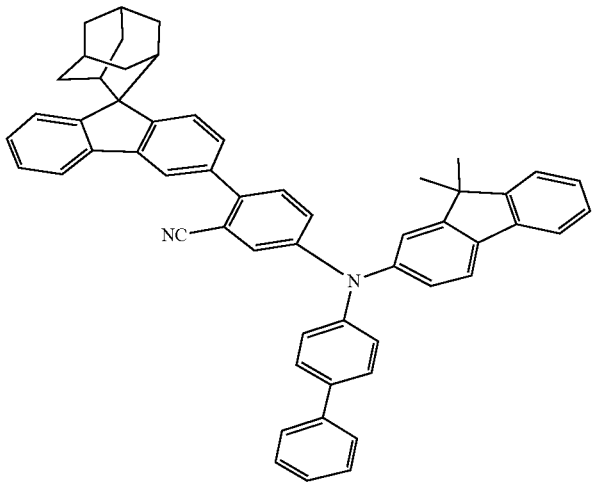
800
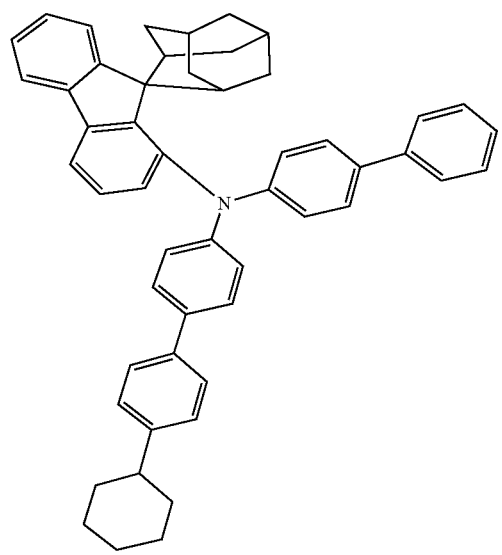
801
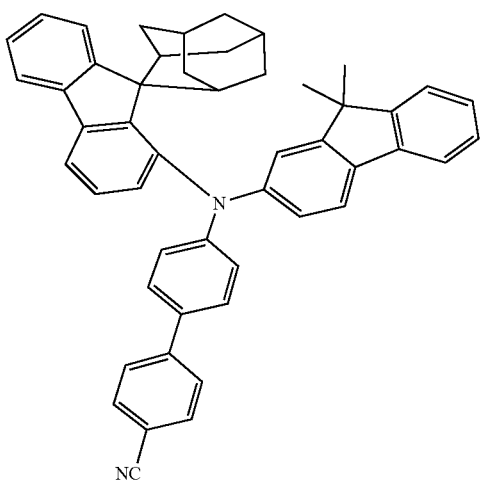

-continued
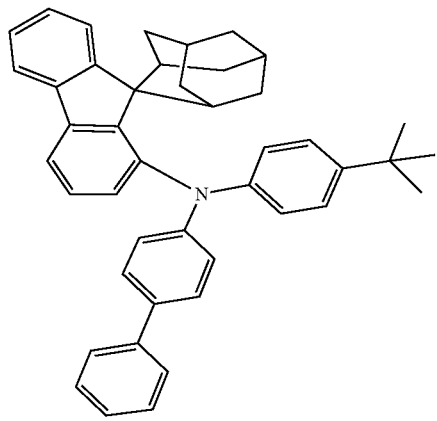
802
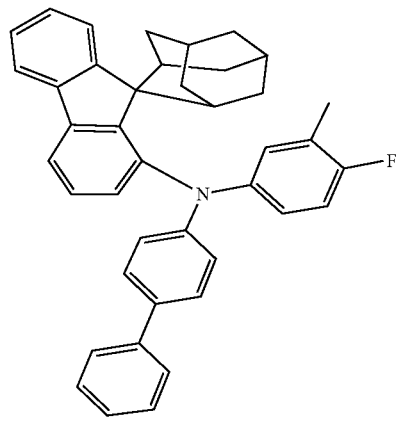
803
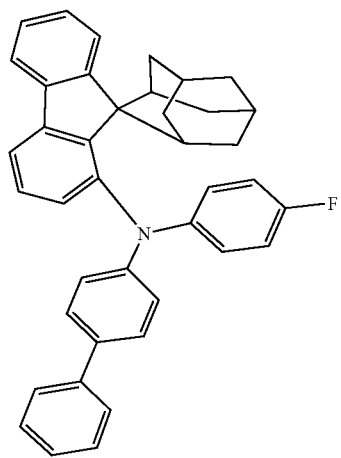
804
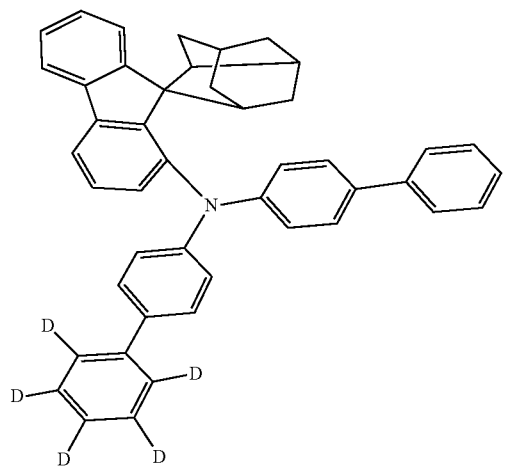
805
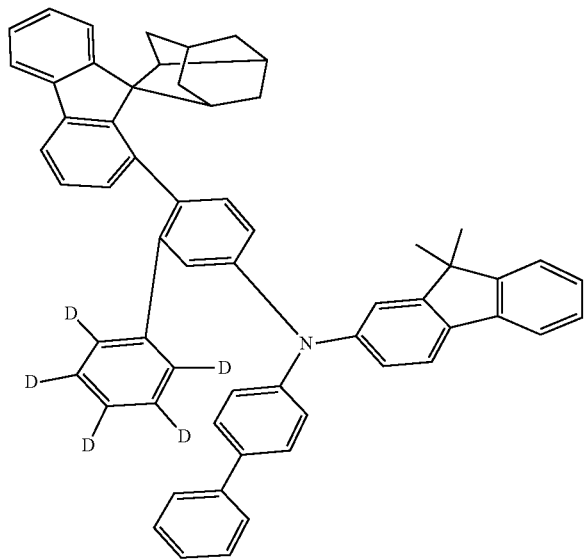
806
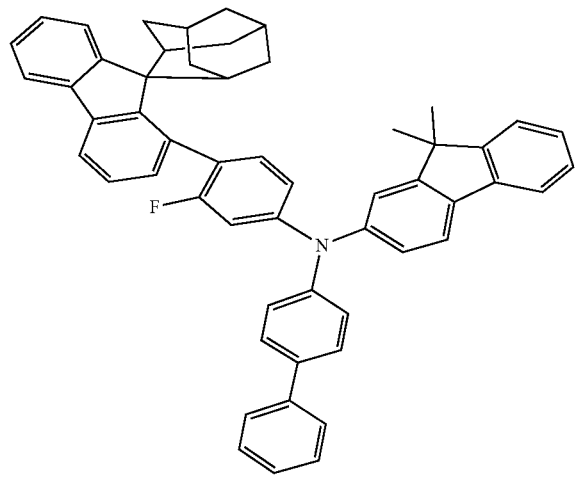
807

-continued
808
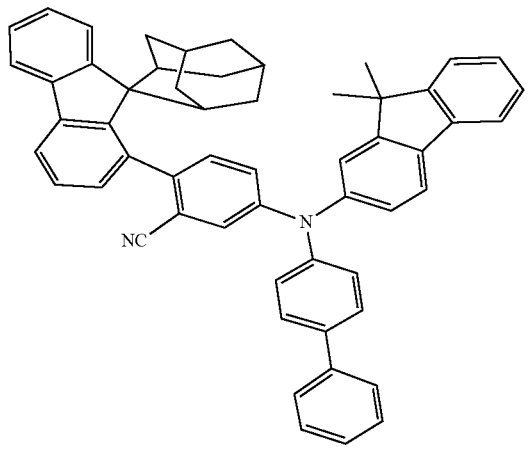
809
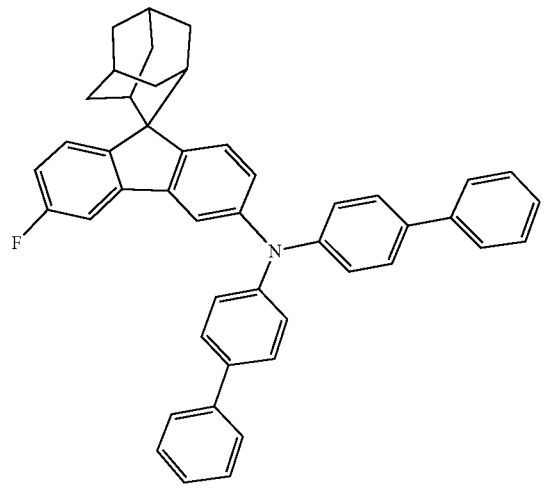
810
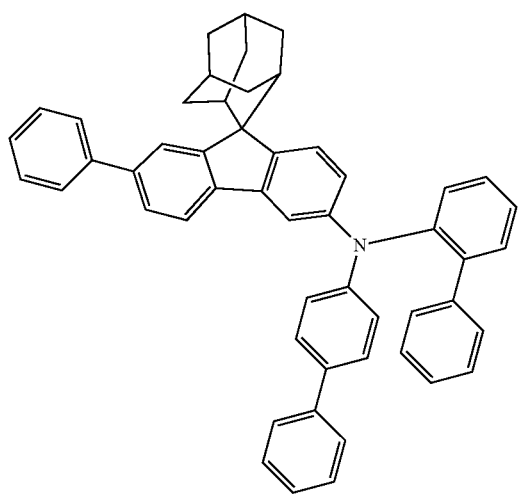
811
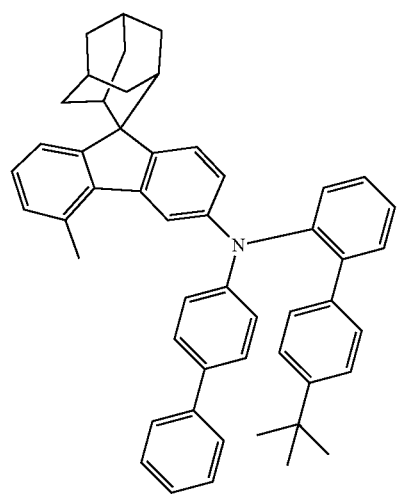
812
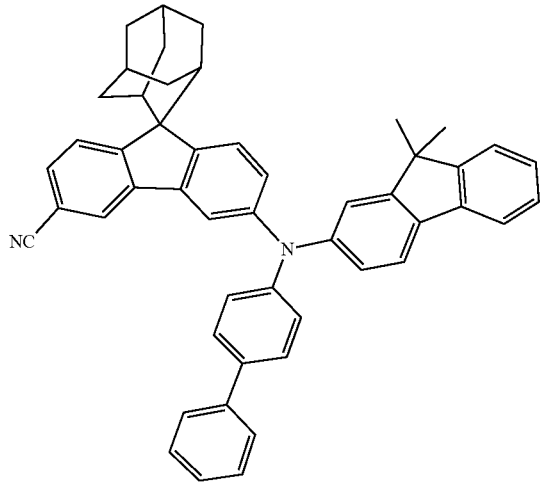
813
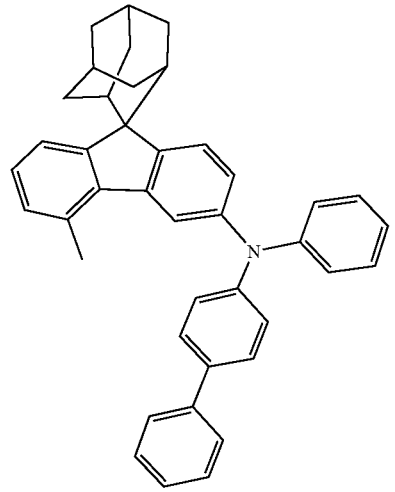

-continued
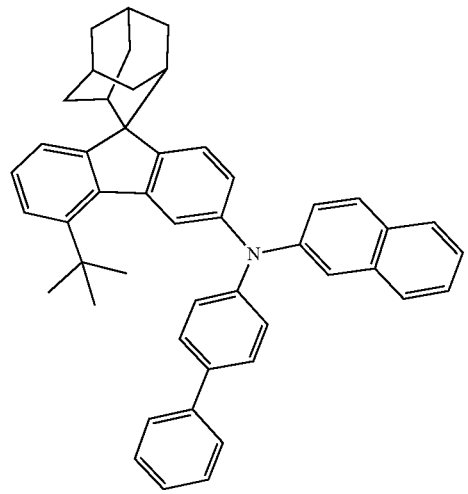
814
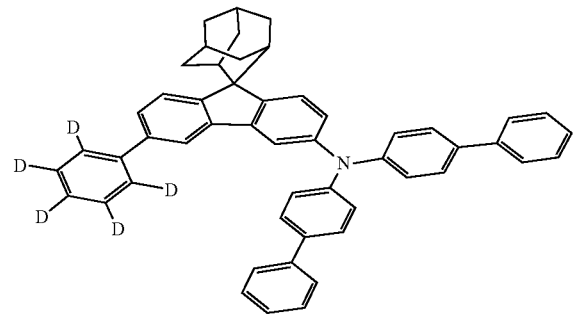
815
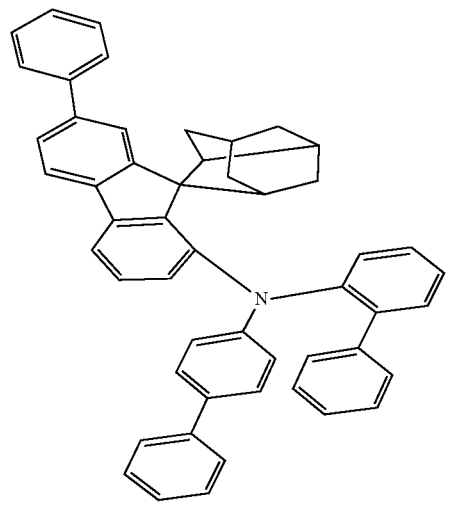
816
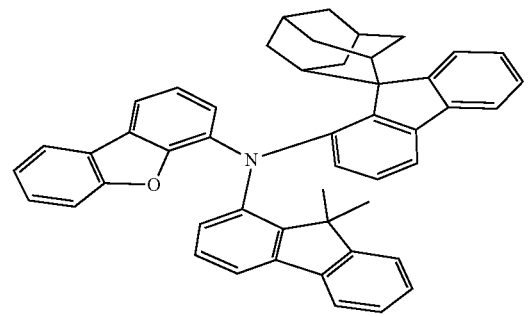
817
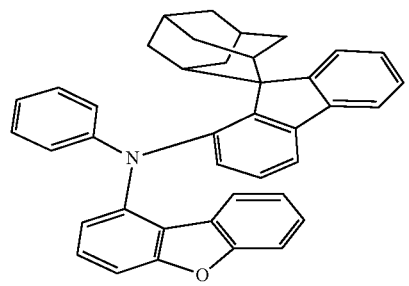
818
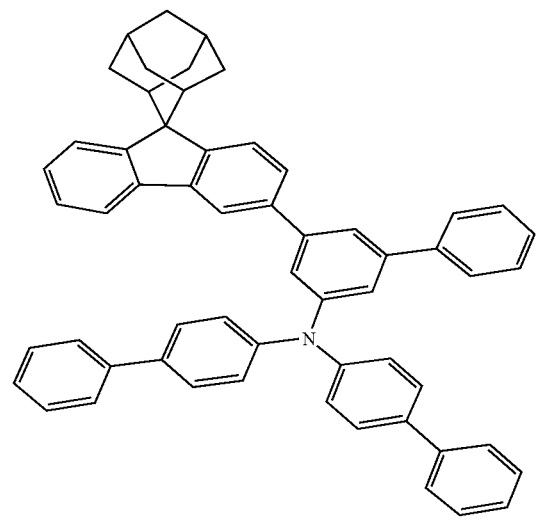
819

-continued
820
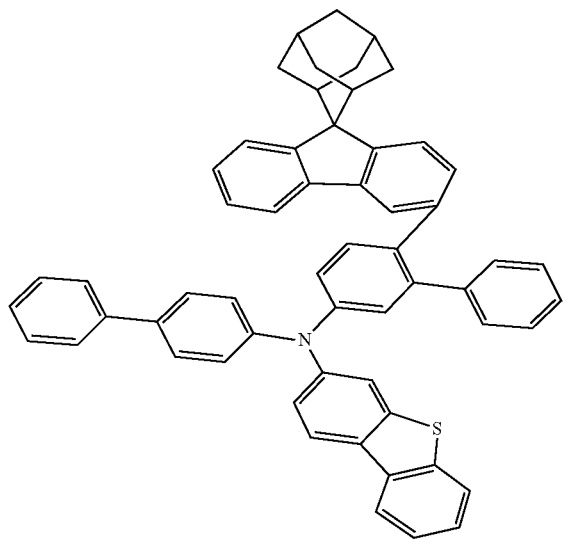
821
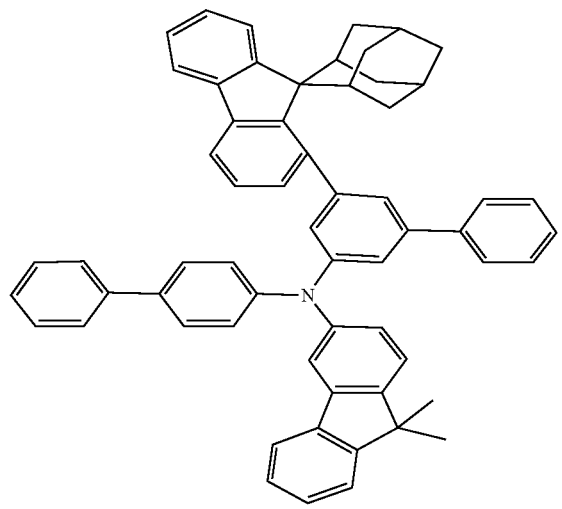
822
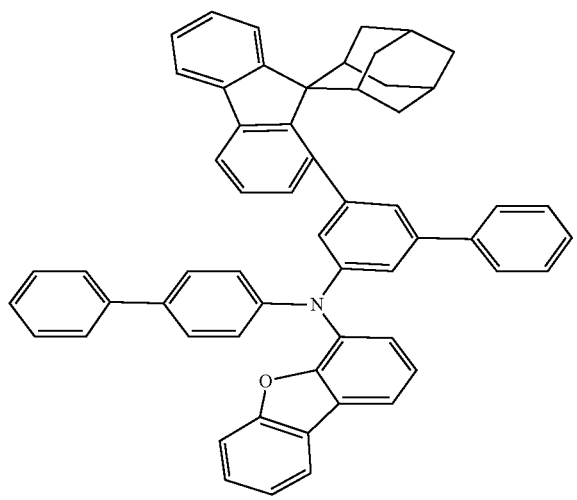
823
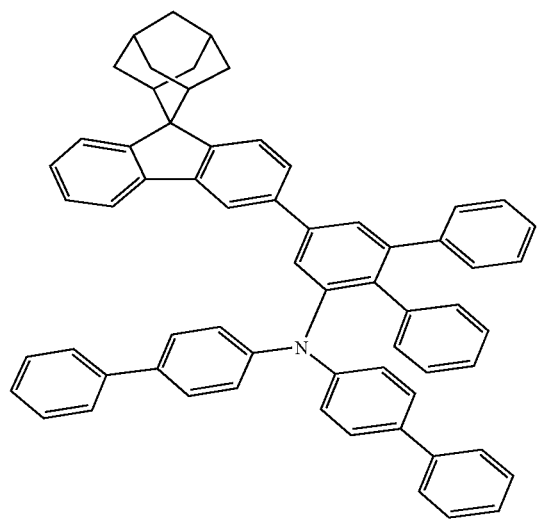
824
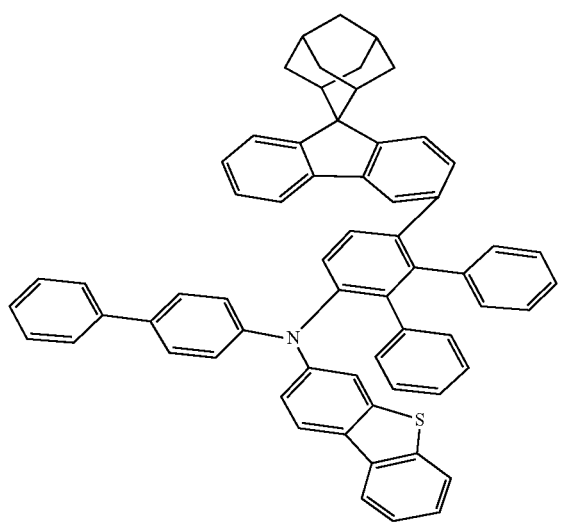
825
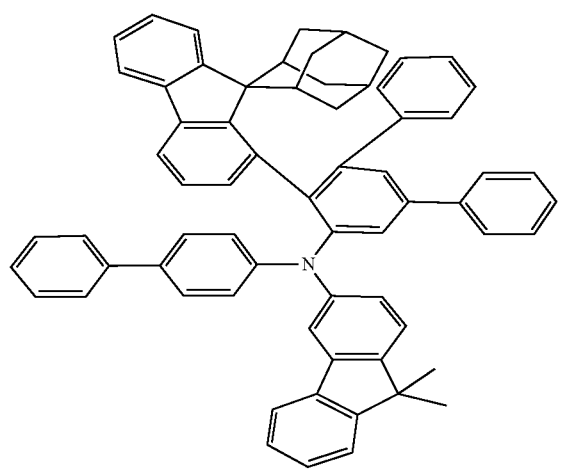

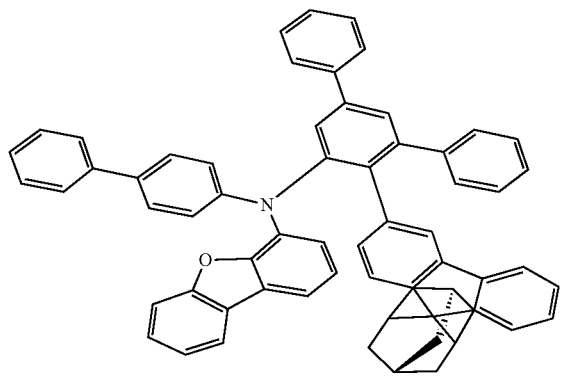

826

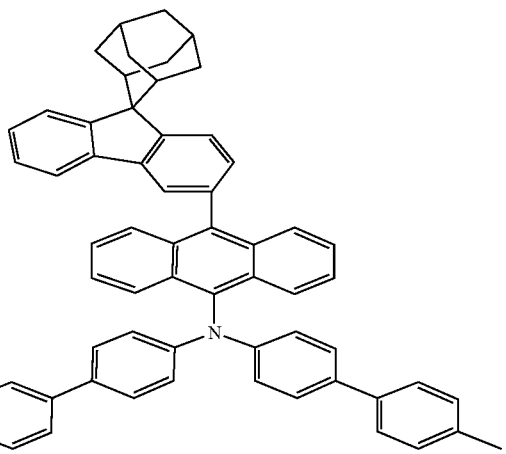

827

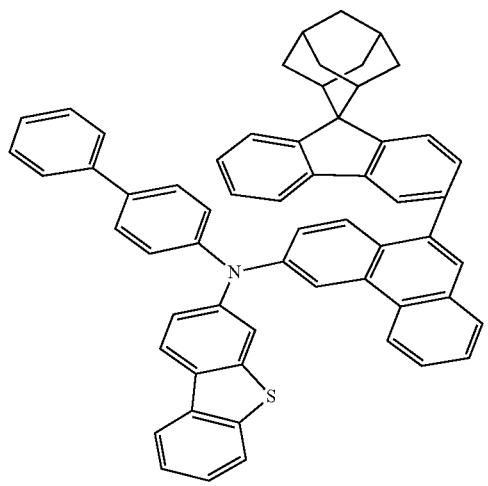

828

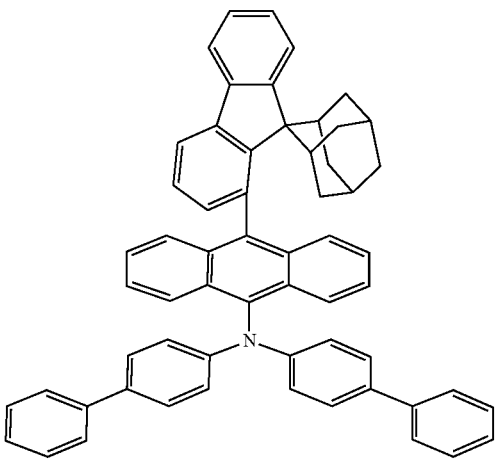

829

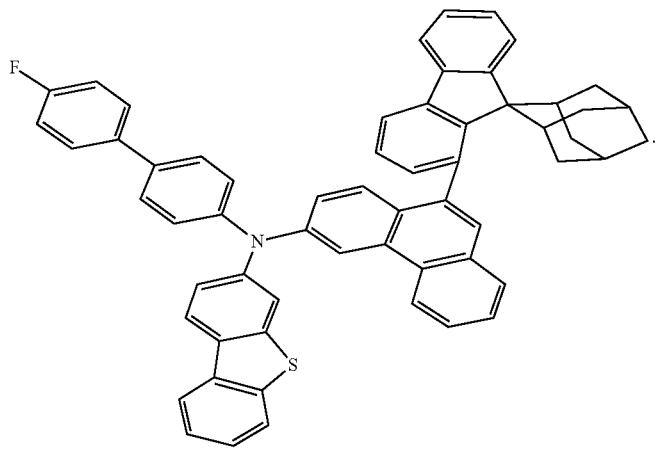

830

The present disclosure also provides an electronic element including an anode and a cathode disposed opposite to each other, and a functional layer disposed between the anode and the cathode; the functional layer contains the nitrogen-containing compound of the present disclosure. The electronic element may be used for implementing photoelectric conversion or electro-optic conversion.

According to an embodiment, the electronic element is an organic electroluminescent device. As shown in FIG. 1, the organic electroluminescent device includes an anode 100 and a cathode 200 disposed opposite to each other, and a functional layer 300 disposed between the anode 100 and the cathode 200; and the functional layer 300 contains the nitrogen-containing compound provided by the present disclosure.

Optionally, the functional layer 300 includes an electron blocking layer 322, and the electron blocking layer 322 contains the nitrogen-containing compound provided by the present disclosure. The electron blocking layer 322 may be composed of the nitrogen-containing compound provided by the present disclosure, or may be composed of the nitrogen-containing compound provided by the present disclosure and other materials.

Optionally, the functional layer 300 includes a hole transporting layer 321 and/or a hole injecting layer 310. The hole transporting layer 321 may contain the nitrogen-containing compound provided by the present disclosure to improve the hole transmission capacity in the electronic element.

In one embodiment of the present disclosure, the organic electroluminescent device may include an anode 100, a hole transporting layer 321, an electron blocking layer 322, an organic electroluminescent layer 330 as the energy conversion layer, an electron transporting layer 350 and cathode 200 that are sequentially stacked. The nitrogen-containing compound provided by the present disclosure may be applied to the electron blocking layer 322, which can effectively improve the luminous efficiency and lifetime of the organic electroluminescent device and reduce the driving voltage of the organic electroluminescent device.

Optionally, the anode 100 includes the anode material. Preferably, it is a material having a large work function that facilitates hole injection into the functional layer. Specific examples of anode materials include: metals such as nickel, platinum, vanadium, chromium, copper, zinc and gold, or their alloys; metal oxides such as zinc oxide, indium oxide, indium tin oxide (ITO) and indium zinc oxide (IZO); combination of metals and oxides such as ZnO:Al or $SnO_2$:Sb; or conductive polymers such as poly(3-methylthiophene), poly[3,4-(ethylene-1,2-dioxy)thiophene] (PEDT), polypyrrole and polyaniline, but not limited thereto. It preferably includes a transparent electrode containing indium tin oxide (ITO) as the anode.

Optionally, the hole transport layer 321 may contain one or more hole transport materials. The hole transporting material may be selected from carbazole polymers, carbazole-linked triarylamine compounds, or other types of compounds, which is not specially limited in the present disclosure. For example, the hole transporting layer 321 is composed of the compound NPB.

Optionally, the organic light-emitting layer 330 may be composed of a single light-emitting material, and may also comprise a host material and a guest material. Alternatively, the organic light-emitting layer 330 is composed of a host material and a guest material. The holes injected into the organic light-emitting layer 330 and the electrons injected into the organic light-emitting layer 330 may combine in the organic light-emitting layer 330 to form excitons, and the excitons transfer energy to the host material, the host material transfers energy to the guest material, which in turn enables the guest material to emit light.

The host material of the organic light-emitting layer 330 may be a metal chelate compound, a bisstyryl derivative, an aromatic amine derivative, a dibenzofuran derivative, or other types of materials, which is not specially limited in the present disclosure. For example, the host material of the organic light-emitting layer 330 may be CBP.

The guest material of the organic light-emitting layer 330 may be a compound having a condensed aryl ring or a derivative thereof, a compound having a heteroaryl ring or a derivative thereof, an aromatic amine derivative or other materials, which is not specially limited in the present disclosure. For example, the guest material of the organic light-emitting layer 330 may be $Ir(ppy)_3$.

The electron transporting layer 350 may have a single layer structure or a multilayer structure, which may comprise one or more electron transporting materials, and the electron transporting materials may be selected from benzimidazole derivatives, oxadiazole derivatives, quinoxaline derivatives or other electron transporting materials, which are not specifically limited in the present disclosure. For example, the electron transporting layer 340 may be composed of ET-1 and LiQ.

Optionally, the cathode 200 includes the cathode material, which is a material having a small work function that facilitates electron injection into the functional layer. Specific examples of cathode materials include: metals such as magnesium, calcium, sodium, potassium, titanium, indium, yttrium, lithium, gadolinium, aluminum, silver, tin and lead, or their alloys; or multilayer materials such as LiF/Al, Liq/Al, $LiO_2$/Al, LiF/Ca, LiF/Al, and $BaF_2$/Ca, but not limited thereto. It is preferable to include a metal electrode containing aluminum as the cathode.

Optionally, as shown in FIG. 1, a hole injecting layer 310 may also be provided between the anode 100 and the hole transporting layer 321 to enhance the ability to inject holes into the hole transporting layer 321. The hole injecting layer 310 may be selected from benzidine derivatives, starburst arylamine compounds, phthalocyanine derivatives, or other materials, which is not specially limited in the present disclosure. For example, the hole injecting layer 310 may be composed of m-MTDATA.

Optionally, as shown in FIG. 1, an electron injecting layer 360 may also be provided between the cathode 200 and the electron transport layer 340 to enhance the ability to inject electrons into the electron transport layer 350. The electron injecting layer 360 may include an inorganic material such as an alkali metal sulfide or an alkali metal halide, or may include a complex compound of an alkali metal and an organic compound. For example, the electron injecting layer 360 may include LiQ.

Optionally, a hole blocking layer 340 may be further provided between the organic electroluminescent layer 330 and the electron transporting layer 350.

Figure 2:
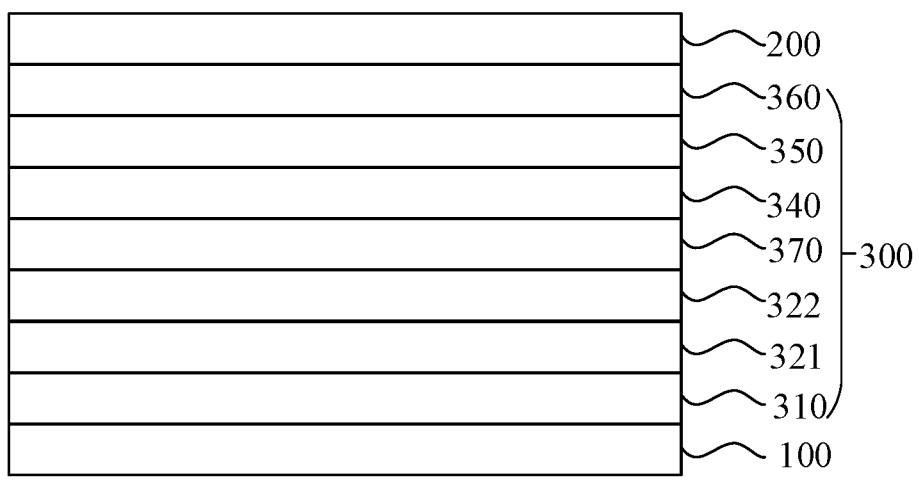
FIG. 2 is a schematic structural diagram of a photoelectric conversion device according to an embodiment of the present disclosure.

According to another embodiment, the electronic element may be a photoelectric conversion device. As shown in FIG. 2, the photoelectric conversion device may include an anode 100 and a cathode 200 disposed opposite to each other, and a functional layer 300 disposed between the anode 100 and the cathode 200; the functional layer 300 contains the nitrogen-containing compound provided in the present disclosure.

Optionally, the functional layer 300 includes an electron blocking layer 322, and the electron blocking layer 322 contains the nitrogen-containing compound provided by the present disclosure. The electron blocking layer 322 may be composed of the nitrogen-containing compound provided by the present disclosure, or may be composed of the nitrogen-containing compound provided by the present disclosure and other materials.

Optionally, as shown in FIG. 2, the photoelectric conversion device may include an anode 100, a hole transporting layer 321, an electron blocking layer 322, a photoelectric conversion layer 370 as the energy conversion layer, an electron transporting layer 350 and a cathode 200 that are sequentially stacked. The nitrogen-containing compound provided in the present disclosure may be applied to the electron blocking layer 322 of the photoelectric conversion device, which can effectively improve the luminous efficiency and lifetime of the photoelectric conversion device and increase the open circuit voltage of the photoelectric conversion device.

Optionally, a hole injecting layer 310 may also be provided between the anode 100 and the hole transporting layer 321.

Optionally, an electron injecting layer 360 may also be provided between the cathode 200 and the electron transporting layer 350.

Optionally, a hole blocking layer 340 may also be provided between the photoelectric conversion layer 370 and the electron transport layer 350.

Optionally, the photoelectric conversion device may be a solar cell, especially an organic thin film solar cell. According to a specific embodiment, the solar cell includes an anode 100, a hole transport layer 321, an electron blocking layer 322, a photoelectric conversion layer 370, an electron transport layer 350 and a cathode 200 that are sequentially stacked, wherein the electron blocking layer 322 contains the nitrogen-containing compound of the present disclosure.

The present disclosure further provides an electronic device including the above-mentioned electronic element. Since the electronic device has the electronic element, it has the same beneficial effects, which will not be repeated here.

Figure 3:
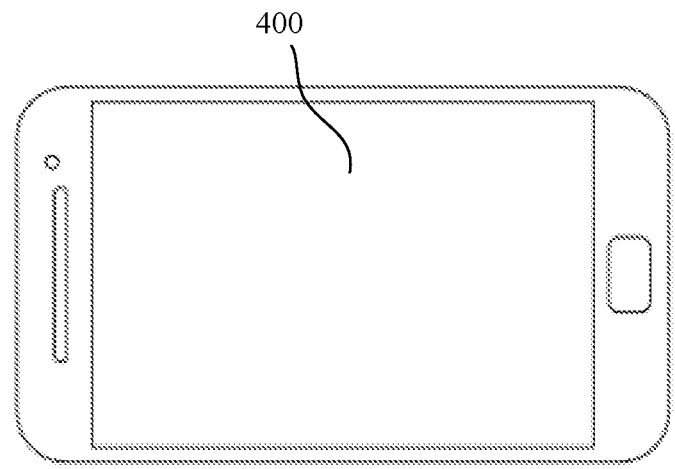
FIG. 3 is a schematic structural diagram of an electronic device according to an embodiment of the present disclosure.

According to an embodiment, as shown in FIG. 3, the electronic device is a first electronic device 400 comprising the above-mentioned organic electroluminescent device. The first electronic device 400 may be a display device, a lighting device, an optical communication device, or other types of electronic devices. For example, the electronic device 400 may include, but is not limited to, a computer screen, a mobile phone screen, a television, an electronic paper, an emergency lighting lamp and an optical module, etc.

Figure 4:
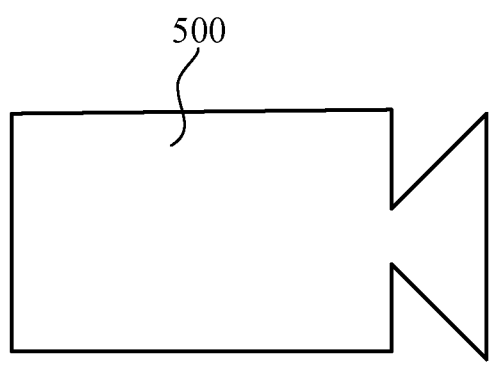
FIG. 4 is a schematic structural diagram of an electronic device according to another embodiment of the present disclosure.

According to another embodiment, as shown in FIG. 4, the electronic device is a second electronic device 500 comprising the above-mentioned photoelectric conversion device. The second electronic device 500 may be a solar power generation device, a light detector, a fingerprint recognition device, an optical module, a CCD camera, or other types of electronic devices.

Hereinafter, the present disclosure will be described in further detail through examples. However, the following examples are merely exemplary of the present disclosure, and do not limit the present disclosure.

Compound Synthesis

The compounds shown in Table 1 were synthesized by the following synthetic route.

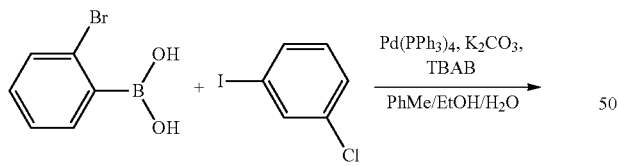

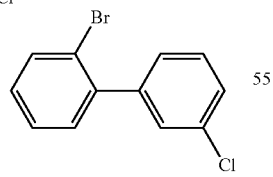

Intermediate I-A-1

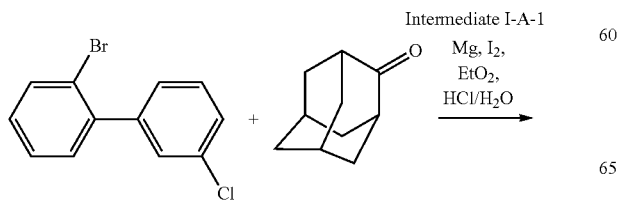

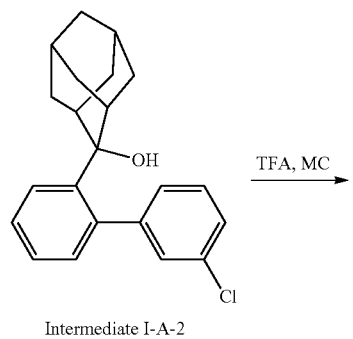

Intermediate I-A-2

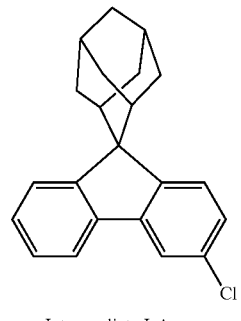

Intermediate I-A

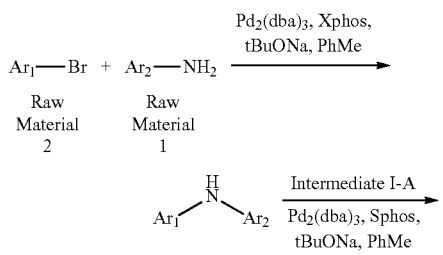

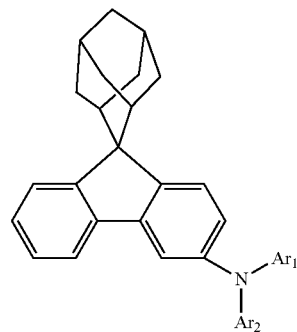

Synthesis of Compound 1

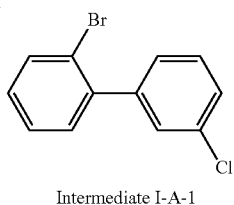

Intermediate I-A-1

2-bromophenylboronic acid (100.0 g, 500.0 mmol), 1-chloro-3-iodobenzene (142.6 g, 597.6 mmol), tetrakis(triphenylphosphine)palladium (11.5 g, 9.97 mmol), potassium carbonate (102 g 746 mmol), tetrabutylammonium bromide (32.1 g, 99.6 mmol), toluene (800 mL), ethanol (200 mL) and deionized water (200 mL) were added to the round bottom flask, heated to 78° C. under nitrogen, and stirred for 2 hours, then the obtained reaction solution was cooled to room temperature, and extracted with toluene (500 mL). The organic phases were combined, dried over anhydrous magnesium sulfate, and filtered. The solvent was removed under reduced pressure. The crude product obtained was purified through silica gel column chromatography using n-heptane as the mobile phase, and then was purified by recrystallization with dichloromethane/ethanol system to obtain intermediate I-A-1 as a light yellow solid (64.0 g, yield 48%).

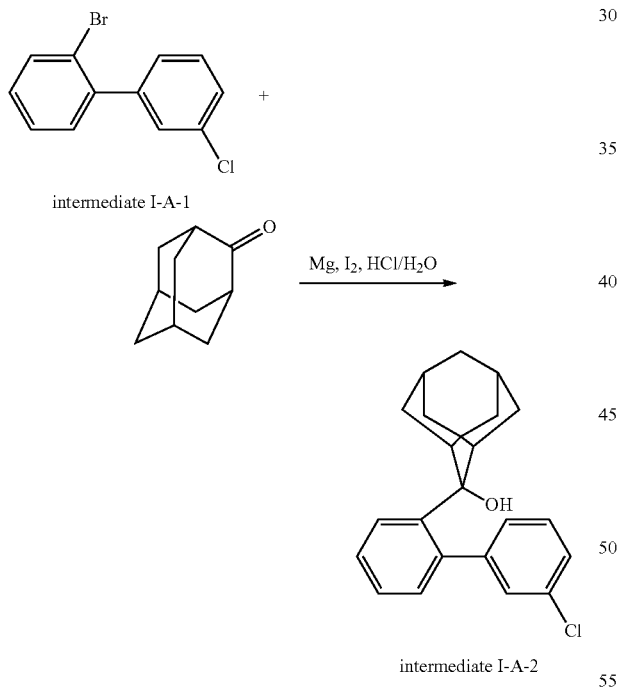

The magnesium bar (13.54 g, 564 mmol) and ether (100 mL) were placed in a dry round bottom flask under nitrogen, and iodine (100 mg) was added. Then, a solution of ether (200 mL) in which intermediate I-A-1 (64.00 g, 187.0 mmol) was dissolved was slowly dropped into the flask. After the addition was completed, the temperature was raised to 35° C. and the content was stirred for 3 hours. The obtained reaction solution was lowered to 0° C., and thereto was slowly added dropwise an ether (200 mL) solution of amantadone (22.45 g, 149 mmol) After the dropwise addition, the temperature was raised to 35° C., and stirred for 6 hours. Then, the reaction solution was cooled to room temperature, and 5 wt % hydrochloric acid was added to pH<7. After stirring for 1 hour, ether (200 mL) was added for extraction. The organic phases were combined, dried over anhydrous magnesium sulfate, filtered, and the solvent was removed under reduced pressure. The crude product obtained was purified by silica gel column chromatography using n-heptane as the mobile phase to obtain a solid intermediate I-A-2 (24 g yield 48%).

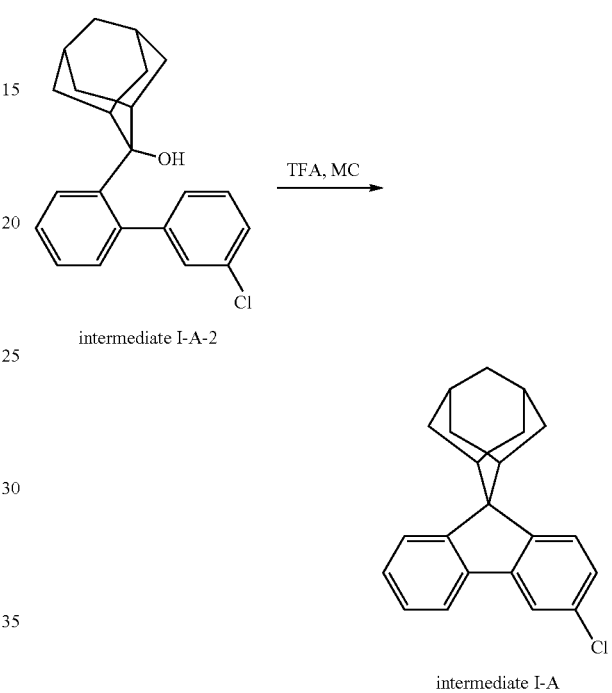

Intermediate I-A-2 (24 g, 71.0 mmol), trifluoroacetic acid (40.48 g, 355.0 mmol) and dichloromethane (200 mL) were added to a round bottom flask, and stirred for 2 hours under nitrogen. Then, sodium hydroxide aqueous solution was added to pH=8. After liquid separation, the organic phase was dried over anhydrous magnesium sulfate, filtered, and the solvent was removed under reduced pressure. The crude product obtained was purified by recrystallization using dichloromethane/n-heptane (1:2) to obtain intermediate I-A as a white solid (21 g, yield 92.5%). $^1$HNMR (400 MHz, CD$_2$Cl$_2$): 8.11 (d, 1H), 8.03 (d, 1H), 7.41-7.63 (m, 2H), 7.37-7.39 (m, 1H), 7.30-7.33 (m, 1H), 7.23-7.24 (m, 1H), 2.88-2.93 (m, 2H), 2.81-2.85 (m, 2H), 2.19 (s, 2H), 1.99 (s, 2H), 1.77-1.83 (m, 4H), 1.54 (s, 2H).

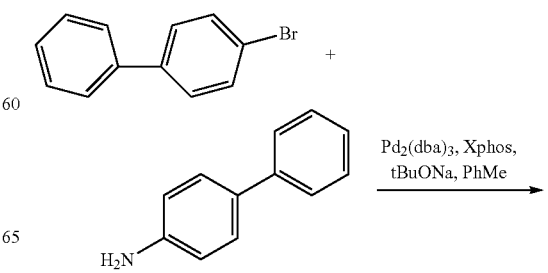

357
-continued

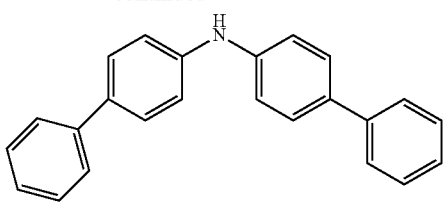

intermediate II-A 4-bromobiphenyl (4.0 g, 17.16 mmol), 4-aminobiphenyl (2.96 g, 17.5 mmol), tris(dibenzylideneacetone)dipalladium (0.16 g, 0.17 mmol), 2-dicyclohexylphosphino-2',4',6'-tri-isopropylbiphenyl (0.16 g, 0.34 mmol) and sodium tert-butoxide (2.47 g, 25.74 mmol) were added to toluene (40 mL) and heated to 108° C. under nitrogen protection, and stirred for 2 h. Then the obtained reaction solution was cooled to room temperature, and washed with water and dried over magnesium sulfate. After filtration, the solvent was removed from the filtrate under reduced pressure. The crude product obtained was purified by recrystallization using dichloromethane/ethyl acetate system to obtain intermediate II-A as a light yellow solid (4.1 g, yield 72.6%).

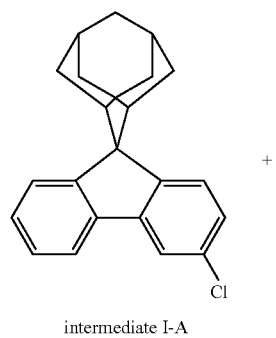

intermediate I-A

+

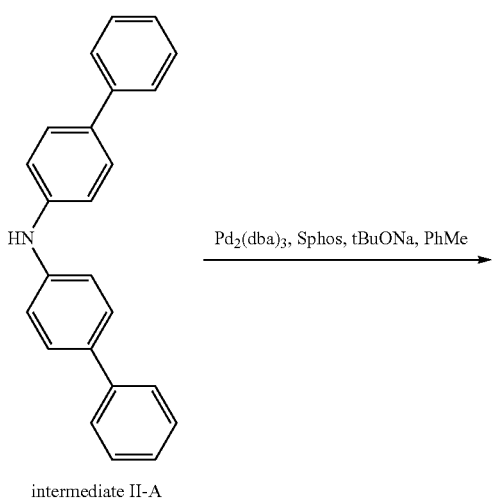

intermediate II-A $\xrightarrow{Pd_2(dba)_3, Sphos, tBuONa, PhMe}$

358
-continued

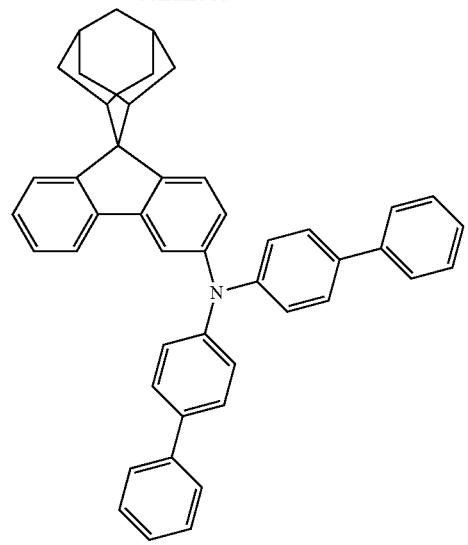

Compound 1

Intermediate I-A (4.1 g, 12.77 mmol), intermediate II-A (4.1 g, 12.77 mmol), tris(dibenzylideneacetone)dipalladium (0.12 g, 0.13 mmol), 2-dicyclohexylphosphino-2',6'-dimethoxybiphenyl (0.10 g, 0.25 mmol) and sodium tert-butoxide (1.84 g, 19.17 mmol) were added to toluene (40 mL), heated to 108° C. under nitrogen protection, and stirred for 1 h. After cooling to room temperature, the obtained reaction solution was washed with water and then dried over magnesium sulfate. After filtration, the solvent was removed from the filtrate under reduced pressure. The crude product obtained was purified by recrystallization using toluene system to obtain Compound 1 as a white solid (4.35 g, yield 56.2%). Mass spectrum (MS): m/z=606.3 [M+H]$^+$. $^1$H NMR (400 MHz, CD$_2$Cl$_2$): 8.11 (d, 1H), 8.02 (d, 1H), 7.64-7.60 (m, 6H), 7.55 (d, 4H), 7.43 (t, 4H), 7.33-7.24 (m, 8H), 7.06 (dd, 1H), 2.91 (m, 4H), 2.19 (m, 2H), 2.00 (s, 2H), 1.82 (d, 4H), 1.61 (s, 2H).

Referring to the synthesis method of Compound 1, and using raw material 2 to replace 4-bromobiphenyl, using raw material 1 to replace 4-aminobiphenyl, the intermediates in the fourth column of Table 1 were synthesized. The intermediates in the fourth column, which were used to replace intermediate II-A, and intermediate I-A were used to prepare other compounds in Table 1. The specific compound number, structure, raw materials, final step synthesis yield, characterization data, etc. are shown in Table 1.

TABLE 1

Compound structure, preparation and characterization data

| Compound No. | Raw material 1 | Raw material 2 | Intermediate |
|---|---|---|---|
| 3 | 4-aminobiphenyl | 2-bromo-9,9-dimethylfluorene | N-([1,1'-biphenyl]-4-yl)-9,9-dimethyl-9H-fluoren-2-amine |
| 7 | | 3-bromodibenzofuran | N-([1,1'-biphenyl]-4-yl)dibenzo[b,d]furan-3-amine |
| 15 | | 2-bromodibenzofuran | N-([1,1'-biphenyl]-4-yl)dibenzo[b,d]furan-2-amine |
| 9 | | 9-(4-bromophenyl)-9H-carbazole | N-([1,1'-biphenyl]-4-yl)-4-(9H-carbazol-9-yl)aniline |
| 23 | | 4-(4-bromophenyl)dibenzofuran | N-([1,1'-biphenyl]-4-yl)-4-(dibenzo[b,d]furan-4-yl)aniline |

TABLE 1-continued
Compound structure, preparation and characterization data
487 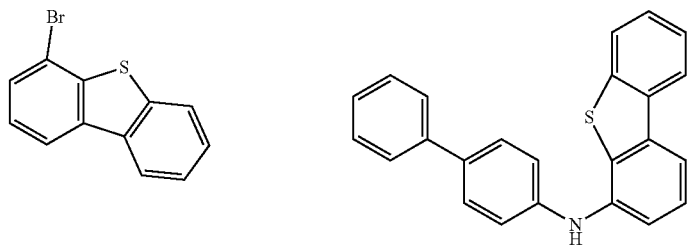
745 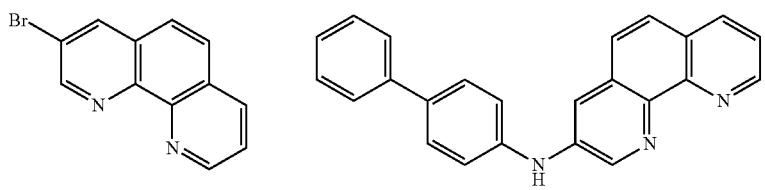
36 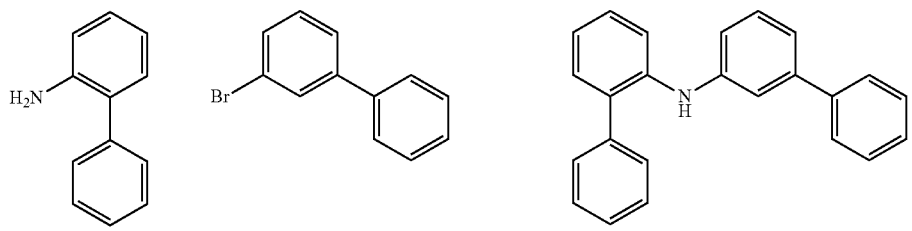
31 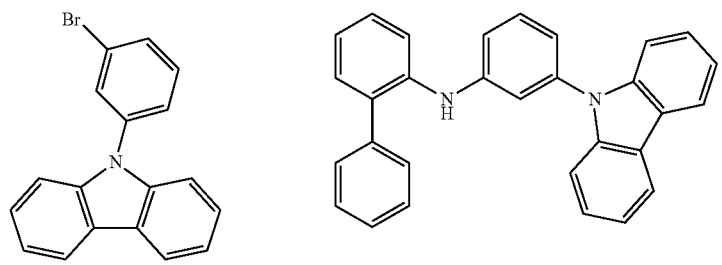
54 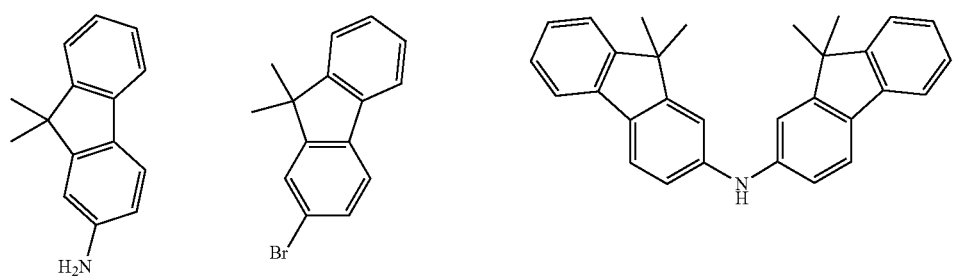
60 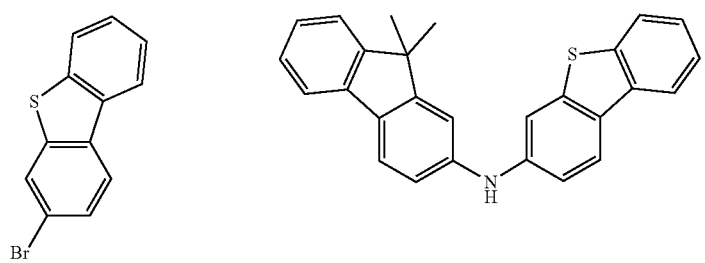

TABLE 1-continued
Compound structure, preparation and characterization data
66 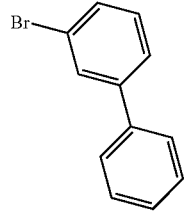 [SMILES: Brc1cccc(-c2ccccc2)c1] 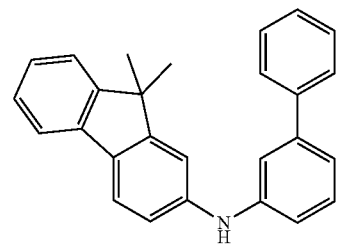 [SMILES: CC1(C)c2ccccc2-c2ccc(Nc3cccc(-c4ccccc4)c3)cc21]
71 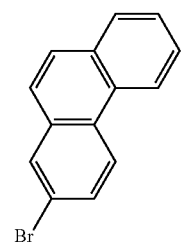 [SMILES: Brc1ccc2c(ccc3ccccc32)c1] 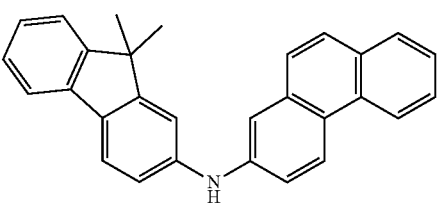 [SMILES: CC1(C)c2ccccc2-c2ccc(Nc3ccc4c(ccc5ccccc54)c3)cc21]
87 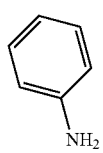 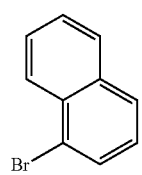 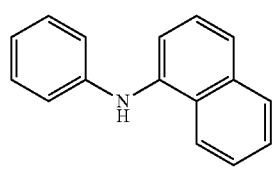 [SMILES: c1ccc(Nc2cccc3ccccc23)cc1]
92 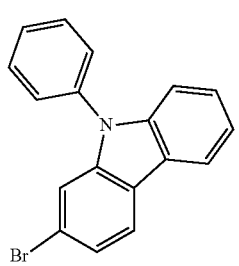 [SMILES: Brc1ccc2c3ccccc3n(-c3ccccc3)c2c1] 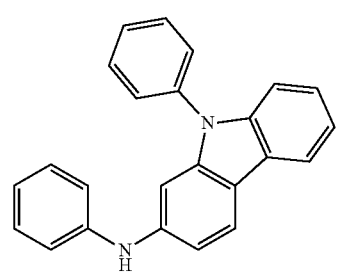 [SMILES: c1ccc(Nc2ccc3c4ccccc4n(-c4ccccc4)c3c2)cc1]
95 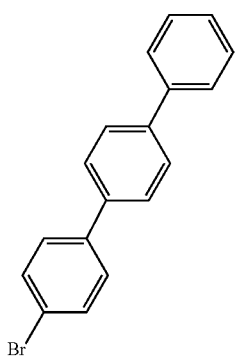 [SMILES: Brc1ccc(-c2ccc(-c3ccccc3)cc2)cc1] 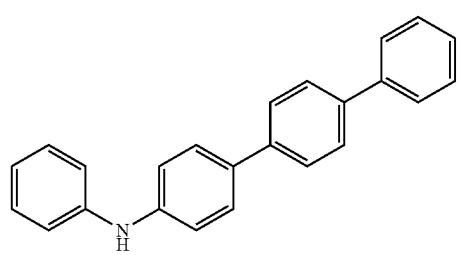 [SMILES: c1ccc(Nc2ccc(-c3ccc(-c4ccccc4)cc3)cc2)cc1]
115 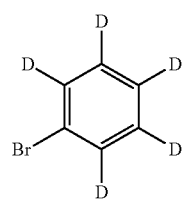 [SMILES: [2H]c1c([2H])c([2H])c(Br)c([2H])c1[2H]] 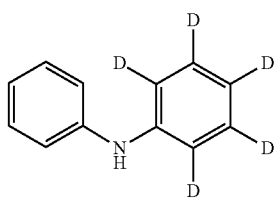 [SMILES: [2H]c1c([2H])c([2H])c(Nc2ccccc2)c([2H])c1[2H]]

TABLE 1-continued
Compound structure, preparation and characterization data
| 116 | 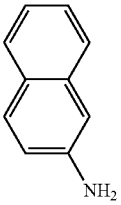 [SMILES: Nc1ccc2ccccc2c1] | 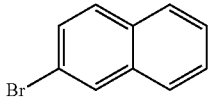 | 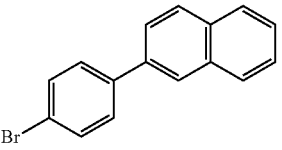 [SMILES: Brc1ccc(-c2ccc3ccccc3c2)cc1] |
| 128 | | 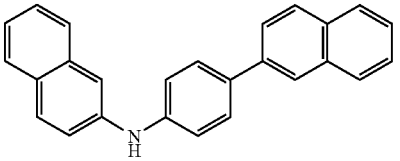 [SMILES: c1ccc2cc(Nc3ccc(-c4ccc5ccccc5c4)cc3)ccc2c1] | 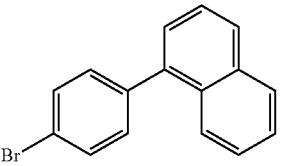 [SMILES: Brc1ccc(-c2cccc3ccccc23)cc1] |
| 127 | | 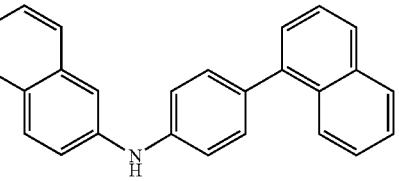 | 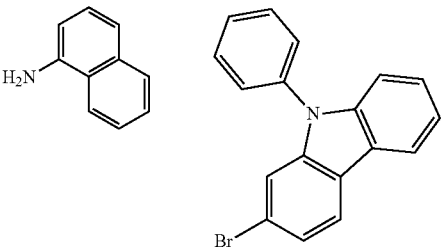 |
| 147 | 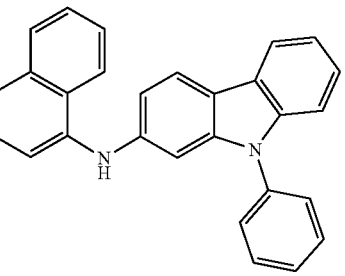 | 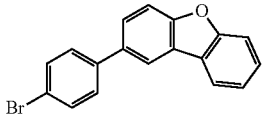 [SMILES: Brc1ccc(-c2ccc3oc4ccccc4c3c2)cc1] | 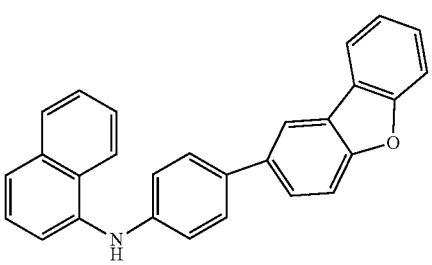 [SMILES: c1ccc2c(Nc3ccc(-c4ccc5oc6ccccc6c5c4)cc3)cccc2c1] |
| 160 | | 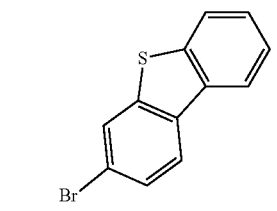 [SMILES: Brc1ccc2c(c1)sc1ccccc12] | 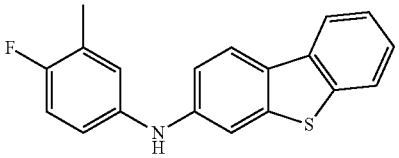 [SMILES: Cc1cc(Nc2ccc3c(c2)sc2ccccc23)ccc1F] |
| 195 | 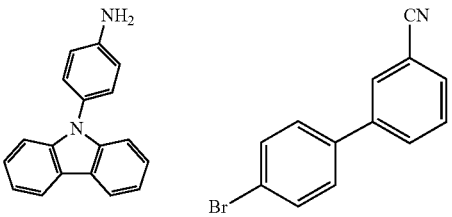 | 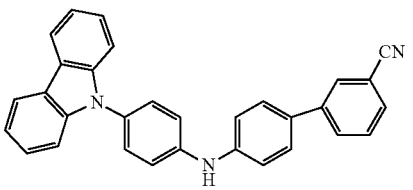 [SMILES: N#Cc1cccc(-c2ccc(Nc3ccc(-n4c5ccccc5c5ccccc54)cc3)cc2)c1] | |
| 206 | | | |

TABLE 1-continued

Compound structure, preparation and characterization data

| Compound No. | Compound Structure | Yield (%) | MS (m/z) [M + H]+ |
|---|---|---|---|
| 3 | 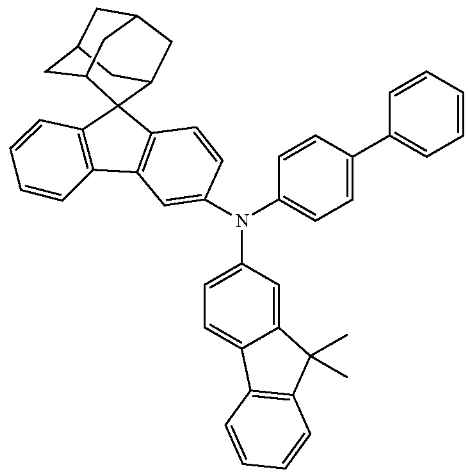 [SMILES: CC1(C)c2ccccc2-c2ccc(N(c3ccc(-c4ccccc4)cc3)c3ccc4c(c3)-c3ccccc3C43C4CC5CC(C4)CC3C5)cc21] | 67 | 646.3 |
| 7 | 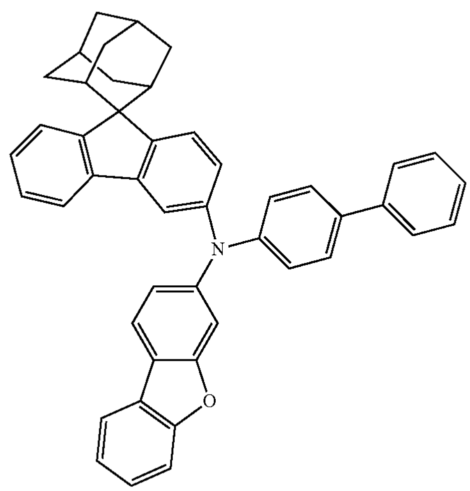 [SMILES: c1ccc(-c2ccc(N(c3ccc4c(c3)-c3ccccc3C43C4CC5CC(C4)CC3C5)c3ccc4c(c3)oc3ccccc34)cc2)cc1] | 69 | 620.3 |
| 15 | 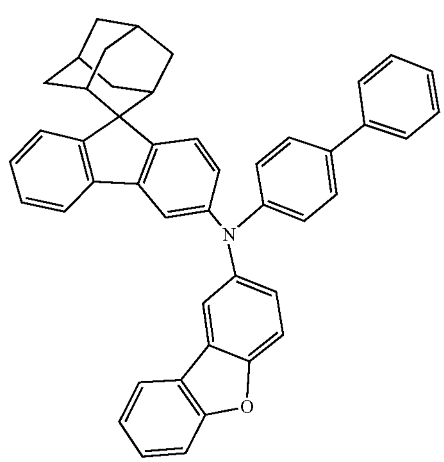 [SMILES: c1ccc(-c2ccc(N(c3ccc4c(c3)-c3ccccc3C43C4CC5CC(C4)CC3C5)c3ccc4oc5ccccc5c4c3)cc2)cc1] | 72 | 620.3 |

TABLE 1-continued
Compound structure, preparation and characterization data
| 9 | 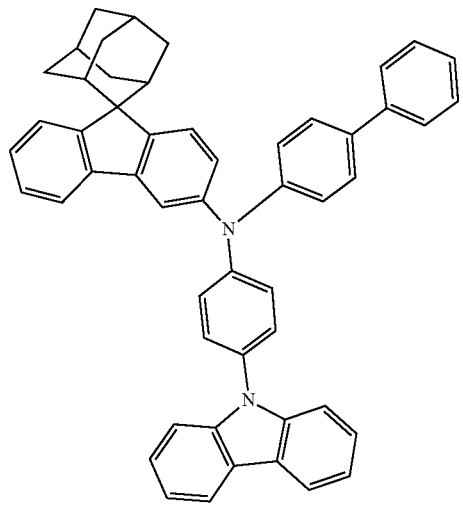 [SMILES: c1ccc(-c2ccc(N(c3ccc(-n4c5ccccc5c5ccccc54)cc3)c3ccc4c(c3)-c3ccccc3C43C4CC5CC(C4)CC3C5)cc2)cc1] | 67 | 695.3 |
| 23 | 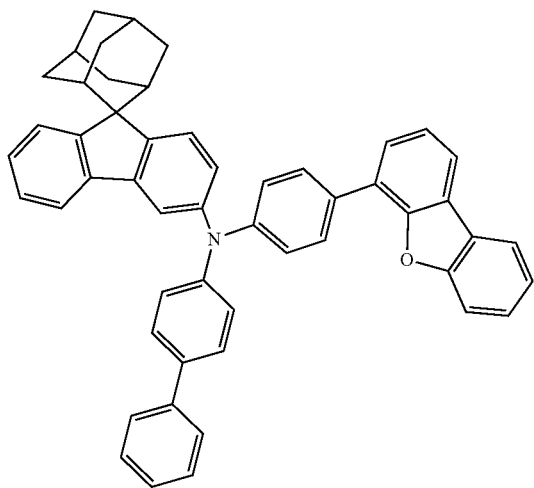 [SMILES: c1ccc(-c2ccc(N(c3ccc(-c4cccc5c4oc4ccccc45)cc3)c3ccc4c(c3)-c3ccccc3C43C4CC5CC(C4)CC3C5)cc2)cc1] | 54 | 696.3 |
| 487 | 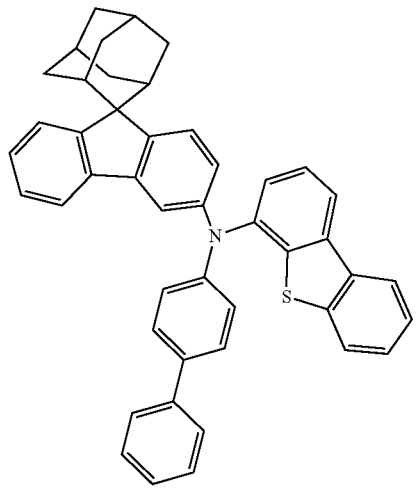 [SMILES: c1ccc(-c2ccc(N(c3ccc4c(c3)-c3ccccc3C43C4CC5CC(C4)CC3C5)c3cccc4c3sc3ccccc34)cc2)cc1] | 61 | 636.3 |

TABLE 1-continued
Compound structure, preparation and characterization data
| | | | |
|---|---|---|---|
| 745 | 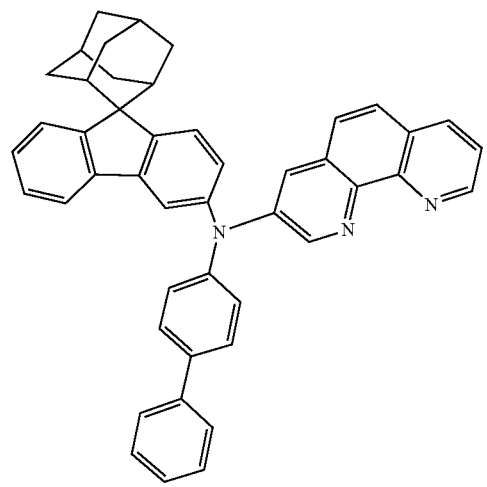 [SMILES: c1ccc(-c2ccc(N(c3ccc4c(c3)-c3ccccc3C43C4CC5CC(C4)CC3C5)c3cnc4c(ccc5cccnc54)c3)cc2)cc1] | 53 | 632.3 |
| 36 | 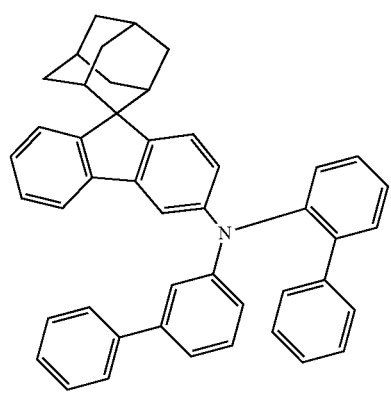 [SMILES: c1ccc(-c2cccc(N(c3ccc4c(c3)-c3ccccc3C43C4CC5CC(C4)CC3C5)c3ccccc3-c3ccccc3)c2)cc1] | 55 | 606.3 |
| 31 | 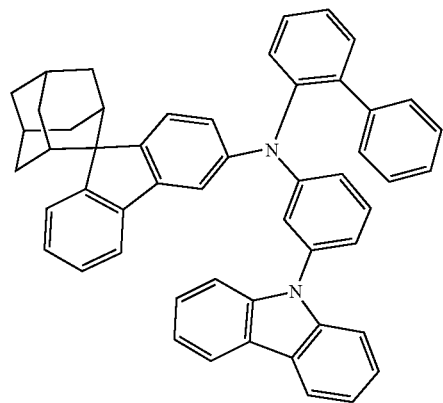 [SMILES: c1ccc(-c2ccccc2N(c2cccc(-n3c4ccccc4c4ccccc43)c2)c2ccc3c(c2)-c2ccccc2C32C3CC4CC(C3)CC2C4)cc1] | 59 | 695.3 |

TABLE 1-continued
Compound structure, preparation and characterization data
| | | | |
|---|---|---|---|
| 54 | 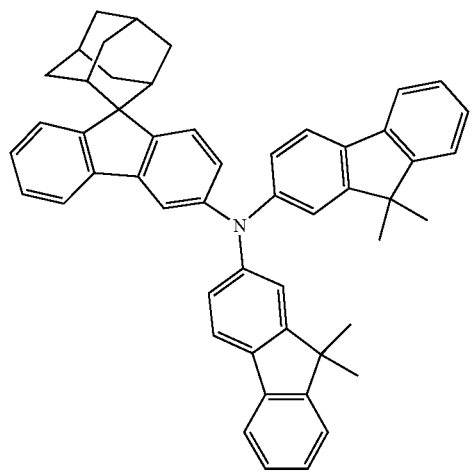 [SMILES: CC1(C)c2ccccc2-c2ccc(N(c3ccc4c(c3)-c3ccccc3C43C4CC5CC(C4)CC3C5)c3ccc4c(c3)C(C)(C)c3ccccc3-4)cc21] | 61 | 686.4 |
| 60 | 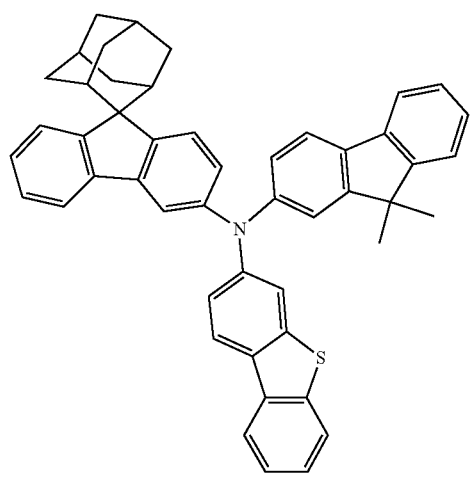 [SMILES: CC1(C)c2ccccc2-c2ccc(N(c3ccc4c(c3)-c3ccccc3C43C4CC5CC(C4)CC3C5)c3ccc4c(c3)sc3ccccc34)cc21] | 62 | 676.3 |
| 66 | 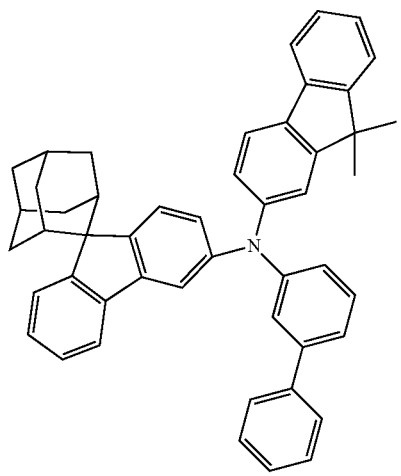 [SMILES: CC1(C)c2ccccc2-c2ccc(N(c3cccc(-c4ccccc4)c3)c3ccc4c(c3)-c3ccccc3C43C4CC5CC(C4)CC3C5)cc21] | 47 | 646.3 |

TABLE 1-continued
Compound structure, preparation and characterization data
| 71 | 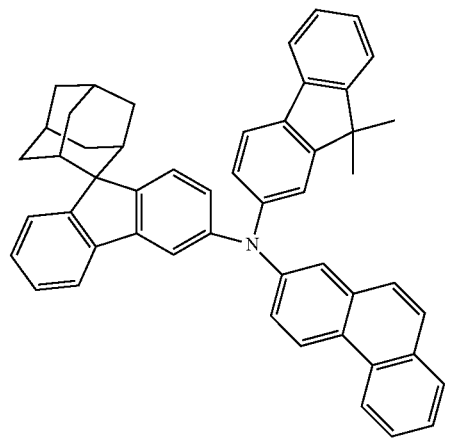 [SMILES: CC1(C)c2ccccc2-c2ccc(N(c3ccc4c(c3)-c3ccccc3C43C4CC5CC(C4)CC3C5)c3ccc4c(ccc5ccccc54)c3)cc21] | 49 | 670.3 |
| 87 | 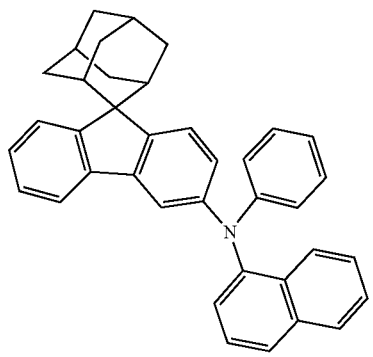 [SMILES: c1ccc(N(c2ccc3c(c2)-c2ccccc2C32C3CC4CC(C3)CC2C4)c2cccc3ccccc23)cc1] | 53 | 504.3 |
| 92 | 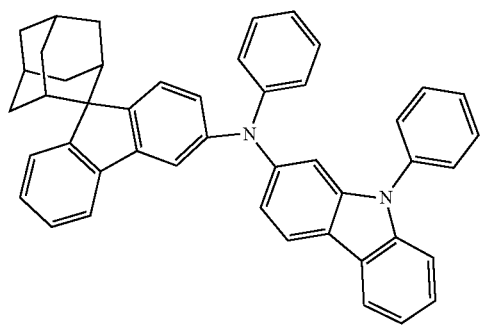 [SMILES: c1ccc(N(c2ccc3c(c2)-c2ccccc2C32C3CC4CC(C3)CC2C4)c2ccc3c4ccccc4n(-c4ccccc4)c3c2)cc1] | 55 | 619.3 |
| 95 | 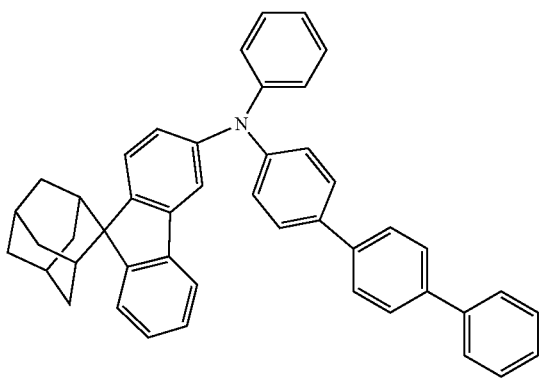 [SMILES: c1ccc(-c2ccc(-c3ccc(N(c4ccccc4)c4ccc5c(c4)-c4ccccc4C54C5CC6CC(C5)CC4C6)cc3)cc2)cc1] | 67 | 606.3 |

TABLE 1-continued

Compound structure, preparation and characterization data

| | | | |
|---|---|---|---|
| 115 | (structure) | 69 | 459.3 |
| 116 | (structure) | 70 | 554.3 |
| 128 | (structure) | 50 | 630.3 |
| 127 | (structure) | 43 | 630.3 |

TABLE 1-continued
Compound structure, preparation and characterization data
| | | | |
|---|---|---|---|
| 147 | 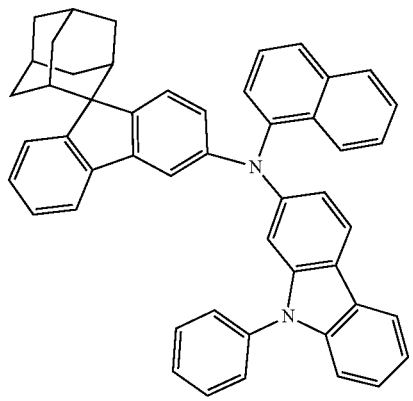 [SMILES: c1ccc(-n2c3ccccc3c3ccc(N(c4ccc5c(c4)-c4ccccc4C54C5CC6CC(C5)CC4C6)c4cccc5ccccc45)cc32)cc1] | 49 | 669.3 |
| 160 | 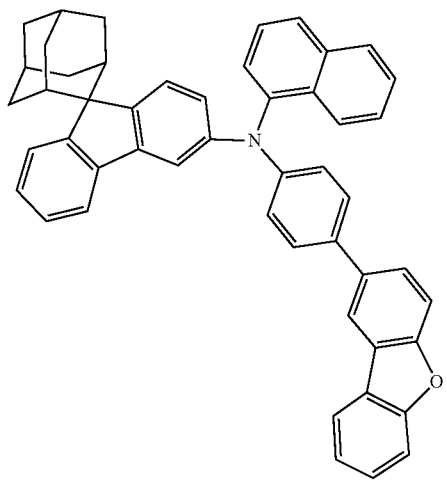 [SMILES: c1ccc2c(c1)-c1cc(N(c3ccc(-c4ccc5oc6ccccc6c5c4)cc3)c3cccc4ccccc34)ccc1C21C2CC3CC(C2)CC1C3] | 48 | 670.3 |
| 195 | 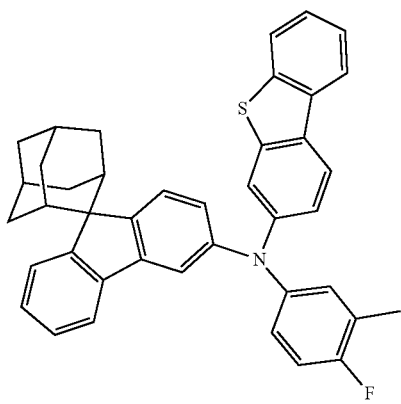 [SMILES: Cc1cc(N(c2ccc3c(c2)-c2ccccc2C32C3CC4CC(C3)CC2C4)c2ccc3c(c2)sc2ccccc23)ccc1F] | 54 | 592.2 |

NMR data of Compound 3: ¹H NMR (CD$_2$Cl$_2$, 400 MHz): 8.10 (d, 1H), 8.00 (d, 1H), 7.67-7.59 (m, 6H), 7.54 (d, 2H), 7.45-7.42 (m, 3H), 7.36-7.25 (m, 8H), 7.12 (br, 1H), 7.06 (br, 1H), 2.92 (t, 4H), 2.19 (d, 2H), 2.00 (s, 2H), 1.82 (d, 4H), 1.61 (s, 2H), 1.44 (s, 6H).

NMR data of Compound 7: ¹H NMR (CD$_2$Cl$_2$, 400 MHz): 8.11 (d, 1H), 8.03 (d, 1H), 7.91 (d, 1H), 7.85 (d, 1H), 7.62-7.60 (m, 4H), 7.56 (d, 2H), 7.51 (d, 1H), 7.45-7.39 (m, 3H), 7.36-7.26 (m, 7H), 7.21 (d, 1H), 7.07 (d, 1H), 2.92 (t, 4H), 2.19 (d, 2H), 2.00 (s, 2H), 1.82 (d, 4H), 1.62 (s, 2H).

NMR data of Compound 54: ¹H NMR (400 MHz, CD$_2$Cl$_2$): 8.11 (d, 1H), 7.99 (d, 1H), 7.66 (d, 2H), 7.63-7.62 (m, 3H), 7.58 (d, 1H), 7.41 (d, 2H), 7.35 (s, 2H), 7.32 (t, 2H), 7.28-7.24 (m, 4H), 7.12 (d, 2H), 7.07 (d, 1H), 2.92 (t, 4H), 2.19 (d, 2H), 2.00 (s, 2H), 1.82 (d, 4H), 1.62 (s, 2H), 1.42 (s, 12H).

Synthesis of Compound 295

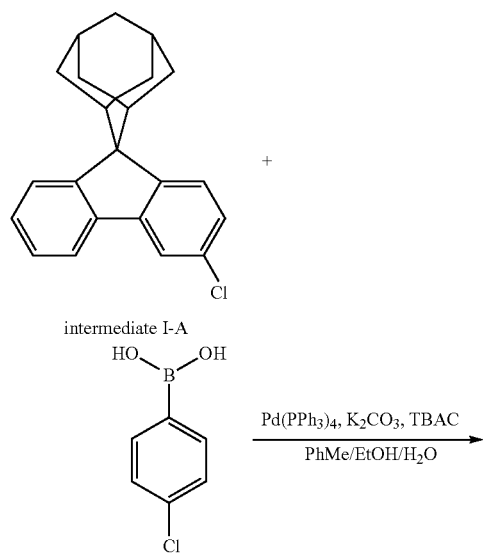

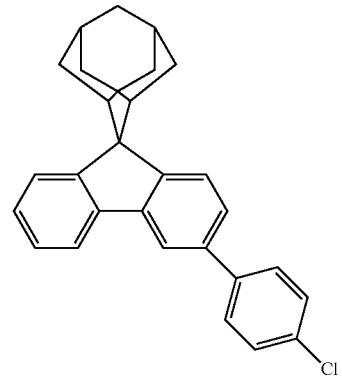

intermediate I-B

Intermediate I-A (10 g, 31.17 mmol), p-chlorophenylboronic acid (3.89 g, 24.93 mmol), tetrakis(triphenylphosphine)palladium (0.72 g, 0.62 mmol), potassium carbonate (6.45 g 46.75 mmol), Tetrabutylammonium chloride (1.73 g, 6.23 mmol), toluene (80 mL), ethanol (20 mL) and deionized water (20 mL) were added to the round-bottom flask, heated to 78° C. under nitrogen protection, and stirred for 6 hours. The obtained reaction solution was cooled to room temperature, and toluene (100 mL) was added for extraction. The organic phases were combined, dried over anhydrous magnesium sulfate, filtered, and the solvent was removed under reduced pressure. The obtained crude product was purified by silica gel column chromatography using n-heptane as the mobile phase, and then was purified by recrystallization using chloromethane/ethyl acetate system to obtain intermediate I-B as a white solid (7.5 g, yield 40.6%).

Referring to the synthesis method of intermediate I-B, the intermediates shown in the third column of Table 2 below were synthesized except that the raw materials 3 in the second column of Table 2 below were used to replace p-chlorophenylboronic acid.

TABLE 2

| Intermediate No. | Raw material 3 | Intermediate Structure | Yield (%) |
|---|---|---|---|
| Intermediate I-C | 3-chlorophenylboronic acid | (adamantyl-fluorene-3-chlorophenyl structure) | 37 |
| Intermediate I-D | 2-chlorophenylboronic acid | (adamantyl-fluorene-2-chlorophenyl structure) | 41 |
| Intermediate I-E | 4-chloronaphthalen-1-ylboronic acid | (adamantyl-fluorene-4-chloronaphthyl structure) | 44 |
| Intermediate I-F | 3'-chloro-[1,1'-biphenyl]-3-ylboronic acid | (adamantyl-fluorene-chlorobiphenyl structure) | 39 |

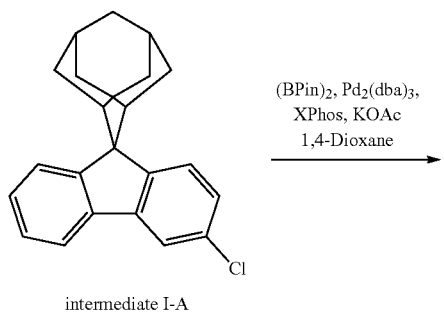

intermediate I-A

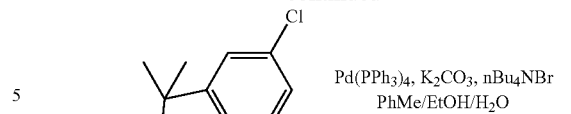

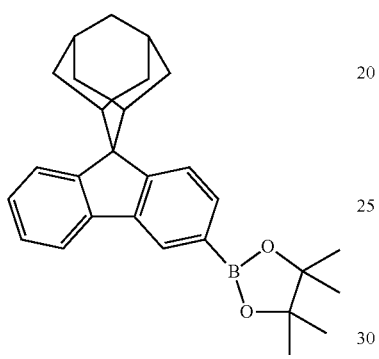

intermediate I-A-1

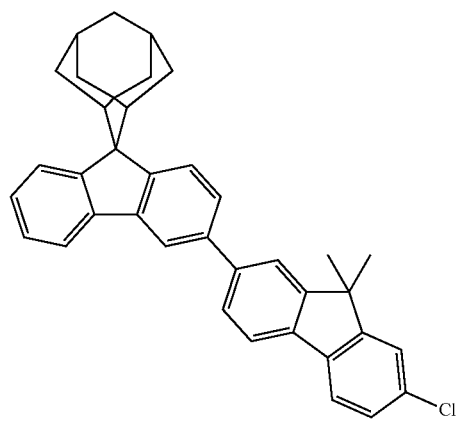

intermediate I-A-2

Intermediate I-A (20.4 g, 63.7 mmol), bis(pinacolato) diboron (19.4 g, 76.5 mmol), tris(dibenzylideneacetone) dipalladium (0.6 g, 0.6 mmol), 2-dicyclohexylphosphino-2',4',6'-triisopropylbiphenyl (0.6 g; 1.3 mmol), potassium acetate (12.5 g; 127.4 mmol) and 1,4-dioxane (150 mL) were added to the flask, and stirred at 100° C. with reflux for 16 hours under nitrogen. After cooling to room temperature, dichloromethane and water were added into the obtained reaction solution to separate the layers, the resulting organic phase was washed with water and dried over anhydrous magnesium sulfate, and the solvent was removed under reduced pressure to obtain the crude product. The crude product was purified through silica gel column chromatography using dichloromethane/n-heptane system to obtain intermediate I-A-1 as a white solid (13.3 g, yield 51%).

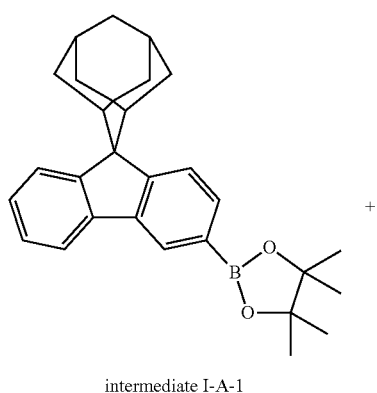

intermediate I-A-1

+

Intermediate I-A-1 (13.3 g, 32.3 mmol), 2-bromo-7-chloro-9,9-dimethylfluorene (7.1 g, 35.5 mmol), tetrakis(triphenylphosphine)palladium (0.7 g, 0.6 mmol), potassium carbonate (11.1 g, 80.7 mmol) and tetrabutylammonium bromide (2.1 g, 6.5 mmol) were added to the flask, and then added a mixed solvent of toluene (80 mL), ethanol (20 mL) and water (20 mL), heated to 80° C. and stirred for 24 hours maintaining the temperature under nitrogen protection. After cooling to room temperature, the stirring was stopped, the resulting reaction solution was washed with water, then the organic phase was separated from it and dried over anhydrous magnesium sulfate, and the solvent was removed under reduced pressure to obtain a crude product. The crude product was purified by silica gel column chromatography using dichloromethane/n-heptane as the mobile phase to obtain product intermediate I-A-2 as a white solid (9.0 g, yield 54.5%).

Referring to the synthesis method of intermediate I-A-2, the intermediates shown in the third column of Table 3 below were synthesized except that the raw material 41 in the second column of Table 3 below were used to replace 2-bromo-7-chloro-9,9-dimethylfluorene.

TABLE 3
Raw materials and intermediates
| Intermediate No. | Raw material 41 | Intermediate structure | Yield (%) |
|---|---|---|---|
| Intermediate I-A-3 | 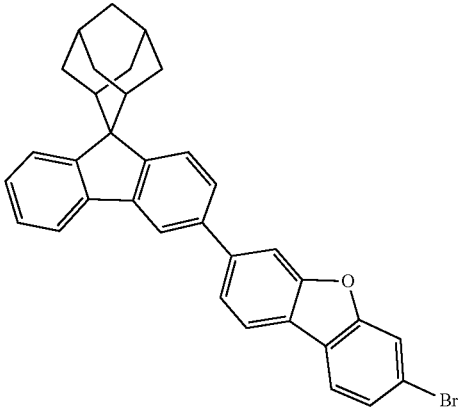 [SMILES: Brc1ccc2c(c1)oc1cc(-c3ccc4c(c3)-c3ccccc3C43C4CC5CC(C4)CC3C5)ccc12] | 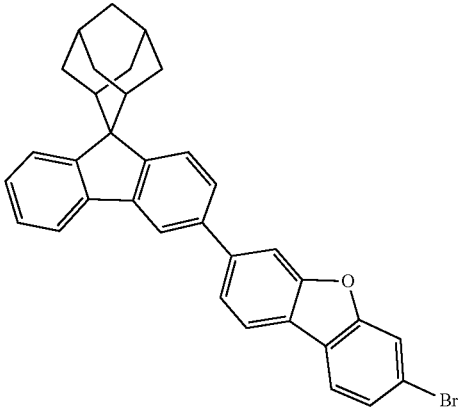 [SMILES: Brc1ccc2c(c1)oc1cc(-c3ccc4c(c3)-c3ccccc3C43C4CC5CC(C4)CC3C5)ccc12] | 59 |
| Intermediate I-A-4 | 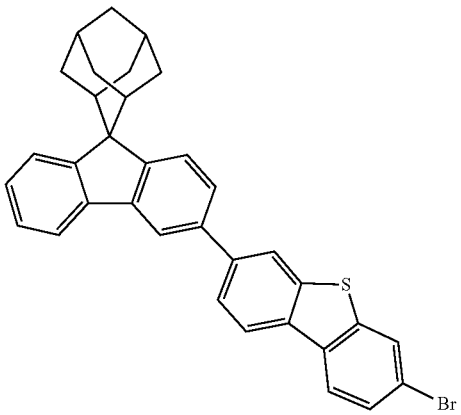 [SMILES: Brc1ccc2c(c1)sc1cc(-c3ccc4c(c3)-c3ccccc3C43C4CC5CC(C4)CC3C5)ccc12] | 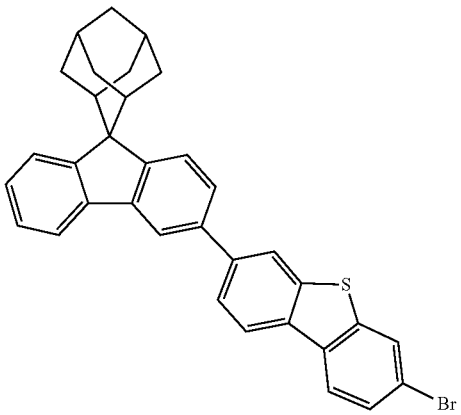 [SMILES: Brc1ccc2c(c1)sc1cc(-c3ccc4c(c3)-c3ccccc3C43C4CC5CC(C4)CC3C5)ccc12] | 62 |
| Intermediate I-A-5 | 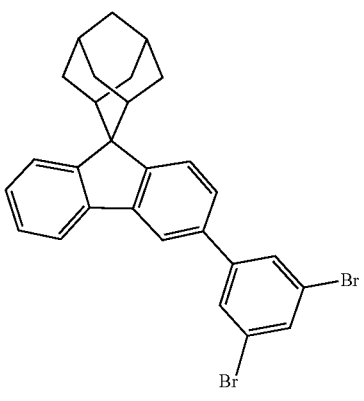 [SMILES: Brc1cc(Br)cc(-c2ccc3c(c2)-c2ccccc2C32C3CC4CC(C3)CC2C4)c1] | 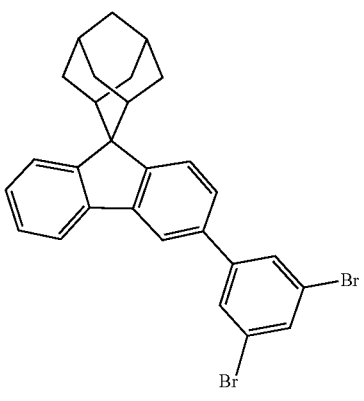 [SMILES: Brc1cc(Br)cc(-c2ccc3c(c2)-c2ccccc2C32C3CC4CC(C3)CC2C4)c1] | 31 |

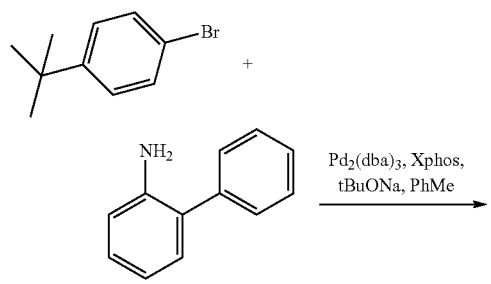

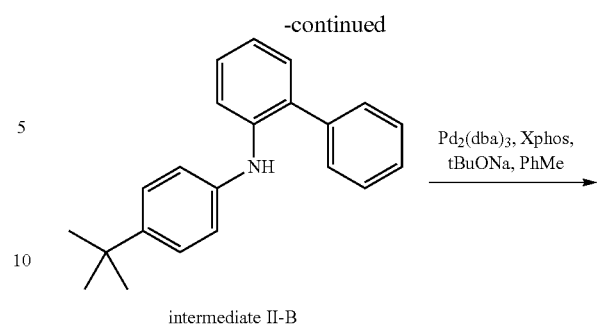

intermediate II-B

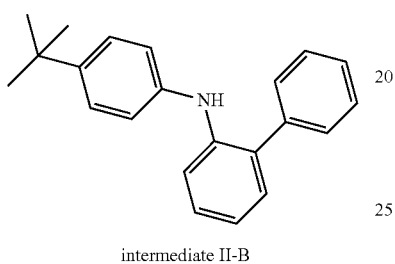

intermediate II-B 4-tert-butylbromobenzene (4.0 g, 25.5 mmol), 2-aminobiphenyl(4.39 g, 25.9 mmol), tris(dibenzylideneacetone)dipalladium (0.23 g, 0.25 mmol), 2-dicyclohexylphosphino-2',4',6'-triisopropylbiphenyl (0.24 g, 0.50 mmol) and sodium tert-butoxide (3.67 g, 38.22 mmol) were added to toluene (40 mL), heated to 108° C. and stirred for 2 h under nitrogen. After cooling to room temperature, the obtained reaction solution was washed with water and dried by adding magnesium sulfate. After filtration, the solvent was removed from the filtrate under reduced pressure. The crude product obtained was purified by recrystallization using dichloromethane/ethyl acetate system to obtain Intermediate II-B as a light yellow solid (3.2 g, yield 56.6%).

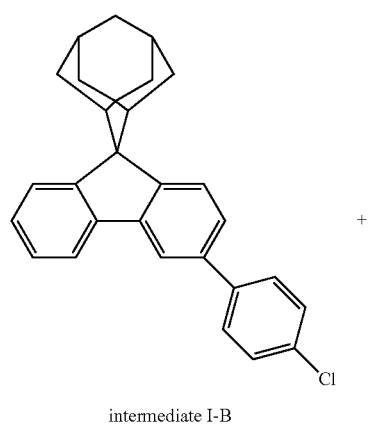

intermediate I-B

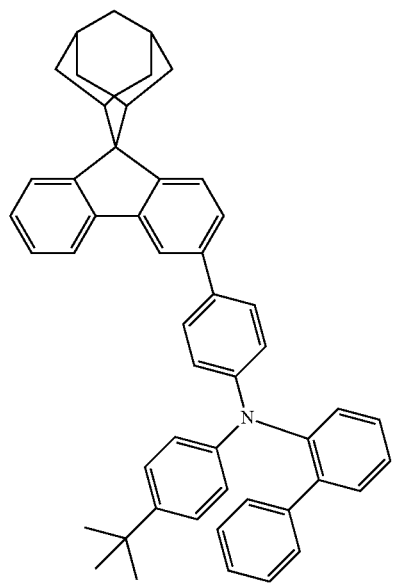

Compound 295

Intermediate I-B (1.50 g, 3.78 mmol), intermediate II-B (0.95 g, 3.85 mmol), tris(dibenzylideneacetone) dipalladium (0.03 g, 0.04 mmol), 2-dicyclohexylphosphinodicyclohexylphosphino-2',6'-dimethoxybiphenyl (0.03 g, 0.07 mmol) and sodium tert-butoxide (0.55 g, 5.67 mmol) were added to toluene (20 mL), heated to 108° C. and stirred for 5 h under nitrogen protection. After cooling to room temperature, the obtained reaction solution was washed with water and dried by adding magnesium sulfate. After filtration, the solvent was removed from the filtrate under reduced pressure. The crude product obtained was purified by recrystallization using toluene system to obtain Compound 295 as a white solid (1.7 g, 74%). Mass spectrum: m/z=662.4 [M+H]f.

Referring to the synthesis method of Compound 295, and using the raw materials 4 to replace 2-aminobiphenyl, and the raw material 5 to replace 4-tert-butylbromobenzene, the intermediates in the fourth column in the following table were synthesized. Other compounds in Table 4 were prepared by replacing the intermediate II-B with the intermediates in the fourth column. The specific compound number, structure, raw materials, synthesis yield of the last step, characterization data, etc. are shown in Table 4.

TABLE 4

Compound number, structure, preparation and characterization data

| Compound No. | Raw material 4 | Raw material 5 | Intermediate |
|---|---|---|---|
| 304 | | | |
| 316 | | | |
| 341 | | | |
| 351 | | | |

TABLE 4-continued
Compound number, structure, preparation and characterization data
384
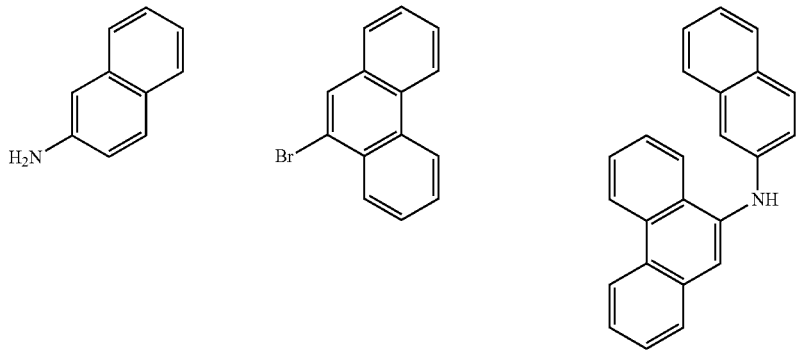
369
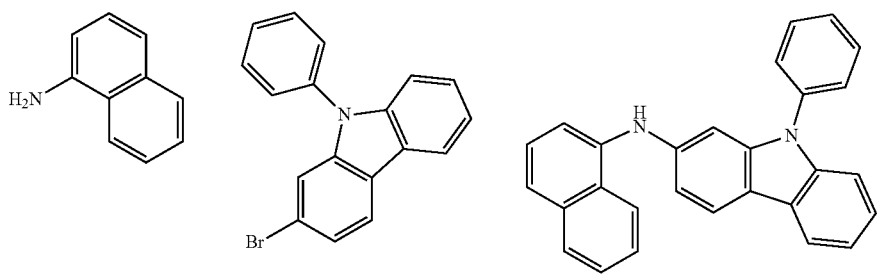
| Compound No. | Structure | Yield (%) | MS (m/z) [M + H]+ |
|---|---|---|---|
| 304 | 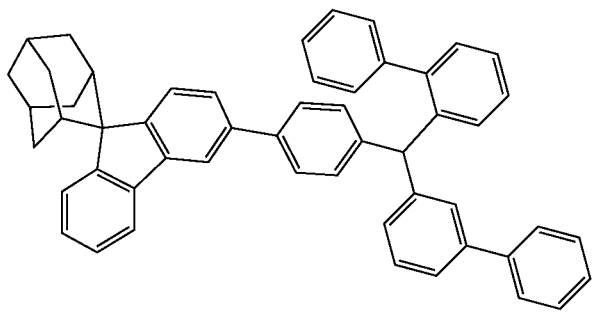 [SMILES: c1ccc(-c2cccc(C(c3ccc(-c4ccc5c(c4)-c4ccccc4C54C5CC6CC(C5)CC4C6)cc3)c3ccccc3-c3ccccc3)c2)cc1] | 61 | 682.3 |
| 316 | 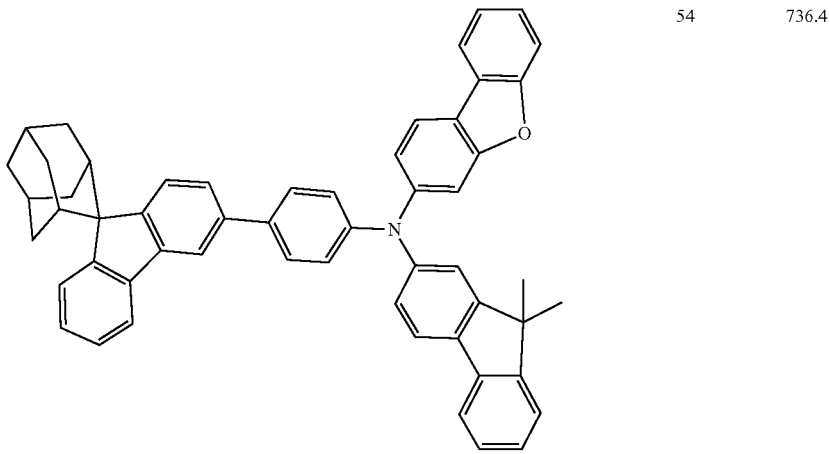 | 54 | 736.4 |

TABLE 4-continued
Compound number, structure, preparation and characterization data
| 341 | 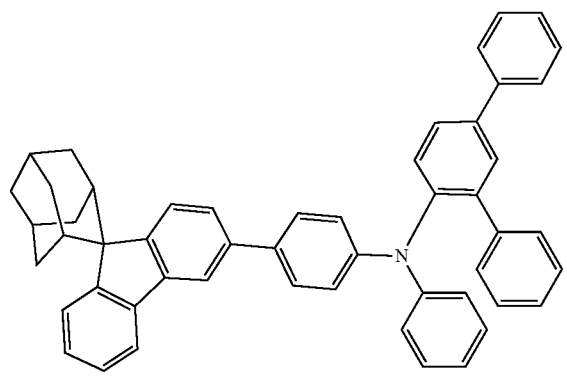 [SMILES: c1ccc(-c2ccc(N(c3ccccc3)c3ccc(-c4ccc5c(c4)-c4ccccc4C54C5CC6CC(C5)CC4C6)cc3)c(-c3ccccc3)c2)cc1] | 59 | 682.3 |
| 351 | 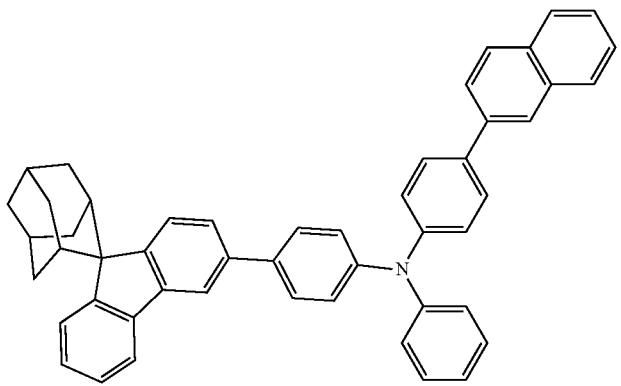 [SMILES: c1ccc(N(c2ccc(-c3ccc4c(c3)-c3ccccc3C43C4CC5CC(C4)CC3C5)cc2)c2ccc(-c3ccc4ccccc4c3)cc2)cc1] | 63 | 656.3 |
| 384 | 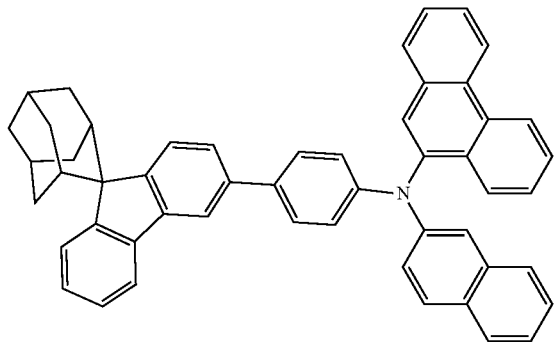 [SMILES: c1ccc2c(c1)-c1cc(-c3ccc(N(c4ccc5ccccc5c4)c4cc5ccccc5c5ccccc45)cc3)ccc1C21C2CC3CC(C2)CC1C3] | 66 | 680.3 |
| 369 | 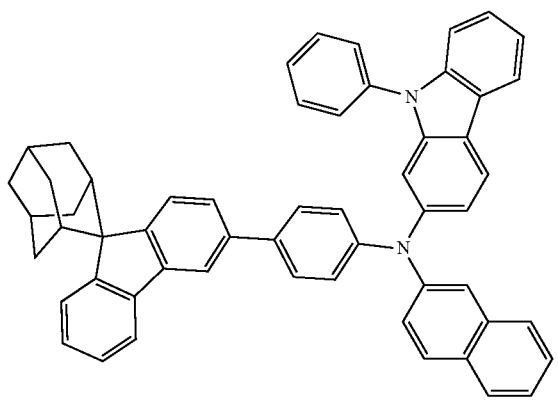 [SMILES: c1ccc(-n2c3ccccc3c3ccc(N(c4ccc(-c5ccc6c(c5)-c5ccccc5C65C6CC7CC(C6)CC5C7)cc4)c4ccc5ccccc5c4)cc32)cc1] | 41 | 745.4 |

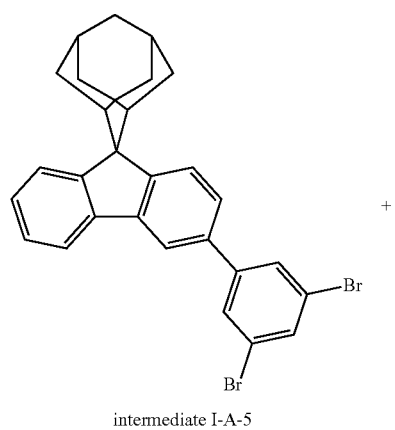

intermediate I-A-5

+

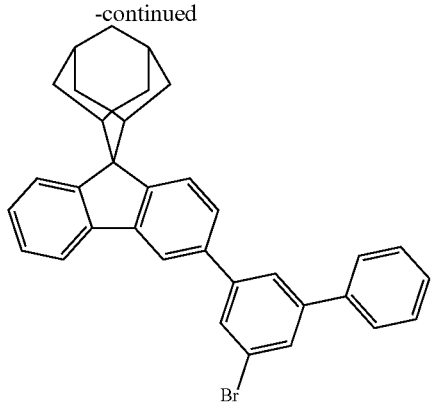

intermediate I-A-6

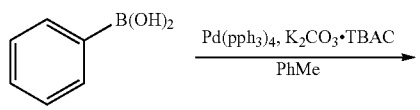

Intermediate I-A-6 was prepared according to the synthesis method of intermediate I-B, except that intermediate I-A was replaced by intermediate I-A-5, and p-chlorophenylboronic acid was replaced by phenylboronic acid to obtain intermediate I-A-6.

Referring to the synthesis method of Compound 1, the compounds shown in the forth column of Table 5 below were prepared, except that the intermediate shown in the third column of Table 5 below replaces the intermediate I-A to react with the intermediate II-A. The specific compound number, structure, raw materials, the synthetic yield of last step and characterization data are shown in Table 5.

TABLE 5

| | | Compound number, structure, preparation and characterization data | | | |
|---|---|---|---|---|---|
| Compound No. | Intermediate No. | Intermediate Structure | Compound Structure | Yield (%) | MS (m/z) [M + H]+ |
| 496 | Intermediate I-C | | | 61 | 682.3 |
| 499 | Intermediate I-D | | | 57 | 682.3 |

TABLE 5-continued

Compound number, structure, preparation and characterization data

| Compound No. | Intermediate No. | Intermediate Structure | Compound Structure | Yield (%) | MS (m/z) [M + H]+ |
|---|---|---|---|---|---|
| 508 | Intermediate I-E | | 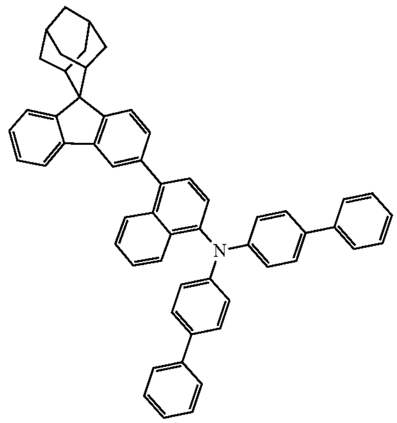 [SMILES: c1ccc(-c2ccc(N(c3ccc(-c4ccccc4)cc3)c3ccc(-c4ccc5c(c4)-c4ccccc4C54C5CC6CC(C5)CC4C6)c4ccccc34)cc2)cc1] | 69 | 732.4 |
| 581 | Intermediate I-F | | 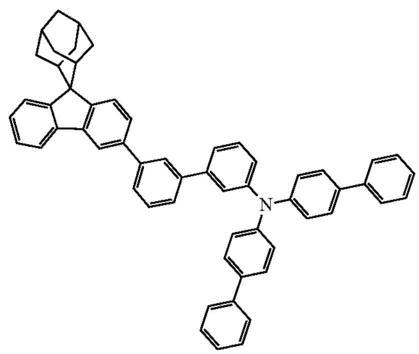 [SMILES: c1ccc(-c2ccc(N(c3ccc(-c4ccccc4)cc3)c3cccc(-c4cccc(-c5ccc6c(c5)-c5ccccc5C65C6CC7CC(C6)CC5C7)c4)c3)cc2)cc1] | 54 | 758.4 |
| 651 | Intermediate I-A-2 | | 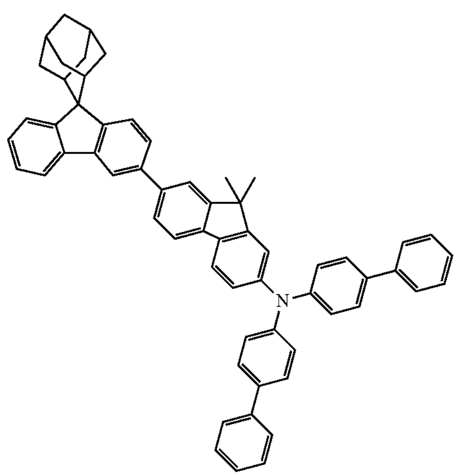 [SMILES: CC1(C)c2cc(-c3ccc4c(c3)-c3ccccc3C43C4CC5CC(C4)CC3C5)ccc2-c2ccc(N(c3ccc(-c4ccccc4)cc3)c3ccc(-c4ccccc4)cc3)cc21] | 49 | 798.4 |

TABLE 5-continued
Compound number, structure, preparation and characterization data
| Compound No. | Intermediate No. | Intermediate Structure | Compound Structure | Yield (%) | MS (m/z) [M + H]+ |
|---|---|---|---|---|---|
| 670 | Intermediate I-A-3 | 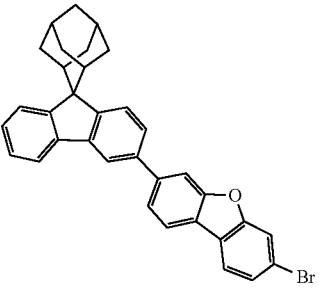 [SMILES: Brc1ccc2c(c1)oc1cc(-c3ccc4c(c3)-c3ccccc3C43C4CC5CC(C4)CC3C5)ccc12] | 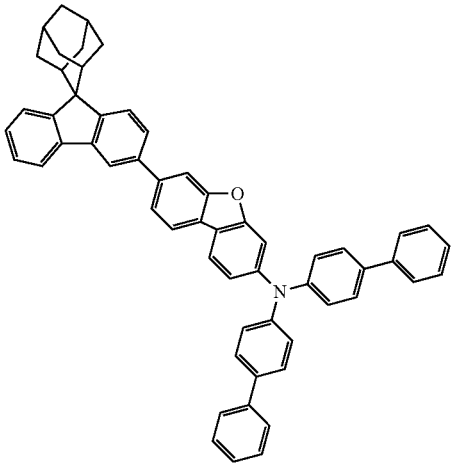 [SMILES: c1ccc(-c2ccc(N(c3ccc(-c4ccccc4)cc3)c3ccc4c(c3)oc3cc(-c5ccc6c(c5)-c5ccccc5C65C6CC7CC(C6)CC5C7)ccc34)cc2)cc1] | 44 | 772.4 |
| 710 | Intermediate I-A-4 | 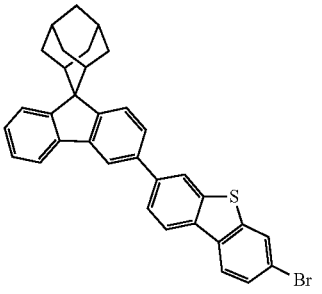 [SMILES: Brc1ccc2c(c1)sc1cc(-c3ccc4c(c3)-c3ccccc3C43C4CC5CC(C4)CC3C5)ccc12] | 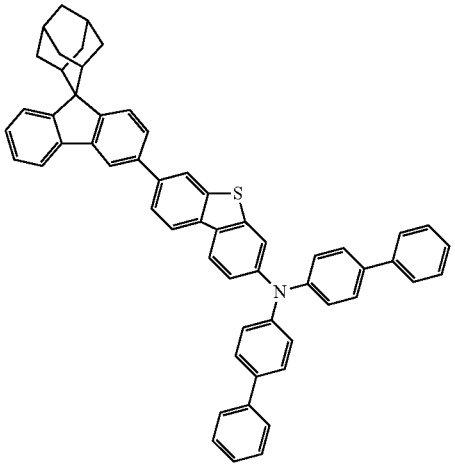 | 51 | 788.3 |
| 819 | Intermediate I-A-6 | 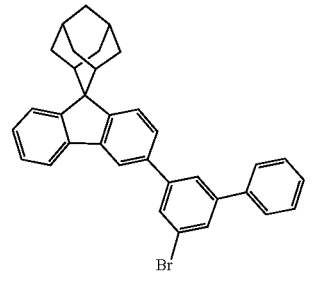 [SMILES: Brc1cc(-c2ccccc2)cc(-c2ccc3c(c2)-c2ccccc2C32C3CC4CC(C3)CC2C4)c1] | 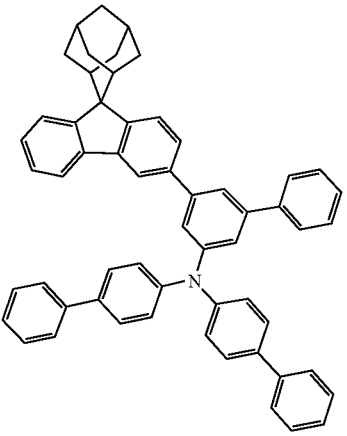 [SMILES: c1ccc(-c2ccc(N(c3ccc(-c4ccccc4)cc3)c3cc(-c4ccccc4)cc(-c4ccc5c(c4)-c4ccccc4C54C5CC6CC(C5)CC4C6)c3)cc2)cc1] | 49 | 758.4 |

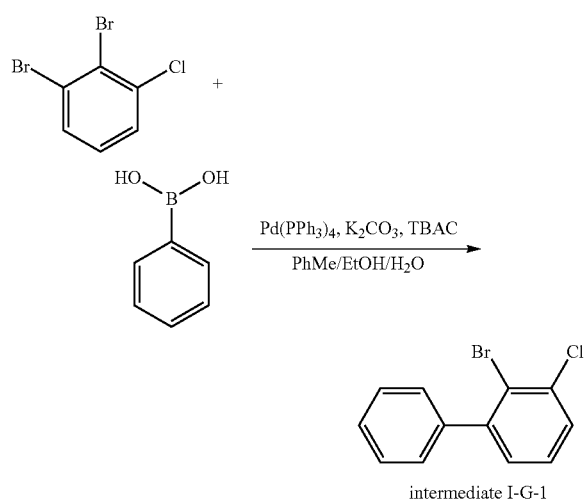

intermediate I-G-1

1,2-dibromo-3-chlorobenzene (80.0 g, 298.7 mmol), phenylboronic acid (36.5 g, 298.7 mmol), tetrakis(triphenylphosphine)palladium (6.9 g, 6.0 mmol), potassium carbonate (103.2 g, 746.7 mmol), and tetrabutylamnmonium bromide (19.2 g; 59.7 mmol) were added to the flask, and then added a mixed solvent of toluene (600 mL), ethanol (150 mL) and water (150 mL), heated to 80° C. and stirred for 18 hours maintaining the temperature under nitrogen protection. After cooling to room temperature, stopped stirring, the resulting reaction liquid was washed with water, then the organic phase was separated from it and dried over anhydrous magnesium sulfate, and the solvent was removed under reduced pressure to obtain a crude product. The crude product was purified by silica gel column chromatography using dichloromethane/n-heptane as the mobile phase to obtain product intermediate I-G-1 as a white solid (42.0 g, yield 53%).

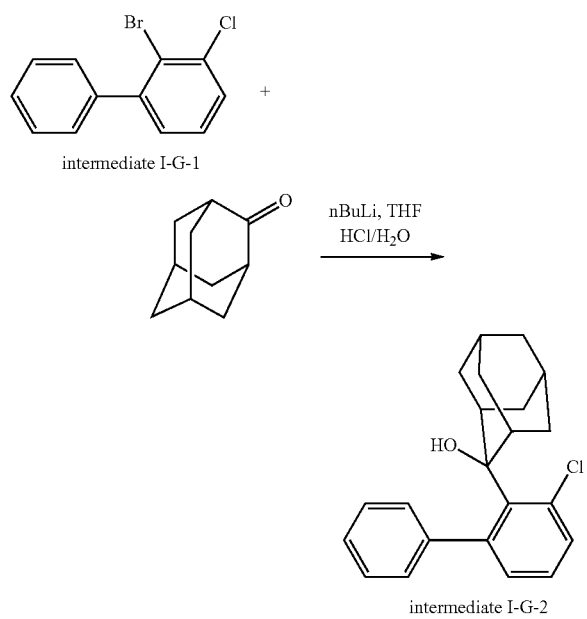

intermediate I-G-2

Intermediate I-G-1 (42.0 g, 157.9 mmol) and tetrahydrofuran (300 mL) were added to the flask, cooled down −78° C. under nitrogen protection, and a solution of n-butyllithium in tetrahydrofuran (2.5M) (95 mL, 236.9 mmol) was added dropwise under stirring. The stirring was maintained for 1 hour after the dropwise addition. Keeping at −78° C., adamantanone-(19.0 g, 126.3 mmol) solution in tetrahydrofuran (100 mL) was added dropwise. After the addition, the temperature was maintained for 1 hour, and then warmed up to room temperature and stirred for 24 hours. A solution of hydrochloric acid (12M) (26.3 mL, 315.8 mmol) in water (100 mL) was added to the resulting reaction solution and stirred for 1 hour. Separating the liquid, the obtained organic phase was washed to neutrality with water, and anhydrous magnesium sulfate was added for drying. The solvent was removed under reduced pressure to obtain a crude product. The crude product was purified by silica gel column chromatography using ethyl acetate/n-heptane system to obtain product intermediate I-G-2 as a white solid (25.8 g, yield 48%).

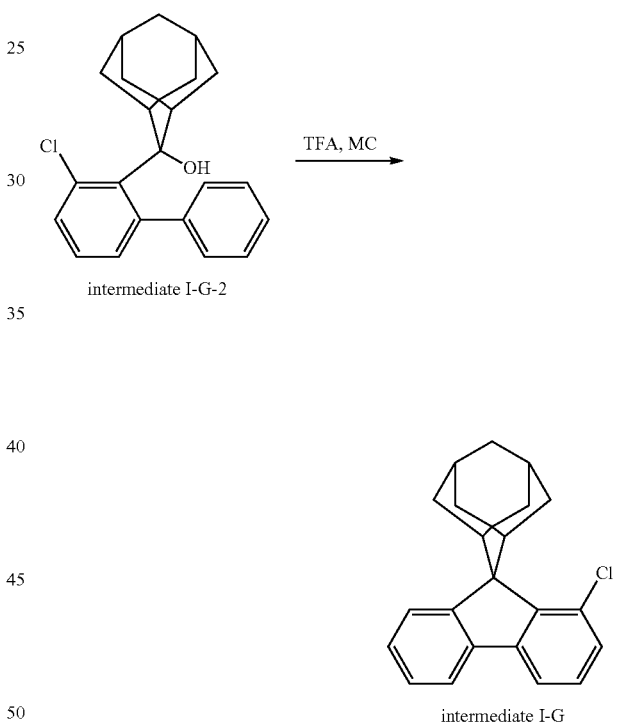

intermediate I-G

Intermediate I-G was synthesized referring to the synthesis method of intermediate I-A, except that intermediate I-G-2 was used to replace intermediate I-A-2.

Referring to the synthesis method of Compound 1, the compounds shown in the fifth column of Table 6 were prepared in which intermediate I-A was replaced by intermediate I-G, 4-aminobiphenyl was replaced by raw material 6 in the second column in the following table, 4-bromobiphenyl was replaced by raw material 7 in the third column, and intermediate II-A was replaced by the intermediates in the fourth column synthesized by raw material 6 and raw material 7. The specific compound number, structure, final step synthesis yield, characterization data, etc. are shown in Table 6.

TABLE 6

Compound number, structure, preparation and characterization data

| Compound No. | Raw material 6 | Raw material 7 | Intermediate |
|---|---|---|---|
| 817 | (4-aminodibenzofuran) | (1-bromo-9,9-dimethylfluorene) | (N-(9,9-dimethylfluoren-1-yl)dibenzofuran-4-amine) |
| 818 | (aniline) | (1-bromodibenzofuran) | (N-phenyldibenzofuran-1-amine) |

| Compound No. | Compound Structure | Yield (%) | MS (m/z) [M + H]⁺ |
|---|---|---|---|
| 817 | 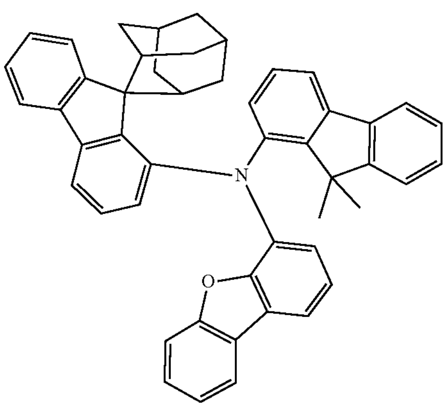 [SMILES: CC1(C)c2ccccc2-c2cccc(N(c3cccc4c3C3(c5ccccc5-4)C4CC5CC(C4)CC3C5)c3cccc4c3oc3ccccc34)c21] | 43 | 660.3 |
| 818 | 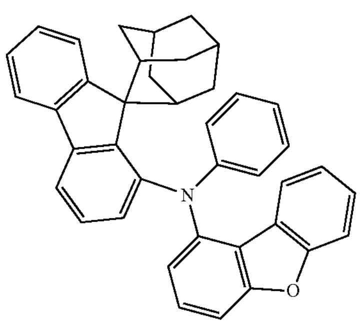 [SMILES: c1ccc(N(c2cccc3c2C2(c4ccccc4-3)C3CC4CC(C3)CC2C4)c2cccc3oc4ccccc4c23)cc1] | 51 | 544.3 |

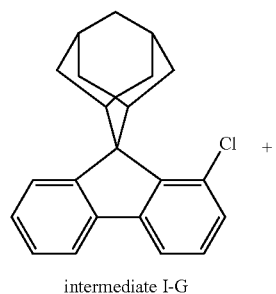

intermediate I-G

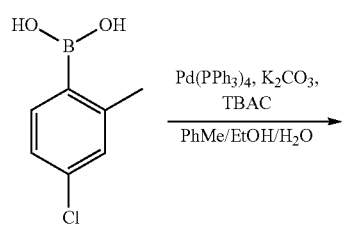

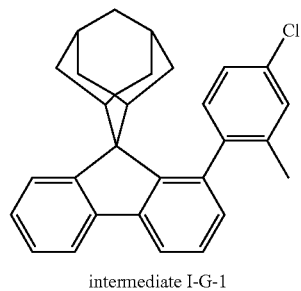

intermediate I-G-1

Intermediate I-G-1 was synthesized referring to the synthesis method of intermediate I-B, except that intermediate I-G was used to replace intermediate I-A.

Compound 439 was synthesized referring to the synthesis method of Compound 295, except that intermediate I-G-1 was used to replace intermediate I-B. The specific compound number, structure, final step synthesis yield, characterization data, etc. are shown in Table 7.

Preparation and Evaluation of Organic Electroluminescent Devices

Example 1

The green organic electroluminescent device was manufactured by the following method.

The ITO substrate (made by Corning) with an ITO thickness of 1500 Å was cut into a size of 40 mm (length)× 40 mm (width)×0.7 mm (thickness), then making it into an experimental substrate with cathode, anode and insulating layer patterns by the photolithography process. The experimental substrate was treated with ultraviolet ozone and $O_2:N_2$ plasma to increase the work function of the anode (experimental substrate) and remove scum.

m-MTDATA was vacuum-evaporated on the experimental substrate (anode) to form a hole injecting layer (HIL) with a thickness of 100 Å, and NPB was vacuum-evaporated on the hole injection layer to form a first hole transporting layer with a thickness of 1000 Å.

Compound 1 was evaporated on the first hole transporting layer to form a second hole transporting layer with a thickness of 350 Å.

CBP as the host material was doped with $Ir(ppy)_3$ at a film thickness ratio of 100:5 simultaneously to form a light-emitting layer (EML) with a thickness of 380 Å.

ET-1 and LiQ were mixed in a weight ratio of 1:1 and evaporated to form an electron transporting layer (ETL) with a thickness of 300 Å. LiQ was vapor-deposited on the electron transporting layer to form an electron injecting layer (EIL) with a thickness of 10 Å. Magnesium (Mg) and silver (Ag) were then mixed and vacuum-evaporated at a vapor deposition rate of 1:9 on the electron injecting layer to form a cathode with a thickness of 120 Å.

In addition, CP-1 was vapor-deposited on the cathode with a thickness of 650 Å, thereby completing the manufacture of the organic light-emitting device.

The chemical structures of some materials used during the manufacture of the above electroluminescent device are shown as follows:

TABLE 7

Compound number, structure, preparation and characterization data

| Compound No. | Compound Structure | yield (%) | Mass (m/z) [M + H]⁺ |
|---|---|---|---|
| 439 | 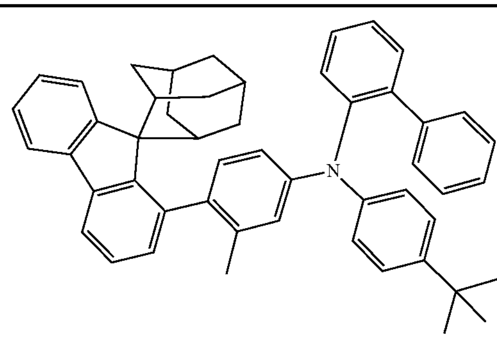 | 37 | 676.4 |

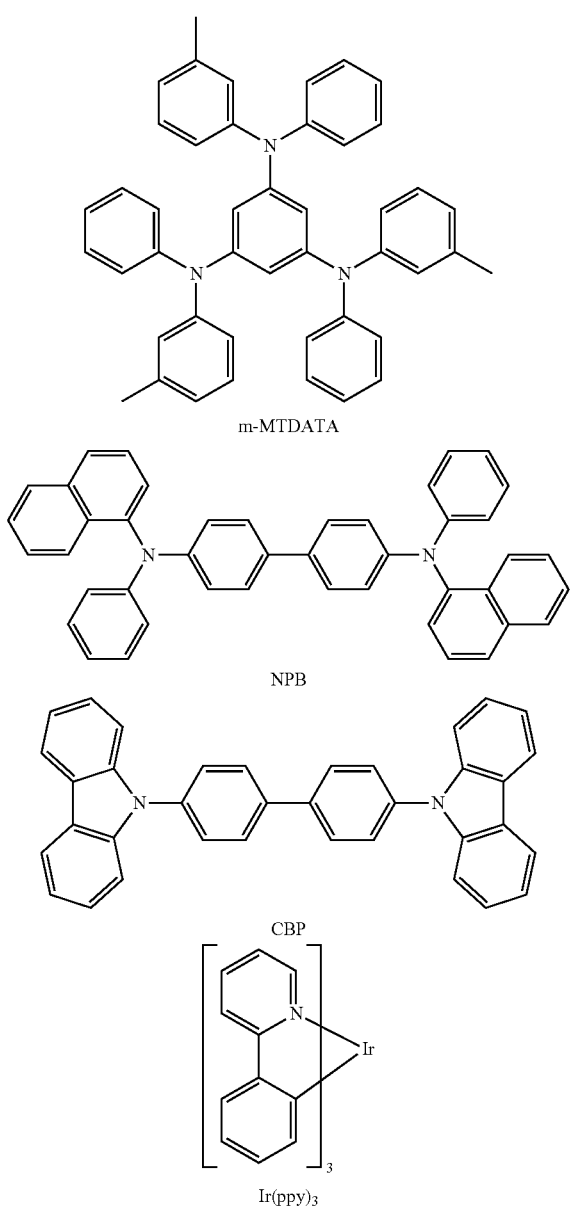
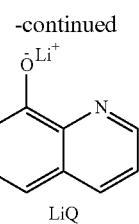
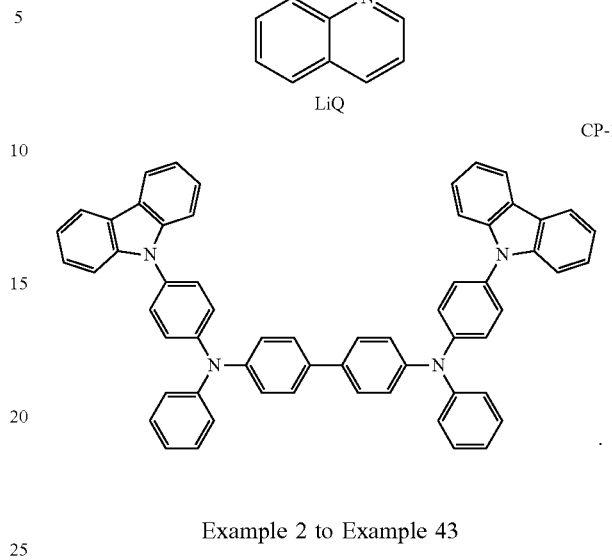

Example 2 to Example 43

The devices of Examples 2 to 43 were manufactured by referring to the method of Example 1, except that the compounds synthesized shown in Table 8 below were used to replace Compound 1, respectively, to form the second hole transporting layer with a thickness of 350 Å, thereby completing the manufacture of corresponding green organic electroluminescent devices.

Comparative Example 1 to Comparative Example 7

The devices of Comparative Example 1 to Comparative Example 7 were manufactured by referring to the method of Example 1, except that Compound A, Compound B, Compound C, Compound D, Compound E, Compound F and Compound G were used to replace Compound 1, respectively, thereby completing the manufacture of corresponding green organic electroluminescent devices.

The chemical structures of Compound A, Compound B, Compound C, Compound D, Compound E, Compound F and Compound G are shown as follows:

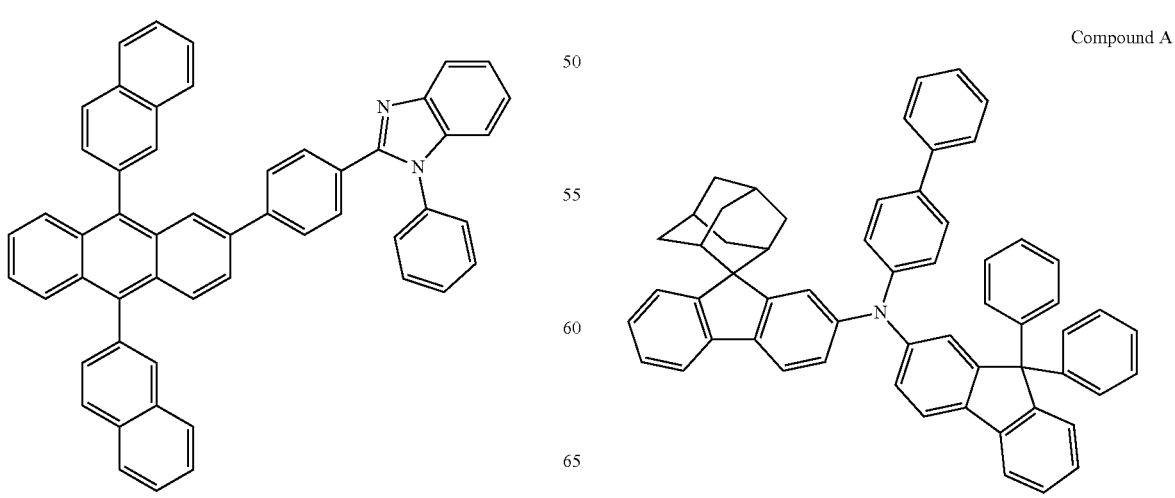

Compound B

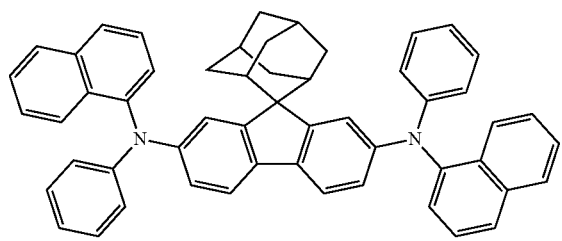

Compound C

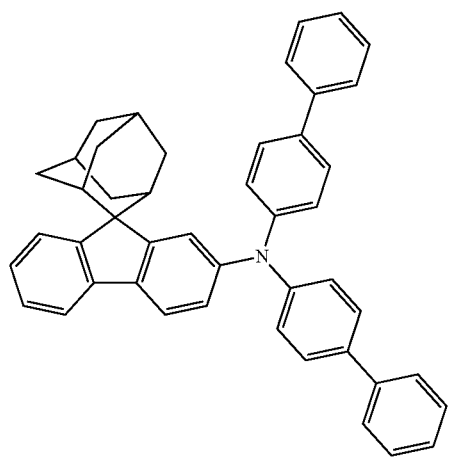

Compound D

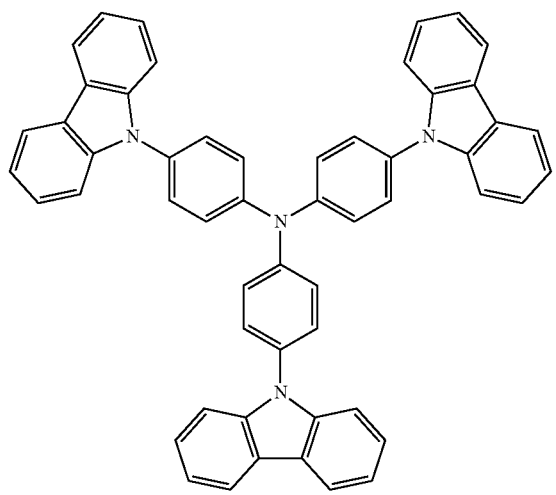

Compound E

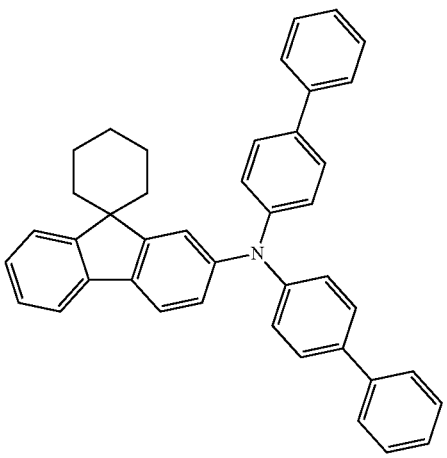

Compound F

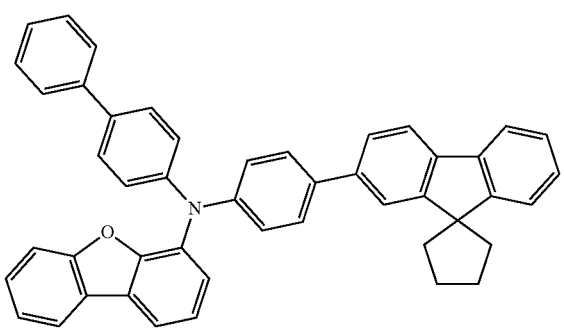

Compound G

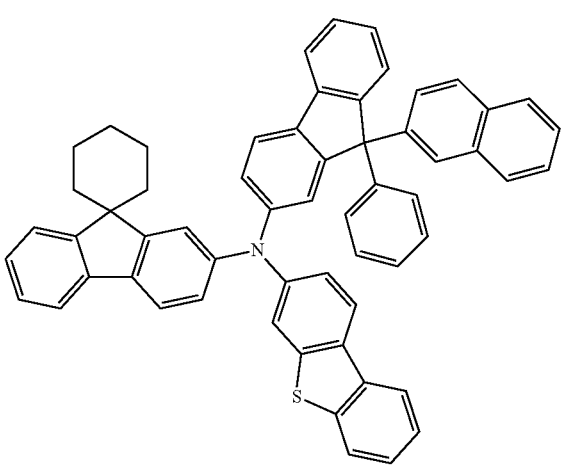

The green organic electroluminescent devices manufacture in Examples 1 to 43 and Comparative Examples 1 to 7 were tested for performance. Specifically, the IVL performance of the devices was tested under the condition of 10 mA/cm$^2$, and the T95 lifetime of the devices was tested under the initial brightness of 17,000 nit. The test results are shown in Table 8.

TABLE 8

Performance test results of green organic electroluminescent devices

| Examples | Second hole transporting layer material | Driving voltage (V) | Current efficiency (Cd/A) | Color coordinate CIEx, CIEy | External quantum efficiency EQE (%) | T95 lifetime (h) |
|---|---|---|---|---|---|---|
| Example 1 | Compound 1 | 4.11 | 86.92 | 0.266, 0.700 | 32.7 | 160 |
| Example 2 | Compound 3 | 4.14 | 86.84 | 0.266, 0.701 | 32.5 | 158 |
| Example 3 | Compound 7 | 4.10 | 87.01 | 0.265, 0.700 | 33.1 | 161 |
| Example 4 | Compound 9 | 4.13 | 86.96 | 0.262, 0.702 | 32.9 | 155 |
| Example 5 | Compound 15 | 4.12 | 86.92 | 0.262, 0.702 | 32.9 | 160 |
| Example 6 | Compound 23 | 4.14 | 86.78 | 0.261, 0.704 | 32.5 | 158 |
| Example 7 | Compound 36 | 4.09 | 87.01 | 0.266, 0.700 | 33.1 | 161 |
| Example 8 | Compound 31 | 4.07 | 86.93 | 0.266, 0.700 | 32.5 | 162 |
| Example 9 | Compound 54 | 4.09 | 86.80 | 0.266, 0.701 | 32.5 | 158 |
| Example 10 | Compound 60 | 4.08 | 87.01 | 0.265, 0.700 | 33.1 | 162 |
| Example 11 | Compound 66 | 4.12 | 86.95 | 0.262, 0.702 | 32.8 | 156 |
| Example 12 | Compound 71 | 4.15 | 86.92 | 0.262, 0.702 | 32.9 | 160 |
| Example 13 | Compound 87 | 4.14 | 86.78 | 0.261, 0.704 | 32.5 | 158 |
| Example 14 | Compound 92 | 4.18 | 87.04 | 0.266, 0.700 | 32.9 | 163 |
| Example 15 | Compound 95 | 4.07 | 86.92 | 0.266, 0.700 | 32.7 | 160 |
| Example 16 | Compound 115 | 4.09 | 86.84 | 0.266, 0.701 | 32.5 | 158 |
| Example 17 | Compound 116 | 4.12 | 87.02 | 0.265, 0.700 | 33.0 | 160 |
| Example 18 | Compound 128 | 4.14 | 86.94 | 0.262, 0.702 | 32.9 | 155 |
| Example 19 | Compound 127 | 4.09 | 86.92 | 0.262, 0.702 | 32.9 | 160 |
| Example 20 | Compound 147 | 4.11 | 86.79 | 0.261, 0.704 | 32.4 | 158 |
| Example 21 | Compound 162 | 4.15 | 87.01 | 0.266, 0.700 | 33.1 | 161 |
| Example 22 | Compound 195 | 4.12 | 86.78 | 0.261, 0.704 | 32.5 | 158 |
| Example 23 | Compound 206 | 4.11 | 87.00 | 0.266, 0.700 | 33.3 | 165 |
| Example 24 | Compound 295 | 4.08 | 86.89 | 0.262, 0.702 | 32.9 | 155 |
| Example 25 | Compound 304 | 4.14 | 86.92 | 0.263, 0.702 | 33.0 | 160 |
| Example 26 | Compound 316 | 4.17 | 86.80 | 0.261, 0.704 | 32.4 | 158 |
| Example 27 | Compound 341 | 4.15 | 87.12 | 0.266, 0.700 | 33.1 | 161 |
| Example 28 | Compound 351 | 4.18 | 87.12 | 0.266, 0.700 | 33.1 | 161 |
| Example 29 | Compound 384 | 4.12 | 86.83 | 0.262, 0.703 | 32.8 | 155 |
| Example 30 | Compound 369 | 4.10 | 86.90 | 0.262, 0.703 | 32.9 | 160 |
| Example 31 | Compound 439 | 4.15 | 84.90 | 0.263, 0.703 | 32.8 | 155 |
| Example 32 | Compound 487 | 4.15 | 84.73 | 0.262, 0.703 | 31.8 | 161 |
| Example 33 | Compound 496 | 4.06 | 83.17 | 0.262, 0.700 | 32.9 | 160 |
| Example 34 | Compound 499 | 4.09 | 85.44 | 0.262, 0.704 | 30.2 | 159 |
| Example 35 | Compound 508 | 4.18 | 86.32 | 0.266, 0.701 | 31.5 | 160 |
| Example 36 | Compound 581 | 4.11 | 83.69 | 0.263, 0.703 | 32.8 | 155 |
| Example 37 | Compound 651 | 4.17 | 82.7 | 0.262, 0.702 | 31.9 | 159 |
| Example 38 | Compound 670 | 4.10 | 83.62 | 0.262, 0.702 | 30.2 | 157 |
| Example 39 | Compound 710 | 4.09 | 85.17 | 0.263, 0.703 | 32.5 | 155 |
| Example 40 | Compound 745 | 4.17 | 82.69 | 0.263, 0.703 | 31.5 | 154 |
| Example 41 | Compound 817 | 4.11 | 85.74 | 0.262, 0.702 | 30.9 | 160 |
| Example 42 | Compound 818 | 4.07 | 87.19 | 0.261, 0.704 | 32.2 | 159 |
| Example 43 | Compound 819 | 4.14 | 86.81 | 0.261, 0.704 | 32.2 | 159 |
| Comparative Example 1 | Compound A | 4.67 | 86.89 | 0.262, 0.702 | 25.8 | 149 |
| Comparative Example 2 | Compound B | 4.73 | 85.04 | 0.262, 0.702 | 24.2 | 145 |
| Comparative Example 3 | Compound C | 4.62 | 85.54 | 0.263, 0.703 | 24.4 | 155 |
| Comparative Example 4 | Compound D | 4.66 | 82.69 | 0.263, 0.703 | 24.5 | 154 |
| Comparative Example 5 | Compound E | 4.65 | 85.04 | 0.262, 0.702 | 24.2 | 140 |
| Comparative Example 6 | Compound F | 4.68 | 85.64 | 0.263, 0.703 | 24.4 | 143 |
| Comparative Example 7 | Compound G | 4.72 | 84.54 | 0.263, 0.703 | 24.4 | 150 |

According to the above table, the luminous efficiency (Cd/A) and lifetime of the organic electroluminescent devices manufactured in Examples 1 to 43 are comparable to those of Comparative Examples 1 to 7 in the case of little difference in the color coordinates, while the overall device voltages of Comparative Examples 1 to 7 are relatively high. As shown in the table above, the driving voltages of Examples 1 to 43 are reduced by at least 0.45V compared to those of Comparative Examples 1 to 7. Therefore, an organic electroluminescent device with a lower operating voltage can be produced by using the nitrogen-containing compound of the present disclosure in the second hole transporting layer.

The nitrogen-containing compound of the present disclosure introduces an adamantane structure at the fluorene to enhance the electron density of the fluorene ring and the conjugate system of the entire compound through the hyperconjugation effect, which can enhance the hole conductivity and electron tolerance of the nitrogen-containing compound. In addition, the introduction of adamantyl can also increase the molecular weight of the nitrogen-containing compound and reduce the molecular symmetry, can increase the glass transition temperature and evaporation temperature of the compound of the present disclosure, control the crystallinity of the nitrogen-containing compound, makes the nitrogen-containing compound has higher physical and thermal stability when being mass-produced, which is convenient for mass production stability of organic electroluminescent devices and photoelectric conversion devices. Compared with Comparative Examples 1, 2 and 3, connecting amine to fluorene at positions 1 and 3 can increase the steric hindrance of the arylamine structure to a certain extent, and increase the twist angles of the fluorene plane and the arylamine plane (especially the triarylamine plane), which reduces the conjugation degree of the nitrogen-containing compound. When the nitrogen-containing compound is used as the second hole transporting layer (also known as the electron blocking layer), it may better match the HOMO energy level of the adjacent layer, thereby reducing the operating voltage of the organic electroluminescent device.

The organic electroluminescent devices manufactured in Example 1 were divided into two groups, and one group of devices was directly subjected to performance tests without heat treatment, and the test results are shown in Table 9. The other group was subjected to heat-treated (placed at 110° C. for 1 hour) before performance tests. The test results for performance are shown in Table 10. Referring to the aforementioned method, the performance parameters without heat treatment and performance parameters after heat treatment were also obtained for the organic electroluminescent devices manufactured in Example 14, Example 21, Example 32, Example 35, Example 38, Example 41, and Comparative Examples 1 to 7.

TABLE 9

Performance parameters of organic electroluminescent devices without heat treatment

| Example | Compound | Operating voltage (V) | Current efficiency (Cd/A) | External quantum efficiency EQE (%) | Color coordinate CIEx, CIEy | T95 lifetime (hr) |
|---|---|---|---|---|---|---|
| Example 1 | Compound 1 | 4.11 | 86.92 | 32.7 | 0.266, 0.700 | 160 |
| Example 14 | Compound 92 | 4.18 | 87.04 | 32.9 | 0.266, 0.700 | 163 |
| Example 21 | Compound 162 | 4.17 | 87.01 | 33.1 | 0.266, 0.700 | 161 |
| Example 31 | Compound 439 | 4.15 | 84.90 | 32.8 | 0.263, 0.703 | 155 |
| Example 35 | Compound 508 | 4.18 | 86.32 | 31.5 | 0.266, 0.701 | 160 |
| Example 38 | Compound 670 | 4.10 | 83.62 | 30.2 | 0.262, 0.702 | 157 |
| Example 41 | Compound 817 | 4.11 | 85.74 | 30.9 | 0.262, 0.702 | 160 |
| Comparative Example 1 | Compound A | 4.67 | 86.89 | 25.8 | 0.262, 0.702 | 149 |
| Comparative Example 2 | Compound B | 4.73 | 85.04 | 24.2 | 0.262, 0.702 | 145 |
| Comparative Example 3 | Compound C | 4.62 | 85.54 | 24.4 | 0.263, 0.703 | 155 |
| Comparative Example 4 | Compound D | 4.66 | 82.69 | 24.5 | 0.263, 0.703 | 154 |
| Comparative Example 5 | Compound E | 4.65 | 85.04 | 24.2 | 0.262, 0.702 | 140 |
| Comparative Example 6 | Compound F | 4.68 | 85.64 | 24.4 | 0.263, 0.703 | 143 |
| Comparative Example 7 | Compound G | 4.72 | 84.54 | 24.4 | 0.263, 0.703 | 150 |

TABLE 10

Performance parameters of organic electroluminescent devices after heat treatment

| Example | Compound | Operating voltage (V) | Current efficiency (Cd/A) | External quantum efficiency EQE (%) | Color coordinate CIEx, CIEy | T95 lifetime (h) |
|---|---|---|---|---|---|---|
| Example 1 | Compound 1 | 4.05 | 83.25 | 32.7 | 0.263, 0.703 | 160 |
| Example 14 | Compound 92 | 4.07 | 86.84 | 32.9 | 0.266, 0.700 | 154 |
| Example 21 | Compound 162 | 4.13 | 86.72 | 33.1 | 0.266, 0.700 | 167 |
| Example 31 | Compound 439 | 4.08 | 87.01 | 31.5 | 0.263, 0.703 | 164 |
| Example 35 | Compound 508 | 4.10 | 86.32 | 31.5 | 0.266, 0.701 | 160 |
| Example 38 | Compound 670 | 4.06 | 84.62 | 30.2 | 0.262, 0.702 | 157 |
| Example 41 | Compound 817 | 4.03 | 85.94 | 30.9 | 0.262, 0.702 | 160 |
| Comparative Example 1 | Compound A | 4.66 | 66.89 | 16.7 | 0.262, 0.702 | 134 |
| Comparative Example 2 | Compound B | 4.75 | 65.04 | 16.0 | 0.262, 0.702 | 130 |
| Comparative Example 3 | Compound C | 4.65 | 80.54 | 20.4 | 0.263, 0.703 | 145 |
| Comparative Example 4 | Compound D | 4.68 | 62.69 | 16.1 | 0.263, 0.703 | 134 |
| Comparative Example 5 | Compound E | 4.67 | 65.04 | 16.8 | 0.262, 0.702 | 127 |

TABLE 10-continued

Performance parameters of organic electroluminescent devices after heat treatment

| Example | Compound | Operating voltage (V) | Current efficiency (Cd/A) | External quantum efficiency EQE (%) | Color coordinate CIEx, CIEy | T95 lifetime (h) |
|---|---|---|---|---|---|---|
| Comparative Example 6 | Compound F | 4.68 | 62.64 | 16.0 | 0.263, 0.703 | 123 |
| Comparative Example 7 | Compound G | 4.73 | 64.54 | 15.6 | 0.263, 0.703 | 125 |

From the results in Table 9 and Table 10, it can be seen that for the organic electroluminescent devices of Comparative Examples 1, Comparative Examples 2, and Comparative Examples 4 to 7, compared with those without heat treatment, the luminous efficiency and external quantum efficiency are reduced by more than 23% after heat treatment, and the lifetimes are reduced by more than 10% after heat treatment. Compared with that without heat treatment, the efficiency and lifetime of the organic electroluminescent device of Comparative Example 3 after heat treatment are reduced by 5.8%, and the lifetime is reduced by 6.5%. However, for the organic electroluminescent devices of Example 1, Example 14, Example 21, Example 35, Example 38 and Example 41 after heat treatment, they maintained the comparable efficiency and lifetime as those without heat treatment.

From the device results in Table 8 to Table 10, it can be seen that the voltages of the devices using the compounds of the present disclosure are reduced, comparing those of the devices using the compounds of Comparative Example 1 and Comparative Example 3. The reason may be that the compounds of the present disclosure in which the aromatic amine is connected at the 1st or 3rd positions of adamantane fluorene have a deeper HOMO than the compounds in which the aromatic amine is connected at the 2nd position of adamantane fluorene, so as to make the injection of holes into the light-emitting layer smoother. Compared with the compounds of Comparative Example 5, Comparative Example 6 and Comparative Example 7, the application of the compounds of the present disclosure can reduce the voltage and improve the thermal stability for the device. The reason may be that the cycloalkyl group formed on the 9,9-dimethylfluorene of the present disclosure is the rigid and large-volume adamantyl group, which has a stronger ability to reduce the molecular stacking, compared with the single ring structure. The material can achieve a more stable film state.

It can be seen that, according to Table 8 to Table 10 for the results of the organic electroluminescent device of the examples, when the arylamine compound with adamantane-fluorene as the core is used as the second hole transporting layer material of the green light device, it can produce organic electroluminescent devices with excellent characteristics in terms of driving voltage, luminous efficiency, external quantum efficiency and thermal stability, etc. For example, it can produce a organic electroluminescent device with high-efficiency, high heat-resistance and long lifetime.

It should be understood that the present disclosure should not be limited to the detailed structure and arrangement of the components proposed in this specification. The present disclosure can have other embodiments, and can be implemented and executed in various ways. The aforementioned modified forms and modified forms fall within the scope of the present disclosure. It should be understood that the disclosed and defined in this specification of the disclosure extends to all alternative combinations of two or more individual features which are mentioned or obvious in the text and/or drawings. All of these different combinations constitute multiple alternative aspects of the present disclosure. The embodiments described in this specification illustrate the best ways known to implement the present disclosure, and will enable those skilled in the art to utilize the present disclosure.

What is claimed is:

1. A nitrogen-containing compound having a structure shown in Chemical Formula 1:

Chemical Formula 1

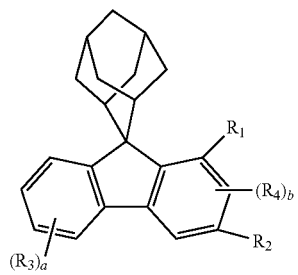

Chemical Formula 1-1

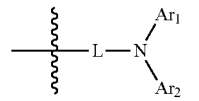

wherein

represents a chemical bond;

$R_1$ and $R_2$ are each independently selected from hydrogen or a group represented by Chemical Formula 1-1, and one and only one of $R_1$ and $R_2$ has the group represented by Chemical Formula 1-1;

when $R_1$ or $R_2$ is selected from hydrogen, said $R_1$ and $R_2$ may be replaced by $R_4$;

$R_3$, $R_4$ are each independently selected from an aryl having 6 to 20 carbon atoms;

a is 1, b is 0, or a is 0, b is 1;

L is selected from single bond, a substituted or unsubstituted arylene having 6 to 30 carbon atoms, or a substituted or unsubstituted heteroarylene having 3 to 30 carbon atoms; and Ar$_1$ and Ar$_2$ are each independently selected from the following substituted or unsubstituted groups: an aryl having 6 to 30 carbon atoms, or a heteroaryl having 3 to 30 carbon atoms.
2. The nitrogen-containing compound of claim 1, wherein L is single bond or selected from the group consisting of the following groups:
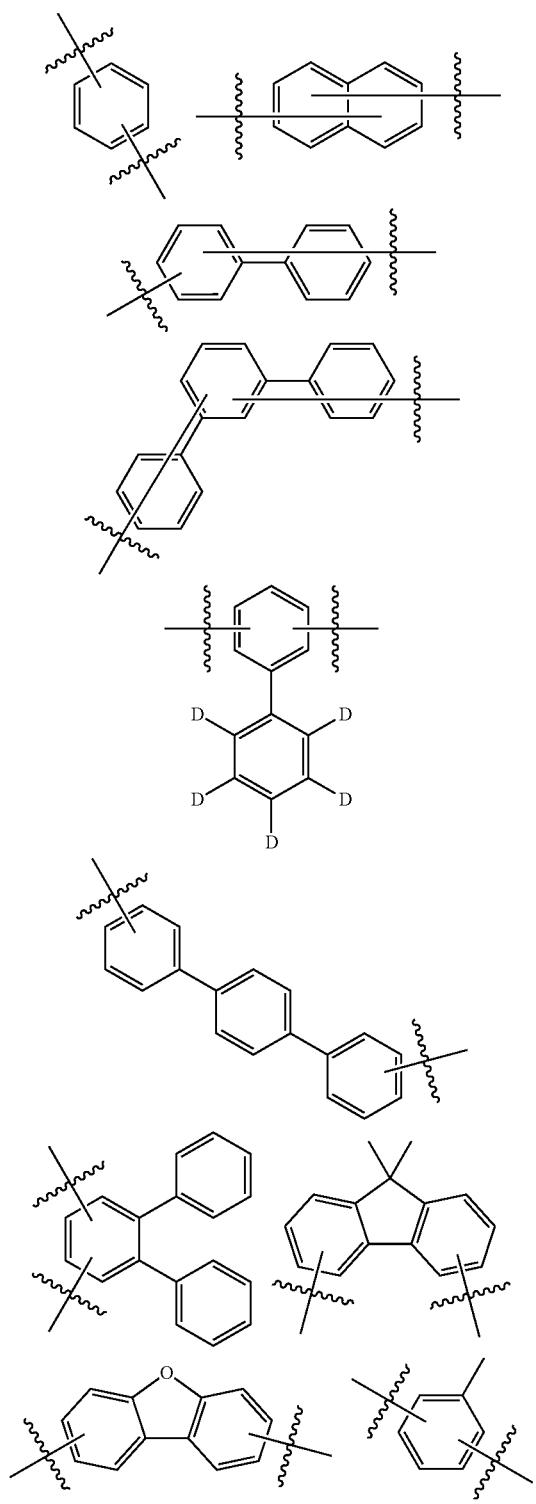
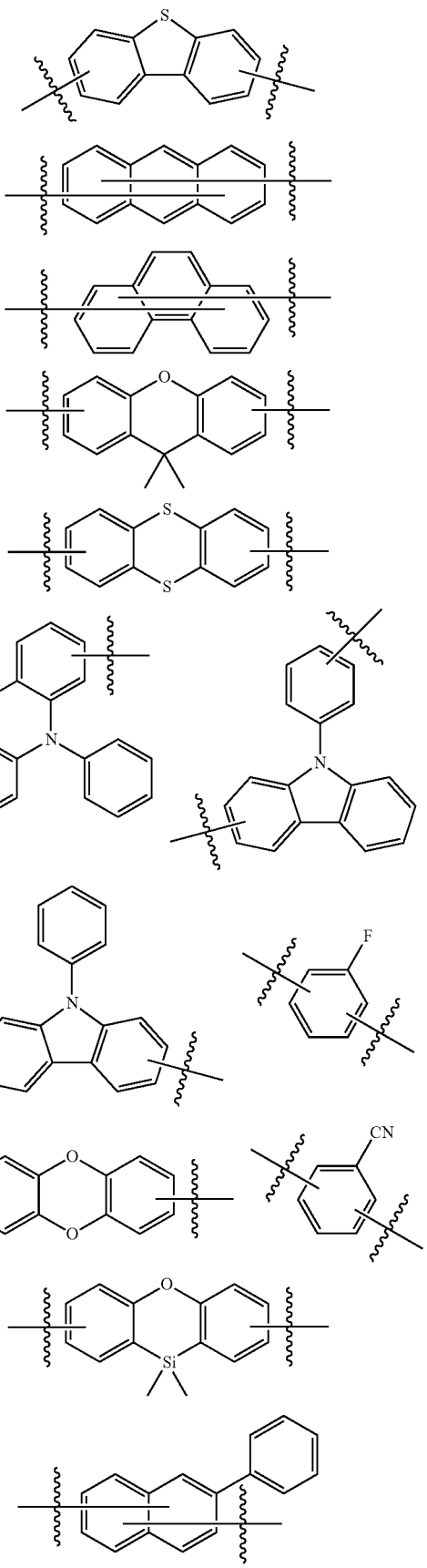

421
-continued
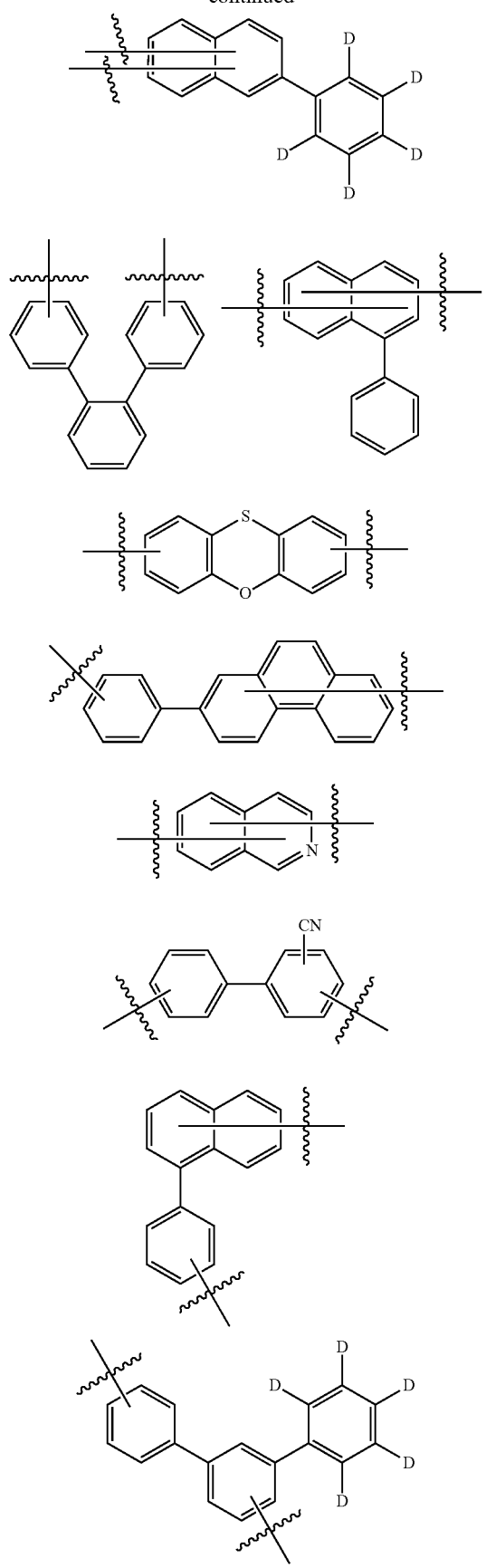
422
-continued
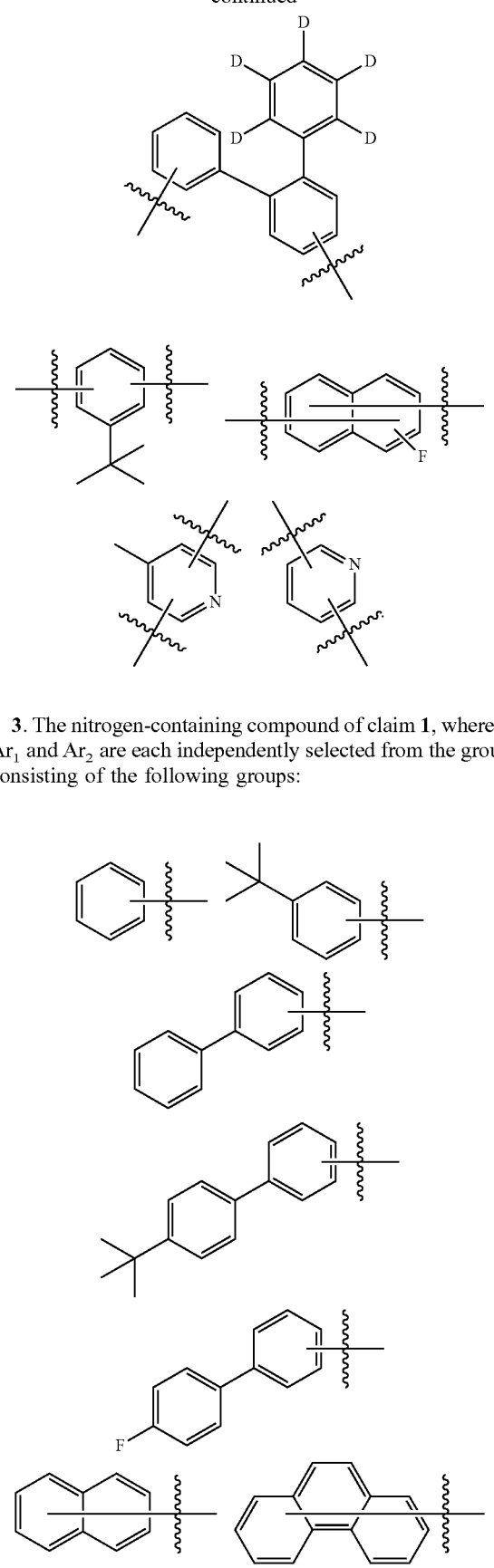
3. The nitrogen-containing compound of claim 1, wherein $Ar_1$ and $Ar_2$ are each independently selected from the group consisting of the following groups:

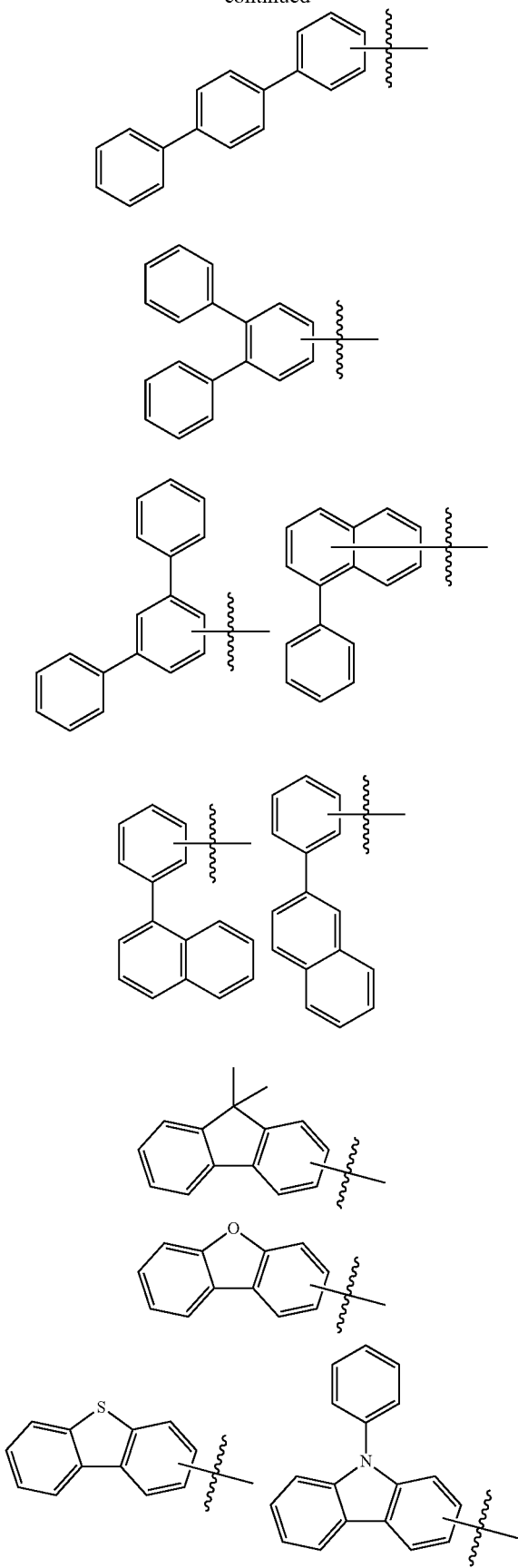
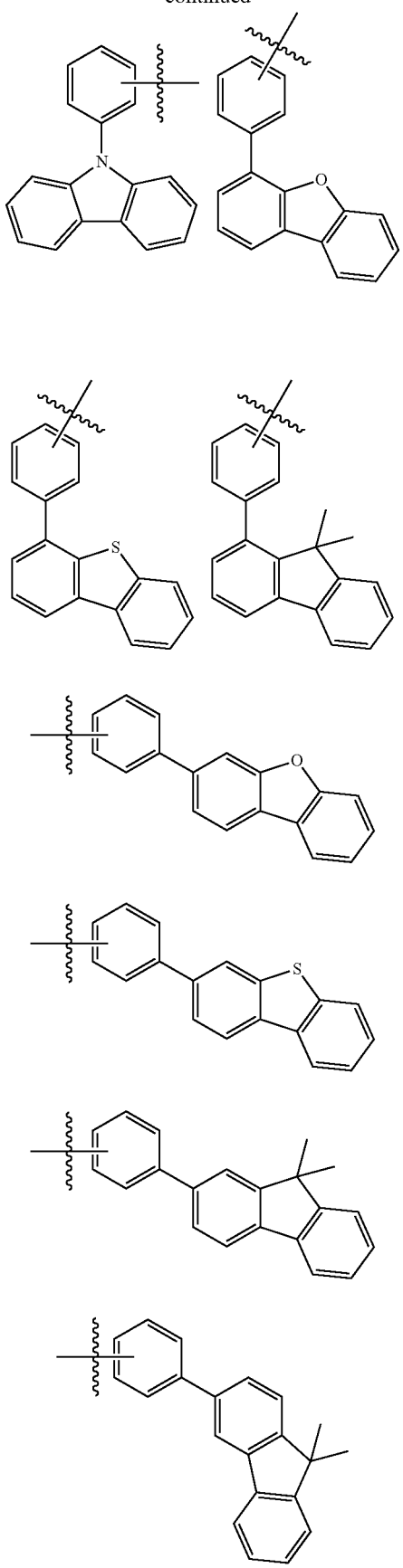

425
-continued

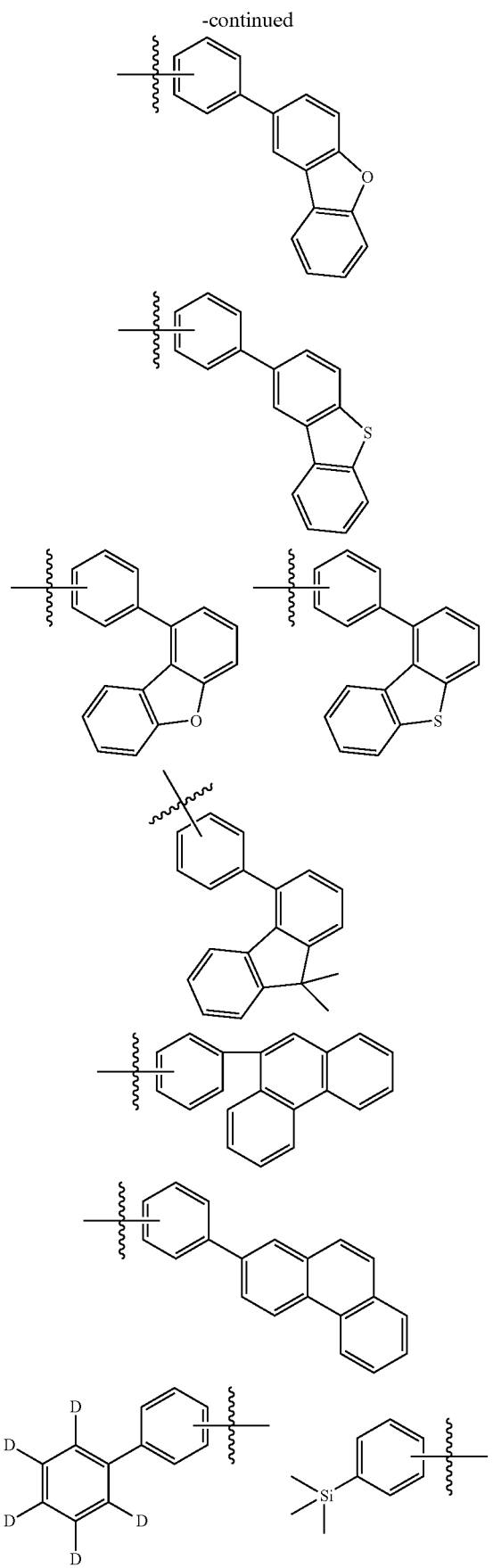

426
-continued

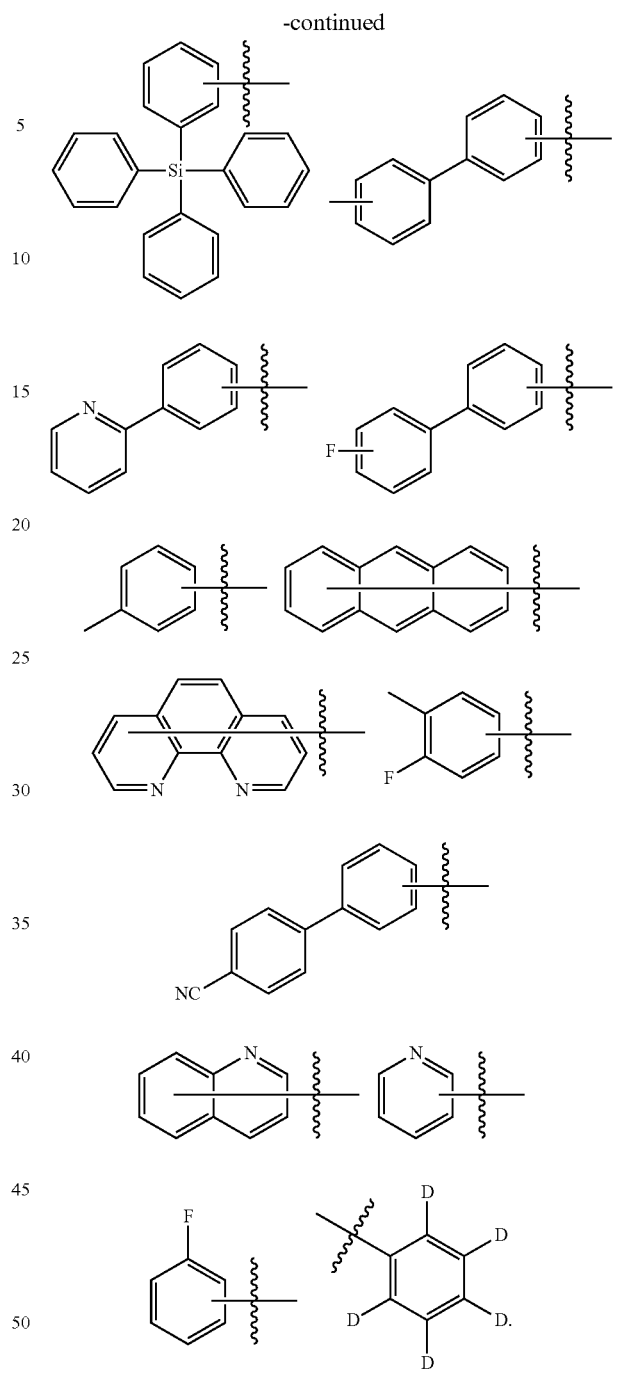

4. The nitrogen-containing compound of claim 1, wherein $R_3$ and $R_4$ are each independently selected from an aryl having 6 to 18 carbon atoms.

5. The nitrogen-containing compound of claim 1, wherein $R_3$ and/or $R_4$ are an aryl having 6 carbon atoms.

6. The nitrogen-containing compound of claim 1, wherein $R_3$ is an aryl having 6 carbon atoms, and a is 1, b is 0.

7. The nitrogen-containing compound of claim 1, wherein $R_4$ is an aryl having 6 carbon atoms, and a is 0, b is 1.

8. The nitrogen-containing compound of claim 1, wherein the nitrogen-containing compound selected from the group consisting of the following compounds:

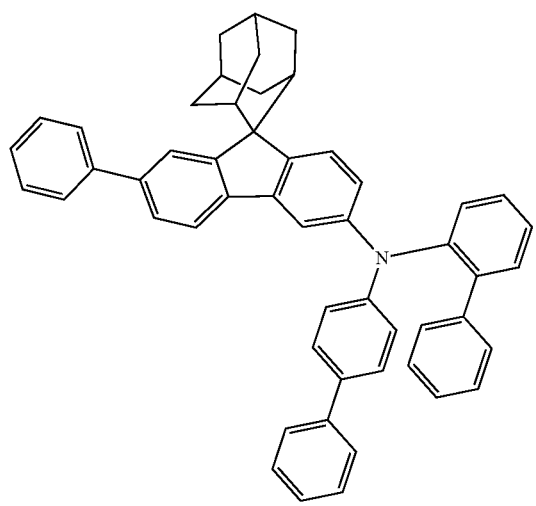

810

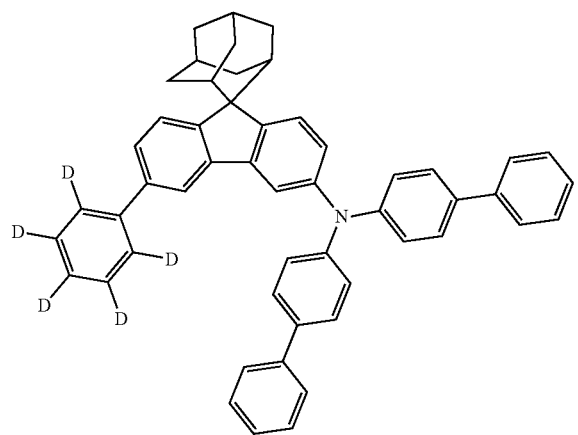

815

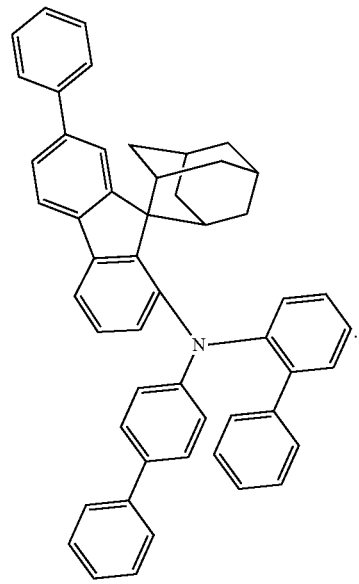

816

9. An electronic element, comprising:
an anode;
a cathode, wherein the anode and the cathode are disposed opposite to each other; and
a functional layer disposed between the anode and the cathode, wherein the functional layer contains the nitrogen-containing compound of claim 1.

10. The electronic element of claim 9, wherein the functional layer includes an electron blocking layer, and the electron blocking layer contains the nitrogen-containing compound.

11. The electronic element of claim 9, wherein the electronic element is an organic electroluminescence device.

12. An electronic device including the electronic element of claim 9.

\* \* \* \* \*